(12) United States Patent
Bennett et al.

(10) Patent No.: US 10,221,163 B2
(45) Date of Patent: Mar. 5, 2019

(54) METALLO-BETA-LACTAMASE INHIBITORS

(71) Applicant: Merck Sharp & Dohme Corp., Rahway, NJ (US)

(72) Inventors: Frank Bennett, Cranford, NJ (US); Jinlong Jiang, Scotch Plains, NJ (US); Alexander Pasternak, Princeton, NJ (US); Shuzhi Dong, Plainsboro, NJ (US); Xin Gu, Scotch Plains, NJ (US); Jack D. Scott, Scotch Plains, NJ (US); Haiqun Tang, Belle Mead, NJ (US); Zhiqiang Zhao, Scotch Plains, NJ (US); Yuhua Huang, Westfield, NJ (US); Dexi Yang, Livingston, NJ (US); Katherine Young, Metuchen, NJ (US); Li Xiao, Cranbury, NJ (US); Zhibo Zhang, Beijing (CN); Jianmin Fu, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/737,351

(22) PCT Filed: Jun. 24, 2016

(86) PCT No.: PCT/US2016/039156
§ 371 (c)(1),
(2) Date: Dec. 18, 2017

(87) PCT Pub. No.: WO2016/210215
PCT Pub. Date: Dec. 29, 2016

(65) Prior Publication Data
US 2018/0244656 A1    Aug. 30, 2018

(30) Foreign Application Priority Data

Jun. 26, 2015  (WO) ................ PCT/CN2015/082514

(51) Int. Cl.
*C07D 403/14* (2006.01)
*C07D 403/10* (2006.01)
(Continued)

(52) U.S. Cl.
CPC .......... *C07D 403/10* (2013.01); *A61K 31/198* (2013.01); *A61K 31/407* (2013.01); *A61K 31/41* (2013.01); *A61K 31/416* (2013.01); *A61K 31/4184* (2013.01); *A61K 31/4192* (2013.01); *A61K 31/4196* (2013.01); *A61K 31/421* (2013.01); *A61K 31/423* (2013.01); *A61K 31/428* (2013.01); *A61K 31/4245* (2013.01); *A61K 31/431* (2013.01); *A61K 31/437* (2013.01); *A61K 31/439* (2013.01); *A61K 31/4375* (2013.01); *A61K 31/4439* (2013.01);
(Continued)

(58) Field of Classification Search
CPC .................................................... C07D 403/14
USPC .............................................................. 514/196
See application file for complete search history.

(56) References Cited

U.S. PATENT DOCUMENTS 4,746,353 A    5/1988 Levitt
4,786,311 A    11/1988 Levitt
(Continued)

FOREIGN PATENT DOCUMENTS

CN    1095549    11/1994
CN    103130686    6/2013
(Continued)

OTHER PUBLICATIONS

English language abstract for CN1095549, published Nov. 30, 1994.
(Continued)

*Primary Examiner* — Kahsay Habte
(74) *Attorney, Agent, or Firm* — Eric A. Meade; John C. Todaro

(57) ABSTRACT

The present invention relates to metallo-beta-lactamase inhibitor compounds of Formula I: and pharmaceutically acceptable salts thereof, wherein Z, $R^A$, $X_1$, $X_2$ and $R^1$ are as defined herein. The present invention also relates to compositions which comprise a metallo-beta-lactamase inhibitor compound of the invention or a pharmaceutically acceptable salt thereof, and a pharmaceutically acceptable carrier, optionally in combination with a beta-lactam antibiotic and/or a beta-lactamase inhibitor. The invention further relates to methods for treating a bacterial infection comprising administering to a patient a therapeutically effective amount of a compound of the invention, in combination with a therapeutically effective amount of one or more β-lactam antibiotics and optionally in combination with one or more beta-lactamase inhibitor compounds. The compounds of the invention are useful in the methods described herein for overcoming antibiotic resistance.

(I)

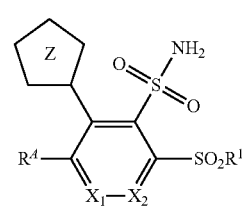

67 Claims, No Drawings

(51) Int. Cl.

| | | |
|---|---|---|
| C07D 403/12 | (2006.01) | |
| C07D 413/14 | (2006.01) | |
| C07D 401/10 | (2006.01) | |
| C07D 407/14 | (2006.01) | |
| C07D 413/10 | (2006.01) | |
| C07D 417/10 | (2006.01) | |
| C07D 417/14 | (2006.01) | |
| C07D 471/04 | (2006.01) | |
| A61P 31/04 | (2006.01) | |
| A61K 31/416 | (2006.01) | |
| A61K 31/4184 | (2006.01) | |
| A61K 31/423 | (2006.01) | |
| A61K 31/428 | (2006.01) | |
| A61K 31/437 | (2006.01) | |
| A61K 31/4375 | (2006.01) | |
| A61K 31/4439 | (2006.01) | |
| A61K 31/454 | (2006.01) | |
| A61K 31/4545 | (2006.01) | |
| A61K 31/4709 | (2006.01) | |
| A61K 31/4725 | (2006.01) | |
| A61K 31/498 | (2006.01) | |
| A61K 31/5025 | (2006.01) | |
| A61K 31/506 | (2006.01) | |
| A61K 31/517 | (2006.01) | |
| A61K 31/5377 | (2006.01) | |
| A61K 45/06 | (2006.01) | |
| C07D 401/14 | (2006.01) | |
| C07D 487/04 | (2006.01) | |
| A61K 31/198 | (2006.01) | |
| A61K 31/407 | (2006.01) | |
| A61K 31/41 | (2006.01) | |
| A61K 31/4192 | (2006.01) | |
| A61K 31/4196 | (2006.01) | |
| A61K 31/421 | (2006.01) | |
| A61K 31/4245 | (2006.01) | |
| A61K 31/431 | (2006.01) | |
| A61K 31/439 | (2006.01) | |
| A61K 31/496 | (2006.01) | |
| A61K 31/541 | (2006.01) | |
| A61K 31/546 | (2006.01) | |
| C07D 405/14 | (2006.01) | |
| C07D 453/02 | (2006.01) | |
| C07D 487/10 | (2006.01) | |
| C07D 493/04 | (2006.01) | |
| C07D 493/08 | (2006.01) | |
| C07D 495/08 | (2006.01) | |

(52) U.S. Cl.
CPC ........ *A61K 31/454* (2013.01); *A61K 31/4545* (2013.01); *A61K 31/4709* (2013.01); *A61K 31/4725* (2013.01); *A61K 31/496* (2013.01); *A61K 31/498* (2013.01); *A61K 31/506* (2013.01); *A61K 31/5025* (2013.01); *A61K 31/517* (2013.01); *A61K 31/5377* (2013.01); *A61K 31/541* (2013.01); *A61K 31/546* (2013.01); *A61K 45/06* (2013.01); *A61P 31/04* (2018.01); *C07D 401/10* (2013.01); *C07D 401/14* (2013.01); *C07D 403/12* (2013.01); *C07D 403/14* (2013.01); *C07D 405/14* (2013.01); *C07D 407/14* (2013.01); *C07D 413/10* (2013.01); *C07D 413/14* (2013.01); *C07D 417/10* (2013.01); *C07D 417/14* (2013.01); *C07D 453/02* (2013.01); *C07D 471/04* (2013.01); *C07D 487/04* (2013.01); *C07D 487/10* (2013.01); *C07D 493/04* (2013.01); *C07D 493/08* (2013.01); *C07D 495/08* (2013.01)

(56) References Cited

U.S. PATENT DOCUMENTS

| | | |
|---|---|---|
| 4,838,925 A | 6/1989 | Tseng |
| 9,708,336 B2 | 7/2017 | Mandal et al. |
| 9,839,642 B2 | 12/2017 | Tang et al. |
| 2003/0199541 A1 | 10/2003 | Lampilas et al. |
| 2004/0157826 A1 | 8/2004 | Lampilas et al. |
| 2016/0333021 A1 | 11/2016 | Mandal et al. |
| 2017/0173035 A1 | 6/2017 | Tang et al. |
| 2018/0179180 A1 | 6/2018 | Shao et al. |

FOREIGN PATENT DOCUMENTS

| | | |
|---|---|---|
| CN | 103191091 | 7/2013 |
| EP | 204513 | 12/1986 |
| EP | 244166 | 11/1987 |
| WO | WO2008039420 | 4/2008 |
| WO | WO2013103760 | 7/2013 |
| WO | WO2014198849 | 12/2014 |
| WO | 2015112441 A1 | 7/2015 |
| WO | 2016210234 | 6/2016 |
| WO | 2016206101 A1 | 12/2016 |
| WO | WO2016210215 A1 | 12/2016 |

OTHER PUBLICATIONS

Fast and Sutton, Proteins and Proteomics, Biochimica et Biophysica Acta, NPL-FAST-2013-1834, p. 1834, 8.
Fast et al., Metallo-β-lactamase: inhibitors and reporter substrates, Biochimica et Biophysica Acta—Proteins and Proteomics, 2013, 1648-1659, 1834(8).
Green et al., Inhibition of bacterial peptide deformylase by biaryl acid analogs, Archives of Biochemistry and Biophysics, 2000, 355-358, 375(2).
International Search Report and Written Opinion for PCT/US2016/039156, dated Sep. 13, 2016, 14 pages.
J. D. Buynak, Beta-Lacatamase inhibitors: A review of the patent literature (2010-2013), Expert Opinion on Therapeutic Patents, Nov. 1, 2013, pp. 1469-1481, vol. 23, No. 11.
King, Dustin T., et al., Targeting metallo-b-lactamase enzymes in, Future Med. Chem., 2013, pp. 1243-1263, 5(11).
Olsen et al., Docking and scoring of metallo-beta-lactamases inhibitors, Journal of Computer-Aided Molecular Design, 2004, 287-302, 18(4).
Shen et al., Inhibitor Discovery of Full-Length New Delhi Metallo-Beta-Lactamase-1 (NDM-1), PLOS One, May 2013, pp. 1-7, vol. 8, Issue 5.
Toney et al., Antibiotic sensitization using biphenyl tetrazoles as potent inhibitors of Bacteroides fragilis metallo-beta-lactamase, Chemistry & Biology, 1998, 185-196, 5(4).
Toney et al., Structure-activity relationships of biphenyl tetrazoles as metallo-beta-lactamase inhibitors, Bioorganic & Medicinal Chemistry Letters, 1999, 2741-2746, 18(9).
Yang, S.-K., et al., Azolylthioacetamide: A Highly Promising Scaffold for the Development of Metallo-beta-lactamase Inhibitors, ACS Medicinal Chemistry Letters, 2015, pp. 455-460, 6.
Zhang, Y.; et al., Diaryl-Substituted Azolylthioacetamides: Inhibitor, ChemMedChem, 2014, pp. 2445-2448, 9.
English language abstract for CN103130686, published Jun. 5, 2013.
English Language abstract of CN103191091, published Jul. 10, 2013.
Gilchrist, T.L., "Five-Membered Ring Compounds With Two or More Heteroatoms", Heterocyclic Chemistry, 1985, pp. 187-188, Chapter 7.1, London.
Japanese Translation of Office Action Corresponding Japanese Patent Application No. 2017-56836—dated May 29, 2018.

(56) References Cited

OTHER PUBLICATIONS

Jones, Maitland Jr., Introduction to Amino Acids and Polyamino Acids (Peptides and Proteins), Organic Chemistry, 2000, pp. 1273-1275, Chapter 25.1.
International Search Report and Written Opinion for PCT/CN2015/82514, dated Feb. 16, 2016.

METALLO-BETA-LACTAMASE INHIBITORS

CROSS REFERENCE TO RELATED APPLICATIONS

This application is a U.S. National Phase application under 35 U.S.C. § 371 of PCT Application No. PCT/US2016/039156, filed Jun. 24, 2016, which claims priority under 35 U.S.C. § 119(e) from International Application No. PCT/CN2015/082514, filed Jun. 26, 2015.

FIELD OF THE INVENTION

This invention relates to novel metallo-β-lactamase inhibitors and their uses. A preferred use of the metallo-β-lactamase inhibitors is for reducing bacterial beta-lactam antibiotic resistance.

BACKGROUND OF THE INVENTION

Bacterial antibiotic resistance has become one of the most serious threats to modern health care. Infections caused by resistant bacteria frequently result in longer hospital stays, higher mortality and increased cost of treatment. See, e.g., Cohen, *Science* 1992, 257:1051-1055. The need for new antibiotics will continue to escalate because bacteria have a remarkable ability to develop resistance to new agents, rendering them quickly ineffective. See, e.g., Neu, *Science* 1992, 257: 1064-1073. The spread of antibiotic resistance has been referred to as a pandemic. A solution to the growing public health threat will require an interdisciplinary approach. See, e.g., Anderson, *Nature America* 1999, 5: 147-149. See also Bush et al., *Nature Reviews in Microbiology* 2011, 9: 894-896; Levy and Marshall, *Nature Medicine* 2004, 10: S122-S129; Livermore, *Clinical Infectious Diseases* 2003, 36: S11-S23; and Roberts et al., *Clinical Infectious Diseases* 2009, 49: 1175-1184.

The present crisis has prompted various efforts to elucidate the mechanisms responsible for bacterial resistance. The widespread use of penicillins and cephalosporins has resulted in the emergence of β-lactamases, a family of bacterial enzymes that catalyze the hydrolysis of the β-lactam ring common to numerous presently used antibiotics. See, Coulton et al., *Progress in Medicinal Chemistry* 1994, 31: 297-349. This family of bacterial β-lactamases is further divided into four sub-families: A, C, and D families, which comprise β-lactamases that have a serine at the active site that catalyzes the hydrolysis of β-lactam antibiotics, and B family, which comprises β-lactamases that are zinc metalloenzymes. Resistance mediated by β-lactamases is a critical aspect at the core of the development of bacterial antibiotic resistance. See, Dudley, *Pharmacotherapy* 1995, 15: 9S-14S. Clavulanic acid, which is a metabolite of *Streptomyces clavuligerus*, and two semi-synthetic inhibitors, sulbactam and tazobactam, are currently available semi-synthetic or natural product β-lactamase inhibitors. Synthetic β-lactamase inhibitors have also been described. See, U.S. Pat. Nos. 5,698,577; 5,510,343; 6,472,406; Hubschwerlen et al., *J. Med. Chem.* 1998, 41: 3961; and Livermore et al., *J. Med. Chem.* 1997, 40: 335-343. Poole (*Cell. Mol. Life Sci.* 2004, 61: 2200-2223) provides a review of the resistance of bacterial pathogens to β-lactam antibiotics and approaches for overcoming resistance. For a review of inhibitors of metallo β-lactamases, see Fast and Sutton, *Biochimica et Biophysica Acta Proteins and Proteomics* 2013, 1834(8): 1648-1659.

U.S. Patent Application Publication No. US 2003/0199541 discloses certain azabicyclic compounds including certain 7-oxo-6-diazabicyclic[3.2.1]octane-2-carboxamides and their use as anti-bacterial agents. U.S. Patent Application Publication No. US 2004/0157826 discloses heterobicyclic compounds including certain diazepine carboxamide and diazepine carboxylate derivatives and their use as anti-bacterials and β-lactamase inhibitors. International Patent Application Publication No. WO 2008/039420 discloses 7-oxo-2,6-diazabicyclo[3.2.0]heptane-6-sulfooxy-2-carboxamides and their use as β-lactamase inhibitors.

Zheng et al. (*PLOS One* 2013, 8(5), e62955) disclose substituted 2,5-bis-tetrazolylmethyl-thiophenes and their use as β-lactamse inhibitors. Chinese Patent Application Publication No. CN103130686 A discloses N,N'-diarylureas and their use as inhibitors of metallo β-lactamases. Chinese Patent Application Publication No. CN103191091 A discloses substituted arylsulfonamides and their use as inhibitors of metallo β-lactamases.

U.S. Pat. Nos. 4,786,311; 4,746,353; 4,838,925; European Patent Application Publication Nos. EP204513; EP244166; and Chinese Patent Application Publication No. CN1095549A disclose substituted 2-(1H-tetrazol-5-yl)benzenesulfonamides and their use as herbicides.

International Patent Application Publication No. WO 2015/112441 discloses substituted 1H- and 2H-tetrazol-5-yl sulfonamide compounds as metallo β-lactamase inhibitors.

SUMMARY OF THE INVENTION

The present invention is directed to substituted 1H- and 2H-tetrazol-5-yl sulfonamide compounds and related compounds which are metallo-β-lactamase inhibitors. The compounds, and their pharmaceutically acceptable salts, are useful, for example, in combination with β-lactam antibiotics, and optionally serine β-lactamase inhibitors, for the treatment of bacterial infections, particularly antibiotic-resistant bacterial infections. More particularly, the present invention includes compounds of Formula I:

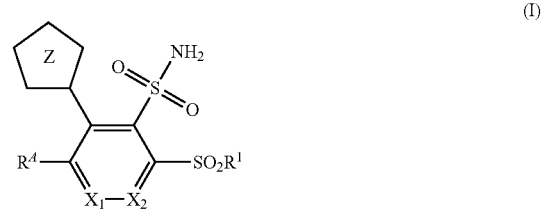

or a pharmaceutically acceptable salt thereof, wherein:

$X^1$ is N or CH;

$X^2$ is N or CH;

Z is tetrazolyl, wherein Z is linked through a carbon to carbon bond to the six-membered core ring having $X_1$ and $X_2$;

$R^A$ is —$(CH_2)_n$-AryA1, —$(CH_2)_n$-HetA1, —$(CH_2)_n$—$C_4$-$C_6$cycloalkyl, or —$(CH_2)_n$—$C_4$-$C_6$cycloalkenyl, wherein said —$(CH_2)_n$—$C_4$-$C_6$cycloalkyl and —$(CH_2)_n$—$C_4$-$C_6$cycloalkenyl are optionally substituted with 1, 2, or 3 substituents independently selected from —$NH_2$, —OH, —F, and —$NR^aC(O)C_1$-$C_6$alkyl optionally substituted with 1 or 2 substituents independently selected from —F, —$CF_3$, —$NR^aR^b$, and —$OR^a$;

$R^1$ is
1) —NH$_2$;
2) —NR$^a$—C$_1$-C$_6$alkyl optionally substituted with 1, 2, 3, or 4 substituents independently selected from —F, —CF$_3$, —CH(NH$_2$)C(O)NH$_2$, —C(O)NR$^a$R$^b$, —C(O)OH, —(CH$_2$)$_{1-2}$NH$_2$, —NR$^a$(CH$_2$)$_{2-3}$NH$_2$, —NR$^a$R$^b$, —N$^+$R$^a$R$^b$CH$_3$, —NHCH$_2$CH$_2$OCH$_3$, —OR$^a$, and —O(CH$_2$)$_{2-3}$NH$_2$;
3) —NR$^a$C(O)C$_1$-C$_6$alkyl optionally substituted with 1 or 2 substituents independently selected from —F, —CF$_3$, —C(O)NR$^a$R$^b$, —C(O)OH, —NR$^a$R$^b$, —N$^+$R$^a$R$^b$CH$_3$, —NHCH$_2$CH$_2$OCH$_3$, —OR$^a$, and —O(CH$_2$)$_{2-3}$NH$_2$;
4) —NR$^a$(CH$_2$)$_n$—C$_3$-C$_6$cycloalkyl, wherein the C$_3$-C$_6$cycloalkyl is optionally substituted with —CH$_2$OH or —NH$_2$;
5) a nitrogen-linked 4-6 membered monocyclic heterocycloalkyl with 0, 1, or 2, additional heteroatom ring atoms independently selected from N, O and S, or a nitrogen-linked 6- to 10-membered bicyclic heterocycloalkyl with 0, 1, 2, or 3 additional heteroatom ring atoms selected from N, O and S wherein the bicyclic ring may be bridged, fused or spirocyclic, wherein the 4-6 membered monocyclic heterocycloalkyl and the 6- to 10-membered bicyclic heterocycloalkyl are optionally substituted with one to three substituents, independently selected from: —F, —NR$^a$R$^b$, oxo, —(CH$_2$)$_{1-2}$OH, —CH$_2$NH$_2$, —SO$_2$CH$_3$, and C$_1$-C$_6$ alkyl and wherein a ring sulfur atom is optionally substituted with one or two oxo;
6) —NR$^a$—(C$_1$-C$_3$alkyl)$_n$-AryB1, wherein the C$_1$-C$_3$alkyl is optionally substituted with —NH$_2$; and
7) —NR$^a$—(C$_1$-C$_3$alkyl)$_n$-HetB1;

AryA1 is an aromatic ring system selected from:
1) a 5-6 membered monocyclic ring with 0, 1, 2, or 3 heteroatom ring atoms independently selected from N, O, and S, optionally substituted with 1, 2, or 3 substituents independently selected from:
 a) halogen,
 b) —C$_1$-C$_6$alkyl,
 c) —CN,
 d) —CH$_2$OH,
 e) —C(O)NR$^a$R$^b$,
 f) —C(O)NH(CH$_2$)$_{2-4}$NH$_2$ optionally substituted with one or two substituents independently selected from —NR$^a$R$^b$ and —(CH$_2$)$_n$OR$^a$,
 g) —C(O)OR$^a$,
 h) —(CH$_2$)$_p$NHR$^a$ optionally substituted with one or two substituents independently selected from —NR$^a$R$^b$ or —OR$^a$,
 i) —(CH$_2$)$_p$NR$^a$C($=$NH)NH$_2$,
 j) —NR$^a$C(O)C$_1$-C$_6$ alkyl optionally substituted with one or two substituents independently selected from —NR$^a$R$^b$ or —OR$^a$,
 k) —NR$^a$SO$_2$—C$_1$-C$_6$alkyl,
 l) —NR$^a$SO$_2$-cyclopropyl,
 m) —OR$^a$,
 n) oxo,
 o) —SC$_1$-C$_6$ alkyl optionally substituted with one or two substituents independently selected from —NR$^a$R$^b$ or —OR$^a$;
 p) —SO$_2$R$^a$,
 q) —SO$_2$NR$^a$R$^b$,
 r) —SO$_2$NH-cyclopropyl,
 s) -AryA2,
 t) —(CH$_2$)$_n$NR$^a$AryA2,
 u) —C(O)NR$^a$HetA2 and
 v) -HetA2, and 2) an 8- to 10-membered bicyclic ring with 1, 2, 3 or 4 heteroatom ring atoms selected from N, O and S, wherein an S atom optionally has one or two oxo substituents and a N atom is optionally in the form of an N-oxide, and wherein the ring is optionally substituted with 1 or 2 substituents independently selected from
 a) halogen;
 b) C$_1$-C$_6$alkyl optionally substituted with one to three substituents independently selected from —NR$^a$R$^b$, —F and —OR$^a$;
 c) —(CH$_2$)$_n$CF$_3$;
 d) —C($=$NH)NH$_2$;
 e) —CN;
 f) —C(O)CF$_3$;
 g) —C(O)NR$^a$R$^b$;
 h) —C(O)NHCH$_2$C(O)OR$^a$;
 i) —C(O)NH—C$_2$-C$_4$alkyl-NH$_2$,
 j) —C(O)OR$^a$;
 k) —NR$^a$R$^b$;
 l) —NHCH$_2$SO$_3$H;
 m) —(CH$_2$)—NHC($=$NH)NH$_2$;
 n) —NHC(O)C$_1$-C$_6$alkyl;
 o) —NHC(O)NH$_2$;
 p) —NHC(O)OR$^a$;
 q) —NHSO$_2$CH$_3$;
 r) —OR$^a$;
 s) oxo;
 t) —SO$_2$R$^a$,
 u) —CH$_2$-phenyl-OCH$_3$; and
 v) -HetA2;

HetA1 is dihydrothiopyranyl or tetrahydropyranyl;

AryA2 is a 5-6-membered aromatic monocyclic ring with 1, 2, or 3 heteroatom ring atoms independently selected from N, N as a quaternary salt, and S, or 4 N ring atoms, optionally substituted with —CH$_2$OH, —COOH, —CONH$_2$, —C(O)OC$_1$-C$_6$alkyl, and —(CH$_2$)$_p$NHR$^a$ optionally substituted with one or two substituents independently selected from —NR$^a$R$^b$ and —OR$^a$;

HetA2 is a 4-6-membered saturated monocyclic ring with 1 or 2 heteroatom ring atoms independently selected from N, O and S, wherein the S is optionally substituted with two oxo groups, and wherein the ring is optionally substituted with 1 or 2 substituents independently selected from C$_1$-C$_6$alkyl, —CN, —OH, and oxo;

AryB1 is an aromatic ring selected from:
1) a 5-6 membered monocyclic aromatic ring with 0, 1, 2, or 3 N ring atoms, optionally substituted with 1 substituent selected from —CF$_3$, C$_1$-C$_6$ alkyl, —(CH$_2$)$_n$NH$_2$ and —OCH$_3$; or
2) a 9-membered bicyclic ring with 2 N ring atoms;

HetB1 is a saturated ring selected from:
1) a 4-6 membered saturated monocyclic ring with 1 or 2 heteroatom ring atoms independently selected from N, O and S, wherein a N ring atom is optionally in the form of a quaternary amine, wherein the S is substituted with two oxo groups, and wherein the ring is optionally substituted with 1 or 2 substituents independently selected from —F, C$_1$-C$_6$ alkyl, C$_1$-C$_6$ hydroxyalkyl, —C(O)OR$^a$, —(CH$_2$)$_k$NR$^a$R$^b$, —OR$^a$, and oxo; or
2) a 6-10-membered bicyclic ring with 1 or 2 heteroatom ring atoms independently selected from N and O, optionally substituted with —OH or —NH$_2$, wherein the bicyclic ring is bridged or fused;

$R^a$ and $R^b$ are independently H or $C_1$-$C_6$ alkyl;

k is 0, 1, 2, 3, or 4;

each n is independently 0 or 1; and each p is independently 0, 1, 2, or 3.

Compounds of Formula I inhibit metallo-β lactamases and can synergize the antibacterial effects of β lactam antibiotics (e.g., imipenem, ceftazidime, ceftolozane, and piperacillin) against microorganisms normally resistant to β lactam antibiotics as a result of the presence of the metallo-β lactamases. Compounds of the present invention are effective against metallo-β lactamases and their combination with a β-lactam antibiotic, such as imipenem, ceftazidime, ceftolozane, or piperacillin, can provide effective treatment of bacterial infections caused by metallo-β lactamase-producing microorganisms. Accordingly, in certain embodiments, the present invention provides compositions comprising a compound of Formula I, IA, or IB with a β-lactam antibiotic, and optionally one or more additional β-lactamase inhibitors, suitable for use against metallo-β lactamase producing bacteria such as *Pseudomonas* spp. and *Klebsiella* spp. In some embodiments, the additional one or more β-lactamase inhibitor(s) is a serine (Class A, C and D) β-lactamase inhibitor. The invention also includes compositions comprising a compound of Formula I, IA, or IB or a pharmaceutically acceptable salt thereof, and a pharmaceutically acceptable carrier. The invention further includes methods for treating bacterial infections and inhibiting bacterial growth by administration of a compound of Formula I, IA, or IB, or a pharmaceutically acceptable salt thereof, to a patient in need thereof, or by administration of a pharmaceutical composition comprising a compound of Formula I, IA, or IB or its salt and a pharmaceutically acceptable carrier.

Embodiments, sub-embodiments, aspects and features of the present invention are either further described in or will be apparent from the ensuing description, examples and appended claims.

DETAILED DESCRIPTION OF THE INVENTION

As noted above, the present invention includes compounds of Formula I, IA, and IB, wherein the compounds are metallo-β-lactamase inhibitors suitable for use in combination with β-lactam antibiotics and optionally class A, C, and/or D β-lactamase inhibitors for the treatment of bacterial infections.

The invention is based, in part, on the presence of a sulfur linker at the 6-position of the core ring as a sulfonamide. The presence of a sulfur at this position results in improved enzyme potency compared to when the linker is carbon and also provides improved activity on difficult to penetrate *Pseudomonas* bacterial strains. The improved Pseudomonal activity is likely due to a decrease in efflux from the cells as a result of the sulfonamide linker.

In each of the various embodiments of the compounds of the invention described herein, each variable including those of Formulas I, IA and IB and the various embodiments thereof, is selected independently of the other variables unless otherwise indicated.

The present invention encompasses for each of the various embodiments of the compounds of the invention described herein, including those of Formulas I, IA and IB, and the various embodiments thereof and the compounds of the examples, all forms of the compounds such as, for example, any solvates, hydrates, stereoisomers, and tautomers of said compounds and of any pharmaceutically acceptable salts thereof, unless otherwise indicated. Additionally, in the examples described herein, the compounds of the invention may be depicted in the salt form. In such cases, it is to be understood that the compounds of the invention include the free acid or free base forms of such salts, and any pharmaceutically acceptable salt of said free acid or free base forms. In addition, in instances where an acidic group such as tetrazole and a basic group such as an amine are present within the same compound, these compounds may be drawn herein for convenience as the free acid and base forms but it should be understood that these can also be alternatively depicted in their zwitterionic forms in which the tetrazole bears a negative charge and the amine bears a positive charge, which are also included as compounds of the invention.

The Compounds of Formula (I):

In one aspect, the present invention includes compounds of Formula I:

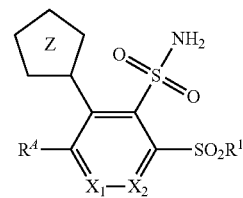

(I)

or a pharmaceutically acceptable salt thereof, wherein $X_1$, $X_2$, Z, $R^A$ and $R^1$ are as defined herein for the Compounds of Formula (I) (i.e. as defined in the Summary of the Invention); wherein the compounds may be suitable for use for the treatment of bacterial infections.

A first embodiment of the invention (Embodiment E1) is a compound of Formula I, or a pharmaceutically acceptable salt thereof, wherein $X_1$, $X_2$, Z, $R^A$ and $R^1$ are as defined in Formula (I) in the Summary of the Invention.

A second embodiment (Embodiment E2) is a compound of Formula I, or a pharmaceutically acceptable salt thereof, wherein $X_1$ is CH, and all other variables are as defined in Embodiment E1.

A third embodiment (Embodiment E3) is a compound of Formula I, or a pharmaceutically acceptable salt thereof, wherein $X_1$ is N, and all other variables are as defined in Embodiment E1.

A fourth embodiment (Embodiment E4) is a compound of Formula I, or a pharmaceutically acceptable salt thereof, wherein $X_1$ is defined in Embodiment E2 or E3, $X_2$ is CH, and all other variables are as defined in Embodiment E1.

A fifth embodiment (Embodiment E5) is a compound of Formula I, or a pharmaceutically acceptable salt thereof, wherein $X_1$ is defined in Embodiment E2 or E3, $X_2$ is N, and all other variables are as defined in Embodiment E1.

A sixth embodiment (Embodiment E6) is a compound of Formula I, or a pharmaceutically acceptable salt thereof, wherein $X_1$ is defined in Embodiment E2 or E3, $X_2$ is defined in Embodiment E4 or E5, $R^A$ is —$(CH_2)_n$-AryA1 and all other variables are as defined in Embodiment E1.

A seventh embodiment (Embodiment E7) is a compound of Formula I, or a pharmaceutically acceptable salt thereof, wherein $X_1$ is defined in Embodiment E2 or E3, $X_2$ is defined in Embodiment E4 or E5, $R^A$ is —$(CH_2)_n$-HetA1 and all other variables are as defined in Embodiment E1.

An eighth embodiment (Embodiment E8) is a compound of Formula I, or a pharmaceutically acceptable salt thereof, wherein $X_1$ is defined in Embodiment E2 or E3, $X_2$ is defined in Embodiment E4 or E5, $R^A$ is —$(CH_2)_n$—$C_4$-$C_6$cycloalkyl, wherein said —$(CH_2)_n$—$C_4$-$C_6$cycloalkyl is optionally substituted with 1, 2, or 3 substituents independently selected from —$NH_2$, —OH, —F, and —$NR^aC(O)$ $C_1$-$C_6$alkyl optionally substituted with 1 or 2 substituents independently selected from —F, —$CF_3$, —$NR^aR^b$, and —$OR^a$ and all other variables are as defined in Embodiment E1.

In one sub-embodiment of Embodiment E8, —$(CH_2)_n$—$C_4$-$C_6$cycloalkyl is unsubstituted. In another sub-embodiment of Embodiment E8, —$(CH_2)_n$—$C_4$-$C_6$cycloalkyl is substituted with 1 substituent. In another sub-embodiment of Embodiment E8, —$(CH_2)_n$—$C_4$-$C_6$cycloalkyl is substituted with 2 substituents. In another sub-embodiment of Embodiment E8, —$(CH_2)_n$—$C_4$-$C_6$cycloalkyl is substituted with 3 substituents.

In another sub-embodiment of Embodiment E8 —$(CH_2)_n$—$C_4$-$C_6$cycloalkyl is substituted with at least one occurrence of $NH_2$.

In a further sub-embodiment of Embodiment E8 —$(CH_2)_n$—$C_4$-$C_6$cycloalkyl is substituted with at least one occurrence of —OH.

In yet another sub-embodiment of Embodiment E8 —$(CH_2)_n$—$C_4$-$C_6$cycloalkyl is substituted with at least one occurrence of —F.

In one sub-embodiment of Embodiment E8 —$(CH_2)_n$—$C_4$-$C_6$cycloalkyl is substituted with at least one occurrence of —$NR^aC(O)C_1$-$C_6$alkyl optionally substituted with 1 or 2 substituents independently selected from —F, —$CF_3$, —$NR^aR^b$, and —$OR^a$.

A ninth embodiment (Embodiment E9) is a compound of Formula I, or a pharmaceutically acceptable salt thereof, wherein $X_1$ is defined in Embodiment E2 or E3, $X_2$ is defined in Embodiment E4 or E5, $R^A$ is —$(CH_2)_n$—$C_4$-$C_6$cycloalkenyl, wherein —$(CH_2)_n$—$C_4$-$C_6$cycloalkenyl is optionally substituted with 1, 2, or 3 substituents independently selected from —$NH_2$, —OH, —F, and —$NR^aC(O)$ $C_1$-$C_6$alkyl optionally substituted with 1 or 2 substituents independently selected from —F, —$CF_3$, —$NR^aR^b$, and —$OR^a$ and all other variables are as defined in Embodiment E1.

In one sub-embodiment of Embodiment E9, —$(CH_2)_n$—$C_4$-$C_6$cycloalkenyl is unsubstituted. In another sub-embodiment of Embodiment E9, —$(CH_2)_n$—$C_4$-$C_6$cycloalkenyl is substituted with 1 substituent. In another sub-embodiment of Embodiment E9, —$(CH_2)_n$—$C_4$-$C_6$cycloalkenyl is substituted with 2 substituents. In another sub-embodiment of Embodiment E9, —$(CH_2)_n$—$C_4$-$C_6$cycloalkenyl is substituted with 3 substituents.

In another sub-embodiment of Embodiment E9 —$(CH_2)_n$—$C_4$-$C_6$cycloalkenyl is substituted with at least one occurrence of $NH_2$.

In a further sub-embodiment of Embodiment E9 —$(CH_2)_n$—$C_4$-$C_6$cycloalkenyl is substituted with at least one occurrence of —OH.

In yet another sub-embodiment of Embodiment E9 —$(CH_2)_n$—$C_4$-$C_6$cycloalkenyl is substituted with at least one occurrence of —F.

In one sub-embodiment of Embodiment E9 —$(CH_2)_n$—$C_4$-$C_6$cycloalkenyl is substituted with at least one occurrence of —$NR^aC(O)C_1$-$C_6$alkyl optionally substituted with 1 or 2 substituents independently selected from —F, —$CF_3$, —$NR^aR^b$, and —$OR^a$.

A tenth embodiment (Embodiment E10) is a compound of Formula I, or a pharmaceutically acceptable salt thereof, wherein $X_1$ is defined in Embodiment E2 or E3, $X_2$ is defined in Embodiment E4 or E5, $R^A$ is AryA1 and all other variables are as defined in Embodiment E1.

An eleventh embodiment (Embodiment E11) is a compound of Formula I, or a pharmaceutically acceptable salt thereof, wherein $X_1$ is defined in Embodiment E2 or E3, $X_2$ is defined in Embodiment E4 or E5, $R^A$ is $C_4$-$C_6$cycloalkyl optionally substituted with —$NH_2$ or $NHC(O)(CH_2)_{1-3}NH_2$, and all other variables are as defined in Embodiment E1.

A twelfth embodiment (Embodiment E12) is a compound of Formula I, or a pharmaceutically acceptable salt thereof, wherein $X_1$ is defined in Embodiment E2 or E3, $X_2$ is defined in Embodiment E4 or E5, $R^A$ is $C_4$-$C_6$cycloalkenyl optionally substituted with —$NH_2$ or $NHC(O)(CH_2)_{1-3}NH_2$, and all other variables are as defined in Embodiment E1.

A thirteenth embodiment (Embodiment E13) is a compound of Formula I, or a pharmaceutically acceptable salt thereof, wherein $X_1$ is defined in Embodiment E2 or E3, $X_2$ is defined in Embodiment E4 or E5, $R^A$ is HetA1 and all other variables are as defined in Embodiment E1.

A fourteenth embodiment (Embodiment E14) is a compound of Formula I, or a pharmaceutically acceptable salt thereof, wherein $X_1$ is defined in Embodiment E2 or E3, $X_2$ is defined in Embodiment E4 or E5, $R^A$ is: selected from the group consisting of:

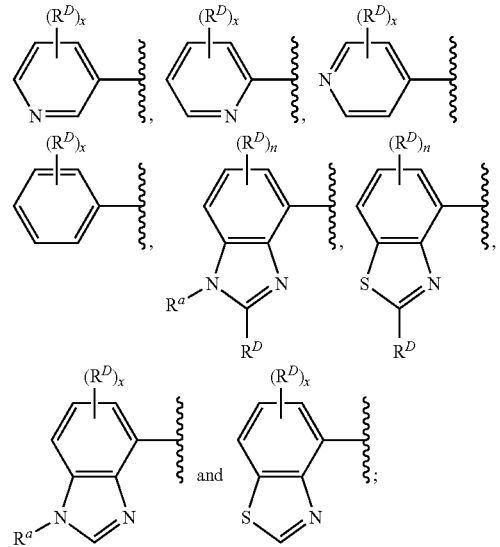

$R^D$ is F, —$C_1$-$C_6$ alkyl, —CONH—$C_2$-$C_4$alkyl-$NH_2$, —$NHR^a$ or —$(CH_2)$—$NHR^a$, each x is independently 0, 1, or 2, n is 0 or 1, and all other variables are as defined in Embodiment E1.

A fifteenth embodiment (Embodiment E15) is a compound of Formula I, or a pharmaceutically acceptable salt thereof, wherein $X_1$ is defined in Embodiment E2 or E3, $X_2$ is defined in Embodiment E4 or E5, $R^A$ is:

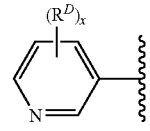

$R^D$ is F, —$C_1$-$C_6$ alkyl, —CONH—$C_2$-$C_4$alkyl-$NH_2$, —$NHR^a$ or —$(CH_2)_xNHR^a$, each x is independently 0, 1, or 2, and all other variables are as defined in Embodiment E1.

A sixteenth embodiment (Embodiment E16) is a compound of Formula I, or a pharmaceutically acceptable salt thereof, wherein $X_1$ is defined in Embodiment E2 or E3, $X_2$ is defined in Embodiment E4 or E5, $R^A$ is:

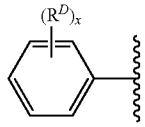

$R^D$ is F, —$C_1$-$C_6$ alkyl, —CONH—$C_2$-$C_4$alkyl-$NH_2$, —$NHR^a$ or —$(CH_2)_x NHR^a$, each x is independently 0, 1, or 2, and all other variables are as defined in Embodiment E1.

A seventeenth embodiment (Embodiment E17) is a compound of Formula I, or a pharmaceutically acceptable salt thereof, wherein $X_1$ is defined in Embodiment E2 or E3, $X_2$ is defined in Embodiment E4 or E5, $R^A$ is:

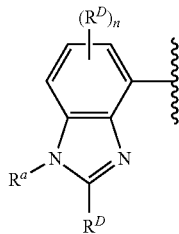

$R^D$ is —F, —$C_1$-$C_6$ alkyl, —CONH—$C_2$-$C_4$alkyl-$NH_2$, —$NHR^a$ or —$(CH_2)_x NHR^a$, x is 0, 1, or 2, n is 0 or 1, and all other variables are as defined in Embodiment E1.

An eighteenth embodiment (Embodiment E18) is a compound of Formula I, or a pharmaceutically acceptable salt thereof, wherein $X_1$ is defined in Embodiment E2 or E3, $X_2$ is defined in Embodiment E4 or E5, $R^A$ is:

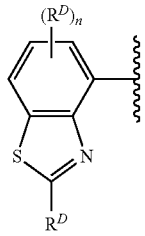

$R^D$ is F, —$C_1$-$C_6$ alkyl, —CONH—$C_2$-$C_4$alkyl-$NH_2$, —$NHR^a$ or —$(CH_2)_x NHR^a$, x is 0, 1, or 2, n is 0 or 1, and all other variables are as defined in Embodiment E1.

In sub-embodiments of Embodiments E17 and E18, n is 0.

In other sub-embodiments of Embodiments E17 and E18, at least one occurrence of $R^D$ is $NH_2$. In other sub-embodiments of Embodiment E17 and E18, at least one occurrence of $R^D$ is —$(CH_2)_x NHR^a$. In further sub-embodiments of Embodiments E17 and E18, at least one occurrence of $R^D$ is methyl. In yet other sub-embodiments of Embodiments E17 and E18, at least one occurrence of $R^D$ is —$CH_2NH_2$. In further sub-embodiments of Embodiments E17 and E18, at least one occurrence of $R^D$ is —F. In yet further sub-embodiments of Embodiments E17 and E18, at least one occurrence of $R^D$ is —CONH—$C_2$-$C_4$alkyl-$NH_2$. In other sub-embodiments of Embodiments E17 and E18, at least one occurrence of $R^D$ is —$C_1$-$C_6$ alkyl.

A nineteenth embodiment (Embodiment E19) is a compound of Formula I, or a pharmaceutically acceptable salt thereof, wherein $X_1$ is defined in Embodiment E2 or E3, $X_2$ is defined in Embodiment E4 or E5, $R^A$ is:

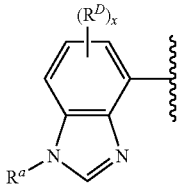

$R^D$ is F, —$C_1$-$C_6$ alkyl, —CONH—$C_2$-$C_4$alkyl-$NH_2$, —$NHR^a$ or —$(CH_2)_x NHR^a$, each x is independently 0, 1, or 2, and all other variables are as defined in Embodiment E1.

A twentieth embodiment (Embodiment E20) is a compound of Formula I, or a pharmaceutically acceptable salt thereof, wherein $X_1$ is defined in Embodiment E2 or E3, $X_2$ is defined in Embodiment E4 or E5, $R^A$ is:

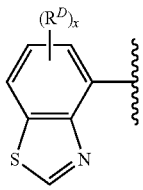

$R^D$ is F, —$C_1$-$C_6$ alkyl, —CONH—$C_2$-$C_4$alkyl-$NH_2$, —$NHR^a$ or —$(CH_2)_x NHR^a$, each x is independently 0, 1, or 2, and all other variables are as defined in Embodiment E1.

A twenty-first embodiment (Embodiment E21) is a compound of Formula I, or a pharmaceutically acceptable salt thereof, wherein $X_1$ is defined in Embodiment E2 or E3, $X_2$ is defined in Embodiment E4 or E5, $R^A$ is:

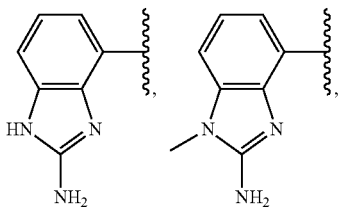

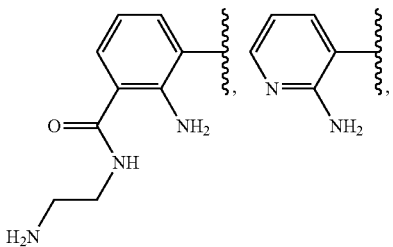

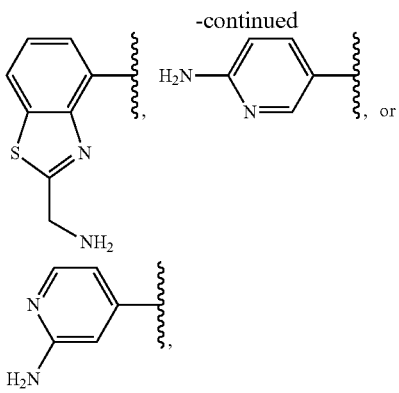

and all other variables are as defined in Embodiment E1.

A twenty-second embodiment (Embodiment E22) is a compound of Formula I, or a pharmaceutically acceptable salt thereof, wherein $X_1$ is defined in Embodiment E2 or E3, $X_2$ is defined in Embodiment E4 or E5, $R^A$ is a 5-6 membered aromatic monocyclic ring with 0, 1, 2, or 3 heteroatom ring atoms independently selected from N, O, and S, optionally substituted with 1, 2, or 3 substituents independently selected from: halogen, —$C_1$-$C_6$alkyl, —CN, —$CH_2$OH, —C(O)$NR^aR^b$, —C(O)NH($CH_2$)$_{2-4}NH_2$ optionally substituted with one or two substituents independently selected from —$NR^aR^b$ and —($CH_2$)$_n$$OR^a$, —C(O)$OR^a$, —($CH_2$)$_p$$NHR^a$ optionally substituted with one or two substituents independently selected from —$NR^aR^b$ or —$OR^a$, —($CH_2$)$_p$$NR^aC(=NH)NH_2$, —$NR^aC(O)C_1$-$C_6$ alkyl optionally substituted with one or two substituents independently selected from —$NR^aR^b$ or —$OR^a$, —$NR^aSO_2$—$C_1$-$C_6$alkyl, —$NR^aSO_2$-cyclopropyl, —$OR^a$, oxo, —$SC_1$-$C_6$ alkyl optionally substituted with one or two substituents independently selected from —$NR^aR^b$ or —$OR^a$; —$SO_2R^a$, —$SO_2NR^aR^b$, —$SO_2$NH-cyclopropyl, -AryA2, —($CH_2$)$_n$$NR^a$AryA2, —C(O)$NR^a$HetA2 and -HetA2, and all other variables are as defined in Embodiment E1.

A twenty-third embodiment (Embodiment E23) is a compound of Formula I, or a pharmaceutically acceptable salt thereof, wherein $X_1$ is defined in Embodiment E2 or E3, $X_2$ is defined in Embodiment E4 or E5, $R^A$ is an 8- to 10-membered bicyclic aromatic ring system with 1, 2, 3 or 4 heteroatom ring atoms selected from N, O and S, wherein an S atom optionally has one or two oxo substituents and a N atom is optionally in the form of an N-oxide, and wherein the ring is optionally substituted with 1 or 2 substituents independently selected from halogen; $C_1$-$C_6$alkyl optionally substituted with one to three substituents independently selected from —$NR^aR^b$, —F and —$OR^a$; —($CH_2$)$_n$$CF_3$; —C(=NH)$NH_2$; —CN; C(O)$CF_3$; —C(O)$NR^aR^b$; —C(O)NH$CH_2$C(O)$OR^a$; —C(O)NH—$C_2$-$C_4$alkyl-$NH_2$; —C(O)$OR^a$; —$NR^aR^b$; —NH$CH_2$$SO_3$H; —($CH_2$)$_n$NHC(=NH)$NH_2$; —NHC(O)$C_1$-$C_6$alkyl; —NHC(O)$NH_2$; —NHC(O)$OR^a$; —NH$SO_2CH_3$; —$OR^a$; oxo; —$SO_2R^a$, —$CH_2$-phenyl-$OCH_3$; and -HetA2; and all other variables are as defined in Embodiment E1.

A twenty-fourth embodiment (Embodiment E24) is a compound of Formula I, or a pharmaceutically acceptable salt thereof, wherein $X_1$ is defined in Embodiment E2 or E3, $X_2$ is defined in Embodiment E4 or E5, $R^A$ is dihydrothiopyranyl, and all other variables are as defined in Embodiment E1.

A twenty-fifth embodiment (Embodiment E25) is a compound of Formula I, or a pharmaceutically acceptable salt thereof, wherein $X_1$ is defined in Embodiment E2 or E3, $X_2$ is defined in Embodiment E4 or E5, $R^A$ is tetrahydropyranyl, and all other variables are as defined in Embodiment E1.

A twenty-sixth embodiment (Embodiment E26) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^1$ is $NH_2$ and all other variables are as defined in Embodiment E1.

A twenty-seventh embodiment (Embodiment E27) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^1$ is —$NR^a$—$C_1$-$C_6$alkyl optionally substituted with 1, 2, 3, or 4 substituents independently selected from —F, —$CF_3$, $C_1$-$C_6$alkyl, —CH($NH_2$)C(O)$NH_2$, —C(O)$NR^aR^b$, —C(O)OH, —($CH_2$)$_{1-2}NH_2$, —$NR^a$($CH_2$)$_{2-3}NH_2$, —$NR^aR^b$, —$N^+R^aR^bCH_3$, —NH$CH_2CH_2OCH_3$, —$OR^a$, and —O($CH_2$)$_{2-3}NH_2$ and all other variables are as defined in Embodiment E1.

A twenty-eighth embodiment (Embodiment E28) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^1$ is —$NR^aC(O)C_1$-$C_6$alkyl optionally substituted with 1 or 2 substituents independently selected from —F, —$CF_3$, —C(O)$NR^aR^b$, —C(O)OH, —$NR^aR^b$, —$N^+R^aR^bCH_3$, —NH$CH_2CH_2OCH_3$, —$OR^a$, and —O($CH_2$)$_{2-3}NH_2$ and all other variables are as defined in Embodiment E1.

A twenty-ninth embodiment (Embodiment E29) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^1$ is —$NR^a$($CH_2$)$_n$—$C_3$-$C_6$cycloalkyl, wherein the $C_3$-$C_6$cycloalkyl is optionally substituted with —$CH_2$OH or —$NH_2$ and all other variables are as defined in Embodiment E1.

A thirtieth embodiment (Embodiment E30) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^1$ is a nitrogen-linked 4-6 membered monocyclic heterocycloalkyl with 0, 1, or 2, additional heteroatom ring atoms independently selected from N, O and S, or a nitrogen-linked 6- to 10-membered bicyclic heterocycloalkyl with 0, 1, 2, or 3 additional heteroatom ring atoms selected from N, O and S wherein the bicyclic ring may be bridged, fused or spirocyclic, wherein the 4-6 membered monocyclic heterocycloalkyl and the 6- to 10-membered bicyclic heterocycloalkyl are optionally substituted with one to three substituents, independently selected from: —F, —$NR^aR^b$, oxo, —($CH_2$)$_{1-2}$OH, —$CH_2NH_2$, —$SO_2CH_3$, and $C_1$-$C_6$ alkyl and wherein a ring sulfur atom is optionally substituted with one or two oxo and all other variables are as defined in Embodiment E1.

A thirty-first embodiment (Embodiment E31) is a compound of Formula I, or a pharmaceutically acceptable salt thereof, wherein $X_1$ is defined in Embodiment E2 or E3, $X_2$ is defined in Embodiment E4 or E5, $R^A$ is defined in any of Embodiments E6-E25, $R^1$ is —$NR^a$—($C_1$-$C_3$alkyl)$_n$-AryB1, wherein the $C_1$-$C_3$alkyl is optionally substituted with —$NH_2$ and all other variables are as defined in Embodiment E1.

In a sub-embodiment of Embodiment E31, $R^a$ is H and AryB1 is a 5-6 membered monocyclic aromatic ring with 0, 1, 2, or 3 N ring atoms, optionally substituted with 1 substituent selected from —CF$_3$, C$_1$-C$_6$ alkyl, —(CH$_2$)$_n$NH$_2$ and —OCH$_3$.

In a further sub-embodiment of Embodiment E31, R$^a$ is H and AryB1 is a 9-membered bicyclic aromatic ring system with 2 N ring atoms.

A thirty-second embodiment (Embodiment E32) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NR$^a$—(C$_1$-C$_3$alkyl)$_n$-HetB1 and all other variables are as defined in Embodiment E1.

In a sub-embodiment of Embodiment E32, R$^a$ is H and HetB1 is a 4-6 membered saturated monocyclic ring with 1 or 2 heteroatom ring atoms independently selected from N, O and S, wherein a N ring atom is optionally in the form of a quaternary amine, wherein the S is substituted with two oxo groups, and wherein the ring is optionally substituted with 1 or 2 substituents independently selected from —F, C$_1$-C$_6$ alkyl, C$_1$-C$_6$ hydroxyalkyl, —C(O)OR$^a$, —(CH$_2$)$_k$N-R$^a$R$^b$, —OR$^a$, and oxo.

In another sub-embodiment of Embodiment E32, R$^a$ is H and HetB1 is a 6-10-membered saturated bicyclic ring with 1 or 2 heteroatom ring atoms independently selected from N and O, optionally substituted with —OH or —NH$_2$, wherein the bicyclic ring is bridged or fused.

In another sub-embodiment of Embodiment E32, R$^a$ is H and HetB1 is:

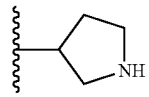

and all other variables are as defined in Embodiment E1.

A thirty-third embodiment (Embodiment E33) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NH-HetB1 optionally substituted with NH$_2$ and all other variables are as defined in Embodiment E1.

A thirty-fourth embodiment (Embodiment E34) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is NH—C$_1$-C$_3$alkylNH$_2$, optionally substituted with —CH$_3$, —OH or —NH$_2$ and all other variables are as defined in Embodiment E1.

A thirty-fifth embodiment (Embodiment E35) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is NH-HetB1, wherein HetB1 is a 4-6 membered saturated monocyclic ring with 1 or 2 heteroatom ring atoms independently selected from N and O, optionally substituted with —NH$_2$, and all other variables are as defined in Embodiment E1.

A thirty-sixth embodiment (Embodiment E36) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NH(CH$_2$)$_2$NH$_2$, and all other variables are as defined in Embodiment E1.

A thirty-seventh embodiment (Embodiment E37) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NHCH(CH$_2$NH$_2$)CH$_2$NH$_2$, and all other variables are as defined in Embodiment E1.

A thirty-eighth embodiment (Embodiment E38) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NHCH$_2$CH(OH)CH$_2$NH$_2$, and all other variables are as defined in Embodiment E1.

A thirty-ninth embodiment (Embodiment E39) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NHCH$_2$CH(NH$_2$)CH$_2$NH$_2$, and all other variables are as defined in Embodiment E1.

A fortieth embodiment (Embodiment E40) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NHCH(CH$_2$OH)CH$_2$NH$_2$, and all other variables are as defined in Embodiment E1.

A forty-first embodiment (Embodiment E41) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NHCH(CH$_3$)CH$_2$NH$_2$, and all other variables are as defined in Embodiment E1.

A forty-second embodiment (Embodiment E42) is a compound of Formula I, or a pharmaceutically acceptable salt thereof, wherein X$_1$ is defined in Embodiment E2 or E3, X$_2$ is defined in Embodiment E4 or E5, R$^A$ is defined in any of Embodiments E6-E25, R$^1$ is —NH2, —NH-HetB1 saturated bicyclic ring optionally substituted with —NH$_2$, or —NH—C$_2$-C$_3$alkylNH$_2$, optionally substituted with —CH$_3$, —OH or —NH$_2$, and all other variables are as defined in Embodiment E1.

A forty-third embodiment (Embodiment E43) is a compound or a pharmaceutically acceptable salt thereof, having the Formula IA:

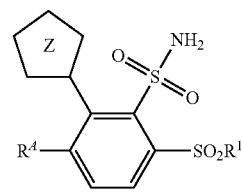

(IA)

wherein:

R$^A$ is AryA1, C$_4$-C$_6$cycloalkyl, or C$_4$-C$_6$cycloalkenyl, wherein said C$_4$-C$_6$cycloalkyl and C$_4$-C$_6$cycloalkenyl are optionally substituted with —NH$_2$ or NHC(O)(CH$_2$)$_{1-3}$NH$_2$;

AryA1 is an aromatic ring system selected from:
1) a 5-6 membered monocyclic ring with 0, 1, or 2 heteroatom ring atoms independently selected from N and S, optionally substituted with 1 or 2 substituents independently selected from:
   a) F,
   b) —C$_1$-C$_6$ alkyl,
   c) —CN, d) —CH$_2$OH,
e) —C(O)NR$^a$R$^b$,
f) —C(O)NH(CH$_2$)$_{2-4}$NH$_2$,
g) —C(O)OR$^a$,
h) —(CH$_2$)$_n$NHR$^a$,
i) —NHC(=NH)NH$_2$;
j) —NHC(O)CH$_3$;
k) —NR$^a$SO$_2$—C$_1$-C$_6$alkyl,
l) —NHSO$_2$-cyclopropyl,
m) —OR$^a$,
n) —SO$_2$NR$^a$R$^b$,
o) —SC$_1$-C$_6$alkyl,
p) —SO$_2$NH-cyclopropyl,
q) -AryA2,
r) —(CH$_2$)$_n$NR$^a$AryA2,
s) —C(O)NR$^a$HetA2 and
t) -HetA2, and 2) a 8- to 10-membered bicyclic ring with 1, 2, 3 or 4 heteroatom ring atoms selected from N, O and S, wherein an S atom is optionally substituted with one or two oxo substituents and a N atom is optionally in the form of an N-oxide, and wherein the ring is optionally substituted with 1 or 2 substituents independently selected from F, C$_1$-C$_6$ alkyl, —CH$_2$CF$_3$, —CF$_2$CH$_2$NH$_2$, —CF$_3$, —C(=NH)NH$_2$, —CH(NH$_2$)CH$_3$, —CN, —C(O)CF$_3$, —C(O)NR$^a$R$^b$, —C(O)NHCH$_2$C(O)OR$^a$, —C(O)OR$^a$, —(CH$_2$)$_{0-2}$NR$^a$R$^b$, —NHC(O)CH$_3$, —NHC(O)NH$_2$, —NHC(O)OR$^a$, —NHCH$_2$SO$_3$H, —NHSO$_2$CH$_3$, —OR$^a$, oxo, —CH$_2$-phenyl-OCH$_3$, and -HetA2;

wherein all other variables are defined in Embodiment E1.

A forty-fourth embodiment (Embodiment E44) is a compound, or a pharmaceutically acceptable salt thereof, having the Formula IB:

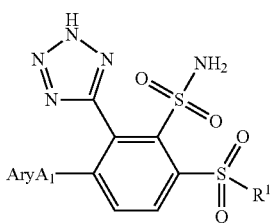

(IB)

wherein:
AryA1 is an aromatic ring system selected from:
1) a 5-6 membered monocyclic ring with 0 or 1 N ring atoms substituted with 1 or 2 substituents independently selected from F, —C$_1$-C$_6$ alkyl, —CONH—C$_{2-4}$alkyl-NH$_2$, or —NHR$^a$; or
2) a 9-membered bicyclic ring with 2 heteroatom ring atoms selected from N and S, wherein the ring is optionally substituted with 1 or 2 substituents independently selected from F, C$_1$-C$_6$ alkyl, and —(CH$_2$)$_x$NR$^a$R$^b$;
R$^1$ is
1) —NH$_2$;
2) —NR$^a$—C$_{1-6}$alkyl optionally substituted with 1 or 2 F substituents and optionally substituted with 1 or 2 substituents independently selected from —CF$_3$, —CH(NH$_2$)C(O)NR$^a$R$^b$; —C(O)NR$^a$R$^b$; —C(O)OH; —NR$^a$(CH$_2$)$_{2-3}$NH$_2$, —NR$^a$R$^b$, —N$^+$R$^a$R$^b$CH$_3$, —NHCH$_2$CH$_2$OCH$_3$, —OR$^a$, and —O(CH$_2$)$_{2-3}$NH$_2$;

3) —NR$^a$(CH$_2$)$_n$—C$_3$-C$_6$cycloalkyl, wherein the C$_3$-C$_6$cycloalkyl is optionally substituted with —CH$_2$OH or —NH$_2$;
4) —NR$^a$—(C$_1$-C$_3$alkyl)$_n$-AryB1; and
5) —NR$^a$—(C$_1$-C$_3$alkyl)$_n$-HetB1;

R$^a$ and R$^b$ are H or —CH$_3$; x is 0, 1 or 2, and all other variables are defined in Embodiment E1.

A forty-fifth embodiment (Embodiment E45) is a compound, or a pharmaceutically acceptable salt thereof, having the Formula (IB):

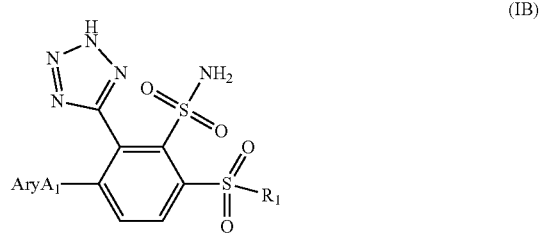

(IB)

wherein:
AryA1 is an aromatic ring system selected from:
1) a 5-6 membered monocyclic ring with 0 or 1 N ring atoms substituted with 1 or 2 substituents independently selected from F, —C$_1$-C$_6$ alkyl, —CONH—C$_{2-4}$alkyl-NH$_2$, or —NHR$^a$; or
2) a 9-membered bicyclic ring with 2 heteroatom ring atoms selected from N and S, wherein the ring is optionally substituted with 1 or 2 substituents independently selected from F, C$_1$-C$_6$ alkyl, and —(CH$_2$)$_{0-2}$NR$^a$R$^b$;
R$^1$ is
1) NH$_2$;
2) —NR$^a$—C$_1$-C$_6$alkyl optionally substituted with 1 or 2 F substituents and optionally substituted with 1 or 2 substituents independently selected from —CF$_3$, —CH(NH$_2$)C(O)NH$_2$; —C(O)NR$^a$R$^b$; —C(O)OH; —NR$^a$R$^b$, —N$^+$R$^a$R$^b$CH$_3$, —OR$^a$, and —O(CH$_2$)$_{1-2}$NH$_2$;
3) —NR$^a$(CH$_2$)$_{0-1}$—C$_{3-6}$cycloalkyl, wherein the C$_{3-6}$cycloalkyl is optionally substituted with —CH$_2$OH or —NH$_2$;
4) —NR$^a$—C$_{0-3}$alkyl-AryB1; and
5) —NR$^a$—C$_{0-3}$alkyl-HetB1;
HetB1 is:
1) a 4-6 membered saturated monocyclic ring with 1 or 2 heteroatom ring atoms independently selected from N, O and S, wherein the S is substituted with two oxo groups, and wherein the ring is optionally substituted with 1 or 2 substituents independently selected from F, C$_1$-C$_6$ alkyl, C$_1$-C$_6$ hydroxyalkyl, —NR$^a$R$^b$, —OH, C$_{1-6}$alkoxy, —C(O)OR$^a$, and oxo; or
2) a 6-8-membered bicyclic ring with 1 or 2 heteroatom ring atoms independently selected from N and O, optionally substituted with —OH or —NH$_2$, wherein the bicyclic ring is bridged or fused;

R$^a$ and R$^b$ are H or —CH$_3$, and all other variables are as provided in Embodiment E1.

A forty-sixth embodiment of the invention (Embodiment E46) is: (1) a compound having a structure of any of the compounds numbered 1-500 in the Examples herein, (2) the free acid or free base base form (when a basic amine group is present) of any compound numbered 1-500 herein that is depicted as a salt, (3) the zwitterionic form of any of compounds 1-500 which contains a basic amine group, wherein the tetrazole bears a negative charge and the amine group bears a positive charge, or (4) a pharmaceutically acceptable salt of the compounds described in (1), (2), and/or (3).
A forty-seventh embodiment of the invention (Embodiment E47) is a compound having the structure:
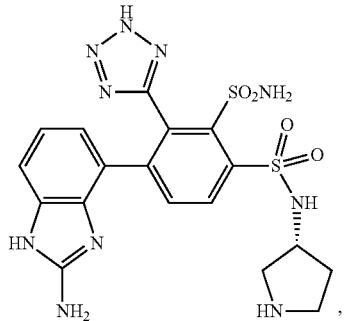
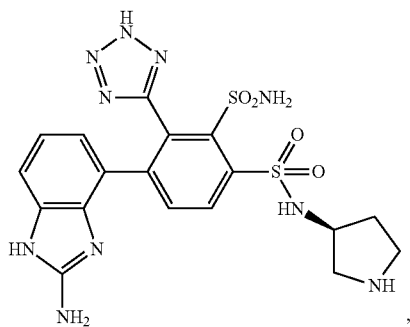
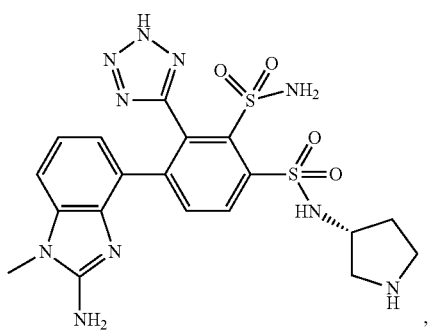
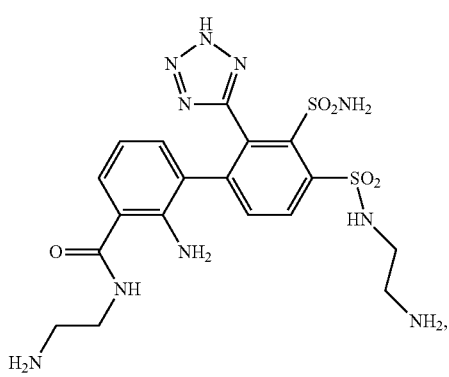
-continued
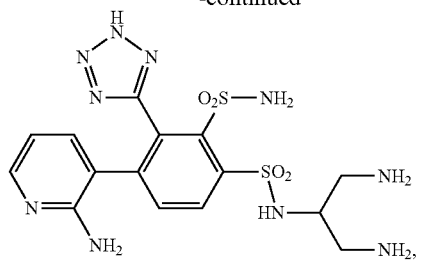
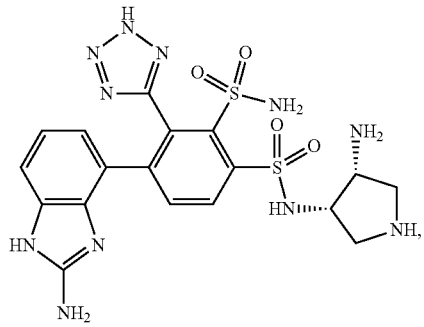
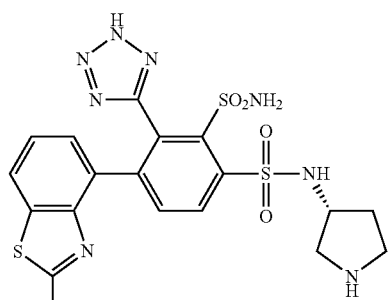
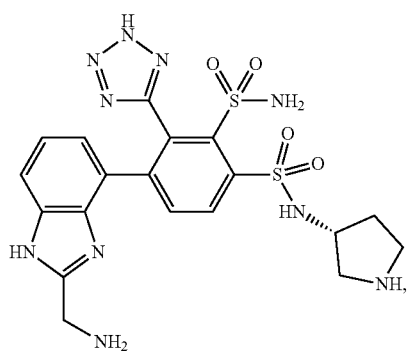
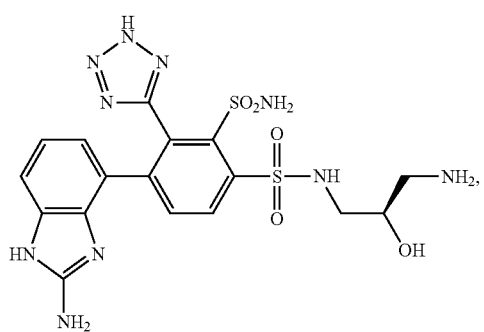

19
-continued
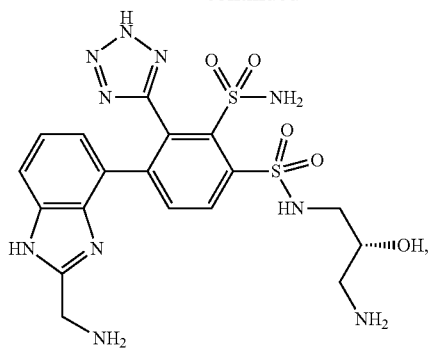
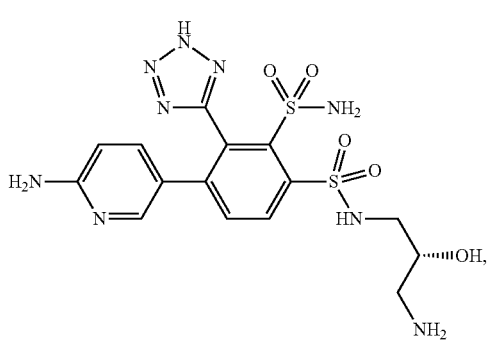
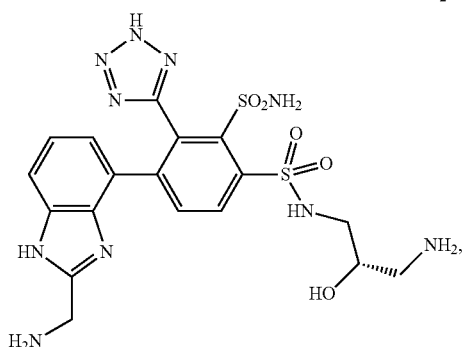
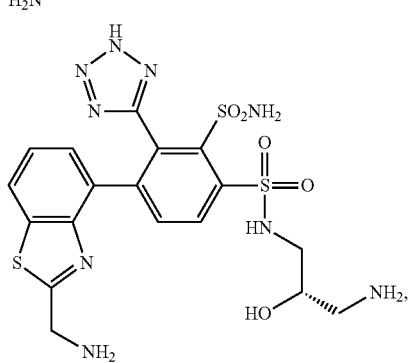
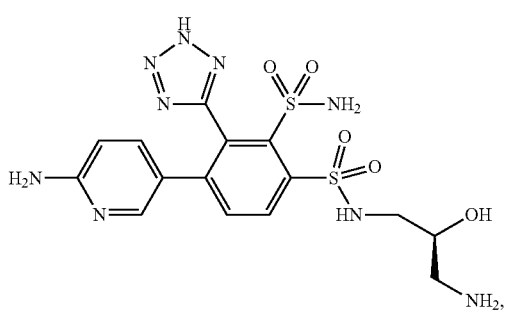
20
-continued
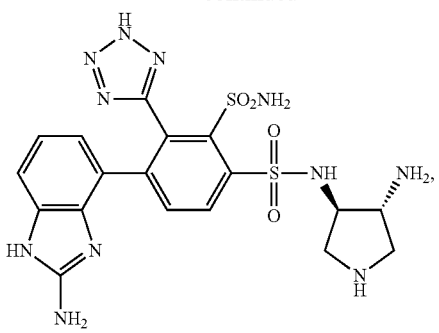
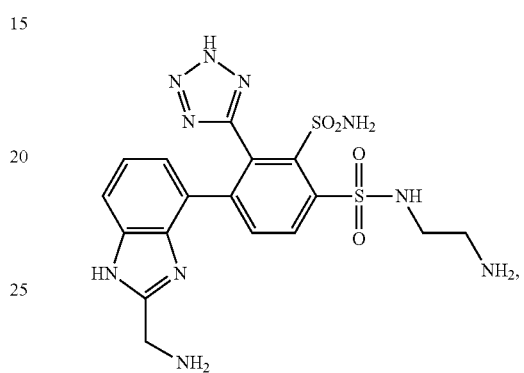
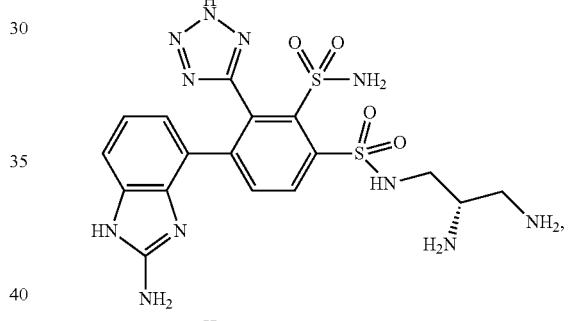
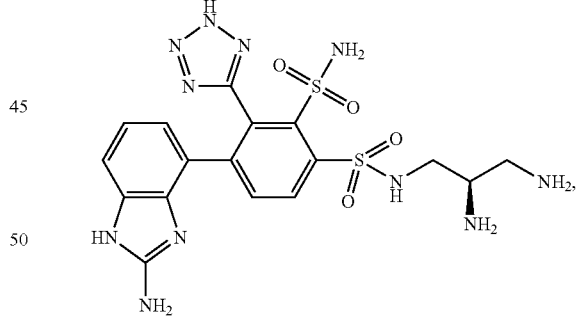
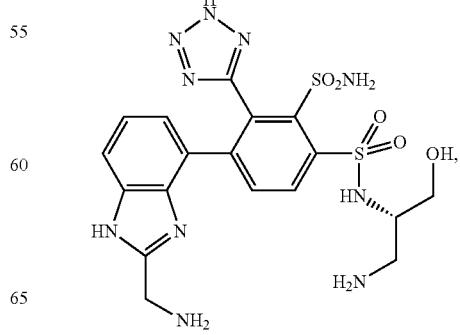

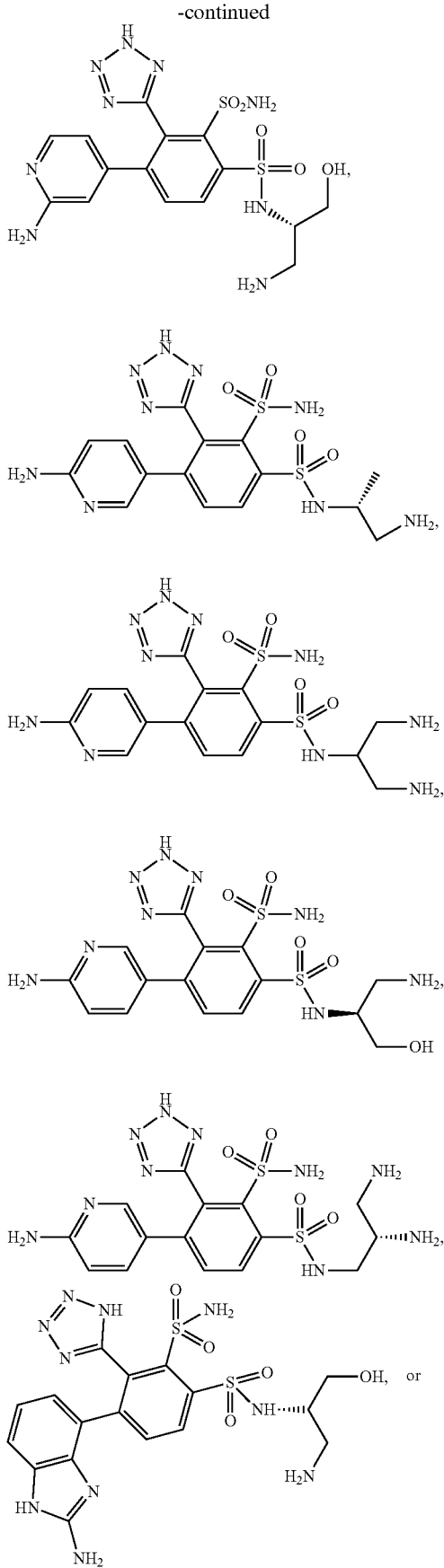

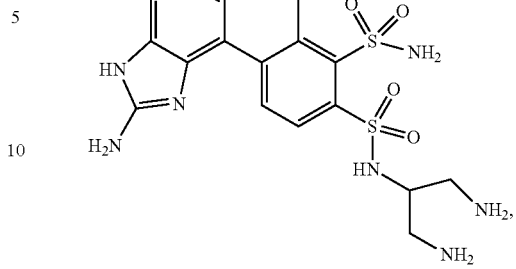

or a pharmaceutically acceptable salt thereof.

Other embodiments of the present invention include the following:

(a) A pharmaceutical composition comprising an effective amount of a compound of Formula I, IA, or IB as defined above, or a pharmaceutically acceptable salt thereof, and a pharmaceutically acceptable carrier.

(b) The pharmaceutical composition of (a), further comprising an effective amount of a β-lactam antibiotic and optionally further comprising an effective amount of a compound which is a class A β-lactamase inhibitor, class C β-lactamase inhibitor, and/or class D β-lactamase inhibitor.

(c) The pharmaceutical composition of (b), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, cefepime, ceftolozane, and ceftazidime, and the class A, C and D β-lactamase inhibitor is selected from the group consisting of relebactam, avibactam, vaborbactam, tazobactam, sulbactam, clavulanic acid, or CB-618.

(d) The pharmaceutical composition of (b), wherein the β-lactam antibiotic is imipenem.

(e) The pharmaceutical composition of (b), wherein the β-lactam antibiotic is ceftazidime.

(f) The pharmaceutical composition of (b), wherein the β-lactam antibiotic is ceftolozane.

(g) The pharmaceutical composition of (b), wherein the β-lactam antibiotic is piperacillin.

(h) The pharmaceutical composition of (a), further comprising a compound which is a class A β-lactamase inhibitor, class C β-lactamase inhibitor, and/or class D β-lactamase inhibitor.

The pharmaceutical composition of any of (b)-(h), wherein the β-lactamase inhibitor compound is relebactam.

The pharmaceutical composition of any of (b)-(h), wherein the β-lactamase inhibitor compound is tazobactam.

(k) The pharmaceutical composition of (a), further comprising effective amounts of a β-lactam antibiotic, a renal dehydropeptidase (DHP) inhibitor, and optionally, a class A, C and D β-lactamase inhibitor.

(l) The pharmaceutical composition of (k), wherein the β-lactam antibiotic is imipenem, the DHP inhibitor is cilastatin or a pharmaceutically acceptable salt thereof, and the class A, C and D β-lactamase inhibitor is relebactam.

(m) A combination of effective amounts of a compound of Formula I as defined above, or a pharmaceutically acceptable salt thereof, a β-lactam antibiotic, and optionally, a class A, C and/or D β-lactamase inhibitor.

(n) The combination of (j), wherein the β-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, ticarcillin, cefoperazone, cefotaxime, ceftriaxone, cefipime, ceftolozane, and ceftazidime.

(o) The combination of (n), wherein the β-lactam antibiotic is imipenem, optionally in combination with cilistatin, and the class A, C, D β-lactamase inhibitor is relebactam.

(p) The combination of (n), wherein the β-lactam antibiotic is ceftazidime and the class A, C, D β-lactamase inhibitor is avibactam.

(q) The combination of (n), wherein the β-lactam antibiotic is ceftolozane and the class A, C, D β-lactamase inhibitor is avibactam or relebactam.

(r) The combination of (n), wherein the β-lactam antibiotic is piperacillin.

(s) A combination of effective amounts of a compound of Formula I, IA or IB as defined above, or a pharmaceutically acceptable salt thereof, and a class A, C and/or D β-lactamase inhibitor.

(t) A combination of effective amounts of a compound of Formula I, IA, or IB as defined above, or a pharmaceutically acceptable salt thereof, a β-lactam antibiotic, a DHP inhibitor, and optionally a class A, C and/or D β-lactamase inhibitor.

(u) The combination of (t), wherein the β-lactam antibiotic is imipenem, the DHP inhibitor is cilastatin or a pharmaceutically acceptable salt thereof, and the class A, C and D β-lactamase inhibitor is relebactam.

(v) A method for treating a bacterial infection which comprises administering to a subject in need of such treatment a therapeutically effective amount of a compound of Formula I, IA, or IB as defined above, or a pharmaceutically acceptable salt thereof, in combination with an effective amount of a β-lactam antibiotic and optionally in combination with a class A, C and D β-lactamase inhibitor.

(w) A method for treating a bacterial infection which comprises administering to a subject in need of such treatment a therapeutically effective amount of a compound of Formula I, IA, or IB as defined above, or a pharmaceutically acceptable salt thereof, in combination with effective amounts of a β-lactam antibiotic and a DHP inhibitor, and optionally in combination with a class A, C and D β-lactamase inhibitor.

(x) A method for treating a bacterial infection which comprises administering to a subject in need of such treatment a therapeutically effective amount of the composition of (a), (b), (c), (d), (e), (f), (g), (h), (i), (j), (k), or (l).

(y) A method for treating a bacterial infection which comprises administering to a subject in need of such treatment a therapeutically effective amount of the combination of (m), (n), (o), (p), (q), (r), (s), (t), or (u).

(z) A method of treating a bacterial infection as set forth in (v), (w), (x), (y) or (z) wherein the bacterial infection is due to *Pseudomonas* spp., *Klebsiella* spp., *Enterobacter* spp., *Escherichi* spp.a, *Morganella* spp., *Citrobacter* spp., *Serratia*, spp. or *Acintetobacter* spp.

The present invention also includes a compound of Formula I, IA, or IB, or a pharmaceutically acceptable salt thereof, (i) for use in, (ii) for use as a medicament for, or (iii) for use in the preparation (or manufacture) of a medicament for, inhibiting beta-lactamase activity or treating bacterial infection. In these uses, the compounds of the present invention can optionally be employed in combination with one or more β-lactam antibiotics, and may further be employed in combination with a class A, C, and/or D serine β-lactamase inhibitor and/or one or more DHP inhibitors.

Additional embodiments of the invention include the pharmaceutical compositions, combinations and methods set forth in (a)-(z) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments. In addition, the compound may optionally be used in the form of a prodrug that releases the active parent compound after dosing by intravenous or oral administration.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (z) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I, IA, or IB or its salt and a pharmaceutically acceptable carrier and optionally one or more excipients, it is understood that the term "substantially pure" is in reference to a compound of Formula I, IA, or IB or its salt per se; i.e., the purity of the active ingredient in the composition. Definitions and Abbreviations:

The term "β-lactamase inhibitor" refers to a compound which is capable of inhibiting enzyme activity from β-lactamases. As used herein, inhibiting β-lactamase activity means inhibiting the activity of a class A, B, C, and/or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I. Page, Ed.; Chapman and Hall, London, (1992) 198-228.

The term "metallo-β-lactamase inhibitor" refers to a compound which is capable of inhibiting metallo-β-lactamase activity. As used herein, inhibiting metallo-β-lactamase activity means inhibiting the activity of a class B metallo-β-lactamase. For antimicrobial applications inhibition at a 50% inhibitory concentration is preferably achieved at or below about 100 μg/mL, or at or below about 50 μg/mL, or at or below about 25 μg/mL.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include a metallo-β-lactamases of *Escherichia coli* (such as New Delhi Metallo-b-lactamase, NDM), *Serratia marcescens* (such as IMP), *Klebsiella* spp. (such as Verona integron-encoded metallo-β-lactamase, VIM)) and *Pseudomonas* spp (such as Verona integron-encoded metallo-β-lactamase, VIM)). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

Another embodiment of the present invention is a compound of Formula I, IA, or IB, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I, IA or IB, or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula I, IA and IB. Unless a specific stereochemistry is indicated, the present invention is meant to comprehend all such isomeric forms of these compounds. Centers of asymmetry that are present in the compounds of Formula I, IA and IB can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers, diastereomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, IA and IB or it can be done on a final racemic product. Absolute stereochemistry may be determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Aminoalkyl" means saturated carbon chains which may be linear or branched or combinations thereof which are substituted with one amino group which may be terminal (—NH$_2$) or internal (—NH—).

"Hydroxyalkyl" means saturated carbon chains which may be linear or branched or combinations thereof which are substituted with one hydroxyl (—OH) group.

"Diaminoalkyl" means saturated carbon chains which may be linear or branched or combinations thereof which are substituted with two amino (—NH$_2$) groups.

"Dihydroxyalkyl" means saturated carbon chains which may be linear or branched or combinations thereof which are substituted with two hydroxyl (—OH) groups.

"Hydroxyaminoalkyl" means saturated carbon chains which may be linear or branched or combinations thereof which are substituted with one hydroxyl (—OH) group and one amino (—NH$_2$) group.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Aromatic ring system" means monocyclic, bicyclic or tricyclic aromatic ring or ring system containing 5-14 ring atoms, wherein at least one of the rings is aromatic. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quarternary amine. In certain embodiments, a N ring atom can be in the form of an N-oxide.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, 1,2,3,4-tetrahydronaphthyl and the like. In one embodiment of the present invention, cycloalkyl is selected from: cyclopropane, cyclobutane, cyclopentane and cyclohexane.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" or "heterocycloalkyl" means a saturated or partly unsaturated non-aromatic monocyclic, bicyclic (including spirocyclic) or bridged carbocyclic ring or ring system comprising 3 to about 11 ring atoms, containing at least one ring heteroatom selected from N, S and O and the remainder of the ring atoms are carbon atoms. The nitrogen or sulfur atom of the heterocycloalkyl can be optionally oxidized to the corresponding N-oxide, S-oxide or S-dioxide. A heterocycloalkyl group can be joined via a ring carbon, or ring nitrogen atom, unless specified otherwise. The cycloheteroalkyl ring may be substituted on the ring carbons and/or the ring nitrogen(s). In one embodiment, a heterocycloalkyl group is monocyclic and has from about 3 to about 7 ring atoms (a "3 to 7-membered monocyclic heterocycloalkyl" group). In another embodiment, a heterocycloalkyl group is monocyclic has from about 4 to about 7 ring atoms (a "4 to 7-membered monocyclic heterocycloalkyl" group). In other embodiments, the heterocycloalkyl group is bicyclic and has 7-10 ring atoms, 8-10 ring atoms, or 9 or 10 ring atoms (a "9 or 10-membered bicyclic heterocycloalkyl" group). In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Examples of cycloheteroalkyl include tetrahydrofuran, piperazine, piperidine, morpholine, oxetane, tetrahydropyran, indolinyl, isoindolinyl, azabicyclooctane, hexahydrofuro[3,2-b]furan, and 2,3, 3a,5,6,6a-hexahydrofuro[3,2-b]furan. Where the ring or ring system contains one or more N atoms, the N can be in the form of quarternary amine.

As used herein, a "nitrogen-linked heterocycloalkyl" refers to a nitrogen-containing heterocycloalkyl that is linked to the rest of the compound through a sulfur-nitrogen bond to an SO$_2$ linker, which is connected to the 6-membered core ring containing X$_1$ and X$_2$. For example, the following compounds of the invention contain a nitrogen-linked heterocycloalkyl:

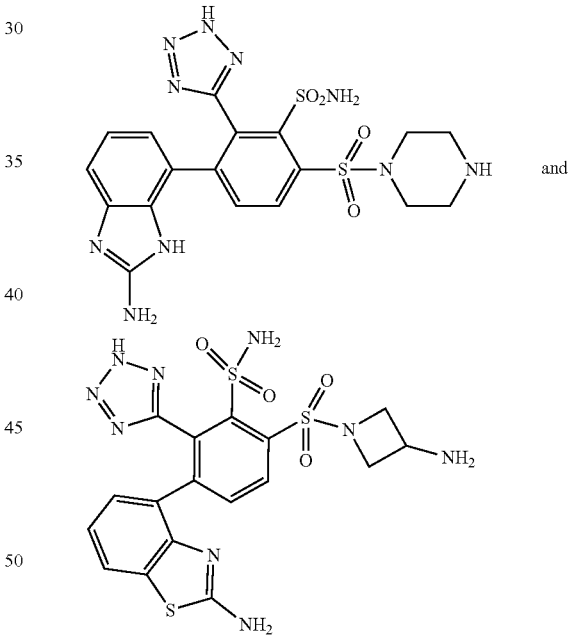

A nitrogen-linked heterocycloalkyl may be a 4-6 membered monocyclic ring, which may contain 0, 1, or 2, additional heteroatom ring atoms independently selected from N, O and S or a 7- to 10-membered bicyclic ring with 0, 1, 2, or 3 additional heteroatom ring atoms selected from N, O and S. A bicyclic nitrogen-linked heterocycloalkyl may be bridged, fused or spirocyclic. A nitrogen-linked heterocycloalkyl may optionally be substituted with one to three substituents as defined herein.

"Heteroaryl" means monocyclic, bicyclic or tricyclic ring or ring system containing 5-14 carbon atoms and containing at least one ring heteroatom selected from N, S (including SO and SO$_2$) and O, wherein at least one of the heteroatom containing rings is aromatic. In the case of a heteroaryl ring system where one or more of the rings are saturated and contain one or more N atoms, the N can be in the form of quarternary amine. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. Examples of bicyclic heteroaryl rings include:

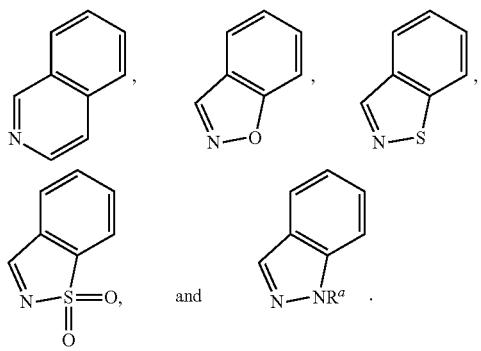

"Halogen" includes fluorine, chlorine, bromine and iodine.

"Oxo" means an oxygen atom connected to another atom by a double bond and is can be represented "=O".

Where any amine is present in the compound, the N atom may be optionally in the form of a quaternary amine having one or more appropriate additional substitutions, as further described herein.

When any ring atom is specified as being optionally substituted with, or in a specified form, for example, S substituted with oxo groups, or N in the form of a N-oxide, this does not preclude the substitution of any ring atom with the other listed optional substituents when not substituted with oxo groups or in the form of a N-oxide.

When any variable (e.g., n, $R^a$, $R^b$, etc.) occurs more than one time in any constituent or in Formula I, IA, or IB, its definition on each occurrence is independent of its definition at every other occurrence. Also, combinations of substituents and/or variables are permissible only if such combinations result in stable compounds.

A wavy line 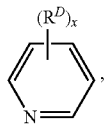, as used herein, indicates a point of attachment to the rest of the compound. Lines drawn into a ring system, for example:

$$\underset{N}{\overset{(R^D)_x}{\diagdown}}$$

indicate that the bond may be attached to any of the substitutable ring atoms.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^A$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds of Formula I, IA, or IB, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I, IA, or IB. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I, IA, or IB, can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic ring and ring system variables or substituents described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formulas I, IA and IB.

The term "compound" refers to the compound and, in certain embodiments, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. Those skilled in the art will recognize those instances in which the compounds of the invention may form salts. The term "pharmaceutically acceptable salt" refers to a salt (including an inner salt such as a zwitterion) which possesses effectiveness similar to the parent compound and which is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is undertood that certain compounds of the invention may exist in zwitterionic form, having both anionic and cationic centers within the same compound and a net neutral charge. Such zwitterions are included within the invention.

The compounds of Formula I, IA, and IB may exist as rapidly interconverting tautomers with different points of attachment of hydrogen accompanied by one or more double bond shifts. The individual tautomers as well as mixtures thereof are encompassed by the present invention. The ratio between the tautomeric forms will vary depending on the conditions. As is well known to one of ordinary skill in the art, such compounds may be drawn and named in different ways. For example, the following structures depicted below show different ways that an illustrative compound of the invention may be drawn:

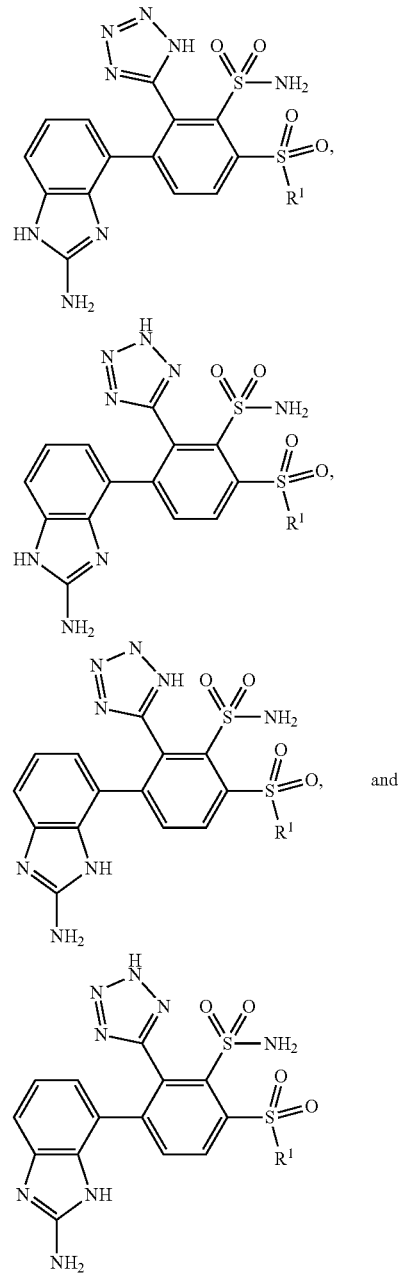

and

It is understood that all possible tautomeric forms of the compounds of Formula I, IA, and IB are contemplated as being within the scope of the instant invention, as well as mixtures thereof. It is further understood that while only one said tautomeric form of each example compound and embodiment of the invention may be depicted in the specification and appended claims, such depiction includes reference to all tautomeric forms of said compounds, which are included within the scope of the invention.

As set forth above, the present invention includes pharmaceutical compositions comprising a compound of Formula I, IA, or IB of the present invention, optionally one or more other active components (e.g., a β-lactam antibiotic), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, IA, or IB, or a pharmaceutically acceptable salt thereof, in combination with a β-lactam antibiotic and optionally a DHP inhibitor. The term "subject" (or, alternatively, "patient") as used herein refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In select embodiment, the subject is a human. In select embodiments, the subject has been the object of treatment, observation or experiment. The term "administration" and variants thereof (e.g., "administering" a compound) in reference to a compound of Formula I, IA, or IB mean providing the compound, or a pharmaceutically acceptable salt thereof, to the individual in need of treatment. When a compound or a salt thereof is provided in combination with one or more other active agents (e.g., a carbapenem antibiotic or a DHP inhibitor or both), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount," when used with a β-lactamase inhibitor (including a DHP inhibitor), means the amount of active compound sufficient to inhibit β-lactamase and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance) in combination with a β-lactam antibiotic. In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound. An "effective amount" of a β-lactam antibiotic is an amount sufficient to alleviate the symptoms of the disease or condition being treated (e.g., the healing of conditions associated with bacterial infection, and/or bacterial drug resistance).

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, 21$^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 μg/mL, and in additional embodiment at least about 10 μg/mL, and at least about 25 μg/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula I. Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula I, IA or IB to an experimental cell culture in vitro to prevent the growth of β-lactam resistant bacteria. The method can alternatively involve administration of a compound of Formula I, IA, or IB to an animal, including a human, to prevent the growth of β-lactam resistant bacteria in vivo. In these cases, the compound of Formula I, IA or IB is typically co-administered with a β-lactam antibiotic.

Compounds of the invention can be employed for the treatment, prophylaxis or inhibition of bacterial growth or infections due to bacteria that are resistant to β-lactam antibiotics in combination with a β-lactam antibiotic. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 μg/mL, and bacterial strains which are slightly resistant to imipenem are those against which the MIC of imipenem is >4 μg/mL.

Compounds of the invention can be used in combination with antibiotic agents for the treatment of infections caused by Class B-β-lactamase producing strains, in addition to those infections which are subsumed within the antibacterial spectrum of the antibiotic agent. Examples of class B-metallo-β-lactamase producing bacteria are *Pseudomonas aeruginosa, Pseudomonas putida, Enterobacter cloacae, Klebsiella pneumoniae, Klebsiella oxytoca, Escherichia coli, Serratia marcescens, Enterobacter aerogenes, Enterobacter asburiae, Citrobacter freundii, Proteus mirabilis, Morganella morganii, Providencia rettgeri*, and *Acinetobacter baumannii*.

It is generally advantageous to use a compound of Formula I, IA, or IB in admixture or conjunction with a carbapenem, penicillin, cephalosporin, or other β-lactam antibiotic, or a prodrug thereof. It is advantageous to use a compound of Formula I, IA, or IB in combination with one or more β-lactam antibiotics because of the class B β-lactamase inhibitory properties of the compounds. It is also advantageous to use a compound of Formula I, IA, or IB in combination with one or more Class A, C, and D β-lactamase inhibitors to further limit β-lactam susceptability. As already noted, the compound of Formula I, IA, or IB and the β-lactam antibiotic can be administered separately (at the same time or as different times) or in the form of a single composition containing both active ingredients.

Carbapenems, penicillins, cephalosporins and other β-lactam antibiotics suitable for use in the present invention include both those known to show instability to or to be otherwise susceptible to class B-β-lactamases.

When the compounds of Formula I, IA, or IB are combined with a carbapenem antibiotic, a dehydropeptidase (DHP) inhibitor can also be combined. Many carbapenems are susceptible to attack by a renal enzyme known as DHP. This attack or degradation may reduce the efficacy of the carbapenem antibacterial agent. Inhibitors of DHP and their use with carbapenems are disclosed in, e.g., U.S. Pat. Nos. 4,539,208; 4,616,038; 4,880,793; and 5,071,843. A preferred DHP inhibitor is 7-(L-2-amino-2-carboxyethylthio)-2-(2,2-dimethylcyclopropanecarboxamide)-2-heptenoic acid or a pharmaceutically acceptable salt thereof.

Carbapenems suitable for co-administration with compounds of the present invention include imipenem, ertapenem, meropenem, biapenem, (4R,5S,6S)-3-[3S,5S)-5-(3-carboxyphenyl-carbamoyl)pyrrolidin-3-ylthio]-6-(1R)-1-hydroxyethyl]-4-methyl-7-oxo-1-azabicyclo[3.2.0]hept-2-ene-2-carboxylic acid, (1S,5R,6S)-2-(4-(2-(((carbamoylmethyl)-1,4-diazoniabicyclo[2.2.2]oct-1-yl)-ethyl(1,8-naphthosultam)methyl)-6-[1(R)-hydroxyethyl]-1-methylcarbapen-2-em-3-carboxylate chloride, BMS181139 ([4R-[4α,5β,6β(R*)]]-4-[2-[(aminoiminomethyl)amino] ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S*(R*)], 4α,5β,6β(R*)]]-6-(1-hydroxyethyl)-3-[[5-[1-hydroxy-3-(methylamino)propyl]-3-pyrrolidinyl] thio]-4-methyl-7-oxo-1-azabicyclo[3.2.0]hept-2-ene-2-carboxylic acid monohydrochloride), E1010 ((1R,5S,6S)-6-[1 (R)-hydroxymethyl]-2-[2(S)-[1(R)-hydroxy-1-[pyrrolidin-3 (R)-yl] methyl]pyrrolidin-4(S)-ylsulfanyl]-1-methyl-1-carba-2-penem-3-carboxylic acid hydrochloride) and S4661 ((1R,5S,6S)-2-[(3S,5S)-5-(sulfamoylaminomethyl) pyrrolidin-3-yl]thio-6-[(1R)-1-hydroxyethyl]-1-methylcarbapen-2-em-3-carboxylic acid), (1S,5R,6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3 carboxylate chloride.

Penicillins suitable for co-administration with compounds of the present invention include benzylpenicillin, phenoxymethylpenicillin, carbenicillin, azidocillin, propicillin, ampicillin, amoxicillin, epicillin, ticarcillin, cyclacillin, pirbenicillin, azlocillin, mezlocillin, sulbenicillin, piperacillin, and other known penicillins. The penicillins may be used in the form of pro-drugs thereof; for example as in vivo hydrolysable esters, for example the acetoxymethyl, pivaloyloxymethyl, α-ethoxycarbonyloxy-ethyl and phthalidyl esters of ampicillin, benzylpenicillin and amoxicillin; as aldehyde or ketone adducts of penicillins containing a 6-α-aminoacetamido side chain (for example hetacillin, metampicillin and analogous derivatives of amoxicillin); and as esters of carbenicillin and ticarcillin, for example the phenyl and indanyl α-esters.

Cephalosporins suitable for co-administration with compound of the present invention include cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftolozane, ceftazidime, cefuroxime, cefmetazole, cefotaxime, ceftriaxone, cefipime, and other known cephalosporins, all of which may be used in the form of pro-drugs thereof.

β-Lactam antibiotics other than penicillins and cephalosporins that may be co-administered with compounds of the present invention include aztreonam, latamoxef (MOXALACTAM), and other known β-lactam antibiotics such as carbapenems like imipenem, ertapenem, meropenem or (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, all of which may be used in the form of pro-drugs thereof.

In one embodiment, the antibiotic co-administered with a compound of the present invention is selected from the group consisting of imipenem, ertapenem, meropenem and (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid.

In another embodiment, the antibiotic co-administered with a compound of the present invention is selected from the group of penicillins consisting of ampicillin, amoxicillin, carbenicillin, piperacillin, azlocillin, mezlocillin, and ticarcillin. Such penicillins can optionally be used in the form of their pharmaceutically acceptable salts, for example their sodium salts. Ampicillin or amoxicillin can alternatively be employed in the form of fine particles of the zwitterionic form (generally as ampicillin trihydrate or amoxicillin trihydrate) for use in an injectable or infusable suspension. In an aspect of this embodiment, the penicillin co-administered with a compound of the present invention is amoxicillin, optionally in the form of its sodium salt or the trihydrate.

In another embodiment, the antibiotic co-administered with a compound of the present invention is selected from the group of cephalosporins consisting of cefotaxime, ceftriaxone, cefipime, and ceftazidime, which are optionally used in the form of their pharmaceutically acceptable salts, for example their sodium salts.

In certain embodiments of the invention, the compounds of the invention in combination with serine β-lactamase inhibitors (which can inhibit class A, C, D beta lactamases) in addition to β-lactam antiobiotics. Serine β-lactamase inhibitors include but are not limited to avibactam, vaborbactam, relebactam, tazobactam, and clavulanic acid.

When co-administered with a β-lactam antibiotic, and optionally a β-lactamase inhibitor, the combination of the compound of the invention and the antibiotic can provide a synergistic effect. The terms "synergistic effect" and "synergy" indicate that the effect produced when two or more drugs are co-administered is greater than would be predicted based on the effect produced when the compounds are administered individually. While not wishing to be bound by theory, it is believed that the compounds of the present invention are β-lactamase inhibitors that act to prevent degradation of β-lactam antibiotics, thereby enhancing their efficacy and producing a synergistic effect.

Abbreviations employed herein include the following: Ac=acetyl=CH$_3$C(=O); AcOH=acetic acid; ACN=MeCN=acetonitrile; aq=aqueous; BH3 DMS=borane dimethyl sulfide; BINAP=(2,2'-bis(diphenylphosphino)-1,1'-binaphthyl); BLI=β-lactamase inhibitor; Bn=benzyl; BOC (or Boc)=tert-butyloxycarbonyl; Boc anhydride=Boc$_2$O=di-tert-butyl dicarbonate; BrettPhos precatalyst generation 3=[(2-Di-cyclohexylphosphino-3,6-dimethoxy-2',4',6'-triisopropyl-1,1'-biphenyl)-2-(2'-amino-1,1'-biphenyl)]palladium(II) methanesulfonate; BPBD=N,N'-{bis(pyridin-2-yl)benzylidene}butane-1,4-diamine; CBZ (or Cbz)=carbobenzoxy (alternatively, benzyloxycarbonyl); CH$_3$CN=acetonitrile; CELITE=diatomaceous earth; conc.=concentrated; DBU=1,8-diazabicyclo[5.4.0]undec-7-ene; DCM=dichloromethane; DEAD=diethyl azodicarboxylate; DIAD=diisopropyl azodicarboxylate; DIBAL-H=diisobutylaluminum hydride; DIEA=N,N-Diisopropylethylamine; DIPEA=diisopropylethylamine (or Hunig's base); DMA=dimethylacetamide; DMAP=4-dimethylaminopyridine or N,N-dimethylaminopyridine; DME=1,2-dimethoxyethane; DMF=N,N-dimethylformamide; DMSO=dimethyl sulfoxide; DPPA=diphenyl- phosphoryl azide; EA=AcOEt=EtOAc=ethyl acetate; EDC=1-ethyl-3-(3-dimethylaminopropyl) carbodiimide; Et=ethyl; EtOH=ethanol; HATU=(1-[Bis(dimethylamino)methylene]-1H-1,2,3-triazolo[4,5-b]pyridinium 3-oxid hexafluorophosphate); hex=hexane; HOAt=1-Hydroxy-7-azabenzotriazole; HPLC=high-performance liquid chromatography; h or hr or hrs=hours; i-Pr=isopropyl alcohol; KOAc=potassium acetate; LCMS=LC-MS=liquid chromatography/mass spectrometry; LDA=lithium di-isopropyl amide; mCPBA=meta-chloroperoxybenzoic acid; Me=methyl; MeCN=acetonitrile; MeOH=methanol; MIC=minimum inhibitory concentration; min or mins=minutes; MPLC=medium pressure liquid chromatography; Ms=methanesulfonyl; MsCl=methane sulfonyl chloride; n-BuLi=n-butyllithium; NCS=N-Chlorosuccinimide; NIS=N-Iodosuccinimide; NMP=N-Methyl-2-pyrrolidone; NMR=nuclear magnetic resonance; PCy3 Pd G2=2nd Generation PCy$_3$ precatalyst=Chloro[(tricyclohexylphosphine)-2-(2'-aminobiphenyl)]palladium(II); Pd(dppf)Cl$_2$=[1,1'-Bis(diphenylphosphino)ferrocene]dichloropalladium(II); PE=Pet. ether=petroleum ether; Ph=phenyl; PMB=p-Methoxybenzyl; PPh$_3$ precatalyst generation 2=2$^{nd}$ PPh3 precatalyst=Chloro(triphenylphosphine) [2-(2'-amino-1,1'-biphenyl)]palladium(II); prep-HPLC=preparative HPLC; RBF=round bottom flask; RPLC=reverse phase liquid chromatography; RT=room temp.=room temperature; SFC=supercritical fluid chromatography; SM=starting material; TBAF=tetrabutylammonium fluoride; tBuXPhos precatalyst generation 3=[(2-Di-tert-butylphosphino-2',4',6'-triisopropyl-1,1'-biphenyl)-2-(2'-amino-1,1'-biphenyl)] palladium(II) methanesulfonate; TEA=triethylamine; TFA= trifluoroacetic acid; THF=tetrahydrofuran; TLC=thin layer chromatography; TMS=trimethylsilane; TMSN$_3$=azidotrimethylsilane; XPhos-Pd-2G or XPHOS Pd G2 precatalyst or Xphos precatalyst generation 2=Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst.

The compounds of the present invention can be readily prepared according to the following reaction schemes and examples, or modifications thereof, using readily available starting materials, reagents and conventional synthesis procedures. In these reactions, it is also possible to make use of known variants. Other methods for preparing compounds of the invention will be readily apparent to the person of ordinary skill in the art in light of the following reaction schemes and examples.

Scheme I:

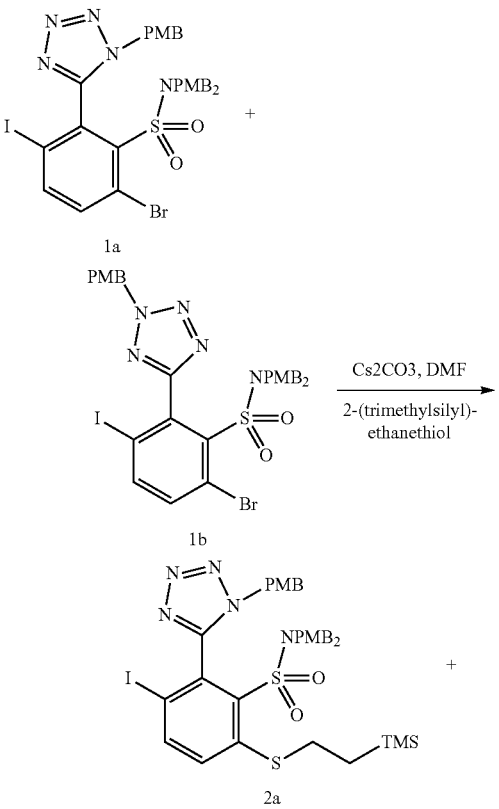

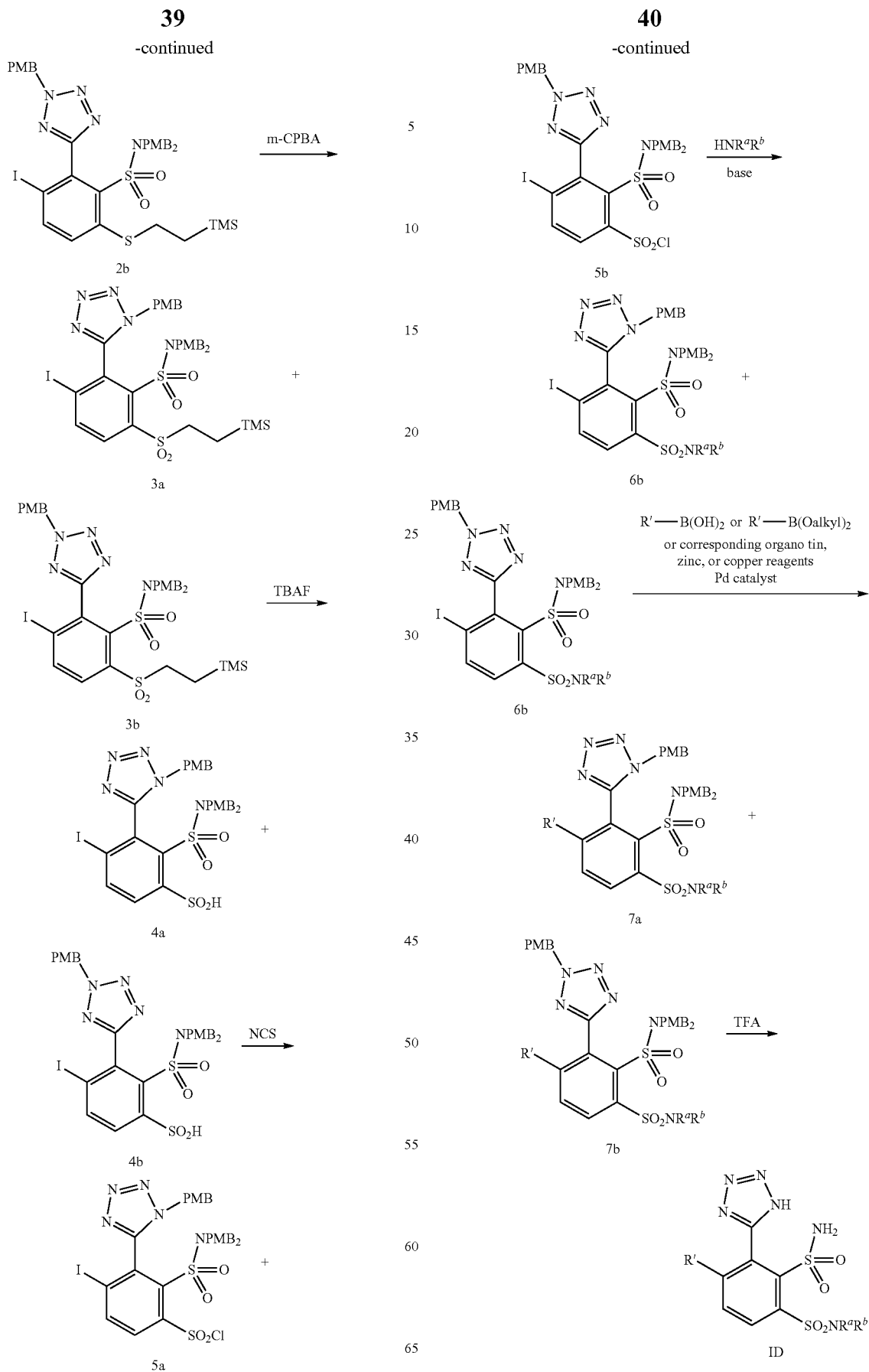

Sulfonamide compounds of the current invention, ID, may be prepared according to general Scheme I. According to the Scheme, bromide intermediates 1a and 1b may be selectively reacted at the bromo position with 2(trimethylsilyl)enthanethiol in the presence of a base (such as cesium carbonate) to afford sulfides 2a and 2b. Oxidation, for example by using meta-chloroperoxybenzoic acid gives sulfones 3a and 3b. Treatment with tetrabutylammonium fluoride (TBAF) gives the coreesponding sulfinic acids 4a and 4b. The sulfinic acids may be converted to the corresponding sulfonyl chlorides in a variety of ways, for example by treatment with N-chlorosuccinimide. Treatment of the resulting sulfonyl chlorides 5a and 5b with an amine in the presence of a base such as triethyl amine affords the sulfonamides 6a and 6b. Alternatively, sulfinic acids 4a and 4b may be directly converted in one pot to the sulfonamides 6a and 6b by reaction with N-chlorosuccinimide in the presence of the amine reactant. Metal mediated coupling, for example using palladium catalysts, with alkyl, aryl, heteroaryl or vinyl boronic acids, boronic esters, organostannanes, organocopper or organo zinc reagents affords intermediates 7a and 7b. Final PMB protective group removal can be achieved under acidic conditions such as by using TFA in the optional presence of a carbocation scavenger, such as anisole or triethylsilane, providing target compounds ID.

Scheme II:

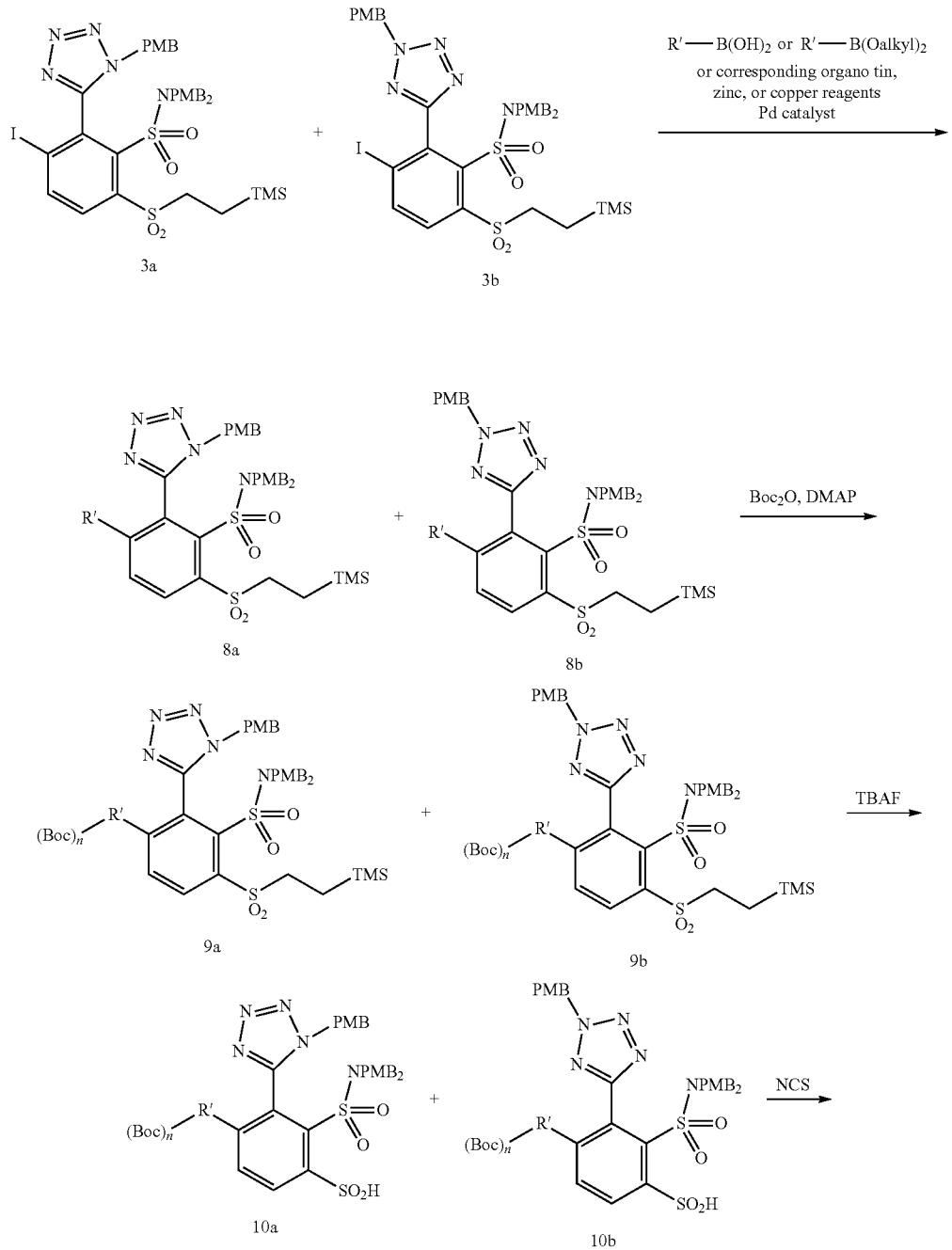

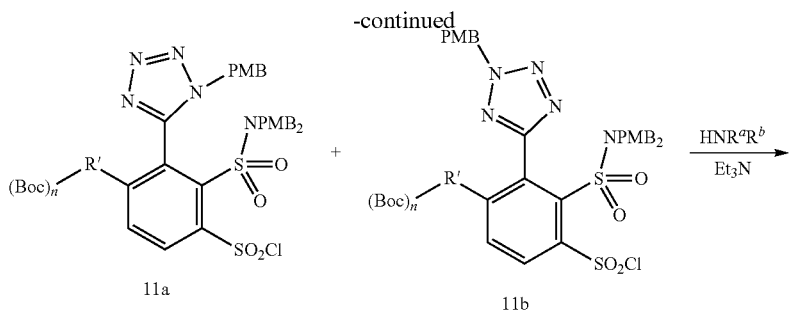

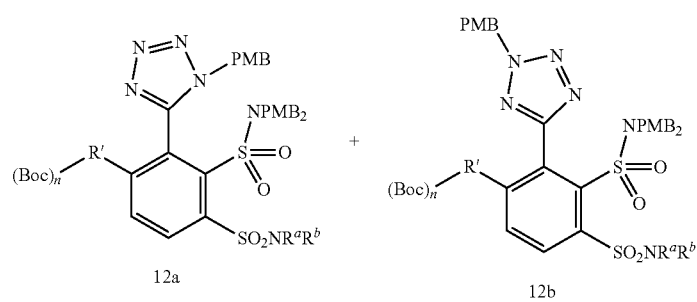

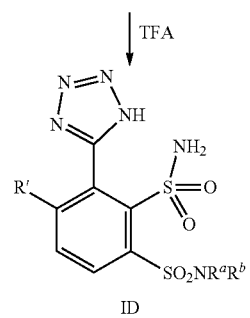

Alternatively, sulfonamide compounds ID may be prepared according to Scheme II. According to the Scheme, iodo intermediates 3a and 3b are subjected to metal mediated coupling, for example using palladium catalysts, with alkyl, aryl, heteroaryl or vinyl boronic acids, boronic esters, organostannanes, organocopper or organo zinc reagents to give intermediates 8a and 8b. When R' contains active NH groups, these may optionally be protected as tert-butoxycarbamates using Boc anhydride and a base such as 4-dimethylaminopyridine, affording 9a and 9b. Conversion of the trimethylsilylethane sulfones to the corresponding sulfonyl chlorides can be accomplished in two steps (as described in Scheme I) to give 11a and 11b. Coupling of the sulfonyl chlorides with amines can then be accomplished in the presence of a base (such as trimethylamine), giving 12a and 12b. Final PMB protective group removal under acidic conditions such as by using TFA in the optional presence of a carbocation scavenger, such as anisole or triethylsilane, provides target compounds ID. Again, when intermediates 12a and 12b contain an acid labile protecting group (like tert-butoxycarbonyl), concurrent removal of this protecting group occurs in the final acidic removal of the PMB groups. This can be done in one step, or in stepwise fashion by treatment with TFA at room temperature to remove a group such as tert-butoxycarbonyl, then heating with TFA and anisole or thioanisole to remove the PMB group.

Scheme III:

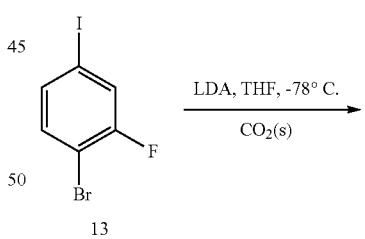

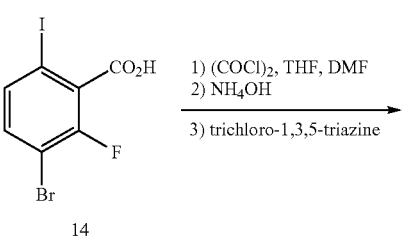

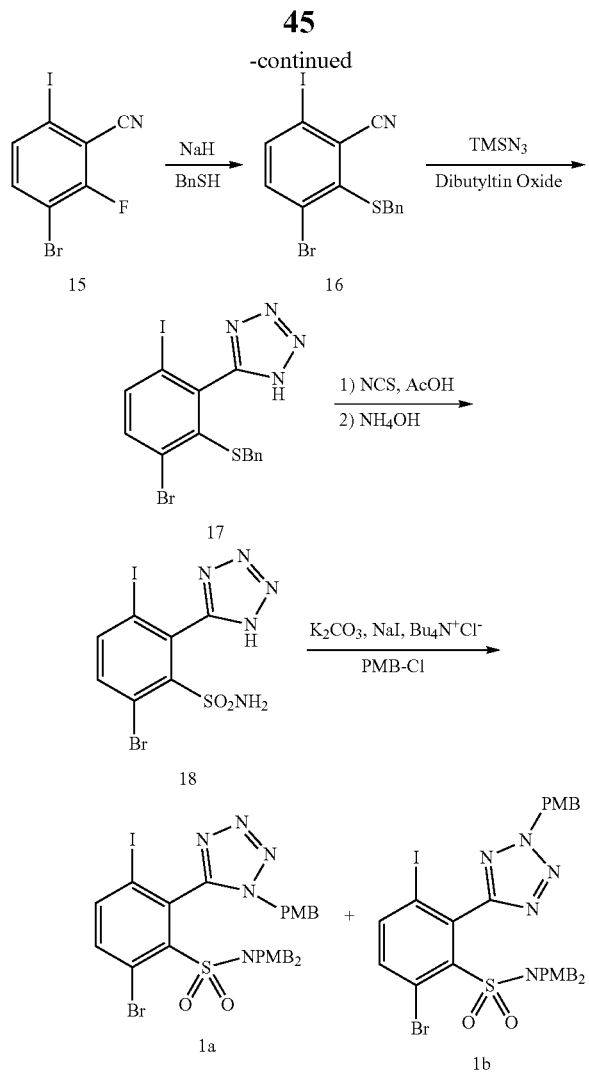

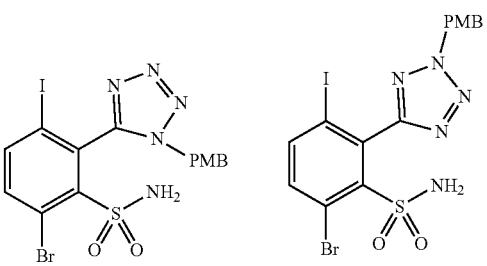

Intermediates 1a and 1b can be prepared according to Scheme III. According to the Scheme, commercially available aryl fluoride 13 can be converted to the carboxylic acid 14 by treatment with LDA, followed by dry ice. The carboxylic acid functionality can be transformed to the corresponding nitrile 15 in numerous ways known in the art. One approach involves conversion to the acid chloride, for example using oxalyl chloride, followed by treatment with ammonium hydroxide to afford the carboxamide, and finally, dehydration, for example using trichloro-1,3,5-triazine, to give the nitrile 15. Nucleophilic aromatic substitution of the fluoride using benzyl mercaptan and a base such as sodium hydride provides the sulfide 16. The nitrile present in 16 can be converted to the tetrazole 17 using one of several methods, for example by treatment with trimethylsilyl azide and dibutyltin oxide. Conversion of the benzyl sulfide to the sulfonyl chloride can be accomplished in several ways, for example, by treatment with N-chloro succinimide in acetic acid. Treatment with ammonium hydroxide then affords the sulfonamide 18. Concomittant protection of the tetrazole and sulfonamide to afford positional isomer mixture 1a and 1b can be achieved by treatment with excess of para-methoxybenzyl chloride in the presence of a base, such as potassium carbonate, and NaI and tetrabutyl ammonium chloride as catalysts. Typically 1a and 1b are used as a mixture of regioisomers, but the isomers can optionally be separated and used individually in the same way. In the examples below, it should be understood that the mixture of regioisomers or the individual regioisomers may be used interchangeably (occasionally only one isomer is shown for the sake of simplicity).

Reference Example 1

6-bromo-3-iodo-2-(1-(4-methoxybenzyl)-1H-tetrazol-5-yl)benzenesulfonamide and 6-bromo-3-iodo-2-(2-(4-methoxybenzyl)-2H-tetrazol-5-yl)benzenesulfonamide Step A: 3-bromo-2-fluoro-6-iodobenzoic acid Into a 2000-mL 3-necked round-bottom flask purged and maintained with an inert atmosphere of nitrogen was placed a solution of (i-Pr)$_2$NH (40.4 g, 400.00 mmol, 1.20 equiv) in THF (400 mL). This was followed by the addition of n-butyl lithium (146 mL, 1.10 equiv) dropwise with stirring at −20° C. over 30 minutes. To this was added a solution of 1-bromo-2-fluoro-4-iodobenzene (100 g, 332.34 mmol, 1.00 equiv) in THF (600 mL) dropwise with stirring at −78° C. The resulting solution was stirred for 90 minutes at −78° C. The reaction mixture was then poured into 1.5 L of dry ice. The resulting mixture was concentrated under vacuum. The residue was diluted with 2000 mL of aq. sodium hydroxide (4 M), then washed with 2×800 mL of ether. The aq. solution was adjusted to pH 2 with HCl (2 M), then extracted with 3×800 mL of ethyl acetate. The organic layers were combined, washed with 3×500 mL of water, dried, and concentrated under vacuum to afford the title compound.

Step B: 3-bromo-2-fluoro-6-iodobenzoyl Chloride

Into a 3000-mL round-bottom flask was placed 3-bromo-2-fluoro-6-iodobenzoic acid (235 g, 681.35 mmol, 1.00 equiv) and thionyl chloride (1175 mL). The resulting solution was stirred for 2 hours at 80° C. in an oil bath. The resulting mixture was cooled and concentrated under vacuum to afford the title compound.

Step C: 3-bromo-2-fluoro-6-iodobenzamide

Into a 10000-mL 4-necked round-bottom flask was placed a solution of NH$_4$OH (840 g) in THF (2000 mL), followed by the addition of a solution of 3-bromo-2-fluoro-6-iodobenzoyl chloride (223 g, 614 mmol, 1.00 equiv) in THF (2460 mL) dropwise with stirring at 0° C. The resulting solution was stirred for 60 minutes at room temperature. The resulting mixture was concentrated under vacuum. The solids were collected by filtration to afford the title compound.

Step D: 3-bromo-2-fluoro-6-iodobenzonitrile

Into a 10000-mL 4-necked round-bottom flask was placed a solution of 3-bromo-2-fluoro-6-iodobenzamide (223 g, 648 mmol, 1.00 equiv) in N,N-dimethylformamide (4460 mL), trichloro-1,3,5-triazine (840 g, 4.56 mol, 7.00 equiv). The resulting solution was stirred overnight at room temperature. The reaction mixture was poured into 10 L of aq. sodium bicarbonate. The solids were collected by filtration to afford the title compound.

Step E: 2-(benzylsulfanyl)-3-bromo-6-iodobenzonitrile

Into a 5000-mL 4-necked round-bottom flask purged and maintained with an inert atmosphere of nitrogen was placed a solution of sodium hydride (14.8 g, 617 mmol, 1.20 equiv) in 1,4-dioxane (1000 mL). A solution of phenylmethanethiol (38.1 g, 306.76 mmol, 1.00 equiv) in 1,4-dioxane (100 mL) was added dropwise with stirring at 0° C. over 20 minutes. To this was added a solution of 3-bromo-2-fluoro-6-iodobenzonitrile (100 g, 306.84 mmol, 1.00 equiv) in 1,4-dioxane (400 mL) dropwise with stirring at 0° C. The resulting solution was stirred for 60 minutes at room temperature and for an additional 60 minutes at 60° C. The reaction was then quenched by the addition of 750 mL of HCl (1 M). The resulting solution was diluted with 3 L of water, then extracted with 3×1 L of ethyl acetate. The organic layers were combined, dried and concentrated under vacuum. The residue was applied onto a silica gel column and eluted with ethyl acetate/petroleum ether (1:4) to afford the title compound.

Step F: 5-[2-(benzylsulfanyl)-3-bromo-6-iodophenyl]-1H-1,2,3,4-tetrazole

Into a 3000-mL 4-necked round-bottom flask was placed a solution of 2-(benzylsulfanyl)-3-bromo-6-iodobenzonitrile (54.0 g, 126 mmol, 1.00 equiv) in toluene (750 mL), $TMSN_3$ (43.4 g, 3.00 equiv) and dibutyltin oxide (6.3 g, 0.20 equiv). The resulting solution was stirred for 48 hour at 105° C. in an oil bath. The reaction mixture was cooled to room temperature. The resulting solution was diluted with 3 L of aq. sodium hydroxide, then extracted with ethyl acetate. The aqueous layer was adjusted to pH 3 with HCl (2 M), then extracted with 2×1 L of ethyl acetate. The organic layers were combined, washed with 2×1 L of water, dried over anhydrous sodium sulfate and concentrated under vacuum to provide the title compound.

Step G: 5-[2-(benzylsulfanyl)-3-bromo-6-iodophenyl]-1-[(4-methoxyphenyl)methyl]-1H-1,2,3,4-tetrazole and 5-[2-(benzylsulfanyl)-3-bromo-6-iodophenyl]-2-[(4-methoxyphenyl)methyl]-2H-1,2,3,4-tetrazole Into a 3000-mL 3-necked round-bottom flask purged and maintained with an inert atmosphere of nitrogen was placed a solution of 5-[2-(benzylsulfanyl)-3-bromo-6-iodophenyl]-1H-1,2,3,4-tetrazole (84.4 g, 178 mmol, 1.00 equiv) in chloroform (700 mL), a solution of potassium carbonate (49.0 g, 355 mmol, 2.00 equiv) in water (520 mL), and tetrabutylammonium chloride (10.2 g, 0.20 equiv). This was followed by the addition of para-methoxybenzyl chloride (42.2 g, 1.50 equiv) dropwise with stirring at 15° C. The resulting solution was stirred for 180 min at 50° C. in an oil bath. The reaction mixture was cooled to room temperature. The resulting solution was diluted with 200 mL of water, then extracted with 2×200 mL of DCM. The organic layers were combined, dried over sodium sulfate and concentrated under vacuum. The residue was applied onto a silica gel column and eluted with ethyl acetate/petroleum ether (1:2), resulting in the title compound as a mixture of two isomers.

Step H: 6-bromo-3-iodo-2-(1-(4-methoxybenzyl)-1H-tetrazol-5-yl)benzene-1-sulfonyl chloride and 6-bromo-3-iodo-2-(2-(4-methoxybenzyl)-2H-tetrazol-5-yl)benzene-1-sulfonyl chloride Into a 2000-mL 4-necked round-bottom flask purged and maintained with an inert atmosphere of nitrogen was placed mixture of 5-[2-(benzylsulfanyl)-3-bromo-6-iodophenyl]-1-[(4-methoxyphenyl)methyl]-1H-1,2,3,4-tetrazole and 5-[2-(benzylsulfanyl)-3-bromo-6-iodophenyl]-2-[(4-methoxyphenyl)methyl]-2H-1,2,3,4-tetrazole (50.0 g, 84.3 mmol, 1.00 equiv, 60%), DCM (750 mL), AcOH (12.7 g, 211 mmol, 2.50 equivalents), and water (3.8 g, 2.5 equiv). $SO_2Cl_2$ (28.3 g, 2.50 equivalents) was then added dropwise with stirring at 0° C. The resulting solution was stirred for 60 minutes at room temperature. The resulting mixture was concentrated under vacuum to afford the title compound isomer mixture.

Step I: 6-bromo-3-iodo-2-(1-(4-methoxybenzyl)-1H-tetrazol-5-yl)benzenesulfonamide and 6-bromo-3-iodo-2-(2-(4-methoxybenzyl)-2H-tetrazol-5-yl)benzenesulfonamide Into a 2000-mL 4-necked round-bottom flask purged and maintained with an inert atmosphere of nitrogen was placed a solution of 6-bromo-3-iodo-2-(1-(4-methoxybenzyl)-1H-tetrazol-5-yl)benzene-1-sulfonyl chloride and 6-bromo-3-iodo-2-(2-(4-methoxybenzyl)-2H-tetrazol-5-yl)benzene-1-sulfonyl chloride (isomer mixture, 50.0 g, 52.7 mmol, 1.00 equiv, 60%) in THF (300 mL) and a solution of $NH_4OH$ (200 mL) in THF (200 mL). The resulting solution was stirred for 60 minutes at room temperature. The resulting solution was extracted with 3×150 mL of ethyl acetate. The organic layers were combined, dried over anhydrous sodium sulfate and concentrated under vacuum. The crude product was purified with Flash-Prep-HPLC under the following conditions: Column, C18 silica gel; mobile phase, $H_2O$: MeCN=25 increasing to $H_2O$: MeCN=55 within 30 min; Detector, UV 210 nm, to afford the title compound. H-NMR (DMSO-d6, 300 MHz, ppm): δ 3.727-3.748 (3H, d), 5.001-5.068 (0.78H, m), 5.428-5.477 (0.75H, m), 5.941 (0.5H, m), 6.823-6.958 (2H, m), 7.148-7.363 (2H, m), 7.732-7.864 (1.6H, m), 7.993-8.117 (3H, m).

Reference Example 2

6-bromo-3-iodo-N,N-bis(4-methoxybenzyl)-2-(1-(4-methoxybenzyl)-1H-tetrazol-5-yl)benzenesulfonamide and 6-bromo-3-iodo-N,N-bis(4-methoxybenzyl)-2-(2-(4-methoxybenzyl)-2H-tetrazol-5-yl)benzenesulfonamide

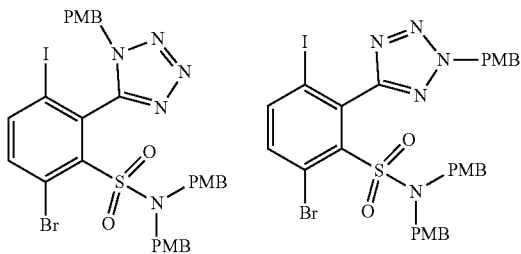

Step A: 3-bromo-2-fluoro-6-iodobenzoic acid

Into a 5000-mL 4-necked round-bottom flask purged and maintained with an inert atmosphere of nitrogen, were placed bis(propan-2-yl)amine (121.2 g, 1.20 mol, 1.20 equiv) and THF (1000 mL). This was followed by the addition of n-butyllithium (440 mL, 2.5 M in hexanes, 1.10 mol, 1.10 equiv) dropwise with stirring at −78° C. for 20 minutes. After 60 minutes, a solution of 1-bromo-2-fluoro-4-iodobenzene (300 g, 997 mmol, 1.00 equiv) in THF (2000 mL) was added dropwise with stirring at −78° C. for 30 minutes. The resulting solution was stirred for 2 hours at −78° C. in a liquid nitrogen bath. The reaction progress was monitored by LCMS. The reaction was then quenched by pouring into 5000 g of dry ice. After stirring for 2 hours, the resulting mixture was concentrated under vacuum. The residue was dissolved in 3000 mL of 4 M sodium hydroxide aqueous solution. The resulting solution was extracted with 2×1000 mL of ether. The pH value of the aqueous solution was adjusted to 2-3 with hydrogen chloride aqueous solution (1 M). The resulting solution was extracted with 4×1000 mL of ethyl acetate, and the organic layers were combined and dried over anhydrous sodium sulfate and concentrated under vacuum. The crude product was purified by re-crystallization from hexanes to afford the title compound.

Step B: 3-bromo-2-fluoro-6-iodobenzoyl Chloride

Into a 5000-mL 3-necked round-bottom flask, purged and maintained with an inert atmosphere of nitrogen, was placed 3-bromo-2-fluoro-6-iodobenzoic acid (273 g, 791.5 mmol, 1.00 equiv), THF (2730 mL), and N,N-dimethylformamide (27.3 mL). This was followed by the addition of oxalyl chloride (110.9 g, 873.7 mmol, 1.10 equiv) dropwise with stirring at 20° C. for 20 minutes. The resulting solution was stirred for 1 hour at room temp. The reaction progress was monitored by LCMS. The resulting mixture was concentrated under vacuum to afford the title compound.

Step C: 3-bromo-2-fluoro-6-iodobenzamide

Into a 5000-mL 4-necked round-bottom flask purged and maintained with an inert atmosphere of nitrogen, was placed NH$_4$OH (1200 g). This was followed by the addition of a solution of 3-bromo-2-fluoro-6-iodobenzoyl chloride (280 g, 771 mmol, 1.00 equiv) in THF (2800 mL) dropwise with stirring at 0° C. for 30 minutes. The resulting solution was stirred for 1 hour at room temperature. The reaction progress was monitored by LCMS. The resulting mixture was concentrated under vacuum. The solids were collected by filtration, and washed with H$_2$O to afford the title compound.

Step D: 3-bromo-2-fluoro-6-iodobenzonitrile

Into a 10000-mL 4-necked round-bottom flask purged and maintained with an inert atmosphere of nitrogen, was placed 3-bromo-2-fluoro-6-iodobenzamide (270 g, 785.1 mmol, 1.00 equiv), N,N-dimethylformamide (5400 mL). This was followed by the addition of trichloro-1,3,5-triazine (1014 g, 5.50 mol, 7.00 equiv) in portions at 0° C. The resulting solution was stirred for 2 hours at room temperature. The reaction progress was monitored by LCMS. The reaction was then quenched by the addition of 15000 mL of saturated sodium bicarbonate aqueous solution. The solids were collected by filtration to afford the title compound.

Step E: 2-(benzylsulfanyl)-3-bromo-6-iodobenzonitrile

Into a 5000-mL 4-necked round-bottom flask purged and maintained with an inert atmosphere of nitrogen, was placed sodium hydride (34 g, 60% dispersion in mineral oil, 850 mmol, 1.20 equiv) and 1,4-dioxane (700 mL). This was followed by the addition of a solution of phenylmethanethiol (88.7 g, 714.2 mmol, 1.00 equiv) in 1,4-dioxane (950 mL) dropwise with stirring at 10° C. for 15 minutes. After 30 minutes, to this reaction mixture was added a solution of 3-bromo-2-fluoro-6-iodobenzonitrile (230 g, 705.7 mmol, 1.00 equiv) in 1,4-dioxane (1800 mL) dropwise with stirring at 10° C. The resulting solution was stirred for 2 hours at room temperature. The reaction was then quenched by pouring into 5000 mL of water/ice. The resulting solution was extracted with 5×1000 mL of ethyl acetate, and the organic layers were combined. The organic layers were washed with 2×1000 mL of water and 2×1000 mL of saturated sodium bicarbonate solution and 2×1000 mL of brine. The resulting mixture was dried over anhydrous sodium sulfate and concentrated under vacuum. The crude product was purified by re-crystallization from ether to afford the title compound.

Step F: 5-[2-(benzylsulfanyl)-3-bromo-6-iodophenyl]-1H-1,2,3,4-tetrazole

Into a 2000-mL 4-necked round-bottom flask, was placed 2-(benzylsulfanyl)-3-bromo-6-iodobenzonitrile (66 g, 153.5 mmol, 1.00 equiv), toluene (660 mL), azidotrimethylsilane (44.2 g, 383.6 mmol, 2.50 equiv), and dibutylstannanone (7.7 g, 30.93 mmol, 0.20 equiv). The resulting solution was stirred for 48 hours at 105° C. in an oil bath. The reaction progress was monitored by LCMS. The reaction mixture was cooled to room temperature, and concentrated under vacuum. The residue was purified by silica gel column chromatography with tetrahydrofuran:PE (100:1) as eluent to afford the title compound.

Step G: 6-bromo-3-iodo-2-(1H-1,2,3,4-tetrazol-5-yl)benzene-1-sulfonyl chloride Into a 2000-mL 4-necked round-bottom flask purged and maintained with an inert atmosphere of nitrogen, were placed 5-[2-(benzylsulfanyl)-3-bromo-6-iodophenyl]-1H-1, 2,3,4-tetrazole (100 g, 211.4 mmol, 1.00 equiv), acetic acid (1000 mL) and water (100 mL). This was followed by the addition of NCS (70.7 g, 529.5 mmol, 2.50 equiv), in portions using an ice/water bath to contain exotherms occurring on addition of NCS, and maintaining the internal temperature approximately between 20-30° C. The resulting solution was stirred for 2 hours at room temperature using an ice/water bath as needed to maintain the temperature following addition of NCS which is exothermic. The reaction progress was monitored by LCMS. The resulting mixture was concentrated under vacuum and then was diluted with 2000 mL of EtOAc. The resulting mixture was washed with 2×1000 mL of water and 2×1000 mL of brine. The mixture was dried over anhydrous sodium sulfate and concentrated under vacuum to afford the title compound.

Step H: 6-bromo-3-iodo-2-(1H-1,2,3,4-tetrazol-5-yl) benzene-1-sulfonamide

Into a 3000-mL 4-necked round-bottom flask purged and maintained with an inert atmosphere of nitrogen, were placed NH$_4$OH (1180 mL) and THF (290 mL). This was followed by the addition of a solution of 6-bromo-3-iodo-2-(1H-1,2,3,4-tetrazol-5-yl)benzene-1-sulfonyl chloride (118 g, 262.5 mmol, 1.00 equiv) in THF (300 mL) dropwise with stirring at 0° C. The resulting solution was stirred for 2 hours at 0-25° C. in an ice/salt bath (slowly warming to room temperature). The reaction progress was monitored by LCMS. The resulting mixture was concentrated under vacuum, and diluted with 500 mL ether. After stirring for 30 minutes, the solids were collected by filtration to afford the title compound.

Step I: 6-bromo-3-iodo-N,N-bis[(4-methoxyphenyl) methyl]-2-[1-[(4-methoxyphenyl)methyl]-1H-1,2,3, 4-tetrazol-5-yl]benzene-1-sulfonamide and 6-bromo-3-iodo-N,N-bis[(4-methoxyphenyl) methyl]-2-[2-[(4-methoxyphenyl)methyl]-2H-1,2,3, 4-tetrazol-5-yl]benzene-1-sulfonamide Into a 3000-mL 4-necked round-bottom flask purged and maintained with an inert atmosphere of nitrogen, were placed 6-bromo-3-iodo-2-(1H-1,2,3,4-tetrazol-5-yl)benzene-1-sulfonamide (105 g, 244.2 mmol, 1.00 equiv), chloroform (1050 mL), potassium carbonate (168.9 g, 1.22 mol, 5.00 equiv), water (525 mL), NaI (11 g, 73.4 mmol, 0.30 equiv), tetrabutylammonium chloride (20.4 g, 73.4 mmol, 0.30 equiv), and 1-(chloromethyl)-4-methoxybenzene (230 g, 1.47 mol, 6.00 equiv). The resulting solution was stirred overnight at 50° C. in an oil bath. The reaction progress was monitored by LCMS. The reaction mixture was cooled to room temperature. The resulting solution was extracted with 2×1000 mL DCM. The organic layers were combined and dried over anhydrous sodium sulfate and concentrated under vacuum to afford the title compounds. $^1$H-NMR: (300 MHz, CDCl$_3$, ppm): δ 7.956-7.928 (m, 0.5H), 7.852-7.824 (m, 1H), 7.656-7.612 (m, 1.5H), 7.323-7.282 (m, 1.5H), 7.195-7.224 (m, 2H), 6.944-6.908 (m, 6H), 6.822-6.760 (m, 9H), 5.791 (m, 1H), 5.570-5.521 (m, 1H), 5.149-5.100 (m, 1H), 4.769-4.718 (m, 2H), 4.232-4.221 (m, 2H), 3.900-3.848 (m, 2H), 3.789-3.742 (m, 14H).

In the experimental procedures below, the compound of REFERENCE EXAMPLE 2 can be used as a mixture of 4-methoxylbenzyl tetrazole regioisomers. Alternatively, the two regioisomers may be separated and each can be used as described below in the same fashion. In some REFERENCE EXAMPLES and EXAMPLES below, both regioisomers are explicitly used; however, in other cases, for the sake of simplicity, only one regioisomer is shown. It should be understood that in these cases the mixture of regioisomers was typically used.

Reference Example 3

3-iodo-N,N-bis(4-methoxybenzyl)-2-(2-(4-methoxybenzyl)-2H-tetrazol-5-yl)-6-((2-(trimethylsilyl)ethyl) sulfonyl)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)sulfonyl) benzenesulfonamide

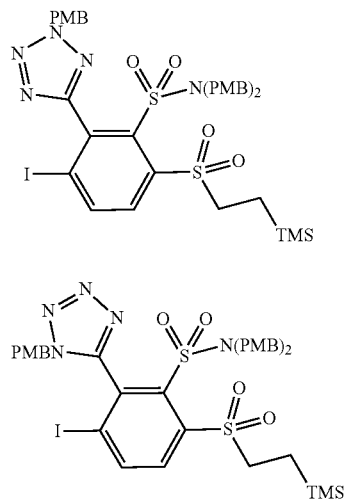

Step A: 3-iodo-N,N-bis(4-methoxybenzyl)-2-(2-(4-methoxybenzyl)-2H-tetrazol-5-yl)-6-(2-(trimethylsilyl)ethylthio)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)thio) benzenesulfonamide Commercially available (for example, from Sigma-Aldrich order #364681), known (Canadian Journal of Chemistry, 1994, 72(2), 325; Journal of Organic Chemistry, 2005, 70(14), 5611) 2-(trimethylsilyl)ethanethiol (21.24 g, 158 mmol) was added to a mixture of NaH (7.59 g, 60% dispersion in mineral oil, 190 mmol) in DMF (350 mL). The resulting mixture was stirred at 0° C. for 30 minutes. After that, 6-bromo-3-iodo-N,N-bis[(4-methoxyphenyl)methyl]-2-[1-[(4-methoxyphenyl)methyl]-1H-1,2,3,4-tetrazol-5-yl] benzene-1-sulfonamide and 6-bromo-3-iodo-N,N-bis[(4-methoxyphenyl)methyl]-2-[2-[(4-methoxyphenyl)methyl]-2H-1,2,3,4-tetrazol-5-yl]benzene-1-sulfonamide (50 g, 63.4 mmol) was added in portions. The resulting mixture was stirred at room temperature for 2 hours under an atmosphere of nitrogen. The reaction was monitored by LCMS, and was quenched with water (500 mL). The resulting mixture was extracted with EtOAc (2×300 mL). The organic layers were combined and concentrated under vacuum to afford the title compound: LCMS [M+H]$^+$: 844.

Step B: 3-iodo-N,N-bis(4-methoxybenzyl)-2-(2-(4-methoxybenzyl)-2H-tetrazol-5-yl)-6-(2-(trimethylsilyl)ethylsulfonyl)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)sulfonyl)benzenesulfonamide m-CPBA (654 g, 379 mmol) was added to a solution of 3-iodo-N,N-bis(4-methoxybenzyl)-2-(2-(4-methoxybenzyl)-2H-tetrazol-5-yl)-6-(2-(trimethylsilyl)ethylthio)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)thio)benzenesulfonamide (160 g, 190 mmol) in DCM (2000 mL) at 0° C. The resulting mixture was stirred at room temperature overnight under an atmosphere of nitrogen. The reaction was monitored by LCMS. The resulting mixture was quenched with saturated $Na_2S_2O_3$ solution (150 mL), and washed with saturated $Na_2CO_3$ solution (1 L) and water (1 L). The organic layer was collected and concentrated under vacuum. The residue was purified by silica gel column chromatography with EtOAc/PE (1/2) as eluent to afford the title compound: LCMS (ESI) calc'd for $C_{36}H_{42}IN_5O_7S_2Si$ $[M+H]^+$: 876, found 876; $^1H$ NMR (300 MHz, $CDCl_3$): δ 8.62 (d, J=8.7 Hz, 1H), 8.26 (d, J=8.4 Hz, 1H), 7.90-7.88 (m, 1H), 7.69-7.68 (m, 0.5H), 7.56-7.53 (m, 0.5H), 7.27-7.20 (m, 2H), 6.91-6.79 (m, 12H), 5.44-5.39 (m, 1H), 5.20-5.15 (m, 1H), 4.58-4.53 (m, 2H), 3.98-3.79 (m, 2H), 3.75-3.66 (m, 9H), 2.50-2.48 (m, 2H), 1.19-1.03 (m, 1H), 0.83-0.82 (m, 1H), 0.01 (s, 9H).

Reference Example 4

2-(N,N-bis(4-methoxybenzyl)sulfamoyl)-4-iodo-3-(2-(4-methoxybenzyl)-2H-tetrazol-5-yl)benzenesulfinic acid and 2-(N,N-bis(4-methoxybenzyl)sulfamoyl)-4-iodo-3-(1-(4-methoxybenzyl)-1H-tetrazol-5-yl)benzenesulfinic acid

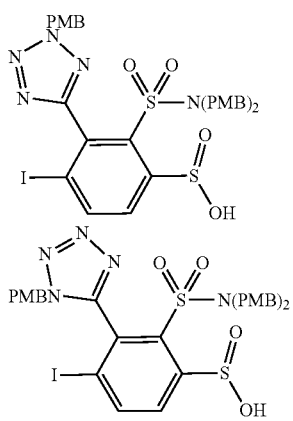

To a solution of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide and 3-iodo-N,N-bis(4-methoxybenzyl)-2-(1-(4-methoxybenzyl)-1H-tetrazol-5-yl)-6-((2-(trimethylsilyl)ethyl)sulfonyl)benzenesulfonamide (2.0 g, 2.28 mmol) in THF (23 mL) was added tetrabutylammonium fluoride (5.02 mL, 1.0 M in THF, 5.02 mmol) dropwise at 0° C. The reaction mixture was stirred at room temperature under $N_2$ for 30 minutes. The resulting mixture was diluted with ethyl acetate, washed with saturated $KHSO_4$ aqueous solution, dried over $MgSO_4$, and concentrated under vacuum to afford the crude product as a solid. The crude material was used directly for to make compounds of the invention: LCMS $[M+H]^+$: 776.

Reference Example 5

2-(N,N-bis(4-methoxybenzyl)sulfamoyl)-4-iodo-3-(2-(4-methoxybenzyl)-2H-tetrazol-5-yl)benzenesulfonyl chloride and 2-(N,N-bis(4-methoxybenzyl)sulfamoyl)-4-iodo-3-(1-(4-methoxybenzyl)-1H-tetrazol-5-yl)benzenesulfonyl chloride

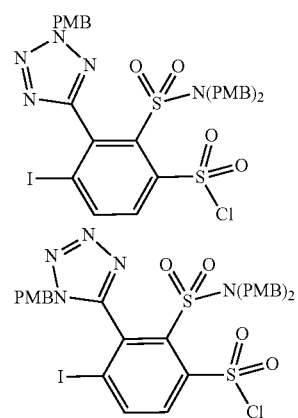

2-(N,N-bis(4-methoxybenzyl)sulfamoyl)-4-iodo-3-(2-(4-methoxybenzyl)-2H-tetrazol-5-yl)benzenesulfinic acid (800 mg, 1.031 mmol) in THF (10 mL) was cooled to 0° C. 1-chloropyrrolidine-2,5-dione (275 mg, 2.063 mmol) in THF (2 mL) was added over 5 minutes. The mixture was stirred at the same temperature for 30 minutes, then diluted with ethyl acetate, washed with saturated $NaHCO_3$ and brine, dried over $MgSO_4$, and concentrated to afford the crude product: LCMS (ESI) $[M+H]^+$: 810.

Reference Example 6 tert-Butyl (4-(3-(N,N-bis(4-methoxybenzyl)sulfamoyl)-4-(chlorosulfonyl)-2-(2-(4-methoxybenzyl)-2H-tetrazol-5-yl)phenyl)benzo[d]thiazol-2-yl)(tert-butoxycarbonyl)carbamate

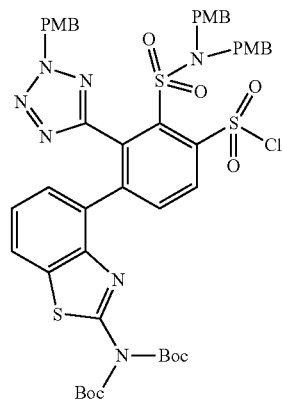

Step A: 3-iodo-N,N-bis(4-methoxybenzyl)-2-(2-(4-methoxybenzyl)-2H-tetrazol-5-yl)-6-((2-(trimethylsilyl)ethyl)thio)benzenesulfonamide A suspension of 6-bromo-3-iodo-N,N-bis(4-methoxybenzyl)-2-(2-(4-methoxybenzyl)-2H-tetrazol-5-yl)benzenesulfonamide (10 g, 12.65 mmol), cesium carbonate (8.24 g, 25.3 mmol) and 2-(trimethylsilyl)ethanethiol (6.08 ml, 38.0 mmol) in DMF (100 ml) was stirred at room temperature overnight. The mixture was diluted with ether and washed with brine. The organic layer was dried (MgSO$_4$), and concentrated to give crude 3-iodo-N,N-bis(4-methoxybenzyl)-2-(2-(4-methoxybenzyl)-2H-tetrazol-5-yl)-6-((2-(trimethylsilyl)ethyl)thio)benzenesulfonamide, which was used directly in the next step. LCMS [M+1]: 844.63.

Step B: 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide The crude 3-iodo-N,N-bis(4-methoxybenzyl)-2-(2-(4-methoxybenzyl)-2H-tetrazol-5-yl)-6-((2-(trimethylsilyl)ethyl)thio)benzenesulfonamide (10.5 g, 12.5 mmol) was dissolved in DCM (100 ml), and cooled to 0° C. m-CPBA (10.92 g, 63.3 mmol) was added in portions. The mixture was stirred overnight. Precipitate was filtered off through a CELITE pad, and the filtrate was diluted with DCM (100 ml), washed with 1N NaOH and brine. The organic layer was dried and concentrated. The residue was purified by ISCO (120 g, 0-50% EtOAc in hexane, the 50% hexane). LCMS [M+1]: 876.49.

Step C: 3-(2-aminobenzo[d]thiazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide A suspension of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (9 g, 10.28 mmol), (2-aminobenzo[d]thiazol-4-yl)boronic acid (3.99 g, 20.55 mmol), TETRAKIS(triphenylphosphine)Palladium(0) (1.187 g, 1.028 mmol) and sodium carbonate (3.27 g, 30.8 mmol) in dioxane (75 ml) and Water (25 ml) was degassed and heated at 80° C. for 3 hr. The mixture was diluted with AcOEt, washed with brine. The organic layer was dried (MgSO$_4$) and concentrated. The crude material was purified by ISCO (220 g, 0-50% then 50% EtOAc in hexane. LCMS: 898.74.

Step D: tert-butyl (4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)benzo[d]thiazol-2-yl)(tert-butoxycarbonyl)carbamate To a mixture of 3-(2-aminobenzo[d]thiazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (7 g, 7.79 mmol), di-tert-butyl dicarbonate (5.95 g, 27.3 mmol) and TEA (3.80 ml, 27.3 mmol) in DCM (80 ml) was added DMAP (0.952 g, 7.79 mmol). The mixture was stirred at room temperature for 1 hour, diluted with ether, washed with KHSO$_4$, saturated aqueous and brine. The organic layer was dried over MgSO$_4$ and concentrated. The crude material was purified by ISCO (120 g, 0-30% then 30% EtOAc in hexane). LCMS [M+1]: 1098.56.

Step E: 2-(N,N-bis(4-methoxybenzyl)sulfamoyl)-4-(2-(N,N-bis(tert-butoxycarbonyl)amido)benzo[d]thiazol-4-yl)-3-(2-(4-methoxybenzyl)-2H-tetrazol-5-yl)benzenesulfinic acid A solution of tert-butyl (4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)benzo[d]thiazol-2-yl)(tert-butoxycarbonyl)carbamate (6.9 g, 6.28 mmol) in THF (100 mL) was stirred with tetrabutylammonium fluoride (25.1 mL, 25.1 mmol) at room temperature under N$_2$ for 0.5 hour. The mixture was diluted with AcOEt, washed with KHSO$_4$, saturated aqueous, then dried over MgSO$_4$, and concentrated. The crude material was purified by ISCO (0-50% then 50% EtOH-EtOAc (1:3) in hexane. LCMS [M+1]: 998.51.

Step F: tert-butyl (4-(3-(N,N-bis(4-methoxybenzyl)sulfamoyl)-4-(chlorosulfonyl)-2-(2-(4-methoxybenzyl)-2H-tetrazol-5-yl)phenyl)benzo[d]thiazol-2-yl)(tert-butoxycarbonyl)carbamate A mixture of sodium acetate (0.789 g, 9.62 mmol), acetic acid (0.551 ml, 9.62 mmol) and 2-(N,N-bis(4-methoxybenzyl)sulfamoyl)-4-(2-(N,N-bis(tert-butoxycarbonyl)amido)benzo[d]thiazol-4-yl)-3-(2-(4-methoxybenzyl)-2H-tetrazol-5-yl)benzenesulfinic acid (3.2 g, 3.21 mmol) in THF (75 ml) was cooled to 0° C. NCS solid (0.856 g, 6.41 mmol) was added. The mixture was stirred at the same temperature for 30 minutes, diluted with Et$_2$O, washed with KHSO$_4$ and brine, then dried over MgSO$_4$, and concentrated. The crude material was purified by ISCO 0-30% EtOAc then 30% EtOAc in hexane). LCMS [M+1]: 1032.67. The isolated material contained a small amount of mono-Boc compound. LCMS [M+1]: 932.57.

Reference Example 7

2-amino-7-methylbenzo[d]thiazol-4-ylboronic acid

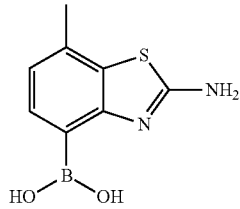

Step A: N-((2-bromo-5-methylphenyl)carbamothioyl)benzamide 2-bromo-5-methylbenzenamine (10 g, 54 mmol) was added into the solution of benzoic cyanic thioanhydride (8.8 g, 54 mmol) in acetone (100 ml) at ambient temperature and stirred at 80° C. for 1 hour. The reaction solution was cooled and filtered. The filtrate was washed with EA and dried to give the title compound as a solid. LCMS (ESI) [M+1]$^+$ 349; $^1$H NMR (DMSO-d6, 400 MHZ): δ 12.54 (s, 1H), 9.16 (s, 1H), 8.06 (s, 1H), 7.90 (d, J=8.4 Hz, 2H), 7.73-7.65 (m, 1H), 7.60-7.54 (m, 3H), 7.20 (dd, J=8.0 Hz, 1H), 2.42 (s, 3H).

Step B: 1-(2-bromo-5-methylphenyl)thiourea

A solution of N-((2-bromo-5-methylphenyl)carbamothioyl)benzamide (5 g, 14 mmol) and NaOH (5.6 g, 140 mmol) in water (100 ml) and MeOH (100 ml) was stirred at 80° C. for 3 hour. The reaction mixture was diluted with water (80 mL) and extracted with DCM (3×80 mL). The combined organic layers were washed with water (3×10 mL) and brine (3×10 mL), dried over anhydrous sodium sulfate and filtered. The filtrate was concentrated under vacuum to give the title compound as a solid. LCMS (ESI): [M+1]$^+$ 245; $^1$H NMR (DMSO-d6, 400 MHZ): δ 9.20 (s, 1H), 7.94 (d, J=7.2 Hz, 1H), 7.50 (d, J=8.0 Hz, 2H), 7.53 (s, 1H), 6.99 (dd, J=1.2 Hz, 1H), 2.26 (s, 3H).

Step C: 4-bromo-7-methylbenzo[d]thiazol-2-amine

Br$_2$ (4.20 ml, 82 mmol) in chloroform (50 mL) was added in drops to a stirred solution of 1-(2-bromo-5-methylphenyl)thiourea (3.1 g, 13 mmol) in chloroform (200 mL) in an ice bath and then stirred at 80° C. for 4 hours. The reaction mixture was concentrated under vacuum and washed with EA (3×30 ml). The mixture was filtered and the filter cake was dried to give the title compound as a solid. LCMS (ESI): [M+1]$^+$ 243; $^1$H NMR (DMSO-d6, 300 MHZ): δ 7.81 (s, 2H), 7.34 (d, J=10.8 Hz, 1H), 6.77 (d, J=10.8 Hz, 1H), 2.30 (s, 3H).

Step D: (2-amino-7-methylbenzo[d]thiazol-4-yl)boronic acid

A solution of 4-bromo-7-methylbenzo[d]thiazol-2-amine (2.0 g, 8.3 mmol), 5,5,5',5'-tetramethyl-2,2'-bi(1,3,2-dioxaborinane) (2.79 g, 12.3 mmol), PCy3 Pd G2 (0.972 g, 1.645 mmol) and potassium acetate (2.422 g, 24.7 mmol) in 1,4-dioxane (40 ml) was stirred at 80° C. for 16 hours. The reaction mixture was concentrated under vacuum and the solid was dissolved with EA (300 ml). The solution was washed with water (15% NaOH) and the aqueous phase was adjusted to pH 3 with 2 M HCl, and then extracted with EA (3×100 ml). The organic layers were dried over anhydrous sodium sulfate and filtered. The filtrate was concentrated under vacuum to give the title compound as a solid. LCMS (ESI): [M+1]$^+$ 209; $^1$H NMR (DMSO-d6, 300 MHZ): δ 7.84 (s, 2H), 7.33 (d, J=8.0 Hz, 1H), 6.78 (d, J=8.0 Hz, 1H), 2.31 (s, 3H).

Reference Example 8

2-aminobenzo[d]oxazol-4-ylboronic acid

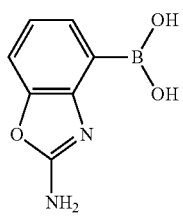

Step A: 4-bromobenzo[d]oxazol-2-amine

A mixture of 2-amino-3-bromophenol (5 g, 26.6 mmol) and cyanic bromide (1.673 ml, 31.9 mmol) in DCM (25 ml) and MeOH (50 ml) was stirred at ambient temperature for 4 hours. The resulting mixture was quenched with aq. sodium hydrogen carbonate (500 mL), diluted with water (20 mL) and extracted with DCM (3×20 mL). The combined organic layers were washed with water (3×10 mL) and brine (3×10 mL), dried over anhydrous sodium sulfate and filtered. The filtrate was concentrated under reduced pressure to give the title compound as a solid. LCMS (ESI): [M+1]$^+$ 213; $^1$H NMR (DMSO-d6, 400 MHZ): 7.70 (s, 2H), 7.35 (s, J=7.6 Hz, 1H), 7.30 (s, J=8.4 Hz, 1H), 6.93-6.89 (m, 1H).

Step B: 2-aminobenzo[d]oxazol-4-ylboronic acid

A solution of 4-bromobenzo[d]oxazol-2-amine (1.00 g, 4.69 mmol), Pd(dppf)Cl$_2$.CH$_2$Cl$_2$ (0.686 g, 0.939 mmol), bis(nneopentylglycolato)diboron (1.060 g, 4.69 mmol) and potassium acetate (0.921 g, 9.39 mmol) in 1,4-dioxane (30 ml) was stirred at 80° C. for 24 hours under nitrogen. The reaction mixture was concentrated under reduced pressure and the residue was purified by Prep-HPLC with the following conditions: Column, Sunfire C 18, 19×150 mm; mobile phase: water (0.05% TFA) and acetonitrile (Gradient time: 7 min. B %: 10%-20%); Detector, UV 220 and 254 nm. The collected fractions were combined and concentrated under reduced pressure to give the title compound as a solid. LCMS (ESI): [M+1]$^+$ 179.

Reference Example 9

(2-aminoquinolin-8-yl)boronic acid

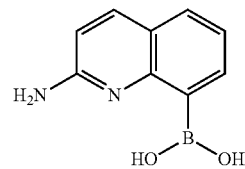 [SMILES: Nc1ccc2cccc(B(O)O)c2n1]

A solution of 8-bromoquinolin-2-amine (500 mg, 2.241 mmol), Pd(dppf)Cl$_2$ (328 mg, 0.448 mmol), bis(pinacolato)diboron (1138 mg, 4.48 mmol) and potassium acetate (440 mg, 4.48 mmol) in 1,4-Dioxane (20 ml) was stirred at 80° C. for 2 hours under nitrogen. The reaction mixture was filtered and the filtrate was concentrated under vacuum to give crude product. The crude product was purified by column C18 eluting with acetonitrile/water with 0.05% TFA (15/85). The collected fractions were combined and concentrated under vacuum to give the title compound as a solid. LCMS (ESI) [M+H]$^+$: 189; $^1$H NMR (300 MHz, CD$_3$OD): δ 8.32 (d, J=9.6 Hz, 1H), 8.20-8.10 (m, 1H), 7.94 (d, J=8.0 Hz, 1H), 7.64 (t, J=7.6 Hz, 1H), 7.13 (d, J=8.0 Hz, 1H).

Reference Example 10

2-aminobenzo[d]thiazol-7-ylboronic acid

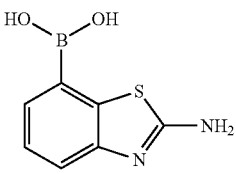 [SMILES: Nc1nc2cccc(B(O)O)c2s1]

A mixture of 4-bromobenzo[d]thiazol-2-amine (commercially available, 2000 mg, 8.73 mmol) and bispinacolatodiboron (6651 mg, 26.2 mmol), potassium acetate (2570 mg, 26.2 mmol) and PCy3 Pd G2 (516 mg, 0.873 mmol) in dry dioxane (80 ml) was degassed, and heated at 80° C. for 48 hours. The mixture was concentrated, and the residue was dissolved in hydrochloric acid (2N, 100 mL). The aqueous was washed with ethyl acetate (60 mL), and concentrated. The residue was dissolved in methanol (50 ml). The solid was filtered off and the filtrate was concentrated to give a solid which was directly used. LCMS (M+1): 195.12.

REFERENCE EXAMPLES 11-12 in the Table immediately below were prepared in an analagous fashion as described for 2-aminobenzo[d]thiazol-7-ylboronic acid (REFERENCE EXAMPLE 10) from the aryl bromide starting materials (SM) indicated.

| REF EX. NO. | SM | Structure | Name | LC/MS m/e [M + H]⁺ |
|---|---|---|---|---|
| 11 | ![Br-NH2-CN structure] | ![boronic acid structure] | (2-amino-3-cyanophenyl)boronic acid | 162.99 |
| 12 | ![Br-benzimidazole structure] | ![boronic acid structure] | (1H-benzo[d]imidazo-4-yl)boronic acid | 163.08 |

Reference Example 13

(2-amino-1H-benzo[d]imidazol-4-yl)boronic acid

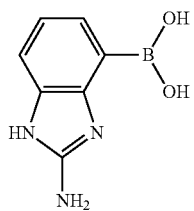

A mixture of 5,5,5',5'-tetramethyl-2,2'-bi(1,3,2-dioxaborinane) (5.59 g, 24.7 mmol), KOAc (4.86 g, 49.5 mmol), and commercially available (for example, from Sigma-Aldrich order #ARK379288552), known (PCT Int. Appl. WO 2015177367) 4-bromo-1H-benzo[d]imidazol-2-amine (3.50 g, 16.5 mmol) in 1,4-dioxane (82 mL) was degassed with $N_2$ before addition of chloro(triphenylphosphine) [2-(2'-amino-1,1'-biphenyl)]palladium(II) (945 mg, 1.65 mmol). The resulting mixture was heated at 80° C. overnight under $N_2$. After cooling to room temperature the reaction mixture was filtered through CELITE, and rinsed with MeOH. The filtrate was concentrated under vacuum, and the residue was purified by reverse phase column chromatography (ISCO RediSep Rf Gold 150 g HP C18 column) eluting with 0-100% MeCN/water (no acid additive) to afford the title compound. LC/MS [M+1]⁺: 178.38.

Reference Example 14

2-amino-1-methyl-1H-benzo[d]imidazol-4-ylboronic acid

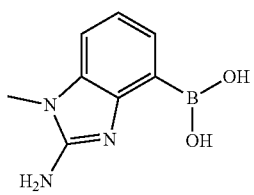

Step A: 3-bromo-N-methyl-2-nitrobenzenamine

A solution of 1-bromo-3-fluoro-2-nitrobenzene (10 g, 45.6 mmol) in $NH_2CH_3$ in THF (2 M, 100 ml) was stirred at 80° C. for 2 hours. The reaction mixture was concentrated under vacuum to give 3-bromo-N-methyl-2-nitrobenzenamine. LCMS (ESI) [M+1]⁺: 231, ¹H NMR (CDCl₃, 400 MHZ): 7.21-7.16 (m, 1H), 6.97 (d, J=7.6 Hz, 1H), 6.76 (d, J=7.6 Hz, 1H), 2.94 (s, 3H).

Step B: 3-bromo-N1-methylbenzene-1,2-diamine

HCl (12 M) was added in drops into a stirred solution of 3-bromo-N-methyl-2-nitrobenzenamine (10.1 g, 44 mmol) and Zn dust (14 g, 0.2 mmol) in methanol (200 ml) at room temperature and stirred at ambient temperature for 2 hours. The reaction mixture was filtered and the filtrate was concentrated under vacuum to give 3-bromo-N1-methylbenzene-1,2-diamine. LCMS (ESI) [M+1]⁺: 201, ¹H NMR (DMSO, 400 MHZ): 6.70 (d, J=8.0 Hz, 1H), 6.47 (t, J=8.0 Hz, 1H), 6.37 (d, J=8.0 Hz, 1H), 4.99 (s, 1H), 4.62 (s, 2H), 2.70 (s, 3H).

Step C: 4-bromo-1-methyl-1H-benzo[d]imidazol-2-amine

A solution of 3-bromo-N1-methylbenzene-1,2-diamine (3.2 g, 16 mmol) and BrCN (1.68 g, 16 mmol) in methanol (100 ml) was stirred at ambient temperature for 4 hours. The reaction mixture was poured into a saturated $NaHCO_3$ solution and filtered. The filter cake was dried to give 4-bromo-1-methyl-1H-benzo[d]imidazol-2-amine. LCMS (ESI) [M+1]⁺: 226, ¹H NMR (DMSO, 400 MHZ): 7.14-7.11 (m, 2H), 6.83-6.79 (m, 1H), 6.71 (s, 1H), 4.99 (s, 2H), 3.49 (s, 3H).

Step D: 2-amino-1-methyl-1H-benzo[d]imidazol-4-ylboronic acid

A mixture of 4-bromo-1-methyl-1H-benzo[d]imidazol-2-amine (3.5 g, 15.5 mmol), bis(pinacolato)diboron (4.7 g, 18.6 mmol) and potassium acetate (4.5 g, 46.5 mmol) in 1,4-Dioxane (100 ml) was stirred at 80° C. for 4 hours under nitrogen. The reaction mixture was concentrated under vacuum to give the crude product. The product was purified by Prep-HPLC with the following conditions: Column, Sunfire C 18, 19×150 mm; mobile phase: water (0.05%

TFA) and acetonitrile (Gradient time: 7 min. B %: 10%-20%); Detector, UV 220 and 254 nm. The collected fractions were combined and concentrated under vacuum to give 2-amino-1-methyl-1H-benzo[d]imidazol-4-ylboronic acid. LCMS (ESI) [M+1]$^+$: 192.

Reference Example 15

(2-amino-6-fluoro-1H-benzo[d]imidazol-4-yl)boronic acid

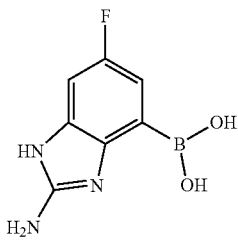 [SMILES: Nc1nc2c(B(O)O)cc(F)cc2[nH]1]

To a 200 mL RBF was charged a solution of 3-bromo-5-fluorobenzene-1,2-diamine (5 g, 24.39 mmol) in ethanol (100 ml), followed by addition of cyanic bromide (5.17 g, 48.8 mmol). The reaction mixture was heated at 80° C. for overnight. The reaction mixture was cooled to room temperature, concentrated in vacuo, then was purified by column chromatography (ISCO, 80 g, 0-20% MeOH in DCM) to give 4-bromo-6-fluoro-1H-benzo[d]imidazol-2-amine (4.2 g, 18.26 mmol), LC-MS [M+H]$^+$: 230.08. The intermediate was dissolved in 50 mL of anhydrous ethanol, followed by addition of 5,5,5',5'-tetramethyl-2,2'-bi(1,3,2-dioxaborinane) (7.86 g, 34.8 mmol), potassium acetate (3.41 g, 34.8 mmol), PCy3 Pd G2 (2.054 g, 3.48 mmol) and anhydrous ethanol (50 ml). The mixture was degassed for 20 minutes, and then was heated at 80° C. for 18 hours. The reaction mixture was acidified with 1.0 M HCl to ~pH 4, then was washed with EtOAc. The crude product was chromatographed over C18 column to give the desired product (2-amino-6-fluoro-1H-benzo[d]imidazol-4-yl)boronic acid. LC/MS (M+H)$^+$: 196.07.

Reference Example S 16A and 16B

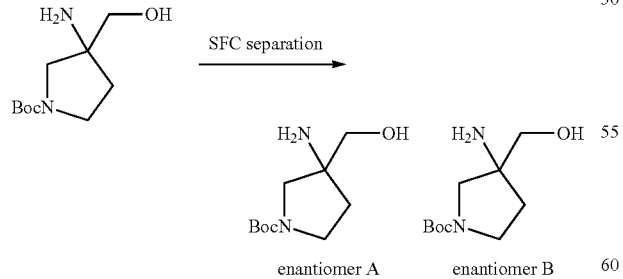

Racemic tert-butyl 3-amino-3-(hydroxymethyl)pyrrolidine-1-carboxylate was separated into individual enantiomers A and B via SFC (Column: AD-H 50×250 mm, UV detection: 210 nm, Solvent: 25% EtOH (with 0.2% DIPA) in CO$_2$, Flow 230 g CO$_2$/min 120 bar). Absolute stereochemistry was not confirmed for the two pure enantiomers. Both enantiomers were useful for preparing metallo-β-lactamase inhibitors.

Reference Example S 17A and 17B

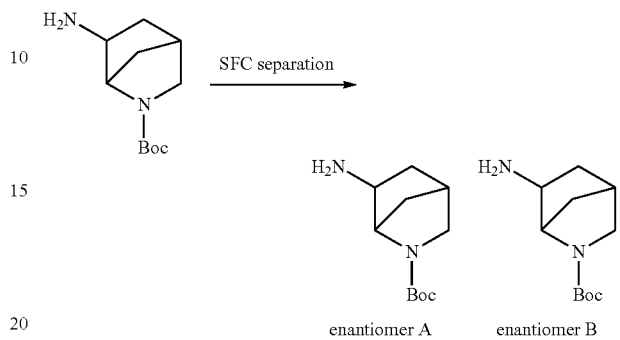

Commercially available racemic tert-butyl 6-amino-2-azabicyclo[2.2.1]heptane-2-carboxylate was separated into individual enantiomers A and B via SFC (Column: AD-H 50×250 mm, UV detection: 210 nm, Solvent: 15% EtOH (with 0.2% DIPA) in CO$_2$, Flow 230 g CO$_2$/min 120 bar). Absolute stereochemistry was not confirmed for the two pure enantiomers. Both enantiomers were useful for preparing metallo-β-lactamase inhibitors.

Reference Example 18

2-(N,N-bis(4-methoxybenzyl)sulfamoyl)-4-(2-((tert-butoxycarbonyl)amino)-1H-benzo[d]imidazol-4-yl)-3-(2-(4-methoxybenzyl)-2H-tetrazol-5-yl)benzenesulfinic acid

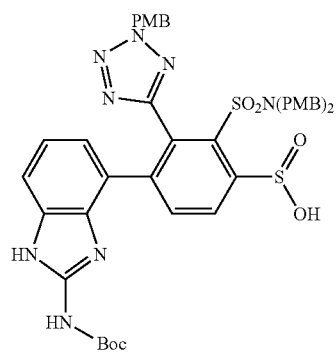

Step A: 3-(2-amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide The mixture of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (5.0 g, 5.71 mmol), (2-amino-1H-benzo[d]imidazol-4-yl)boronic acid (2.02 g, 11.42 mmol), Na2CO3 (1.82 g, 17.13 mmol) and 1,1'-bis(diphenylphosphino)ferrocene-palladium(ii)dichloride dichloromethane complex (0.699 g, 0.856 mmol) in dioxane (60 mL) and water (15 mL) was degassed with N₂ for 5 minutes. The resulting mixture was heated at 90° C. for 6 hours. The reaction mixture was filtered and extracted with EtOAc (2×100 mL). The organic phases were dried (MgSO4) and concentrated. The residue was purified by column chromatography on silica gel 220 g, eluting with EtOAc/isohexane (0-100% in 45 min) to give a solid. LC/MS [M+H]+: 881.

Step B: tert-butyl (4-(3-(N,N-bis(4-methoxybenzyl) sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)carbamate To 3-(2-amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (6.22 g, 7.06 mmol) in DCM (60 mL) at room temperature, was added BOC-Anhydride (1.69 g, 7.77 mmol), TEA (2.46 mL, 17.65 mmol) and DMAP (0.86 g, 7.1 mmol). The mixture was stirred at room temperature for 2 hours, diluted with ether, washed with aqueous KHSO4 and brine. The organic layer was dried over MgSO4 and concentrated. The crude product was purified by column chromatography on silica gel 220 g, eluting with 0-80% EtOAc in hexane to afford pure product. LC/MS [M+H]: 981.

Step C: 2-(N,N-bis(4-methoxybenzyl)sulfamoyl)-4-(2-((tert-butoxycarbonyl)amino)-1H-benzo[d]imidazol-4-yl)-3-(2-(4-methoxybenzyl)-2H-tetrazol-5-yl)benzenesulfinic acid TBAF (10.1 mL, 10.1 mmol) was added to a stirred solution of tert-butyl (4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)carbamate (4.5 g, 4.6 mmol) in THF (50 mL) at room temperature. The mixture was stirred at room temperature for 45 minutes. The mixture was diluted with AcOEt, washed with saturated KHSO4 aqueous (3×60 mL), dried over MgSO4, and concentrated to get the crude product as a solid after concentration. The crude material was used directly for the next step. LC/MS [M+H]+: 881.

Reference Example 19

2-(N,N-bis(4-methoxybenzyl)sulfamoyl)-4-(2-((tert-butoxycarbonyl)amino)pyridin-3-yl)-3-(2-(4-methoxybenzyl)-2H-tetrazol-5-yl)benzenesulfinic acid

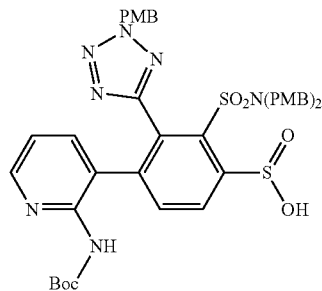

Step A: 3-(2-aminopyridin-3-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (REFERENCE EXAMPLE 3; 2.69 g, 3.07 mmol), N-(3-(4,4,5,5-tetramethyl-1,3,2-dioxaborolan-2-yl)pyridin-2-yl)acetamide (1.610 g, 6.14 mmol), Na2CO3 (0.977 g, 9.21 mmol), 1,1'-bis(diphenylphosphino)ferrocene-palladium(ii)dichloride dichloromethane complex (0.376 g, 0.461 mmol) were added to a 100 mL round bottle flask in dioxane (12 mL) and water (3 mL) at room temperature and the mixture was stirred at 80° C. overnight. The mixture was filtered, washed with EtOAc, diluted with water (50 mL), and extracted with ethyl acetate (2×50 mL). The combined organic layers were washed with brine (60 mL), dried (MgSO₄) and filtered and the solvent was evaporated under reduced pressure. The residue was purified by column chromatography on silica gel 40 g, eluting with EtOAc/isohexane to give the product as foam after concentration. LC/MS [M+H]+: 842

Step B: tert-butyl (3-(3-(N,N-bis(4-methoxybenzyl) sulfamoyl)-2-(2-(4-methoxybenzyl)-2H-tetrazol-5-yl)-4-((2-(trimethylsilyl)ethyl)sulfonyl)phenyl)pyridin-2-yl)carbamate Boc-anhydride (0.31 mL, 1.33 mmol) and DMAP (0.148 g, 1.211 mmol) were added to a stirred solution of starting material 3-(2-aminopyridin-3-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (1.02 g, 1.211 mmol) in DCM (10 mL) at room temperature and the mixture was stirred at room temperature overnight. The mixture was diluted with water (50 mL), and extracted with DCM (2×50 mL). The residue was purified by column chromatography on silica gel 24 g, eluting with EtOAc/isohexane to give a foam after concentration. LC/MS [M+H]+: 942

Step C: 2-(N,N-bis(4-methoxybenzyl)sulfamoyl)-4-(2-((tert-butoxycarbonyl)amino)pyridin-3-yl)-3-(2-(4-methoxybenzyl)-2H-tetrazol-5-yl)benzenesulfinic acid A solution of tert-butyl (3-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)pyridin-2-yl)carbamate (0.92 g, 0.97 mmol) in THF (9 mL) was stirred with TBAF (2.153 mL, 2.153 mmol) at room temperature under N₂ for 30 minutes. The mixture was diluted with AcOEt, washed with saturated KHSO₄ aqueous (3×50 mL), dried over MgSO4, and concentrated to give the crude product as a solid. The crude material was used directly for the next step.

Reference Example 20

Step A: (9-methyl 3-amino-2-(((benzyloxy)carbonyl)amino)propanoate

To a solution of (S)-3-amino-2-(((benzyloxy)carbonyl)amino)propanoic acid (6 g, 25.2 mmol) in MeOH (60 mL) was added SOCl₂ (9.19 mL, 126 mmol) at 0° C. The mixture was stirred at room temperature for 2 hours. The resulting mixture was quenched with water (300 mL) and extracted with EA (3×300 mL). The combined organic layers were washed with brine (300 mL), dried over anhydrous Na₂SO₄ and filtered. The filtrate was concentrated under vacuum to afford crude product (9-methyl 3-amino-2-(((benzyloxy)carbonyl)amino)propanoate as a solid, which was directly used in the next step without further purification: LC/MS [M+1]⁺: 253.

Step B: (S)-methyl-2-(((benzyloxy)carbonyl) amino)-3-((tert-butoxycarbonyl)amino) propanoate To a solution of (S)-methyl-3-amino-2-(((benzyloxy)carbonyl)amino)propanoate (4.0 g, 13.85 mmol) in MeOH (50 mL) were added (Boc)₂O (6.4 mL, 27.70 mmol) and TEA (7.7 mL, 55.40 mmol) at 0° C. The mixture was stirred at room temperature for 12 hours. The resulting mixture was quenched with water (200 mL), and then extracted with EA (3×200 mL). The combined organic layers were washed with brine (2×200 mL), dried over anhydrous Na₂SO₄ and filtered. The filtrate was concentrate under vacuum. The residue was purified by silica gel column chromatography and eluted with 70% EA in PE. The fractions containing desired product were combined and concentrated under vacuum to afford (S)-methyl-2-(((benzyloxy)carbonyl)amino)-3-((tert-butoxycarbonyl) amino)propanoate as an oil: LC/MS [M+1]⁺: 353.

Step C: (S)-benzyl-tert-butyl (3-hydroxypropane-1,2-diyl)dicarbamate

To a solution of (S)-methyl-2-(((benzyloxy)carbonyl) amino)-3-((tert-butoxycarbonyl) amino)propanoate (4.3 g, 12.2 mmol) in THF (45 mL) was added LiBH₄ (0.8 g, 36.6 mmol) at 0° C. The mixture was stirred at room temperature for 1 hour. The resulting mixture was quenched with saturated aqueous NH₄Cl (200 mL) and extracted with EA (3×300 mL). The combined organic layers were washed with brine (300 mL), dried over anhydrous Na₂SO₄ and filtered. The filtrate was concentrated under vacuum. The residue was purified by silica gel column chromatography, eluted with 60% EA in PE. The fractions containing desired product were combined and concentrated under vacuum to afford (S)-benzyl-tert-butyl(3-hydroxypropane-1,2-diyl)dicarbamate as an oil. LC/MS [M+1]⁺: 325.

Step D: (S)-2-(((benzyloxy)carbonyl)amino)-3-((tert-butoxycarbonyl)amino)propyl methanesulfonate To a solution of (S)-benzyl-tert-butyl (3-hydroxypropane-1,2-diyl)dicarbamate (4.0 g, 12.33 mmol) in DCM (40 mL) were added MsCl (1.9 mL, 24.66 mmol), TEA (5.2 mL, 37.0 mmol) and DMAP (0.301 g, 2.47 mmol) at 0° C. The mixture was stirred at 50° C. for 1 hour. The resulting mixture was quenched with water (200 mL), and then extracted with EA (3×300 mL). The combined organic layers were washed with brine (300 mL), dried over anhydrous Na₂SO₄ and filtered. The filtrate was concentrated under vacuum. The residue was purified by silica gel column chromatography, eluted with 60% EA in PE. The fractions containing desired product were combined and concentrated under vacuum to afford (S)-2-(((benzyloxy)carbonyl) amino)-3-((tert-butoxycarbonyl)amino)propyl methanesulfonate as a solid: LCMS [M+1]⁺: 403.

Step E: (S)-benzyl-tert-butyl (3-(1,3-dioxoisoindolin-2-yl)propane-1,2-diyl) dicarbamate To a solution of (S)-2-(((benzyloxy)carbonyl)amino)-3-((tert-butoxycarbonyl) amino)propyl methanesulfonate (3.8 g, 9.44 mmol) in DMF (60 mL) was added potassium 1,3-dioxoisoindolin-2-ide (3.5 g, 18.88 mmol) at room temp. The mixture was stirred at 60° C. for 3 hours. The resulting mixture was quenched with water (200 mL), and then extracted with EA (3×200 mL). The combined organic layers were washed with brine (300 mL), dried over anhydrous Na₂SO₄ and filtered. The filtrate was concentrated under vacuum. The residue was purified by silica gel column chromatography, eluted with 60% EA in PE. The fractions containing desired product were combined and concentrated under vacuum to afford (S)-benzyl tert-butyl (3-(1,3-dioxoisoindolin-2-yl)propane-1,2-diyl)dicarbamate as a solid: LCMS [M+1]⁺: 454.

Step F: (R)-benzyl-tert-butyl (3-aminopropane-1,2-diyl)dicarbamate

To a solution of (S)-benzyl-tert-butyl (3-(1,3-dioxoisoindolin-2-yl)propane-1,2-diyl) dicarbamate (3.0 g, 6.62 mmol) in EtOH (50 mL) was added N₂H₄.H₂O (80%, 0.99 g, 19.85 mmol) at room temperature. The mixture was stirred at 70° C. for 2 h. The resulting mixture was allowed to cool down to room temperature. The resulting mixture was quenched with water (200 mL), and then extracted with EA (3×200 mL). The combined organic layers were washed with brine (3×200 mL), dried over anhydrous Na₂SO₄ and filtered. The filtrate was concentrated under vacuum. The residue was purified by silica gel column chromatography, eluted with 30% EA in PE. The fractions containing desired product were combined and concentrated under vacuum to afford (R)-benzyl tert-butyl (3-aminopropane-1,2-diyl)dicarbamate as a solid: LC/MS [M+1]⁺: 324.

Reference Example 21

(R)-benzyl (1-amino-3-hydroxypropan-2-yl)carbamate hydrochloride

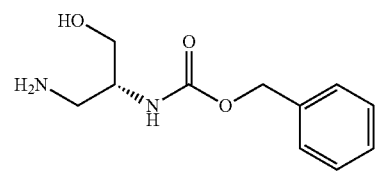 [SMILES: NC[C@H](CO)NC(=O)OCc1ccccc1]

HCl (4 mL, 1.25 M in dioxane, 5.00 mmol) was added to a stirred solution of starting material (R)-benzyl tert-butyl (3-hydroxypropane-1,2-diyl)dicarbamate (1.0 g, 3.08 mmol) in DCM (10 mL) and the mixture was stirred at room temperature for 2 hours. The mixture was concentrated. The product was used as is. LC/MS [M+H]+: 225.

Reference Example 22 tert-butyl (R)-(2-amino-3-hydroxypropyl)carbamate

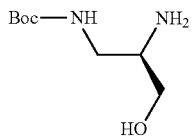

To a solution of (R)-benzyl tert-butyl (3-hydroxypropane-1,2-diyl)dicarbamate (1.05 g, 3.24 mmol) in MeOH (20 mL) in a RBF at room temperature under N₂, was added Pd—C (10% wt/wt, 0.689 g, 0.65 mmol) and hydrogenated at 1 atm. (balloon pressure) overnight. The reaction mixture was filtered through a CELITE pad, and washed with EtOAc (3×50 mL). The filtrate was concentrated under reduced pressure. The crude product was used as is. LC/MS [M+H]+: 191.

Reference Example 23 tert-butyl (R)-(3-amino-2-hydroxypropyl)carbamate

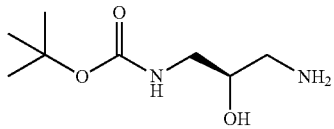

To a solution of the epoxide (S)-tert-butyl (oxiran-2-ylmethyl)carbamate (2.0 g, 11.55 mmol) in ethanol (20 mL) was added ammonium hydroxide (20 mL, 114 mmol) at room temperature. The reaction mixture was stirred for 2 hours, and concentrated in vacuo. The residue was dissolved in DCM (40 mL), dried (MgSO4) and concentrated in vacuo. The crude product was chromatographed over silica gel (40 g), eluting with 0-10% MeOH in DCM to give the desired product. LC/MS [M+H]+: 191.

Reference Example 24

(3-(5-amino-1H-1,2,4-triazol-3-yl)phenyl)boronic acid

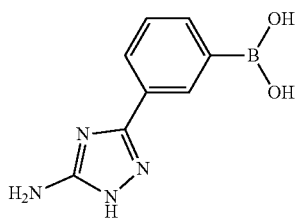 [SMILES: Nc1nc(-c2cccc(B(O)O)c2)n[nH]1]

Potassium acetate (1.232 g, 12.55 mmol) and PCy3 Pd G2 (0.371 g, 0.627 mmol), 4,4,4',4',5,5,5',5'-octamethyl-2,2'-bi(1,3,2-dioxaborolane) (2.124 g, 8.37 mmol), were added to a stirred solution of 3-(3-bromophenyl)-1H-1,2,4-triazol-5-amine (1.0 g, 4.18 mmol) in dimethylsulfoxide (15 mL) at room temperature and the mixture was stirred at 90° C. overnight. The reaction mixture was filtered through a pad of CELITE, diluted with water (100 mL) and extracted with ethyl acetate (3×100 mL). The residue was purified by reverse phase column chromatography on silica gel 240 g C18, eluting with acetonitrile/water, 0-100% in 45 minutes to give the desired product as a solid after concentration. LC/MS [M+H]+: 205.

Reference Example 25 tert-butyl (3R,4S)-3-amino-4-(((benzyloxy)carbonyl)amino)pyrrolidine-1-carboxylate

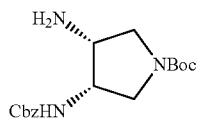

Step A: tert-butyl (3S,4S)-3-(((benzyloxy)carbonyl)amino)-4-hydroxypyrrolidine-1-carboxylate To a solution of (3S,4S)-tert-butyl 3-amino-4-hydroxypyrrolidine-1-carboxylate (1000 mg, 4.94 mmol) in dioxane (12.4 mL) and water (12.4 mL) was added sodium carbonate (629 mg, 5.93 mmol) and Cbz-Cl (0.847 mL, 5.93 mmol) at 0° C. The reaction was stirred at room temperature for 2 hours. EtOAc (20 mL) was added. The organic layer was separated, washed with brine, dried, filtered, and concentrated under reduced pressure. The residue was purified by flash chromatography on silica gel (0-10% MeOH/DCM as eluent) to give the title compound. LC/MS [M+H]⁺: 337.38.

Step B: tert-butyl (3S,4S)-3-(((benzyloxy)carbonyl)amino)-4-((methylsulfonyl)oxy)pyrrolidine-1-carboxylate To the solution of (3S,4S)-tert-butyl 3-(((benzyloxy)carbonyl)amino)-4-hydroxypyrrolidine-1-carboxylate (1200 mg, 3.57 mmol) in DCM (17.8 mL) was added triethylamine (0.796 mL, 5.71 mmol) and MsCl (0.445 mL, 5.71 mmol) at 0° C. The reaction was stirred at room temperature for 2 hours. After evaporation, the residue was purified by flash chromatography on silica gel (40 g gold column, 0-10% MeOH/DCM as eluent) to give the title compound. LC/MS [M+H]⁺: 415.38.

Step C: tert-butyl (3R,4S)-3-azido-4-(((benzyloxy)carbonyl)amino)pyrrolidine-1-carboxylate To the solution of (3S,4S)-tert-butyl 3-(((benzyloxy)carbonyl)amino)-4-((methylsulfonyl)oxy)pyrrolidine-1-carboxylate (1470 mg, 3.55 mmol) in DMF (17.7 mL) was added sodium azide (922 mg, 14.19 mmol) at room temperature. The reaction was stirred at 100° C. for 4 hours. EtOAc (20 mL) and water (20 mL) were added. The organic layer was separated, washed with water and brine, dried, filtered, and concentrated under reduced pressure to give the title compound. LC/MS [M+H]⁺: 362.44.

Step D: tert-butyl (3R,4S)-3-amino-4-(((benzyloxy)carbonyl)amino)pyrrolidine-1-carboxylate To the solution of (3R,4S)-tert-butyl 3-azido-4-(((benzyloxy)carbonyl)amino)pyrrolidine-1-carboxylate (1200 mg, 3.32 mmol) in THF (15.1 mL) and Water (1.51 mL) was added triphenylphosphine (1045 mg, 3.98 mmol) at room temperature. The reaction was stirred at 60° C. overnight. After concentration under reduced pressure, the residue was purified by flash chromatography on silica gel (0-10% MeOH/DCM as eluent) to give the title compound. LC/MS [M+H]+: 336.36.

Reference Example 26 tert-butyl (3S,4R)-3-amino-4-(((benzyloxy)carbonyl)amino)pyrrolidine-1-carboxylate

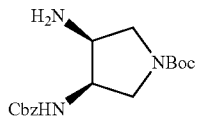

The title compound was prepared in an analogous fashion to the above intermediate (REFERENCE EXAMPLE 25) using (3R,4R)-tert-butyl 3-amino-4-hydroxypyrrolidine-1-carboxylate. LC/MS [M+H]+: 336.42.

Reference Example 27

(1H-benzo[d][1,2,3]triazol-4-yl)boronic acid

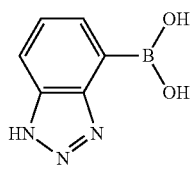

A mixture of 5,5,5',5'-tetramethyl-2,2'-bi(1,3,2-dioxaborinane) (1027 mg, 4.54 mmol), potassium acetate (446 mg, 4.54 mmol), and 4-bromo-1H-benzo[d][1,2,3]triazole (300 mg, 1.515 mmol) in dioxane (7.6 mL) was degassed with nitrogen before addition of chloro(triphenylphosphine) [2-(2'-amino-1,1'biphenyl)] palladium (II) (130 mg, 0.227 mmol). The resulting mixture was further degassed by nitrogen and heated at 80° C. overnight. After cooling to room temperature the reaction mixture was filtered through CELITE, and rinsed with EtOAc. The filtrate was concentrated and the residue was purified by reverse phase C18 column chromatography eluting with 0-100% MeCN/water (no acid additive) to afford the title compound. LC/MS [M+H]+: 164.05.

Reference Example 28 benzo[c][1,2,5]oxadiazol-4-ylboronic acid

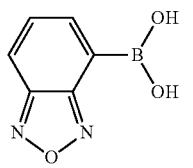 [SMILES: OB(O)c1cccc2nonc12]

The title compound was prepared in an analogous fashion to REFERENCE EXAMPLE 27 using 4-chlorobenzo[c][1,2,5]oxadiazole. LC/MS [M+H]+: 165.20.

Reference Example 29

(R)-benzyl-tert-butyl (3-aminopropane-1,2-diyl)dicarbamate

Step A: (S)-3-(((benzyloxy)carbonyl)amino)-2-((tert-butoxycarbonyl)amino)propanoic (isobutyl carbonic) anhydride To a stirred solution of (S)-3-(((benzyloxy)carbonyl)amino)-2-((tert-butoxycarbonyl) amino) propanoic acid (20 g, 59 mmol) in THF (200 mL) was added isobutyl carbonochloridate (9.60 g, 71 mmol) and 4-methylmorpholine (7.20 g, 71 mmol) at 0° C. The reaction mixture was stirred for 6 hours at 0° C. The reaction mixture was filtered. The filtrate was concentrated under vacuum to afford (S)-3-(((benzyloxy)carbonyl) amino)-2-((tert-butoxycarbonyl)amino)propanoic (isobutyl carbonic) anhydride as an oil. The crude product was used directly in the next step without further purification.

Step B: (S)-benzyl tert-butyl (3-hydroxypropane-1,2-diyl)dicarbamate

To a stirred solution of (S)-3-(((benzyloxy)carbonyl)amino)-2-((tert-butoxycarbonyl) amino)propanoic (isobutyl carbonic) anhydride (15 g, 34 mmol) in THF (100 mL) was added NaBH4 (5.0 g, 136 mmol) at 0° C. The reaction mixture was stirred at room temperature for 2 hours. The resulting mixture was quenched with water (500 mL) and then extracted with EA (3×800 mL). The combined organic layers were washed with water (3×500 mL) and brine (3×500 mL), dried over anhydrous Na2SO4 and filtered. The filtrate was concentrated under vacuum. The residue was purified by silica gel column chromatography, and eluted with 5% MeOH in DCM. The fractions containing desired product were combined and concentrated under vacuum to afford (S)-benzyl tert-butyl (3-hydroxypropane-1,2-diyl)carbamate as an oil: LCMS (ESI) calc'd for $C_{16}H_{24}N_2O_5$ [M+1]+: 325, found 325.

Step C: (S)-3-(((benzyloxy)carbonyl)amino)-2-((tert-butoxycarbonyl)amino)propyl methanesulfonate To a stirred solution of (S)-benzyl tert-butyl (3-hydroxypropane-1,2-diyl)dicarbamate (8.20 g, 25 mmol) in DCM (100 mL) was added TEA (10.4 mL, 75 mmol) and MsCl (2.38 mL, 30 mmol) at 0° C. The mixture was stirred at room temperature for 2 hours. The resulting mixture was quenched with water (500 mL), and then extracted with EA (3×800 mL). The combined organic layers were washed with water (3×500 mL) and brine (3×500 mL), dried over anhydrous Na2SO4 and filtered. The filtrate was concentrated under vacuum. The residue was purified by silica gel column chromatography, and eluted with 5% MeOH in DCM. The fractions containing desired product were combined and concentrated under vacuum to afford (S)-3-(((benzyloxy)carbonyl)amino)-2((tert-butoxycarbonyl)amino)propyl methanesulfonate as an oil: LCMS [M+1]⁺: 403.

Step D: (S)-benzyl-tert-butyl (3-(1,3-dioxoisoindolin-2-yl)propane-1,2-diyl) dicarbamate To a solution of (S)-3-(((benzyloxy)carbonyl)amino)-2-((tert-butoxycarbonyl) amino)propyl methanesulfonate (2.00 g, 4.97 mmol) in DMF (20 mL) was added potassium 1,3-dioxoisoindolin-2-ide (1.38 g, 7.45 mmol). The mixture was stirred at 60° C. for 2 hours. The resulting mixture was quenched with water (100 mL) and extracted with EA (3×100 mL). The combined organic layers were washed with water (3×100 mL) and brine (3×100 mL), dried over anhydrous Na₂SO₄ and filtered. The filtrate was concentrated under vacuum to afford (S)-benzyl-tert-butyl (3-(1,3-dioxoisoindolin-2-yl) propane-1,2-diyl)dicarbamate as a solid: LC/MS [M+1]⁺: 454.

Step E: (R)-benzyl tert-butyl (3-aminopropane-1,2-diyl)dicarbamate

To a solution of (S)-benzyl tert-butyl (3-(1,3-dioxoisoindolin-2-yl) propane-1,2-diyl) dicarbamate (1.80 g, 3.97 mmol) in EtOH (2 mL) was added N₂H₄.H₂O (80%, 5 mL, 3.97 mmol). The mixture was stirred at 80° C. for 1 hour. The resulting mixture was quenched with water (50 mL) and extracted with EA (3×100 mL). The combined organic layers were washed with water (3×100 mL) and brine (3×100 mL), dried over anhydrous Na₂SO₄ and filtered. The filtrate was concentrated under vacuum. The residue was purified by silica gel column chromatography, eluted with 10% MeOH and 1% aqueous NH₃ in DCM. The fractions containing desired product were combined and concentrated under vacuum to afford (R)-benzyl-tert-butyl (3-aminopropane-1,2-diyl)dicarbamate as a solid: LC/MS [M+1]⁺: 323.

Reference Example 30

Di-tert-butyl (2-aminopropane-1,3-diyl)dicarbamate

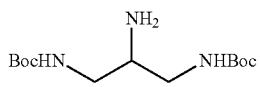

Step A: Di-tert-butyl (2-hydroxypropane-1,3-diyl)dicarbamate

To a solution of 1,3-diaminopropan-2-ol (10.0 g, 11 mmol) and KOH (16.0 g, 28 mmol) in THF (50 mL) and water (50 mL) was added (Boc)₂O (64 mL, 28 mmol) at room temperature. The reaction mixture was stirred at room temperature overnight. The resulting mixture was diluted with water (100 mL), extracted with EA (2×300 mL). The combined organic layers were dried over anhydrous Na₂SO₄ and filtered. The filtrate was concentrated under vacuum. The residue was purified by silica gel column chromatography, eluted with 30% EA in PE. The fractions containing desired product were combined and concentrated under vacuum to afford di-tert-butyl (2-hydroxypropane-1,3-diyl) dicarbamate as an oil: LC/MS [M+1]⁺: 291.

Step B: 2,2,12,12-Tetramethyl-4,10-dioxo-3,11-dioxa-5,9-diazatridecan-7-ylmethanesulfonate To a solution of di-tert-butyl (2-hydroxypropane-1,3-diyl) dicarbamate (20.0 g, 68.9 mmol) in DCM (200 mL) was added MsCl (8.1 mL, 103 mmol) dropwise at 0° C. The mixture was stirred at room temperature for 5 hours under nitrogen. The resulting mixture was diluted with EA (400 mL), and then washed with water (3×200 mL) and brine (3×150 mL). The collected organic layer was dried over anhydrous Na₂SO₄ and filtered. The filtrate was concentrated under vacuum to afford 2,2,12,12-tetramethyl-4,10-dioxo-3,11-dioxa-5,9-diazatridecan-7-yl methanesulfonate as an oil, which was used in the next step directly without further purification: LC/MS [M+1]⁺: 369.

Step C: Di-tert-butyl (2-(1,3-dioxoisoindolin-2-yl) propane-1,3-diyl)dicarbamate To a solution of 2,2,12,12-tetramethyl-4,10-dioxo-3,11-dioxa-5,9-diazatridecan-7-yl methanesulfonate (20.0 g, 54.3 mmol) in DMF (200 mL) was added potassium 1,3-dioxoisoindolin-2-ide (10.0 g, 54.3 mmol) at room temperature. The reaction mixture was stirred for 16 hours at 80° C. under nitrogen. The resulting mixture was quenched with water (300 mL). The aqueous layer was extracted with EA (3×100 mL), and then the combined organic layers were washed with brine (3×150 mL), dried over anhydrous Na₂SO₄ and filtered. The filtrate was concentrated under vacuum to afford di-tert-butyl(2-(1,3-dioxoisoindolin-2-yl)propane-1,3-diyl) dicarbamate as a solid, which was used in the next step directly without further purification: LC/MS [M+1]⁺: 420.

Step D: Di-tert-butyl (2-aminopropane-1,3-diyl)dicarbamate

To a solution of di-tert-butyl (2-(1,3-dioxoisoindolin-2-yl) propane-1,3-diyl) dicarbamate (14.0 g, 33.4 mmol) in EtOH (100 mL) was added N₂H₄.H₂O (80%, 6.7 g, 167 mmol) at room temperature. The reaction was allowed to warm to 80° C. The reaction mixture was stirred for 4 hours at 80° C. under nitrogen. The resulting mixture was cooled to room temperature. The mixture was filtered. The filter cake was washed with EtOH (2×50 mL). The filtrate was concentrated under vacuum. The residue was re-crystallized with EA/PE (1:2) to afford di-tert-butyl(2-aminopropane-1,3-diyl) dicarbamate as a solid: LC/MS [M+1]⁺: 290.

Reference Example 31

(R)-di-tert-butyl (3-aminopropane-1,2-diyl)dicarbamate

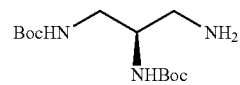 [SMILES: CC(C)(C)OC(=O)N[C@H](CN)CNC(=O)OCc1ccccc1]

Step A: (S)-di-tert-butyl (3-hydroxypropane-1,2-diyl)dicarbamate

To a solution of (S)-methyl 2,3-bis((tert-butoxycarbonyl) amino)propanoate (commercially available or prepared as described in WO 2006076706, 1.5 g, 4.71 mmol) in THF (15 mL) was added LiAlH$_4$ (0.27 g, 7.07 mmol) in several portions at 5° C. under nitrogen. The mixture was stirred for 2 hours at 5° C. under nitrogen. The resulting mixture was quenched with water (30 mL) and extracted with EA (3×30 mL). The combined organic layers were washed with brine (3×30 mL), dried over anhydrous Na$_2$SO$_4$ and filtered. The filtrate was concentrated under vacuum. The residue was purified by silica gel column chromatography, eluted with 30% EA in PE. The fractions containing desired product were combined and concentrated under vacuum to afford (S)-di-tert-butyl (3-hydroxypropane-1,2-diyl)dicarbamate as a liquid: LC/MS/[M+1]$^+$: 291.

Step B: (S)-2,3-bis((tert-butoxycarbonyl)amino)propyl methanesulfonate

To a solution of (S)-di-tert-butyl (3-hydroxypropane-1,2-diyl)dicarbamate (0.8 g, 2.76 mmol) and TEA (0.84 g, 8.27 mmol) in DCM (8 mL) was added MsCl (0.47 g, 4.13 mmol) at 0° C. The reaction mixture was stirred at room temperature for 1 hour. The resulting mixture was quenched with water (50 mL) and extracted with EA (3×50 mL). The combined organic layers were washed with brine (3×50 mL), dried over anhydrous Na$_2$SO$_4$ and filtered. The filtrate was concentrated under vacuum to afford (S)-2,3-bis((tert-butoxycarbonyl)amino)propyl methanesulfonate as a solid, which was directly used in the next step without further purification: LC/MS [M+1]$^+$: 369.

Step C: (S)-di-tert-butyl (3-(1,3-dioxoisoindolin-2-yl)propane-1,2-diyl)dicarbamate To a solution of (S)-2,3-bis((tert-butoxycarbonyl)amino) propyl methanesulfonate (1.1 g, 2.99 mmol) in DMF (10 mL) was added potassium 1,3-dioxoisoindolin-2-ide (0.83 g, 4.48 mmol) at room temperature. Then the mixture was stirred at 60° C. for 16 hours. The reaction mixture was cooled to room temperature. The resulting mixture was quenched with water (50 mL) and extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography, eluted with 30% EA in PE. The fractions containing desired product were combined and concentrated under vacuum to afford the desired product as a solid: LC/MS [M+1]$^+$: 420.

Step D: (R)-di-tert-butyl (3-aminopropane-1,2-diyl)dicarbamate

To a solution of (S)-di-tert-butyl (3-(1,3-dioxoisoindolin-2-yl)propane-1,2-diyl) dicarbamate (0.5 g, 1.19 mmol) in EtOH (5 mL) was added N$_2$H$_4$.H$_2$O (80%, 0.12 g, 3.58 mmol) at room temperature. The reaction was allowed to warm to 80° C. The reaction mixture was stirred for 4 hours at 80° C. under nitrogen. The resulting mixture was cooled to room temperature. The mixture was filtered. The filter cake was washed with EtOH (2×50 mL). The filtrate was concentrated under vacuum to afford (R)-di-tert-butyl (3-aminopropane-1,2-diyl)dicarbamate as a solid, which was directly used for next step without further purification: LC/MS [M+1]$^+$: 290.

Reference Example 32

(S)-benzyl-tert-butyl (3-aminopropane-1,2-diyl)dicarbamate

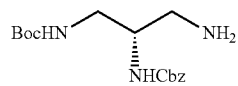

Step A: (R)-2-(((benzyloxy)carbonyl)amino)-3-((tert-butoxycarbonyl)amino)propyl methanesulfonate To a solution of (R)-benzyl-tert-butyl (3-hydroxypropane-1,2-diyl)dicarbamate (2 g, 6.17 mmol) in DCM (20 mL) was added TEA (2.6 mL, 18.50 mmol), MsCl (0.96 mL, 12.33 mmol) and DMAP (0.15 g, 1.23 mmol) at 0° C. The mixture was stirred at room temperature for 1 hour. The resulting mixture was quenched with water (100 mL) and extracted with EA (3×100 mL). The combined organic layers were washed with brine (100 mL), dried over anhydrous Na$_2$SO$_4$ and filtered. The filtrate was concentrated under vacuum to afford crude product as an oil, which was directly used in the next step without further purification: LC/MS [M+1]$^+$: 403.

Step B: (R)-benzyl tert-butyl (3-(1,3-dioxoisoindolin-2-yl)propane-1,2-diyl) dicarbamate To a solution of (R)-2-(((benzyloxy)carbonyl)amino)-3-((tert-butoxycarbonyl) amino)propyl methanesulfonate (3.0 g, 7.45 mmol) in DMF (50 mL) was added potassium 1,3-dioxoisoindolin-2-ide (2.76 g, 14.90 mmol) at room temperature. The mixture was stirred at 60° C. for 12 hours. The resulting mixture was allowed to cool down to room temperature, diluted with water (200 mL) and extracted with EA (3×200 mL). The combined organic layers were washed with brine (200 mL), dried over anhydrous Na$_2$SO$_4$ and filtered. The filtrate was concentrated under vacuum. The residue was purified by silica gel column chromatography, and eluted with 60% EA in PE to afford the desired compound as a solid: LC/MS [M+1]$^+$: 454.

Step C: (S)-benzyl tert-butyl (3-aminopropane-1,2-diyl)dicarbamate

To a solution of (R)-benzyl-tert-butyl(3-(1,3-dioxoisoindolin-2-yl)propane-1,2-diyl) dicarbamate (3.0 g, 6.62 mmol) in EtOH (50 mL), was added N$_2$H$_4$.H$_2$O (80%, 0.99 g, 19.85 mmol) at room temperature. The mixture was stirred at 70° C. for 2 hours. The resulting mixture was allowed to cool down to room temperature. The resulting reaction was quenched with water (200 mL) and extracted with EA (3×200 mL). The combined organic layers were washed with brine (3×200 mL), dried over anhydrous Na$_2$SO$_4$ and filtered. The filtrate was concentrated under vacuum. The residue was purified by silica gel column chromatography, eluted with 30% EA in PE to afford (S)-benzyl-tert-butyl(3-aminopropane-1,2-diyl)dicarbamate as a solid: LC/MS [M+1]$^+$: 324.

Reference Example 33

(S)-di-tert-butyl 2-(aminomethyl)piperazine-1,4-dicarboxylate

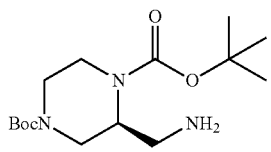 [SMILES: CC(C)(C)OC(=O)N1CCN(C(=O)OC(C)(C)C)[C@@H](CN)C1]

Step A: (R)-1,4-di-tert-butyl 2-methyl piperazine-1,2,4-tricarboxylate

To a solution of (R)-1-tert-butyl 2-methyl piperazine-1,2-dicarboxylate (2.00 g, 8.19 mmol) and TEA (3.42 mL, 24.57 mmol) in DCM (20 mL) was added (Boc)$_2$O (2.28 mL, 9.83 mmol) at 0° C. The reaction mixture was stirred at room temperature for 6 hours. The resulting mixture was diluted with water (100 mL), and then extracted with EA (3×70 mL). The combined organic layers were washed with brine (3×150 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the desired product as an oil: LC/MS [M+1]$^+$: 345.

Step B: (R)-di-tert-butyl 2-(hydroxymethyl)piperazine-1,4-dicarboxylate

To a solution of (R)-1,4-di-tert-butyl 2-methyl piperazine-1,2,4-tricarboxylate (2.00 g, 5.81 mmol) in THF (30 mL) was added LiAlH$_4$ (0.44 g, 11.61 mmol) at 0° C. The reaction mixture was stirred at 0° C. for 1 hour. The resulting mixture was quenched with NaOH (1 M, 50 mL), and then extracted with EA (3×50 mL). The combined organic layers were washed with brine (3×70 mL), dried over anhydrous Na$_2$SO$_4$ and filtered. The filtrate was concentrated under vacuum. The residue was purified by silica gel column chromatography, and eluted with 40% EA in PE. The fractions containing desired product were combined and concentrated under vacuum to afford the desired product as an oil: LC/MS [M+1]$^+$: 317.

Step C: (S)-di-tert-butyl2-((1,3-dioxoisoindolin-2-yl)methyl)piperazine-1,4-dicarboxylate To a solution of (R)-di-tert-butyl2-(hydroxymethyl)piperazine-1,4-dicarboxylate (1.00 g, 3.16 mmol), triphenylphosphine (0.83 g, 3.16 mmol) and isoindoline-1,3-dione (0.47 g, 3.16 mmol) in THF (20 mL) was added DIAD (0.62 mL, 3.16 mmol) at 0° C. The reaction mixture was stirred at room temperature for 16 h under nitrogen. The resulting mixture was quenched with water (50 mL), and then extracted with EA (3×30 mL). The combined organic layers were washed with brine (3×70 mL), dried over anhydrous Na$_2$SO$_4$ and filtered. The filtrate was concentrated under vacuum. The residue was purified by silica gel column chromatography, eluted with 40% EA in PE. The fractions containing desired product were combined and concentrated under vacuum to afford the desired compound as a solid: LC/MS [M+1]$^+$: 446.

Step D: (S)-di-tert-butyl 2-(aminomethyl)piperazine-1,4-dicarboxylate

To a solution of (S)-di-tert-butyl 2-((1,3-dioxoisoindolin-2-yl)methyl)piperazine-1,4-dicarboxylate (1.30 g, 2.92 mmol) in EtOH (30 mL) was added N$_2$H$_4$.H$_2$O (80%, 0.58 g, 14.59 mmol) at room temperature. The reaction mixture was stirred at 50° C. for 1 hour. The resulting mixture was filtered. The filtrate was concentrated under vacuum. The residue was diluted with EA (100 mL), washed with brine (3×80 mL), dried over anhydrous Na$_2$SO$_4$ and filtered. The filtrate was concentrated under vacuum to afford the title compound as an oil, which was used directly in the next step without further purification: LC/MS [M+1]$^+$: 316.

Reference Example 34

(R)-di-tert-butyl 2-(aminomethyl)piperazine-1,4-dicarboxylate

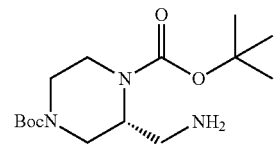 [SMILES: CC(C)(C)OC(=O)N1CCN(C(=O)OC(C)(C)C)[C@H](CN)C1]

Step A: (S)-1,4-di-tert-butyl-2-methyl-piperazine-1,2,4-tricarboxylate

To a solution of (S)-1-tert-butyl-2-methyl-piperazine-1,2-dicarboxylate (2.0 g, 8.19 mmol) and TEA (2.28 mL, 16.37 mmol) in DCM (20 mL) was added (Boc)$_2$O (2.85 mL, 12.28 mmol) at 0° C. The reaction mixture was stirred at room temperature for 6 hours. The resulting mixture was quenched with water (100 mL) and extracted with EA (3×70 mL). The combined organic layers was washed with brine (3×150 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the desired product as an oil: LC/MS [M+1]$^+$: 345.

Step B: (S)-di-tert-butyl-2-(hydroxymethyl)piperazine-1,4-dicarboxylate

To a solution of (S)-1,4-di-tert-butyl-2-methyl-piperazine-1,2,4-tricarboxylate (1.50 g, 4.36 mmol) in THF (20 mL) was added LiAlH$_4$ (0.33 g, 8.71 mmol) at 0° C. The reaction mixture was stirred at 0° C. for 1 hour. The resulting mixture was quenched with NaOH (1 M, 40 mL), and then extracted with EA (3×30 mL). The combined organic layers were washed with brine (3×70 mL), dried over anhydrous Na$_2$SO$_4$ and filtered. The filtrate was concentrated under vacuum. The residue was purified by silica gel column chromatography, eluted with 40% EA in PE. The fractions containing desired product were combined and concentrated under vacuum to afford (S)-di-tert-butyl-2-(hydroxymethyl)piperazine-1,4-dicarboxylate as an oil: LC/MS [M+1]$^+$: 317.

Step C: (R)-di-tert-butyl-2-((1,3-dioxoisoindolin-2-yl)methyl)piperazine-1,4-dicarboxylate To a solution of (S)-di-tert-butyl-2-(hydroxymethyl)piperazine-1,4-dicarboxylate (1.10 g, 3.48 mmol), triphenylphosphine (1.82 g, 6.95 mmol) and isoindoline-1,3-dione (1.02 g, 6.95 mmol) in THF (15 mL) was added DIAD (1.35 mL, 6.95 mmol) at 0° C. The mixture was degassed with nitrogen for three times. The reaction mixture was stirred at room temperature for 16 h under nitrogen. The resulting mixture was quenched with water (50 mL) and extracted with EA (3×30 mL). The combined organic layers were washed with brine (3×70 mL), dried over anhydrous $Na_2SO_4$ and filtered. The filtrate was concentrated under vacuum. The residue was purified by silica gel column chromatography, eluted with 40% EA in PE. The fractions containing desired product were combined and concentrated under vacuum to afford the desired compound as an oil: LC/MS/ [M+1]$^+$: 446.

Step D: (R)-di-tert-butyl-2-(aminomethyl)piperazine-1,4-dicarboxylate

To a solution of (R)-di-tert-butyl-2-((1,3-dioxoisoindolin-2-yl)methyl)piperazine-1,4-dicarboxylate (1.20 g, 2.69 mmol) in EtOH (10 mL) was added $N_2H_4.H_2O$ (0.26 g, 8.08 mmol) at room temperature. The reaction mixture was stirred at 50° C. for 1 hour. The mixture was cooled to room temperature. The resulting mixture was filtered and the filtration was evaporated under vacuum. The residue was diluted with EA (100 mL), washed with brine (3×80 mL), dried over anhydrous $Na_2SO_4$ and filtered. The filtrate was concentrated under vacuum to afford the desired product as an oil, which was used directly in the next step without further purification: LC/MS [M+1]$^+$: 316.

Reference Example 35

(S)-benzyl (3-aminobutyl)carbamate 2,2,2-trifluoroacetate

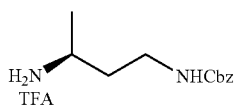 [SMILES: C[C@H](N)CCNC(=O)OCc1ccccc1]

Step A: (S)-tert-butyl (4-hydroxybutan-2-yl)carbamate

To a solution of (S)-3-((tert-butoxycarbonyl)amino)butanoic acid (5.0 g, 24.60 mmol) in THF (30 mL) was added $BF_3.THF$ (49 mL, 49 mmol, 1 M) dropwise at 0° C. The reaction mixture was stirred at room temperature for 1 hour. The resulting mixture was quenched with water (50 mL), and then extracted with EA (3×50 mL). The combined organic layers were washed with water (3×50 mL) and brine (3×50 mL), dried over $Na_2SO_4$ and filtered. The filtrate was concentrated under vacuum. The residue was purified by silica gel column chromatography, and eluted with 25% EA in PE. The fractions containing desired product were combined and concentrated under vacuum to afford the desired product as an oil: LC/MS [M+1]$^+$: 190.

Step B: (S)-3-((tert-butoxycarbonyl)amino)butyl methanesulfonate

To a solution of (S)-tert-butyl(4-hydroxybutan-2-yl)carbamate (2.5 g, 13.21 mmol) and TEA (5.5 mL, 39.60 mmol) in DCM (50 mL) was added MsCl (1.5 mL, 19.81 mmol) dropwise at 0° C. The reaction mixture was stirred at room temperature for 1 hour. The resulting mixture was diluted with EA (100 mL), washed with brine (3×30 mL), dried over $Na_2SO_4$ and filtered. The filtrate was concentrated under vacuum to afford the desired product as an oil, which was used directly in the next step without further purification: LC/MS [M+1]$^+$: 268.

Step C: (S)-tert-butyl (4-(1,3-dioxoisoindolin-2-yl)butan-2-yl)carbamate

To a solution of (S)-3-((tert-butoxycarbonyl)amino)butylmethanesulfonate (3.0 g, 11.22 mmol) in DMF (40 mL) was added potassium 1,3-dioxoisoindolin-2-ide (3.0 g, 16.83 mmol) at room temperature. The reaction mixture was stirred at 50° C. for 3 hours. The resulting mixture was quenched with water (100 mL), and then extracted with EA (3×50 mL). The combined organic layers were washed with brine (3×50 mL), dried over $Na_2SO_4$ and filtered. The filtrate was concentrated under vacuum. The residue was purified by silica gel column chromatography, and eluted with 20% EA in PE. The fractions containing desired product were combined and concentrated under vacuum to afford the desired compound as a solid: LC/MS [M+1]$^+$: 319.

Step D: (S)-tert-butyl (4-aminobutan-2-yl)carbamate

To a solution of (S)-tert-butyl (4-(1,3-dioxoisoindolin-2-yl)butan-2-yl)carbamate (2.7 g, 8.48 mmol) in EtOH (50 mL) was added $N_2H_4.H_2O$ (80%, 0.85 g, 16.96 mmol). The reaction mixture was stirred at 80° C. for 2 hours. The resulting mixture was filtered. The filtrate was concentrated under vacuum to afford (S)-tert-butyl (4-aminobutan-2-yl)carbamate as an oil, which was used directly in the next step without further purification: LC/MS [M+1]$^+$: 189.

Step E: (S)-benzyl tert-butyl butane-1,3-diyldicarbamate

To a solution of (S)-tert-butyl(4-aminobutan-2-yl)carbamate (1.4 g, 7.44 mmol) in DCM (15 mL) was added TEA (1.5 g, 14.87 mmol) and CbzCl (1.5 g, 8.55 mmol) at room temperature. The reaction mixture was stirred at room temperature for 0.5 hour. The resulting mixture was concentrated under vacuum. The residue was diluted with EA (100 mL), washed with brine (3×30 mL), dried over anhydrous $Na_2SO_4$ and filtered. The filtrate was concentrated under vacuum to afford the desired product as an oil, which was used directly in the next step without further purification: LC/MS [M+1]$^+$: 323.

Step F: (S)-benzyl (3-aminobutyl)carbamate 2,2,2-trifluoroacetate

A solution of (S)-benzyl tert-butyl butane-1,3-diyldicarbamate (1 g, 3.1 mmol) in TFA (8 mL) was stirred at room temperature for 1 hour. The resulting mixture was concentrated under vacuum to afford (S)-benzyl(3-aminobutyl) carbamate 2,2,2-trifluoroacetate as an oil, which was used directly in the next step without further purification: LC/MS [M+1−TFA]$^+$: 223

Reference Example 36

(S)-di-tert-butyl (3-aminopropane-1,2-diyl)dicarbamate

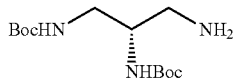

Step A: (R)-2,3-bis((tert-butoxycarbonyl)amino)propyl methanesulfonate

MsCl (0.59 g, 5.16) was added to di-tert-butyl (3-hydroxypropane-1,2-diyl)(R)-dicarbamate (*J. Med. Chem.* 2010, 53(8), 3198-3213; 1.0 g, 3.44 mmol) and TEA (1.0 g, 10.34 mmol) in DCM (10 mL) at 0° C. The reaction mixture was allowed to warm to room temperature and was stirred for 1 h. The resulting mixture was quenched with water (50 mL), and then extracted with EA (3×50 mL). The combined organic layers were washed with water (3×50 mL) and brine (3×50 mL), dried over anhydrous $Na_2SO_4$ and filtered. The filtrate was concentrated under vacuum to afford the desired compound, which was directly used in the next step without further purification: LC/MS $[M+1]^+$: 369.

Step B: (R)-di-tert-butyl (3-(1,3-dioxoisoindolin-2-yl)propane-1,2-diyl)dicarbamate To a solution of (R)-2,3-bis((tert-butoxycarbonyl)amino)propyl methanesulfonate (1.4 g, 0.38 mmol) in DMF (15 mL) was added potassium 1,3-dioxoisoindolin-2-ide (1.41 g, 7.60 mmol) at room temperature. Then the mixture was stirred at 60° C. for 16 h. The resulting mixture was quenched with water (50 mL), and then extracted with EA (3×50 mL). The combined organic layers was washed with water (3×50 mL) and brine (3×50 mL), dried over anhydrous $Na_2SO_4$ and filtered. The filtrate was concentrated under vacuum. The residue was purified by silica gel column chromatography, eluted with 30% EA in PE. The fractions containing desired product were combined and concentrated under vacuum to afford the desired compound as a solid: LC/MS $[M+1]^+$: 420.

Step C: (S)-di-tert-butyl (3-aminopropane-1,2-diyl)dicarbamate

To a solution of (R)-di-tert-butyl (3-(1,3-dioxoisoindolin-2-yl)propane-1,2-diyl)dicarbamate (1.0 g, 2.38 mmol) in EtOH (10 mL) was added $N_2H_4 \cdot H_2O$ (80%, 0.36 g, 7.15 mmol). The mixture was stirred at 70° C. for 1 h. The reaction mixture was filtered. The filtrate was concentrated under vacuum to the desired compound as a solid, which was used to make compounds of the invention without further purification: LC/MS $[M+1]^+$: 290.

Reference Example 37

(R)-benzyl (2-aminobutyl)carbamate hydrochloride

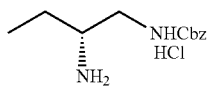

Step A: (R)-tert-butyl (1-amino-1-oxobutan-2-yl)carbamate

TEA (13.7 mL, 98 mmol) and $Boc_2O$ (15.8 g, 72.2 mmol) were added to a solution of (R)-2-aminobutanamide hydrochloride (5.0 g, 36.1 mmol) in MeOH (100 mL). The mixture was stirred at room temp. for 3 hours. The resulting mixture was quenched with water (100 mL) and extracted with EA (3×100 mL). The combined organic layers were washed with aqueous HCl (1 M, 2×50 mL), dried over anhydrous $Na_2SO_4$ and filtered. The filtrate was concentrated under vacuum to afford the desired compound as a solid, which was used in the next step without further purification: LC/MS $[M+1]^+$: 203.

Step B: (R)-tert-butyl (1-aminobutan-2-yl)carbamate $BH_3 \cdot DMS$ (9.39 g, 124 mmol) was added dropwise to a stirred solution of (R)-tert-butyl (1-amino-1-oxobutan-2-yl)carbamate (5.0 g, 24.72 mmol) in THF (50 mL) at 0° C. The mixture was degassed with nitrogen three times. The reaction mixture was stirred for 12 hours at room temperature under nitrogen. The resulting mixture was quenched with aqueous NaOH (1 M, 150 mL), and then extracted with EA (3×100 mL). The combined organic layers were washed with brine (2×100 mL), dried over anhydrous $Na_2SO_4$, and filtered. The filtrate was concentrated under vacuum to afford the title compound, which was directly used in the next step without further purification: LC/MS $[M+1]^+$: 189.

Step C: (R)-benzyl tert-butyl butane-1,2-diyldicarbamate

Benzyl carbonochloridate (8.16 g, 47.8 mmol) and TEA (10 mL, 71.7 mmol) were added to a solution of (R)-tert-butyl (1-aminobutan-2-yl)carbamate (4.50 g, 23.90 mmol) in DCM (50 mL). The mixture was stirred at room temperature for 1 hour under nitrogen. The resulting mixture was quenched with water (200 mL), and then extracted with EA (3×200 mL). The combined organic layers were washed with water (3×100 mL) and brine (3×200 mL), dried over anhydrous $Na_2SO_4$, and filtered. The filtrate was concentrated under vacuum. The residue was purified by silica gel column chromatography and eluted with 20% EA in PE. The fractions containing desired product were combined and concentrated under vacuum to afford the title compound: LC/MS $[M+1]^+$: 323.

Step D: (R)-benzyl (2-aminobutyl)carbamate hydrochloride

A solution of (R)-benzyl tert-butyl butane-1,2-diyldicarbamate (1.0 g, 3.10 mmol) in HCl (1M in dioxane) (10 mL) was stirred at room temperature for 1 hour. The resulting mixture was concentrated under vacuum to afford crude (R)-benzyl (2-aminobutyl)carbamate hydrochloride as a solid, which was directly used in the next step without further purification: LC/MS $[M+1-HCl]^+$: 223.

Reference Example 38

(S)-tert-butyl (2-(3-aminopyrrolidin-1-yl)ethyl)carbamate

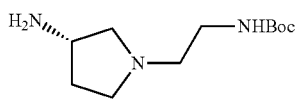

Step A: benzyl (S)-(1-(2-((tert-butoxycarbonyl)amino)ethyl)pyrrolidin-3-yl)carbamate Tert-butyl (2-bromoethyl)carbamate (4.5 g, 20 mmol) and Na$_2$CO$_3$ (2.9 g, 27 mmol) were added to a solution of (S)-benzylpyrrolidin-3-ylcarbamate (3 g, 13.5 mmol) in DMF (15 mL). The mixture was stirred for 10 hours at room temp. Then the mixture was poured into water (60 mL). The aqueous phase was extracted with EA (2×50 mL). The combined organic layers were washed with brine (3×50 mL), dried over anhydrous Na$_2$SO$_4$ and filtered. The filtrate was concentrated under vacuum to afford the title compound, which was used in the next step directly without further purification: LC/MS [M+1]$^+$: 364.

Step B: (S)-tert-butyl (2-(3-aminopyrrolidin-1-yl)ethyl)carbamate

To a solution of benzyl (S)-(1-(2-((tert-butoxycarbonyl)amino)ethyl)pyrrolidin-3-yl)carbamate (4.8 g, 13 mmol) in MeOH (15 mL) was added Pd(OH)$_2$/C (20% Pd, 2 g). The mixture was degassed with hydrogen for three times. Then the mixture was stirred at room temperature under hydrogen for 16 hours. The resulting mixture was filtered through CELITE. The filtrate was concentrated under vacuum. The residue was purified by silica gel column chromatography, eluted with 10% MeOH in DCM. The fractions containing desired product were combined and concentrated under vacuum to afford the title compound: LC/MS [M+1−100]$^+$: 130.

Reference Example 39

(R)-tert-butyl (2-(3-aminopyrrolidin-1-yl)ethyl)carbamate

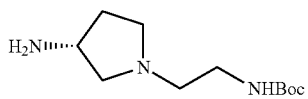

Step A: tert-butyl (R)-(2-(3-(((benzyloxy)carbonyl)amino)pyrrolidin-1-yl)ethyl)carbamate Tert-butyl (2-bromoethyl)carbamate (4.48 g, 19.98 mmol) was added to a mixture of (R)-benzylpyrrolidin-3-ylcarbamate (2.2 g, 9.99 mmol) and K$_2$CO$_3$ (4.14 g, 30.0 mmol) in DMF (40 mL). The reaction mixture was stirred for 4 hours at room temperature under nitrogen. The reaction mixture was diluted with water (100 mL) and extracted with EA (3×100 mL). The combined organic layers were washed with brine (2×100 mL), dried over anhydrous Na$_2$SO$_4$ and filtered. The filtrate was concentrated under vacuum. The residue was purified by silica gel column chromatography and eluted with 10% MeOH in DCM. The fractions containing desired product were combined and concentrated under vacuum to afford the desired compound: LC/MS [M+1]$^+$: 364.

Step B: (R)-tert-butyl (2-(3-aminopyrrolidin-1-yl)ethyl)carbamate

Pd(OH)2/C (20% Pd, 0.30 g, 2.14 mmol) was added to a solution of tert-butyl (R)-(2-(3-(((benzyloxy)carbonyl)amino)pyrrolidin-1-yl)ethyl)carbamate (2.96 g, 8.14 mmol) in MeOH (30 mL). The reaction mixture was degassed with hydrogen three times and stirred for 6 hours at room temperature under hydrogen (about 1.5 atm.). The resulting solution was filtered and the filter cake was washed with MeOH (3×100 mL). The filtrate was concentrated under vacuum to afford the desired compound as an oil, which was used directly in next step without further purification: LC/MS [M+1]$^+$: 230.

Reference Example 40

(R)-benzyl(3-aminobutyl)carbamate hydrochloride

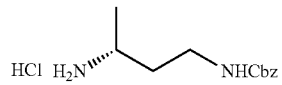

Step A: (R)-tert-butyl (4-hydroxybutan-2-yl)carbamate

BF$_3$.THF (84 mL, 84.0 mmol, 1 M) was added dropwise at 0° C. to a solution of (R)-3-((tert-butoxycarbonyl)amino)butanoic acid (8.5 g, 41.8 mmol) in THF (10 mL). The reaction mixture was stirred at room temperature for 1 hour. The resulting mixture was quenched with water (50 mL), and then extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography and eluted with 30% EA in PE. The fractions containing desired product were combined and concentrated under vacuum to afford the desired compound as an oil: LC/MS [M+1−56]$^+$: 134.

Step B: (R)-3-((tert-butoxycarbonyl)amino)butyl methanesulfonate

TEA (7.0 g, 69.7 mmol) and MsCl (2.7 mL, 34.9 mmol) were added to a solution of (R)-tert-butyl (4-hydroxybutan-2-yl)carbamate (4.4 g, 23.3 mmol) in DCM (100 mL) at 0° C. The reaction mixture was stirred for 1 hour at room temperature. The resulting mixture was concentrated under vacuum. The residue was diluted with EA (300 mL), washed with brine (3×200 mL), dried over anhydrous Na$_2$SO$_4$ and filtered. The filtrate was concentrated under vacuum. The residue was purified by silica gel column chromatography, eluted with 10% EA in PE. The fractions containing desired product were combined and concentrated under vacuum to afford (R)-3-((tert-butoxycarbonyl) amino)butyl methanesulfonate as a solid: LCMS [M+1]+: 268.

Step C: (R)-tert-butyl (4-(1,3-dioxoisoindolin-2-yl)butan-2-yl)carbamate

Potassium 1,3-dioxoisoindolin-2-ide (5.7 g, 30.0 mmol) was added to a solution of (R)-3-((tert-butoxycarbonyl)amino)butyl methanesulfonate (5.5 g, 20.0 mmol) in DMF (20 mL). The mixture was stirred at 60° C. for 2 hours, diluted with water (100 mL), and then extracted with EA (3×200 mL). The combined organic fractions were washed with brine (3×200 mL), dried over anhydrous Na$_2$SO$_4$ and filtered. The filtrate was concentrated under vacuum to afford the desired compound as a solid, which was directly used in the next step without further purification: LC/MS [M+1]+: 319.

Step D: (R)-tert-butyl (4-aminobutan-2-yl)carbamate

N$_2$H$_4$.H$_2$O (1.44 g, 28.30 mmol) was added to a solution of (R)-tert-butyl (4-(1,3-dioxoisoindolin-2-yl)butan-2-yl)carbamate (4.5 g, 14.10 mmol) in EtOH (2 mL). The mixture was stirred at 80° C. for 1 hour, then allowed to cool to room temperature. The resulting mixture was filtered and the filtrate was concentrated under vacuum to afford (R)-tert-butyl (4-aminobutan-2-yl)carbamate as an oil, which was directly used in the next step without further purification: LCMS [M+1]+: 189.

Step E: (R)-benzyl tert-butyl butane-1,3-diyldicarbamate

TEA (4.4 mL, 31.90 mmol) and CbzCl (1.7 mL, 12.20 mmol) were added to a solution of (R)-tert-butyl (4-aminobutan-2-yl)carbamate (2.0 g, 10.60 mmol) in THF (10 mL) and water (10 mL) at 0° C. over 5 minutes. The reaction was stirred for 30 minutes at room temperature. The resulting mixture was diluted with water (100 mL) and extracted with EA (3×30 mL). The combined organic layers were washed with water (3×30 mL), saturated aqueous NaHCO$_3$ (3×30 mL) and brine (3×30 mL), dried over anhydrous Na$_2$SO$_4$ and filtered. The filtrate was concentrated under vacuum to afford (R)-benzyl tert-butyl butane-1,3-diyldicarbamate as a solid, which was used in the next step directly without further purification: LCMS [M+1]+: 323.

Step F: (R)-benzyl (3-aminobutyl)carbamate hydrochloride

To a solution of (R)-benzyl tert-butyl butane-1,3-diyldicarbamate (1.0 g, 3.10 mmol) in 1,4-dioxane (10 mL) was added concentrated HCl (1 mL, 12 M). The mixture was stirring at room temperature for 1.5 hours. The resulting mixture was concentrated under vacuum to afford (R)-benzyl (3-aminobutyl)carbamate hydrochloride as an oil, which was used in the preparation of final compounds without further purification: LCMS [M+1−HCl]+: 223.

Reference Example S 41 and 42

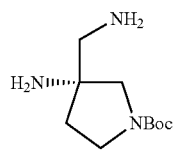

41

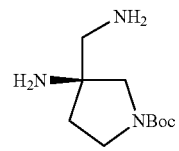

42

(R)- and (S)-tert-butyl-3-amino-3-(aminomethyl)pyrrolidine-1-carboxylate

Tert-butyl 3-amino-3-(aminomethyl)pyrrolidine-1-carboxylate (2.0 g, 9.29 mmol), prepared by following details described in *Bioorganic and Medicinal Chemistry Letters,* 2007, 17, 1181-1184), was separated by Chiral Prep-HPLC with the following conditions: Column: Chiralpak AD-H, 2×25 cm; Mobile Phase A: CO$_2$ (70%), Mobile Phase B: MeOH (2 mmol/L NH$_3$/MeOH): 30%; Flow rate: 40 mL/min; Detector: 210 nm; Retention time: RT$_1$: 2.27 min; RT$_2$: 3.30 min; Temperature: 25° C. The faster-eluting enantiomer 41 was obtained (R)-tert-butyl 3-amino-3-(aminomethyl) pyrrolidin e-1-carboxylate at 2.27 min as an oil: LCMS (ESI) calc'd for C$_{10}$H$_{21}$N$_3$O$_2$ [M+1]+: 216, found 216. The slower-eluting enantiomer 42 was obtained (S)-tert-butyl 3-amino-3-(aminomethyl)pyrrolidine-1-carboxylate at 3.30 min as an oil: LCMS (ESI) calc'd for C$_{10}$H$_{21}$N$_3$O$_2$ [M+1]+: 216, found 216.

Reference Example 43

(S)-tert-butyl-(3-amino-2-hydroxypropyl)carbamate

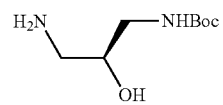

25% NH$_3$.H$_2$O (20 mL) was added to a stirred solution of (R)-tert-butyl-(oxiran-2-ylmethyl)carbamate (1.50 g, 8.70 mmol) in EtOH (5 mL) at 0° C. The reaction solution was stirred for 2 hours at room temp, then concentrated under vacuum to afford (S)-tert-butyl-(3-amino-2-hydroxypropyl)carbamate as a solid, which was used to make final compounds of the invention without further purification: LCMS [M+1]+: 191.

Reference Example 44

(3S,4R)-tert-butyl-amino-4-(((benzyloxy)carbonyl)amino)pyrrolidine-1-carboxylate

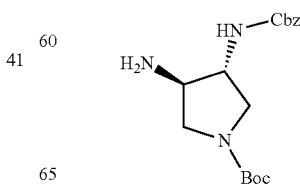

Step A: tert-butyl (3R,4R)-3-(((benzyloxy)carbonyl) amino)-4-hydroxypyrrolidine-1-carboxylate Cbz-Cl (10.12 g, 59.3 mmol) was added dropwise to a mixture of (3R,4R)-tert-butyl 3-amino-4-hydroxypyrrolidine-1-carboxylate (10.0 g, 49.40 mmol) and Na₂CO₃ (6.29 g, 59.30 mmol) in 1,4-dioxane (100 mL) and water (100 mL) at 0° C. The reaction mixture was degassed with nitrogen three times. The reaction mixture was stirred at room temperature for 1 hour under nitrogen. The resulting solution was extracted with EA (3×100 mL). The combined organic layer was washed with aqueous NaOH (1 M, 2×100 mL) and brine (2×100 mL), dried over anhydrous Na₂SO₄ and filtered. The filtrate was concentrated under vacuum. The residue was purified by a silica gel column chromatography, eluted with 10% MeOH in DCM. The fractions containing desired product were combined and concentrated under vacuum to afford the desired compound: LCMS [M+23]⁺: 359.

Step B: (3R,4R)-tert-butyl-3-(((benzyloxy)carbonyl) amino)-4-((methylsulfonyl)oxy) pyrrolidine-1-carboxylate MsCl (10.9 g, 95 mmol) was added dropwise to a solution of tert-butyl (3R,4R)-3-(((benzyloxy)carbonyl)amino)-4-hydroxypyrrolidine-1-carboxylate (16.0 g, 47.6 mmol) and TEA (13.2 mL, 95 mmol) in DCM (200 mL) at 0° C. The reaction mixture was stirred at room temperature for 1 h under nitrogen. The resulting solution was quenched with water (100 mL) and extracted with EA (3×100 mL). The combined organic layers were washed with brine (2×100 mL), dried over anhydrous Na₂SO₄ and filtered. The filtrate was concentrated under vacuum. The residue was purified by silica gel column chromatography, eluted with 32% EA in PE. The fractions containing desired product were combined and concentrated under vacuum to afford (3R,4R)-tert-butyl-3-(((benzyloxy)carbonyl)amino)-4-((methylsulfonyl)oxy) pyrrolidine-1-carboxylate as a solid: LCMS [M+23]⁺: 437.

Step C: (3S,4R)-tert-butyl 3-azido-4-(((benzyloxy) carbonyl)amino)pyrrolidine-1-carboxylate NaN₃ (12.8 g, 198 mmol) was added to a solution of (3R,4R)-tert-butyl-3-(((benzyloxy)carbonyl)amino)-4-((methylsulfonyl)oxy)pyrrolidine-1-carboxylate (20.5 g, 49.5 mmol) in DMF (200 mL) at room temperature. The reaction mixture was stirred at 100° C. for 3 hours under nitrogen. The resulting solution was quenched with water (200 mL) and extracted with EA (3×100 mL). The combined organic layers were washed with brine (2×100 mL), dried over anhydrous Na₂SO₄ and filtered. The filtrate was concentrated under vacuum to afford (3S,4R)-tert-butyl-3-azido-4-(((benzyloxy)carbonyl)amino)pyrrolidine-1-carboxylate as an oil, which was used in the next step directly without further purification: LCMS [M+23]⁺: 384.

Step D: (3S,4R)-tert-butyl 3-amino-4-(((benzyloxy) carbonyl)amino)pyrrolidine-1-carboxylate To a solution of (3S,4R)-tert-butyl-3-azido-4-(((benzyloxy)carbonyl)amino) pyrrolidine-1-carboxylate (17.8 g, 49.30 mmol) in THF (200 mL) and water (20 mL) was added triphenylphosphine (15.5 g, 59.10 mmol) at room temperature. The mixture was stirred at 60° C. for 16 hours under nitrogen. The resulting solution was concentrated under vacuum. The residue was purified by silica gel column chromatography, eluted with 5% MeOH in DCM. The fractions containing desired product were combined and concentrated under vacuum to afford the title compound as an oil: LCMS [M+23]⁺: 358.

Reference Example 45

(S)-tert-butyl(1-amino-3-hydroxypropan-2-yl)carbamate

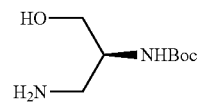

Pd(OH)₂/C (20% Pd, 0.46 g) was added to a solution of (S)-benzyl-tert-butyl(3-hydroxypropane-1,2-diyl)dicarbamate (2.10 g, 6.47 mmol) in MeOH (20 mL) at room temperature. The reaction mixture was degassed with hydrogen three times. The reaction mixture was stirred for 12 hours at room temperature under hydrogen (1.5 atm). The resulting mixture was filtered. The filter cake was washed with MeOH (3×20 mL). The filtrate was concentrated under vacuum. The residue was purified by silica gel column chromatography, and eluted with 45% MeOH and 5% NH₃.H₂O in DCM. The fractions containing desired product were combined and concentrated under vacuum to afford methyl-2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylate as a solid: LCMS [M+1]⁺: 191.

Reference Example 46

S)-benzyl (2-amino-3-hydroxypropyl)carbamate 2,2,2-trifluoroacetate

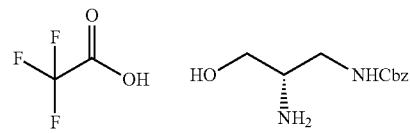 [SMILES: O=C(O)C(F)(F)F ; N[C@H](CO)CNC(=O)OCc1ccccc1]

TFA (3.3 mL) was added to a stirred solution of (S)-benzyl-tert-butyl (3-hydroxypropane-1,2-diyl)dicarbamate (1.20 g, 3.70 mmol) in DCM (10 mL) at 0° C. The reaction solution was stirred for 2 hours at 0° C. The solution was concentrated under vacuum to afford (S)-benzyl (2-amino-3-hydroxypropyl)carbamate 2,2,2-trifluoroacetate as a solid, which was used to make final compounds of the invention directly without further purification: LCMS [M+1−TFA]⁺: 225.

Reference Example 47

(R)-benzyl (2-aminopropyl)carbamate 2,2,2-trifluoroacetate

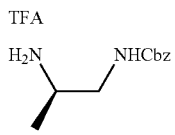

Step A: (R)-tert-butyl (1-amino-1-oxopropan-2-yl) carbamate

To a suspension of (R)-2-aminopropanamide hydrochloride (100 g, 0.80 mmol) in MeOH (1000 mL) were added TEA (244 g, 2.41 mol) and (Boc)$_2$O (263 g, 1.20 mol) at 0° C. The reaction mixture was stirred for 2 h at room temperature. The resulting mixture was diluted with water (1 L) and extracted with EA (3×1.5 L). The combined organic layers were washed with brine (3×2 L), dried over anhydrous Na$_2$SO$_4$ and filtered. The filtrate was concentrated under vacuum to afford the desired product as a solid: LCMS [M+1]$^+$: 189.

Step B: (R)-tert-butyl (1-aminopropan-2-yl)carbamate

BH$_3$-DMS (128 mL, 1.28 mol, 10 M) was added to a suspension of (R)-tert-butyl(1-amino-1-oxopropan-2-yl)carbamate (120 g, 0.64 mol) in THF (200 mL) at 0° C. The reaction mixture was stirred for 4 hours at 45° C. The resulting mixture was quenched with aqueous NaOH (1.0 M, 1.0 L) and extracted with EA (3×1 L). The combined organic layers were washed with brine (3×1.5 L), dried over anhydrous Na$_2$SO$_4$ and filtered. The filtrate was concentrated under vacuum to afford (R)-tert-butyl (1-aminopropan-2-yl) carbamate as an oil, which was used in the next step directly without further purification: LCMS [M+1]$^+$: 175.

Step C: (R)-benzyl-tert-butyl propane-1,2-diyldicarbamate

TEA (7.20 mL, 51.70 mmol) and Cbz-Cl (5.87 g, 34.4 mmol) were added to a solution of (R)-tert-butyl (1-aminopropan-2-yl)carbamate (3 g, 17.2 mmol) in DCM (40 mL). The reaction mixture was stirred at room temperature for 3 hours. The resulting mixture was concentrated under vacuum. The residue was purified by silica gel column chromatography with 20% EA in PE. The fractions containing desired product were combined and concentrated under vacuum to afford (R)-benzyl-tert-butyl propane-1,2-diyldicarbamate as a solid; LCMS [M+1]$^+$: 309.

Step D: (R)-benzyl (2-aminopropyl)carbamate 2,2,2-trifluoroacetate

A solution of (R)-benzyl-tert-butyl-propane-1,2-diyldicarbamate (1.10 g, 3.57 mmol) in TFA (15.0 ml, 214 mmol) and DCM (15.0 ml) was stirred at room temperature for 1 hour. The resulting mixture was concentrated under vacuum to afford the title compound as an oil, which was used to make final compounds of the invention without further purification: LCMS [M−TFA+1]$^+$: 209.

Reference Example 48

(R)-benzyl (2-aminobutyl)carbamate hydrochloride

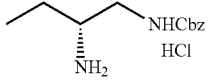

Step A: (R)-tert-butyl (1-amino-1-oxobutan-2-yl) carbamate (Boc)$_2$O (15.8 g, 72.20 mmol) and TEA (13.7 mL, 98.00 mmol) were added to a solution of (R)-2-aminobutanamide hydrochloride (5.0 g, 36.10 mmol) in MeOH (50 mL). The mixture was stirred at room temp. for 3 h. The resulting mixture was quenched with H$_2$O (100 mL) and extracted with EA (3×50 mL). The combined organic layers were washed with HCl (1 M, 2×50 mL), dried over Na$_2$SO$_4$ and filtered. The filtrate was concentrated under vacuum to afford the desired product as a solid, which was used in the next step directly without further purification: LCMS [M+1]$^+$: 203.

Step B: (R)-tert-butyl (1-aminobutan-2-yl)carbamate

BH$_3$.Me$_2$S (9.39 g, 124.0 mmol, 10 M) was added dropwise to a solution of (R)-tert-butyl(1-amino-1-oxobutan-2-yl)carbamate (5.0 g, 24.7 mmol) in THF (50 mL) at 0° C. The reaction mixture was stirred for 12 hours at room temperature. The resulting reaction mixture was quenched with aqueous NaOH (1 M, 150 mL), and then extracted with EA (3×100 mL). The combined organic layers was washed with brine (2×50 mL), dried over anhydrous Na$_2$SO$_4$ and filtered. The filtrate was concentrated under vacuum to afford (R)-tert-butyl(1-aminobutan-2-yl)carbamate as a solid, which was used in the next step directly without further purification: LCMS [M+1]$^+$: 189.

Step C: (R)-benzyl tert-butyl butane-1,2-diyldicarbamate

CbzCl (8.16 g, 47.80 mmol) and TEA (7.26 g, 71.70 mmol) were added to a solution of (R)-tert-butyl (1-aminobutan-2-yl)carbamate (4.5 g, 23.90 mmol) in DCM (50 mL). The mixture was stirred at room temperature for 3 h. The resulting mixture was quenched with water (50 mL), and then extracted with EA (3×50 mL). The combined organic layers were washed with brine (2×10 mL), dried over anhydrous Na$_2$SO$_4$ and filtered. The filtrate was concentrated under vacuum. The residue was purified by silica gel column chromatography, eluted with 20% EA in PE. The fractions containing desired product were combined and concentrated under vacuum to afford (R)-benzyl tert-butyl butane-1,2-diyldicarbamate as a solid: LCMS [M+1]$^+$: 323.

Step D: (R)-benzyl(2-aminobutyl)carbamate hydrochloride

A solution of (R)-benzyl-tert-butylbutane-1,2-diyldicarbamate (1.0 g, 3.10 mmol) in HCl (1 M in dioxane) (10 mL)

was stirred at room temperature for 2 h. The resulting mixture was concentrated under vacuum to afford the title compound as a solid: LCMS [M+1−HCl]⁺: 223.

Reference Example 49

(S)-benzyl(2-aminobutyl)carbamate hydrochloride

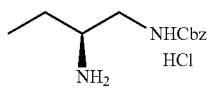

Step A: (S)-tert-butyl(1-amino-1-oxobutan-2-yl) carbamate

The title compound was prepared as described in REFERENCE EXAMPLE 48 step A using (S)-2-aminobutanamide hydrochloride (10 g, 65.50 mmol): LCMS [M+1]⁺: 203.

Step B: (S)-tert-butyl (1-aminobutan-2-yl)carbamate

The title compound was prepared as described in REFERENCE EXAMPLE 48 step B using (S)-tert-butyl(1-amino-1-oxobutan-2-yl)carbamate (3 g, 14.83 mmol): LCMS [M+1]⁺: 189.

Step C: (S)-benzyl tert-butylbutane-1,2-diyldicarbamate

The title compound was prepared as described in REFERENCE EXAMPLE 48 step C using (S)-tert-butyl(1-aminobutan-2-yl)carbamate (1.0 g, 5.31 mmol): LCMS [M+1]⁺: 323.

Step D: (S)-benzyl (2-aminobutyl)carbamate hydrochloride

The title compound was prepared as described in REFERENCE EXAMPLE 48 step D using (S)-benzyl tert-butyl butane-1,2-diyldicarbamate (1 g, 3.10 mmol): LCMS [M+1−HCl]⁺: 223.

Reference Example 50

(3R,4S)-tert-butyl 3-amino-4-((tert-butoxycarbonyl) amino)pyrrolidine-1-carboxylate

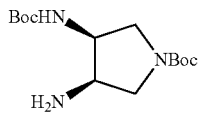

Step A: (3R,4S)-tert-butyl-3-(((benzyloxy)carbonyl) amino)-4-((tert-butoxycarbonyl) amino)pyrrolidine-1-carboxylate TEA (1.02 g, 10.10 mmol) and (Boc)₂O (1.76 g, 8.07 mmol) were added to a stirred solution of (3S,4R)-tert-butyl-3-amino-4-(((benzyloxy)carbonyl) amino)pyrrolidine-1-carboxylate (REFERENCE EXAMPLE 44, 2.3 g, 6.72 mmol) in 1,4-dioxane (15 mL) and water (15 mL) in an ice bath. The reaction mixture was stirred for 16 hours at room temperature. The reaction mixture was diluted with water (100 mL) and extracted with Et₂O (3×200 mL). The combined organic layers were washed with saturated aqueous Na₂CO₃ (2×100 mL), brine (2×100 mL), dried over anhydrous Na₂SO₄ and filtered. The filtrate was concentrated under vacuum to afford the title compound, which was used in the next step directly without further purification: LCMS [M+1]⁺: 436.

Step B: (3R,4S)-tert-butyl 3-amino-4-((tert-butoxycarbonyl)amino)pyrrolidine-1-carboxylate Pd(OH)₂/C (20% Pd, 0.35 g, 0.50 mmol) was added to a solution of (3R,4S)-tert-butyl-3-(((benzyloxy)carbonyl) amino)-4-((tert-butoxycarbonyl)amino)pyrrolidine-1-carboxylate (2.20 g, 4.95 mmol) in MeOH (20 mL) at room temperature. The reaction mixture was degassed with hydrogen for three times. The reaction mixture was stirred for 16 hours at room temperature under hydrogen (1.5 atm). The resulting mixture was filtered. The filtrate was concentrated under vacuum to afford (3R,4S)-tert-butyl-3-amino-4-((tert-butoxycarbonyl)amino) pyrrolidine-1-carboxylate as a solid, which was used to make compounds of the invention without further purification: LCMS [M+1]⁺: 302.

Reference Example 51

(2-Carbamoyl-1H-benzo[d]imidazol-4-yl)boronic acid

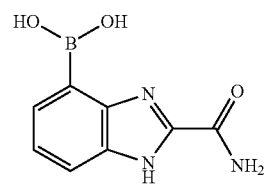 [SMILES: NC(=O)c1nc2c(B(O)O)cccc2[nH]1]

Step A: 4-Bromo-2-(trichloromethyl)-1H-benzo[D] imidazole

Benzyl 2,2,2-trichloroacetimidate (13.50 g, 53.50 mmol) was added to a stirred solution of 3-bromobenzene-1,2-diamine (10.0 g, 53.50 mmol) in AcOH (50 mL) at room temperature. The reaction solution was stirred at room temp. for 4 hours. The resulting mixture was poured into water (300 mL) and the solid was precipitated. The resulting mixture was filtered. The filter cake was washed with water (3×50 mL) and dried under vacuum to afford the desired product as a solid, which was used in the next step directly without further purification: LCMS [M+1]⁺: 315.

Step B: 4-Bromo-1H-benzo[d]imidazole-2-carbonitrile 4-bromo-2-(trichloromethyl)-1H-benzo[d]imidazole (10.00 g, 31.80 mmol) was added to a solution of liquid NH₃ (20 mL) at −78° C. The mixture was stirred at −78° C. for 20 min. The reaction mixture was allowed to warm to room temperature. After the ammonia was evaporated, the residue was dissolved in EA (300 mL). The organic layer was washed with brine (3×200 mL), dried over anhydrous Na$_2$SO$_4$ and filtered. The filtrate was concentrated under vacuum. The residue was purified by silica gel column chromatography, eluted with 30% EA in PE. The fractions containing desired product were combined and concentrated under vacuum to afford 4-bromo-1H-benzo[d]imidazole-2-carbonitrile as a solid: LCMS [M+1]$^+$: 222, 224.

Step C: 4-Bromo-1H-benzo[d]imidazole-2-carboxamide

30% H$_2$O$_2$ (0.3 mL, 2.25 mmol) and KOH (0.63 g, 11.26 mmol) were added to a solution of 4-bromo-1H-benzo[d]imidazole-2-carbonitrile (0.50 g, 2.25 mmol) in MeOH (10 mL) and water (5 mL). The reaction mixture was stirred at 25° C. for 4 hours. The resulting mixture was concentrated under vacuum. The residue was purified by silica gel column chromatography, eluted with 10% MeOH in DCM. The fractions containing desired product were combined and concentrated under vacuum to afford the desired product as a solid: LCMS [M+1]$^+$: 240, 242.

Step D: (2-Carbamoyl-1H-benzo[d]imidazol-4-yl) boronic acid

KOAc (1.23 g, 12.50 mmol), Pd(dppf)Cl$_2$ (0.51 g, 0.63 mmol) and 5,5,5',5'-tetramethyl-2,2'-bi(1,3,2-dioxaborinane) (2.12 g, 9.37 mmol) were added to a solution of 4-bromo-1H-benzo[d]imidazole-2-carboxamide (0.75 g, 3.12 mmol) in 1,4-dioxane (6 mL). The mixture was degassed with nitrogen three times and stirred for 16 h at 80° C. under nitrogen. The resulting mixture was concentrated under vacuum. The residue was purified by RPLC with the following conditions: Column: C18; mobile phase: ACN/water (0.5% TFA); Flow rate: 60 mL/min; Gradiate: 5%-30% ACN in water in 30 min; Retention time: 20 min; Detector: UV 254 nm. The fractions containing desired product were combined and concentrated under vacuum to afford (2-carbamoyl-1H-benzo[d]imidazol-4-yl)boronic acid as a solid: LCMS [M+1]$^+$: 206.

Reference Example 52

Tert-butyl (2-(4-(4,4,5,5-tetramethyl-1,3,2-dioxaborolan-2-yl)-2H-benzo[d][1,2,3]triazol-2-yl)ethyl)carbamate

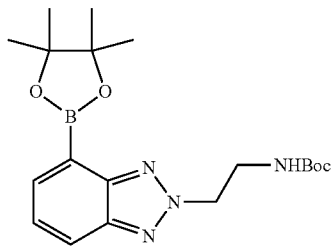 [SMILES: CC(C)(C)OC(=O)NCCn1nc2cccc(B3OC(C)(C)C(C)(C)O3)c2n1]

Step A: 4-Bromo-1H-benzo[d][1,2,3]triazole

Sodium nitrite (1.7 g, 25.0 mmol) was added in several portions to a solution of 3-bromobenzene-1,2-diamine (2.3 g, 12.5 mmol) in AcOH (10 mL) and water (4 mL) at 0° C. The reaction mixture was stirred at room temp. for 4 h. The resulting mixture was quenched with water (100 mL) and extracted with EA (3×100 mL). The combined organic layers were washed with brine (3×100 mL), dried over anhydrous Na$_2$SO$_4$ and filtered. The filtrate was concentrated under vacuum to afford 4-bromo-1H-benzo[d][1,2,3]triazole as a solid, which was used in the next step directly without further purification: LCMS [M+1]$^+$: 198, 200.

Step B: Tert-butyl (2-(4-bromo-2H-benzo[d][1,2,3]triazol-2-yl)ethyl)carbamate

Na$_2$CO$_3$ (2.6 g, 25 mmol) was added to a solution of 4-bromo-1H-benzo[d][1,2,3]triazole (2 g, 10 mmol) and tert-butyl (2-bromoethyl) carbamate (3.4 g, 15 mmol) in DMF (15 mL) at 0° C. The reaction mixture was stirred at room temp. for 5 hours. The resulting mixture diluted with water (100 mL) and extracted with EA (3×100 mL). The combined organic layers were washed with brine (3×80 mL), dried over anhydrous Na$_2$SO$_4$ and filtered. The filtrate was concentrated under vacuum. The residue was purified by silica gel column chromatography, eluted with 15% EA in PE. The fractions containing desired product were combined and concentrated under vacuum to afford the desired product as a solid: LCMS [M+1]$^+$: 341, 343.

Step C: Tert-butyl (2-(4-(4,4,5,5-tetramethyl-1,3,2-dioxaborolan-2-yl)-2H-benzo[d][1,2,3]triazol-2-yl) ethyl)carbamate 4,4,4',4',5,5,5',5'-octamethyl-2,2'-bi(1,3,2-dioxaborolane) (4.47 g, 17.58 mmol), KOAc (0.86 g, 8.79 mmol) and Pd(dppf)Cl$_2$ adduct CH$_2$Cl$_2$ (0.48 g, 0.59 mmol) were added to a solution of tert-butyl(2-(4-bromo-2H-benzo[d][1,2,3]triazol-2-yl)ethyl) carbamate (1.0 g, 2.93 mmol) in 1,4-dioxane (10 mL) at room temperature. The mixture was degassed with nitrogen three times and stirred for 16 hours at 80° C. The resulting mixture was concentrated under vacuum. The residue was purified by silica gel column chromatography, and eluted with 20% EA in PE. The fractions containing desired product were combined and concentrated under vacuum to afford tert-butyl (2-(4-(4,4,5,5-tetramethyl-1,3,2-dioxaborolan-2-yl)-2H-benzo[d][1,2,3]triazol-2-yl) ethyl)carbamate as an oil: LCMS [M+1]$^+$: 389.

Reference Example 53

2-Amino-7-methyl-1H-benzo[d]imidazol-4-ylboronic acid

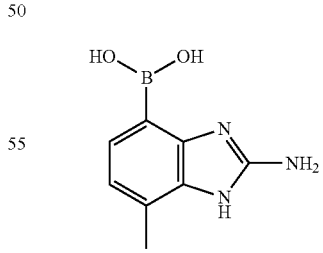

Step A: 4-Methylbenzo[c][1,2,5]thiadiazole

SOCl$_2$ (18 mL, 246 mmol) was added dropwise very slowly to a solution of 3-methylbenzene-1,2-diamine (10.0 g, 82 mmol) and TEA (45.6 mL, 327 mmol) in DCM (200 mL). The reaction mixture was refluxed for 4 hours. The resulting mixture was concentrated under vacuum. The residue was diluted with water (700 mL), and then extracted with DCM (3×200 mL). The combined organic layers were washed with water (2×200 mL), brine (2×200 mL), dried over anhydrous Na$_2$SO$_4$ and filtered. The filtrate was concentrated under vacuum. The residue was purified by silica gel column chromatography, and eluted with 1% EA in PE. The fractions containing desired product were combined and concentrated under vacuum to afford 4-methylbenzo[c][1,2,5]thiadiazole as an oil: LCMS [M+1]$^+$: 151.

Step B: 4-Bromo-7-methylbenzo[c][1,2,5]thiadiazole

Br$_2$ (7.6 mL, 146 mmol) was added to a solution of 4-methylbenzo[c][1,2,5]thiadiazole (11 g, 73.2 mmol) in 48% aqueous HBr (120 mL, 1.06 mol). The reaction mixture was stirred for 16 hours at 80° C. The resulting mixture was diluted with water (100 mL), and then extracted with DCM (3×100 mL). The combined organic layers were washed with water (2×200 mL) and brine (2×200 mL), dried over anhydrous MgSO$_4$ and filtered. The filtrate was concentrated under vacuum to afford the desired product as a solid, which was used in the next step without further purification: LCMS [M+1]$^+$: 229, 231.

Step C: 3-Bromo-6-methylbenzene-1,2-diamine

NaBH$_4$ (1.3 g, 34.90 mmol) and cobalt (II) chloride hexahydrate (0.4 g, 1.75 mmol) were added to a solution of 4-bromo-7-methylbenzo[c][1,2,5]thiadiazole (4.0 g, 17.46 mmol) in MeOH (80 mL) were added at 0° C. The reaction mixture was stirred at 70° C. for 3 hours. The resulting mixture was cooled to room temperature, and then filtered to remove the solid. The filtrate was concentrated under vacuum. The residue was dissolved in water (100 mL). The aqueous phase was extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography, eluting with 20% EA in PE. The fractions containing desired product were combined and concentrated under vacuum to afford 3-bromo-6-methylbenzene-1,2-diamine as an oil: LCMS [M+1]$^+$: 201, 203.

Step D: 4-Bromo-7-methyl-1H-benzo[d]imidazol-2-amine

BrCN (1.05 g, 9.95 mmol) was added to a solution of 3-bromo-6-methylbenzene-1,2-diamine (2.00 g, 9.95 mmol) in MeOH (20 mL) at 0° C. The reaction mixture was stirred at room temperature for 90 min. The reaction mixture was poured into saturated aqueous NaHCO$_3$ (50 mL). The solid was precipitated and filtered. The filter cake was dried under vacuum to afford the desired product, which was used in the next step without further purification: LCMS [M+1]$^+$: 226, 228.

Step E: 2-Amino-7-methyl-1H-benzo[d]imidazol-4-ylboronic acid 5,5,5',5'-tetramethyl-2,2'-bi(1,3,2-dioxaborinane) (4.50 g, 19.91 mmol), 2nd Generation PPh$_3$ precatalyst (0.69 g, 1.19 mmol) and KOAc (2.3 g, 23.90 mmol) were added to a solution of 4-bromo-7-methyl-1H-benzo[d]imidazol-2-amine (1.80 g, 7.96 mmol) in 1,4-dioxane (18 mL) at room temperature. The reaction mixture was degassed with nitrogen three times. The reaction mixture was stirred at 80° C. for 16 hours under nitrogen. The resulting mixture was concentrated under vacuum. The residue was purified by RPLC with the following conditions: Column: C18; mobile phase: ACN/water (0.5% TFA); Flow rate: 60 mL/min; Gradiate: 5%-30% ACN in water in 30 min; Retention time: 20 min; Detector: 254 nm. The fractions containing the desired product were concentrated under vacuum to afford the title compound acid as a solid: LCMS [M+1 192.

Reference Example 54

Tert-butyl (4-(3-(4,4,5,5-tetramethyl-1,3,2-dioxaborolan-2-yl)phenyl)-1H-imidazol-2-yl)carbamate

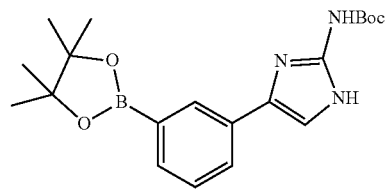 [SMILES: CC(C)(C)OC(=O)Nc1nc(-c2cccc(B3OC(C)(C)C(C)(C)O3)c2)c[nH]1]

Step A: Tert-butyl (4-(3-bromophenyl)-1H-imidazol-2-yl)carbamate

To a solution of 2-bromo-1-(3-bromophenyl)ethanone (3 g, 10.79 mmol) in DMF (30 mL) was added tert-butyl-N-carbamimidoylcarbamate (3.5 g, 21.59 mmol). The reaction mixture was stirred at room temperature for 16 hours. The resulting mixture was diluted with water (60 mL), and then extracted with EA (3×30 mL). The combined organic layers were washed with brine (3×30 mL), dried over anhydrous Na$_2$SO$_4$ and filtered. The filtrate was concentrated under vacuum. The residue was purified by silica gel column chromatography, eluted with 15% EA in PE. The fractions containing desired product were combined and concentrated under vacuum to afford tert-butyl (4-(3-bromophenyl)-1H-imidazol-2-yl)carbamate as a solid: LCMS [M+1]$^+$: 338, 340.

Step B: Tert-butyl(4-(3-(4,4,5,5-tetramethyl-1,3,2-dioxaborolan-2-yl)phenyl)-1H-imidazole-2-yl)carbamate To a solution of tert-butyl (4-(3-bromophenyl)-1H-imidazol-2-yl)carbamate (1.5 g, 4.44 mmol) in 1,4-dioxane (20 mL) were added 4,4,4',4',5,5,5',5'-octamethyl-2,2'-bi(1,3,2-dioxaborolane) (2.3 g, 8.87 mmol), Pd(dppf)Cl$_2$ adduct CH$_2$Cl$_2$ (0.6 g, 0.68 mmol) and KOAc (1.3 g, 13.31 mmol). The reaction mixture was degassed with nitrogen three times. The reaction mixture was stirred for 16 hours under nitrogen at 80° C. The resulting mixture was concentrated under vacuum to afford the title compound as a solid: LCMS [M+1]$^+$: 386.

Reference Example 55

(1H-pyrrolo[3,2-b]pyridin-6-yl)boronic acid

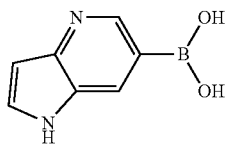 [SMILES: OB(O)c1cnc2cc[nH]c2c1]

KOAc (1.5 g, 15.20 mmol), 2nd Generation XPhosprecatalyst (1.2 g, 1.52 mmol) and 4,4,4',4',5,5,5',5'-octamethyl-2,2'-bi(1,3,2-dioxaborolane) (2.6 g, 10.15 mmol) were added to a solution of 6-bromo-1H-pyrrolo[3,2-b]pyridine (1.0 g, 5.08 mmol) in 1,4-dioxane (4 mL). The reaction mixture was degassed with nitrogen three times. The reaction mixture was stirred at 80° C. for 16 hours under nitrogen. The resulting mixture was diluted with EA (30 mL), and then extracted with aqueous NaOH (2N, 2×100 mL). The combined aqueous layers were concentrated under vacuum. The residue was stirred in MeOH/DCM (1/10, 100 mL) for 20 min. The resulting mixture was filtered and the filtrate was concentrated under vacuum to afford the title compound as a solid: [M+1]$^+$: 163.

Reference Example 56

5-(4,4,5,5-Tetramethyl-1,3,2-dioxaborolan-2-yl)benzo[d]thiazol-2-amine

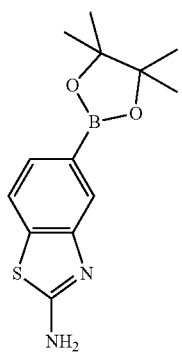 [SMILES: CC1(C)OB(c2ccc3sc(N)nc3c2)OC1(C)C]

Step A: N-((3-bromophenyl)carbamothioyl)benzamide 3-bromoaniline (3.50 mL, 32.1 mmol) was added dropwise to a solution of benzoyl isothiocyanate (5.81 g, 35.7 mmol) in acetone (50 mL) at 70° C. The reaction mixture was stirred at 70° C. for 1 hour. The resulting solution was poured into ice-water (100 mL), stirred for 10 minutes, and filtered. The filter cake was washed with water (10 mL) and dried under vacuum to afford the desired product as a solid, which was used in the next step without further purification: LCMS [M+1]$^+$: 335, 337.

Step B: 1-(3-Bromophenyl)thiourea

N-((3-bromophenyl)carbamothioyl)benzamide (10.0 g, 29.8 mmol) was added to a solution of NaOH (10.0 g, 250 mmol) in water (100 mL) at 80° C. The reaction mixture was stirred at 80° C. for 1 hour under nitrogen. The resulting mixture was poured into ice aqueous HCl (6M, 30 mL) and stirred for 10 minutes. The pH value was adjusted to 10 with 25% NH$_3$.H$_2$O. The solid was precipitated and filtered. The filter cake was washed with water (10 mL) and dried under vacuum. The crude solid was purified by silica gel column chromatography, eluted with 50% EA in PE. The fractions containing desired product were combined and concentrated under vacuum to afford 1-(3-bromophenyl)thiourea as a solid: LCMS [M+1]$^+$: 231, 233.

Step C: 5-Bromobenzo[d]thiazol-2-amine

A solution of bromine (0.86 mL, 16.79 mmol) in AcOH (17.5 mL) was added dropwise at 0° C. to a solution of 1-(3-bromophenyl)thiourea (4.00 g, 17.31 mmol) in ACN (350 mL). The reaction mixture was stirred at room temperature for 18 hours under nitrogen. The resulting mixture was filtered. The filter cake was washed with EA (10 mL) and dried under vacuum to afford the crude product. The crude product was purified by Prep-HPLC with the following conditions: Column: X Select CSH Prep C18 OBD Column 19×150 mm, 5 µm, 13 nm, Phase A: water with 0.05% TFA, Phase B: MeOH; Flow rate: 20; Injection volumn: 200 µL; Gradient: 30-100% of B; Rentation time: 28 min (faster peak). The fractions containing the desired product were combined and concentrated under vacuum to afford 5-bromobenzo[d]thiazol-2-amine as a solid: LCMS [M+1]$^+$: 229, 231.

Step D: 5-(4,4,5,5-Tetramethyl-1,3,2-dioxaborolan-2-yl)benzo[d]thiazol-2-amine KOAc (5.27 g, 53.70 mmol) and 2nd Generation PCy$_3$ precatalyst (2.11 g, 3.58 mmol) were added to a solution of 5-bromobenzo[d]thiazol-2-amine (4.10 g, 17.90 mmol) and 4,4,4',4',5,5,5',5'-octamethyl-2,2'-bi(1,3,2-dioxaborolane) (9.09 g, 35.80 mmol) in 1,4-dioxane (100 mL) at room temperature. The reaction mixture was stirred for 4 hours at 80° C. under nitrogen. The resulting mixture was concentrated under vacuum. The residue was purified by silica gel column chromatography, eluted with 50% EA in PE. The fractions containing desired product were combined and concentrated under vacuum to afford the title compound as a solid: LCMS [M+1]$^+$: 277.

Reference Example 57

2-Methyl-4-(4,4,5,5-tetramethyl-1,3,2-dioxaborolan-2-yl)-2H-benzo[d][1,2,3]triazole

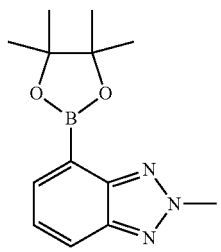

Step A: 4-Bromo-2-methyl-2H-benzo[d][1,2,3]triazole

Iodomethane (2.87 g, 20.20 mmol) was added to a mixture of 4-bromo-2H-benzo[d][1,2,3]triazole (4.0 g, 20.20 mmol) and potassium carbonate (5.58 g, 40.40 mmol) in DMF (40 mL) at room temperature for 2 min. The reaction mixture was stirred at room temperature for 16 h under nitrogen, then concentrated under vacuum. The residue was purified by silica gel column chromatography and eluted with 7% EA in PE. The fractions containing desired product were combined and concentrated under vacuum to afford 4-bromo-2-methyl-2H-benzo[d][1,2,3]triazole as a solid: LCMS [M+1]$^+$: 212, 214.

Step B: 2-Methyl-4-(4,4,5,5-tetramethyl-1,3,2-dioxaborolan-2-yl)-2H-benzo[d][1,2,3]triazole 4,4,4',4',5,5,5',5'-octamethyl-2,2'-bi(1,3,2-dioxaborolane) (1.72 g, 6.79 mmol), KOAc (1.67 g, 16.98 mmol) and Pd(dppf)Cl$_2$ adduct CH$_2$Cl$_2$ (0.46 g, 0.57 mmol) were added to a solution of 4-bromo-2-methyl-2H-benzo[d][1,2,3]triazole (1.20 g, 5.66 mmol) in 1,4-dioxane (16 mL) at room temperature. The mixture was degassed with nitrogen three times. The reaction mixture was stirred at 80° C. for 16 hours under nitrogen. The resulting mixture was concentrated under vacuum. The residue was purified by silica gel column chromatography and eluted with 10% EA in PE. The fractions containing desired product were combined and concentrated under vacuum to afford the title compound as an oil: LCMS [M+1]$^+$: 260.

Reference Example 58

3-Oxocyclohex-1-enylboronic acid

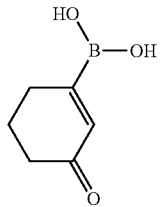

Step A: 3-Oxocyclohex-1-enyl-trifluoromethanesulfonate

TEA (9.03 g, 89.4 mmol) and Tf$_2$O (15.1 g, 53.6 mmol) were added to a solution of cyclohexane-1,3-dione (5.00 g, 44.6 mmol) in DCM (50 mL) at −78° C. for 10 minutes under nitrogen. The reaction mixture was stirred at −78° C. for 1 hour. The resulting mixture was quenched with saturated aqueous NaHCO$_3$ (50 mL) and extracted with DCM (3×50 mL). The combined organic layers were dried over anhydrous Na$_2$SO$_4$ and filtered. The filtrate was concentrated under vacuum. The residue was purified by silica gel column and eluted with 10% EA in PE. The fractions containing desired product were combined and concentrated under vacuum to afford 3-oxocyclohex-1-enyl-trifluoromethanesulfonate as an oil: LCMS [M+1]$^+$: 245.

Step B: 3-Oxocyclohex-1-enylboronic acid 4,4,4',4',5,5,5',5'-octamethyl-2,2'-bi(1,3,2-dioxaborolane) (15.2 g, 60 mmol), KOAc (8.80 g, 90 mmol), Pd(dppf)Cl$_2$ adduct CH$_2$Cl$_2$ (2.50 g, 3.0 mmol) were added to a solution of 3-oxocyclohex-1-enyl-trifluoromethanesulfonate (7.30 g, 30 mmol) in 1,4-dioxane (100 mL) at room temperature. The reaction mixture was degassed with nitrogen three times. The reaction mixture was stirred at 80° C. for 2 hours under nitrogen. The resulting mixture was diluted with EA (100 mL) and extracted with aqueous NaOH (2 M, 3×50 mL). The combined aqueous layers were concentrated under vacuum. The residue was purified by RPLC with the following conditions: Column: C18; mobile phase: ACN/water (1‰ TFA); Flow rate: 60 mL/min; Gradiate: 10%-40% ACN in water in 30 min; Retention time: 23 min; Detector: 254 nm. The fractions containing desired product were combined and concentrated under vacuum to afford 3-oxocyclohex-1-enylboronic acid as an oil: LCMS [M+1]$^+$: 141.

Reference Example 59

2-((2-((3-(4,4,5,5-Tetramethyl-1,3,2-dioxaborolan-2-yl)phenyl)amino)thiazol-4-yl)methyl)isoindoline-1,3-dione

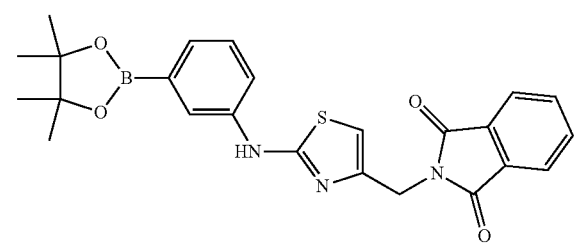 [SMILES: CC1(C)OB(c2cccc(Nc3nc(CN4C(=O)c5ccccc5C4=O)cs3)c2)OC1(C)C]

Step A: 2-((2-((3-Bromophenyl)amino)thiazol-4-yl)methyl)isoindoline-1,3-dione 1,3-dibromopropan-2-one (2.2 g, 10 mmol) was added to a stirred solution of 1-(3-bromophenyl)thiourea (2.3 g, 10 mmol) in NMP (20 mL) at room temperature. The reaction mixture was stirred at 50° C. for 2 hours. The resulting mixture was allowed to cool to room temperature. Isoindoline-1,3-dione (2.2 g, 14.9 mmol) and K$_2$CO$_3$ (2.8 g, 19.9 mmol) were added at room temperature to the reaction solution. The reaction mixture was stirred at room temperature for 3 days. The resulting mixture was diluted with water (100 mL) and extracted with EA (3×50 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography and eluted with 70% EA in PE. The fractions containing desired product were combined and concentrated under vacuum to afford 2-((2-((3-bromophenyl)amino)thiazol-4-yl) methyl)isoindoline-1,3-dione as a solid: LCMS [M+1]$^+$: 414, 416.

Step B: 2-((2-((3-(4,4,5,5-Tetramethyl-1,3,2-dioxaborolan-2-yl)phenyl)amino)thiazol-4-yl) methyl)isoindoline-1,3-dione 4,4,4',4',5,5,5',5'-octamethyl-2,2'-bi(1,3,2-dioxaborolane) (2.5 g, 9.66 mmol), KOAc (1.4 g, 14.5 mmol) and 2nd Generation PPh$_3$ precatalyst (0.57 g, 0.97 mmol) were added to a stirred solution of 2-((2-((3-bromophenyl)amino)thiazol-4-yl)methyl) isoindoline-1,3-dione (2.0 g, 4.83 mmol) in 1,4-dioxane (15 mL) at room temperature. The mixture was degassed with nitrogen three times. The reaction mixture was stirred at 80° C. for 16 hours under nitrogen. The resulting mixture was diluted with water (100 mL) and extracted with EA (3×50 mL). The combined organic layers were washed with water (3×50 mL) and brine (3×50 mL), dried over anhydrous $Na_2SO_4$ and filtered. The filtrate was concentrated under vacuum. The residue was purified by silica gel column chromatography and eluted with 50% EA in PE. The fractions containing desired product were combined and concentrated under vacuum to afford ((2-((3-(4,4,5,5-tetramethyl-1,3,2-dioxaborolan-2-yl)phenyl) amino) thiazol-4-yl)methyl)isoindoline-1,3-dione as a solid: LCMS [M+1]$^+$: 462.

Reference Example 60

Imidazo[1,2-a]pyridin-8-ylboronic acid

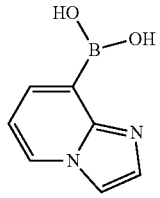 [SMILES: OB(O)c1cccn2ccnc12]

Step A: 3-(4,4,5,5-tetramethyl-1,3,2-dioxaborolan-2-yl)pyridin-2-amine $Pd_2$(dba)$_3$ (2.10 g, 2.30 mmol), 3-bromopyridin-2-amine (2.00 g, 11.56 mmol), 4,4,4',4',5,5,5',5'-octamethyl-2,2'-bi(1,3,2-dioxaborolane) (5.87 g, 23.12 mmol) and KOAc (3.40 g, 34.7 mmol) were added to a solution of tricyclohexylphosphine (1.10 g, 4.10 mmol) in 1,4-dioxane (15 mL) at room temp. The mixture was degassed with nitrogen three times and stirred at 95° C. for 16 h. The resulting mixture was filtered. The filtrate was concentrated under vacuum to afford the title compound, which was used in the next step without further purification: LCMS [M+1]$^+$: 139.

Step B: Imidazo[1,2-a]pyridin-8-ylboronic acid 2-chloroacetaldehyde (13.7 g, 68.20 mmol) was added to a solution of 3-(4,4,5,5-tetramethyl-1,3,2-dioxaborolan-2-yl)pyridin-2-amine (1.00 g, 4.54 mmol) in EtOH (15 mL) at room temperature. The reaction mixture was stirred at 70° C. for 16 hours. The resulting mixture was concentrated under vacuum. The residue was diluted with EA (100 mL) and extracted with aqueous HCl (1 N, 3×30 mL). The combined aqueous layers were concentrated under vacuum to afford the title compound as a solid, which was used in the next step without further purification: LCMS [M+1]$^+$: 163.

Reference Example 61

Tert-butyl ((4-(5,5-dimethyl-1,3,2-dioxaborinan-2-yl)-1H-benzo[d]imidazol-2-yl)methyl)carbamate

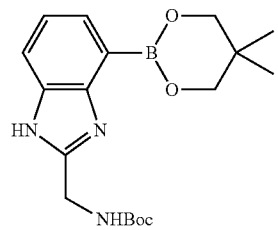 [SMILES: CC1(C)COB(c2cccc3[nH]c(CNC(=O)OC(C)(C)C)nc23)OC1]

Step A: Tert-butyl (2-((2-amino-3-bromophenyl) amino)-2-oxoethyl)carbamate 2-((tert-butoxycarbonyl)amino)acetic acid (94 g, 535 mmol), HATU (610 g, 1.6 mol) and TEA (223 mL, 1.6 mol) were added to a solution of 3-bromobenzene-1,2-diamine (100 g, 535 mmol) in THF (1 L) at room temperature. The reaction mixture was degassed with nitrogen three times and stirred for overnight at room temperature. The resulting mixture was diluted with water (500 mL) and extracted with EA (3×600 mL). The combined organic layers was washed with water (3×500 mL) and brine (3×500 mL), dried over anhydrous $Na_2SO_4$ and filtered. The filtrate was concentrated under vacuum. The residue was purified by silica gel column chromatography, eluted with 60% EA in PE. The fractions containing desired product were combined and concentrated under vacuum to afford tert-butyl(2-((2-amino-3-bromophenyl) amino)-2-oxoethyl)carbamate as a solid, which was used in the next step directly without further purification: LCMS [M+1]$^+$: 344, 346.

Step B: Tert-butyl ((4-bromo-1H-benzo[d]imidazol-2-yl)methyl)carbamate

A solution of tert-butyl (2-((2-amino-3-bromophenyl)amino)-2-oxoethyl)carbamate (180 g, 523 mmol) in AcOH (250 mL) was stirred for 0.5 h at 60° C. The resulting mixture was concentrated under vacuum. The residue was crystallized from EA/PE (50:1, 200 mL). The solid was collected by filtration and dried under vacuum to afford tert-butyl ((4-bromo-1H-benzo[d]imidazol-2-yl)methyl)carbamate as a soild: LCMS [M+1]$^+$: 326, 328.

Step C: Tert-butyl((4-(5,5-dimethyl-1,3,2-dioxaborinan-2-yl)-1H-benzo[d]imidazol-2-yl) methyl)carbamate To a solution of tert-butyl((4-bromo-1H-benzo[d]imidazol-2-yl)methyl)carbamate (70.0 g, 215 mmol) in 1,4-dioxane (350 mL) was added Chloro(triphenylphosphine)[2-(2'-amino-1,1-biphenyl)]Palladium (II) (24.6 g, 42.9 mmol), 5,5,5',5'-tetramethyl-2,2'-bi(1,3,2-dioxaborinane) (72.7 g, 322 mmol) and KOAc (63.2 g, 644 mmol) at room temperature. The reaction mixture was degassed with nitrogen three times and stirred at 80° C. for 16 h. The resulting mixture was diluted with water (500 mL) and extracted with EA (3×400 mL). The combined organic layers was washed with water (3×800 mL) and brine (3×500 mL), dried over anhydrous $Na_2SO_4$ and filtered. The filtrate was concentrated under vacuum. The residue was purified by silica gel column chromatography, eluted with 60% EA in PE. The fractions containing desired product were combined and concentrated under vacuum to afford tert-butyl((4-(5,5-dimethyl-1,3,2-dioxaborinan-2-yl)-1H-benzo[d]imidazol-2-yl)methyl)carbamate: LCMS [M+1]$^+$: 360.

Reference Example 62

Tert-butyl (2-(4-(4,4,5,5-tetramethyl-1,3,2-dioxaborolan-2-yl)-1H-benzo[d][1,2,3]triazol-1-yl)ethyl) carbamate

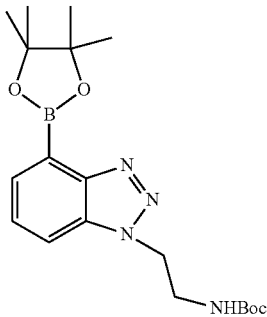 [SMILES: CC(C)(C)OC(=O)NCCn1nnc2c(B3OC(C)(C)C(C)(C)O3)cccc21]

Step A: Tert-butyl (2-((3-bromo-2-nitrophenyl)amino)ethyl)carbamate

Tert-butyl (2-aminoethyl)carbamate (3.3 g, 21 mmol) and Na$_2$CO$_3$ (2.9 g, 27 mmol) were added to a solution of 1-bromo-3-fluoro-2-nitrobenzene (3.0 g, 14 mmol) in DMF (15 mL). The mixture was stirred at room temperature for 5 hours. The resulting mixture was diluted with water (200 mL), and then extracted with EA (3×150 mL). The combined organic layers was washed with water (3×150 mL), brine (3×150 mL), dried over anhydrous Na$_2$SO$_4$ and filtered. The filtrate was concentrated under vacuum to afford tert-butyl (2-((3-bromo-2-nitrophenyl)amino)ethyl)carbamate as an oil, which was used in the next step without further purification: LCMS [M+1]$^+$: 360, 362 (1:1).

Step B: Tert-butyl (2-((2-amino-3-bromophenyl)amino)ethyl)carbamate

Zn dust (5.9 g, 84.0 mmol) was slowly added in several portions to a solution of tert-butyl(2-((3-bromo-2-nitrophenyl)amino)ethyl)carbamate (5.5 g, 14.0 mmol) in concentrated HCl and MeOH (1:4, 30 mL). The reaction mixture was stirred for 2 hours at 50° C. The resulting mixture was filtered. The filtrate was concentrated under vacuum to afford crude N1-(2-aminoethyl)-3-bromobenzene-1,2-diamine as an oil, which was used in the next step directly without further purification. To the solution of the crude N1-(2-aminoethyl)-3-bromobenzene-1,2-diamine in DCM (50 mL) was added (Boc)$_2$O (4.5 g, 21 mmol) and TEA (2.8 g, 28 mmol) at 0° C. The reaction mixture was stirred at room temperature for 2 hours. The resulting mixture was diluted with water (100 mL), and then extracted with DCM (3×250 mL). The combined organic layers were washed with water (3×250 mL) and brine (3×100 mL), dried over anhydrous Na$_2$SO$_4$ and filtered. The filtrate was concentrated under vacuum to afford tert-butyl (2-((2-amino-3-bromophenyl)amino)ethyl)carbamate as a solid, which was used in the next step without further purification: LCMS [M+1−100]$^+$: 230, 232.

Step C: Tert-butyl (2-(4-bromo-1H-benzo[d][1,2,3]triazol-1-yl)ethyl)carbamate

NaNO$_2$ (1.9 g, 28.0 mmol) was added to a solution of tert-butyl(2-((2-amino-3-bromophenyl)amino)ethyl)carbamate (5.0 g, 14.0 mmol) in AcOH and H$_2$O (1:3, 15 mL) at 0° C. The reaction mixture was stirred at room temperature for 1 hour. The resulting mixture was diluted with water (100 mL), and then extracted with EA (3×200 mL). The combined organic fractions were washed with brine (2×100 mL), dried over anhydrous Na$_2$SO$_4$ and filtered. The filtrate was concentrated under vacuum. The residue was purified by silica gel column chromatography and eluted with 10% EA in PE. The fractions containing desired product were combined and concentrated under vacuum to afford tert-butyl(2-(4-bromo-1H-benzo[d][1,2,3]triazol-1-yl)ethyl) carbamate as a solid: LCMS [M+1]$^+$: 341, 343.

Step D: Tert-butyl(2-(4-(4,4,5,5-tetramethyl-1,3,2-dioxaborolan-2-yl)-1H-benzo[d][1,2,3]triazol-1-yl)ethyl)carbamate 4,4,4',4',5,5,5',5'-octamethyl-2,2'-bi(1,3,2-dioxaborolane) (4.5 g, 17.70 mmol), Pd(dppf)Cl$_2$ adduct CH$_2$Cl$_2$ (0.5 g, 0.60 mmol) and KOAc (0.8 g, 8.70 mmol) were added to a solution of tert-butyl(2-(4-bromo-1H-benzo[d][1,2,3]triazol-1-yl)ethyl) carbamate (1.0 g, 2.90 mmol) in 1,4-dioxane (15 mL). The mixture was degassed with nitrogen three times and stirred at 80° C. for 16 hours. The resulting mixture was concentrated under vacuum. The residue was purified by silica gel column chromatography and eluted with 30% EA in PE. The fractions containing desired product were combined and concentrated under vacuum to afford tert-butyl (2-(4-(4,4,5,5-tetramethyl-1,3,2-dioxaborolan-2-yl)-1H-benzo[d][1,2,3]triazol-1-yl) ethyl)carbamate as an oil: LCMS [M+1]$^+$: 389.

Reference Example 63

(2-((2-Amino-5-(4,4,5,5-tetramethyl-1,3,2-dioxaborolan-2-yl)phenyl)amino)ethyl) carbamate

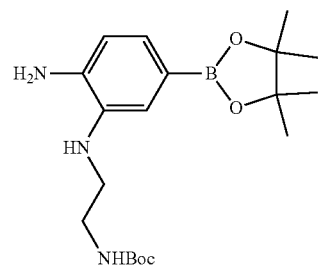 [SMILES: CC(C)(C)OC(=O)NCCNc1cc(B2OC(C)(C)C(C)(C)O2)ccc1N]

Step A: Tert-butyl (2-((5-bromo-2-nitrophenyl)amino)ethyl)carbamate

Cs$_2$CO$_3$ (22.2 g, 68.2 mmol) and tert-butyl(2-aminoethyl)carbamate (8.74 g, 54.5 mmol) were added to a stirred solution of 4-bromo-2-fluoro-1-nitrobenzene (10 g, 45.5 mmol) in NMP (35 mL) at room temperature. The reaction mixture was stirred at 100° C. for 16 hours under nitrogen. The resulting mixture was diluted with water (200 mL), and then extracted with EA (3×200 mL). The combined organic layers were washed with water (3×200 mL) and brine (3×200 mL), dried over anhydrous Na$_2$SO$_4$ and filtered. The filtrate was concentrated under vacuum. The residue was purified by silica gel column chromatography and eluted with 30% EA in PE. The fractions containing desired product were combined and concentrated under vacuum to afford tert-butyl (2-((5-bromo-2-nitrophenyl)amino)ethyl) carbamate as a solid: LCMS [M+1]$^+$: 360, 362.

Step B: Tert-butyl(2-((2-nitro-5-(4,4,5,5-tetramethyl-1,3,2-dioxaborolan-2-yl)phenyl)amino) ethyl) carbamate Pd(dppf)Cl$_2$ (1.22 g, 1.67 mmol), 4,4,4',4',5,5,5',5'-octamethyl-2,2'-bi(1,3,2-dioxaborolane) (4.23 g, 16.70 mmol) and KOAc (2.45 g, 25.00 mmol) were added to a stirred solution of tert-butyl(2-((5-bromo-2-nitrophenyl)amino)ethyl)carbamate (3.0 g, 8.33 mmol) in 1,4-dioxane (30 mL) at room temperature. The mixture was degassed with nitrogen three times. The reaction mixture was stirred at 80° C. for 16 h under nitrogen. The resulting mixture was diluted with water (100 mL) and extracted with EA (3×50 mL). The combined organic layers was washed with water (3×100 mL) and brine (3×100 mL), dried over anhydrous Na$_2$SO$_4$ and filtered. The filtrate was concentrated under vacuum. The residue was purified by silica gel column chromatography, eluted with 30% EA in PE. The fractions containing desired product were combined and concentrated under vacuum to afford tert-butyl (2-((2-nitro-5-(4,4,5,5-tetramethyl-1,3,2-dioxaborolan-2-yl)phenyl)amino)ethyl)carbamate as an oil: LCMS [M+1]$^+$: 408.

Step C: Tert-butyl(2-((2-amino-5-(4,4,5,5-tetramethyl-1,3,2-dioxaborolan-2-yl)phenyl)amino) ethyl) carbamate Pd/C (10% wt, 0.3 g, 0.28 mmol) was added to a solution of tert-butyl(2-((2-nitro-5-(4,4,5,5-tetramethyl-1,3,2-dioxaborolan-2-yl) phenyl)amino)ethyl)carbamate (3 g, 7.37 mmol) in MeOH (30 mL) at room temperature under nitrogen. The mixture was degassed with hydrogen three times. The reaction mixture was stirred at room temperature for 16 hours under hydrogen (1.5 atm). The solid was removed by filtration. The filtrate was concentrated under vacuum to afford the title compound as an oil, which was used to make compounds of the invention without further purification: LCMS [M+1]$^+$: 378.

Reference Example 64

(2-Aminobenzo[d]thiazol-4-yl)boronic acid

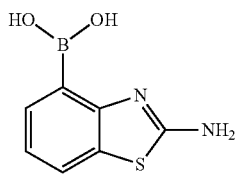 [SMILES: Nc1nc2c(B(O)O)cccc2s1]

4,4,4',4',5,5,5',5'-octamethyl-2,2'-bi(1,3,2-dioxaborolane) (4.43 g, 17.46 mmol), KOAc (2.84 g, 28.90 mmol) and 2nd Generation PCy$_3$ precatalyst (1.03 g, 1.75 mmol) were added to a solution of commercially available 4-bromobenzo[d]thiazol-2-amine (2.0 g, 8.8 mmol) in 1,4-dioxane (20 mL) at room temperature. The reaction mixture was degassed with nitrogen three times and stirred at 90° C. for 24 h under nitrogen. The resulting mixture was diluted with water (100 mL) and extracted with EA (3×150 mL). The combined organic layers was washed with water (3×300 mL) and brine (3×300 mL), dried over anhydrous Na$_2$SO$_4$ and filtered. The filtrate was concentrated under vacuum. The residue was purified by RPLC with the following conditions: Column: C18 column chromatography; Flow rate: 60 mL/min; Gradiate: 25%-30% ACN in water with 0.5% TFA in 20 min; Detector: 254 nm. The fractions containing desired product were combined and concentrated under vacuum to afford (2-aminobenzo[d]thiazol-4-yl)boronic acid as a solid: LCMS [M+1]$^+$: 195.

Reference Example 65

Tert-butyl ((5-(3-(4,4,5,5-tetraethyl-1,3,2-dioxaborolan-2-yl)phenyl)-1H-imidazol-2-yl)methyl)carbamate

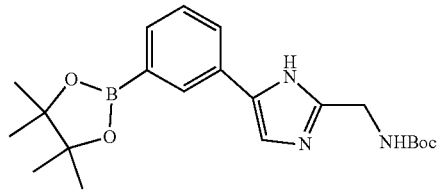 [SMILES: CC(C)(C)OC(=O)NCc1ncc(-c2cccc(B3OC(C)(C)C(C)(C)O3)c2)[nH]1]

Step A: 2-(3-bromophenyl)-2-oxoethyl (tert-butoxycarbonyl)glycinate

To a solution of 2-((tert-butoxycarbonyl)amino)acetic acid (1.26 g, 7.20 mmol) in EtOH (20 mL) was added Cs$_2$CO$_3$ (1.17 g, 3.60 mmol) at room temperature. The reaction mixture was stirred at room temperature. The resulting solution was concentrated under vacuum to afford a cesium salt. To a solution of 2-bromo-1-(3-bromophenyl)ethanone (1.98 g, 7.20 mmol) in DMF (20 mL) was added the caesium salt. The reaction mixture was stirred for 2 hours at room temp. The resulting mixture was diluted with water (100 mL) and extracted with EA (3×100 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 26% EA in PE. The fractions containing desired product were combined and concentrated under vacuum to afford the title compound: LCMS [M+1]$^+$: 372, 374.

Step B: Tert-butyl ((4-(3-bromophenyl)-1H-imidazol-2-yl)methyl)carbamate

To a solution of the 2-(3-bromophenyl)-2-oxoethyl (tert-butoxycarbonyl)glycinate (2 g, 5.37 mmol) in toluene (20 mL) was added ammonium acetate (4.14 g, 53.70 mmol). The reaction mixture was stirred at 110° C. for 16 hours. The reaction mixture was then cooled to room temp., and then diluted with EA (50 mL). The resulting solution was washed with aqueous NaHCO$_3$ (5% W/V) (3×30 mL) and brine (3×30 mL). The organic layer was dried over anhydrous Na₂SO₄ and filtered. The filtrate was concentrated under vacuum. The residue was purified by silica gel column chromatography, eluting with 40% EA in PE. The fractions containing desired product were combined and concentrated under vacuum to afford the title compound: LCMS [M+1]⁺: 352, 354.

Step C: Tert-butyl((5-(3-(4,4,5,5-tetramethyl-1,3,2-dioxaborolan-2-yl)phenyl)-1H-imidazole-2-yl)methyl)carbamate To a solution of tert-butyl((4-(3-bromophenyl)-1H-imidazol-2-yl)methyl)carbamate (1 g, 2.84 mmol) in 1,4-dioxane (30 mL) were added 4,4,4',4',5,5,5',5'-octamethyl-2,2'-bi(1,3,2-dioxaborolane) (1.44 g, 5.68 mmol), 2nd Generation PCy₃ precatalyst (0.50 g, 0.85 mmol) and KOAc (0.84 g, 8.52 mmol) at room temp. The reaction mixture was degassed with nitrogen three times. The reaction mixture was stirred at 80° C. for 16 hours under nitrogen. The resulting mixture was diluted with water (100 mL) and extracted with EA (3×100 mL). The combined organic layers were washed with water (3×100 mL) and brine (3×100 mL), dried over anhydrous Na₂SO₄ and filtered. The filtrate was concentrated under vacuum. The residue was purified by silica gel column chromatography, eluted with 40% EA in PE. The fractions containing desired product were combined and concentrated under vacuum to afford tert-butyl ((5-(3-(4,4,5,5-tetramethyl-1,3,2-dioxaborolan-2-yl)phenyl)-1H-imidazol-2-yl)methyl)carbamate as a solid: LCMS [M+1]⁺: 400.

Reference Example 66

(2-(Methylamino)-1H-benzo[d]imidazol-4-yl)boronic acid

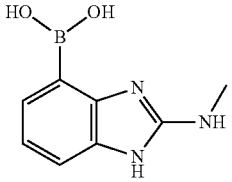

Step A: 7-Bromo-N-methyl-1H-benzo[d]imidazol-2-amine

To a solution of commercially available 7-bromo-2-chloro-1H-benzo[d]imidazole (0.50 g, 2.16 mmol) in THF (10 mL) was added methanamine (2 M in THF, 5.40 mL, 10.80 mmol). The reaction solution was stirred for 24 hours at 80° C. The resulting solution was concentrated under vacuum. The residue was purified by silica gel column chromatography, eluted with 2% MeOH in EA. The fractions containing desired product were combined and concentrated under vacuum to afford 7-bromo-N-methyl-1H-benzo[d]imidazole-2-amine as a solid: LCMS [M+H]⁺: 226, 228.

Step B: (2-(Methylamino)-1H-benzo[d]imidazol-4-yl)boronic acid

To a solution of 7-bromo-N-methyl-1H-benzo[d]imidazole-2-amine (0.30 g, 1.33 mmol) in dioxane (4 mL) were added 2nd PPh₃ precatalyst (76 mg, 0.13 mmol), 5,5,5',5'-tetramethyl-2,2'-bi(1,3,2-dioxaborinane) (0.45 g, 1.99 mmol) and KOAc (0.39 g, 3.98 mmol). The reaction mixture was degassed with nitrogen three times. The reaction mixture was stirred for 16 hours at 80° C. under nitrogen. The resulting mixture was filtered. The filtrate was purified by RPLC with the following conditions: Column: C18; Mobile phase: water (0.5% TFA)/ACN; Gradiate: 5%-30% ACN in water in 25 min; Retention time: 18 min; Flow rate: 60 mL/min; Detector: 254 nm and 220 nm. The fractions containing desired product were combined and concentrated under vacuum to afford (2-(methylamino)-1H-benzo[d]imidazol-4-yl) boronic acid as a solid: LCMS [M+1]⁺: 192.

Reference Example 67 tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate

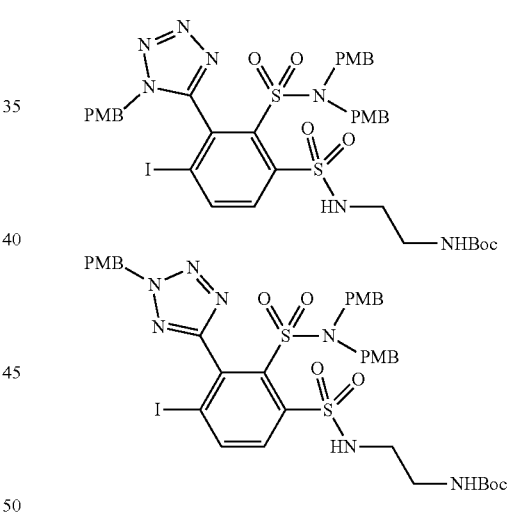

To a solution of 2-(N,N-bis(4-methoxybenzyl)sulfamoyl)-4-iodo-3-(2-(4-methoxybenzyl)-2H-tetrazol-5-yl)benzenesulfinic acid and 2-(N,N-bis(4-methoxybenzyl)sulfamoyl)-4-iodo-3-(1-(4-methoxybenzyl)-1H-tetrazol-5-yl)benzenesulfinic acid (3 g, 3.87 mmol) in THF (38.7 ml) was added tert-butyl (2-aminoethyl)carbamate (1.239 g, 7.74 mmol), triethylamine (1.078 ml, 7.74 mmol), and NCS (1.033 g, 7.74 mmol) in sequence at 0° C. under nitrogen. The mixture was stirred at the same temperature for 30 minutes. The reaction mixture was diluted with EtOAc, washed with NaHCO₃ solution and brine. The organic layer was dried over MgSO₄, evaporated, and the crude product was purified by silica gel column eluting with 0-100% EtOAc/hex to give the title compound. LC/MS [M+H]⁺: 934.53.

Reference Example 68 tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate

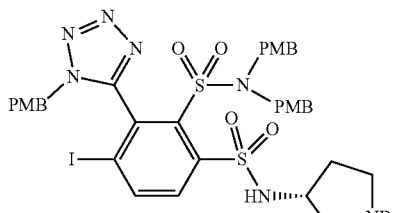

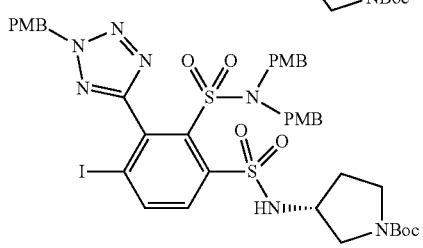

To a solution of a mixture of 2-(N,N-bis(4-methoxybenzyl)sulfamoyl)-4-iodo-3-(2-(4-methoxybenzyl)-2H-tetrazol-5-yl)benzene-1-sulfonyl chloride and 2-(N,N-bis(4-methoxybenzyl)sulfamoyl)-4-iodo-3-(2-(4-methoxybenzyl)-1H-tetrazol-5-yl)benzene-1-sulfonyl chloride (0.46 g, 0.48 mmol) in THF (10 mL) was added (R)-tert-butyl 3-aminopyrrolidine-1-carboxylate (90 mg, 0.48 mmol) at ambient temperature. The reaction was kept at 25° C. for 30 minutes. The mixture was concentrated under vacuum. The residue was diluted with EA (3×20 mL), washed with brine (3×20 mL), dried and filtered. The filtrate was concentrated under vacuum. The residue was applied onto silica gel column chromatography with ethyl acetate/petroleum ether (1:50 to 1:1) to give the title compound: LCMS [M+11]⁺ 960; ¹H NMR (400 MHz, DMSO-d₆) δ 8.52 (d, J=8.4 Hz, 1H), 8.29 (d, J=8.4 Hz, 1H), 7.29-7.25 (m, 2H), 6.83-6.69 (m, 10H), 5.95 (brs, 1H), 5.55-5.50 (m, 0.5H), 5.24-5.19 (m, 0.5H), 4.58-4.53 (m, 1H), 4.05-3.81 (m, 5H), 3.85 (s, 9H), 3.48-3.35 (m, 4H), 2.02-1.82 (m, 2H), 1.44 (s, 9H).

Reference Example 69 tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate

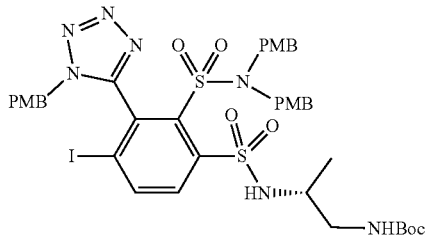

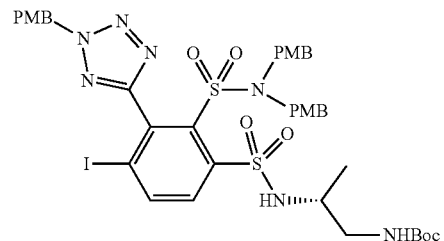

To a solution of 2-(N,N-bis(4-methoxybenzyl)sulfamoyl)-4-iodo-3-(2-(4-methoxybenzyl)-2H-tetrazol-5-yl)benzenesulfinic acid and 2-(N,N-bis(4-methoxybenzyl)sulfamoyl)-4-iodo-3-(1-(4-methoxybenzyl)-1H-tetrazol-5-yl)benzenesulfinic acid (1.0 g, 1.289 mmol) in DCM (20 ml) was added (R)-tert-butyl (2-aminopropyl)carbamate (0.337 g, 1.934 mmol), triethylamine (0.261 g, 2.58 mmol), and NCS (0.344 g, 2.58 mmol) in sequence at 0° C. under nitrogen. The reaction mixture was stirred at 0° C. for 30 minutes. The reaction mixture was washed with 10 ml of sat. aq. NaHCO₃. The organic phase was dried over MgSO₄, concentrated, and the crude product was purified by silica gel column chromatography eluting with 0-10% MeOH in DCM to give the title compound. LC/MS [M+H]⁺: 948.48.

Reference Example 70 tert-butyl (3S,4R)-3-(((benzyloxy)carbonyl)amino)-4-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (3S,4R)-3-(((benzyloxy)carbonyl)amino)-4-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate

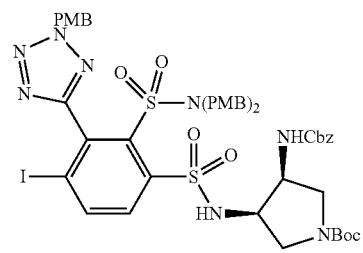

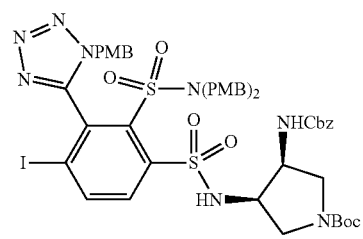

The title compound was prepared in an analogous fashion to REFERENCE EXAMPLE 67 using tert-butyl (3R,4S)-3-amino-4-(((benzyloxy)carbonyl)amino)pyrrolidine-1-carboxylate. LC/MS [M+H]⁺: 1109.80.

Reference Example 71 tert-butyl (3R,4S)-3-(((benzyloxy)carbonyl)amino)-4-((2-(N,N-bis(4-methoxybenzyl)sulfamoyl)-4-iodo-3-(2-(4-methoxybenzyl)-2H-tetrazol-5-yl)phenyl) sulfonamido)pyrrolidine-1-carboxylate and tert-butyl (3R,4S)-3-(((benzyloxy)carbonyl)amino)-4-((2-(N,N-bis(4-methoxybenzyl)sulfamoyl)-4-iodo-3-(1-(4-methoxybenzyl)-1H-tetrazol-5-yl)phenyl) sulfonamido)pyrrolidine-1-carboxylate

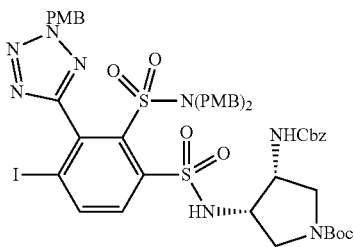

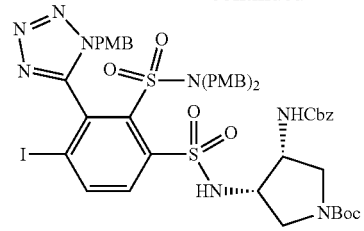

The title compound was prepared in an analogous fashion to REFERENCE EXAMPLE 67 using tert-butyl (3S,4R)-3-amino-4-(((benzyloxy)carbonyl)amino)pyrrolidine-1-carboxylate. LC/MS [M+H]⁺: 1109.8.

REFERENCE EXAMPLES 68 (alternative preparation) and 72-84 in the Table below were similarly prepared in an analogous fashion to that described for REFERENCE EXAMPLE 67 using 2-(N,N-bis(4-methoxybenzyl)sulfamoyl)-4-iodo-3-(2-(4-methoxybenzyl)-2H-tetrazol-5-yl) benzenesulfinic acid (as a mixture of two tetrazole-PMB regioisomers) and the corresponding amines, which were prepared as described herein, or which were available from commercial sources. While a single regioisomer of the PMB-protected tetrazole is shown for simplicity, it should be understood that the intermediates prepared here are in fact mixtures of both possible regioisomeric PMB substituted tetrazoles.

| Ex # | Structure | Chemical Name | LC/MS [M + H]⁺ |
|---|---|---|---|
| 68 | 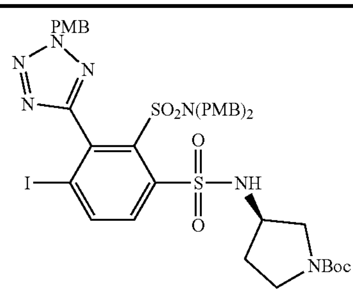 | (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate | 960 |
| 72 | 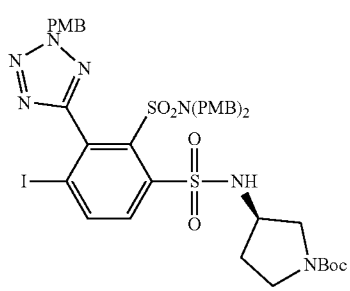 | (S)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate | 960 |
| 73 | 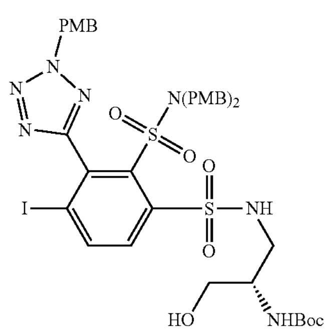 | (S)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl)carbamate | 964 |

| Ex # | Structure | Chemical Name | LC/MS [M + H]+ |
|---|---|---|---|
| 74 | 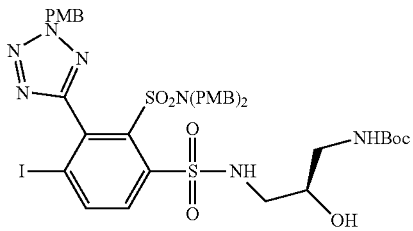 | (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl)carbamate | 964 |
| 75 | 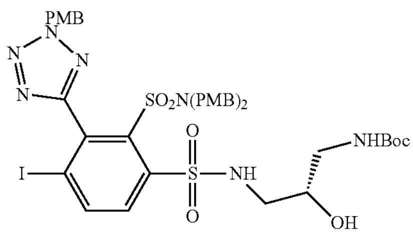 | (S)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl)carbamate | 964 |
| 76 | 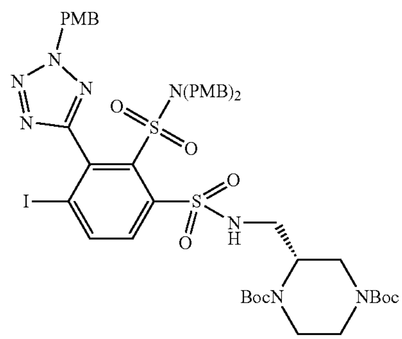 | (S)-di-tert-butyl 2-((2-(N,N-bis(4-methoxybenzyl)sulfamoyl)-4-iodo-3-(2-(4-methoxybenzyl)-2H-tetrazol-5-yl)phenylsulfonamido)methyl)piperazine-1,4-dicarboxylate | 1089 |
| 77 | 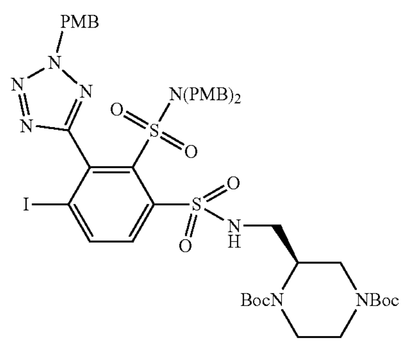 | (R)-di-tert-butyl 2-((2-(N,N-bis(4-methoxybenzyl)sulfamoyl)-4-iodo-3-(2-(4-methoxybenzyl)-2H-tetrazol-5-yl)phenylsulfonamido)methyl)piperazine-1,4-dicarboxylate | 1089 |
| 78 | 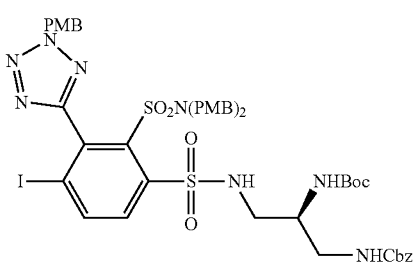 | (S)-benzyl tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate | 1097 |

-continued

| Ex # | Structure | Chemical Name | LC/MS [M + H]+ |
|---|---|---|---|
| 79 | 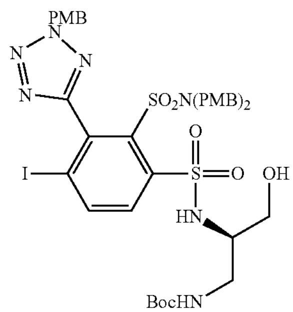 | (R)-tert-butyl (2-(2-(N,N-bis(4-methoxybenzyl)sulfamoyl)-4-iodo-3-(2-(4-methoxybenzyl)-2H-tetrazol-5-yl)phenylsulfonamido)-3-hydroxypropyl)carbamate | 964 |
| 80 | 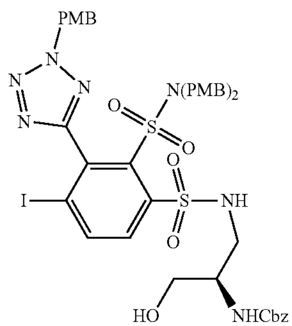 | (R)-benzyl (1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl)carbamate | 998 |
| 81 (R) form | 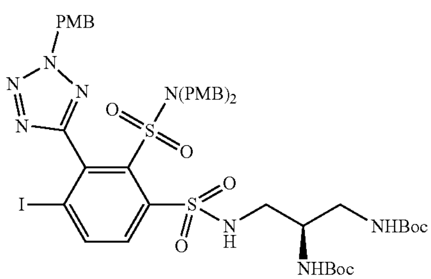 | (R)-di-tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate | 1063 |
| 81 (S) form | 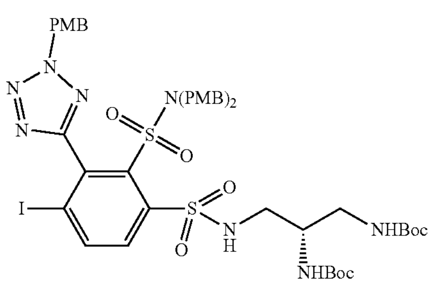 | (S)-di-tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate | |
| 82 | 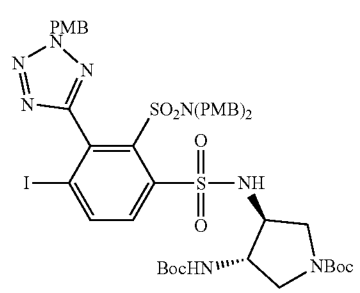 | (3R,4S)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)-4-((tert-butoxycarbonyl)amino)pyrrolidine-1-carboxylate | 1075 |

| Ex # | Structure | Chemical Name | LC/MS [M + H]+ |
|---|---|---|---|
| 83 | 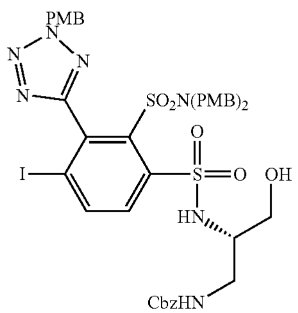 | (S)-benzyl (2-(2-(N,N-bis(4-methoxybenzyl)sulfamoyl)-4-iodo-3-(2-(4-methoxybenzyl)-2H-tetrazol-5-yl)phenylsulfonamido)-3-hydroxypropyl)carbamate | 998 |
| 84 | 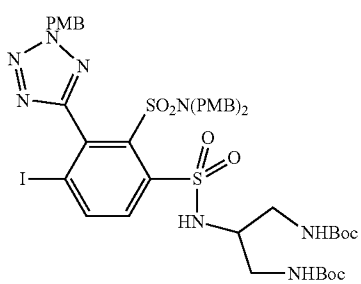 | di-tert-butyl (2-(2-(N,N-bis(4-methoxybenzyl)sulfamoyl)-4-iodo-3-(2-(4-methoxybenzyl)-2H-tetrazol-5-yl)phenylsulfonamido)propane-1,3-diyl)dicarbamate | 1063 |
| 85 | 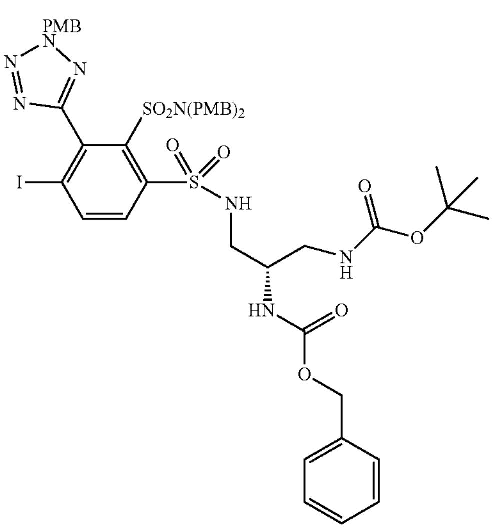 | benzyl tert-butyl (3-((2-(N,N-bis(4-methoxybenzyl)sulfamoyl)-4-iodo-3-(2-(4-methoxybenzyl)-2H-tetrazol-5-yl)phenyl)sulfonamido)porpane-1,2-diyl)(S)-dicarbamate | |

Reference Example 86 tert-butyl (S)-(2-((2-(N,N-bis(4-methoxybenzyl)
sulfamoyl)-4-iodo-3-(1-(4-methoxybenzyl)-1H-tetrazol-5-yl)phenyl)sulfonamido)propyl)carbamate and
tert-butyl (S)-(2-((2-(N,N-bis(4-methoxybenzyl)
sulfamoyl)-4-iodo-3-(2-(4-methoxybenzyl)-2H-tetrazol-5-yl)phenyl)sulfonamido)propyl)carbamate

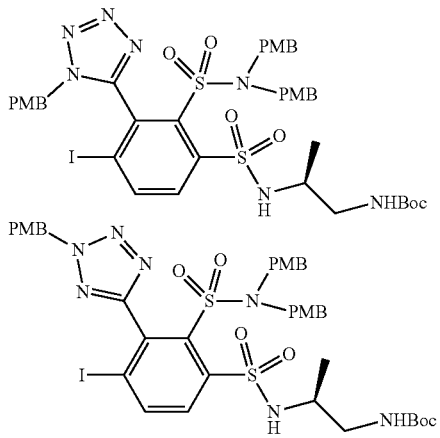

The title compounds were prepared in the same way as REFERENCE EXAMPLE 69 using tert-butyl (S)-(2-aminopropyl)carbamate. LC/MS [M+H]+: 948.45.

Reference Example 87 tert-butyl (S)-(2-amino-3-hydroxypropyl)carbamate

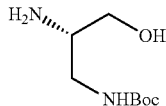

To a solution of (S)-benzyl tert-butyl (3-hydroxypropane-1,2-diyl)dicarbamate (1.5 g, 4.62 mmol) in 20 ml of ethanol was added Pd/C (0.325 g, 0.231 mmol). The mixture was stirred at 45 psi of H$_2$ for 4 hours. The volatile was removed in vacuo and the residue was dissolved in 10 mL of EtOAc, then concentrated again to give the desired product as a a powder. LC/MS [M+H]+: 191.22.

Reference Example 88 tert-butyl (S)-(2-((2-(N,N-bis(4-methoxybenzyl)
sulfamoyl)-4-iodo-3-(1-(4-methoxybenzyl)-1H-tetrazol-5-yl)phenyl)sulfonamido)-3-hydroxypropyl)carbamate and tert-butyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)-3-hydroxypropyl)carbamate

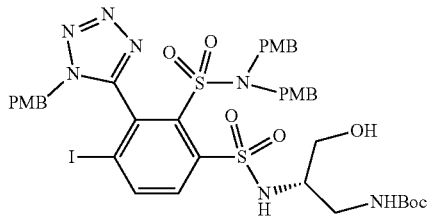

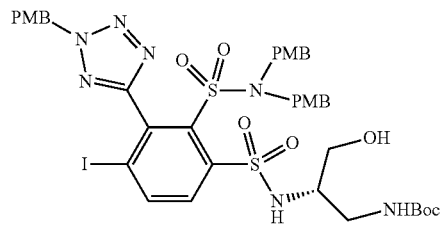

The title compounds were prepared in the same way as REFERENCE EXAMPLE 69 using tert-butyl (S)-(2-amino-3-hydroxypropyl)carbamate. LC/MS [M+H]+: 964.58.

Reference Example 89 tert-butyl (2S,4R)-4-((2-(N,N-bis(4-methoxybenzyl)
sulfamoyl)-4-iodo-3-(1-(4-methoxybenzyl)-2H-tetrazol-5-yl)phenyl)sulfonamido)-2-(hydroxymethyl)
pyrrolidine-1-carboxylate and tert-butyl (2S,4R)-4-
((2-(N,N-bis(4-methoxybenzyl)sulfamoyl)-4-iodo-3-
(2-(4-methoxybenzyl)-2H-tetrazol-5-yl)phenyl)
sulfonamido)-2-(hydroxymethyl)pyrrolidine-1-
carboxylate

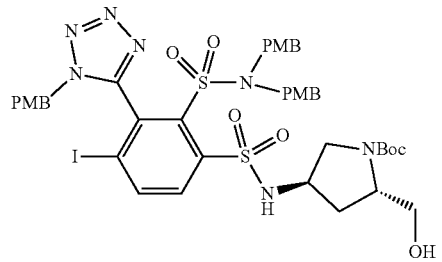

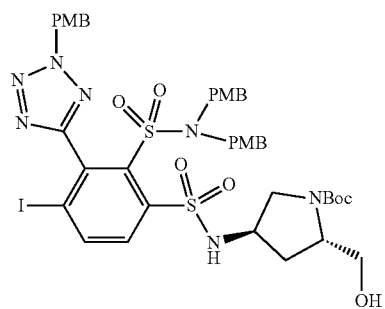

The title compounds were prepared in the same way as REFERENCE EXAMPLE 69 using commercially available tert-butyl (2S,4R)-4-amino-2-(hydroxymethyl)pyrrolidine-1-carboxylate. LC/MS [M+H]+: 990.31.

Reference Example 90

2-(N,N-bis(4-methoxybenzyl)sulfamoyl)-4-(6-((tert-butoxycarbonyl)amino)pyridin-3-yl)-3-(2-(4-methoxybenzyl)-2H-tetrazol-5-yl)benzenesulfinic acid

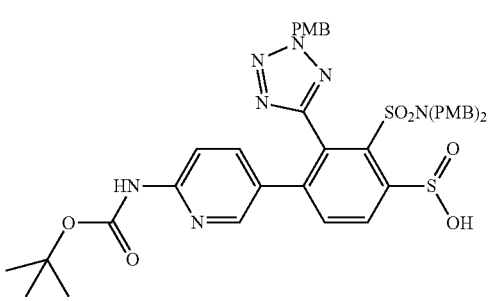

Step A. tert-butyl (5-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)pyridin-2-yl)carbamate (6-((tert-butoxycarbonyl)amino)pyridin-3-yl)boronic acid (0.707 g, 2.97 mmol) and sodium carbonate (0.726 g, 6.85 mmol) and Pd(dppf)Cl$_2$ (0.373 g, 0.457 mmol) were added to a stirred solution of starting material 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (2.0 g, 2.283 mmol) in dioxane (16 mL) and water (4 ml) at room temp. and the mixture was degased for 5 minutes and then stirred at 90° C. overnight. The mixture was diluted with water (50 mL), extracted with EtOAc (2×50 mL). The combined organic phases were washed with brine, dried (MgSO$_4$) and concentrated under reduced pressure. The residue was purified by column chromatography on silica gel 120 g, eluting with EtOAc/isohexane, 0-40% in 30 minutes to give the product as a foam. LC/MS [M+H]+: 942.

Step B. 2-(N,N-bis(4-methoxybenzyl)sulfamoyl)-4-(6-((tert-butoxycarbonyl)amino)pyridin-3-yl)-3-(2-(4-methoxybenzyl)-2H-tetrazol-5-yl)benzenesulfinic acid A solution of tert-butyl (5-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)pyridin-2-yl)carbamate (1.76 g, 1.87 mmol) in THF (16 mL) was stirred with TBAF (4.11 mL, 4.11 mmol) at RT under N$_2$ for 30 minutes. The mixture was diluted with EtOAc, washed with KHSO$_4$ aqueous (3×), dried over MgSO$_4$, and concentrated to give the product. LC/MS [M+H]+: 842.

Reference Example 91

3'-(5-amino-1H-1,2,4-triazol-3-yl)-3-(N,N-bis(4-methoxybenzyl)sulfamoyl)-2-(2-(4-methoxybenzyl)-2H-tetrazol-5-yl)-[1,1'-biphenyl]-4-sulfinic acid

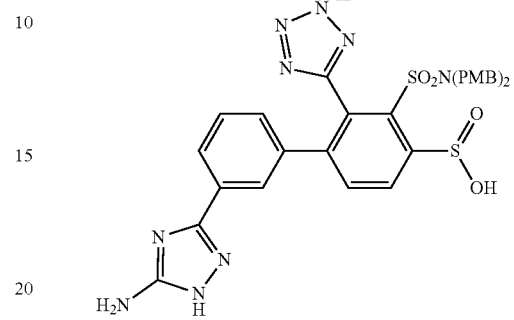

Step A. (3-(5-amino-1H-1,2,4-triazol-3-yl)phenyl)boronic acid

Potassium acetate (1.232 g, 12.55 mmol) and PCy3 Pd G2 (0.371 g, 0.627 mmol), 4,4,4',4',5,5,5',5'-octamethyl-2,2'-bi(1,3,2-dioxaborolane) (2.124 g, 8.37 mmol), were added to a stirred solution of starting material 3-(3-bromophenyl)-1H-1,2,4-triazol-5-amine (1.0 g, 4.18 mmol) in dimethyl sulfoxide (15 mL) at room temp. and the mixture was stirred at 90° C. overnight. The reaction mixture was filtered through a pad of CELITE, diluted with water (100 mL) and extracted with EtOAc (3×100 mL). The residue was purified by reverse phase LC column chromatography on silica gel 240 g C18, eluting with Acetonitrile/Water, 0-100% in 45 minutes to give desired product. LC/MS [M+H]+: 205.

Step B. 3'-(5-amino-1H-1,2,4-triazol-3-yl)-N,N-bis(4-methoxybenzyl)-2-(2-(4-methoxybenzyl)-2H-tetrazol-5-yl)-4-((2-(trimethylsilyl)ethyl)sulfonyl)-[1,1'-biphenyl]-3-sulfonamide The mixture of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (1.0 g, 1.142 mmol), (3-(5-amino-1H-1,2,4-triazol-3-yl)phenyl)boronic acid (0.419 g, 2.055 mmol), Na$_2$CO$_3$ (0.363 g, 3.43 mmol) and 1,1'-bis(diphenylphosphino)ferrocene-palladium(ii)dichloride dichloromethane complex (0.140 g, 0.171 mmol) in dioxane (10 mL) and water (2 mL) was degassed with N$_2$ for 5 minutes. The resulting mixture was stirred at 95° C. for 16 hours. This reaction was filtered and extracted with EtOAc (2×100 mL), organic phase was dried (MgSO$_4$), and concentrated. The residue was purified by column chromatography on silica gel 40 g, eluting with EtOAc/isohexane, B=0-100% in 45 min to give the title compound. LC/MS [M+H]+: 909.

Step C. 3'-(5-amino-1H-1,2,4-triazol-3-yl)-3-(N,N-bis(4-methoxybenzyl)sulfamoyl)-2-(2-(4-methoxybenzyl)-2H-tetrazol-5-yl)-[1,1'-biphenyl]-4-sulfinic acid TBAF (2.0 mL, 2.0 mmol) was added to a stirred solution of starting material 3'-(5-amino-1H-1,2,4-triazol-3-yl)-N,N- bis(4-methoxybenzyl)-2-(2-(4-methoxybenzyl)-2H-tetrazol-5-yl)-4-((2-(trimethylsilyl)ethyl)sulfonyl)-[1,1'-biphenyl]-3-sulfonamide (855 mg, 0.941 mmol) in THF at 0° C. and the mixture was stirred at 0° C. for 45 minutes. The mixture was diluted with KHSO$_4$ (saturated, 3×40 mL) and was extracted with EtOAc (3×40 mL). The organic phase was concentrated to give the title compound. LC/MS [M+H]+: 809.

Reference Example 92 benzyl tert-butyl (3-aminopropane-1,2-diyl)(S)-dicarbamate

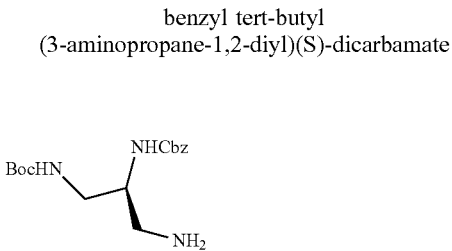

This intermediate was prepared in an analogous fashion to (R)-benzyl tert-butyl (3-aminopropane-1,2-diyl)dicarbamate (REFERENCE EXAMPLE 20) using (R)-benzyl tert-butyl (3-hydroxypropane-1,2-diyl)dicarbamate. LC/MS [M+H]$^+$: 324.42.

Reference Example 93 benzyl tert-butyl (3-((2-(N,N-bis(4-methoxybenzyl)sulfamoyl)-4-iodo-3-(1-(4-methoxybenzyl)-1H-tetrazol-5-yl)phenyl)sulfonamido)propane-1,2-diyl)(R)-dicarbamate and benzyl tert-butyl (3-((2-(N,N-bis(4-methoxybenzyl)sulfamoyl)-4-iodo-3-(2-(4-methoxybenzyl)-2H-tetrazol-5-yl)phenyl)sulfonamido)propane-1,2-diyl)(R)-dicarbamate

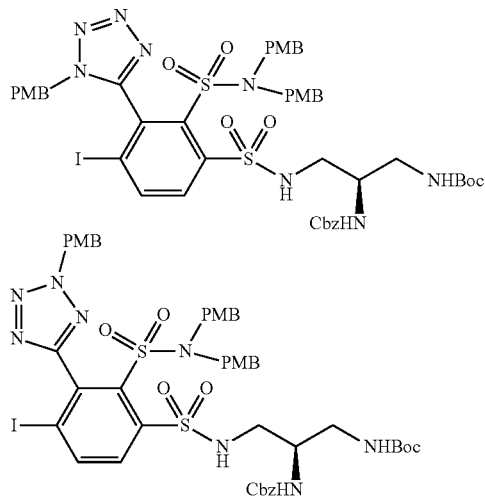

The title compounds were prepared in an analogous fashion to REFERENCE EXAMPLE 69 using benzyl tert-butyl (3-aminopropane-1,2-diyl)(S)-dicarbamate. LC/MS [M+H]$^+$: 1097.98.

Reference Example 94 tert-butyl (3S,4R)-3-((2-(N,N-bis(4-methoxybenzyl)sulfamoyl)-4-iodo-3-(1-(4-methoxybenzyl)-1H-tetrazol-5-yl)phenyl)sulfonamido)-4-hydroxypyrrolidine-1-carboxylate and tert-butyl (3S,4R)-3-((2-(N,N-bis(4-methoxybenzyl)sulfamoyl)-4-iodo-3-(2-(4-methoxybenzyl)-2H-tetrazol-5-yl)phenyl)sulfonamido)-4-hydroxypyrrolidine-1-carboxylate

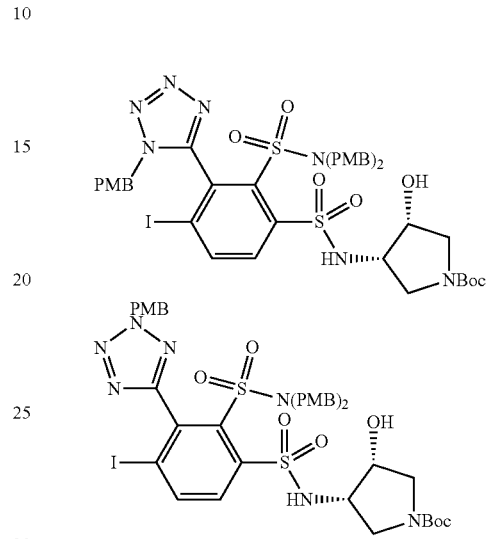

The title compounds were prepared in an analogous fashion to REFERENCE EXAMPLE 69 using commercially available tert-butyl (3S,4R)-3-amino-4-hydroxypyrrolidine-1-carboxylate. LC/MS [M+H]$^+$: 976.30.

Reference Example 95 tert-butyl (3R,4S)-3-((2-(N,N-bis(4-methoxybenzyl)sulfamoyl)-4-iodo-3-(1-(4-methoxybenzyl)-1H-tetrazol-5-yl)phenyl)sulfonamido)-4-hydroxypyrrolidine-1-carboxylateand tert-butyl (3R,4S)-3-((2-(N,N-bis(4-methoxybenzyl)sulfamoyl)-4-iodo-3-(2-(4-methoxybenzyl)-2H-tetrazol-5-yl)phenyl)sulfonamido)-4-hydroxypyrrolidine-1-carboxylate

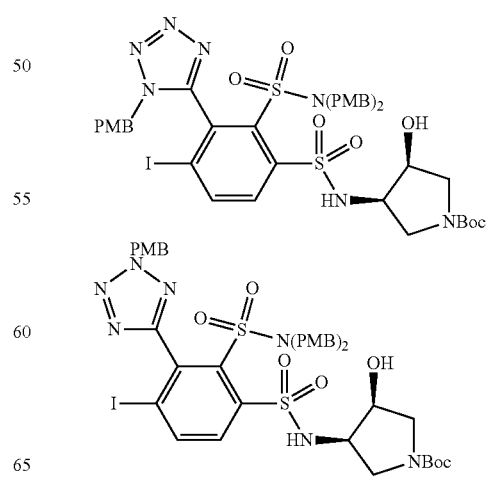

The title compounds were prepared in an analogous fashion to REFERENCE EXAMPLE 69 using commercially available tert-butyl (3S,4R)-3-amino-4-hydroxypyrrolidine-1-carboxylate. LC/MS [M+H]⁺: 976.44.

Reference Example 96 tert-butyl (3-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (3-((2-(N,N-bis(4-methoxybenzyl)sulfamoyl)-4-iodo-3-(2-(4-methoxybenzyl)-1H-tetrazol-5-yl)phenyl)sulfonamido)propyl)carbamate

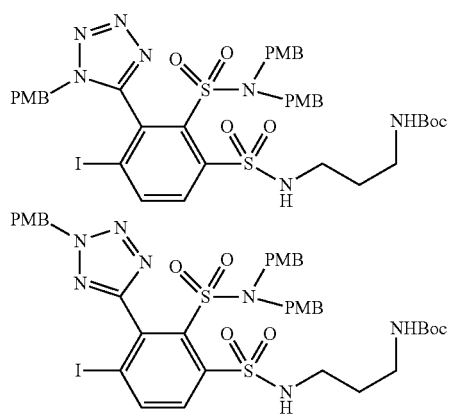

The title compounds were prepared in an analogous fashion to REFERENCE EXAMPLE 69 using tert-butyl (3-aminopropyl)carbamate. LC/MS [M+H]⁺: 948.45.

Reference Example 97 tert-butyl (R)-(1-((2-(N,N-bis(4-methoxybenzyl)sulfamoyl)-4-iodo-3-(1-(4-methoxybenzyl)-1H-tetrazol-5-yl)phenyl)sulfonamido)propan-2-yl)carbamate and tert-butyl (R)-(1-((2-(N,N-bis(4-methoxybenzyl)sulfamoyl)-4-iodo-3-(2-(4-methoxybenzyl)-1H-tetrazol-5-yl)phenyl)sulfonamido)propan-2-yl)carbamate

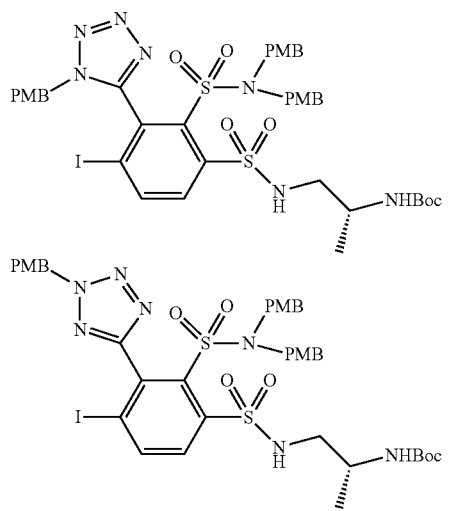

The title compounds were prepared in an analogous fashion to REFERENCE EXAMPLE 69 using tert-butyl (R)-(1-aminopropan-2-yl)carbamate. LC/MS [M+H]⁺: 948.49.

Reference Example 98 tert-butyl (S)-(1-((2-(N,N-bis(4-methoxybenzyl)sulfamoyl)-4-iodo-3-(1-(4-methoxybenzyl)-1H-tetrazol-5-yl)phenyl)sulfonamido)propan-2-yl)carbamate and tert-butyl (S)-(1-((2-(N,N-bis(4-methoxybenzyl)sulfamoyl)-4-iodo-3-(2-(4-methoxybenzyl)-1H-tetrazol-5-yl)phenyl)sulfonamido)propan-2-yl)carbamate

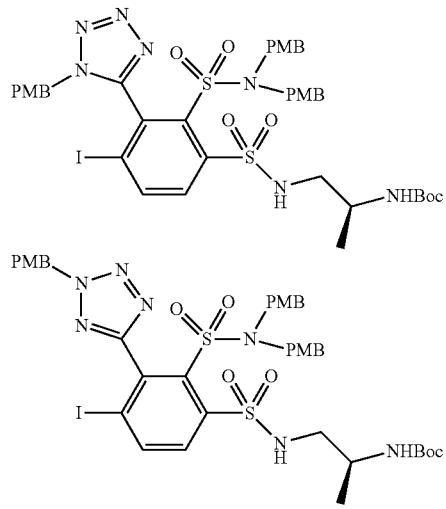

The title compounds were prepared in an analogous fashion to REFERENCE EXAMPLE 69 using tert-butyl (S)-(1-aminopropan-2-yl)carbamate. LC/MS [M+H]⁺: 948.37.

Reference Example 99 tert-butyl (3R,4R)-3-(((2-(N,N-bis(4-methoxybenzyl)sulfamoyl)-4-iodo-3-(1-(4-methoxybenzyl)-1H-tetrazol-5-yl)phenyl)sulfinyl)amino)-4-((tert-butoxycarbonyl)amino)pyrrolidine-1-carboxylate and tert-butyl (3R,4R)-3-(((2-(N,N-bis(4-methoxybenzyl)sulfamoyl)-4-iodo-3-(2-(4-methoxybenzyl)-1H-tetrazol-5-yl)phenyl)sulfinyl)amino)-4-((tert-butoxycarbonyl)amino)pyrrolidine-1-carboxylate

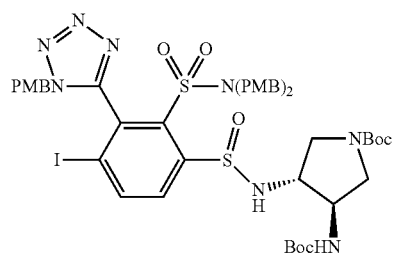

-continued

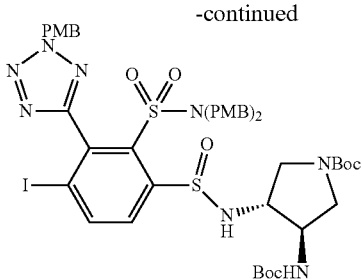

The title compounds were prepared in an analogous fashion to REFERENCE EXAMPLE 69 using commercially available tert-butyl ((3R,4R)-4-amino-1-benzylpyrrolidin-3-yl)carbamate. LC/MS [M+H]$^+$: 1065.77.

Reference Example 100 tert-butyl (2S,4R)-4-amino-2-((1,3-dioxoisoindolin-2-yl)methyl)pyrrolidine-1-carboxylate

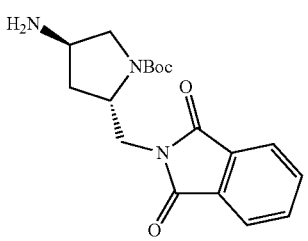 [SMILES: CC(C)(C)OC(=O)N1C[C@H](N)C[C@H]1CN1C(=O)c2ccccc2C1=O]

Step A: tert-butyl (2S,4R)-4-(((benzyloxy)carbonyl)amino)-2-(hydroxymethyl)pyrrolidine-1-carboxylate To a solution of (2S,4R)-tert-butyl 4-amino-2-(hydroxymethyl)pyrrolidine-1-carboxylate (2.0 g, 9.25 mmol) in dioxane (20 ml) and water (20 ml) was added sodium carbonate (1.176 g, 11.10 mmol) and Cbz-Cl (1.584 ml, 11.10 mmol) at 0° C. The reaction was stirred at room temp. for 2 hours. EtOAc (20 mL) was added. The organic layer was separated, washed with brine, dried (MgSO$_4$), filtered, and concentrated under reduced pressure. The residue was purified by column chromatography on silica gel eluting with 0-100% EtOAc/hexanes to give the title compound. LC-MS: [M+H−56]$^+$: 295.28.

Step B: tert-butyl (2S,4R)-4-(((benzyloxy)carbonyl)amino)-2-((1,3-dioxoisoindolin-2-yl)methyl)pyrrolidine-1-carboxylate To a solution of (2S,4R)-tert-butyl 4-(((benzyloxy)carbonyl)amino)-2-(hydroxymethyl)pyrrolidine-1-carboxylate (2.67 g, 7.62 mmol), PPh$_3$ (2.60 g, 9.91 mmol) and isoindoline-1,3-dione (1.345 g, 9.14 mmol) in THF (40 ml) was added DEAD (2.062 ml, 9.91 mmol) at 0° C. dropwise. The reaction completed in 30 min. The reaction mixture was concentrated in vacuo and the residue was chromatographed over silic gel eluting with 0-60% EtOAc in hexanes to give the desired product (2S,4R)-tert-butyl 4-(((benzyloxy)carbonyl)amino)-2-((1,3-dioxoisoindolin-2-yl)methyl)pyrrolidine-1-carboxylate. LC-MS: [M+H]$^+$: 480.29.

Step C: tert-butyl (2S,4R)-4-amino-2-((1,3-dioxoisoindolin-2-yl)methyl)pyrrolidine-1-carboxylate To a solution of (2S,4R)-tert-butyl 4-(((benzyloxy)carbonyl)amino)-2-((1,3-dioxoisoindolin-2-yl)methyl)pyrrolidine-1-carboxylate (3.0 g, 6.26 mmol) in 20 ml of ethanol was added Pd/C (0.44 g, 0.313 mmol), the mixture was stirred at 45 psi of H$_2$ for 8 hours. The catalyst was removed by filting through a CELITE pad. The filtrate was concentrated and chromatographed over silica gel eluting with 0-20% MeOH in DCM to give the desired product. LC-MS [M+H]$^+$: 346.41.

Reference Example 101 tert-butyl (2S,4R)-4-(((2-(N,N-bis(4-methoxybenzyl)sulfamoyl)-4-iodo-3-(1-(4-methoxybenzyl)-1H-tetrazol-5-yl)phenyl)sulfinyl)amino)-2-((1,3-dioxoisoindolin-2-yl)methyl)pyrrolidine-1-carboxylate and tert-butyl (2S,4R)-4-(((2-(N,N-bis(4-methoxybenzyl)sulfamoyl)-4-iodo-3-(2-(4-methoxybenzyl)-2H-tetrazol-5-yl)phenyl)sulfinyl)amino)-2-((1,3-dioxoisoindolin-2-yl)methyl)pyrrolidine-1-carboxylate

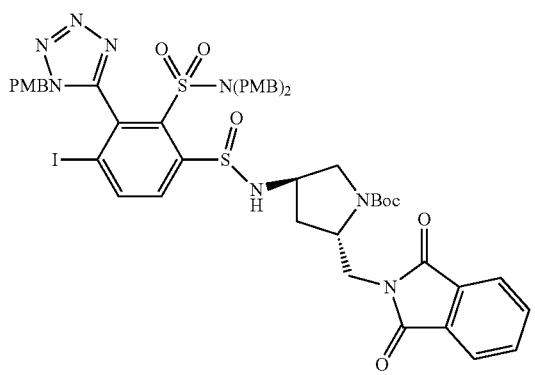

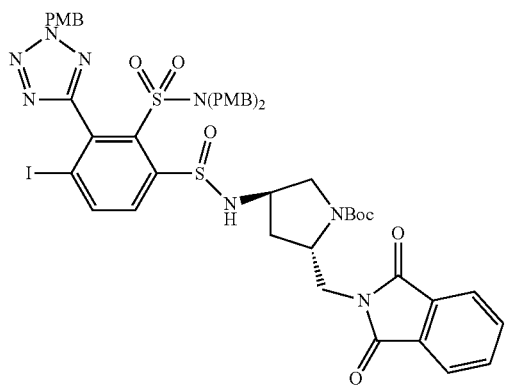

This intermediate was prepared in an analogous fashion to REFERENCE EXAMPLE 69 using tert-butyl (2S,4R)-4-amino-2-((1,3-dioxoisoindolin-2-yl)methyl)pyrrolidine-1-carboxylate. LC/MS [M+H]$^+$: 1120.07.

Reference Example 102

(3-(2-Amino-1H-imidazol-4-yl)phenyl)boronic acid

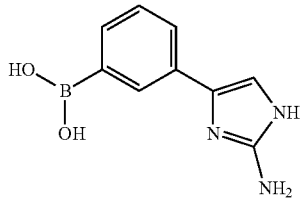 [SMILES: Nc1nc(-c2cccc(B(O)O)c2)c[nH]1]

Step A: N-(4-(3-Bromophenyl)-1H-imidazol-2-yl)acetamide

2-Bromo-1-(3-bromophenyl)ethanone (3000 mg, 10.79 mmol) was stirred with N-carbamimidoylacetamide (3274 mg, 32.4 mmol) in DMF (8995 µl) at room temperature for 48 h. The reaction mixture was diluted with EtOAc and washed with saturated NH$_4$Cl aqueous solution and brine. The organic layer was separated and concentrated and the resulting residue was purified by column chromatography (eluting with 0-100% EtOAc/hexane) to give the title compound. LC/MS [M+H]+: 280.1, 282.1.

Step B: 4-(3-Bromophenyl)-1H-imidazol-2-amine

N-(4-(3-Bromophenyl)-1H-imidazol-2-yl)acetamide (1.2 g, 4.28 mmol) was dissolved in MeOH (8 mL), and HCl in dioxane (4 N, 8 mL) and water (8 mL) were added. The mixture was heated at 100° C. in a sealed bottle for 1 hour. LC-MS showed that the acyl group was removed. The reaction was cooled and concentrated to remove the solvents. The resulting residue was dissolved in MeOH, and purified by column chromatography (eluting with 100% hexane to 100% EtOAc/EtOH (3/1) to hexane) to give the title compound. LC/MS [M+H]+: 238.1, 240.1

Step C: (3-(2-Amino-1H-imidazol-4-yl)phenyl)boronic acid 4-(3-Bromophenyl)-1H-imidazol-2-amine (561 mg, 2.356 mmol), 5,5,5',5'-tetramethyl-2,2'-bi(1,3,2-dioxaborinane) (1331 mg, 5.89 mmol), Ph$_3$PPdG2 (202 mg, 0.353 mmol), and potassium acetate (925 mg, 9.43 mmol) were placed in a vial, Dioxane (3927 µl) was added. The reaction was degassed for 20 min, then heated at 90° C. for 1 h. The reaction was then cooled to room temperature, and filtered. The filtrates were concentrated and the residue was purified with reverse C18 column eluting with 0-60% CH3CN/water. The correct fractions were combined and lypholized. LC/MS [M+H]+: 204.2.

Reference Example 103

(3-(2-Amino-5-(ethoxycarbonyl)thiazol-4-yl)phenyl)boronic acid

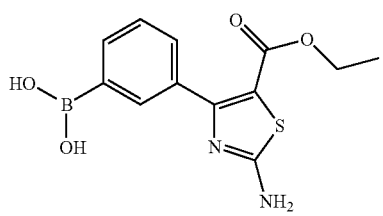 [SMILES: CCOC(=O)c1sc(N)nc1-c1cccc(B(O)O)c1]

Step A: Ethyl 2-bromo-3-(3-bromophenyl)-3-oxopropanoat

Ethyl 3-(3-bromophenyl)-3-oxopropanoate (3.72 g, 13.72 mmol) was dissolved in DCM (35.4 ml), and 1-bromopyrrolidine-2,5-dione (2.93 g, 16.47 mmol) was added. The reaction mixture was stirred at room temperature under N$_2$ for 6 hours. The reaction mixture was partitioned between DCM and saturated NaHCO3 aqueous solution. The organic layer was separated, concentrated and purified by column chromatography (eluting with 0-20% EtOAc/hexane) to give the title compound. LC/MS [M+H]+: 351.2.

Step B: Ethyl 2-amino-4-(3-bromophenyl)thiazole-5-carboxylate

Ethyl 2-bromo-3-(3-bromophenyl)-3-oxopropanoate (3.26 g, 9.31 mmol) and thiourea (0.723 g, 9.50 mmol) were heated in ethanol (74.5 ml) at 75° C. for 1 h. LC-MS showed the formation of the desired product. The reaction mixture was concentrated and partitioned between DCM and water. The organic layer was separated, washed with brine, and concentrated to afford the title compound. LC/MS [M+H]+: 327.2, 329.2.

Step C: (3-(2-amino-5-(ethoxycarbonyl)thiazol-4-yl)phenyl)boronic acid

Ethyl 2-amino-4-(3-bromophenyl)thiazole-5-carboxylate (250 mg, 0.764 mmol), 5,5,5',5'-tetramethyl-2,2'-bi(1,3,2-dioxaborinane) (431 mg, 1.910 mmol), Ph$_3$PPdG2 (65.6 mg, 0.115 mmol), and potassium acetate (300 mg, 3.06 mmol) were placed in a reaction vial. Dioxane (5458 µl) was added. The reaction mixture was degassed and heated at 90° for 1 hour 45 minutes. The reaction mixture was cooled to room temperature, and the product was used as crude for the next step. LC/MS [M+H]+: 293.2.

Reference Example 104

(3-(2-((tert-Butoxy carbonyl)amino)-5-(((ter t-butoxycarbonyl)amino)methyl)thiazol-4-yl)phenyl) boronic acid

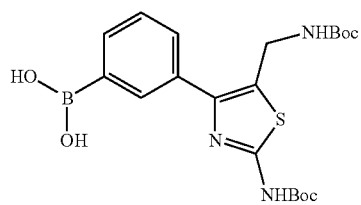 [SMILES: CC(C)(C)OC(=O)NCc1sc(NC(=O)OC(C)(C)C)nc1-c1cccc(B(O)O)c1]

Step A: Ethyl 4-(3-bromophenyl)-2-((tert-butoxycarbonyl)amino)thiazole-5-carboxylate Ethyl 2-amino-4-(3-bromophenyl)thiazole-5-carboxylate (Step B, Intermediate 103) (2 g, 6.11 mmol) was suspended in THF (30.6 ml). DMAP (0.075 g, 0.611 mmol) was added followed by BOC-Anhydride (3.12 ml, 13.45 mmol). The mixture was stirred at room temperature under $N_2$ for 1 h. LC-MS showed the reaction was completed. The reaction was partitioned between EtOAc and water. The organic layer was separated and concentrated and the residue was purified by column chromatography (100% hexane to 25% EtOAc/Hexane) to give the title compound. LC/MS [M+H]+: 427.3, 429.3.

Step B: tert-Butyl (4-(3-bromophenyl)-5-(hydroxymethyl)thiazol-2-yl)carbamate Ethyl 4-(3-bromophenyl)-2-((tert-butoxycarbonyl)amino) thiazole-5-carboxylate (1.17 g, 2.74 mmol) was suspended in DCM (21.06 ml) and cooled to −78° C. DIBAL-H (8.21 ml, 8.21 mmol) (1.0 M in toluene) was added dropwise under $N_2$. The mixture was allowed to warm up to room temperature for 12 hours. LC-MS showed about ⅓ of starting material remained. The reaction was cooled to −78° C., another 1.5 eq of DIBAL (4 mL, 1.0M in toluene) was added. The reaction mixture was stirred at −78° C. for 1 hour and then the cold bath was removed and the reaction mixture was warmed to room temperature. The reaction was quenched with EtOAc and MeOH. The resulting mixture was stirred with CELITE and filtered. The filter cake was washed with MeOH. The filtrates were concentrated and the rsidue was purified by column chromatography (100% hexane to 40% EtOAc/Hexane) to give the product. LC/MS [M+H]+: 385.3, 387.3.

Step C: tert-Butyl (5-(azidomethyl)-4-(3-bromophenyl)thiazol-2-yl)carbamate tert-Butyl (4-(3-bromophenyl)-5-(hydroxymethyl)thiazol-2-yl)carbamate (450 mg, 1.168 mmol) in DCM (1.17E+04 µl) was treated with DIEA (306 µl, 1.752 mmol) and cooled to −78° C. Ms-Cl (109 µl, 1.402 mmol) was added under $N_2$. After stirred at −78° C. for 5 minutes, the reaction mixture was allowed to warm up to room temperature and stirred at room temp. for 1 hour. The reaction mixture was concentrated and redissolved in DMF (4 mL). Sodium azide (228 mg, 3.50 mmol) was added. The mixture was heated at 80° C. for 20 minutes and continued to stir at room temperature for 12 hours. LC-MS showed that majority of starting material was converted to the product. The reaction was partitioned between EtOAc and water. The organic layer was seaparated and concentrated. The resulting residue was purified by column chromatography (100% hexane to 45% then to 80% EtOAc/Hexane) to give the title compound. LC/MS [M+H]+: 410.2, 412.2.

Step D: tert-Butyl ((4-(3-bromophenyl)-2-((tert-butoxycarbonyl)amino)thiazol-5-yl)methyl)carbamate tert-Butyl (5-(azidomethyl)-4-(3-bromophenyl)thiazol-2-yl)carbamate (195 mg, 0.475 mmol) was dissolved in THF (1584 µl). Triphenylphosphine (249 mg, 0.951 mmol) and water (1 ml) were added. The mixture was stirred at 60° C. for 12 hours under $N_2$. LC-MS showed the desired mass. BOC-Anhydride (221 µl, 0.951 mmol) and 1 mL of saturtaed $NaHCO_3$ aqueous solution were added. The reaction was stirred at room temperature under $N_2$ for 1 hour. LC-MS showed the formation of the desired product. The reaction mixture was partitioned between EtOAc and water. The organic layer was separated and concentrated and the resulting residue was purified by column chromatography (100% hexane to 100% EtOAc/EtOH (3/1)) to give the title compound. LC/MS [M+H]+: 484.4, 486.4

Step E: (3-(2-((tert-Butoxycarbonyl)amino)-5-(((tert-butoxycarbonyl)amino)methyl)thiazol-4-yl) phenyl)boronic acid tert-Butyl ((4-(3-bromophenyl)-2-((tert-butoxycarbonyl) amino)thiazol-5-yl)methyl)carbamate (148 mg, 0.306 mmol), 5,5,5′,5′-tetramethyl-2,2′-bi(1,3,2-dioxaborinane) (173 mg, 0.764 mmol), $Ph_3PPdG2$ (26.2 mg, 0.046 mmol), and potassium acetate (120 mg, 1.222 mmol) were placed in a reaction vial. Dioxane (2182 µl) was added. The reaction was degassed and heated at 90° for 45 minutes. The reaction mixture was cooled to room temp., and used directly in the next reaction. LC/MS [M+H]+: 450.5.

Reference Example 105

(3-(2-((tert-Butoxycarbonyl)amino)-5-(((2-((tert-butoxycarbonyl)amino)ethyl)amino)methyl)thiazol-4-yl)phenyl)boronic acid

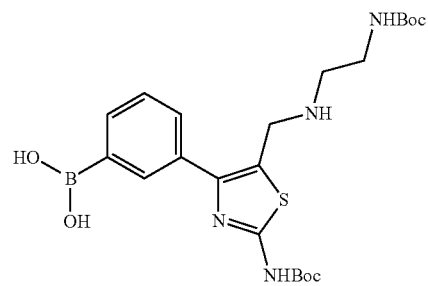 [SMILES: CC(C)(C)OC(=O)NCCNCc1sc(NC(=O)OC(C)(C)C)nc1-c1cccc(B(O)O)c1]

Step A: tert-Butyl (4-(3-bromophenyl)-5-(((2-((tert-butoxycarbonyl)amino)ethyl)amino)methyl) thiazol-2-yl)carbamate tert-Butyl (4-(3-bromophenyl)-5-(hydroxymethyl)thiazol-2-yl)carbamate (Step B REFERENCE EXAMPLE 104) (320 mg, 0.831 mmol) in DCM (8306 μl) was cooled to −78° C. and treated with triethylamine (109 mg, 1.080 mmol), and Ms-Cl (78 μl, 0.997 mmol) was added under $N_2$. After stirring at −78° C. for 20 minutes, the reation mixture was allowed to warm to room temperature. tert-Butyl (2-aminoethyl)carbamate (266 mg, 1.661 mmol) was then added. After the reaction was stirred at room temperature for 15 min, LC-MS showed the desired mass, and the major product was the reactive intermediate. Excess amount of tert-butyl (2-aminoethyl)carbamate was added. The reaction mixture was stirred at room temperature under $N_2$ for 40 min. The reaction mixture was concentrated and the residue was purified by column chromatography twice (100% hexane to 50% EtOAc/Hexane) to give the title compound. LC/MS [M+H]+: 527.4, 529.4.

Step B: (3-(2-((tert-Butoxycarbonyl)amino)-5-(((2-((tert-butoxycarbonyl)amino)ethyl)amino)methyl) thiazol-4-yl)phenyl)boronic acid tert-Butyl (4-(3-bromophenyl)-5-(((2-((tert-butoxycarbonyl)amino)ethyl)amino)methyl)thiazol-2-yl)carbamate (135 mg, 0.256 mmol), 5,5,5',5'-tetramethyl-2,2'-bi(1,3,2-dioxaborinane) (145 mg, 0.640 mmol), $Ph_3PPdG2$ (21.97 mg, 0.038 mmol), and potassium acetate (100 mg, 1.024 mmol) were placed in a reaction vial. Dioxane (1828 μl) was added. The reaction mixture was degassed and heated at 90° for 45 minutes. The reaction mixture was cooled to room temperature, and used directly in the next reaction. LC/MS [M+H]+: 493.5.

Reference Example 106 tert-butyl 4-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)-2-(bis(tert-butoxycarbonyl)amino)-1H-benzo[d]imidazole-1-carboxylate and tert-butyl 4-(3-(N,N-bis(4-methoxybenzyl)sulfamoyl)-2-(2-(4-methoxybenzyl)-1H-tetrazol-5-yl)-4-((2-(trimethylsilyl)ethyl)sulfonyl)phenyl)-2-(bis(tert-butoxycarbonyl)amino)-1H-benzo[d]imidazole-1-carboxylate

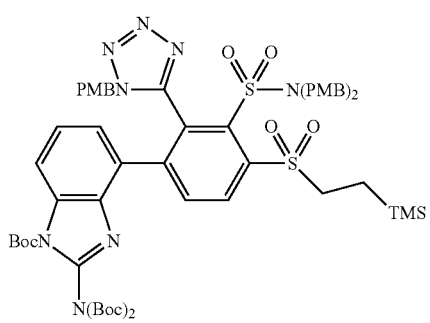

-continued

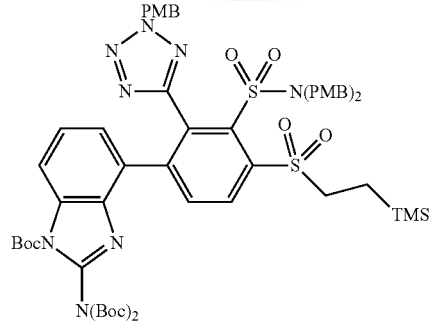

Step A: 3-(2-amino-1H-benzo[d]imidazol-4-yl)-N,N-bis(4-methoxybenzyl)-2-(1-(4-methoxybenzyl)-2H-tetrazol-5-yl)-6-((2-(trimethylsilyl)ethyl)sulfonyl)benzenesulfonamide and 3-(2-amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide A suspension of 3-iodo-N,N-bis(4-methoxybenzyl)-2-(1-(4-methoxybenzyl)-1H-tetrazol-5-yl)-6-((2-(trimethylsilyl)ethyl)sulfonyl)benzenesulfonamide and 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (2.0 g, 2.283 mmol), (2-amino-1H-benzo[d]imidazol-4-yl)boronic acid (0.808 g, 4.57 mmol), $PdCl_2$ (dppf) (0.251 g, 0.343 mmol) and sodium carbonate (0.726 g, 6.85 mmol) in dioxane (30 mL) and water (6 ml) was degassed and heated at 100° C. for 2 hours. The mixture was diluted with 20 ml of EtOAc, then filtered through a CELITE pad. The organic layer was dried ($MgSO_4$) and concentrated. The crude material was purified by silica gel column chromatography eluting with 0-20% methanol in DCM to give the desired product. LC/MS [M+H]$^+$: 881.53.

Step B: tert-butyl 4-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)-2-(bis(tert-butoxycarbonyl)amino)-1H-benzo[d]imidazole-1-carboxylate and tert-butyl 4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-2-(bis(tert-butoxycarbonyl)amino)-1H-benzo[d]imidazole-1-carboxylate To a solution of 3-(2-amino-1H-benzo[d]imidazol-4-yl)-N,N-bis(4-methoxybenzyl)-2-(1-(4-methoxybenzyl)-1H-tetrazol-5-yl)-6-((2-(trimethylsilyl)ethyl)sulfonyl)benzenesulfonamide and 3-(2-amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (1.4 g, 1.589 mmol) in DCM (20 ml) was added N,N-dimethylpyridin-4-amine (0.582 g, 4.77 mmol) and di-tert-butyl dicarbonate (1.040 g, 4.77 mmol) at 0° C. The reaction mixture was stirred at room temp. for 30 minutes. NMR shown conversion to the desired product. The volatile was removed and the residue was chromatographed over silica gel eluting with 0-100% EtOAc in hexanes to give the desired products. [M+H]$^+$: 1181.87.

Reference Example 107

2-((3-(4,4,5,5-tetraethyl-1,3,2-dioxaborolan-2-yl)phenyl)amino) thiazole-4-carboxylate

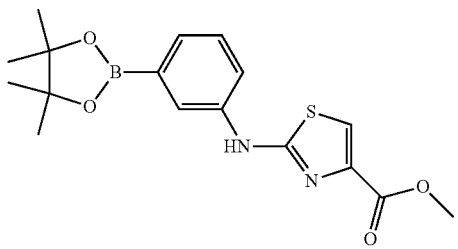

Step A: Methyl 2-((3-bromophenyl)amino)thiazole-4-carboxylate

To a solution of methyl 3-bromo-2-oxopropanoate (3.96 g, 21.89 mmol) in MeOH (200 mL) was added 1-(3-bromophenyl)thiourea (4.6 g, 19.90 mmol) at room temperature. The reaction solution was stirred at 70° C. for 3 hours. The reaction mixture was concentrated under vacuum, and the residue was dissolved in EA (200 mL). The organic layer was washed with saturated aqueous NaHCO$_3$ (3×200 mL), brine (3×200 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+H]$^+$: 313, 315.

Step B: Methyl 2-((3-(4,4,5,5-tetramethyl-1,3,2-dioxaborolan-2-yl)phenyl)amino) thiazole-4-carboxylate To a solution of methyl 2-((3-bromophenyl)amino)thiazole-4-carboxylate (2 g, 6.38 mmol) in 1,4-dioxane (20 mL) were added 4,4,4',4',5,5,5',5'-octamethyl-2,2'-bi (1,3,2-dioxaborolane) (3.24 g, 12.8 mmol), potassium acetate (1.88 g, 19.2 mmol) and 2nd Generation PCy$_3$ precatalyst (0.75 g, 1.278 mmol) at room temperature. The mixture was degassed with nitrogen three times and stirred at 80° C. for 16 hours under nitrogen. The resulting mixture was diluted with water (50 mL) and extracted with EA (3×30 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography, eluted with 75% EA in PE. The fractions containing desired product were combined and concentrated under vacuum to afford the title compound: LCMS [M+H]$^+$: 361.

Reference Example 108

(2-((3-(4,4,5,5-tetramethyl-1,3,2-dioxaborolan-2-yl)phenyl)amino)thiazol-4-yl)methanol

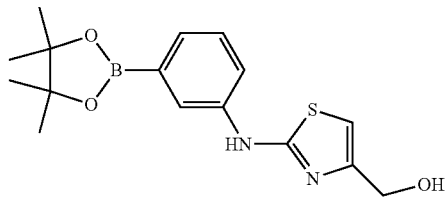 [SMILES: CC1(C)OB(c2cccc(Nc3nc(CO)cs3)c2)OC1(C)C]

Step A: 2-((3-Bromophenyl)amino)thiazole-4-carboxylic acid

To the solution of methyl 2-((3-bromophenyl)amino)thiazole-4-carboxylate (4.5 g, 14.37 mmol) in MeOH (50 mL) and THF (50 mL) was added aqueous NaOH (2 N, 28.7 mL) at room temperature. The reaction mixture was stirred at room temp. for 16 hours. The organic solvent was evaporated under vacuum. The remained aqueous phase was adjusted to pH 5 with 1N HCl and a solid was precipitated. The solid was filtered. The filter cake was washed with water (2×10 mL), dried under an oven to afford the title compound: LCMS [M+1]$^+$: 299, 301 (1:1); $^1$H NMR (400 MHz, DMSO-d$_6$): δ 12.80 (s, 1H), 10.64 (brs, 1H), 8.04-8.01 (m, 1H), 7.75 (s, 1H), 7.59-7.51 (m, 1H), 7.26 (t, J=8.0 Hz, 1H), 7.16-7.11 (m, 1H).

Step B: (2-((3-Bromophenyl)amino)thiazol-4-yl)methanol

A stirred solution of 2-((3-bromophenyl)amino)thiazole-4-carboxylic acid (1.2 g, 4.01 mmol) in THF (10 mL) was degassed with nitrogen three times. Then BH$_3$.THF (20.06 mL, 1 M in THF) was added dropwise to the reaction mixture at 0° C. The resulting mixture was warmed to room temperature and stirred for 16 hours under nitrogen. The resulting mixture was quenched by ice water (100 mL). The aqueous solution NaOH (8 mL, 1N) was added to the mixture and stirred for 2 h. The resulting mixture was extracted with EA (3×100 mL). The combined organic layers were washed with brine (3×100 mL), dried over anhydrous Na$_2$SO$_4$ and filtered. The filtrate was concentrated under vacuum to afford the title compound: LCMS [M+1]+: 285, 287 (1:1).

Step C: (2-((3-(4,4,5,5-Tetramethyl-1,3,2-dioxaborolan-2-yl)phenyl)amino) thiazol-4-yl)methanol To a solution of (2-((3-bromophenyl)amino)thiazol-4-yl)methanol (0.9 g, 3.16 mmol) in 1,4-dioxane (9 mL) were added 4,4,4',4',5,5,5',5'-octamethyl-2,2'-bi (1,3,2-dioxaborolane) (1.6 g, 6.31 mmol), potassium acetate (0.93 g, 9.47 mmol) and 2nd Generation PPh$_3$ precatalyst (0.34 mg, 0.63 mmol) at room temp. The resulting mixture was degassed with nitrogen three times and stirred at 80° C. for 16 hours. The resulting mixture was diluted with water (50 mL) and extracted with EA (3×30 mL). The combined organic layers was washed with water (3×50 mL) and brine (3×50 mL), dried over Na$_2$SO$_4$ and filtered. The filtrate was concentrated Reference Example 109

N-(3-(4,4,5,5-tetramethyl-1,3,2-dioxaborolan-2-yl)phenyl)-1H-imidazol-2-amine

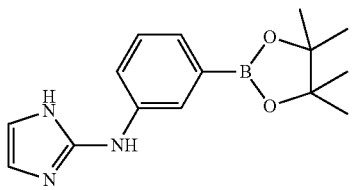 [SMILES: CC1(C)OB(c2cccc(Nc3ncc[nH]3)c2)OC1(C)C]

Step A:
2,2-Diethoxy-N-(iminomethylene)ethanamine

To a stirred solution of the 2,2-diethoxyethanamine (2.5 g, 18.8 mmol) in Et$_2$O (20 mL) and hexane (20 mL) was added cyanic bromide (2.0 g, 18.8 mmol) at 0° C. The reaction mixture was stirred at room temperature for 16 hours. The resulting mixture was filtered and the filtrate was concentrated under vacuum. The residue was purified by silica gel column chromatography, eluted with 5% MeOH in DCM. The fractions containing desired product were combined and concentrated under vacuum to afford the title compound: LCMS [M+1]$^+$: 159; $^1$H NMR (400 MHz, CDCl$_3$): δ 4.59 (t, J=5.2 Hz, 1H), 3.77-3.70 (m, 2H), 3.66-3.53 (m, 2H), 3.18-3.15 (m, 2H), 1.23 (t, J=7.0 Hz, 6H).

Step B:
1-(3-Bromophenyl)-3-(2,2-diethoxyethyl)guanidine

To a solution of 3-bromoaniline (1 g, 5.81 mmol) in EtOH (16 mL) were added the solution of 2,2-diethoxy-N-(iminomethylene)ethanamine (1.8 g, 11.63 mmol) in Et$_2$O (1.6 mL) and methanesulfonic acid (1.1 g, 11.63 mmol) at room temperature. The reaction mixture was stirred at 90° C. for 16 h. The resulting mixture was concentrated under vacuum to afford the title compound. The crude product was used in the next step without further purification: LCMS [M+1]$^+$: 330, 332.

Step C: N-(3-bromophenyl)-1H-imidazol-2-amine 1-(3-Bromophenyl)-3-(2,2-diethoxyethyl)guanidine (0.8 g, 2.42 mmol) was dissolved in conc. HCl (2 mL, 12.00 mmol). The reaction solution was stirred at room temperature for 2 hours. Then aqueous solution NaOH (25%) was added until a precipitate formed (pH=14). The mixture was stirred for 30 minutes. The resulting mixture was poured into aqueous solution NaOH (30 mL, 0.5 M), extracted with DCM (3×20 mL), dried over anhydrous Na$_2$SO$_4$ and filtered. The filtrate was concentrated under vacuum. The crude product was purified by Prep-HPLC with the following conditions: Column: X Bridge Prep C18 OBD Column; Mobile Phase A: water (10 mmoL/L NH$_4$HCO$_3$), Mobile Phase B: ACN; Flow rate: 80 mL/min; Gradient: 0% B to 30% B in 30 min; Detector: UC 254 and 220 nm. The fractions containing desired product were combined and concentrated under vacuum to afford the title compound: LCMS [M+1]$^+$: 238, 240.

Step D: N-(3-(4,4,5,5-tetramethyl-1,3,2-dioxaborolan-2-yl)phenyl)-1H-imidazol-2-amine To a solution of N-(3-bromophenyl)-1H-imidazol-2-amine (0.6 g, 2.52 mmol) in 1,4-dioxane (12 mL) were added 4,4,4',4',5,5,5',5'-octamethyl-2,2'-bi (1,3,2-dioxaborolane) (1.3 g, 5.04 mmol), PCy3 palladium(II) biphenyl-2-amine chloride (0.3 g, 0.50 mmol) and potassium acetate (0.05 g, 0.50 mmol). The reaction mixture was degassed with nitrogen three times and stirred for 16 hours at 80° C. under nitrogen. The resulting mixture was concentrated under vacuum. The residue was purified by silica gel column chromatography, eluted with 50% EA in PE. The fractions containing desired product were combined and concentrated under vacuum to afford the title compound: LCMS [M+1]$^+$: 286

Reference Example 110

2-(N,N-bis(4-methoxybenzyl)sulfamoyl)-4-(2-(((tert-butoxycarbonyl)amino)methyl)-1H-benzo[d]imidazol-4-yl)-3-(2-(4-methoxybenzyl)-2H-tetrazol-5-yl)benzenesulfinic acid

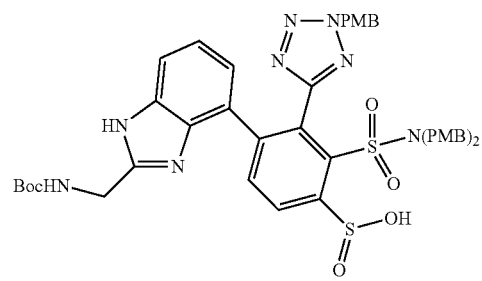

The title compound was prepared in an analogous fashion as described for 2-(N,N-bis(4-methoxybenzyl)sulfamoyl)-4-(6-((tert-butoxycarbonyl)amino)pyridin-3-yl)-3-(2-(4-methoxybenzyl)-2H-tetrazol-5-yl)benzenesulfinic acid (REFERENCE EXAMPLE 90) starting from 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide and tert-butyl ((4-(5,5-dimethyl-1,3,2-dioxaborinan-2-yl)-1H-benzo[d]imidazol-2-yl)methyl)carbamate (REFERENCE EXAMPLE 61). LCMS [M+1]$^+$: 895.

Example 1

4-(2-amino-3H-benzo[d]imidazol-4-yl)-3-(2H-tetrazol-5-yl)benzene-1,2-disulfonamide

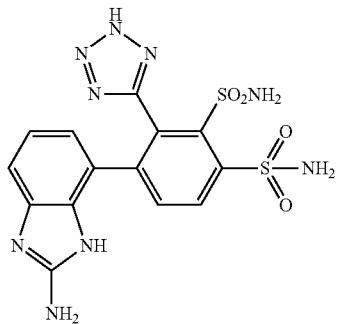 [SMILES: Nc1nc2cccc(-c3ccc(S(N)(=O)=O)c(S(N)(=O)=O)c3-c3nn[nH]n3)c2[nH]1]

Step A: 5-iodo-N$^1$,N$^1$-bis(4-methoxybenzyl)-6-(2-(4-methoxybenzyl)-2H-tetrazol-5-yl)benzene-1,2-disulfonamide and 5-iodo-N$^1$,N$^1$-bis(4-methoxybenzyl)-6-(1-(4-methoxybenzyl)-1H-tetrazol-5-yl)benzene-1,2-disulfonamide To a solution of 2-(N,N-bis(4-methoxybenzyl)sulfamoyl)-4-iodo-3-(2-(4-methoxybenzyl)-2H-tetrazol-5-yl)benzenesulfonyl chloride and 2-(N,N-bis(4-methoxybenzyl)sulfamoyl)-4-iodo-3-(1-(4-methoxybenzyl)-1H-tetrazol-5-yl)benzenesulfonyl chloride (synthesis described above, 400 mg, 0.741 mmol) in THF (10 mL) was added ammonium hydroxide (78 mg, 2.222 mmol) at ambient temperature. The reaction was kept for 30 minutes at room temp. The mixture was concentrated under reduced pressure. The residue was then applied onto silica gel column with DCM/methanol (10:1) to get the product as a mixture of regioisomers on the p-methoxybenzyl tetrazole: LCMS [M+hr−15]$^+$: 791.

Step B: 5-(2-amino-1H-benzo[d]imidazol-4-yl)-N$^1$,N$^1$-bis(4-methoxybenzyl)-6-(2-(4-methoxybenzyl)-2H-tetrazol-5-yl)benzene-1,2-disulfonamide and 5-(2-amino-1H-benzo[d]imidazol-4-yl)-N$^1$,N$^1$-bis(4-methoxybenzyl)-6-(1-(4-methoxybenzyl)-1H-tetrazol-5-yl)benzene-1,2-disulfonamide To a solution of 5-iodo-N$^1$,N$^1$-bis(4-methoxybenzyl)-6-(2-(4-methoxybenzyl)-2H-tetrazol-5-yl)benzene-1,2-disulfonamide and 5-iodo-N$^1$,N$^1$-bis(4-methoxybenzyl)-6-(1-(4-methoxybenzyl)-1H-tetrazol-5-yl)benzene-1,2-disulfonamide (200 mg, 0.253 mmol) in 1,4-Dioxane (2 mL)/water (0.2 mL) (5:1) was added (2-amino-1H-benzo[d]imidazol-4-yl)boronic acid (90 mg, 0.506 mmol), sodium carbonate (80 mg, 0.759 mmol) and 2nd generation Xphos precatalyst (39.8 mg, 0.051 mmol) at ambient temperature. The flask was degassed with nitrogen three times. Then the mixture was stirred for 16 hours at 80° C. under an atmosphere of nitrogen. The solid was filtered out and the filtrate was extracted with ethyl acetate. The organic layers were combined and concentrated under reduced pressure. The residue was then applied onto silica gel column with DCM/methanol (10:1) to obtain the product as a mixture of PMB protected tetrazole regioisomers: LCMS [M+H]$^+$: 796.

Step C: 4-(2-amino-3H-benzo[d]imidazol-4-yl)-3-(2H-tetrazol-5-yl)benzene-1,2-disulfonamide 5-(2-amino-1H-benzo[d]imidazol-4-yl)-N1,N1-bis(4-methoxybenzyl)-6-(2-(4-methoxybenzyl)-2H-tetrazol-5-yl)benzene-1,2-disulfonamide (100 mg, 0.126 mmol) was dissolved in trifluoroacetic acid (3 ml) at ambient temperature. The reaction was kept at 80° C. for 1 hour. The resulting mixture was concentrated under reduced pressure to get the crude product. The crude product was then applied onto Prep-HPLC with the condition (Column: X Bridge RP C18, 19*150 mm, 5 μM; Mobile Phase A: water/10 mM NH$_4$HCO$_3$, Mobile Phase B: ACN; Flow rate: 20 mL/min; Gradient: 10-35% B in 10 min; 254 nm; Retention time: 5.89 min) to get the final product: LCMS [M+H]$^+$: 436; $^1$H NMR (400 MHz, DMSO-d$_6$): δ 8.34 (d, J=8.0 Hz, 1H), 7.90 (d, J=8.4 Hz, 1H), 7.62-7.33 (m, 4H), 7.11-6.94 (m, 2H), 6.78 (t, J=8.0 Hz, 1H), 6.33 (d, J=7.6 Hz, 1H)

EXAMPLES 2-7 in the table below were prepared in an analogous fashion as described for EXAMPLE 1, starting with 5-iodo-N$^1$,N$^1$-bis(4-methoxybenzyl)-6-(2-(4-methoxybenzyl)-2H-tetrazol-5-yl)benzene-1,2-disulfonamide (Step A, or the corresponding N-methyl sulfonamide, 4-iodo-N$^2$,N$^2$-bis(4-methoxybenzyl)-3-(2-(4-methoxybenzyl)-2H-tetrazol-5-yl)-N$^1$-methylbenzene-1,2-disulfonamide, prepared in an analogous fashion) and coupling with boronic acids or boronic esters that are prepared as described herein or that are commercially available.

| EX. No. | Structure | Name | LC/MS [M + H]$^+$ |
|---|---|---|---|
| 2 | 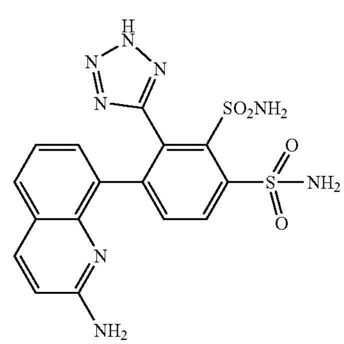 [SMILES: Nc1ccc2cccc(-c3ccc(S(N)(=O)=O)c(S(N)(=O)=O)c3-c3nn[nH]n3)c2n1] | 4-(2-aminoquinolin-8-yl)-3-(2H-tetrazol-5-yl)benzene-1,2-disulfonamide | 447 |

| EX. No. | Structure | Name | LC/MS [M + H]⁺ |
|---|---|---|---|
| 3 | 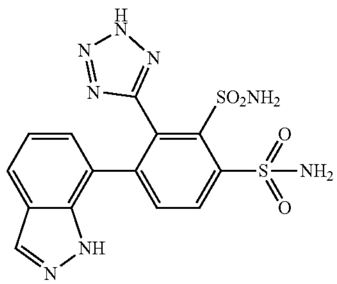 [SMILES: NS(=O)(=O)c1ccc(-c2cccc3cn[nH]c23)c(-c2nn[nH]n2)c1S(N)(=O)=O] | 4-(1H-indazol-7-yl)-3-(2H-tetrazol-5-yl)benzene-1,2-disulfonamide | 421 |
| 4 | 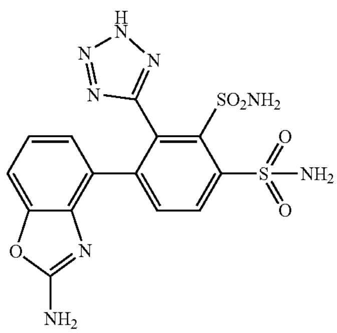 [SMILES: Nc1nc2c(-c3ccc(S(N)(=O)=O)c(S(N)(=O)=O)c3-c3nn[nH]n3)cccc2o1] | 4-(2-aminobenzo[d]oxazol-4-yl)-3-(2H-tetrazol-5-yl)benzene-1,2-disulfonamide | 437 |
| 5 | 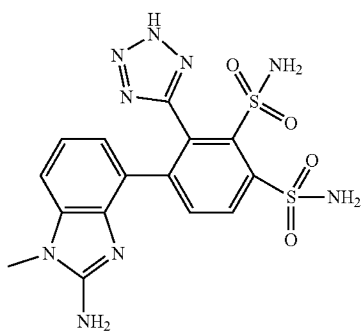 [SMILES: Cn1c(N)nc2c(-c3ccc(S(N)(=O)=O)c(S(N)(=O)=O)c3-c3nn[nH]n3)cccc21] | 4-(2-amino-1-methyl-1H-benzo[d]imidazol-4-yl)-3-(2H-tetrazol-5-yl)benzene-1,2-disulfonamide | 450 |
| 6 | 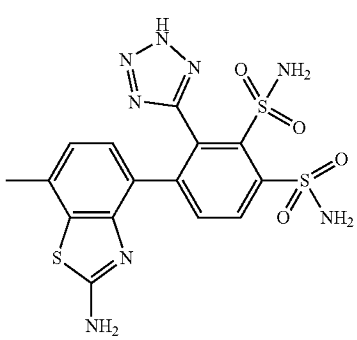 [SMILES: Cc1ccc(-c2ccc(S(N)(=O)=O)c(S(N)(=O)=O)c2-c2nn[nH]n2)c2nc(N)sc12] | 4-(2-amino-7-methylbenzo[d]thiazol-4-yl)-3-(2H-tetrazol-5-yl)benzene-1,2-disulfonamide | 467 |

| EX. No. | Structure | Name | LC/MS [M + H]+ |
|---|---|---|---|
| 7 | 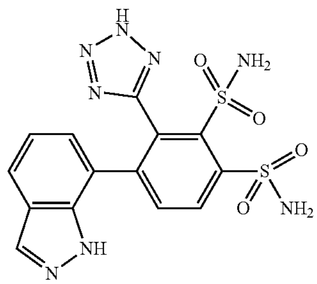 [SMILES: NS(=O)(=O)c1ccc(-c2cccc3cn[nH]c23)c(-c2nn[nH]n2)c1S(N)(=O)=O] | 4-(1H-indazol-7-yl)-N1-methyl-3-(2H-tetrazol-5-yl)benzene-1,2-disulfonamide | 435 |

Example 8

4-(3,4-disulfamoyl-2-(2H-tetrazol-5-yl)phenyl)-1H-benzo[d]imidazole-2-carboxylic acid

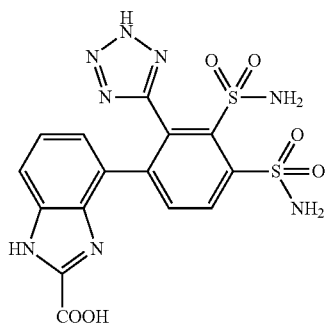 [SMILES: NS(=O)(=O)c1ccc(-c2cccc3[nH]c(C(=O)O)nc23)c(-c2nn[nH]n2)c1S(N)(=O)=O]

Step A: 2',3'-diamino-N,N-bis(4-methoxybenzyl)-2-(2-(4-methoxybenzyl)-2H-tetrazol-5-yl)-4-((2-(trimethylsilyl)ethyl)sulfonyl)-[1,1'-biphenyl]-3-sulfonamide Into a 50 mL RBF was placed 3-(4,4,5,5-tetramethyl-1,3,2-dioxaborolan-2-yl)benzene-1,2-diamine (0.802 g, 3.43 mmol), 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (Synthesis described above, 2.0 g, 2.3 mmol), Pd(PPh$_3$)$_4$ (0.528 g, 0.457 mmol) and sodium carbonate (0.726 g, 6.85 mmol) in 1,4-dioxane (6 ml) and water (1.500 ml). The reaction mixture was degassed with nitrogen for 3 times and stirred at 80° C. for 16 hr. The resulting mixture was extracted with ethyl acetate (300 mL) and washed with water (250 mL). Then the organic layer was concentrated under vacuum. The residue was applied on a silica gel column with ethyl acetate/petrol ether (1/1) to give the title compound: LCMS [M+H]+: 856; $^1$H NMR (300 MHz, d-DMSO): δ 8.57-8.54 (d, J=8.4 Hz, 1H), 7.92-7.89 (d, J=8.4 Hz, 1H), 7.06-6.73 (m, 13H), 6.52-6.39 (m, 1H), 6.23-6.10 (m, 1H), 4.79-4.45 (m, 2H), 4.30-4.11 (m, 2H), 4.08-3.88 (m, 4H), 3.724 (s, 12H), 1.09-0.80 (m, 2H), 0.029 (s, 9H).

Step B: N,N-bis(4-methoxybenzyl)-2-(2-(4-methoxybenzyl)-2H-tetrazol-5-yl)-3-(2-(trichloromethyl)-1H-benzo[d]imidazol-4-yl)-6-((2-(trimethylsilyl)ethyl)sulfonyl) benzenesulfonamide Into a RBF was placed 2',3'-diamino-N,N-bis(4-methoxybenzyl)-2-(2-(4-methoxybenzyl)-2H-tetrazol-5-yl)-4-((2-(trimethylsilyl)ethyl)sulfonyl)-[1,1'-biphenyl]-3-sulfonamide (1.1 g, 1.285 mmol) and benzyl 2,2,2-trichloroacetimidate (0.324 g, 1.285 mmol) in acetic acid (6 ml). Then the mixture was stirred at RT for 6 hours. Then the mixture was concentrated under vacuum to give the title compound: LCMS [M+H]+: 982, 984,985 (3:4:2).

Step C: methyl 4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazole-2-carboxylate Into a 50 mL RBF was placed N,N-bis(4-methoxybenzyl)-2-(2-(4-methoxybenzyl)-2H-tetrazol-5-yl)-3-(2-(trichloromethyl)-1H-benzo[d]imidazol-4-yl)-6-((2-(trimethylsilyl)ethyl)sulfonyl)benzenesulfonamide (500 mg, 0.508 mmol) and sodium carbonate (162 mg, 1.525 mmol) in methanol (0.5 ml). The mixture was stirred at 80° C. overnight, then the solvent was removed under vacuum. The residue was extracted with ethyl acetate (200 mL) and washed with hydrogen chloride (1 mol) in water (5*100 mL). The organic layer was concentrated under vacuum. The residue was applied on a silica gel column with ethyl acetate/petrol ether(2/1) to give the title compound: LCMS [M+H]+: 924; $^1$H NMR (300 MHz, d-DMSO): δ 8.70-8.58 (d, J=8.1 Hz, 1H), 8.14-8.11 (d, J=8.7 Hz, 1H), 7.74-7.40 (m, 3H), 7.10-6.79 (m, 12H), 5.66 (s, 1H), 5.07-4.51 (m, 2H), 4.09-3.87 (m, 7H), 3.73 (s, 9H), 3.21-2.90 (m, 2H), 1.09-0.81 (m, 2H), 0.03 (s, 9H).

Step D: 2-(N,N-bis(4-methoxybenzyl)sulfamoyl)-3-(2-(4-methoxybenzyl)-2H-tetrazol-5-yl)-4-(2-(methoxycarbonyl)-1H-benzo[d]imidazol-4-yl)benzenesulfinic acid To a solution of methyl 4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazole-2-carboxylate (300 mg, 0.325 mmol) in THF (2 ml) was added tetrabutylammonium fluoride (1.623 ml, 1.623 mmol). The mixture was stirred at room temperature for 2 hours, then extracted with ethyl acetate (50 mL) and washed with water (50 mL). The organic layer was dried over sodium sulfate for 2 hours and concentrated under vacuum to give the title compound: LCMS [M+H]⁺: 824.

Step E: methyl 4-(3-(N,N-bis(4-methoxybenzyl) sulfamoyl)-2-(2-(4-methoxybenzyl)-2H-tetrazol-5-yl)-4-sulfamoylphenyl)-1H-benzo[d]imidazole-2-carboxylate Into a 50 mL RBF was placed 2-(N,N-bis(4-methoxybenzyl)sulfamoyl)-3-(2-(4-methoxybenzyl)-2H-tetrazol-5-yl)-4-(2-(methoxycarbonyl)-1H-benzo[d]imidazol-4-yl)benzenesulfinic acid (300 mg, 0.364 mmol) and 1-chloropyrrolidine-2,5-dione (72.9 mg, 0.546 mmol) in THF (2 ml). The mixture was stirred at room temperature for 2 hours, and ammonia (0.350 ml, 0.699 mmol) was added. The resulting mixture was stirred at room temperature for 2 hours, extracted with ethyl acetate (50 mL) and washed with water (50 mL). The organic layer was concentrated under vacuum. The residue was applied on a silica gel column with ethyl acetate/petrol ether (1/1) to give the title compound: LCMS [M+H]⁺: 479; ¹H NMR (300 MHz, d-DMSO): δ 8.70-8.51 (d, J=8.4 Hz, 1H), 8.12-8.03 (d, J=8.4 Hz, 1H), 7.74-7.40 (m, 3H), 7.10-6.65 (m, 12H), 5.66 (s, 2H), 4.12-3.98 (m, 2H), 3.97-3.80 (m, 5H), 3.80-3.59 (m, 9H).

Step F: methyl 4-(3,4-disulfamoyl-2-(2H-tetrazol-5-yl)phenyl)-1H-benzo[d]imidazole-2-carboxylate Into a 50 mL RBF was placed methyl 4-(3-(N,N-bis(4-methoxybenzyl)sulfamoyl)-2-(2-(4-methoxybenzyl)-2H-tetrazol-5-yl)-4-sulfamoylphenyl)-1H-benzo[d]imidazole-2-carboxylate (90 mg, 0.107 mmol) and trifluoroacetic acid (2 ml). The mixture was stirred at 60° C. for 2 hours, then concentrated under vacuum. The residue was pH-adjusted with sodium carbonate (50 mg). Then it was purified by flash chromatography on silica with methanol/DCM (percent of methanol:5-60% in 25 min) to give the title compound: LCMS [M+H]⁺: 465.

Step G: 4-(3,4-disulfamoyl-2-(2H-tetrazol-5-yl)phenyl)-1H-benzo[d]imidazole-2-carboxylic acid To a solution of methyl 4-(3,4-disulfamoyl-2-(2H-tetrazol-5-yl)phenyl)-1H-benzo[d]imidazole-2-carboxylate (40 mg, 0.084 mmol) in methanol (1 ml) was added sodium hydroxide (13.38 mg, 0.334 mmol) in water (0.500 ml). The mixture was stirred at room temp. for 1 hour and concentrated under vacuum. The residue was pH-adjusted with hydrogen chloride (3 mol in methanol, 0.15 mL). The mixture was dissolved in N,N-dimethylformamide and purified by Pre-HPLC (condition: Column: XSelect CSH Prep C18 OBD Column,5 µM, 19*150 mm; Mobile Phase A: water with 10 mmol NH₄HCO₃, Mobile Phase B: MeCN; Flow rate: 20 mL/min; Gradient: 8% B to 35% B in 8 min; 254/220 nm) to give the title compound. LCMS [M+H]⁺: 346; ¹H NMR (300 MHz, d-DMSO): δ 8.59-8.50 (d, J=8.4 Hz, 1H), 8.07-8.04 (d, J=8.4 Hz, 1H), 7.56 (s, 2H), 7.51-7.49 (d, J=8.4 Hz, 1H), 7.30 (s, 2H), 7.20-7.15 (t, J=8.1 Hz, 1H), 6.75-6.72 (d, J=7.8 Hz, 1H).

Example 9

N¹-(2-aminoethyl)-4-(1H-indazol-7-yl)-3-(2H-tetrazol-5-yl)benzene-1,2-disulfonamide

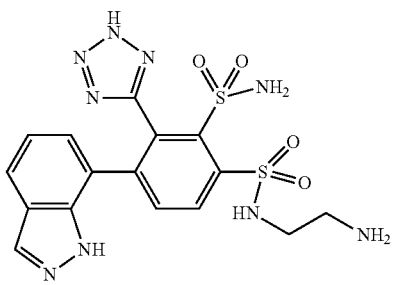 [SMILES: NCCNS(=O)(=O)c1ccc(-c2cccc3cn[nH]c23)c(-c2nn[nH]n2)c1S(N)(=O)=O]

Step A: tert-butyl 2-(2-(N,N-bis(4-methoxybenzyl) sulfamoyl)-4-iodo-3-(2-(4-methoxybenzyl)-2H-tetrazol-5-yl)phenylsulfonamido)ethylcarbamate To a solution of 2-(N,N-bis(4-methoxybenzyl)sulfamoyl)-4-iodo-3-(2-(4-methoxybenzyl)-2H-tetrazol-5-yl)benzenesulfonyl chloride and 2-(N,N-bis(4-methoxybenzyl)sulfamoyl)-4-iodo-3-(1-(4-methoxybenzyl)-1H-tetrazol-5-yl)benzenesulfonyl chloride (synthesis described above, 1.4 g, 1.73 mmol) in THF (20 ml) was added tert-butyl (2-aminoethyl)carbamate (0.554 g, 3.46 mmol) and triethylamine (0.525 g, 5.18 mmol) with stirring at room temperature. The resulting solution was warmed to room temperature and stirred for 1 hour. The reaction mixture was cooled to ambient temperature, diluted with water (20 mL) and extracted with ethyl acetate (3×20 mL). The combined organic layers were washed with brine (50 mL), dried over anhydrous sodium sulfate and filtered. The filtrate was concentrated under vacuum to afford the product as an oil. The residue was purified by silica gel column chromatography 20 g, eluting with EtOAc/petroleum ether (2/1) to afford the title compound (as a mixture of protected tetrazole regioisomers): LCMS [M+H]⁺: 934.

Step B: tert-butyl 2-(2-(N,N-bis(4-methoxybenzyl) sulfamoyl)-4-(1H-indazol-7-yl)-3-(2-(4-methoxybenzyl)-2H-tetrazol-5-yl)phenylsulfonamido)ethylcarbamate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (200 mg, 0.214 mmol) in dioxane (4 ml) and water (1 ml) was added Na₂CO₃ (91 mg, 0.857 mmol) (1H-indazol-7-yl)boronic acid (69.4 mg, 0.428 mmol) and Pd(dppf)Cl₂ (49.5 mg, 0.043 mmol) with stirring at room temp. The reaction mixture was degassed with nitrogen 3 times. The resulting mixture was warmed to 80° C. and stirred for 3 hours. The reaction mixture was cooled to ambient temperature, diluted with water (5 mL) and extracted with ethyl acetate (2×10 mL). The combined organic layers were washed with brine (5 mL), dried over anhydrous sodium sulfate and filtered. The filtrate was concentrated under vacuum to afford an oil. The residue was purified by silica gel column chromatography 12 g, eluted with EtOAc/petroleum ether (2/1) to afford the title compound as a mixture of PMB tetrazole regioisomers: LCMS [M+H]+: 924.

Step C: $N^1$-(2-aminoethyl)-4-(1H-indazol-7-yl)-3-(2H-tetrazol-5-yl)benzene-1,2-disulfonamide To a solution of tert-butyl (2-(2-(N,N-bis(4-methoxybenzyl)sulfamoyl)-4-(1H-indazol-7-yl)-3-(2-(4-methoxybenzyl)-2H-tetrazol-5-yl)phenylsulfonamido)ethyl)carbamate (120 mg, 0.130 mmol) in DCM (3 ml) was added TFA (0.100 ml, 1.299 mmol) with stirring at room temperature. The resulting solution was warmed to room temperature and stirred for 1 hour. The residue was concentrated to afford $N^1$-(2-aminoethyl)-4-(1H-indazol-7-yl)-$N^2$-(4-methoxybenzyl)-3-(2-(4-methoxybenzyl)-2H-tetrazol-5-yl)benzene-1,2-disulfonamide as an oil. The solution of $N^1$-(2-aminoethyl)-4-(1H-indazol-7-yl)-$N^2$-(4-methoxybenzyl)-3-(2-(4-methoxybenzyl)-2H-tetrazol-5-yl)benzene-1,2-disulfonamide (80 mg, 0.114 mmol) in TFA (0.876 ml, 11.37 mmol) was stirring at room temperature. The resulting solution was warmed to 80° C. and stirred for 2 hours. The product was purified by Prep-HPLC with the following conditions: Column: XBridge C18 OBD Prep Column, 100 Å, 5 μm, 19 mm×250 mm; Mobile Phase A: water with 10 mmol $NH_4HCO_3$, Mobile Phase B: MeCN; Flow rate: 15 mL/min; Gradient: 10% B to 35% B in 8 min; 254/220 nm. The collected fractions were combined and concentrated under vacuum to afford the title compound: LCMS [M+H]+: 464; $^1$H NMR (300 MHz, DMSO): δ 8.23 (d, J=8.4 Hz, 1H), 8.04 (d, J=12 Hz, 1H), 7.91-7.89 (m, 6H), 6.80 (d, J=7.8 Hz, 1H), 6.48 (d, J=7.8 Hz, 1H), 3.16-3.14 (m, 2H), 3.05-3.01 (m, 2H).

EXAMPLES 10-12 in the Table below were prepared in an analogous fashion as described for EXAMPLE 9 starting from tert-butyl 2-(2-(N,N-bis(4-methoxybenzyl)sulfamoyl)-4-iodo-3-(2-(4-methoxybenzyl)-2H-tetrazol-5-yl)phenylsulfonamido)ethylcarbamate and boronic acids or boronic esters prepared as described herein or available from commercial sources.

| EX NO | Structure | Name | MW | LC/MS [M + H]+ |
|---|---|---|---|---|
| 10 | 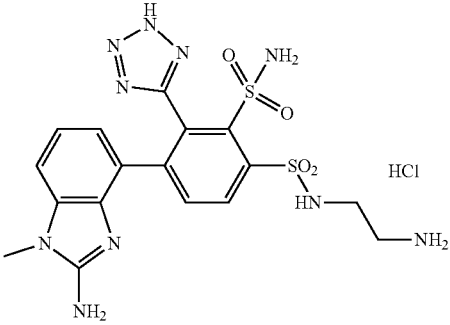 [SMILES: Cn1c(N)nc2c(-c3ccc(S(=O)(=O)NCCN)c(S(N)(=O)=O)c3-c3nn[nH]n3)cccc21 ; Cl] | 4-(2-amino-1-methyl-1H-benzo[d]imidazol-4-yl)-N1-(2-aminoethyl)-3-(2H-tetrazol-5-yl)benzene-1,2-disulfonamide hydrochloride | 492 | 493 |
| 11 | 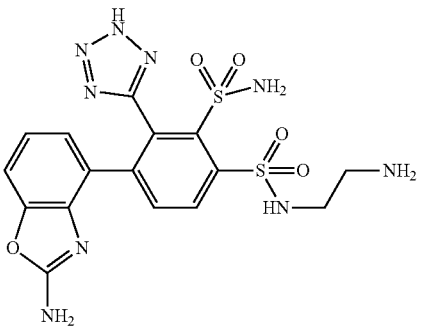 [SMILES: NCCNS(=O)(=O)c1ccc(-c2cccc3oc(N)nc23)c(-c2nn[nH]n2)c1S(N)(=O)=O] | 4-(2-aminobenzo[d]oxazol-4-yl)-$N^1$-(2-aminoethyl)-3-(2H-tetrazol-5-yl)benzene-1,2-disulfonamide | 420 | 421 |
| 12 | 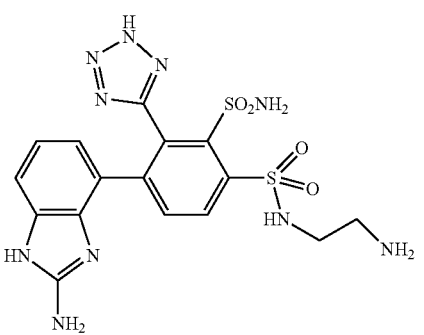 [SMILES: NCCNS(=O)(=O)c1ccc(-c2cccc3[nH]c(N)nc23)c(-c2nn[nH]n2)c1S(N)(=O)=O] | 4-(2-amino-1H-benzo[d]imidazol-4-yl)-$N^1$-(2-aminoethyl)-3-(2H-tetrazol-5-yl)benzene-1,2-disulfonamide | 478 | 479 |

Example 13

4-(4-(N-(2-aminoethyl)sulfamoyl)-3-sulfamoyl-2-(2H-tetrazol-5-yl)phenyl)benzo[d]oxazole-2-carboxylic acid

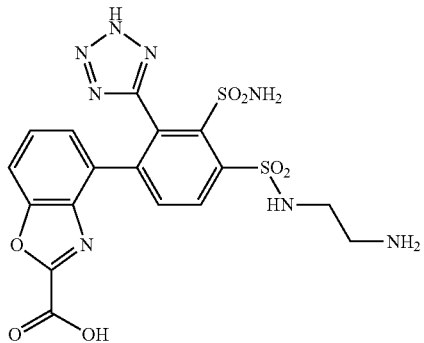 [SMILES: NCCNS(=O)(=O)c1ccc(-c2cccc3oc(C(=O)O)nc23)c(-c2nn[nH]n2)c1S(N)(=O)=O]

Step A: ethyl 4-bromobenzo[d]oxazole-2-carboxylate 2-amino-3-bromophenol (1.0 g, 5.3 mmol) was added to ethyl 2-chloro-2-oxoacetate (1.1 g, 8.0 mmol) in 1,4-dioxane (12.0 ml) at room temperature. The reaction solution was stirred for 1 hour at 150° C. under microwave, cooled, and concentrated. The residue was purified by silica gel chromatography, eluting with ethyl acetate/petroleum ether (1/10). The combined organic fractions were concentrated under reduced pressure to give the title compound: LCMS [M+1]$^+$: 270/272. $^1$H NMR (400 MHz, CDCl$_3$) δ 7.64 (dd, J=8.4 Hz, 2H), 7.42 (dd, J=8.0 Hz, 1H), 4.60-4.55 (m, 2H), 1.51-1.37 (m, 3H).

Step B: (2-(ethoxycarbonyl)benzo[d]oxazol-4-yl)boronic acid

Potassium acetate (0.36 g, 3.7 mmol) was added to a stirred mixture of 4,4,4',4',5,5,5',5'-octamethyl-2,2'-bi(1,3,2-dioxaborolane) (1.9 g, 7.4 mmol), ethyl 4-bromobenzo[d]oxazole-carboxylate (1.0 g, 3.7 mmol) and PdCl$_2$(dppf) (0.54 g, 0.74 mmol) in 1,4-dioxane (15.0 ml) at room temperature under Ar condition. The reaction mixture was stirred 1 hour at 80° C., monitored by LCMS to find product. The reaction mixture was quenched with water (25.0 mL) and extracted with EA (3×30 mL). The product was purified by Prep-MPLC with the following conditions: Column, C-18, 120 g, mobile phase: water (0.05% TFA) and acetonitrile; Detector, UV 210 and 254 nm. The combined organic fractions were concentrated under reduced pressure to give the title compound: LCMS [M+1]$^+$: 236. $^1$H NMR (400 MHz, DMSO d$_6$) δ 8.27 (brs, 2H), 7.95 (dd, J=7.6 Hz, 1H), 7.87 (dd, J=8.0 Hz, 1H), 7.62 (dd, J=7.6 Hz, 1H), 4.49-4.41 (m, 2H), 1.41-1.35 (m, 1H).

Step C: ethyl 4-(3-(N,N-bis(4-methoxybenzyl)sulfamoyl)-4-(N-(2-((tert-butoxycarbonyl)amino)ethyl)sulfamoyl)-2-(2-(4-methoxybenzyl)-2H-tetrazol-5-yl)phenyl)benzo[d]oxazole-2-carboxylate Na$_2$CO$_3$ (68 mg, 0.64 mmol) was added to a stirred mixture of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (200 mg, 0.21 mmol), (2-(ethoxycarbonyl)benzo[d]oxazol-4-yl)boronic acid (100 mg, 0.42 mmol) and Pd(PPh$_3$)$_4$ (5 mg, 0.004 mmol) indioxane (10.0 ml) at room temp. under Ar condition. The reaction mixture was stirred for 13 hours at 80° C. The reaction mixture was quenched with water (20 mL) and extracted with EA (3×20 mL). The combined organic layers were washed with brine (2×20 mL), dried over anhydrous sodium sulfate and filtered. The filtrate was concentrated under vacuum. The residue was purified by silica gel chromatography, eluting with PE/EA (3/1). The combined organic fractions were concentrated under reduced pressure to give the title compound: LCMS [M+1]+: 997; $^1$H NMR (400 MHz, CDCl$_3$) δ 8.45 (dd, J=8.0 Hz, 1H), 7.89 (dd, J=8.4 Hz, 1H), 7.70-7.65 (m, 2H), 7.53-7.34 (m, 5H), 7.05-6.91 (m, 4H), 6.81 (dd, J=8.8 Hz, 3H), 6.70 (dd, J=8.8 Hz, 2H), 6.67-6.46 (m, 1H), 5.43-5.40 (m, 1H), 5.10-4.90 (m, 1H), 4.50-4.40 (m, 2H), 4.30-4.20 (m, 2H), 4.15-4.10 (m, 2H), 3.78 (brs, 9H), 3.40-3.10 (m, 3H), 1.47 (brs, 9H), 1.38-1.24 (m, 3H).

Step D: ethyl 4-(4-(N-(2-aminoethyl)sulfamoyl)-3-sulfamoyl-2-(2H-tetrazol-5-yl)phenyl)benzo[d]oxazole-2-carboxylate TFA (2.0 ml) was added dropwise to a stirred solution of ethyl 4-(3-(N,N-bis(4-methoxybenzyl)sulfamoyl)-4-(N-(2-((tert-butoxycarbonyl)amino)ethyl)sulfamoyl)-2-(2-(4-methoxybenzyl)-2H-tetrazol-5-yl)phenyl)benzo[d]oxazole-2-carboxylate (160 mg, 0.16 mmol) in CH$_2$Cl$_2$ (2.0 ml) at 0° C. The reaction solution was stirred for 1 hour at room temp., then concentrated to afford ethyl 4-(4-(N-(2-aminoethyl)sulfamoyl)-2-(2-(4-methoxybenzyl)-2H-tetrazol-5-yl)-3-(N-(4-methoxybenzyl)sulfamoyl)phenyl)benzo[d]oxazole-2-carboxylate 200 mg (crude) as an oil. TFA (1.5 ml) was added to a stirred solution of ethyl 4-(4-(N-(2-aminoethyl)sulfamoyl)-2-(2-(4-methoxybenzyl)-2H-tetrazol-5-yl)-3-(N-(4-methoxybenzyl)sulfamoyl)phenyl)benzo[d]oxazole-2-carboxylate (160 mg, crude) at 0° C. The reaction solution was stirred for 2 hours at 80° C., then concentrated to afford the title compound: LCMS [M$^+$]$^+$: 537.

Step E: 4-(4-(N-(2-aminoethyl)sulfamoyl)-3-sulfamoyl-2-(2H-tetrazol-5-yl)phenyl)benzo[d]oxazole-2-carboxylic acid NaOH (54 mg, 1.3 mmol) was added to a stirred solution of ethyl 4-(4-(N-(2-aminoethyl)sulfamoyl)-3-sulfamoyl-2-(2H-tetrazol-5-yl)phenyl)benzo[d]oxazole-2-carboxylate (120 mg, 0.224 mmol) in MeOH (1.5 ml) at 0° C. The reaction mixture was stirred for 3 hours at room temperature, adjusted to pH=6.0 with HCl (~1M aq.). The product was purified by Prep-HPLC with the following conditions: Column, Xbridge C 18, 19*150 mm; mobile phase: water (0.05% NH$_4$HCO$_3$) and acetonitrile (hold 34% acetonitrile for 8 min, hold 100% for 2 min, down to 34% in 2 min); Detector, UV 220 and 254 nm. The collected fractions were combined and concentrated under vacuum to give the title compound: LCMS [M+1]$^+$: 509; $^1$H NMR (400 MHz, DMSO d$_6$) δ 8.28-8.20 (m, 1H), 7.93 (dd, J=8.4 Hz, 1H), 7.51 (dd, J=8.0 Hz, 1H), 7.06 (dd, J=8.0 Hz, 1H), 6.52 (dd, J=7.2 Hz, 1H),3.25-3.21 (m, 2H), 2.96-2.92 (m, 2H).

Example S 14-84

General procedure for parallel preparation of sulfonamide Examples 14-84

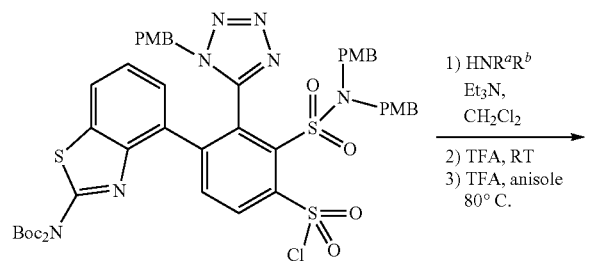

1) HNR$^a$R$^b$
   Et$_3$N,
   CH$_2$Cl$_2$
2) TFA, RT
3) TFA, anisole
   80° C.

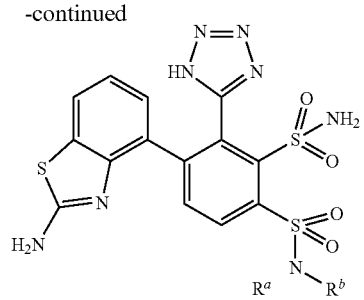

To a set of vials each containing the requisite commercially available or known amine (0.13 mmol) was added a solution of the sulfonyl chloride (45 mg, 0.044 mmol) followed by Et$_3$N (0.018 mL, 0.13 mmol). The vials were capped and the mixtures were stirred at RT for 5 hours. To the reaction mixture was then added TFA (0.5 mL) and the mixtures were stirred at RT for 1.5 hours. After that time, toluene (1 mL) was added to each vial and the mixtures were concentrated in vacuo. To each vial was then added TFA (1.0 mL) and anisole (0.019 mL, 0.17 mmol). The vials were capped and the reaction mixtures were heated to 80° C. with stirring for 45 minutes. After that time, the reaction mixtures were concentrated in vacuo. The crude residues were then dissolved in DMSO (1.0 mL) and filtered. The crude products were purified by mass triggered preparative HPLC [Waters Sunfire C18 column, 5 μm, 19×100 mm, using a gradient range from 8-10% initial to 21-36% final MeCN (0.1% TFA) in water (0.1% TFA), 25 mL/min, 8-12 min run time] to afford EXAMPLES 14-84.

| EX. No. | HNR$^a$R$^b$ | Structure | Name | LC/MS m/e [M + H]$^+$ |
|---|---|---|---|---|
| 14 | (H$_2$N-tetrahydrothiopyran-1,1-dioxide) | (structure) | 4-(2-amino-1,3-benzothiazol-4-yl)-N1-(1,1-dioxidotetrahydro-2H-thiopyran-4-yl)-3-(1H-tetrazol-5-yl)benzene-1,2-disulfonamide | 585.0 |
| 15 | (H$_2$N-ethyl-3-oxopiperazine) | (structure) | 4-(2-amino-1,3-benzothiazol-4-yl)-N1-[2-(3-oxopiperazin-1-yl)ethyl]-3-(1H-tetrazol-5-yl)benzene-1,2-disulfonamide | 579.0 |

-continued

| EX. No. | HNR$^a$R$^b$ | Structure | Name | LC/MS m/e [M + H]$^+$ |
|---|---|---|---|---|
| 16 | 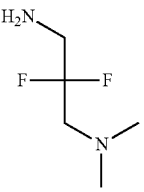 | 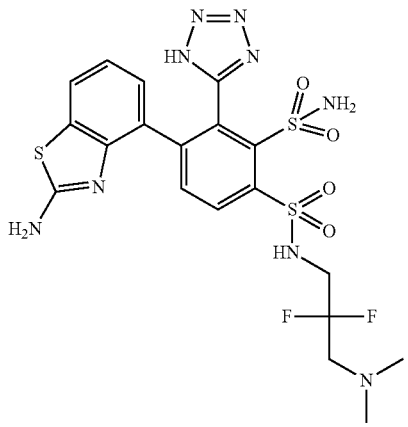 [SMILES: CN(C)CC(F)(F)CNS(=O)(=O)c1ccc(-c2cccc3sc(N)nc23)c(-c2nnn[nH]2)c1S(N)(=O)=O] | 4-(2-amino-1,3-benzothiazol-4-yl)-N1-[3-(dimethylamino)-2,2-difluoropropyl]-3-(1H-tetrazol-5-yl)benzene-1,2-disulfonamide | 574.1 |
| 17 | 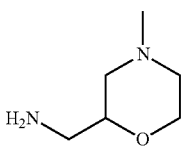 | 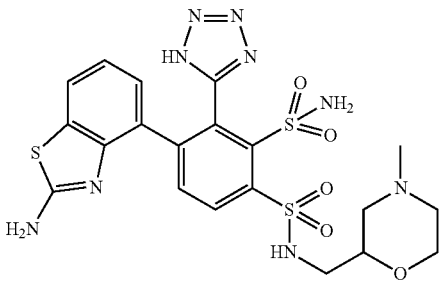 [SMILES: CN1CCOC(CNS(=O)(=O)c2ccc(-c3cccc4sc(N)nc34)c(-c3nnn[nH]3)c2S(N)(=O)=O)C1] | 4-(2-amino-1,3-benzothiazol-4-yl)-N1-[(4-methylmorpholin-2-yl)methyl]-3-(1H-tetrazol-5-yl)benzene-1,2-disulfonamide | 566.0 |
| 18 | 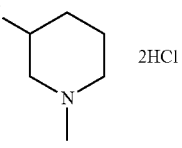 2HCl | 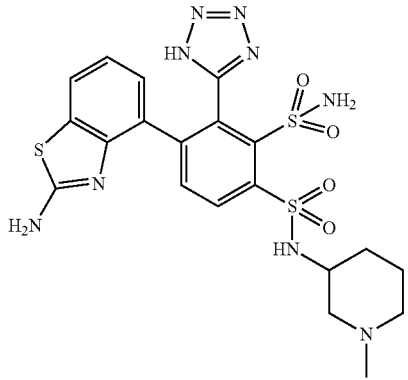 [SMILES: CN1CCCC(NS(=O)(=O)c2ccc(-c3cccc4sc(N)nc34)c(-c3nnn[nH]3)c2S(N)(=O)=O)C1] | 4-(2-amino-1,3-benzothiazol-4-yl)-N1-(1-methylpiperidin-3-yl)-3-(1H-tetrazol-5-yl)benzene-1,2-disulfonamide | 550.1 |
| 19 | 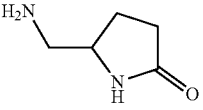 | 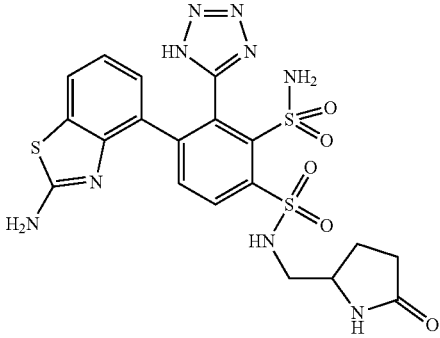 [SMILES: Nc1nc2c(-c3ccc(S(=O)(=O)NCC4CCC(=O)N4)c(S(N)(=O)=O)c3-c3nnn[nH]3)cccc2s1] | 4-(2-amino-1,3-benzothiazol-4-yl)-N1-[(5-oxopyrrolidin-2-yl)methyl]-3-(1H-tetrazol-5-yl)benzene-1,2-disulfonamide | 550.1 |

-continued

| EX. No. | HNR$^a$R$^b$ | Structure | Name | LC/MS m/e [M + H]$^+$ |
|---|---|---|---|---|
| 20 | 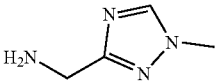 | 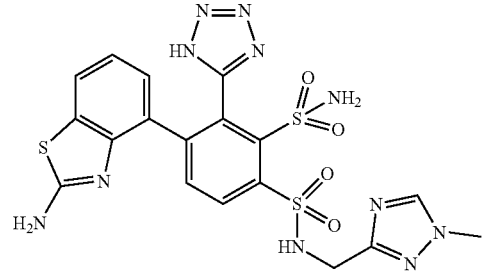 [SMILES: Cn1cnc(CNS(=O)(=O)c2ccc(-c3cccc4sc(N)nc34)c(-c3nnn[nH]3)c2S(N)(=O)=O)n1] | 4-(2-amino-1,3-benzothiazol-4-yl)-N$^1$-[(1-methyl-1H-1,2,4-triazol-3-yl)methyl]-3-(1H-tetrazol-5-yl)benzene-1,2-disulfonamide | 548.0 |
| 21 | 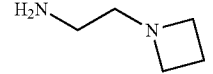 | 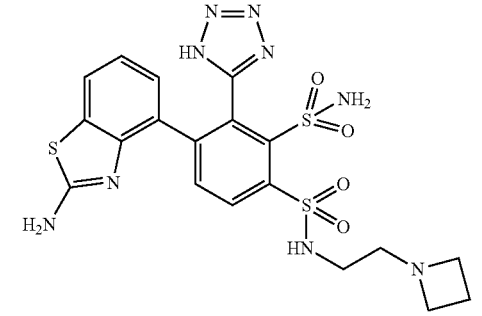 [SMILES: Nc1nc2c(-c3ccc(S(=O)(=O)NCCN4CCC4)c(S(N)(=O)=O)c3-c3nnn[nH]3)cccc2s1] | 4-(2-amino-1,3-benzothiazol-4-yl)-N1-(2-azetidin-1-ylethyl)-3-(1H-tetrazol-5-yl)benzene-1,2-disulfonamide | 536.0 |
| 22 | 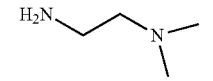 | 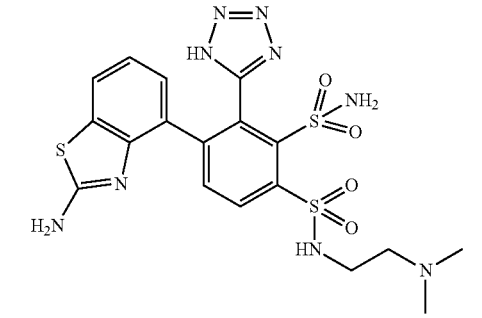 [SMILES: CN(C)CCNS(=O)(=O)c1ccc(-c2cccc3sc(N)nc23)c(-c2nnn[nH]2)c1S(N)(=O)=O] | 4-(2-amino-1,3-benzothiazol-4-yl)-N$^1$-[2-(dimethylamino)ethyl]-3-(1H-tetrazol-5-yl)benzene-1,2-disulfonamide | 524.0 |
| 23 |  | 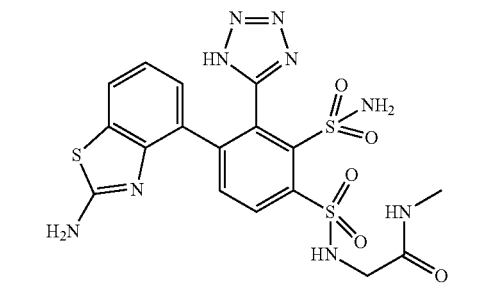 [SMILES: CNC(=O)CNS(=O)(=O)c1ccc(-c2cccc3sc(N)nc23)c(-c2nnn[nH]2)c1S(N)(=O)=O] | N$^2$-{[4-(2-amino-1,3-benzothiazol-4-yl)-2-sulfamoyl-3-(1H-tetrazol-5-yl)phenyl]sulfonyl}-N-methylglycinamide | 524.0 |
| 24 | 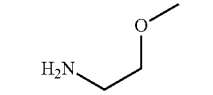 | 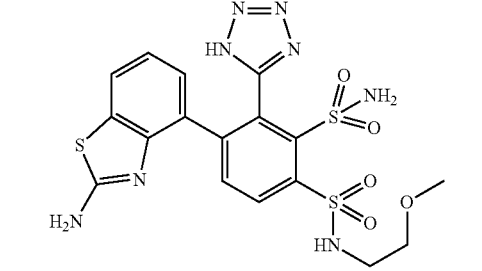 [SMILES: COCCNS(=O)(=O)c1ccc(-c2cccc3sc(N)nc23)c(-c2nnn[nH]2)c1S(N)(=O)=O] | 4-(2-amino-1,3-benzothiazol-4-yl)-N$^1$-(2-methoxyethyl)-3-(1H-tetrazol-5-yl)benzene-1,2-disulfonamide | 511.1 |

-continued

| EX. No. | HNR$^a$R$^b$ | Structure | Name | LC/MS m/e [M + H]$^+$ |
|---|---|---|---|---|
| 25 | 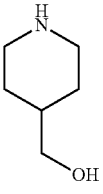 | 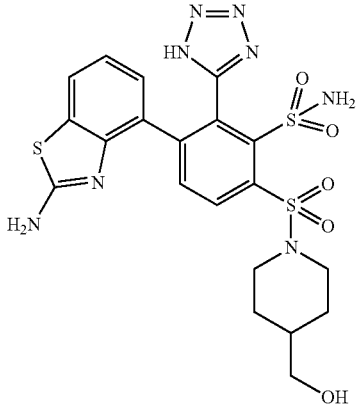 [SMILES: Nc1nc2c(-c3ccc(S(=O)(=O)N4CCC(CO)CC4)c(S(N)(=O)=O)c3-c3nnn[nH]3)cccc2s1] | 3-(2-amino-1,3-benzothiazol-4-yl)-6-{[4-(hydroxymethyl)piperidin-1-yl]sulfonyl}-2-(1H-tetrazol-5-yl)benzenesulfonamide | 551.0 |
| 26 | 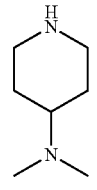 | 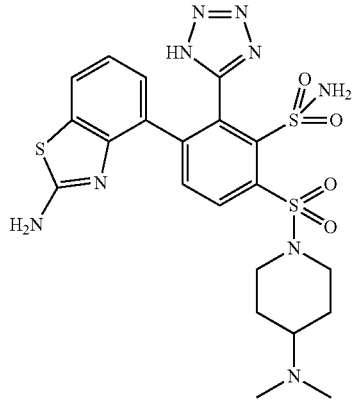 [SMILES: CN(C)C1CCN(S(=O)(=O)c2ccc(-c3cccc4sc(N)nc34)c(-c3nnn[nH]3)c2S(N)(=O)=O)CC1] | 3-(2-amino-1,3-benzothiazol-4-yl)-6-{[4-(dimethylamino)piperidin-1-yl]sulfonyl}-2-(1H-tetrazol-5-yl)benzenesulfonamide | 564.2 |
| 27 | 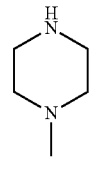 | 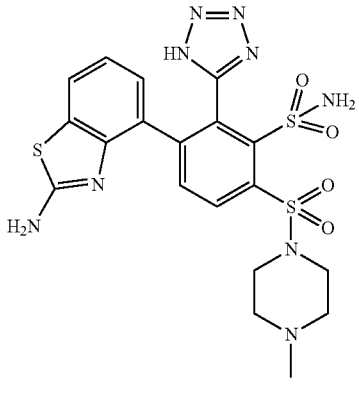 [SMILES: CN1CCN(S(=O)(=O)c2ccc(-c3cccc4sc(N)nc34)c(-c3nnn[nH]3)c2S(N)(=O)=O)CC1] | 3-(2-amino-1,3-benzothiazol-4-yl)-6-[(4-methylpiperazin-1-yl)sulfonyl]-2-(1H-tetrazol-5-yl)benzenesulfonamide | 536.0 |
| 28 | 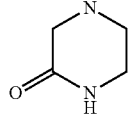 | 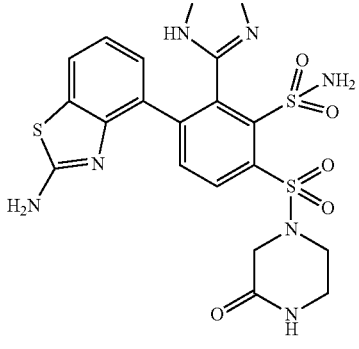 | 3-(2-amino-1,3-benzothiazol-4-yl)-6-[(3-oxopiperazin-1-yl)sulfonyl]-2-(1H-tetrazol-5-yl)benzenesulfonamide | 536.1 |

-continued

| EX. No. | HNR<sup>a</sup>R<sup>b</sup> | Structure | Name | LC/MS m/e [M + H]<sup>+</sup> |
|---|---|---|---|---|
| 29 | 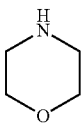 | 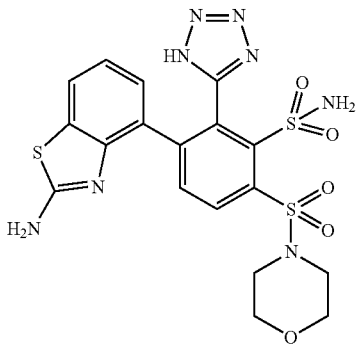 [SMILES: Nc1nc2c(-c3ccc(S(=O)(=O)N4CCOCC4)c(S(N)(=O)=O)c3-c3nnn[nH]3)cccc2s1] | 3-(2-amino-1,3-benzothiazol-4-yl)-6-(morpholin-4-ylsulfonyl)-2-(1H-tetrazol-5-yl)benzenesulfonamide | 523.0 |
| 30 | 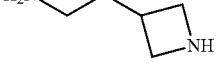 | 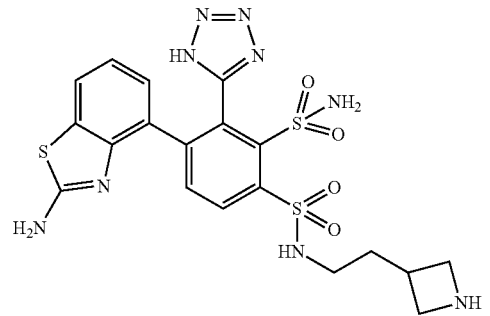 [SMILES: Nc1nc2c(-c3ccc(S(=O)(=O)NCCC4CNC4)c(S(N)(=O)=O)c3-c3nnn[nH]3)cccc2s1] | 4-(2-amino-1,3-benzothiazol-4-yl)-N1-(2-azetidin-3-ylethyl)-3-(1H-tetrazol-5-yl)benzene-1,2-disulfonamide | 536.0 |
| 31 | 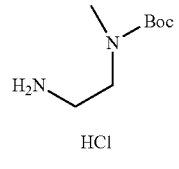 HCl | 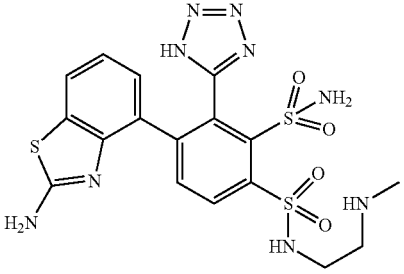 [SMILES: CNCCNS(=O)(=O)c1ccc(-c2cccc3sc(N)nc23)c(-c2nnn[nH]2)c1S(N)(=O)=O] | 4-(2-amino-1,3-benzothiazol-4-yl)-N$^1$-[2-(methylamino)ethyl]-3-(1H-tetrazol-5-yl)benzene-1,2-disulfonamide | 510.0 |
| 32 | 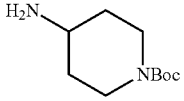 | 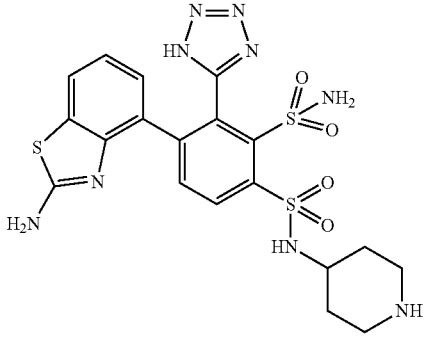 [SMILES: Nc1nc2c(-c3ccc(S(=O)(=O)NC4CCNCC4)c(S(N)(=O)=O)c3-c3nnn[nH]3)cccc2s1] | 4-(2-amino-1,3-benzothiazol-4-yl)-N1-piperidin-4-yl-3-(1H-tetrazol-5-yl)benzene-1,2-disulfonamide | 536.0 |

| EX. No. | HNR$^a$R$^b$ | Structure | Name | LC/MS m/e [M + H]$^+$ |
|---|---|---|---|---|
| 33 | H$_2$N-ethyl-(2-oxopiperidin-1-yl), HCl | 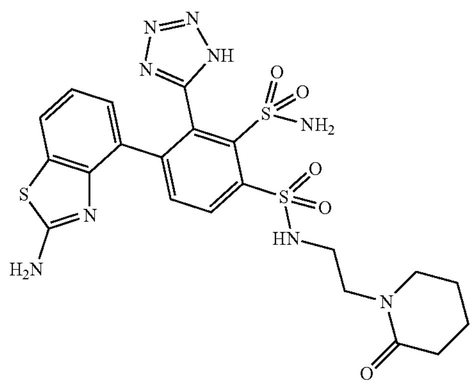 [SMILES: Nc1nc2c(-c3ccc(S(=O)(=O)NCCN4CCCCC4=O)c(S(N)(=O)=O)c3-c3nnn[nH]3)cccc2s1] | 4-(2-amino-1,3-benzothiazol-4-yl)-N1-[2-(2-oxopiperidin-1-yl)ethyl]-3-(1H-tetrazol-5-yl)benzene-1,2-disulfonamide | 578.0 |
| 34 | H$_2$N-CH$_2$-(4-methoxypyrimidin-2-yl), HCl | 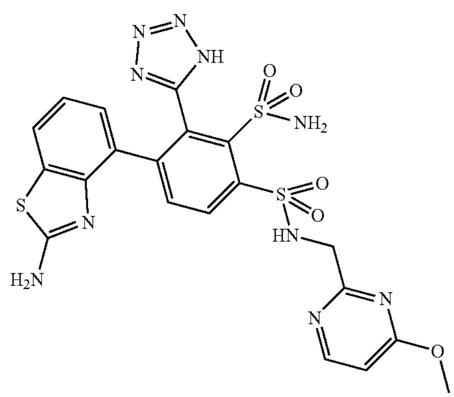 [SMILES: COc1ccnc(CNS(=O)(=O)c2ccc(-c3cccc4sc(N)nc34)c(-c3nnn[nH]3)c2S(N)(=O)=O)n1] | 4-(2-amino-1,3-benzothiazol-4-yl)-N1-[(4-methoxypyrimidin-2-yl)methyl]-3-(1H-tetrazol-5-yl)benzene-1,2-disulfonamide | 575.0 |
| 35 | H$_2$N-(5,6,7,8-tetrahydroimidazo[1,2-a]pyridin-6-yl), HCl | 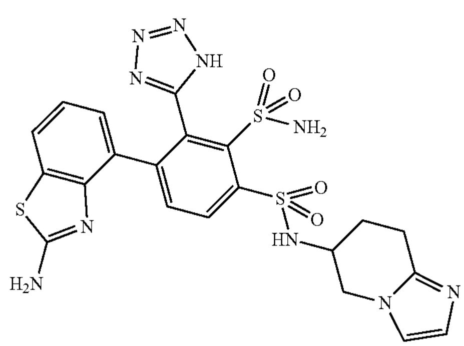 [SMILES: Nc1nc2c(-c3ccc(S(=O)(=O)NC4CCc5nccn5C4)c(S(N)(=O)=O)c3-c3nnn[nH]3)cccc2s1] | 4-(2-amino-1,3-benzothiazol-4-yl)-N1-(5,6,7,8-tetrahydroimidazo[1,2-a]pyridin-6-yl)-3-(1H-tetrazol-5-yl)benzene-1,2-disulfonamide | 573.1 |
| 36 | H$_2$N-CH$_2$-C(O)-N(CH$_3$)$_2$ | 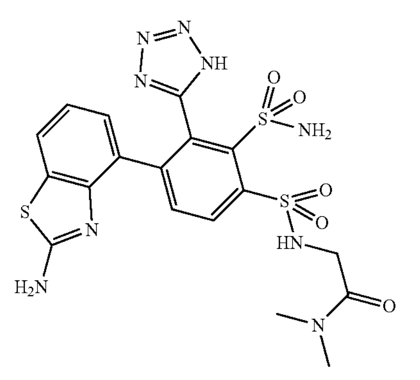 [SMILES: CN(C)C(=O)CNS(=O)(=O)c1ccc(-c2cccc3sc(N)nc23)c(-c2nnn[nH]2)c1S(N)(=O)=O] | N$^2$-{[4-(2-amino-1,3-benzothiazol-4-yl)-2-sulfamoyl-3-(1H-tetrazol-5-yl)phenyl]sulfonyl}-N,N-dimethylglycinamide | 538.0 |

-continued

| EX. No. | HNR$^a$R$^b$ | Structure | Name | LC/MS m/e [M + H]$^+$ |
|---|---|---|---|---|
| 37 | 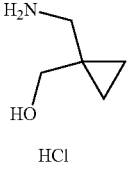 | 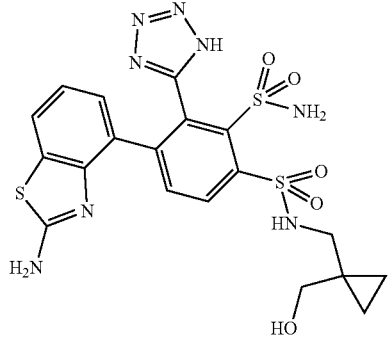 [SMILES: Nc1nc2c(-c3ccc(S(=O)(=O)NCC4(CO)CC4)c(S(N)(=O)=O)c3-c3nnn[nH]3)cccc2s1] | 4-(2-amino-1,3-benzothiazol-4-yl)-N1-{[1-(hydroxymethyl)cyclopropyl]methyl}-3-(1H-tetrazol-5-yl)benzene-1,2-disulfonamide | 537.0 |
| 38 | 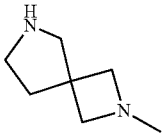 | 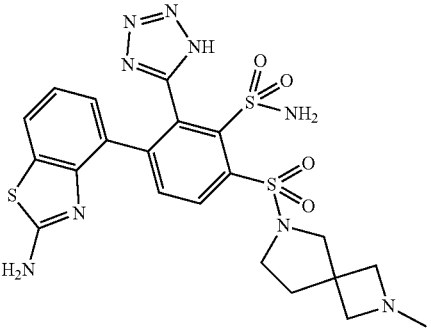 [SMILES: CN1CC2(CCN(S(=O)(=O)c3ccc(-c4cccc5sc(N)nc45)c(-c4nnn[nH]4)c3S(N)(=O)=O)C2)C1] | 3-(2-amino-1,3-benzothiazol-4-yl)-6-[(2-methyl-2,6-diazaspiro[3.4]oct-6-yl)sulfonyl]-2-(1H-tetrazol-5-yl)benzenesulfonamide | 562.1 |
| 39 | 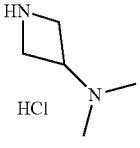 | 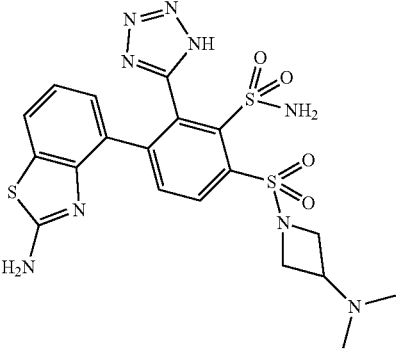 [SMILES: CN(C)C1CN(S(=O)(=O)c2ccc(-c3cccc4sc(N)nc34)c(-c3nnn[nH]3)c2S(N)(=O)=O)C1] | 3-(2-amino-1,3-benzothiazol-4-yl)-6-{[3-(dimethylamino)azetidin-1-yl]sulfonyl}-2-(1H-tetrazol-5-yl)benzenesulfonamide | 536.0 |
| 40 | 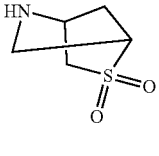 | 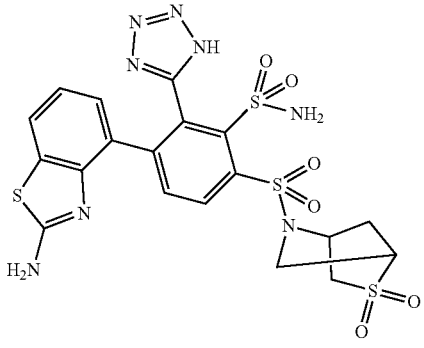 [SMILES: Nc1nc2c(-c3ccc(S(=O)(=O)N4CC5CC4CS5(=O)=O)c(S(N)(=O)=O)c3-c3nnn[nH]3)cccc2s1] | 3-(2-amino-1,3-benzothiazol-4-yl)-6-[(2,2-dioxido-2-thia-5-azabicyclo[2.2.1]hept-5-yl)sulfonyl]-2-(1H-tetrazol-5-yl)benzenesulfonamide | 582.9 |

-continued

| EX. No. | HNR$^a$R$^b$ | Structure | Name | LC/MS m/e [M + H]$^+$ |
|---|---|---|---|---|
| 41 | 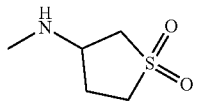 | 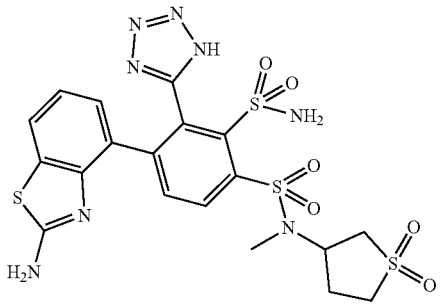 [SMILES: CN(C1CCS(=O)(=O)C1)S(=O)(=O)c1ccc(-c2cccc3sc(N)nc23)c(-c2nnn[nH]2)c1S(N)(=O)=O] | 4-(2-amino-1,3-benzothiazol-4-yl)-N$^1$-(1,1-dioxidotetrahydrothiophen-3-yl)-N~1~-methyl-3-(1H-tetrazol-5-yl)benzene-1,2-disulfonamide | 584.9 |
| 42 | 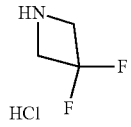 | 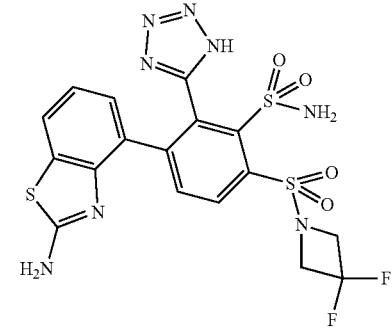 [SMILES: Nc1nc2c(-c3ccc(S(=O)(=O)N4CC(F)(F)C4)c(S(N)(=O)=O)c3-c3nnn[nH]3)cccc2s1] | 3-(2-amino-1,3-benzothiazol-4-yl)-6-[(3,3-difluoroazetidin-1-yl)sulfonyl]-2-(1H-tetrazol-5-yl)benzenesulfonamide | 529.0 |
| 43 | 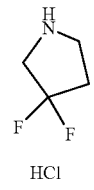 | 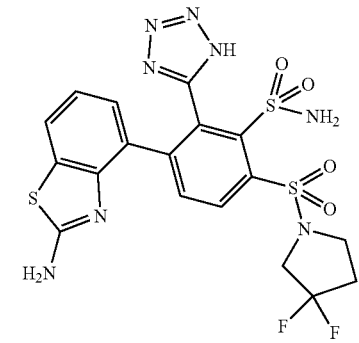 [SMILES: Nc1nc2c(-c3ccc(S(=O)(=O)N4CCC(F)(F)C4)c(S(N)(=O)=O)c3-c3nnn[nH]3)cccc2s1] | 3-(2-amino-1,3-benzothiazol-4-yl)-6-[(3,3-difluoropyrrolidin-1-yl)sulfonyl]-2-(1H-tetrazol-5-yl)benzenesulfonamide | 543.0 |
| 44 | 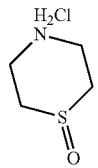 | 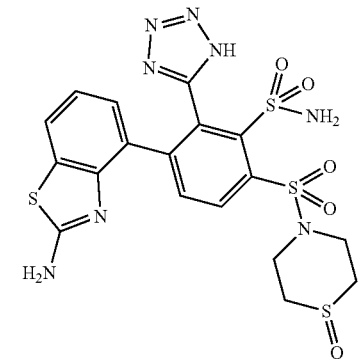 [SMILES: Nc1nc2c(-c3ccc(S(=O)(=O)N4CCS(=O)CC4)c(S(N)(=O)=O)c3-c3nnn[nH]3)cccc2s1] | 3-(2-amino-1,3-benzothiazol-4-yl)-6-[(1-oxidothiomorpholin-4-yl)sulfonyl]-2-(1H-tetrazol-5-yl)benzenesulfonamide | 554.9 |

| EX. No. | HNR^aR^b | Structure | Name | LC/MS m/e [M + H]+ |
|---|---|---|---|---|
| 45 | | 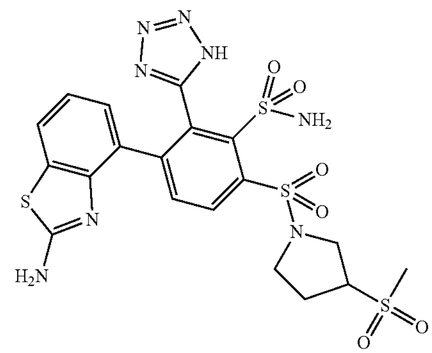 [SMILES: CS(=O)(=O)C1CCN(S(=O)(=O)c2ccc(-c3cccc4sc(N)nc34)c(-c3nnn[nH]3)c2S(N)(=O)=O)C1] | 3-(2-amino-1,3-benzothiazol-4-yl)-6-{[3-(methylsulfonyl)pyrrolidin-1-yl]sulfonyl}-2-(1H-tetrazol-5-yl)benzenesulfonamide | 585.0 |
| 46 | | 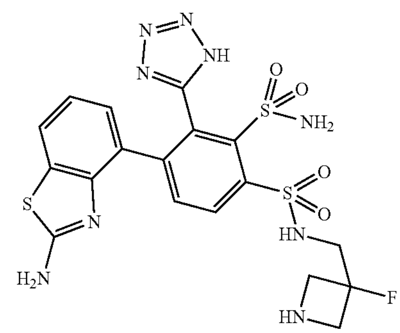 [SMILES: Nc1nc2c(-c3ccc(S(=O)(=O)NCC4(F)CNC4)c(S(N)(=O)=O)c3-c3nnn[nH]3)cccc2s1] | 4-(2-amino-1,3-benzothiazol-4-yl)-$N^1$-[(3-fluoroazetidin-3-yl)methyl]-3-(1H-tetrazol-5-yl)benzene-1,2-disulfonamide | 540.0 |
| 47 | | 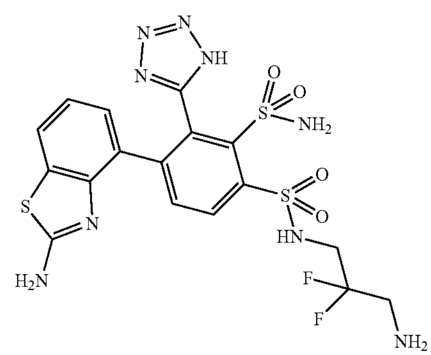 [SMILES: NCC(F)(F)CNS(=O)(=O)c1ccc(-c2cccc3sc(N)nc23)c(-c2nnn[nH]2)c1S(N)(=O)=O] | 4-(2-amino-1,3-benzothiazol-4-yl)-N1-(3-amino-2,2-difluoropropyl)-3-(1H-tetrazol-5-yl)benzene-1,2-disulfonamide | 546.0 |
| 48 | | 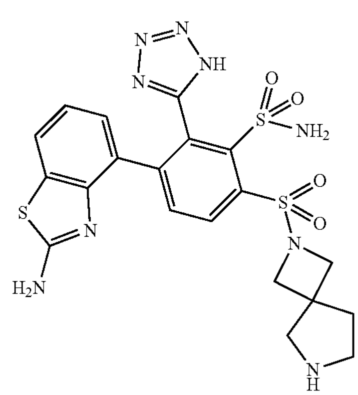 [SMILES: Nc1nc2c(-c3ccc(S(=O)(=O)N4CC5(CCNC5)C4)c(S(N)(=O)=O)c3-c3nnn[nH]3)cccc2s1] | 3-(2-amino-1,3-benzothiazol-4-yl)-6-(2,6-diazaspiro[3.4]oct-2-ylsulfonyl)-2-(1H-tetrazol-5-yl)benzenesulfonamide | 548.0 |

| EX. No. | HNR$^a$R$^b$ | Structure | Name | LC/MS m/e [M + H]$^+$ |
|---|---|---|---|---|
| 49 | | 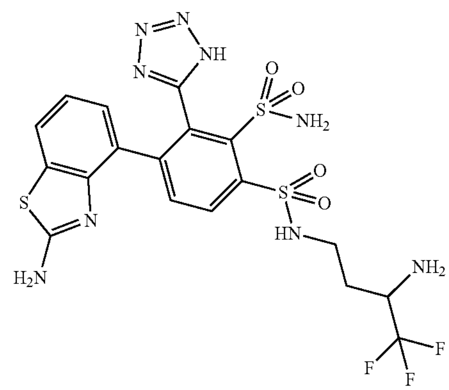 [SMILES: Nc1nc2c(-c3ccc(S(=O)(=O)NCCC(N)C(F)(F)F)c(S(N)(=O)=O)c3-c3nnn[nH]3)cccc2s1] | 4-(2-amino-1,3-benzothiazol-4-yl)-N1-(3-amino-4,4,4-trifluorobutyl)-3-(1H-tetrazol-5-yl)benzene-1,2-disulfonamide | 578.0 |
| 50 | | 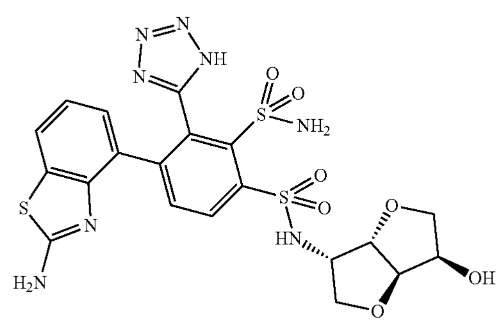 [SMILES: Nc1nc2c(-c3ccc(S(=O)(=O)N[C@H]4CO[C@H]5[C@H]4OC[C@H]5O)c(S(N)(=O)=O)c3-c3nnn[nH]3)cccc2s1] | 2-({[4-(2-amino-1,3-benzothiazol-4-yl)-2-sulfamoyl-3-(1H-tetrazol-5-yl)phenyl]sulfonyl}amino)-1,4:3,6-dianhydro-2-deoxy-D-allitol | 581.1 |
| 51 | | 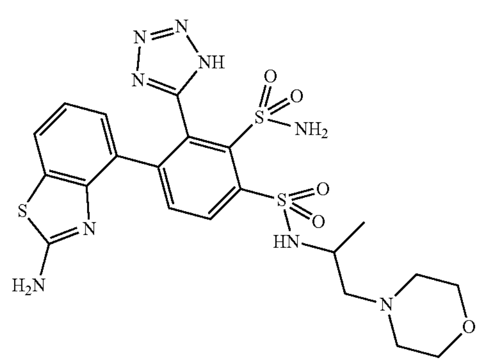 [SMILES: CC(CN1CCOCC1)NS(=O)(=O)c1ccc(-c2cccc3sc(N)nc23)c(-c2nnn[nH]2)c1S(N)(=O)=O] | 4-(2-amino-1,3-benzothiazol-4-yl)-N1-(1-methyl-2-morpholin-4-ylethyl)-3-(1H-tetrazol-5-yl)benzene-1,2-disulfonamide | 580.0 |
| 52 | | 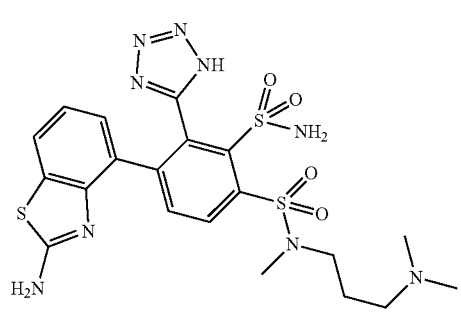 [SMILES: CN(C)CCCN(C)S(=O)(=O)c1ccc(-c2cccc3sc(N)nc23)c(-c2nnn[nH]2)c1S(N)(=O)=O] | 4-(2-amino-1,3-benzothiazol-4-yl)-N1-[3-(dimethylamino)propyl]-N~1~-methyl-3-(1H-tetrazol-5-yl)benzene-1,2-disulfonamide | 552.0 |

-continued

| EX. No. | HNR<sup>a</sup>R<sup>b</sup> | Structure | Name | LC/MS m/e [M + H]<sup>+</sup> |
|---|---|---|---|---|
| 53 | | 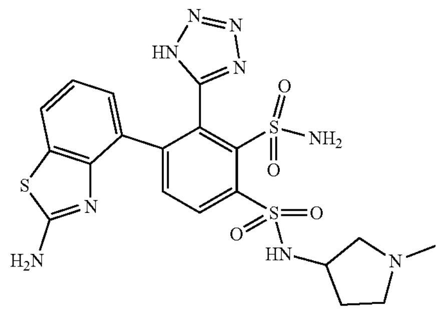 [SMILES: CN1CCC(NS(=O)(=O)c2ccc(-c3cccc4sc(N)nc34)c(-c3nnn[nH]3)c2S(N)(=O)=O)C1] | 4-(2-amino-1,3-benzothiazol-4-yl)-N1-(1-methylpyrrolidin-3-yl)-3-(1H-tetrazol-5-yl)benzene-1,2-disulfonamide | 536.1 |
| 54 | | 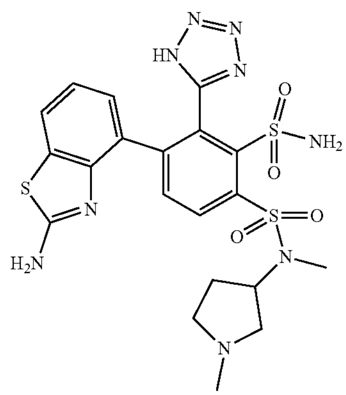 [SMILES: CN1CCC(N(C)S(=O)(=O)c2ccc(-c3cccc4sc(N)nc34)c(-c3nnn[nH]3)c2S(N)(=O)=O)C1] | 4-(2-amino-1,3-benzothiazol-4-yl)-N1-methyl-N1-(1-methylpyrrolidin-3-yl)-3-(1H-tetrazol-5-yl)benzene-1,2-disulfonamide | 550.0 |
| 55 | | 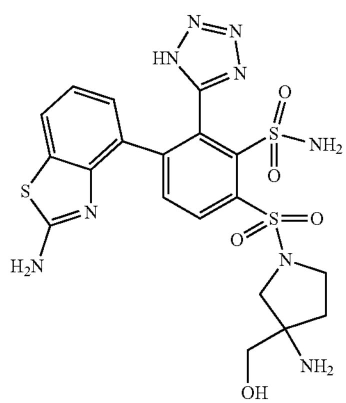 [SMILES: Nc1nc2c(-c3ccc(S(=O)(=O)N4CCC(N)(CO)C4)c(S(N)(=O)=O)c3-c3nnn[nH]3)cccc2s1] | 3-(2-amino-1,3-benzothiazol-4-yl)-6-{[3-amino-3-(hydroxymethyl)pyrrolidin-1-yl]sulfonyl}-2-(1H-tetrazol-5-yl)benzenesulfonamide | 552.1 |
| 56 | | 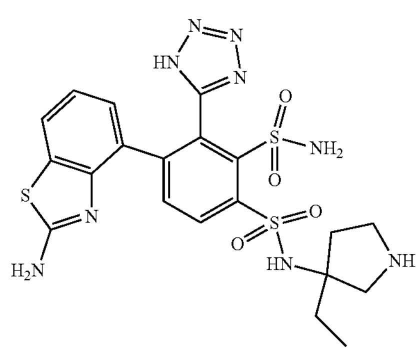 [SMILES: CCC1(NS(=O)(=O)c2ccc(-c3cccc4sc(N)nc34)c(-c3nnn[nH]3)c2S(N)(=O)=O)CCNC1] | 4-(2-amino-1,3-benzothiazol-4-yl)-N1-(3-ethylpyrrolidin-3-yl)-3-(1H-tetrazol-5-yl)benzene-1,2-disulfonamide | 550.1 |

| EX. No. | HNR$^a$R$^b$ | Structure | Name | LC/MS m/e [M + H]$^+$ |
|---|---|---|---|---|
| 57 | 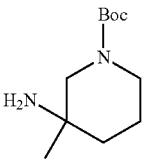 | 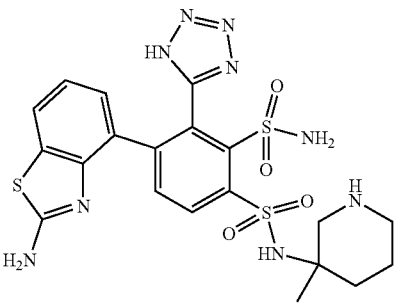 [SMILES: CC1(NS(=O)(=O)c2ccc(-c3cccc4sc(N)nc34)c(-c3nnn[nH]3)c2S(N)(=O)=O)CCCNC1] | 4-(2-amino-1,3-benzothiazol-4-yl)-N1-(3-methylpiperidin-3-yl)-3-(1H-tetrazol-5-yl)benzene-1,2-disulfonamide | 550.0 |
| 58 | 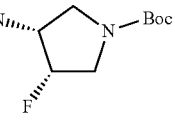 | 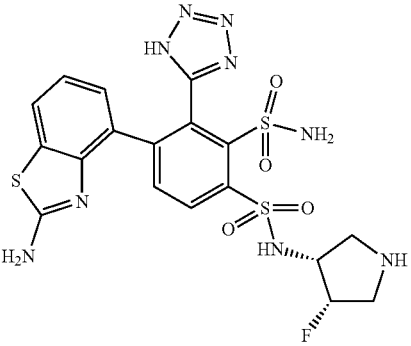 [SMILES: Nc1nc2c(-c3ccc(S(=O)(=O)N[C@@H]4CNC[C@@H]4F)c(S(N)(=O)=O)c3-c3nnn[nH]3)cccc2s1] | 4-(2-amino-1,3-benzothiazol-4-yl)-N1-[(3R,4S)-4-fluoropyrrolidin-3-yl]-3-(1H-tetrazol-5-yl)benzene-1,2-disulfonamide | 540.0 |
| 59 | 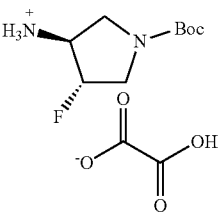 | 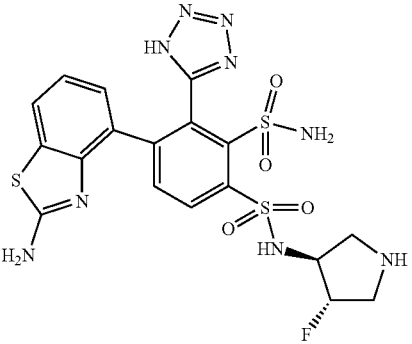 [SMILES: Nc1nc2c(-c3ccc(S(=O)(=O)N[C@H]4CNC[C@@H]4F)c(S(N)(=O)=O)c3-c3nnn[nH]3)cccc2s1] | 4-(2-amino-1,3-benzothiazol-4-yl)-N1-[(3S,4S)-4-fluoropyrrolidin-3-yl]-3-(1H-tetrazol-5-yl)benzene-1,2-disulfonamide | 540.0 |
| 60 | 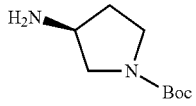 | 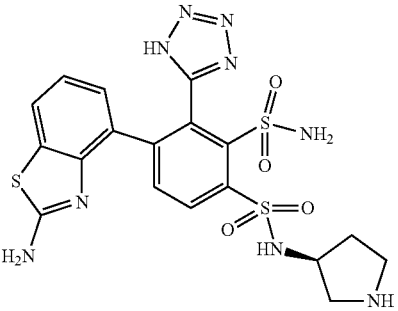 [SMILES: Nc1nc2c(-c3ccc(S(=O)(=O)N[C@H]4CCNC4)c(S(N)(=O)=O)c3-c3nnn[nH]3)cccc2s1] | 4-(2-amino-1,3-benzothiazol-4-yl)-N1-[(3S)-pyrrolidin-3-yl]-3-(1H-tetrazol-5-yl)benzene-1,2-disulfonamide | 522.0 |

-continued

| EX. No. | HNR^aR^b | Structure | Name | LC/MS m/e [M + H]+ |
|---|---|---|---|---|
| 61 | 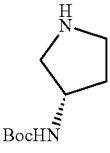 | 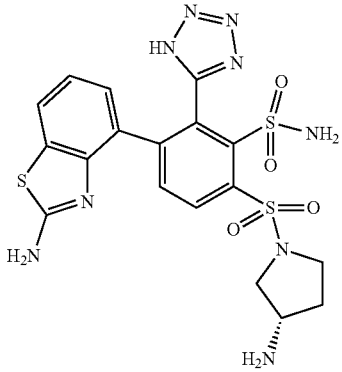 [SMILES: Nc1nc2c(-c3ccc(S(=O)(=O)N4CC[C@H](N)C4)c(S(N)(=O)=O)c3-c3nnn[nH]3)cccc2s1] | 3-(2-amino-1,3-benzothiazol-4-yl)-6-{[(3S)-3-aminopyrrolidin-1-yl]sulfonyl}-2-(1H-tetrazol-5-yl)benzenesulfonamide | 522.1 |
| 62 | 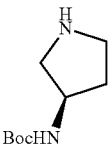 | 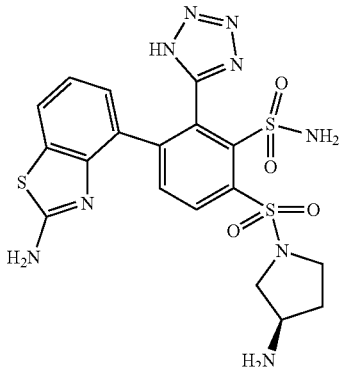 | 3-(2-amino-1,3-benzothiazol-4-yl)-6-{[(3R)-3-aminopyrrolidin-1-yl]sulfonyl}-2-(1H-tetrazol-5-yl)benzenesulfonamide | 521.9 |
| 63 | 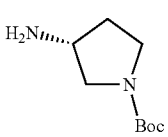 | 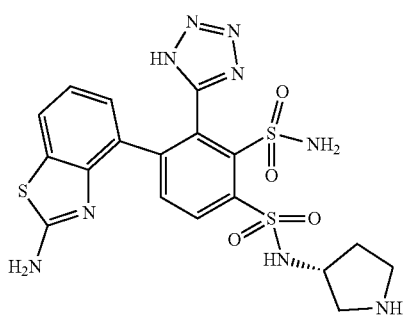 [SMILES: Nc1nc2c(-c3ccc(S(=O)(=O)N[C@@H]4CCNC4)c(S(N)(=O)=O)c3-c3nnn[nH]3)cccc2s1] | 4-(2-amino-1,3-benzothiazol-4-yl)-N1-[(3R)-pyrrolidin-3-yl]-3-(1H-tetrazol-5-yl)benzene-1,2-disulfonamide | 522.1 |
| 64 | 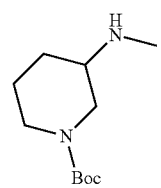 | 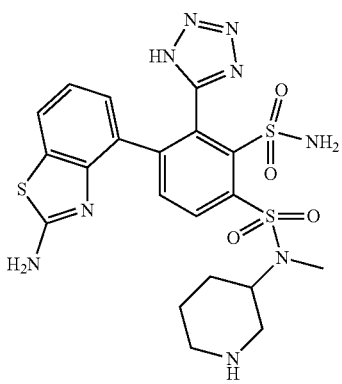 [SMILES: CN(C1CCCNC1)S(=O)(=O)c1ccc(-c2cccc3sc(N)nc23)c(-c2nnn[nH]2)c1S(N)(=O)=O] | 4-(2-amino-1,3-benzothiazol-4-yl)-N1-methyl-N1-piperidin-3-yl-3-(1H-tetrazol-5-yl)benzene-1,2-disulfonamide | 550.1 |

-continued

| EX. No. | HNR<sup>a</sup>R<sup>b</sup> | Structure | Name | LC/MS m/e [M + H]<sup>+</sup> |
|---|---|---|---|---|
| 65 | 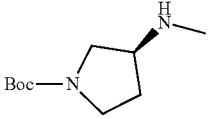 | 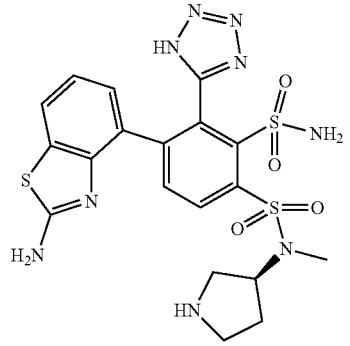 [SMILES: CN([C@H]1CCNC1)S(=O)(=O)c1ccc(-c2cccc3sc(N)nc23)c(-c2nnn[nH]2)c1S(N)(=O)=O] | 4-(2-amino-1,3-benzothiazol-4-yl)-N1-methyl-N1-[(3S)-pyrrolidin-3-yl]-3-(1H-tetrazol-5-yl)benzene-1,2-disulfonamide | 536.1 |
| 66 | 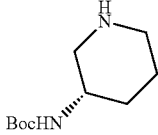 [SMILES: CC(C)(C)OC(=O)N[C@H]1CCCNC1] | 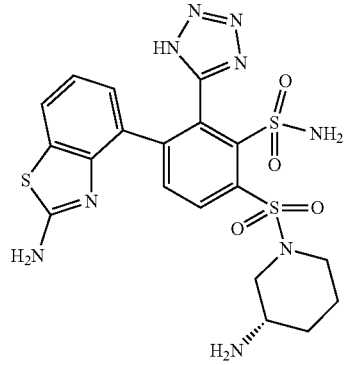 [SMILES: Nc1nc2c(-c3ccc(S(=O)(=O)N4CCC[C@H](N)C4)c(S(N)(=O)=O)c3-c3nnn[nH]3)cccc2s1] | 3-(2-amino-1,3-benzothiazol-4-yl)-6-{[(3S)-3-aminopiperidin-1-yl]sulfonyl}-2-(1H-tetrazol-5-yl)benzenesulfonamide | 536.1 |
| 67 | 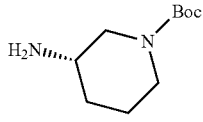 | 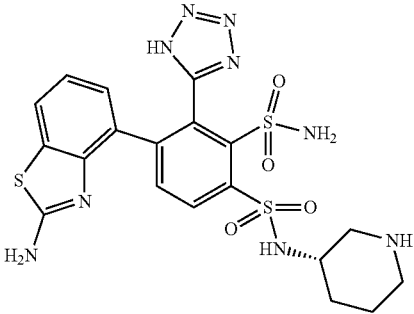 [SMILES: Nc1nc2c(-c3ccc(S(=O)(=O)N[C@H]4CCCNC4)c(S(N)(=O)=O)c3-c3nnn[nH]3)cccc2s1] | 4-(2-amino-1,3-benzothiazol-4-yl)-N1-[(3S)-piperidin-3-yl]-3-(1H-tetrazol-5-yl)benzene-1,2-disulfonamide | 536.2 |
| 68 | 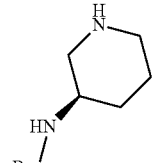 | 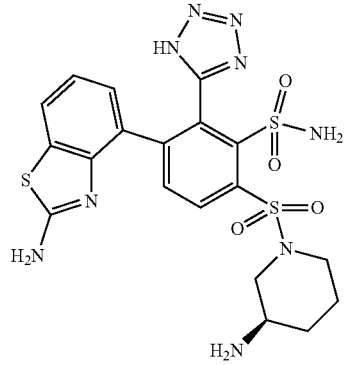 [SMILES: Nc1nc2c(-c3ccc(S(=O)(=O)N4CCC[C@@H](N)C4)c(S(N)(=O)=O)c3-c3nnn[nH]3)cccc2s1] | 3-(2-amino-1,3-benzothiazol-4-yl)-6-{[(3R)-3-aminopiperidin-1-yl]sulfonyl}-2-(1H-tetrazol-5-yl)benzenesulfonamide | 536.1 |

-continued

| EX. No. | HNR$^a$R$^b$ | Structure | Name | LC/MS m/e [M + H]$^+$ |
|---|---|---|---|---|
| 69 | 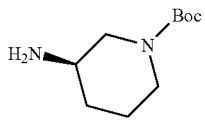 | 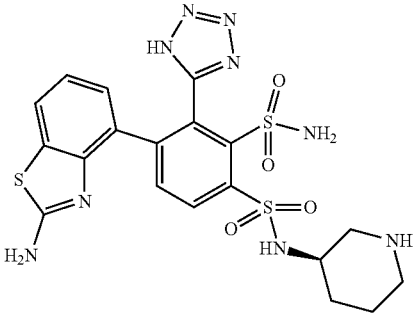 [SMILES: Nc1nc2c(-c3ccc(S(=O)(=O)N[C@@H]4CCCNC4)c(S(N)(=O)=O)c3-c3nnn[nH]3)cccc2s1] | 4-(2-amino-1,3-benzothiazol-4-yl)-N1-[(3R)-piperidin-3-yl]-3-(1H-tetrazol-5-yl)benzene-1,2-disulfonamide | 536.1 |
| 70 | 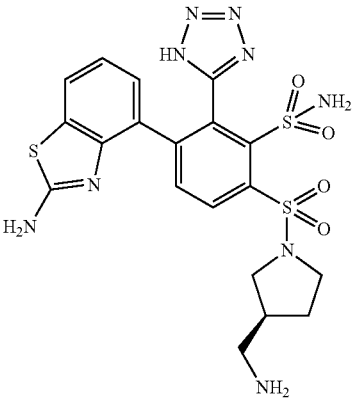 | 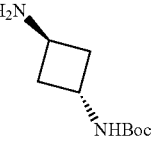 | 3-(2-amino-1,3-benzothiazol-4-yl)-6-{[(3S)-3-(aminomethyl)pyrrolidin-1-yl]sulfonyl}-2-(1H-tetrazol-5-yl)benzenesulfonamide | 536.0 |
| 71 | 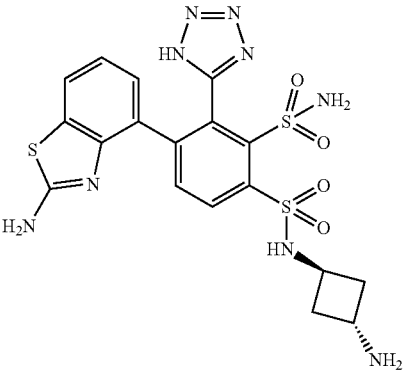 | 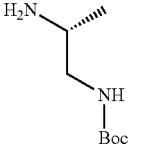 | 4-(2-amino-1,3-benzothiazol-4-yl)-N$^1$-(trans-3-aminocyclobutyl)-3-(1H-tetrazol-5-yl)benzene-1,2-disulfonamide | 521.9 |
| 72 | 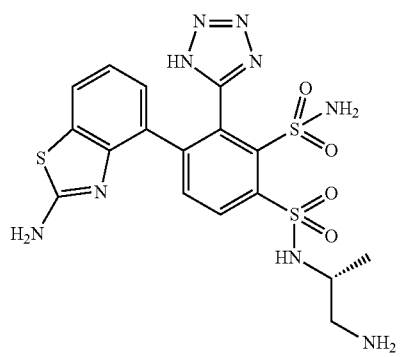 | 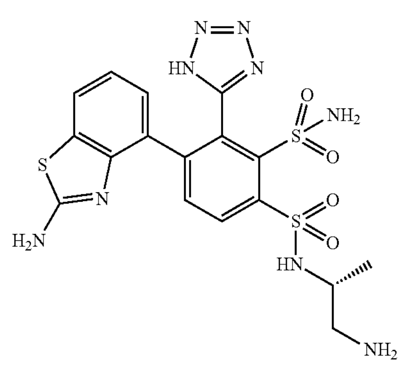 [SMILES: C[C@H](CN)NS(=O)(=O)c1ccc(-c2cccc3sc(N)nc23)c(-c2nnn[nH]2)c1S(N)(=O)=O] | (R)-4-(2-aminobenzo[d]thiazol-4-yl)-N$^1$-(1-aminopropan-2-yl)-3-(1H-tetrazol-5-yl)benzene-1,2-disulfonamide | 510.1 |

-continued

| EX. No. | HNRᵃRᵇ | Structure | Name | LC/MS m/e [M + H]⁺ |
|---|---|---|---|---|
| 73 | H₂N-CH₂-(pyrrolidine-N-Boc) | 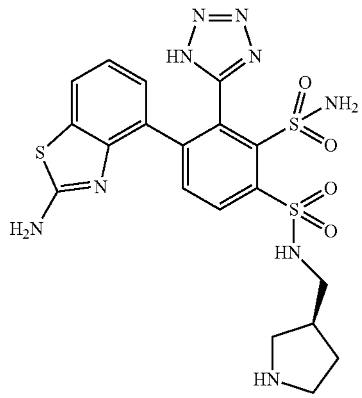 [SMILES: Nc1nc2c(-c3ccc(S(=O)(=O)NC[C@H]4CCNC4)c(S(N)(=O)=O)c3-c3nnn[nH]3)cccc2s1] | 4-(2-amino-1,3-benzothiazol-4-yl)-N¹-[(3S)-pyrrolidin-3-ylmethyl]-3-(1H-tetrazol-5-yl)benzene-1,2-disulfonamide | 535.9 |
| 74 | HCl, pyrrolidine-CH₂-NHBoc | 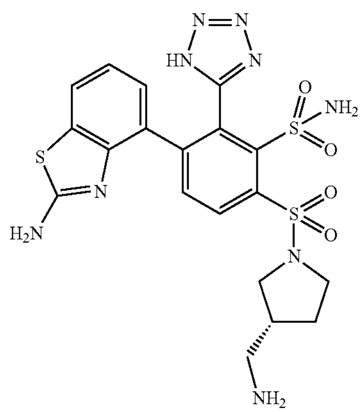 [SMILES: NC[C@H]1CCN(S(=O)(=O)c2ccc(-c3cccc4sc(N)nc34)c(-c3nnn[nH]3)c2S(N)(=O)=O)C1] | 3-(2-amino-1,3-benzothiazol-4-yl)-6-{[(3R)-3-(aminomethyl)pyrrolidin-1-yl]sulfonyl}-2-(1H-tetrazol-5-yl)benzenesulfonamide | 536.0 |
| 75 | H₂N-CH₂-(pyrrolidine-N-Boc) | 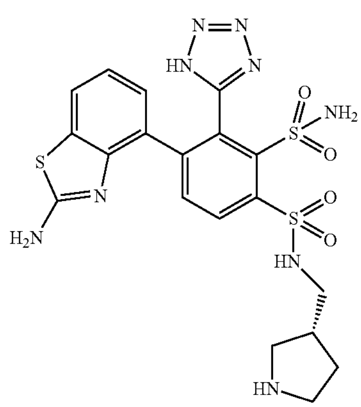 [SMILES: Nc1nc2c(-c3ccc(S(=O)(=O)NC[C@@H]4CCNC4)c(S(N)(=O)=O)c3-c3nnn[nH]3)cccc2s1] | 4-(2-amino-1,3-benzothiazol-4-yl)-N¹-[(3R)-pyrrolidin-3-ylmethyl]-3-(1H-tetrazol-5-yl)benzene-1,2-disulfonamide | 535.9 |

| EX. No. | HNR$^a$R$^b$ | Structure | Name | LC/MS m/e [M + H]$^+$ |
|---|---|---|---|---|
| 76 | 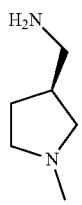 | 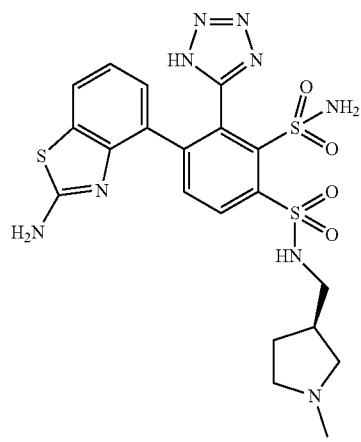 [SMILES: CN1CC[C@@H](CNS(=O)(=O)c2ccc(-c3cccc4sc(N)nc34)c(-c3nnn[nH]3)c2S(N)(=O)=O)C1] | 4-(2-amino-1,3-benzothiazol-4-yl)-N$^1$-{[(3R)-1-methylpyrrolidin-3-yl]methyl}-3-(1H-tetrazol-5-yl)benzene-1,2-disulfonamide | 550.0 |
| 77 | 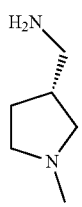 | 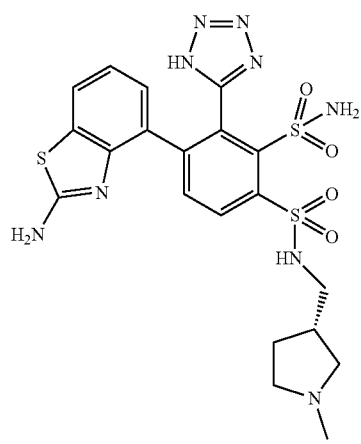 [SMILES: CN1CC[C@H](CNS(=O)(=O)c2ccc(-c3cccc4sc(N)nc34)c(-c3nnn[nH]3)c2S(N)(=O)=O)C1] | 4-(2-amino-1,3-benzothiazol-4-yl)-N1-{[(3S)-1-methylpyrrolidin-3-yl]methyl}-3-(1H-tetrazol-5-yl)benzene-1,2-disulfonamide | 549.9 |
| 78 | 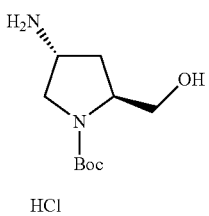 HCl | 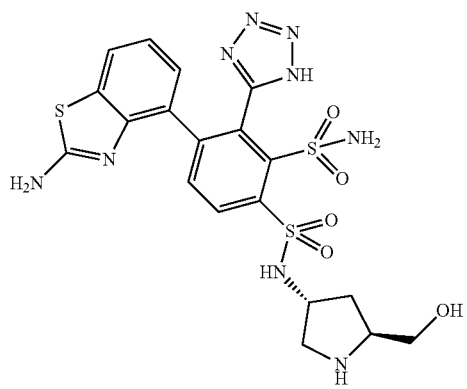 [SMILES: Nc1nc2c(-c3ccc(S(=O)(=O)N[C@H]4CN[C@H](CO)C4)c(S(N)(=O)=O)c3-c3nnn[nH]3)cccc2s1] | 4-(2-amino-1,3-benzothiazol-4-yl)-N1-[(3R,5S)-5-(hydroxymethyl)pyrrolidin-3-yl]-3-(1H-tetrazol-5-yl)benzene-1,2-disulfonamide | 552.0 |

| EX. No. | HNR$^a$R$^b$ | Structure | Name | LC/MS m/e [M + H]$^+$ |
|---|---|---|---|---|
| 79 | 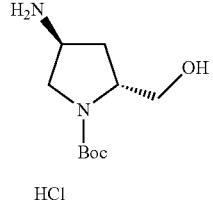 HCl | 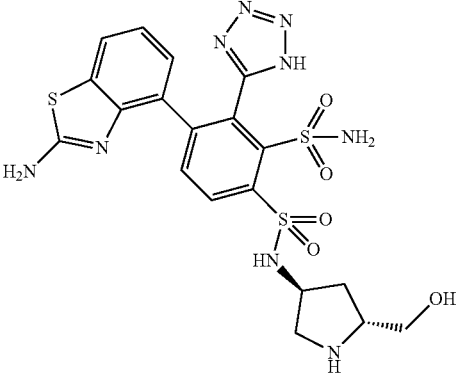 [SMILES: Nc1nc2c(-c3ccc(S(=O)(=O)N[C@@H]4CN[C@@H](CO)C4)c(S(N)(=O)=O)c3-c3nnn[nH]3)cccc2s1] | 4-(2-amino-1,3-benzothiazol-4-yl)-N1-[(3S,5R)-5-(hydroxymethyl)pyrrolidin-3-yl]-3-(1H-tetrazol-5-yl)benzene-1,2-disulfonamide | 522.0 |
| 80 | 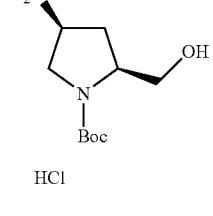 HCl | 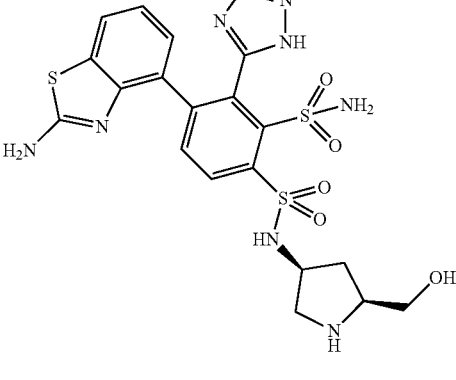 | 4-(2-amino-1,3-benzothiazol-4-yl)-N1-[(3S,5S)-5-(hydroxymethyl)pyrrolidin-3-yl]-3-(1H-tetrazol-5-yl)benzene-1,2-disulfonamide | 552.0 |
| 81 | 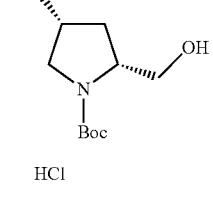 HCl | 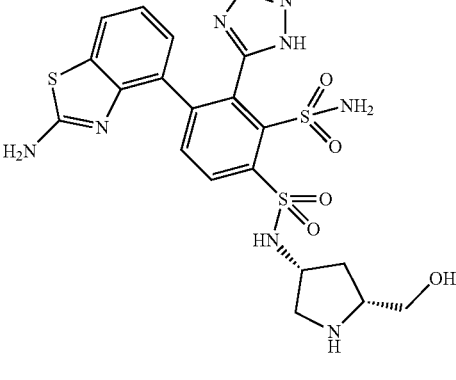 | 4-(2-amino-1,3-benzothiazol-4-yl)-N1-[(3R,5R)-5-(hydroxymethyl)pyrrolidin-3-yl]-3-(1H-tetrazol-5-yl)benzene-1,2-disulfonamide | 552.0 |
| 82 | 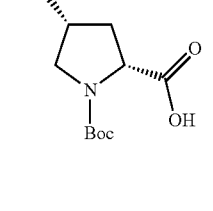 | 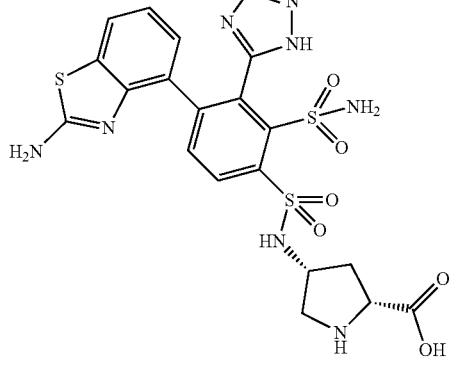 | (4R)-4-({[4-(2-amino-1,3-benzothiazol-4-yl)-2-sulfamoyl-3-(1H-tetrazol-5-yl)phenyl]sulfonyl}amino)-D-proline | 566.0 |

| EX. No. | HNR$^a$R$^b$ | Structure | Name | LC/MS m/e [M + H]$^+$ |
|---|---|---|---|---|
| 83 | H$_2$N–[pyrrolidine with NBoc, CH$_2$OH] Enantiomer A (faster eluting) | [structure] Enantiomer A | 4-(2-amino-1,3-benzothiazol-4-yl)-N1-[3-(hydroxymethyl)pyrrolidin-3-yl]-3-(1H-tetrazol-5-yl)benzene-1,2-disulfonamide | 551.9 |
| 84 | H$_2$N–[pyrrolidine with NBoc, CH$_2$OH] Enantiomer B (slower eluting) | [structure] Enantiomer B | 4-(2-amino-1,3-benzothiazol-4-yl)-N1-[3-(hydroxymethyl)pyrrolidin-3-yl]-3-(1H-tetrazol-5-yl)benzene-1,2-disulfonamide | 551.9 |

Example S 85-127

General procedure for parallel preparation of sulfonamide examples 85-127:

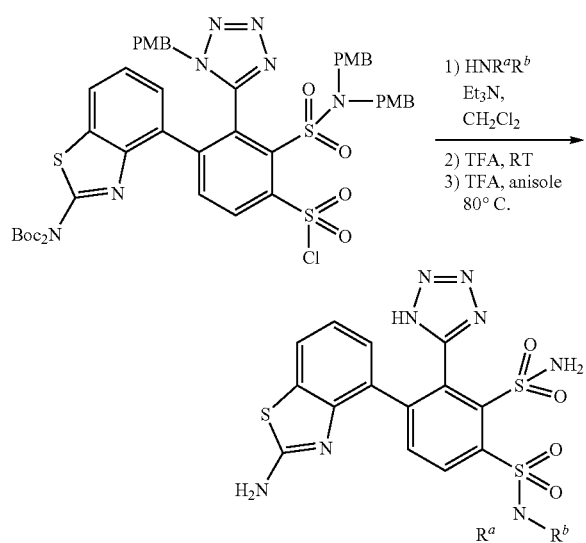

To a set of vials each containing the requisite amine (commercially available, known, or prepared as described herein, 0.13 mmol) was added a solution of the sulfonyl chloride (45 mg, 0.044 mmol) followed by Et$_3$N (0.018 mL, 0.13 mmol). The vials were capped and the mixtures were stirred at RT for 5 hours. To the reaction mixture was then added TFA (0.5 mL) and the mixtures were stirred at RT for 1.5 hours. After that time, toluene (1 mL) was added to each vial and the mixtures were concentrated in vacuo. To each vial was then added TFA (1.0 mL) and anisole (0.019 mL, 0.17 mmol). The vials were capped and the reaction mixtures were heated to 80° C. with stirring for 45 minutes. After that time, the reaction mixtures were concentrated in vacuo. The crude residues were then dissolved in DMSO (1.0 mL) and filtered. The crude products were purified by mass triggered preparative HPLC [Waters Sunfire C18 column, 5 μm, 19×100 mm, using a gradient range from 8% initial to 30% final MeCN (0.1% TFA) in water (0.1% TFA), 25 mL/min, 8 min run time]. The isolated products were each dissolved in MeOH (1 mL) and loaded onto an ion exchange cartridge [Agilent Bond Elut SCX (2 gram)]. The TFA was eluted off the column with MeOH (20 mL). The products were then eluted off using a solution of NH$_3$ in MeOH (7N, 20 mL). This fraction was then concentrated in vacuo. The residue was dissolved in 1:1 MeCN:distilled water (2 mL). These fractions were then frozen and lyophillized overnight to afford Examples 85-127.

| EX. No. | HNR$^a$R$^b$ | Structure | Name | LC/MS m/e [M + H]$^+$ |
|---|---|---|---|---|
| 85 | H$_2$N-CH$_2$CH$_2$-N(Boc)-CH$_2$CH$_2$-O-CH$_3$ | 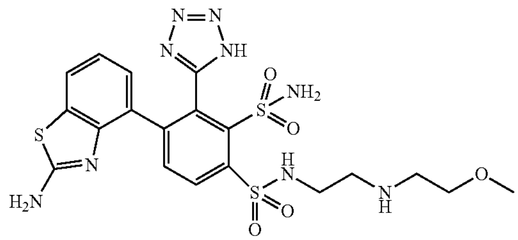 [SMILES: COCCNCCNS(=O)(=O)c1ccc(-c2cccc3sc(N)nc23)c(-c2nnn[nH]2)c1S(N)(=O)=O] | 4-(2-aminobenzo[d]thiazol-4-yl)-N1-(2-((2-methoxyethyl)amino)ethyl)-3-(1H-tetrazol-5-yl)benzene-1,2-disulfonamide | 554.10 |
| 86 | H$_2$N-CH$_2$-(4-hydroxy-1-Boc-piperidin-4-yl) HCl | 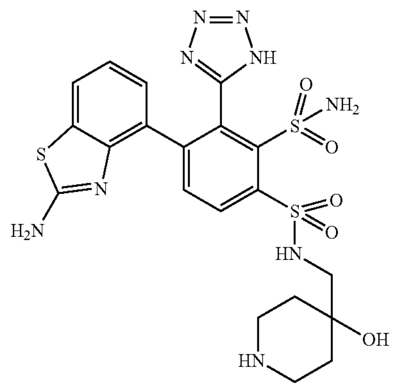 [SMILES: Nc1nc2c(-c3ccc(S(=O)(=O)NCC4(O)CCNCC4)c(S(N)(=O)=O)c3-c3nnn[nH]3)cccc2s1] | 4-(2-aminobenzo[d]thiazol-4-yl)-N$^1$-((4-hydroxypiperidin-4-yl)methyl)-3-(1H-tetrazol-5-yl)benzene-1,2-disulfonamide | 566.1 |
| 87 | H$_2$N-CH$_2$-C(CH$_3$)$_2$-NHBoc HCl | 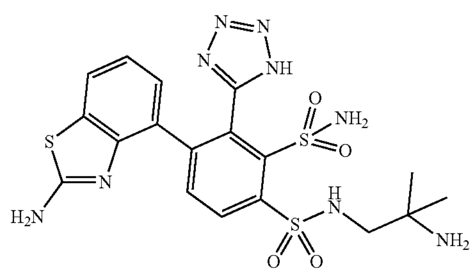 [SMILES: CC(C)(N)CNS(=O)(=O)c1ccc(-c2cccc3sc(N)nc23)c(-c2nnn[nH]2)c1S(N)(=O)=O] | N$^1$-(2-amino-2-methylpropyl)-4-(2-aminobenzo[d]thiazol-4-yl)-3-(1H-tetrazol-5-yl)benzene-1,2-disulfonamide | 524.0 |
| 88 | H$_2$N-(2-Boc-azabicyclo[2.2.1]heptan-6-yl) Enantiomer A (faster eluting) | Enantiomer A | 4-(2-aminobenzo[d]thiazol-4-yl)-N$^1$-(2-azabicyclo[2.2.1]heptan-6-yl)-3-(1H-tetrazol-5-yl)benzene-1,2-disulfonamide | 548.0 |

-continued

| EX. No. | HNR$^a$R$^b$ | Structure | Name | LC/MS m/e [M + H]$^+$ |
|---|---|---|---|---|
| 89 | H$_2$N-[2-azabicyclo[2.2.1]heptane]-Boc<br>Enantiomer B (slower eluting) | Enantiomer B | 4-(2-aminobenzo[d]thiazol-4-yl)-N$^1$-(2-azabicyclo[2.2.1]heptan-6-yl)-3-(1H-tetrazol-5-yl)benzene-1,2-disulfonamide | 548.0 |
| 90 | H$_2$N~~~NHBoc | 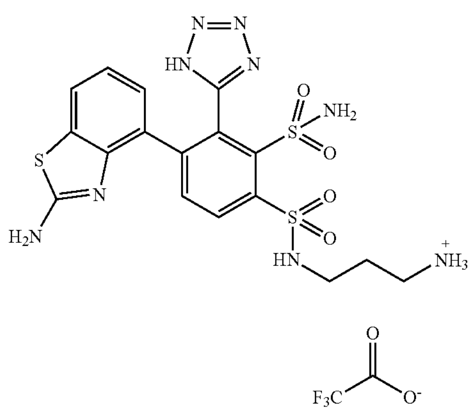 [SMILES: NCCCNS(=O)(=O)c1ccc(-c2cccc3sc(N)nc23)c(-c2nnn[nH]2)c1S(N)(=O)=O ; O=C([O-])C(F)(F)F] | 3-(4-(2-aminobenzo[d]thiazol-4-yl)-2-sulfamoyl-3-(1H-tetrazol-5-yl)phenylsulfonamido)propan-1-aminium 2,2,2-trifluoroacetate | 510.07 |
| 91 | H$_2$N-CH$_2$-[3-fluoroazetidine]-Boc | 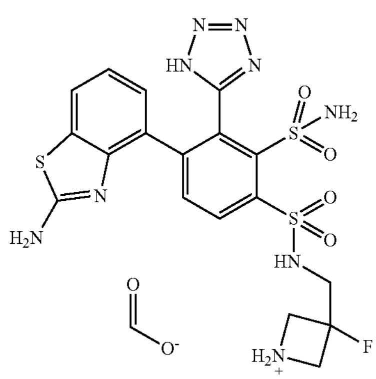 | 3-(((4-(2-aminobenzo[d]thiazol-4-yl)-2-sulfamoyl-3-(1H-tetrazol-5-yl)phenyl)sulfonamido)methyl)-3-fluoroazetidin-1-ium formate | 540.06 |

-continued

| EX. No. | HNR<sup>a</sup>R<sup>b</sup> | Structure | Name | LC/MS m/e [M + H]<sup>+</sup> |
|---|---|---|---|---|
| 92 | | 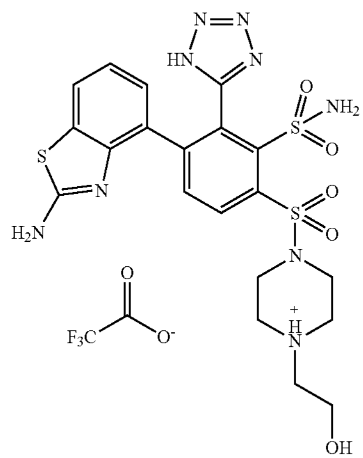 | 4-((4-(2-aminobenzo[d]thiazol-4-yl)-2-sulfamoyl-3-(1H-tetrazol-3-yl)phenyl)sulfonyl)-1-(2-hydroxyethyl)piperazin-1-ium 2,2,2-trifluoroacetate | 566.1 |
| 93 | | 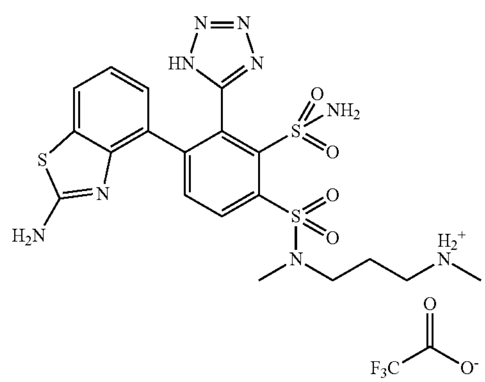 | 3-(4-(2-aminobenzo[d]thiazol-4-yl)-N-methyl-2-sulfamoyl-3-(1H-tetrazol-5-yl)phenylsulfonamido)-N-methylpropan-1-aminium 2,2,2-trifluoroacetate | 538.1 |
| 94 | | 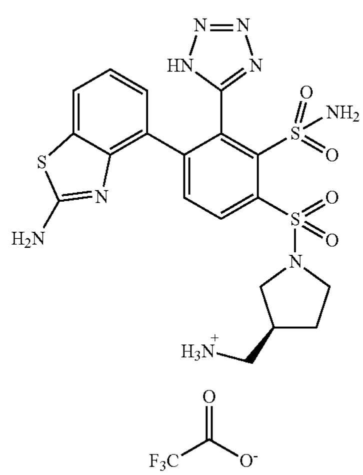 [SMILES: NC[C@@H]1CCN(S(=O)(=O)c2ccc(-c3cccc4sc(N)nc34)c(-c3nnn[nH]3)c2S(N)(=O)=O)C1 ; O=C([O-])C(F)(F)F] | (S)-(1-((4-(2-aminobenzo[d]thiazol-4-yl)-2-sulfamoyl-3-(1H-tetrazol-5-yl)phenyl)sulfonyl)pyrrolidin-3-yl)methanaminium 2,2,2-trifluoroacetate | 536.09 |

-continued

| EX. No. | HNR$^a$R$^b$ | Structure | Name | LC/MS m/e [M + H]$^+$ |
|---|---|---|---|---|
| 95 | | 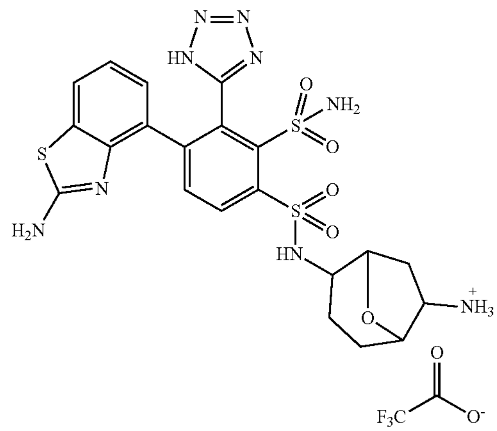 [SMILES: Nc1nc2c(-c3ccc(S(=O)(=O)NC4CCC5OC4CC5N)c(S(N)(=O)=O)c3-c3nnn[nH]3)cccc2s1 ; O=C([O-])C(F)(F)F] | 2-(4-(2-aminobenzo[d]thiazol-4-yl)-2-sulfamoyl-3-(1H-tetrazol-5-yl)phenyl-sulfonamido)-8-oxabicyclo[3.2.1]octan-6-aminium 2,2,2-trifluoroacetate | 578.1 |
| 96 | | 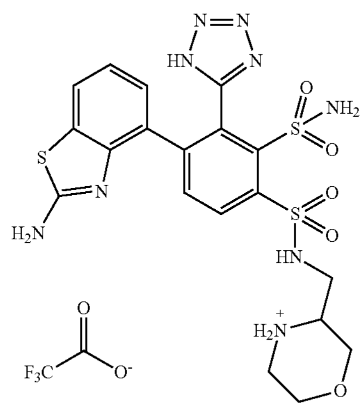 [SMILES: Nc1nc2c(-c3ccc(S(=O)(=O)NCC4COCCN4)c(S(N)(=O)=O)c3-c3nnn[nH]3)cccc2s1 ; O=C([O-])C(F)(F)F] | 3-((4-(2-aminobenzo[d]thiazol-4-yl)-2-sulfamoyl-3-(1H-tetrazol-5-yl)phenylsulfonamido)methyl)morpholin-4-ium 2,2,2-trifluoroacetate | 552.08 |
| 97 | | 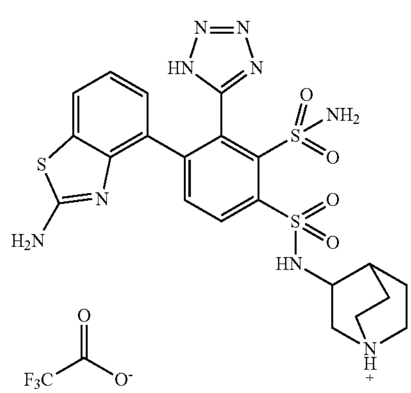 [SMILES: Nc1nc2c(-c3ccc(S(=O)(=O)NC4CN5CCC4CC5)c(S(N)(=O)=O)c3-c3nnn[nH]3)cccc2s1 ; O=C([O-])C(F)(F)F] | 3-(4-(2-amino-benzo[d]thiazol-4-yl)-2-sulfamoyl-3-(1H-tetrazol-5-yl)phenylsulfonamido)quinuclidin-1-ium 2,2,2-trifluoroacetate | 562.1 |

| EX. No. | HNR<sup>a</sup>R<sup>b</sup> | Structure | Name | LC/MS m/e [M + H]<sup>+</sup> |
|---|---|---|---|---|
| 98 | 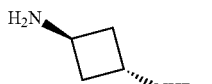 | 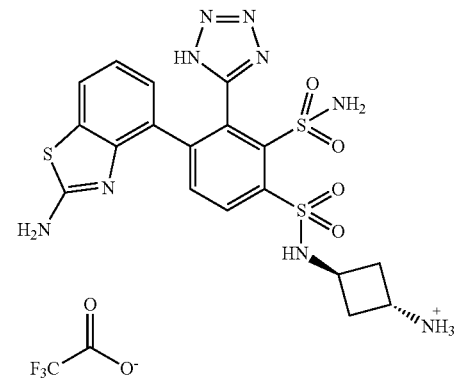 [SMILES: Nc1nc2c(-c3ccc(S(=O)(=O)N[C@H]4C[C@H](N)C4)c(S(N)(=O)=O)c3-c3nnn[nH]3)cccc2s1 ; O=C([O-])C(F)(F)F] | (1r,3r)-3-(4-(2-aminobenzo[d]thiazol-4-yl)-2-sulfamoyl-3-(1H-tetrazol-5-yl)phenylsulfonamido)cyclobutanaminium 2,2,2-trifluoroacetate | 522.07 |
| 99 | 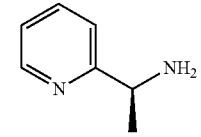 | 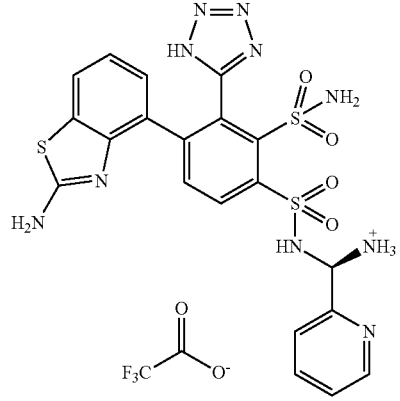 [SMILES: Nc1nc2c(-c3ccc(S(=O)(=O)N[C@@H](N)c4ccccn4)c(S(N)(=O)=O)c3-c3nnn[nH]3)cccc2s1 ; O=C([O-])C(F)(F)F] | (R)-(4-(2-aminobenzo[d]thiazol-4-yl)-2-sulfamoyl-3-(1H-tetrazol-5-yl)phenylsulfonamido)(pyridin-2-yl)methanaminium 2,2,2-trifluoroacetate | 558.07 |
| 100 | 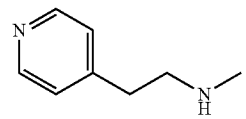 | 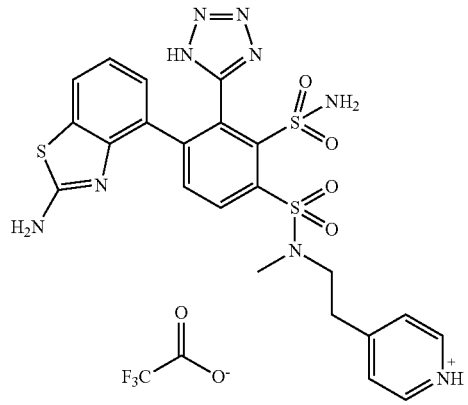 [SMILES: CN(CCc1ccncc1)S(=O)(=O)c1ccc(-c2cccc3sc(N)nc23)c(-c2nnn[nH]2)c1S(N)(=O)=O ; O=C([O-])C(F)(F)F] | 4-(2-(4-(2-aminobenzo[d]thiazol-4-yl)-N-methyl-2-sulfamoyl-3-(1H-tetrazol-5-yl)phenylsulfonamido)ethyl)pyridin-1-ium 2,2,2-trifluoroacetate | 572.09 |

| EX. No. | HNR$^a$R$^b$ | Structure | Name | LC/MS m/e [M + H]$^+$ |
|---|---|---|---|---|
| 101 | 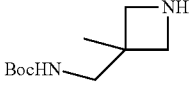 | 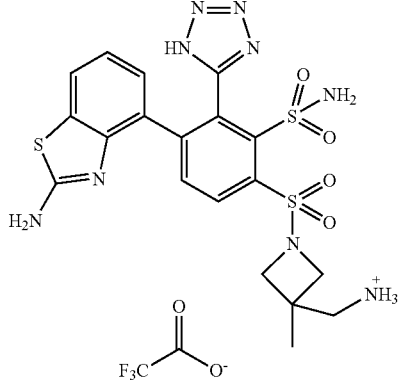 [SMILES: CC1(CN)CN(S(=O)(=O)c2ccc(-c3cccc4sc(N)nc34)c(-c3nnn[nH]3)c2S(N)(=O)=O)C1 ; O=C([O-])C(F)(F)F] | (1-((4-(2-aminobenzo[d]thiazol-4-yl)-2-sulfamoyl-3-(1H-tetrazol-5-yl)phenyl)sulfonyl)-3-methylazetidin-3-yl)methanaminium 2,2,2-trifluoroacetate | 536.09 |
| 102 | 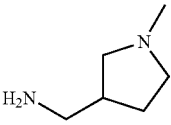 | 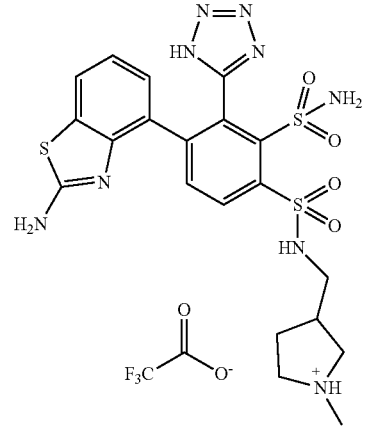 [SMILES: CN1CCC(CNS(=O)(=O)c2ccc(-c3cccc4sc(N)nc34)c(-c3nnn[nH]3)c2S(N)(=O)=O)C1 ; O=C([O-])C(F)(F)F] | 3-((4-(2-aminobenzo[d]thiazol-4-yl)-2-sulfamoyl-3-(1H-tetrazol-5-yl)phenylsulfonamido)methyl)-1-methylpyrrolidin-1-ium 2,2,2-trifluoroacetate | 550.1 |
| 103 | 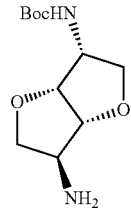 | 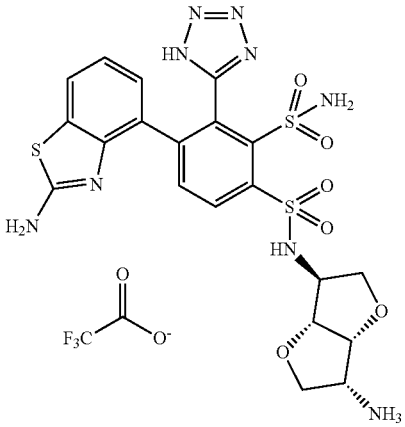 [SMILES: Nc1nc2c(-c3ccc(S(=O)(=O)N[C@H]4CO[C@H]5[C@@H]4OC[C@H]5N)c(S(N)(=O)=O)c3-c3nnn[nH]3)cccc2s1 ; O=C([O-])C(F)(F)F] | (3R,3aR,6S,6aR)-6-(4-(2-aminobenzo[d]thiazol-4-yl)-2-sulfamoyl-3-(1H-tetrazol-5-yl)phenylsulfonamido)hexahydrofuro[3,2-b]furan-3-aminium 2,2,2-trifluoroacetate | 580.08 |

-continued

| EX. No. | HNR$^a$R$^b$ | Structure | Name | LC/MS m/e [M + H]$^+$ |
|---|---|---|---|---|
| 104 | 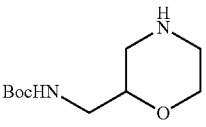 | 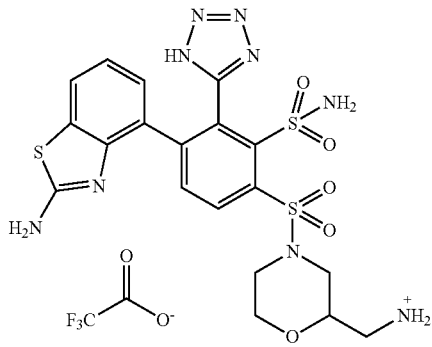 [SMILES: NCC1CN(S(=O)(=O)c2ccc(-c3cccc4sc(N)nc34)c(-c3nnn[nH]3)c2S(N)(=O)=O)CCO1 ; O=C([O-])C(F)(F)F] | (4-((4-(2-aminobenzo[d]thiazol-4-yl)-2-sulfamoyl-3-(1H-tetrazol-5-yl)phenyl)sulfonyl)morpholin-2-yl)methanaminium 2,2,2-trifluoroacetate | 552.08 |
| 105 | 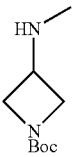 | 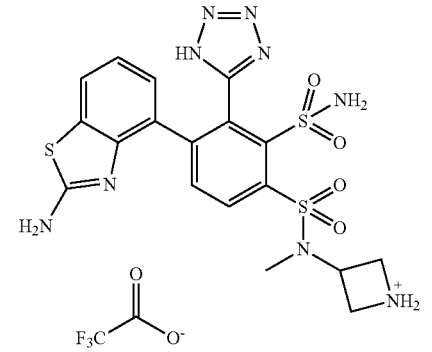 [SMILES: CN(C1CNC1)S(=O)(=O)c1ccc(-c2cccc3sc(N)nc23)c(-c2nnn[nH]2)c1S(N)(=O)=O ; O=C([O-])C(F)(F)F] | 3-(4-(2-aminobenzo[d]thiazol-4-yl)-N-methyl-2-sulfamoyl-3-(1H-tetrazol-5-yl)phenylsulfonamido)azetidin-1-ium 2,2,2-trifluoroacetate | 522.07 |
| 106 | 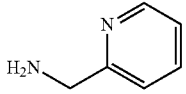 | 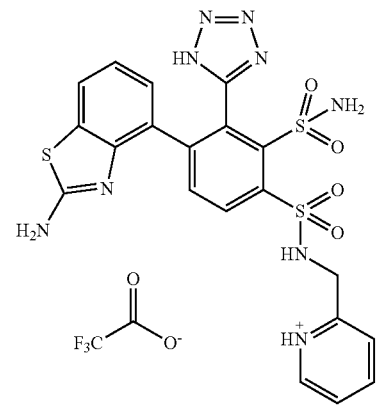 [SMILES: Nc1nc2c(-c3ccc(S(=O)(=O)NCc4ccccn4)c(S(N)(=O)=O)c3-c3nnn[nH]3)cccc2s1 ; O=C([O-])C(F)(F)F] | 2-((4-(2-aminobenzo[d]thiazol-4-yl)-2-sulfamoyl-3-(1H-tetrazol-5-yl)phenylsulfonamido)methyl)pyridin-1-ium 2,2,2-trifluoroacetate | 544.06 |
| 107 | 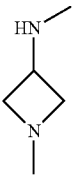 | 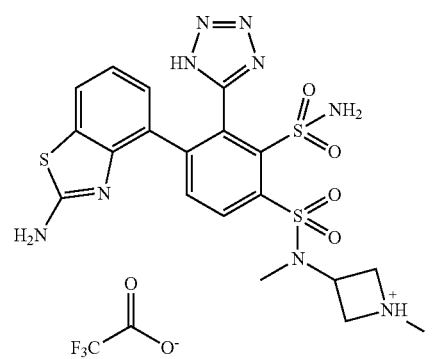 [SMILES: CN1CC(N(C)S(=O)(=O)c2ccc(-c3cccc4sc(N)nc34)c(-c3nnn[nH]3)c2S(N)(=O)=O)C1 ; O=C([O-])C(F)(F)F] | 3-(4-(2-aminobenzo[d]thiazol-4-yl)-N-methyl-2-sulfamoyl-3-(1H-tetrazol-5-yl)phenylsulfonamido)-1-methylazetidin-1-ium 2,2,2-trifluoroacetate | 536.09 |

-continued

| EX. No. | HNR$^a$R$^b$ | Structure | Name | LC/MS m/e [M + H]$^+$ |
|---|---|---|---|---|
| 108 | | 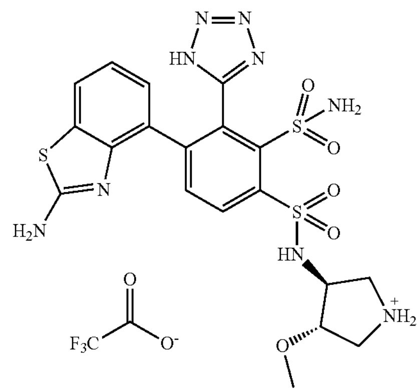 [SMILES: CO[C@H]1CNC[C@@H]1NS(=O)(=O)c1ccc(-c2cccc3sc(N)nc23)c(-c2nnn[nH]2)c1S(N)(=O)=O ; O=C([O-])C(F)(F)F] | (3S,4S)-3-(4-(2-aminobenzo[d]thiazol-4-yl)-2-sulfamoyl-3-(1H-tetrazol-5-yl)phenylsulfonamido)-4-methoxypyrrolidin-1-ium 2,2,2-trifluoroacetate | 552.08 |
| 109 | | 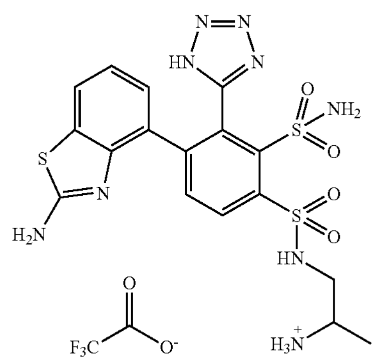 [SMILES: CC(N)CNS(=O)(=O)c1ccc(-c2cccc3sc(N)nc23)c(-c2nnn[nH]2)c1S(N)(=O)=O ; O=C([O-])C(F)(F)F] | 1-(4-(2-aminobenzo[d]thiazol-4-yl)-2-sulfamoyl-3-(1H-tetrazol-5-yl)phenyl-sulfonamido)propan-2-aminium 2,2,2-trifluoroacetate | 510.07 |
| 110 | | 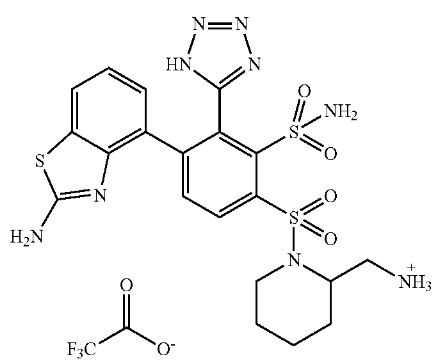 [SMILES: NCC1CCCCN1S(=O)(=O)c1ccc(-c2cccc3sc(N)nc23)c(-c2nnn[nH]2)c1S(N)(=O)=O ; O=C([O-])C(F)(F)F] | (1-((4-(2-aminobenzo[d]thiazol-4-yl)-2-sulfamoyl-3-(1H-tetrazol-5-yl)phenyl)sulfonyl)piperidin-2-yl)methanaminium 2,2,2-trifluoroacetate | 550.1 |
| 111 | | 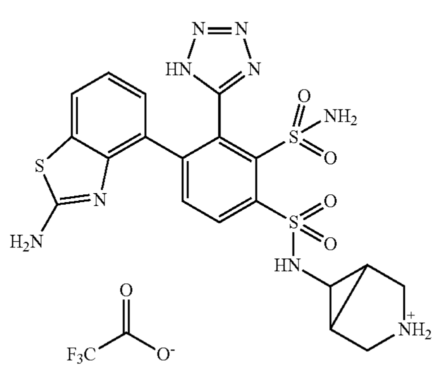 [SMILES: Nc1nc2c(-c3ccc(S(=O)(=O)NC4C5CNCC54)c(S(N)(=O)=O)c3-c3nnn[nH]3)cccc2s1 ; O=C([O-])C(F)(F)F] | 6-(4-(2-aminobenzo[d]thiazol-4-yl)-2-sulfamoyl-3-(1H-tetrazol-5-yl)phenyl-sulfonamido)-3-azabicyclo[3.1.0]hexan-3-ium 2,2,2-trifluoroacetate | 534.07 |

| EX. No. | HNRᵃRᵇ | Structure | Name | LC/MS m/e [M + H]⁺ |
|---|---|---|---|---|
| 112 | 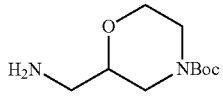 | 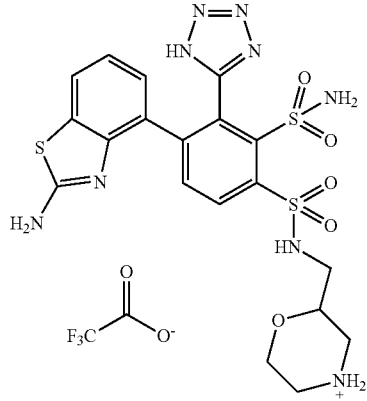 [SMILES: Nc1nc2c(-c3ccc(S(=O)(=O)NCC4CNCCO4)c(S(N)(=O)=O)c3-c3nnn[nH]3)cccc2s1 ; O=C([O-])C(F)(F)F] | 2-((4-(2-aminobenzo[d]thiazol-4-yl)-2-sulfamoyl-3-(1H-tetrazol-5-yl)phenyl-sulfonamido)methyl)morpholin-4-ium 2,2,2-trifluoroacetate | 552.08 |
| 113 | 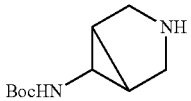 | 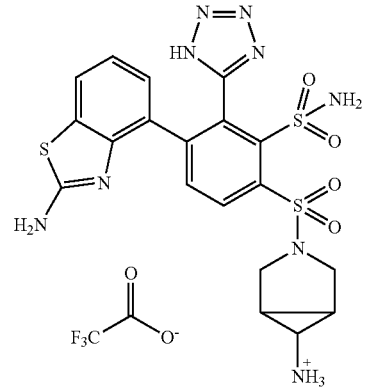 [SMILES: Nc1nc2c(-c3ccc(S(=O)(=O)N4CC5C(N)C5C4)c(S(N)(=O)=O)c3-c3nnn[nH]3)cccc2s1 ; O=C([O-])C(F)(F)F] | (1R,5S,6s)-3-((4-(2-aminobenzo[d]thiazol-4-yl)-2-sulfamoyl-3-(1H-tetrazol-5-yl)phenyl)sulfonyl)-3-azabicyclo[3.1.0]hexan-6-aminium 2,2,2-trifluoroacetate | 534.07 |
| 114 | 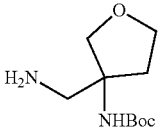 | 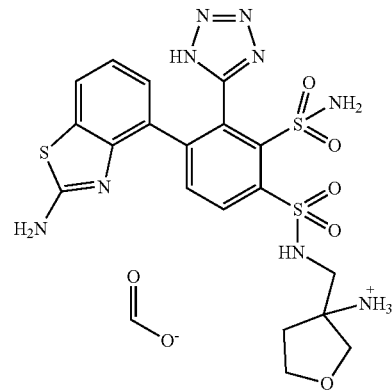 | 3-((4-(2-aminobenzo[d]thiazol-4-yl)-2-sulfamoyl-3-(1H-tetrazol-5-yl)phenyl-sulfonamido)methyl)tetrahydrofuran-3-aminium formate | 552.08 |

| EX. No. | HNRᵃRᵇ | Structure | Name | LC/MS m/e [M + H]⁺ |
|---|---|---|---|---|
| 115 | 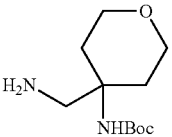 | 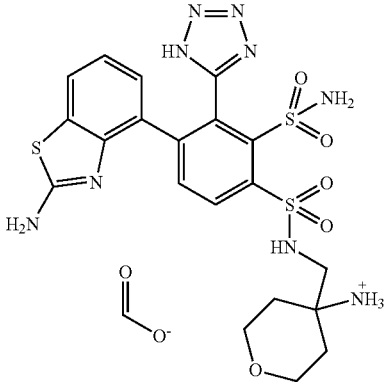 | 4-((4-(2-aminobenzo[d]thiazol-4-yl)-2-sulfamoyl-3-(1H-tetrazol-5-yl)phenyl-sulfonamido)methyl)tetrahydro-2H-pyran-4-aminium formate | 566.1 |
| 116 | 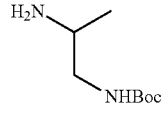 | 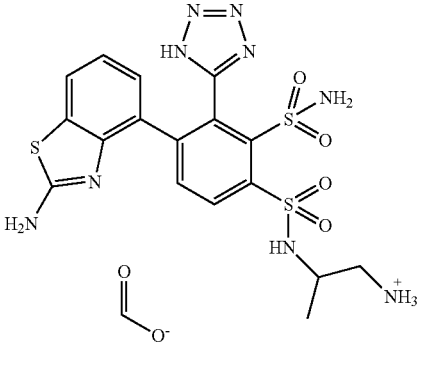 | 2-(4-(2-aminobenzo[d]thiazol-4-yl)-2-sulfamoyl-3-(1H-tetrazol-5-yl)phenyl-sulfonamido)propan-1-aminium formate | 510.07 |
| 117 | 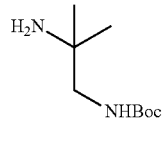 | 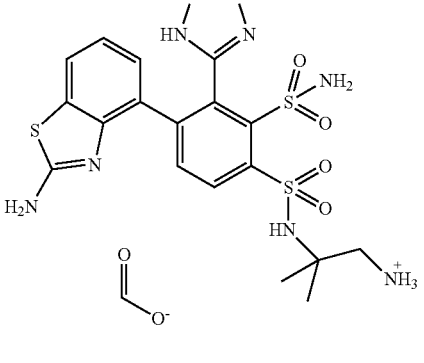 | 2-(4-(2-aminobenzo[d]thiazol-4-yl)-2-sulfamoyl-3-(1H-tetrazol-5-yl)phenyl-sulfonamido)-2-methylpropan-1-aminium formate | 524.09 |
| 118 | 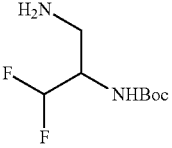 | 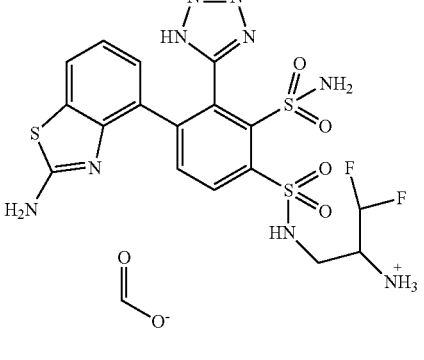 | 3-(4-(2-aminobenzo[d]thiazol-4-yl)-2-sulfamoyl-3-(1H-tetrazol-5-yl)phenyl-sulfonamido)-1,1-difluoropropan-2-aminium formate | 546.05 |

| EX. No. | HNRᵃRᵇ | Structure | Name | LC/MS m/e [M + H]⁺ |
|---|---|---|---|---|
| 119 | | 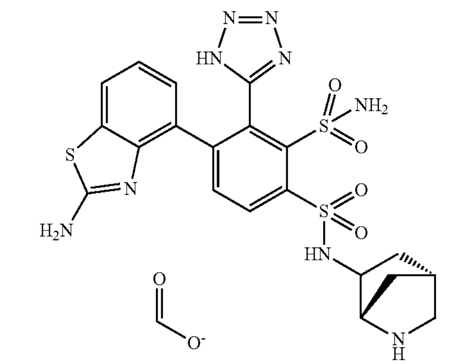 | 4-(2-aminobenzo[d]thiazol-4-yl)-N1-((1S,4R)-2-azabicyclo[2.2.1]heptan-6-yl)-3-(1H-tetrazol-5-yl)benzene-1,2-disulfonamide, formate salt | 548.09 |
| 120 | | 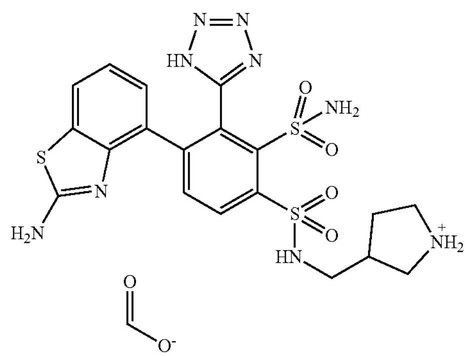 | 3-((4-(2-aminobenzo[d]thiazol-4-yl)-2-sulfamoyl-3-(1H-tetrazol-5-yl)phenyl-sulfonamido)methyl)pyrrolidin-1-ium formate | 536.09 |
| 121 | | 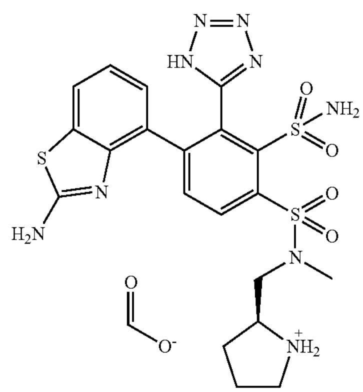 | (S)-2-((4-(2-aminobenzo[d]thiazol-4-yl)-N-methyl-2-sulfamoyl-3-(1H-tetrazol-5-yl)phenylsulfonamido)methyl)pyrrolidin-1-ium formate | 550.1 |
| 122 | | 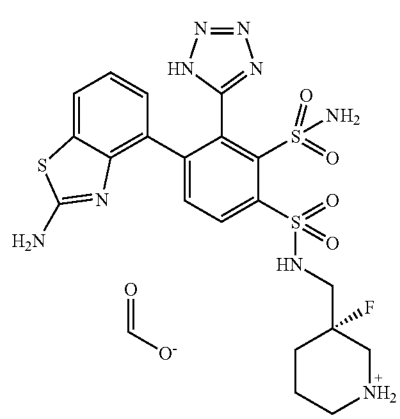 | (S)-3-(((4-(2-aminobenzo[d]thiazol-4-yl)-2-sulfamoyl-3-(1H-tetrazol-5-yl)phenyl)sulfonamido)methyl)-3-fluoropiperidin-1-ium formate | 568.09 |

-continued

| EX. No. | HNR<sup>a</sup>R<sup>b</sup> | Structure | Name | LC/MS m/e [M + H]<sup>+</sup> |
|---|---|---|---|---|
| 123 | H2N-CH2CH2-CH(NHBoc)-CH2F | (structure) | 4-(4-(2-aminobenzo[d]thiazol-4-yl)-2-sulfamoyl-3-(1H-tetrazol-5-yl)phenylsulfonamido)-1-fluorobutan-2-aminium formate | 542.08 |
| 124 | H2N-CH2CH2-CH(NHBoc)-CHF2 | (structure) | 4-(4-(2-aminobenzo[d]thiazol-4-yl)-2-sulfamoyl-3-(1H-tetrazol-5-yl)phenylsulfonamido)-1,1-difluorobutan-2-aminium formate | 560.07 |
| 125 | (S)-N-Boc-2-(aminomethyl)pyrrolidine | (structure) | (S)-2-((4-(2-aminobenzo[d]thiazol-4-yl)-2-sulfamoyl-3-(1H-tetrazol-5-yl)phenylsulfonamido)methyl)pyrrolidin-1-ium formate | 536.09 |
| 126 | (R)-N-Boc-2-(aminomethyl)pyrrolidine | (structure) | (R)-2-((4-(2-aminobenzo[d]thiazol-4-yl)-2-sulfamoyl-3-(1H-tetrazol-5-yl)phenylsulfonamido)methyl)pyrrolidin-1-ium formate | 536.09 |

| EX. No. | HNR^aR^b | Structure | Name | LC/MS m/e [M + H]+ |
|---|---|---|---|---|
| 127 | H2N-CH(CH3)-CH2-NHBoc | (structure shown) | (S)-4-(2-aminobenzo[d]thiazol-4-yl)-N1-(2-aminopropyl)-3-(1H-tetrazol-5-yl)benzene-1,2-disulfonamide, formate salt | |

Example 128

Methyl (2R,4R)-4-((4-(2-aminobenzo[d]thiazol-4-yl)-2-sulfamoyl-3-(1H-tetrazol-5-yl)phenyl)sulfonamido)pyrrolidine-2-carboxylate

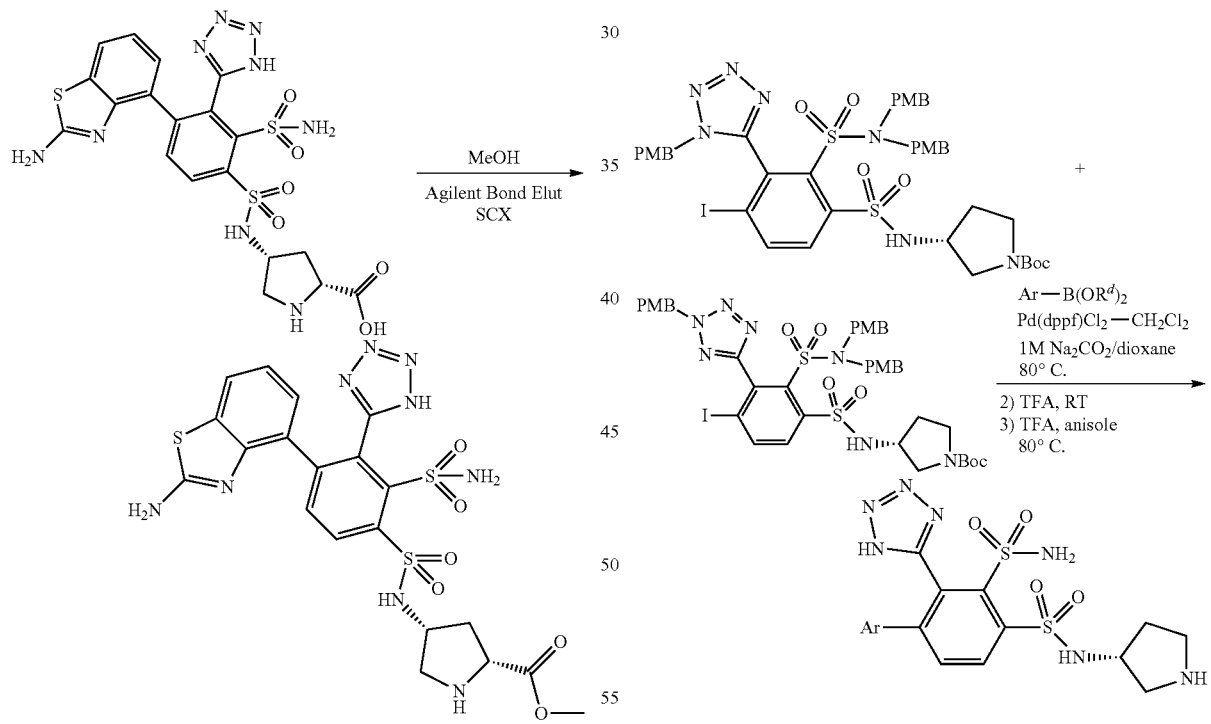

(4R)-4-({[4-(2-amino-1,3-benzothiazol-4-yl)-2-sulfamoyl-3-(1H-tetrazol-5-yl)phenyl]sulfonyl}amino)-D-proline (TFA salt) was dissolved in MeOH (1 mL) and loaded onto an ion exchange cartridge [Agilent Bond Elut SCX (2 gram)]. The TFA was eluted off the column with MeOH (20 mL). The product was then eluted off using a solution of NH3 in MeOH (7N, 20 mL). This fraction was then concentrated in vacuo. The residue was dissolved in 1:1 MeCN: distilled water (2 mL). These fractions were then frozen and lyophillized overnight. The crude product was purified by mass triggered HPLC [Waters Sunfire C18 column, 5 μm, 19×100 mm, using a gradient range from 10% initial to 40% final MeCN (0.1% TFA) in water (0.1% TFA), 25 mL/min, 12 min run time] to afford the title compound. LC/MS m/e [M+H]+ 579.9.

Example S 129-141

General procedure for parallel preparation of Examples 129-141: To a set of vials each containing the requisite boronic acid/ester (commercially available, known or prepared as described herein, 0.31 mmol) was added Pd(dppf)Cl2—CH2Cl2 (8.5 mg, 0.010 mmol). The vials were capped and transferred into a glove box under an atmosphere of nitrogen. To each vial was then added a solution of the iodide (100 mg, 0.104 mmol) in dioxane (1 mL). To each vial was then added a solution of Na2CO3 (1M, 0.156 mL, 0.313 mmol). The vials were capped and placed into a preheated heating block at 80° C. The reaction mixtures were stirred at that temperature overnight. The mixtures were removed from the glove box and allowed to cool to RT. To each vial was added water (2 mL) followed by DCM (2 mL). The mixtures were transferred to a set of fritted barrel filters and the organic layers were drained into a set of vials.

To each mixture was added additional DCM (1 mL). The organic layers were again drained into the vials to combine the extracts. The reaction mixtures were then concentrated in vacuo. The reaction mixtures were dissolved in DMSO (1.0 mL) and filtered. The crude intermediates were purified by mass triggered preparative HPLC [Waters XBridge C18 column, 5 μm, 19×100 mm, gradient ranges from 50-55% initial to 80-90% MeCN (0.1% NH₄OH) in water (0.1% NH₄OH) 25 mL/min, 8 min run time] to provide the requisite intermediates. To a set of vials containing the intermediates was added TFA (1.0 mL) and the mixtures were stirred at RT for 1 hour. After that time, the mixtures were concentrated in vacuo. To each vial was then added TFA (1.0 mL) and anisole (0.055 mL, 0.50 mmol). The vials were capped and the reaction mixtures were heated to 80° C. with stirring for 1 hour. After that time, the reaction mixtures were concentrated in vacuo. The crude residues were then dissolved in DMSO (1.0 mL) and filtered. The crude products were purified by mass triggered preparative HPLC [Waters Sunfire C18 column, 5 μm, 19×100 mm, using a gradient range from a range of 5-8% initial to 15-35% final MeCN (0.1% TFA) in water (0.1% TFA), 25 mL/min, 8 min run time] to afford Examples 129-141

| EX. No. | ArB(OR$^d$)$_2$ | Structure | Name | LC/MS m/e [M + H]⁺ |
|---|---|---|---|---|
| 129 | 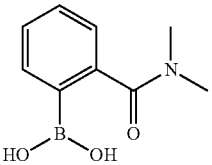 | 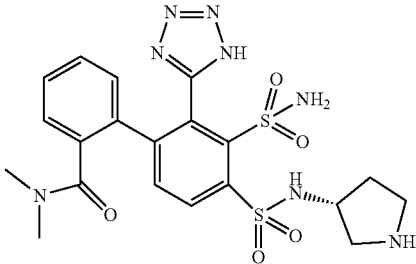 [SMILES: CN(C)C(=O)c1ccccc1-c1ccc(S(=O)(=O)N[C@@H]2CCNC2)c(S(N)(=O)=O)c1-c1nnn[nH]1] | (R)-N,N-dimethyl-4'-(N-(pyrrolidin-3-yl)sulfamoyl)-3'-sulfamoyl-2'-(1H-tetrazol-5-yl)-[1,1'-biphenyl]-2-carboxamide | 521.1 |
| 130 | 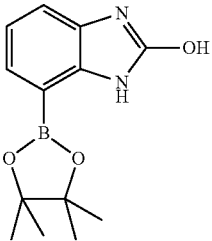 [SMILES: CC1(C)OB(c2cccc3nc(O)[nH]c23)OC1(C)C] | 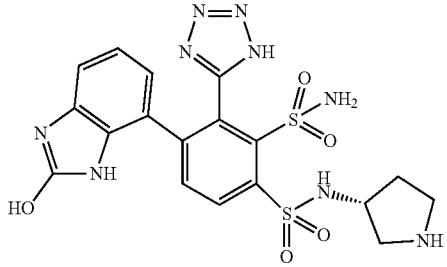 [SMILES: NS(=O)(=O)c1c(S(=O)(=O)N[C@@H]2CCNC2)ccc(-c2cccc3nc(O)[nH]c23)c1-c1nnn[nH]1] | (R)-4-(2-hydroxy-1H-benzo[d]imidazol-7-yl)-N1-(pyrrolidin-3-yl)-3-(1H-tetrazol-5-yl)benzene-1,2-disulfonamide | 506.1 |
| 131 | 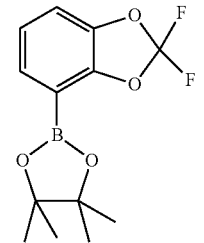 [SMILES: CC1(C)OB(c2cccc3c2OC(F)(F)O3)OC1(C)C] | 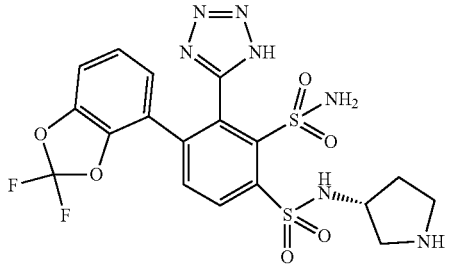 [SMILES: NS(=O)(=O)c1c(S(=O)(=O)N[C@@H]2CCNC2)ccc(-c2cccc3c2OC(F)(F)O3)c1-c1nnn[nH]1] | (R)-4-(2,2-difluorobenzo[d][1,3]dioxol-4-yl)-N1-(pyrrolidin-3-yl)-3-(1H-tetrazol-5-yl)benzene-1,2-disulfonamide | 530.1 |
| 132 | 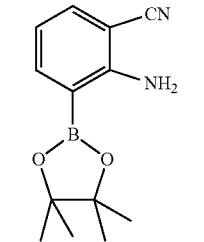 [SMILES: CC1(C)OB(c2cccc(C#N)c2N)OC1(C)C] | 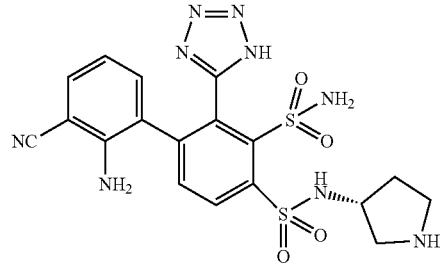 [SMILES: N#Cc1cccc(-c2ccc(S(=O)(=O)N[C@@H]3CCNC3)c(S(N)(=O)=O)c2-c2nnn[nH]2)c1N] | (R)-2'-amino-3'-cyano-N4-(pyrrolidin-3-yl)-2-(1H-tetrazol-5-yl)-[1,1'-biphenyl]-3,4-disulfonamide | 490.1 |

-continued

| EX. No. | ArB(OR^d)_2 | Structure | Name | LC/MS m/e [M + H]+ |
|---|---|---|---|---|
| 133 | 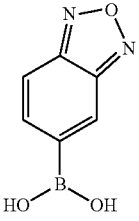 | 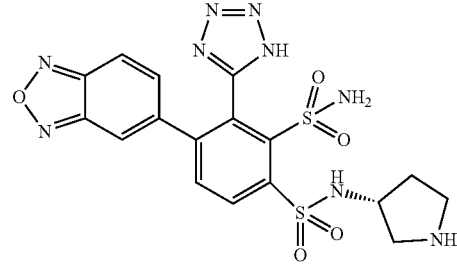 [SMILES: NS(=O)(=O)c1c(S(=O)(=O)N[C@@H]2CCNC2)ccc(-c2ccc3nonc3c2)c1-c1nnn[nH]1] | (R)-4-(benzo[c][1,2,5]oxadiazol-5-yl)-N1-(pyrrolidin-3-yl)-3-(1H-tetrazol-5-yl)benzene-1,2-disulfonamide | 492.1 |
| 134 | 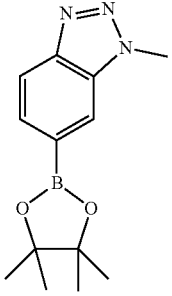 | 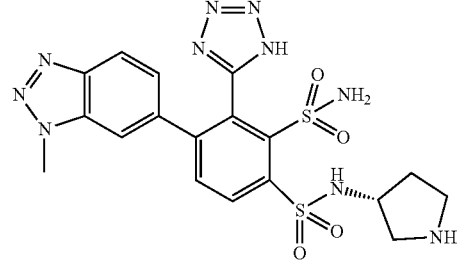 [SMILES: Cn1nnc2ccc(-c3ccc(S(=O)(=O)N[C@@H]4CCNC4)c(S(N)(=O)=O)c3-c3nnn[nH]3)cc21] | (R)-4-(1-methyl-1H-benzo[d][1,2,3]triazol-6-yl)-N1-(pyrrolidin-3-yl)-3-(1H-tetrazol-5-yl)benzene-1,2-disulfonamide | 505.1 |
| 135 | 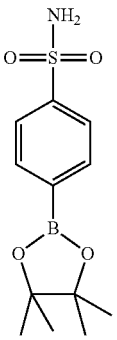 | 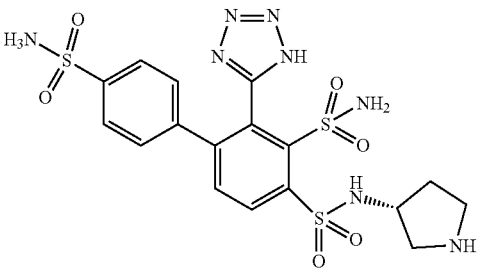 [SMILES: NS(=O)(=O)c1ccc(-c2ccc(S(=O)(=O)N[C@@H]3CCNC3)c(S(N)(=O)=O)c2-c2nnn[nH]2)cc1] | (R)-N4-(pyrrolidin-3-yl)-2-(1H-tetrazol-5-yl)-[1,1'-biphenyl]-3,4,4'-trisulfonamide | 529.1 |
| 136 | 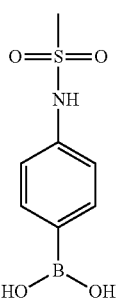 | 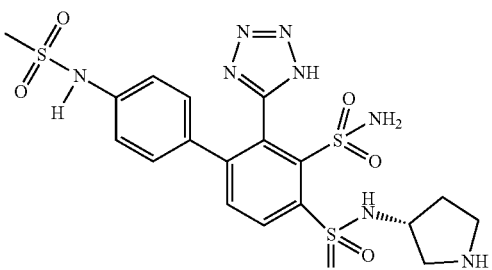 | (R)-4'-(methylsulfonamido)-N4-(pyrrolidin-3-yl)-2-(1H-tetrazol-5-yl)-[1,1'-biphenyl]-3,4-disulfonamide | 543.0 |
| 137 | 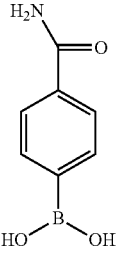 | 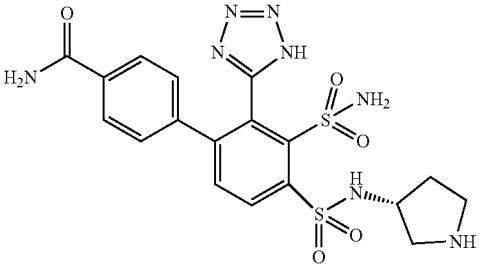 [SMILES: NC(=O)c1ccc(-c2ccc(S(=O)(=O)N[C@@H]3CCNC3)c(S(N)(=O)=O)c2-c2nnn[nH]2)cc1] | (R)-4'-(N-(pyrrolidin-3-yl)sulfamoyl)-3'-sulfamoyl-2'-(1H-tetrazol-5-yl)-[1,1'-biphenyl]-4-carboxamide | 493.1 |

-continued

| EX. No. | ArB(OR$^d$)$_2$ | Structure | Name | LC/MS m/e [M + H]$^+$ |
|---|---|---|---|---|
| 138 | | 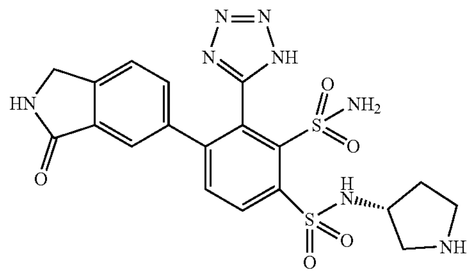 [SMILES: NS(=O)(=O)c1c(S(=O)(=O)N[C@@H]2CCNC2)ccc(-c2ccc3c(c2)C(=O)NC3)c1-c1nnn[nH]1] | (R)-4-(3-oxoisoindolin-5-yl)-N1-(pyrrolidin-3-yl)-3-(1H-tetrazol-5-yl)benzene-1,2-disulfonamide | 505.0 |
| 139 | | 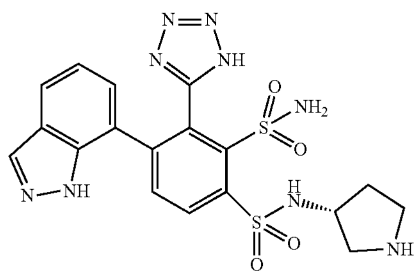 [SMILES: NS(=O)(=O)c1c(S(=O)(=O)N[C@@H]2CCNC2)ccc(-c2cccc3cn[nH]c23)c1-c1nnn[nH]1] | (R)-4-(1H-indazol-7-yl)-N1-(pyrrolidin-3-yl)-3-(1H-tetrazol-5-yl)benzene-1,2-disulfonamide | 490.0 |
| 140 | | 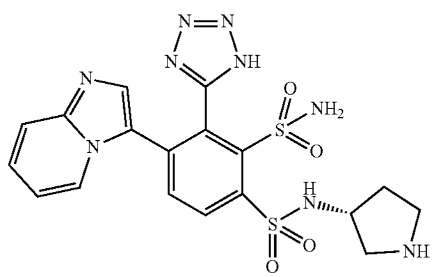 [SMILES: NS(=O)(=O)c1c(S(=O)(=O)N[C@@H]2CCNC2)ccc(-c2cnc3ccccn23)c1-c1nnn[nH]1] | (R)-4-(imidazo[1,2-a]pyridin-3-yl)-N1-(pyrrolidin-3-yl)-3-(1H-tetrazol-5-yl)benzene-1,2-disulfonamide | 490.1 |
| 141 | | 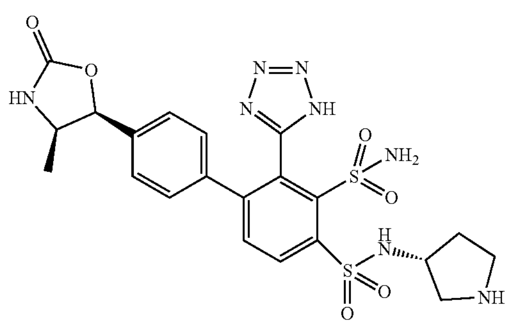 [SMILES: C[C@H]1NC(=O)O[C@H]1c1ccc(-c2ccc(S(=O)(=O)N[C@@H]3CCNC3)c(S(N)(=O)=O)c2-c2nnn[nH]2)cc1] | 4'-((4R,5S)-4-methyl-2-oxooxazolidin-5-yl)-N4-((R)-pyrrolidin-3-yl)-2-(1H-tetrazol-5-yl)-[1,1'-biphenyl]-3,4-disulfonamide | 549.1 |

Example 142

3-(2-Aminobenzo[d]thiazol-4-yl)-6-(piperazin-1-ylsulfonyl)-2-(2H-tetrazol-5-yl)benzenesulfonamide

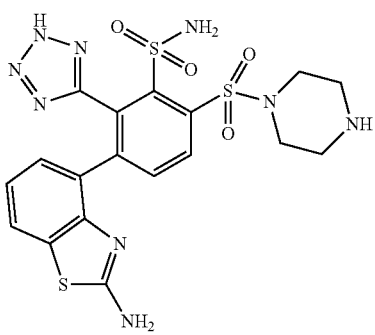 [SMILES: Nc1nc2c(-c3ccc(S(=O)(=O)N4CCNCC4)c(S(N)(=O)=O)c3-c3nn[nH]n3)cccc2s1]

Step A: benzyl 4-((2-(N,N-bis(4-methoxybenzyl)sulfamoyl)-4-(2-(N,N-bis(tert-butoxycarbonyl)amido)benzo[d]thiazol-4-yl)-3-(2-(4-methoxybenzyl)-2H-tetrazol-5-yl)phenyl)sulfonyl)piperazine-1-carboxylate A solution of benzyl piperazine-1-carboxylate (1.14 mL, 5.81 mmol)), and tert-butyl (4-(3-(N,N-bis(4-methoxybenzyl)sulfamoyl)-4-(chlorosulfonyl)-2-(2-(4-methoxybenzyl)-2H-tetrazol-5-yl)phenyl)benzo[d]thiazol-2-yl)(tert-butoxycarbonyl)carbamate (1.5 g, 1.45 mmol) in DCM (25 mL) was stirred at rt for 1 hr. The mixture was diluted with EtOAc (50 mL), washed with saturated KHSO₄ aqueous and brine, dried (MgSO₄) and concentrated. LCMS [M+1]: 1216.71.

Step B: 3-(2-aminobenzo[d]thiazol-4-yl)-6-(piperazin-1-ylsulfonyl)-2-(2H-tetrazol-5-yl)benzenesulfonamide The crude benzyl 4-((2-(N,N-bis(4-methoxybenzyl)sulfamoyl)-4-(2-(N,N-bis(tert-butoxycarbonyl)amido)benzo[d]thiazol-4-yl)-3-(2-(4-methoxybenzyl)-2H-tetrazol-5-yl)phenyl)sulfonyl)piperazine-1-carboxylate was dissolved in DCM (10 ml), stirred at rt for 2 hr with TFA (3 ml) and a few drops of anisole. The mixture was concentrated, and the residue was heated at 80° C. in 2 ml TFA for 40 minutes. TFA was removed, and the crude material was purified by RP-HPLC (7-42% ACN in water with 0.1% TFA). LCMS [M+1]: 522.28.

The following EXAMPLES 143-154 were prepared according to the representative procedure described above for EXAMPLE 142 from tert-butyl (4-(3-(N,N-bis(4-methoxybenzyl)sulfamoyl)-4-(chlorosulfonyl)-2-(2-(4-methoxybenzyl)-2H-tetrazol-5-yl)phenyl)benzo[d]thiazol-2-yl)(tert-butoxycarbonyl)carbamate and corresponding amines. The amines can optionally be protected as their tert-butoxy carbonyl carbamates which are similarly removed under the final deprotection condictions with TFA. The same is true when carboxylates are present and are protected as tert-buthyl esters.

| EX No. | Starting Amines | Structure | Compound Name | LC/MS m/e [M + H]⁺ |
|---|---|---|---|---|
| 143 | NH₃ | 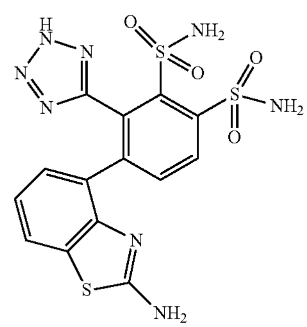 [SMILES: Nc1nc2c(-c3ccc(S(N)(=O)=O)c(S(N)(=O)=O)c3-c3nn[nH]n3)cccc2s1] | 4-(2-aminobenzo[d]thiazol-4-yl)-3-(2H-tetrazol-5-yl)benzene-1,2-disulfonamide | 453.16 |
| 144 | H₂N—CH₂CH₂—OH | 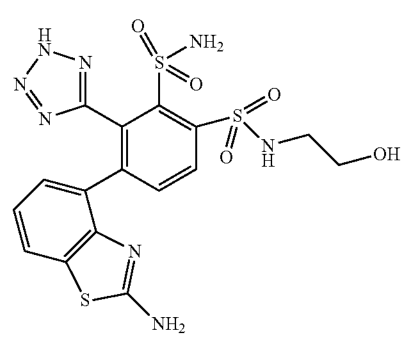 [SMILES: Nc1nc2c(-c3ccc(S(=O)(=O)NCCO)c(S(N)(=O)=O)c3-c3nn[nH]n3)cccc2s1] | 4-(2-aminobenzo[d]thiazol-4-yl)-N1-(2-hydroxyethyl)-3-(2H-tetrazol-5-yl)benzene-1,2-disulfonamide | 497.33 |

| EX No. | Starting Amines | Structure | Compound Name | LC/MS m/e [M + H]⁺ |
|---|---|---|---|---|
| 145 | H₂N-CH₂CH₂-NHBoc | 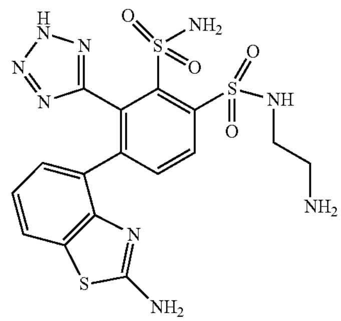 [SMILES: NCCNS(=O)(=O)c1ccc(-c2cccc3sc(N)nc23)c(-c2nn[nH]n2)c1S(N)(=O)=O] | 4-(2-aminobenzo[d]thiazol-4-yl)-N1-(2-aminoethyl)-3-(2H-tetrazol-5-yl)benzene-1,2-disulfonamide | 496.35 |
| 146 | H₂N-azetidine-NBoc | 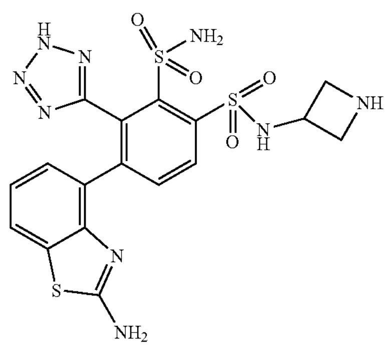 [SMILES: Nc1nc2c(-c3ccc(S(=O)(=O)NC4CNC4)c(S(N)(=O)=O)c3-c3nn[nH]n3)cccc2s1] | 4-(2-aminobenzo[d]thiazol-4-yl)-N1-(azetidin-3-yl)-3-(2H-tetrazol-5-yl)benzene-1,2-disulfonamide | 508.30 |
| 147 | HN-azetidine-NHBoc | 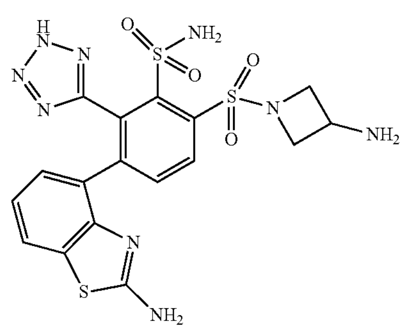 [SMILES: Nc1nc2c(-c3ccc(S(=O)(=O)N4CC(N)C4)c(S(N)(=O)=O)c3-c3nn[nH]n3)cccc2s1] | 6-((3-aminoazetidin-1-yl)sulfonyl)-3-(2-aminobenzo[d]thiazol-4-yl)-2-(2H-tetrazol-5-yl)benzenesulfonamide | 508.38 |
| 148 | HN-piperidine-NHBoc | 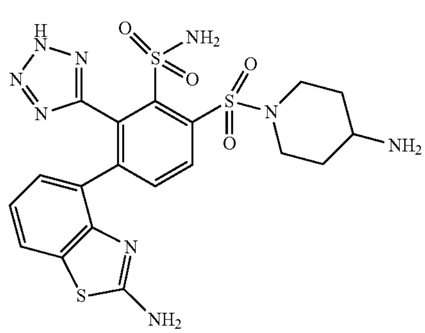 [SMILES: Nc1nc2c(-c3ccc(S(=O)(=O)N4CCC(N)CC4)c(S(N)(=O)=O)c3-c3nn[nH]n3)cccc2s1] | 3-(2-aminobenzo[d]thiazol-4-yl)-6-((4-aminopiperidin-1-yl)sulfonyl)-2-(2H-tetrazol-5-yl)benzenesulfonamide | 536.42 |

-continued

| EX No. | Starting Amines | Structure | Compound Name | LC/MS m/e [M + H]+ |
|---|---|---|---|---|
| 149 | 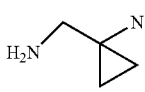 | 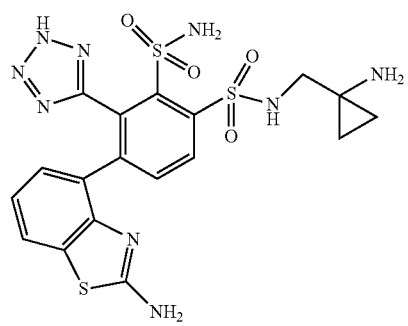 [SMILES: Nc1nc2c(-c3ccc(S(=O)(=O)NCC4(N)CC4)c(S(N)(=O)=O)c3-c3nn[nH]n3)cccc2s1] | 4-(2-aminobenzo[d]thiazol-4-yl)-N1-((1-aminocyclopropyl)methyl)-3-(2H-tetrazol-5-yl)benzene-1,2-disulfonamide | 522.37 |
| 151 |  | 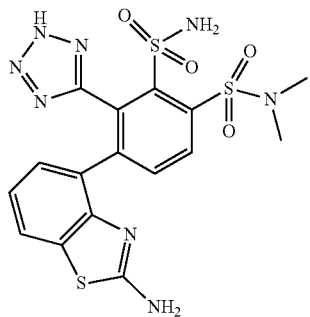 [SMILES: CN(C)S(=O)(=O)c1ccc(-c2cccc3sc(N)nc23)c(-c2nn[nH]n2)c1S(N)(=O)=O] | 4-(2-aminobenzo[d]thiazol-4-yl)-N1,N1-dimethyl-3-(2H-tetrazol-5-yl)benzene-1,2-disulfonamide | 481.16 |
| 152 |  | 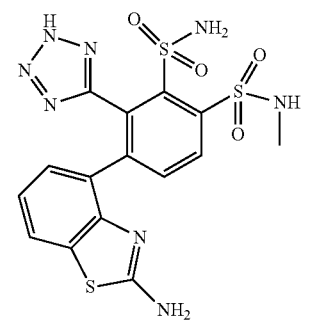 [SMILES: CNS(=O)(=O)c1ccc(-c2cccc3sc(N)nc23)c(-c2nn[nH]n2)c1S(N)(=O)=O] | 4-(2-aminobezno[d]thiazol-4-yl)-N1-methyl-3-(2H-tetrazol-5-yl)benzene-1,2-disulfonamide | 467.16 |
| 153 | 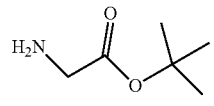 | 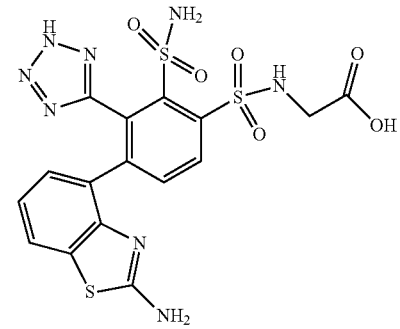 [SMILES: Nc1nc2c(-c3ccc(S(=O)(=O)NCC(=O)O)c(S(N)(=O)=O)c3-c3nn[nH]n3)cccc2s1] | ((4-(2-aminobenzo[d]thiazol-4-yl)-2-sulfamoyl-3-(2H-tetrazol-5-yl)phenyl)sulfonyl)glycine | 511.12 |

| EX No. | Starting Amines | Structure | Compound Name | LC/MS m/e [M + H]+ |
|---|---|---|---|---|
| 154 | 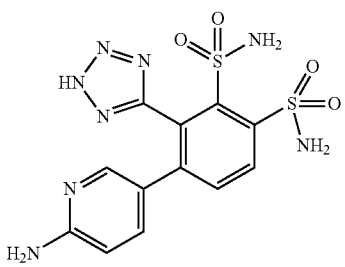 | 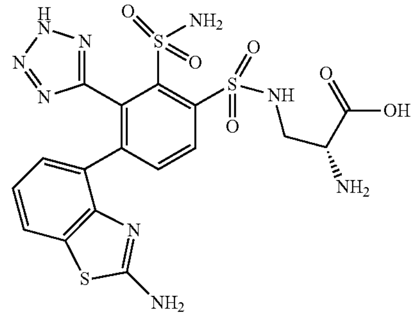 [SMILES: Nc1nc2c(-c3ccc(S(=O)(=O)NC[C@@H](N)C(=O)O)c(S(N)(=O)=O)c3-c3nn[nH]n3)cccc2s1] | (R)-2-amino-3-((4-(2-aminobenzo[d]thiazol-4-yl)-2-sulfamoyl-3-(2H-tetrazol-5-yl)phenyl)sulfonamido)propanoic acid | 540.17 |

Example 155

4-(6-Aminopyridin-3-yl)-3-(2H-tetrazol-5-yl)benzene-1,2-disulfonamide

Step A: 5-iodo-$N^1$,$N^1$-bis(4-methoxybenzyl)-6-(2-(4-methoxybenzyl)-2H-tetrazol-5-yl)benzene-1,2-disulfonamide Under $N_2$, TBAF (9.13 ml, 9.13 mmol) was added to a solution of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (2.0 g, 2.283 mmol) in THF (40 ml). The mixture was stirred at room temp. for 1 hour under $N_2$. Sodium acetate (1.873 g, 22.83 mmol) in water (10 ml) was added followed by solid (aminooxy)sulfonic acid (2.58 g, 22.83 mmol). The resultant mixture was stirred at room temp. under $N_2$ for 3 days. 30% of starting material was not consumed. The reaction mixture was diluted with EtOAc, washed with brine, dried (MgSO$_4$) and concentrated. The crude material was purified by ISCO (0-100% EtOAc in hexane) to give 5-iodo-N1,N1-bis(4-methoxybenzyl)-6-(2-(4-methoxybenzyl)-2H-tetrazol-5-yl)benzene-1,2-disulfonamide. LCMS [M+1]: 791.57.

Step B: 5-(6-aminopyridin-3-yl)-$N^1$,$N^1$-bis(4-methoxybenzyl)-6-(2-(4-methoxybenzyl)-2H-tetrazol-5-yl)benzene-1,2-disulfonamide A suspension of 5-iodo-$N^1$,$N^1$-bis(4-methoxybenzyl)-6-(2-(4-methoxybenzyl)-2H-tetrazol-5-yl)benzene-1,2-disulfonamide (0.1 g, 0.126 mmol), (6-aminopyridin-3-yl)boronic acid (0.035 g, 0.253 mmol), tetrakis(triphenylphosphine)palladium(0) (0.015 g, 0.013 mmol) and sodium carbonate (0.040 g, 0.379 mmol) in dioxane (2 mL) and water (0.6 mL) was heated at 80° C. for 17 hours under $N_2$. The mixture was filtered through a CELITE pad. The filtrate was concentrated, and the residue was dissolved in EtOAc (30 mL), washed with brine, dried (MgSO$_4$) and concentrated. The crude material was directly used for the next deprotection. LCMS [M+1]: 757.80.

Step C: 4-(6-aminopyridin-3-yl)-3-(2H-tetrazol-5-yl)benzene-1,2-disulfonamide 5-(6-Aminopyridin-3-yl)-$N^1$,$N^1$-bis(4-methoxybenzyl)-6-(2-(4-methoxybenzyl)-2H-tetrazol-5-yl)benzene-1,2-disulfonamide (0.08 g, 0.106 mmol) was heated at 80° C. in 2 mL TFA for 40 minutes. TFA was evaporated in vacuo, and the crude material was purified by reverse phase HPLC (2-30% acetonitrile in water with 0.05% TFA). LCMS [M+1]: 397.23.

Example 156

3-(2-(Methylsulfonamido)benzo[d]thiazol-4-yl)-6-(piperazin-1-ylsulfonyl)-2-(2H-tetrazol-5-yl)benzenesulfonamide

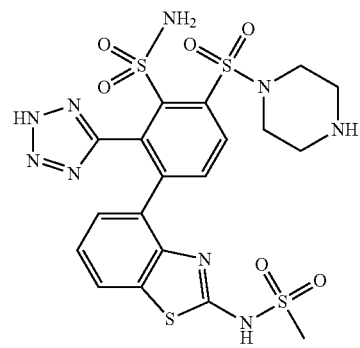 [SMILES: CS(=O)(=O)Nc1nc2c(-c3ccc(S(=O)(=O)N4CCNCC4)c(S(N)(=O)=O)c3-c3nn[nH]n3)cccc2s1]

Benzyl 4-((2-(N,N-bis(4-methoxybenzyl)sulfamoyl)-4-(2-(N,N-bis(tert-butoxycarbonyl)amido)benzo[d]thiazol-4-yl)-3-(2-(4-methoxybenzyl)-2H-tetrazol-5-yl)phenyl)sulfonyl)piperazine-1-carboxylate (0.185 g, 0.116) was dissolved in DCM (30 mL), and stirred at room temperature for 2 hours with 3 mL TFA and a few drops of anisole. The mixture was concentrated. To a mixture of the residue obtained above and methanesulfonyl chloride (0.018 ml, 0.232 mmol) in DMF (10 mL) was added sodium hydride (4.64 mg, 0.116 mmol) at 0° C. The mixture was stirred at room temperature for 1 hour, quenched with water, and diluted with ether. The organic layer was separated, washed with brine, dried over MgSO$_4$, and concentrated. The crude material was heated in 5 mL TFA at 80° C. for 40 minutes. TFA was evaporated under vacuum, and the residue was purified with reverse phase HPLC (10-75% water in AcCN with 0.1% TFA. LCMS [M+1]: 600.28.

Example 157

3-(2-amino-3H-benzo[d]imidazol-4-yl)-6-(piperazin-1-ylsulfonyl)-2-(2H-tetrazol-5-yl)benzenesulfonamide

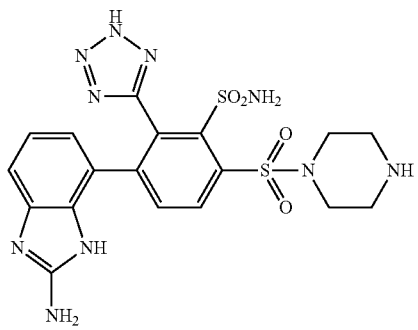 [SMILES: Nc1nc2cccc(-c3ccc(S(=O)(=O)N4CCNCC4)c(S(N)(=O)=O)c3-c3nn[nH]n3)c2[nH]1]

Step A: tert-butyl 4-((2-(N,N-bis(4-methoxybenzyl)sulfamoyl)-4-iodo-3-(2-(4-methoxybenzyl)-2H-tetrazol-5-yl)phenyl)sulfonyl)piperazine-1-carboxylate To a solution of 2-(N,N-bis(4-methoxybenzyl)sulfamoyl)-4-iodo-3-(2-(4-methoxybenzyl)-2H-tetrazol-5-yl)benzene-1-sulfonyl chloride (1.8 g, 2.222 mmol) in THF (34 ml) was added tert-butyl piperazine-1-carboxylate (0.828 g, 4.44 mmol) and Et$_3$N (0.619 ml, 4.44 mmol) at ambient temperature. The reaction was kept for 30 minutes at room temperature. The mixture was concentrated under vacuum. The residue was diluted with EA (300 mL), washed with brine (3×100 mL), dried and filtered. The filtrate was concentrated under vacuum. The residue was applied onto silica gel column chromatography with ethyl acetate/petroleum ether (1:1) to give the title compound: LCMS [M+H]$^+$: 960; $^1$H NMR (400 MHz, $^1$H NMR (400 MHz, DMSO-d$_6$): 8.15-8.13 (m, 1H), 7.91-7.89 (m, 1H), 7.03-6.95 (m, 6H), 6.89-6.82 (m, 2H), 6.81-4.71 (m, 4H), 4.54-4.45 (m, 2H), 4.15-4.09 (m, 4H), 3.88-3.77 (m, 9H), 3.61-3.45 (m, 8H), 1.46-1.45 (m, 9H).

Step B: tert-butyl 4-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)piperazine-1-carboxylate To a solution of tert-butyl 4-((2-(N,N-bis(4-methoxybenzyl)sulfamoyl)-4-iodo-3-(2-(4-methoxybenzyl)-2H-tetrazol-5-yl)phenyl)sulfonyl)piperazine-1-carboxylate (200 mg, 0.208 mmol) in dioxane (1.2 ml)/water (0.300 ml) (4:1) were added (2-amino-1H-benzo[d]imidazol-7-yl)boronic acid (11.06 mg, 0.063 mmol), Na$_2$CO$_3$ (66.3 mg, 0.625 mmol) and Pd(Ph$_3$P)$_4$ (72.2 mg, 0.063 mmol) at ambient temperature. The flask was degassed with nitrogen three times. Then the mixture was stirred for 16 hr at 80° C. under an atmosphere of nitrogen. The reaction mixture was quenched with water (5 mL) and extracted with ethyl acetate (3×15 mL). The combined organic layers were washed with water (1×15 mL) and brine (1×15 mL), dried over anhydrous sodium sulfate and filtered. The filtrate was concentrated under vacuum. The residue was applied onto silica gel column chromatography with CH$_2$Cl$_2$/MeOH (1:10) to give the title compound: LCMS [M+H]$^+$: 965.

Step C: 3-(2-amino-3H-benzo[d]imidazol-4-yl)-6-(piperazin-1-ylsulfonyl)-2-(2H-tetrazol-5-yl)benzenesulfonamide Into a 10 mL two necked RBF were placed a solution of tert-butyl 4-((4-(2-amino-1H-benzo[d]imidazol-7-yl)-2-(N,N-bis(4-methoxybenzyl)sulfamoyl)-3-(2-(4-methoxybenzyl)-2H-tetrazol-5-yl)phenyl)sulfonyl)piperazine-1-carboxylate (200 mg, 0.207 mmol) in DCM (3 ml) and TFA (1 ml) at 0° C. and the mixture was stirred at room temperature for 1 hour. The reaction solution was filtered and the solvent was evaporated under reduced pressure. The residue was added to stirred, cooled TFA (4 ml). The mixture was stirred at 80° C. for 1 hr. The mixture was evaporated under reduced pressure. The product was purified by Prep-HPLC with the following conditions: Column: X Bridge RP18, 19×150 mm, 5 μm; Mobile Phase A: water (0.05% NH$_4$HCO$_3$), Mobile Phase B: MeCN; Flow rate: 20 mL/min; Gradient: 57% B to 92% B in 10 min; Detection: UV 254 nm. The collected fractions were concentrated under vacuum to afford the title compound: LCMS [M−H]$^+$: 503; $^1$H NMR (400 MHz, DMSO): δ 8.09 (d, J=15.0 Hz, 1H), 7.93-7.91 (m, 1H), 7.58 (brs, 2H), 6.94-6.91 (m, 1H), 6.576.53 (m, 1H), 6.47 (brs, 2H), 6.12-6.11 (m, 1H), 3.45-3.42 (m, 4H), 3.16-3.13 (m, 4H).

The EXAMPLES in the Table below were prepared in an analogous fashion as described for 3-(2-amino-3H-benzo[d]imidazol-4-yl)-6-(piperazin-1-ylsulfonyl)-2-(2H-tetrazol-5-yl)benzenesulfonamide (EXAMPLE 157) starting from tert-butyl 4-((2-(N,N-bis(4-methoxybenzyl)sulfamoyl)-4-iodo-3-(2-(4-methoxybenzyl)-2H-tetrazol-5-yl)phenyl)sulfonyl)piperazine-1-carboxylate (EXAMPLE 157, Step A) and the appropriate boronic acids or boronic esters which were prepared as described herein or which were commercially available.

| EX. No. | Structure | Name | MW | LC/MS [M + H]+ |
|---|---|---|---|---|
| 158 | 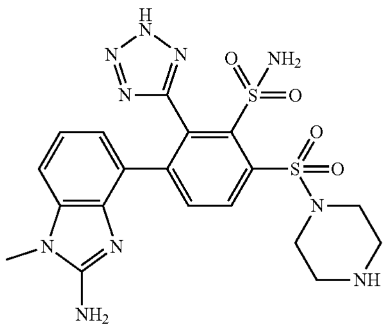 [SMILES: Cn1c(N)nc2c(-c3ccc(S(=O)(=O)N4CCNCC4)c(S(N)(=O)=O)c3-c3nn[nH]n3)cccc21] | 3-(2-amino-1-methyl-1H-benzo[d]imidazol-4-yl)-6-(piperazin-1-ylsulfonyl)-2-(2H-tetrazol-5-yl)benzenesulfonamide | 518 | 519 |
| 159 | 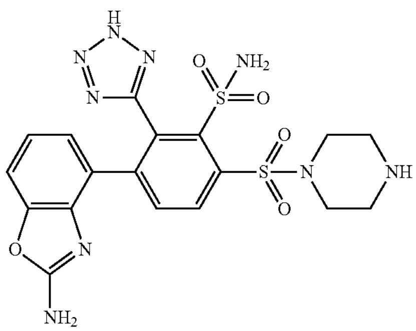 [SMILES: Nc1nc2c(-c3ccc(S(=O)(=O)N4CCNCC4)c(S(N)(=O)=O)c3-c3nn[nH]n3)cccc2o1] | 3-(2-aminobenzo[d]oxazol-4-yl)-6-(piperazin-1-ylsulfonyl)-2-(2H-tetrazol-5-yl)benzenesulfonamide | 505 | 506 |
| 160 | 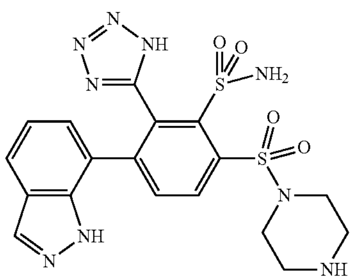 [SMILES: NS(=O)(=O)c1c(S(=O)(=O)N2CCNCC2)ccc(-c2cccc3cn[nH]c23)c1-c1nnn[nH]1] | 3-(1H-indazol-7-yl)-6-(piperazin-1-ylsulfonyl)-2-(1H-tetrazol-5-yl)benzenesulfonamide | 489 | 490 |

Example 161

4-(2-amino-1H-benzo[d]imidazol-4-yl)-N¹—((R)-pyrrolidin-3-yl)-3-(2H-tetrazol-5-yl)benzene-1,2-disulfonamide

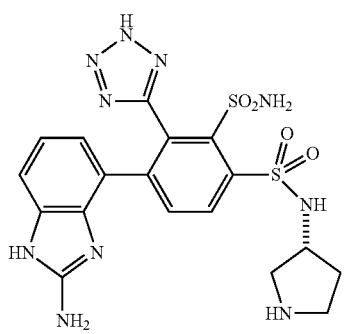

Step A: tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate To a solution of 2-(N,N-bis(4-methoxybenzyl)sulfamoyl)-4-iodo-3-(2-(4-methoxybenzyl)-2H-tetrazol-5-yl) benzenesulfinic acid and 2-(N,N-bis(4-methoxybenzyl)sulfamoyl)-4-iodo-3-(1-(4-methoxybenzyl)-1H-tetrazol-5-yl) benzenesulfinic acid regioisomers (REFERENCE EXAMPLE 4, 0.45 g, 0.58 mmol) in THF (30 mL) was added a solution of NCS (0.16 g, 1.2 mmol) in THF (10 mL) at 0° C. under nitrogen. The reaction mixture was stirred at 0° C. for 0.5 hour. To the resulting mixture was added (R)-tert-butyl 3-aminopyrrolidine-1-carboxylate (90 mg, 0.48 mmol) and TEA (0.16 mL, 1.2 mmol) at room temperature. The reaction mixture was stirred for 0.5 hour at room temperature. The resulting mixture was filtered and the filtrate was concentrated under reduced pressure. The residue was purified by silica gel column chromatography, eluting with EtOAc/PE (1/1). The fractions containing the desired product were combined and concentrated under reduced pressure to afford the title compound: LCMS [M+1]$^+$: 960.

Step B: tert-butyl (R)-3-((4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfonamido)pyrrolidine-1-carboxylate and tert-butyl (R)-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)pyrrolidine-1-carboxylate To a solution of tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate regioisomers (0.20 g, 0.21 mmol) in 1,4-dioxane (3 mL) and water (0.5 mL) was added (2-amino-1H-benzo[d]imidazol-4-yl) boronic acid (92 mg, 0.52 mmol), Na$_2$CO$_3$ (66 mg, 0.63 mmol) and Pd(PPh$_3$)$_4$ (48 mg, 0.04 mmol) at room temperature. The mixture was degassed with argon three times. The reaction mixture was stirred at 80° C. for 3 hours under argon. The resulting mixture was cooled to room temperature and concentrated under vacuum. The residue was purified by silica gel column chromatography, eluting with MeOH/DCM (1/10). The fractions containing desired product were combined and concentrated the reduced pressure to afford the title compound: LCMS [M+1]$^+$: 965.

Step C: 4-(2-amino-1H-benzo[d]imidazol-4-yl)-N$^1$—((R)-pyrrolidin-3-yl)-3-(2H-tetrazol-5-yl)benzene-1,2-disulfonamide A solution of tert-butyl (R)-3-((4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfonamido)pyrrolidine-1-carboxylate and tert-butyl (R)-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)pyrrolidine-1-carboxylate regioisomers (100 mg, 0.10 mmol) in TFA (2 mL) was stirred for 0.5 hour at room temperature. The resulting solution was concentrated under reduced pressure. The residue was co-evaporated with anisole (3×10 mL) under reduced pressure. The residue was dissolved in TFA (2 mL) and the reaction mixture was stirred at 80° C. for 1 hour. The resulting solution was cooled to room temperature and poured into water (50 mL). The aqueous phase was washed with EtOAc (2×30 mL). The aqueous phase was concentrated under reduced pressure. The residue was purified by preparative HPLC with the following conditions: Column: XSelect CSH Prep C18 OBD, 5 μm, 19×150 mm; Mobile Phase A: water with 10 mmol NH$_4$HCO$_3$, Mobile Phase B: ACN; Flow rate: 20 mL/min; Gradient: 5% B to 33% B in 8 min; Detector: UV 254/220 nm. The fractions containing desired product were combined and concentrated under the reduced pressure to afford the title compound: LCMS [M+1]$^+$: 505; $^1$H NMR (300 MHz, DMSO-d$_6$): δ 8.20 (d, J=8.7 Hz, 1H), 8.01 (d, J=8.4 Hz, 1H), 6.93 (d, J=7.5 Hz, 1H), 6.49 (t, J=7.8 Hz, 1H), 6.18 (brs, 2H), 6.07 (d, J=7.5 Hz, 1H), 4.13-4.06 (m, 1H), 3.29-3.04 (m, 4H), 2.15-2.04 (m, 1H), 1.94-1.85 (m, 1H).

The EXAMPLES in the Table below were prepared in an analogous fashion as described for (R)-4-(2-amino-1H-benzo[d]imidazol-4-yl)-N1-(pyrrolidin-3-yl)-3-(2H-tetrazol-5-yl)benzene-1,2-disulfonamide (EXAMPLE 161) starting from (R)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (Step A, or the enantiomeric corresponding pyrolidine, prepared in the same fashion) and the appropriate boronic acids or boronic esters which were prepared as described herein or which were commercially available.

| EX NO | Structure | Name | MW | LC/MS [M + H]$^+$ |
|---|---|---|---|---|
| 162 | 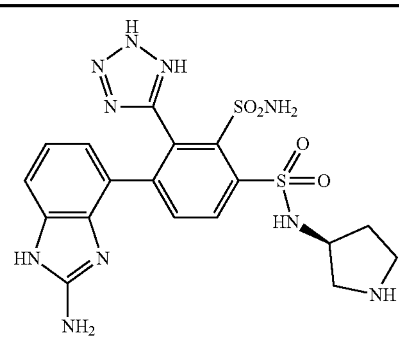 | 4-(2-amino-1H-benzo[d]imidazol-4-yl)-N$^1$-((S)-pyrrolidin-3-yl)-3-(2H-tetrazol-5-yl)benzene-1,2-disulfonamide | 504 | 505 |

| EX NO | Structure | Name | MW | LC/MS [M + H]+ |
|---|---|---|---|---|
| 163 | 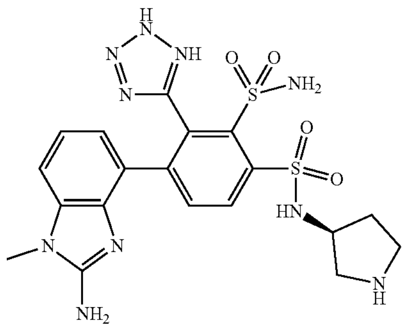 [SMILES: Cn1c(N)nc2c(-c3ccc(S(=O)(=O)N[C@H]4CCNC4)c(S(N)(=O)=O)c3-c3nn[nH]n3)cccc21] | 4-(2-amino-1-methyl-1H-benzo[d]imidazol-4-yl)-N¹-((S)-pyrrolidin-3-yl)-3-(2H-tetrazol-5-yl)benzene-1,2-disulfonamide | 518 | 519 |
| 164 | 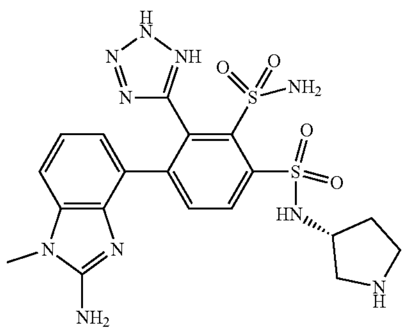 [SMILES: Cn1c(N)nc2c(-c3ccc(S(=O)(=O)N[C@@H]4CCNC4)c(S(N)(=O)=O)c3-c3nn[nH]n3)cccc21] | 4-(2-amino-1-methyl-1H-benzo[d]imidazol-4-yl)-N¹-((R)-pyrrolidin-3-yl)-3-(2H-tetrazol-5-yl)benzene-1,2-disulfonamide | 518 | 519 |

Example 165

4-(4-aminocyclohexyl)-3-(1H-tetrazol-5-yl)benzene-1,2-disulfonamide

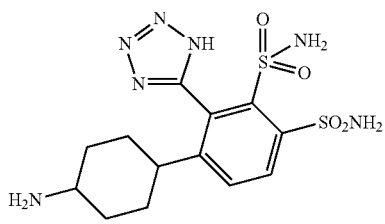 [SMILES: NC1CCC(c2ccc(S(N)(=O)=O)c(S(N)(=O)=O)c2-c2nnn[nH]2)CC1]

Step A: tert-butyl (3'-(N,N-bis(4-methoxybenzyl)sulfamoyl)-2'-(1-(4-methoxybenzyl)-1H-tetrazol-5-yl)-4'-sulfamoyl-2,3,4,5-tetrahydro-[1,1'-biphenyl]-4-yl)carbamate tert-Butyl (4-(4,4,5,5-tetramethyl-1,3,2-dioxaborolan-2-yl)cyclohex-3-en-1-yl)carbamate (82 mg, 0.25 mmol) and sodium carbonate (26.8 mg, 0.253 mmol), and tetrakis(triphenylphosphine)palladium(0) (17.5 mg, 0.015 mmol) were added to a stirred solution of starting material 5-iodo-N¹,N¹-bis(4-methoxybenzyl)-6-(2-(4-methoxybenzyl)-2H-tetrazol-5-yl)benzene-1,2-disulfonamide and 5-iodo-N¹,N¹-bis(4-methoxybenzyl)-6-(1-(4-methoxybenzyl)-1H-tetrazol-5-yl)benzene-1,2-disulfonamide regioisomers (Example 1, Step A; 100 mg, 0.126 mmol) in dioxane at room temp. and the mixture was degassed with N₂ for 10 minutes, then stirred at 80° C. overnight. After the reaction cooled to room temp., the reaction mixture was filtered through CELITE. The liquid was concentrated under reduced pressure. The residue was purified by column chromatography on silica gel (12 g) and eluted with EtOEt/hexane to give the desired product.

Step B: tert-butyl (4-(3-(N,N-bis(4-methoxybenzyl)sulfamoyl)-2-(1-(4-methoxybenzyl)-1H-tetrazol-5-yl)-4-sulfamoylphenyl)cyclohexyl)carbamate Platinum(IV) oxide (46.5 mg, 0.205 mmol) was added to a stirred solution of starting material tert-butyl (3'-(N,N-bis(4-methoxybenzyl)sulfamoyl)-2'-(1-(4-methoxybenzyl)-1H-tetrazol-5-yl)-4'-sulfamoyl-2,3,4,5-tetrahydro-[1,1'-biphenyl]-4-yl)carbamate (176 mg, 0.205 mmol) in EtOAc (2 ml) and MeOH (0.5 ml) at RT. The solution was degassed by reduced pressure, then hydrogenated (using small balloon) at room temperature for 2 hours. The reaction mixture was filtered through CELITE and washed with MeOH, concentrated and the residue was purified by column chromatography on silica gel 12 g, eluting with EtOAc/isohexane to give as a solid.

Step C: 4-(4-aminocyclohexyl)-3-(1-(4-methoxybenzyl)-1H-tetrazol-5-yl)benzene-1,2-disulfonamide TFA (1.5 ml, 19.47 mmol) and anisole (1 ml, 9.15 mmol) were added to a stirred solution of starting material tert-butyl (4-(3-(N,N-bis(4-methoxybenzyl)sulfamoyl)-2-(1-(4-methoxybenzyl)-1H-tetrazol-5-yl)-4-sulfamoylphenyl)cyclohexyl)carbamate (160 mg, 0.186 mmol) in DCM at room temperature and the mixture was stirred at room temperature for 2 hours. The mixture was concentrated. The residue was redissolved in EtOAc (3 ml) and toluene (5 ml). The mixture was concentrated again, and this procedure was repeated two more times. The residue was placed on high vacuum for 3 hours and used as is for next step.

Step D: 4-(4-aminocyclohexyl)-3-(1H-tetrazol-5-yl)benzene-1,2-disulfonamide

TFA (2 mL, 26.0 mmol) and anisole (1 mL, 9.15 mmol) were added to starting material 4-(4-aminocyclohexyl)-3-(1-(4-methoxybenzyl)-1H-tetrazol-5-yl)benzene-1,2-disulfonamide at room temperature and the mixture was stirred at 80° C. for 2 hours. The mixture was concentrated. The residue was purified by preparative reverse phase HPLC (C-18), eluting with Acetonitrile/water+0.1% TFA to give to give the title compound. LCMS: 402.35 [M+H]+

Example S 166 AND 167

(S)-5-(6-(2-amino-1H-benzo[d]imidazol-4-yl)-3-(N-(1,1-dimethylpyrrolidin-1-ium-3-yl)sulfamoyl)-2-sulfamoylphenyl)tetrazol-2-ide and (S)-5-(6-(2-amino-1-methyl-1H-benzo[d]imidazol-4-yl)-3-(N-(1,1-dimethylpyrrolidin-1-ium-3-yl)sulfamoyl)-2-sulfamoylphenyl)tetrazol-2-ide

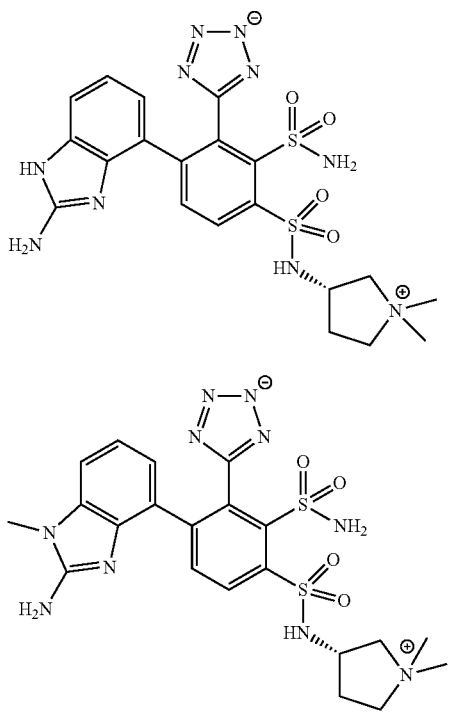

166

167

Step A: (S)-3-((4-(2-amino-1H-benzo[d]imidazol-4-yl)-3-(2-(4-methoxybenzyl)-2H-tetrazol-5-yl)-2-(N-(4-methoxybenzyl)sulfamoyl)phenyl)sulfonamido)-1,1-dimethylpyrrolidin-1-ium 2,2,2-trifluoroacetate and (S)-3-((4-(2-amino-1-methyl-1H-benzo[d]imidazol-4-yl)-3-(2-(4-methoxybenzyl)-2H-tetrazol-5-yl)-2-(N-(4-methoxybenzyl)sulfamoyl)phenyl)sulfonamido)-1,1-dimethylpyrrolidin-1-ium TFA (23.5 g, 206 mmol) was added to a mixture of (S)-tert-butyl 3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate (from synthesis of EXAMPLE 162, Step B, according to procedures for making EXAMPLE 161; 1.99 g, 2.06 mmol) in DCM (10.3 mL) and anisole (1.13 g, 10.29 mmol) and cooled in an ice bath while a stream of nitrogen was bubbling through the solution. When the addition was complete, the mixture was stirred for 1 hour. The volatiles were removed under reduced pressure. To the resulting crude material (0.4 g, 0.27 mmol) in THF (1 mL) was added CH₃I (114 mg, 0.8 mmol) followed by Cs₂CO₃ (175 mg, 0.54 mmol) and stirred at 50° C. for 30 minutes. After cooling, the reaction mixture was filtered and the resulting filtrate was removed solvent under reduced pressure to give the mixture of products. LC/MS [M+H]+: 773.55 and 787.57

Step B: (S)-5-(6-(2-amino-1H-benzo[d]imidazol-4-yl)-3-(N-(1,1-dimethylpyrrolidin-1-ium-3-yl)sulfamoyl)-2-sulfamoylphenyl)tetrazol-2-ide and (S)-5-(6-(2-amino-1-methyl-1H-benzo[d]imidazol-4-yl)-3-(N-(1,1-dimethylpyrrolidin-1-ium-3-yl)sulfamoyl)-2-sulfamoylphenyl)tetrazol-2-ide The products obtained in Step A (above) were treated with TFA at 80° C. and the crude reaction product purified by reverse phase HPLC using a gradient of acetonitrile (containing 0.1% TFA) in water (containing 0.1% TFA) to give the title compounds. LC/MS [M+H]+: 533.4 and 547.36

Example 168

4-(2-amino-1H-benzo[d]imidazol-4-yl)-N¹-(3S,4R)-4-hydroxypyrrolidin-3-yl)-3-(1H-tetrazol-5-yl)benzene-1,2-disulfonamide

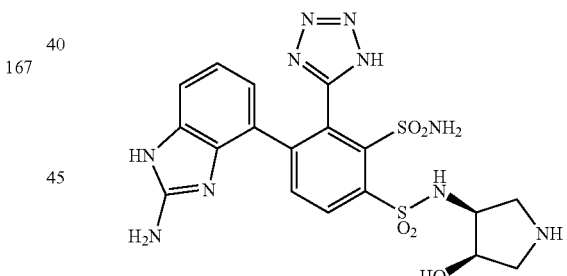

Step A: 3-(2-amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)-benzenesulfonamide A suspension of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (2.0 g, 2.283 mmol), (2-amino-1H-benzo[d]imidazol-4-yl)boronic acid (0.808 g, 4.57 mmol), [1,1'-bis(diphenylphosphino)-ferrocene]dichloropalladium(II) (0.251 g, 0.343 mmol) and sodium carbonate (0.726 g, 6.85 mmol) in dioxane (30 mL) and water (6 ml) was degassed and heated at 120° C. for 2 hours. The mixture was diluted with EtOAc, washed with brine. The organic layer was dried (MgSO₄) and concentrated. The crude product was chromatographed via silica gel (ISCO, 80 g column, 0-20% MeOH in DCM) to give the desired product. LC/MS (M+H)+: 881.53.

Step B: tert-butyl 4-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)-2-((tert-butoxycarbonyl)amino)-1H-benzo[d]imidazole-1-carboxylate To a solution of the Suzuki coupling product 3-(2-amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)-benzenesulfonamide (1.4 g, 1.59 mmol) in DCM (20.00 mL), was added N,N-dimethylpyridin-4-amine (0.582 g, 4.77 mmol) and di-tert-butyl dicarbonate (1.04 g, 4.77 mmol) at 0° C. The reaction mixture was stirred at room temp. for 30 minutes. The volatiles were removed in vacuo and the residue was chromatographed over silica gel (ISCO 80 g, 0-100% EtOAc in hexanes) to give the title compound. LC/MS (M+H)+: 1181.87.

Step C: tert-butyl 4-(3-(N,N-bis(4-methoxybenzyl)sulfamoyl)-4-(N-((3S,4R)-1-(tert-butoxycarbonyl)-4-hydroxypyrrolidin-3-yl)sulfamoyl)-2-(1-(4-methoxybenzyl)-1H-tetrazol-5-yl)phenyl)-2-((tert-butoxycarbonyl)amino)-1H-benzo[d]imidazole-1-carboxylate To a solution of the tri-Boc intermediate tert-butyl 4-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)-2-((tert-butoxycarbonyl)amino)-1H-benzo[d]imidazole-1-carboxylate (0.2 g, 0.169 mmol) in THF (10 mL) was added tetrabutylammonium fluoride (1.0 M in THF, 0.372 ml, 0.372 mmol) at 0° C. under $N_2$. After stirring for 1 hour, the reaction mixture was diluted with 20 mL of EtOAc, washed sequentially with 5 mL of sat. aq. $KHSO_4$, 5 mL of brine, dried ($MgSO_4$) and concentrated. The residue was dissolved in 20 mL of DCM, cooled to 0° C., then to the reaction mixture was added (3S,4R)-tert-butyl 3-amino-4-hydroxypyrrolidine-1-carboxylate (0.034 g, 0.169 mmol), N,N-dimethylpyridin-4-amine (0.021 g, 0.169 mmol) and 1-chloropyrrolidine-2,5-dione (0.045 g, 0.339 mmol). The reaction mixture was stirred for 2 hours. After removing the volatile in vacuo, the residue was chromatographed over silica gel (ISCO, 40 g, 0-20% EtOAc in hexanes) to give the desired product. LC/MS (M+H)+: 1281.50.

Step D: 4-(2-amino-1H-benzo[d]imidazol-4-yl)-$N^1$-((3S,4R)-4-hydroxypyrrolidin-3-yl)-3-(1H-tetrazol-5-yl)benzene-1,2-disulfonamide A solution of tert-butyl 4-(3-(N,N-bis(4-methoxybenzyl)sulfamoyl)-4-(N-((3S,4R)-1-(tert-butoxycarbonyl)-4-hydroxypyrrolidin-3-yl)sulfamoyl)-2-(1-(4-methoxybenzyl)-1H-tetrazol-5-yl)phenyl)-2-((tert-butoxycarbonyl)amino)-1H-benzo[d]imidazole-1-carboxylate (400 mg, 3.70 mmol) in DCM (200 μl) was concentrated in vacuo. The residue was dissolved in anisole (400 mg, 3.7 mmol) and TFA (1000 mg, 8.77 mmol) at 0° C. After stirring at rt for 0.5 hr, the volatile was removed in vacuo. The residue was dissolved in 2 mL of TFA and stirred at 80° C. for 1.0 hour. After removing the volatile, the residue was dissolved in 4 mL of DMSO and purified by reverse phase HPLC directly (3-60% acetonitrile in water) to give the product. LC/MS (M+2H)$^{2+}$: 261.28.

The following EXAMPLES 169-177 were prepared according to the general procedure described above for EXAMPLE 168 using pyrrolidine derivatives that are commercially available, known, or prepared as described herein. Note that all amine moieties are typically protected with a tert-butoxycarbonyl group, which is concurrently removed under the final PMB deprotection step with TFA and anisole. Alternatively, a Boc protected amine may be de-protected by treatment with TFA at room temperature, followed by de-protection of the PMB group with heating as described herein.

| Ex. No. | Structure | Compound Name | Calc'd Mass [M + H]+ | LC/MS [M + 2H]$^{2+}$ |
|---|---|---|---|---|
| 169 | 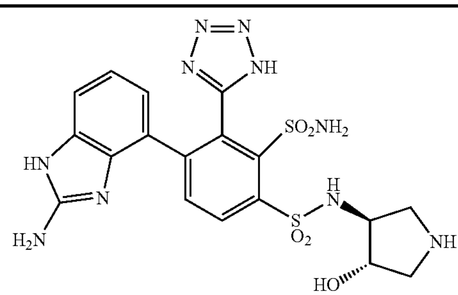 | 4-(2-amino-1H-benzo[d]imidazol-4-yl)-$N^1$-((3S,4S)-4-hydroxypyrrolidin-3-yl)-3-(1H-tetrazol-5-yl)benzene-1,2-disulfonamide | 521.55 | 261.20 |
| 170 | 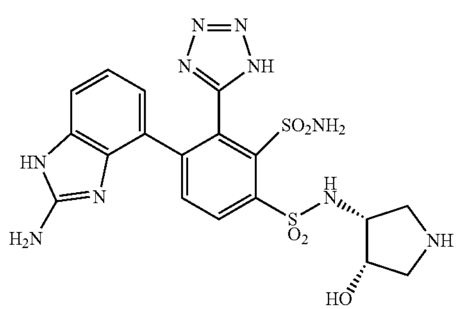 [SMILES: Nc1nc2c(-c3ccc(S(=O)(=O)N[C@@H]4CNC[C@@H]4O)c(S(N)(=O)=O)c3-c3nnn[nH]3)cccc2[nH]1] | 4-(2-amino-1H-benzo[d]imidazol-4-yl)-$N^1$-((3R,4S)-4-hydroxypyrrolidin-3-yl)-3-(1H-tetrazol-5-yl)benzene-1,2-disulfonamide | 521.55 | 261.25 |

-continued

| Ex. No. | Structure | Compound Name | Calc'd Mass [M + H]+ | LC/MS [M + 2H]2+ |
|---|---|---|---|---|
| 171 | 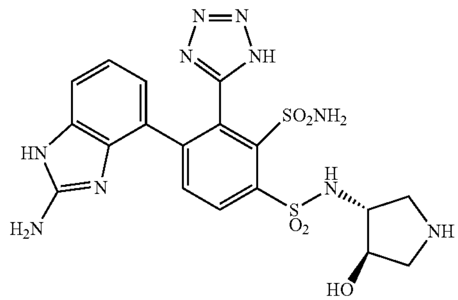 [SMILES: Nc1nc2c(-c3ccc(S(=O)(=O)N[C@@H]4CNC[C@H]4O)c(S(N)(=O)=O)c3-c3nnn[nH]3)cccc2[nH]1] | 4-(2-amino-1H-benzo[d]imidazol-4-yl)-N¹-((3R,4R)-4-hydroxypyrrolidin-3-yl)-3-(1H-tetrazol-5-yl)benzene-1,2-disulfonamide | 521.55 | 261.32 |
| 172 | 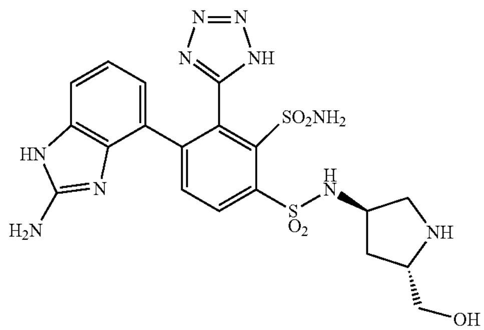 [SMILES: Nc1nc2c(-c3ccc(S(=O)(=O)N[C@H]4CN[C@H](CO)C4)c(S(N)(=O)=O)c3-c3nnn[nH]3)cccc2[nH]1] | 4-(2-amino-1H-benzo[d]imidazol-4-yl)-N¹-((3R,5S)-5-(hydroxymethyl)pyrrolidin-3-yl)-3-(1H-tetrazol-5-yl)benzene-1,2-disulfonamide | 535.58 | 268.30 |
| 173 | 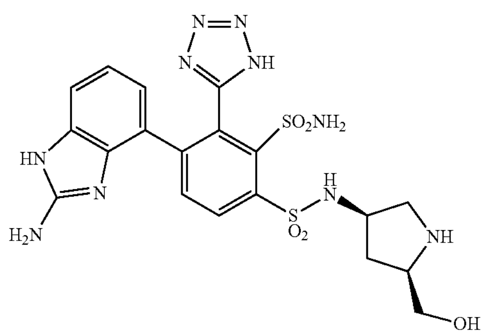 [SMILES: Nc1nc2c(-c3ccc(S(=O)(=O)N[C@H]4CN[C@@H](CO)C4)c(S(N)(=O)=O)c3-c3nnn[nH]3)cccc2[nH]1] | 4-(2-amino-1H-benzo[d]imidazol-4-yl)-N¹-((3R,5R)-5-(hydroxymethyl)pyrrolidin-3-yl)-3-(1H-tetrazol-5-yl)benzene-1,2-disulfonamide | 535.58 | 268.42 |
| 174 | 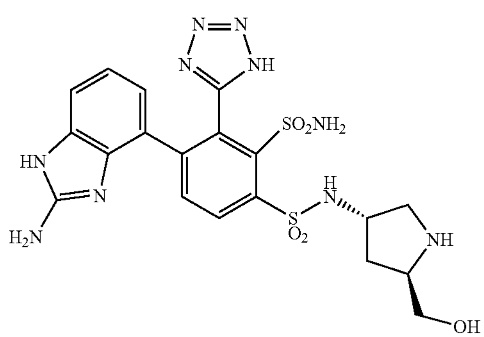 [SMILES: Nc1nc2c(-c3ccc(S(=O)(=O)N[C@@H]4CN[C@@H](CO)C4)c(S(N)(=O)=O)c3-c3nnn[nH]3)cccc2[nH]1] | 4-(2-amino-1H-benzo[d]imidazol-4-yl)-N¹-((3S,5R)-5-(hydroxymethyl)pyrrolidin-3-yl)-3-(1H-tetrazol-5-yl)benzene-1,2-disulfonamide | 535.58 | 268.23 |

-continued

| Ex. No. | Structure | Compound Name | Calc'd Mass [M + H]+ | LC/MS [M + 2H]2+ |
|---|---|---|---|---|
| 175 | 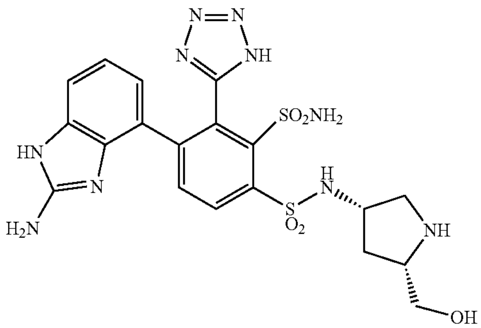 [SMILES: Nc1nc2c(-c3ccc(S(=O)(=O)N[C@@H]4CN[C@H](CO)C4)c(S(N)(=O)=O)c3-c3nnn[nH]3)cccc2[nH]1] | 4-(2-amino-1H-benzo[d]imidazol-4-yl)-N1-((3S,5S)-5-(hydroxymethyl)pyrrolidin-3-yl)-3-(1H-tetrazol-5-yl)benzene-1,2-disulfonamide | 535.58 | 268.42 |
| 176 | 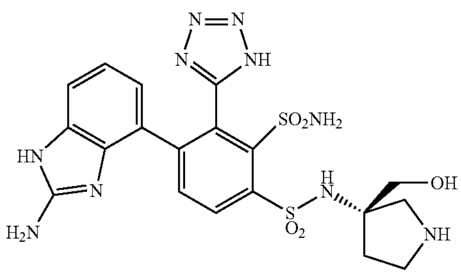 [SMILES: Nc1nc2c(-c3ccc(S(=O)(=O)N[C@@]4(CO)CCNC4)c(S(N)(=O)=O)c3-c3nnn[nH]3)cccc2[nH]1] | (S)-4-(2-amino-1H-benzo[d]imidazol-4-yl)-N1-(3-(hydroxymethyl)pyrrolidin-3-yl)-3-(1H-tetrazol-5-yl)benzene-1,2-disulfonamide | 535.58 | 268.45 |
| 177 | 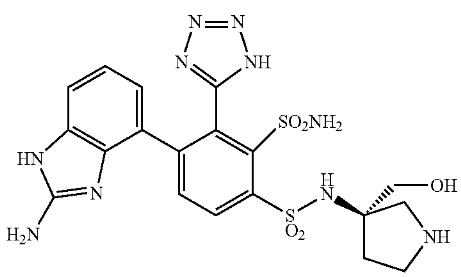 [SMILES: Nc1nc2c(-c3ccc(S(=O)(=O)N[C@]4(CO)CCNC4)c(S(N)(=O)=O)c3-c3nnn[nH]3)cccc2[nH]1] | (R)-4-(2-amino-1H-benzo[d]imidazol-4-yl)-N1-(3-(hydroxymethyl)pyrrolidin-3-yl)-3-(1H-tetrazol-5-yl)benzene-1,2-disulfonamide | 535.58 | 268.42 |

Example 178

(R)-4-(2-amino-1H-benzo[d]imidazol-4-yl)-N$^1$-(piperidin-3-yl)-3-(1H-tetrazol-5-yl)benzene-1,2-disulfonamide

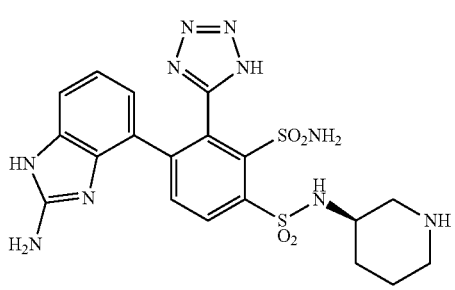 [SMILES: Nc1nc2c(-c3ccc(S(=O)(=O)N[C@@H]4CCCNC4)c(S(N)(=O)=O)c3-c3nnn[nH]3)cccc2[nH]1]

Step A: (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)piperidine-1-carboxylate To a solution of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (1.0 g, 1.142 mmol) in THF (10 ml) was added tetrabutylammonium fluoride (1.0 M in THF, 2.51 ml, 2.51 mmol) at 0° C. under N$_2$. After stirring for 1 hour, the reaction mixture was diluted with 20 mL of EtOAc, washed sequentially with 5 mL of sat. aq. KHSO$_4$, 5 mL of brine, dried (MgSO$_4$) and concentrated. The residue was dissolved in 20 mL of DCM and cooled to 0° C. To the reaction mixture was added (R)-tert-butyl 3-aminopiperidine-1-carboxylate (0.343 g, 1.713 mmol) and N,N-dimethylpyridin-4-amine (0.209 g, 1.713 mmol), followed by 1-chloropyrrolidine-2,5-dione (0.305 g, 2.283 mmol). The reaction mixture was stirred for 2 hours. After removing the volatile in vacuo, the residue was chromatographed over silica gel (ISCO, 40 g, 0-20% EtOAc in hexanes) to give the desired product. LC/MS (M+H)$^+$: 974.53.

Step B: (R)-tert-butyl 3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)piperidine-1-carboxylate A suspension of (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)piperidine-1-carboxylate (935 mg, 0.960 mmol), (2-amino-1H-benzo[d]imidazol-4-yl)boronic acid (340 mg, 1.920 mmol), [1,1'-bis(diphenylphosphino)ferrocene]dichloroPd(II) (0.157 g, 0.192 mmol) and sodium carbonate (0.305 g, 2.88 mmol) in dioxane (10.00 mL) and water (2 ml) was degassed and heated at 120° C. for 2 hours. The reaction mixture was diluted with EtOAc, then was washed with brine. The organic layer was dried (MgSO$_4$) and concentrated. The crude was chromatographed via silica gel (ISCO, 40 g column, 0-20% MeOH in DCM) to give the desired product. LC/MS (M+H)$^+$: 979.73.

Step C: (R)-4-(2-amino-1H-benzo[d]imidazol-4-yl)-N1-(piperidin-3-yl)-3-(2H-tetrazol-5-yl)benzene-1,2-disulfonamide A solution of (R)-tert-butyl 3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-piperidine-1-carboxylate (520 mg, 0.531 mmol) in DCM (200 µl) was concentrated in vacuum. The residue was dissolved in anisole (400 mg, 3.7 mmol) and TFA (1000 mg, 8.77 mmol) at 0° C. After stirring at room temp. for 0.5 hours, the volatile was removed in vacuo. The residue was dissolved in 2 mL of TFA and stirred at 80° C. for 1.0 hour. After removing the volatile, the residue was dissolved in 4 mL of DMSO and purified by reverse phase HPLC directly (3-60% acetonitrile in water) to give the product. LC/MS (M+2H)$^{2+}$: 260.20.

The following EXAMPLES 179-181 were prepared according to the general procedure described above for EXAMPLE 178 using amines that are commercially available, known, or prepared as described herein. Either (2-amino-1H-benzo[d]imidazol-4-yl)boronic acid or (2-amino-6-fluoro-1H-benzo[d]imidazol-4-yl)boronic acid were used for Suzuki coupling reactions. Note that all amine moieties are typically protected with a tert-butoxycarbonyl group, which is concurrently removed under the final PMB deprotection step with TFA and anisole. Alternatively, a Boc protected amine may be de-protected by treatment with TFA at room temperature, followed by de-protection of the PMB group with heating as described herein.

| Ex. No. | Structure | Name | Calc'd Mass [M + H]$^+$ | LC/MS [M + 2H]$^{2+}$ |
|---|---|---|---|---|
| 179 | 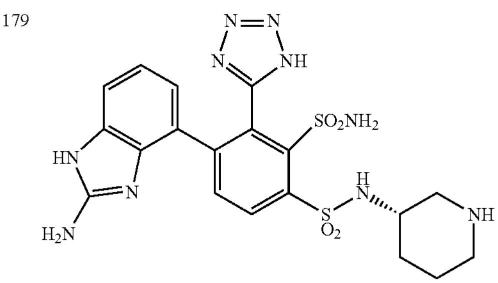 | (S)-4-(2-amino-1H-benzo[d]imidazol-4-yl)-N$^1$-(piperidin-3-yl)-3-(1H-tetrazol-5-yl)benzene-1,2-disulfonamide | 519.13 | 260.21 |
| 180 | 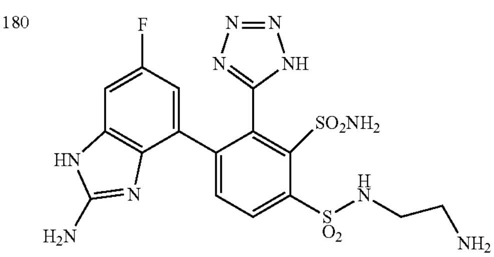 | 4-(2-amino-6-fluoro-1H-benzo[d]imidazol-4-yl)-N$^1$-(2-aminoethyl)-3-(1H-tetrazol-5-yl)benzene-1,2-disulfonamide | 497.09 | 249.37 |
| 181 | 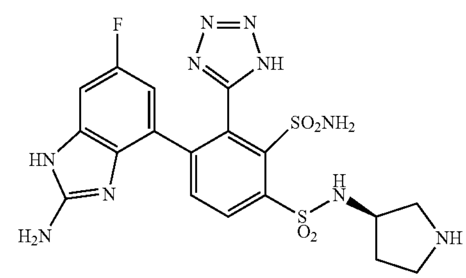 [SMILES: Nc1nc2c(-c3ccc(S(=O)(=O)N[C@@H]4CCNC4)c(S(N)(=O)=O)c3-c3nnn[nH]3)cc(F)cc2[nH]1] | (R)-4-(2-amino-6-fluoro-1H-benzo[d]imidazol-4-yl)-N$^1$-(pyrrolidin-3-yl)-3-(1H-tetrazol-5-yl)benzene-1,2-disulfonamide | 523.54 | 262.47 |

Example 182

4-(2-amino-1H-benzo[d]imidazol-4-yl)-N1-(3-aminopropyl)-3-(2H-tetrazol-5-yl)benzene-1,2-disulfonamide

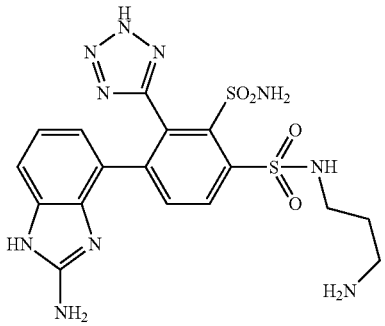 [SMILES: NCCCNS(=O)(=O)c1ccc(-c2cccc3[nH]c(N)nc23)c(-c2nn[nH]n2)c1S(N)(=O)=O]

Step A: tert-butyl-(3-(2-(N,N-bis(4-methoxybenzyl)sulfamoyl)-4-iodo-3-(2-(4-methoxybenzyl)-2H-tetrazol-5-yl)-phenylsulfonamido)propyl)carbamate To a solution of 2-(N,N-bis(4-methoxybenzyl)sulfamoyl)-4-iodo-3-(2-(4-methoxybenzyl)-2H-tetrazol-5-yl)benzene-1-sulfonyl chloride (1.50 g, 1.48 mmol) in THF (10 mL) was added tert-butyl 3-aminopropylcarbamate (0.52 g, 2.96 mmol) at room temp. The resulting solution was stirred at 25° C. for 30 minutes and then concentrated under vacuum. The residue was diluted with water (50 mL) and extracted with ethyl acetate (3×100 mL). The combined organic layers were washed with brine (3×100 mL), dried over anhydrous sodium sulfate, filtered and concentrated under vacuum. The residue was applied onto silica gel column chromatography with ethyl acetate/petroleum ether (1:50 to 1:1) to give the title compound as a solid: LCMS [M+1]$^+$ 948; $^1$H NMR (300 MHz, DMSO-d$_6$) δ 8.57-8.52 (m, 1H), 8.12-8.07 (m, 1H), 7.35-7.21 (m, 2H), 6.99-6.81 (m, 10H), 5.99 (brs, 1H), 5.45-5.09 (m, 1H), 4.95-4.52 (m, 2H), 4.29-4.12 (m, 1H), 3.96-3.92 (m, 2H), 3.83-3.79 (m, 9H), 2.95-2.91 (m, 4H), 1.61-1.55 (m, 2H), 1.34 (s, 9H).

Step B: tert-butyl (3-(4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenylsulfonamido)propyl)carbamate A solution of tert-butyl (3-(2-(N,N-bis(4-methoxybenzyl)sulfamoyl)-4-iodo-3-(2-(4-methoxybenzyl)-2H-tetrazol-5-yl)phenylsulfonamido)propyl)carbamate (0.30 g, 0.32 mmol), (2-amino-1H-benzo[d]imidazol-4-yl)boronic acid (0.14 g, 0.79 mmol), Na$_2$CO$_3$ (0.10 g, 0.95 mmol) and Pd(PPh$_3$)$_4$ (73 mg, 0.06 mmol) in 1,4-dioxane (3 mL) and water (0.5 mL) was stirred at 80° C. for 3 hours under argon. The resulting mixture was diluted with water (50 mL) and extracted with ethyl acetate (3×70 mL). The combined organic layers were washed with brine (3×70 mL), dried over anhydrous sodium sulfate, filtered and concentrated under vacuum. The residue was purified by silica gel chromatography, eluting with methanol/DCM (1/10). The combined organic fractions were concentrated under reduced pressure to give the title compound as a solid: LCMS [M+1]$^+$ 953; $^1$H NMR (400 MHz, DMSO-d$_6$) δ 10.82 (s, 1H), 8.46 (d, J=8.1 Hz, 1H), 8.11 (d, J=8.3 Hz, 1H), 7.09-6.80 (m, 12H), 6.77-6.75 (m, 2H), 6.45-6.42 (m, 1H), 6.35 (s, 2H), 5.76 (brs, 1H), 5.70 (brs, 1H), 4.70-4.52 (m, 2H), 4.10-4.08 (m, 4H), 3.73 (s, 6H), 3.70 (s, 3H), 3.02-2.98 (m, 4H), 1.63-1.61 (m, 2H), 1.36 (s, 9H).

Step C: 4-(2-amino-1H-benzo[d]imidazol-4-yl)-N1-(3-aminopropyl)-N2,N2-bis(4-methoxybenzyl)-3-(1-(4-methoxybenzyl)-1H-tetrazol-5-yl)benzene-1,2-disulfonamide A mixture of tert-butyl-(3-(4-(2-amino-1H-benzo[d]imidazol-4-yl)-2-(N,N-bis(4-methoxybenzyl)-sulfamoyl)-3-(1-(4-methoxybenzyl)-1H-tetrazol-5-yl)phenylsulfonamido)propyl)carbamate (0.16 g, 0.17 mmol) in TFA (2 mL) was stirred at 25° C. for 30 minutes. The reaction mixture was concentrated under reduced pressure to afford the title compound as a solid: LCMS [M+1]$^+$ 733.

Step D: 4-(2-amino-1H-benzo[d]imidazol-4-yl)-N1-(3-aminopropyl)-3-(1H-tetrazol-5-yl)benzene-1,2-disulfonamide A mixture of 4-(2-amino-1H-benzo[d]imidazol-4-yl)-N1-(3-aminopropyl)-N2,N2-bis(4-methoxybenzyl)-3-(1-(4-methoxybenzyl)-1H-tetrazol-5-yl)benzene-1,2-disulfonamide (0.10 g, 0.09 mmol) in TFA (2 mL) was stirred at 80° C. for 1 hour. The reaction mixture was concentrated under reduced pressure, the residue was purified by Prep-HPLC. Column, Xbridge C18, 19×150 mm; mobile phase: acetonitrile in water (0.05% NH$_4$HCO$_3$), 5%-40% in 8 min; Detector, UV 254 nm. RT: 5.5 min. The collected fractions were combined and concentrated under reduced pressure to give the title compound as a solid: LCMS [M+1]$^+$ 493; $^1$H NMR (300 MHz, DMSO-d$_6$) δ 8.49 (d, J=8.1 Hz, 1H), 8.03 (d, J=8.1 Hz, 1H), 7.31 (d, J=7.2 Hz, 1H), 7.02 (t, J=7.8 Hz, 1H), 6.52 (d, J=7.8 Hz, 1H), 3.16-3.12 (m, 2H), 2.85 (t, J=7.5 Hz, 2H), 1.88-1.83 (m, 2H).

Example 183

4-(2-amino-1-methyl-1H-benzo[d]imidazol-4-yl)-N$^1$-(3-aminopropyl)-3-(2H-tetrazol-5-yl)benzene-1,2-disulfonamide

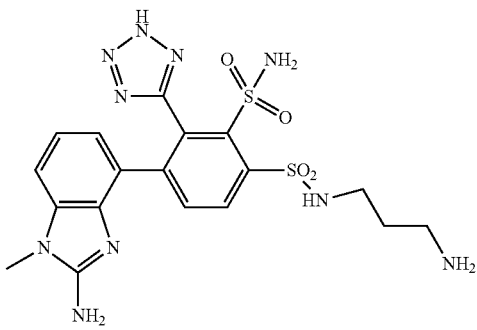 [SMILES: Cn1c(N)nc2c(-c3ccc(S(=O)(=O)NCCCN)c(S(N)(=O)=O)c3-c3nn[nH]n3)cccc21]

Step A: tert-butyl (3-(4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propyl)carbamate A solution of tert-butyl (3-(2-(N,N-bis(4-methoxybenzyl)sulfamoyl)-4-iodo-3-(2-(4-methoxybenzyl)-2H-tetrazol-5- yl)phenylsulfonamido)propyl)carbamate (100 mg, 0.106 mmol), (2-amino-1-methyl-1H-benzo[d]imidazol-4-yl)boronic acid (60.5 mg, 0.317 mmol), Pd(PPh$_3$)$_4$ (24.38 mg, 0.021 mmol) and Na$_2$CO$_3$ (22.36 mg, 0.211 mmol) in 1,4-dioxane (1 mL) and water (0.3 mL) was stirred at 80° C. for 2 hours under argon. The reaction mixture was concentrated under vacuum to give crude product. The residue was purified by silica gel chromatography, eluted with methanol/DCM (10/90). The combined organic fractions were concentrated under reduced pressure to give the title compound as a solid: LCMS [M+1]$^+$: 967; $^1$H NMR (CDCl$_3$, 400 MHZ):

Step B: 4-(2-amino-1-methyl-1H-benzo[d]imidazol-4-yl)-N1-(3-aminopropyl)-N2-(4-methoxybenzyl)-3-(2-(4-methoxybenzyl)-2H-tetrazol-5-yl)benzene-1,2-disulfonamide A solution of tert-butyl (3-(4-(2-amino-1-methyl-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propyl)carbamate (70 mg, 0.072 mmol) and TFA (1 mL, 12.98 mmol) in DCM (5 mL) was stirred at ambient temperature for 2 hours. The reaction mixture was concentrated under vacuum to give the title compound as an oil: LCMS [M+1]$^+$: 967;

Step C: 4-(2-amino-1-methyl-1H-benzo[d]imidazol-4-yl)-N1-(3-aminopropyl)-3-(2H-tetrazol-5-yl)benzene-1,2-disulfonamide A solution of 4-(2-amino-1-methyl-1H-benzo[d]imidazol-4-yl)-N1-(3-aminopropyl)-N2-(4-methoxybenzyl)-3-(2-(4-methoxybenzyl)-2H-tetrazol-5-yl)benzene-1,2-disulfonamide (40 mg, 0.054 mmol) in TFA (5 mL, 64.9 mmol) was stirred at 80° C. for 1 hour. The reaction mixture was concentrated under vacuum to give crude product. The product was purified by Prep-HPLC with the following conditions: Column: XBridge Prep C18 OBD Column 19×150 mm 5 μM 13 nm; Mobile Phase A: water with 10 mmol NH$_4$HCO$_3$, Mobile Phase B: ACN; Flow rate: 20 mL/min; Gradient: 3% B to 30% B in 8 min; 254/220 nm. The collected fractions were combined and concentrated under vacuum to give the title compound as a solid: LCMS [M+1]$^+$: 507; $^1$H NMR (DMSO-d$_6$, 400 MHz): 8.16 (d, J=8.4 Hz, 1H), 8.00 (d, J=8.4 Hz, 1H), 7.70-7.20 (m, 3H), 6.92 (d, J=7.9 Hz, 1H), 6.50 (t, J=8.4 Hz, 1H), 6.43 (brs, 2H), 6.06 (d, J=8.0 Hz, 1H), 3.49 (s, 3H), 3.12 (t, J=6.8 Hz, 2H), 2.86 (t, J=7.6 Hz, 2H), 1.80-1.76 (m, 2H).

Example 184

4-(2-amino-1H-benzo[d]imidazol-4-yl)-N1-((S)-2-aminopropyl)-3-(2H-tetrazol-5-yl)benzene-1,2-disulfonamide

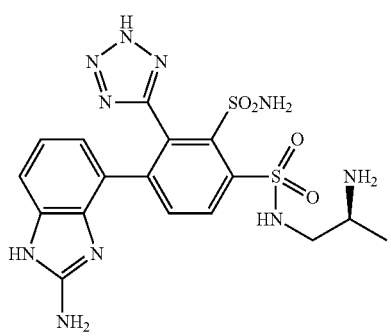 [SMILES: C[C@H](N)CNS(=O)(=O)c1ccc(-c2cccc3[nH]c(N)nc23)c(-c2nn[nH]n2)c1S(N)(=O)=O]

Step A: (S)-tert-butyl (1-amino-1-oxopropan-2-yl)carbamate

Into a 250 mL RBF, di-tert-butyl dicarbonate (13.14 g, 60.2 mmol) was added dropwise to a stirred mixture of triethylamine (12.18 g, 120 mmol), (S)-2-aminopropanamide hydrochloride (5.00 g, 40.1 mmol) in DCM (150 ml). The reaction mixture was stirred at room temperature overnight. The reaction mixture was diluted with water (100 mL) and extracted with DCM (3×100 mL). The combined organic layers were washed with brine (3×50 mL), dried over anhydrous sodium sulfate and filtered. The filtrate was concentrated under vacuum. The residue was purified by silica gel column chromatography and eluted with ethyl acetate/petroleum ether (1/20) to give the title compound as a solid. LCMS [M+H]$^+$: 189. $^1$H NMR (300 MHz, DMSO-d$_6$):7.20 (brs, 1H), 6.90 (brs, 1H), 6.70 (d, J=6.4 Hz, 1H), 3.90-3.85 (m, 1H), 1.40 (s, 9H), 1.18 (d, J=7.2 Hz, 3H)

Step B: (S)-tert-butyl (1-aminopropan-2-yl)carbamate

Into a 250 RBF, borane (6 ml, 60.0 mmol) was added dropwise to a stirred mixture of (S)-tert-butyl (1-amino-1-oxopropan-2-yl)carbamate (6.50 g, 34.5 mmol) in THF (100 ml) at room temperature. After the reaction mixture was stirred at 70° C. for 4 hours, it was cooled to room temperature, quenched with water/ice (100 mL), and extracted with ethyl acetate (3×100 mL). The combined organic layers were washed with brine (3×40 mL), dried over anhydrous sodium sulfate and filtered. The filtrate was concentrated under vacuum. The residue was purified by silica gel column chromatography, eluted with ethyl acetate/petroleum/ether (1/10) to give the title compound as an oil. LCMS [M+H]$^+$: 175. $^1$H NMR (300 MHz, DMSO-d6): 4.97 (s, 1H), 3.46 (d, J=6.6 Hz, 2H), 2.25 (s, 3H), 1.39 (s, 9H), 1.28 (s, 6H). LCMS [M+H]$^+$: 189. $^1$H NMR (300 MHz, DMSO-d$_6$): 7.22 (brs, 1H), 6.93 (brs, 1H), 6.58 (d, J=1.2 Hz, 1H, 3.88-3.81 (m, 1H), 2.48 (d, J=3.3 Hz, 2H), 1.37 (s, 9H), 1.16 (d, J=5.7 Hz, 3H).

Step C: (S)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)propan-2-yl)carbamate Into a 50 mL RBF, 1-chloropyrrolidine-2,5-dione (0.15 g, 1.160 mmol) was added to a stirred mixture of 2-(N,N-bis (4-methoxybenzyl)sulfamoyl)-4-iodo-3-(2-(4-methoxybenzyl)-2H-tetrazol-5-yl)benzenesulfinic acid and 2-(N,N-bis (4-methoxybenzyl)sulfamoyl)-4-iodo-3-(1-(4-methoxybenzyl)-1H-tetrazol-5-yl)benzenesulfinic acid regioisomers (REFERENCE EXAMPLE 4; 0.45 g, 0.580 mmol) in THF (20 ml) at room temperature. After the reaction mixture was stirred at room temperature for 1 hour, (S)-tert-butyl (1-aminopropan-2-yl)carbamate (0.15 g, 0.870 mmol) was added at room temperature. The resulting mixture was stirred at room temperature overnight and then diluted with water (50 mL) and extracted with ethyl acetate (3×100 mL). The combined organic layers were washed with brine (3×20 mL), dried over anhydrous sodium sulfate and filtered. The filtrate was concentrated under vacuum. The residue was purified by silica gel column chromatography, eluted with ethyl acetate/petroleum ether (1/5) to give the title compound as a solid. LCMS [M+H]$^+$: 948. $^1$H NMR (300 MHz, CDCl$_3$): 8.23-8.12 (m, 6H), 7.33-7.26 (m, 4H), 6.96-6.86 (m, 4H), 5.80 (s, 2H), 4.10-3.70 (m, 4H), 3.79 (s, 9H), 3.70-3.68 (m, 3H), 1.47 (s, 9H), 1.16 (d, J=3.0 Hz, 3H).

Step D: (S)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propan-2-yl)carbamate Into a 50 three-necked RBF, [1,1'-bis(diphenylphosphineo)ferrocene]dichoropalladium(II) (46.20 mg, 0.063 mmol) was added to a stirred mixture of sodium carbonate (0.10 g, 0.947 mmol), (S)-tert-butyl 1-(2-(N,N-bis(4-methoxybenzyl)sulfamoyl)-4-iodo-3-(2-(4-methoxybenzyl)-2H-tetrazol-5-yl)phenylsulfonamido)propan-2-ylcarbamate (0.30 g, 0.316 mmol), (2-amino-1H-benzo[d]imidazol-4-yl)boronic acid (0.112 g, 0.632 mmol) in dioxane/water ((1:1)4/1) (12 ml) at room temperature. The reaction mixture was stirred at 80° C. for 2 hours under nitrogen. The solids were filtered out. The filtrate was concentrated. The residue was purified by silica gel column chromatography, eluted with ethyl acetate/petroleum ether (1/1) to give the title compound as a solid. LCMS [M+H]⁺: 953 ¹H NMR (300 MHz, MeOD): δ 8.32-(d, J=8.4 Hz, 1H), 8.19 (d, J=8.4 Hz, 1H), 7.45-7.40 (m, 4H), 7.29-7.22 (m, 6H), 6.87-6.64 (m, 4H), 5.75-5.12 (m, 2H), 4.73-4.68 (m, 2H), 4.21-4.13 (m, 2H), 3.94-3.73 (m, 1H), 3.76 (s, 9H), 3.73 (s, 2H), 1.43 (s, 9H), 0.85 (d, J=6.9 Hz, 3H).

Step E: 4-(2-amino-1H-benzo[d]imidazol-4-yl)-N1-((S)-2-aminopropyl)-3-(2H-tetrazol-5-yl)benzene-1,2-disulfonamide Into a 50 mL RBF, 2,2,2-trifluoroacetic acid (2 ml) was added to a stirred mixture of (S)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propan-2-yl)carbamate (80.00 mg, 0.083 mmol) in DCM (1 ml) at room temperature. The reaction mixture was stirred at 80° C. for 1 hour and then concentrated under vacuum to give the residue (crude) which was purified by Prep-HPLC with the following conditions: Column, Xbridge C¹⁸, 19×150 mm; mobile phase: Phase A: water with 10 mmol NH₄HCO₃, Phase B: MeCN for 11 min, hold 80% to 85% in 11 min); Detector, UV 220 and 254 nm. The collected fractions were combined and concentrated under vacuum to give the title compound. LCMS [M+H]⁺: 493. ¹H NMR (300 MHz, CD₃OD): 8.38 (d, J=7.8 Hz, 1H), 7.87 (d, J=8.4 Hz, 1H), 7.00 (d, J=7.8 Hz, 1H), 6.74-6.69 (m, 1H), 6.41 (d, J=7.8 Hz, 1H), 3.44-3.28 (m, 2H), 3.09-3.03 (m, 1H), 1.13 (d, J=6.6 Hz, 3H).

Example 185

4-(2-amino-1H-benzo[d]imidazol-4-yl)-N1-((R)-2-aminopropyl)-3-(2H-tetrazol-5-yl)benzene-1,2-disulfonamide

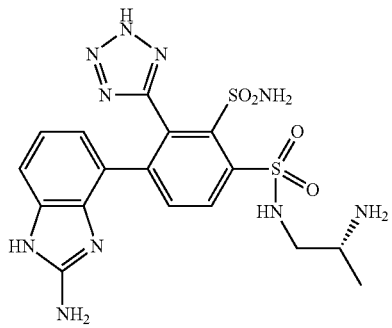 [SMILES: C[C@@H](N)CNS(=O)(=O)c1ccc(-c2cccc3[nH]c(N)nc23)c(-c2nn[nH]n2)c1S(N)(=O)=O]

Step A: (R)-tert-butyl (1-amino-1-oxopropan-2-yl)carbamate

Into a 250 mL RBF, di-tert-butyl dicarbonate (35.0 g, 161 mmol) was added dropwise to a stirred mixture of triethylamine (16.25 g, 161 mmol), (S)-2-aminopropanamide hydrochloride in MeOH (150 ml). After the resulting mixture was stirred at room temperature overnight, it was diluted with water (100 mL) and extracted with DCM (3×100 mL). The combined organic layers were washed with brine (3×50 mL), dried over anhydrous sodium sulfate and filtered. The filtrate was concentrated under vacuum. The residue was purified by silica gel column chromatography, eluted with ethyl acetate/petroleum/ether (1/20) to give the title compound as a solid. LCMS [M+H]⁺: 189. ¹H NMR (300 MHz, DMSO-d₆): 7.21 (brs, 1H), 6.89 (brs, 1H), 6.74 (d, J=6.4 Hz, 1H), 3.89-3.84 (m, 1H), 1.39 (s, 9H), 1.18 (d, J=7.2 Hz, 3H).

Step B: (R)-tert-butyl (1-aminopropan-2-yl)carbamate

Into a 500 mL RBF, borane (20 ml, 200 mmol) was added dropwise to a stirred mixture of (R)-tert-butyl (1-amino-1-oxopropan-2-yl)carbamate (15.00 g, 80 mmol) in THF (150 ml) at room temp. After the resulting mixture was stirred at 70° C. for 4 hours, it was cooled to room temp., quenched with sodium hydroxide (1N) and extracted with ethyl acetate (3×100 mL). The combined organic layers were washed with brine (3×40 mL), dried over anhydrous sodium sulfate and filtered. The filtrate was concentrated under vacuum. The residue was purified by silica gel column chromatography, eluted with ethyl acetate/petroleum/ether (1/1) to give the title compound as an oil. LCMS [M+H]⁺: 175. ¹H NMR (300 MHz, DMSO-d₆): 3.88-3.79 (m, 2H), 2.66-2.62 (m, 1H), 1.49 (s, 9H), 1.16 (d, J=5.7 Hz, 3H).

Step C: (R)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)propan-2-yl)carbamate Into a 50 mL RBF, 1-chloropyrrolidine-2,5-dione (172 mg, 1.289 mmol) was added to a stirred mixture of 2-(N,N-bis(4-methoxybenzyl)sulfamoyl)-4-iodo-3-(2-(4-methoxybenzyl)-2H-tetrazol-5-yl)benzenesulfinic acid (500 mg, 0.645 mmol) in THF (20 ml) at room temperature. The reaction mixture was stirred at room temperature for 1 hour. (R)-tert-butyl 1-aminopropan-2-ylcarbamate (0.17 g, 1.289 mmol) was added to the reaction mixture at room temperature. The reaction mixture was stirred at room temperature overnight. The reaction mixture was diluted with water (50 mL) and extracted with ethyl acetate (3×100 mL). The combined organic layers were washed with brine (1×60 mL), dried over anhydrous sodium sulfate and filtered. The filtrate was concentrated under vacuum. The residue was purified by silica gel column chromatography, eluting with ethyl acetate/petroleum ether(1/5) to give the title compound as a solid. LCMS [M+H]⁺: 948. ¹H NMR (300 MHz, CDCl₃): 8.42-8.24 (m, 4H), 7.33-7.26 (m, 4H), 6.96-6.86 (m, 6H), 5.80 (s, 2H), 4.10-3.70 (m, 4H), 3.79 (s, 9H), 3.70-3.68 (m, 3H), 1.47 (s, 9H), 1.16 (d, J=3.0 Hz, 3H).

Step D: (R)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propan-2-yl)carbamate Into a 50 mL three-necked RBF, tetrakis(triphenylphosphine)palladium (0) (36.60 mg, 0.032 mmol) was added to a stirred mixture of sodium carbonate (0.10 g, 0.950 mmol), (R)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)propan-2-yl)carbamate (0.40 g, 0.422 mmol, (2-amino-1H-benzo[d]imidazol-4-yl)boronic acid (0.11 g, 0.633 mmol) in dioxane/water (4/1) (4 ml) at room temperature. The reaction mixture was stirred at 80° C. for 2 hours under nitrogen. The solids were filtered out. The filtrate was concentrated. The residue was purified by silica gel column chromatography, eluted with methanol/DCM (1/10) to give the title compound as a solid. $^1$H NMR (300 MHz, CDCl$_3$): δ 7.97 (d, J=8.4 Hz, 1H), 7.88 (d, J=8.7 Hz, 1H), 7.48-7.42 (m, 1H), 7.32-7.26 (m, 1H), 6.94-6.90 (m, 4H), 6.82-6.75 (m, 6H), 5.75-5.12 (m, 1H), 4.73-4.68 (m, 2H), 4.21-4.13 (m, 2H), 3.94-3.89 (m, 1H), 3.76 (s, 9H), 3.73 (s, 2H), 1.43 (s, 9H), 1.26 (s, 6H).

Step E: (R)-4-(2-amino-1H-benzo[d]imidazol-4-yl)-N1-(2-aminopropyl)-3-(2H-tetrazol-5-yl)benzene-1,2-disulfonamide Into a 50 mL RBF, 2,2,2-trifluoroacetic acid (5 ml, 0.168 mmol) was added to a stirred mixture of (R)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propan-2-yl) carbamate (0.16 g, 0.168 mmol) in DCM (3 ml) at room temperature. After the reaction mixture was stirred at room temperature for 1 hour, it was concentrated under vacuum to give the residue. Then 3 mL CF$_3$COOH was added to the residue and the resulting solution was stirred for 1 hour at 80° C. The reation mixture was cooled to room temperature and concentrated under vacuum. The residue was purified by Prep-HPLC with the following conditions: Column: Atlantis Prep T3 OBD Column 19×150 mm 5 μM 10 nm; Mobile Phase A: water with 50 mmol NH$_4$HCO$_3$, Mobile Phase B: ACN; Flow rate: 20 mL/min; Gradient: 5% B to 28% B in 10 min; 254 nm. The collected fractions were combined and concentrated under vacuum to give the title compound as a solid.: LCMS [M+H]$^+$: 493. $^1$H NMR (300 MHz, DMSO-d6): 8.18 (d, J=8.4 Hz, 1H), 7.96 (d, J=8.4 Hz, 1H), 7.91-7.10 (brs, 4H), 6.90 (d, J=7.8 Hz, 1H), 6.50-6.45 (m, 1H), 6.11-6.00 (m, 3H), 3.36-3.32 (m, 12H), 3.09-3.03 (m, 2H), 1.17 (d, J=5.4 Hz, 3H).

Example 186

4-(2-amino-1H-benzo[d]imidazol-4-yl)-N$^1$—(S)-1-aminopropan-2-yl)-3-(2H-tetrazol-5-yl)benzene-1,2-disulfonamide

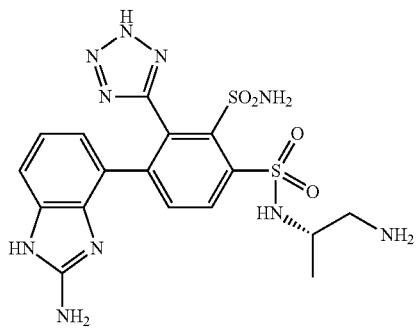 [SMILES: C[C@@H](CN)NS(=O)(=O)c1ccc(-c2cccc3[nH]c(N)nc23)c(-c2nn[nH]n2)c1S(N)(=O)=O]

Step A: benzyl tert-butyl propane-1,2-diyl(S)-dicarbamate

Into a 100 mL RBF, benzyl carbonochloridate (2.94 g, 17.22 mmol) was added dropwise to a stirred mixture of triethylamine (1.16 g, 11.48 mmol) and tert-butyl (S)-(1-aminopropan-2-yl)carbamate (1.00 g, 5.74 mmol) in DCM (20 ml) at room temperature. The reaction mixture was stirred at room temperature for 2 hours. The reaction mixture was diluted with water (50 mL) and extracted with ethyl acetate (3×50 mL). The combined organic layers were washed with brine (2×25 mL), dried over anhydrous sodium sulfate and filtered. The filtrate was concentrated under vacuum. The residue was purified by silica gel column chromatography, eluted with ethyl acetate/petroleum ether (1/10) to give the title compound as a solid. LCMS [M+H]$^+$: 309. $^1$H NMR (300 MHz, CDCl$_3$): 7.29-7.21 (m, 5H), 5.03 (s, 2H), 4.63-4.55 (m, 1H), 3.69-3.51 (m, 1H), 3.25-3.18 (m, 1H), 1.35 (s, 8H), 1.06 (d, J=6.9 Hz 3H).

Step B: (S)-benzyl (2-aminopropyl)carbamate 2,2,2-trifluoroacetate

Into a 50 mL RBF, 2,2,2-trifluoroacetic acid (2 ml, 1.621 mmol) was added to a stirred mixture of benzyl tert-butyl propane-1,2-diyl(S)-dicarbamate (0.50 g, 1.621 mmol) in DCM (1 ml) at room temperature. The reaction mixture was stirred at room temperature for 1 hour. The mixture was concentrated under vacuum to give the title compound. LCMS [M+H]$^+$: 209.

Step C: benzyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate Into a 50 mL RBF, 1-chloropyrrolidine-2,5-dione (0.15 g, 1.160 mmol) was added to a stirred mixture of 2-(N,N-bis(4-methoxybenzyl)sulfamoyl)-4-iodo-3-(2-(4-methoxybenzyl)-2H-tetrazol-5-yl)benzenesulfinic acid (0.45 g, 0.580 mmol) in THF (20 ml) at room temperature. The reaction mixture was stirred at room temperature for 1 hour. Triethymine (2 ml), (S)-benzyl (2-aminopropyl)carbamate 2,2,2-trifluoroacetate (0.15 g, 0.870 mmol) was added to the reaction mixture at room temperature. The reaction mixture was stirred at room temperature 2 hours and then it was diluted with water (50 mL) and extracted with ethyl acetate (3×100 mL). The combined organic layers were washed with brine (2×30 mL), dried over anhydrous sodium sulfate and filtered. The filtrate was concentrated under vacuum. The residue was purified by silica gel column chromatography, eluted with ethyl acetate/petroleum ether (1/5) to give the title compound as a solid. LCMS [M+H]$^+$: 982; $^1$H NMR (300 MHz, CDCl$_3$): δ 8.40-7.91 (m, 7H), 7.34-7.28 (m, 6H), 6.98-6.71 (m, 6H), 5.91 (s, 2H), 5.19-5.12 (m, 2H), 4.21-4.13 (m, 2H), 3.94-3.89 (m, 1H), 3.77 (s, 9H), 3.68-3.51 (m, 2H), 3.31-3.28 (m, 2H), 0.91 (d, J=6.6 Hz, 3H).

Step D: Benzyl (S)-2-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propylcarbamate Into a 50 three-necked RBF, tetrakis(triphenylphosphine) palladium (0) (0.259 g, 0.224 mmol) was added to a stirred mixture of sodium carbonate (23.75 mg, 0.224 mmol), benzyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate (0.22 g, 0.224 mmol), (2-amino-1H-benzo[d]imidazol-4-yl)boronic acid (39.70 mg, 0.224 mmol) in dioxane/water (4/1) (12 ml) at room temperature. The reaction mixture was stirred at 80° C. for 2 hours under nitrogen. The solids were filtered out. The filtrate was concentrated under vacuum. The residue was purified by silica gel column chromatography, eluted with methanol/DCM (1/20) to give the title compound as a solid. LCMS [M+H]+: 987; 1H NMR (300 MHz, CDCl3): δ8.26 (d, J=8.4 Hz, 1H), 7.88 (d, J=8.7 Hz, 1H), 7.48-7.42 (m, 1H), 7.32-7.26 (m, 5H), 6.94-6.90 (m, 5H), 6.82-6.75 (m, 6H), 5.75-5.12 (m, 2H), 5.56-5.41 (m, 2H), 5.21-4.40 (m, 2H), 4.21-4.13 (m, 2H), 3.94-3.89 (m, 1H), 3.76 (s, 9H), 3.73 (s, 2H), 1.24 (d, J=7.2 Hz, 3H).

Step E: (S)-4-(2-amino-1H-benzo[d]imidazol-4-yl)-N-(1-aminopropan-2-yl)-3-(2H-tetrazol-5-yl) benzene-1,2-disulfonamide Into a 50 mL RBF, palladium hydroxide on carbon (49.80 mg, 0.071 mmol) was added to a stirred mixture of benzyl (S)-2-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propylcarbamate (0.14 g, 0.14 mmol) in MeOH (3 ml) at room temperature. The reaction mixture was stirred at room temperature overnight under hydrogen (2 atm). The solid was filtered out and the filtrate was concentrated under vacuum to give the residue. 2,2,2-trifluoroacetic acid (2 ml, 0.094 mmol) was added to the residue and the resulting mixture was stirred at 80° C. After being stirred for 1 hour, the reaction mixture was concentrated under vacuum. The residue was purified by Prep-HPLC with the following conditions: Column: XBridge Shield RP18 OBD Column, 5 μM, 19×150 mm; Mobile Phase A: water with 10 mmol NH4HCO3, Mobile Phase B: ACN; Flow rate: 20 mL/min; Gradient: 0% B to 15% B in 15 min; 254/220 nm. The collected fractions were combined and concentrated under vacuum to give the title compound as a solid. LCMS [M+H]+: 493. 1H NMR (300 MHz, CD3OD): 8.41 (d, J=8.1 Hz, 1H), 7.88 (d, J=8.1 Hz, 1H), 6.99 (d, J=7.8 Hz, 1H), 6.76-6.70 (m, 1H), 6.43-6.40 (m, 1H), 3.69-3.64 (m, 1H), 2.86-2.78 (m, 2H), 1.11 (d, J=6.9 Hz, 3H).

Example 187

4-(2-amino-1H-benzo[d]imidazol-4-yl)-N1—((R)-1-aminopropan-2-yl)-3-(2H-tetrazol-5-yl)benzene-1,2-disulfonamide

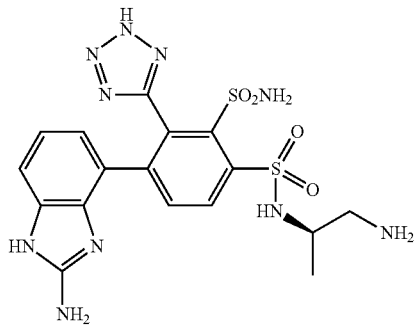 [SMILES: C[C@H](CN)NS(=O)(=O)c1ccc(-c2cccc3[nH]c(N)nc23)c(-c2nn[nH]n2)c1S(N)(=O)=O]

Step A: (R)-benzyl tert-butyl propane-1,2-diyldicarbamate

Into a 100 mL RBF, benzyl carbonochloridate (5.87 g, 34.4 mmol) was added dropwise to a stirred mixture of triethylamine (5.23 g, 51.7 mmol), (R)-tert-butyl 1-aminopropan-2-ylcarbamate (4.00 g,22.00 mmol) in DCM (20 ml) at room temperature. The reaction mixture was stirred at room temperature for 2 hours and then was diluted with water (50 mL) and extracted with ethyl acetate (3×50 mL). The combined organic layers were washed with brine (2×25 mL), dried over anhydrous sodium sulfate and filtered. The filtrate was concentrated under vacuum. The residue was purified by silica gel column chromatography, eluted with ethyl acetate/petroleum ether (1/10) to give the title compound as a solid. LCMS [M+H]+: 309. 1H NMR (300 MHz, DMSO-d6): 7.41-715 (m, 5H), 5.04 (s, 2H), 4.63-4.55 (m, 1H), 3.69-3.51 (m, 1H), 3.25-3.18 (m, 1H), 1.35 (s, 8H), 1.06 (d, J=6.9 Hz 3H).

Step B: (R)-benzyl (2-aminopropyl)carbamate 2,2,2-trifluoroacetate

Into a 50 mL RBF, 2,2,2-trifluoroacetic acid (2 ml) was added to a stirred mixture of (R)-benzyl tert-butyl propane-1,2-diyldicarbamate (1.2 g,3.8 mmol) in DCM (1 ml) at room temperature. The reaction mixture was stirred at room temperature for 1 hour and then it was concentrated under vacuum to the title compound as an oil. LCMS [M+H]+: 209.

Step C: benzyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate Into a 50 mL RBF, 1-chloropyrrolidine-2,5-dione (0.15 g, 1.160 mmol) was added to a stirred mixture of 2-(N,N-bis(4-methoxybenzyl)sulfamoyl)-4-iodo-3-(2-(4-methoxybenzyl)-2H-tetrazol-5-yl)benzenesulfinic acid (0.45 g, 0.580 mmol) in THF (20 ml) at room temperature. The reaction mixture was stirred at room temperature for 1 hour. Triethylamine (2 mL), (R)-benzyl (2-aminopropyl)carbamate 2,2,2-trifluoroacetate (0.15 g, 0.870 mmol) were added to the reaction mixture at room temperature. The reaction mixture was stirred at room temperature overnight, diluted with water (50 mL) and extracted with ethyl acetate (3×100 mL). The combined organic layers were washed with brine (3×20 mL), dried over anhydrous sodium sulfate and filtered. The filtrate was concentrated under vacuum. The residue was purified by silica gel column chromatography, eluted with ethyl acetate/petroleum ether (1/5) to give the title compound as a solid. LCMS [M+H]+: 982; 1H NMR (300 MHz, CDCl3): δ 8.23 (d, J=8.4 Hz, 2H), 7.88 (d, J=8.7 Hz, 4H), 7.48-7.42 (m, 4H), 7.32-7.26 (m, 1H), 6.95-6.85 (m, 4H), 6.76-6.74 (m, 4H), 5.81 (s, 2H), 5.21-5.12 (m, 2H), 4.21-4.13 (m, 2H), 3.94-3.89 (m, 1H), 3.68-3.51 (m, 2H), 3.76 (s, 9H), 0.95 (d, J=6.6 Hz, 3H).

Step D: benzyl (R)-(2-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)propyl)carbamate Into a 50 mL three-necked RBF, tetrakis(triphenylphosphine)palladium (0) (0.25 g, 0.224 mmol) was added to a stirred mixture of sodium carbonate (23.75 mg, 0.224 mmol), benzyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate (0.22 g, 0.224 mmol), (2-amino-1H-benzo[d]imidazol-4-yl)boronic acid (39.70 mg, 0.224 mmol) in 12 ml of dioxane/water (4/1) at room temperature. After the reaction mixture was stirred at 80° C. for 2 hours under nitrogen, the solids were filtered out. The filtrate was concentrated under vacuum. The residue was purified by silica gel column chromatography, eluted with methanol/DCM (1/20) to give the title compound as a solid. LCMS [M+H]$^+$: 987.

Step E: (R)-4-(2-amino-1H-benzo[d]imidazol-4-yl)-N-(1-aminopropan-2-yl)-3-(2H-tetrazol-5-yl)benzene-1,2-disulfonamide Into a 50 mL RBF, conc. HCl (10 mL) was added to a stirred mixture of benzyl (R)-(2-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)propyl)carbamate (0.16 g, 0.162 mmol) in 20 ml of MeOH at room temperature. The reaction mixture was stirred at 80° C. overnight and then concentrated under vacuum to give the residue. The residue was purified by Prep-HPLC with the following conditions: Column, Column: XBridge Shield RP18 OBD Column, 5 μM, 19×150 mm; Mobile Phase A: water with 10 mmol of NH$_4$HCO$_3$, Mobile Phase B: ACN; Flow rate: 20 mL/min; Gradient: 0% B to 15% B in 15 min; 254/220 nm. The collected fractions were combined and concentrated under vacuum to give the title compound as a solid. LCMS [M+H]$^+$: 493. $^1$H NMR (300 MHz, CD$_3$OD): 8.42 (d, J=8.1 Hz, 1H), 7.88 (d, J=8.4 Hz, 1H), 7.00 (d, J=7.8 Hz, 1H), 6.76-6.70 (m, 1H), 6.50-6.42 (m, 1H), 3.77-3.71 (m, 2H), 2.99-2.83 (m, 2H), 1.19 (d, J=9.0 Hz, 3H).

Example 188

(2R)-2-amino-3-(4-(2-amino-1H-benzo[d]imidazol-4-yl)-2-sulfamoyl-3-(2H-tetrazol-5-yl)phenylsulfonamido)propanamide

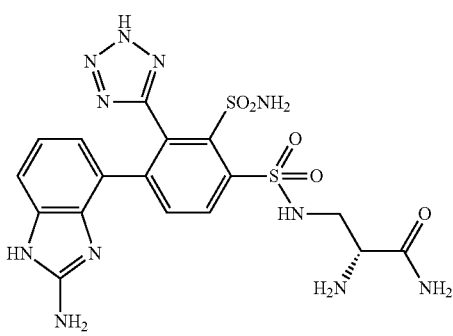 [SMILES: NC(=O)[C@H](N)CNS(=O)(=O)c1ccc(-c2cccc3[nH]c(N)nc23)c(-c2nn[nH]n2)c1S(N)(=O)=O]

Step A: (R)-tert-butyl (1-amino-3-(2-(N,N-bis(4-methoxybenzyl)sulfamoyl)-4-iodo-3-(2-(4-methoxybenzyl)-2H-tetrazol-5-yl)phenylsulfonamido)-1-oxopropan-2-yl)carbamate A solution of (R)-3-(2-(N,N-bis(4-methoxybenzyl)sulfamoyl)-4-iodo-3-(2-(4-methoxybenzyl)-2H-tetrazol-5-yl)phenylsulfonamido)-2-((tert-butoxycarbonyl)amino)propanoic acid (prepared in an analogous fashion as described in EXAMPLE 189, Step A starting from 2-(N,N-bis(4-methoxybenzyl)sulfamoyl)-4-iodo-3-(2-(4-methoxybenzyl)-2H-tetrazol-5-yl)benzene-1-sulfonyl chloride and (R)-3-amino-2-((tert-butoxycarbonyl)amino)propanoic acid; 300 mg, 0.307 mmol), ammonia hydrochloride (65.6 mg, 1.227 mmol), HATU (175 mg, 0.460 mmol) and DIEA (0.107 ml, 0.614 mmol) in DMF (10 ml) was stirred at ambient temperature for 3 hours. The reaction mixture was quenched with water (30 mL), diluted with water (70 mL) and extracted with ethyl acetate (3×50 mL). The combined organic layers were washed with water (3×10 mL) and brine (3×10 mL), dried over anhydrous sodium sulfate and filtered. The filtrate was concentrated under vacuum to give the title compound as a solid: LCMS [M+1]$^+$: 977.

Step B: (R)-tert-butyl (1-amino-3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-1-oxopropan-2-yl)carbamate A solution of (R)-tert-butyl (1-amino-3-(2-(N,N-bis(4-methoxybenzyl)sulfamoyl)-4-iodo-3-(2-(4-methoxybenzyl)-2H-tetrazol-5-yl)phenylsulfonamido)-1-oxopropan-2-yl)carbamate (300 mg, crude), (2-amino-1H-benzo[d]imidazol-4-yl)boronic acid (36.2 mg, 0.205 mmol), Pd(Ph$_3$P)$_4$ (237 mg, 0.205 mmol) and Na$_2$CO$_3$ (21.7 mg, 0.21 mmol) in 1,4-Dioxane (3 ml) and water (0.6 ml) was stirred at 80° C. for 2 hours. The reaction mixture was concentrated under vacuum to give crude product. The residue was purified by silica gel chromatography, eluted with methanol/DCM (10/90). The combined organic fractions were concentrated under reduced pressure to give the title compound as a solid: LCMS [M+1]$^+$: 982.

Step C: (S)-2-amino-3-(4-(2-amino-1H-benzo[d]imidazol-4-yl)-2-sulfamoyl-3-(2H-tetrazol-5-yl)-phenylsulfonamido)-propanamide A solution of (R)-tert-butyl (1-amino-3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-1-oxopropan-2-yl)carbamate (200 mg, crude) and TFA (2 ml, 26.0 mmol) in DMC (10 ml) was stirred at ambient temperature for 2 hours. The reaction mixture was concentrated under vacuum to give 150 mg crude of (R)-2-amino-3-(4-(2-amino-1H-benzo[d]imidazol-4-yl)-3-(2-(4-methoxybenzyl)-2H-tetrazol-5-yl)-2-(N-(4-methoxybenzyl)sulfamoyl)phenylsulfonamido) propanamide as an oil: LCMS [M+1]$^+$: 762. This oil was added to 20 ml of TFA and the resulting solution was stirred at 80° C. for 1 hour. The reaction mixture was concentrated under vacuum. The residue was purified by Prep-HPLC with the following conditions: Column: X-Bridge BEH130 Prep C18 OBD Column 19×150 mm 5 μM 13 nm; Mobile Phase A: water with 10 mmol of NH$_4$HCO$_3$, Mobile Phase B: ACN; Flow rate: 20 mL/min; Gradient: 3% B to 25% B in 8 min; 254 nm. The collected fractions were combined and concentrated under vacuum to give the title compound as a solid LCMS [M+1]$^+$: 522. $^1$H NMR (DMSO-d$_6$/D$_2$O, 400 MHZ): 8.22 (d, J=8.4 Hz, 1H), 7.93 (d, J=8.8 Hz, 1H), 6.96 (d, J=8.4 Hz, 1H), 6.59-6.55 (m, 1H), 6.13 (d, J=7.6 Hz, 1H), 3.64-3.53 (m, 1H), 3.35-3.30 (m, 1H), 3.21-3.16 (m, 1H).

Example 189

(2S)-2-amino-3-(4-(2-amino-1H-benzo[d]imidazol-4-yl)-2-sulfamoyl-3-(2H-tetrazol-5-yl)phenylsulfonamido)propanamide

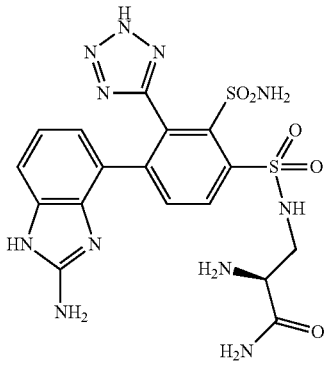 [SMILES: NC(=O)[C@@H](N)CNS(=O)(=O)c1ccc(-c2cccc3[nH]c(N)nc23)c(-c2nn[nH]n2)c1S(N)(=O)=O]

Step A: (S)-3-(2-(N,N-bis(4-methoxybenzyl)sulfamoyl)-4-iodo-3-(2-(4-methoxybenzyl)-2H-tetrazol-5-yl)phenylsulfonamido)-2-((tert-butoxycarbonyl)amino)propanoic acid A solution of 2-(N,N-bis(4-methoxybenzyl)sulfamoyl)-4-iodo-3-(2-(4-methoxybenzyl)-2H-tetrazol-5-yl)benzene-1-sulfonyl chloride (1.5 g, 1.85 mmol), (S)-3-amino-2-((tert-butoxycarbonyl)amino)propanoic acid (1.14 g, 5.56 mmol) and TEA (0.77 ml, 5.56 mmol) in THF (15 ml) was stirred at ambient temperature for 30 minutes. The reaction mixture was quenched with water (40 mL), diluted with water (30 mL) and extracted with DCM (3×50 mL). The combined organic layers were washed with water (2×30 mL) and brine (2×30 mL), dried over anhydrous sodium sulfate and filtered. The filtrate was concentrated under vacuum and the residue was purified by silica gel chromatography and eluted with methanol/DCM (1/10). The combined organic fractions were concentrated under reduced pressure to give the title compound as a solid. LCMS [M+H]$^+$: 978; $^1$H NMR (400 MHz, CDCl$_3$): δ 8.27-8.16 (m, 2H), 6.94-6.65 (m, 12H), 5.85-5.65 (m, 2H), 5.60-5.48 (m, 1H), 4.5-3.5 (m, 15H), 1.44 (s, 9H).

Step B: (S)-tert-butyl (1-amino-3-(2-(N,N-bis(4-methoxybenzyl)sulfamoyl)-4-iodo-3-(2-(4-methoxybenzyl)-2H-tetrazol-5-yl)phenylsulfonamido)-1-oxopropan-2-yl)carbamate A solution of (S)-3-(2-(N,N-bis(4-methoxybenzyl)sulfamoyl)-4-iodo-3-(2-(4-methoxybenzyl)-2H-tetrazol-5-yl)phenylsulfonamido)-2-((tert-butoxycarbonyl)amino)propanoic acid (300 mg, 0.31 mmol), ammonia hydrochloride (65.6 mg, 1.23 mmol), HATU (175 mg, 0.46 mmol) and DIEA (0.11 ml, 0.61 mmol) in DMF (10 ml) was stirred at ambient temperature for 3 hours. The reaction mixture was quenched with water (30 mL), diluted with water (70 mL) and extracted with ethyl acetate (3×50 mL). The combined organic layers were washed with water (2×30 mL) and brine (2×30 mL), dried over anhydrous sodium sulfate and filtered. The filtrate was concentrated under vacuum to give the title compound as a solid. LCMS [M+H]$^+$: 977; $^1$H NMR (400 MHz, CDCl$_3$): δ 8.32-8.15 (m, 2H), 7.00-6.74 (m, 12H), 5.85-5.75 (m, 2H), 5.60-5.50 (m, 1H), 4.5-3.5 (m, 15H), 1.48 (s, 9H).

Step C: (S)-tert-butyl (1-amino-3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-1-oxopropan-2-yl)carbamate A solution of (S)-tert-butyl (1-amino-3-(2-(N,N-bis(4-methoxybenzyl)sulfamoyl)-4-iodo-3-(2-(4-methoxybenzyl)-2H-tetrazol-5-yl)phenylsulfonamido)-1-oxopropan-2-yl)carbamate (200 mg, 0.21 mmol), (2-amino-1H-benzo[d]imidazol-4-yl)boronic acid (36.2 mg, 0.205 mmol), Pd(Ph$_3$P)$_4$ (237 mg, 0.205 mmol) and Na$_2$CO$_3$ (21.70 mg, 0.205 mmol) in 1,4-Dioxane (3 ml) and water (0.6 ml) was stirred at 80° C. for 2 hours. The reaction mixture was concentrated under vacuum and the residue was purified by silica gel chromatography, eluting with methanol/DCM (10/90). The combined organic fractions were concentrated under reduced pressure to give the title compound as a solid. LCMS [M+H]$^+$: 982

Step D: (S)-2-amino-3-(4-(2-amino-1H-benzo[d]imidazol-4-yl)-2-sulfamoyl-3-(2H-tetrazol-5-yl)phenylsulfonamido)propanamide A solution of (S)-tert-butyl (1-amino-3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-1-oxopropan-2-yl)carbamate (160 mg, 0.163 mmol) and TFA (2 ml, 26.0 mmol) in DCM (10 ml) was stirred at ambient temperature for 2 hours. The reaction mixture was concentrated under vacuum to give the title compound as an oil. LCMS [M+H]$^+$: 762.

The solution of (S)-2-amino-3-(4-(2-amino-1H-benzo[d]imidazol-4-yl)-3-(2-(4-methoxybenzyl)-2H-tetrazol-5-yl)-2-(N-(4-methoxybenzyl)sulfamoyl)phenylsulfonamido)propanamide (120 mg, 0.158 mmol) in TFA (20 ml, 260 mmol) was stirred at 80° C. for 1 hr. The reaction mixture was concentrated under vacuum to give crude product. The product was purified by Prep-HPLC with the following conditions: Column: XBridge BEH130 Prep C18 OBD Column 19×150 mm 5 μM 13 nm; Mobile Phase A: water with 10 mmol NH$_4$HCO$_3$, Mobile Phase B: ACN; Flow rate: 20 mL/min; Gradient: 3% B to 25% B in 8 min; 254 nm. The collected fractions were combined and concentrated under vacuum to give the title compound as a solid. LCMS [M+H]$^+$: 977; $^1$H NMR (400 MHz, DMSO-d6): δ 8.23 (d, J=8.4 Hz, 1H), 7.96 (d, J=8.4 Hz, 1H), 7.73 (s, 1H), 7.50 (s, 1H), 6.97 (d, J=8.0 Hz, 1H), 6.64 (t, J=8.0 Hz, 1H), 6.50 (brs, 1H), 6.14 (d, J=8.0 Hz, 1H), 3.66-3.64 (m, 1H), 3.36-3.31 (m, 1H), 3.18-3.13 (m, 1H).

Example 190

4-(2-amino-1H-benzo[d]imidazol-4-yl)-N1-((R)-2-amino-3-hydroxypropyl)-3-(2H-tetrazol-5-yl)benzene-1,2-disulfonamide

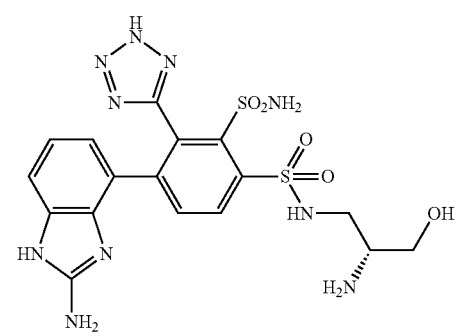 [SMILES: Nc1nc2c(-c3ccc(S(=O)(=O)NC[C@@H](N)CO)c(S(N)(=O)=O)c3-c3nn[nH]n3)cccc2[nH]1]

Step A: (R)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl)carbamate TEA (248 mg, in 0.2 ml THF) was added dropwise to a stirred solution of (R)-3-(2-(N,N-bis(4-methoxybenzyl)sulfamoyl)-4-iodo-3-(2-(4-methoxybenzyl)-2H-tetrazol-5-yl)phenylsulfonamido)-2-((tert-butoxycarbonyl)amino)propanoic acid (800 mg, 0.82 mmol) and isobutyl carbonochloridate (223 mg, 1.64 mmol) in 6.0 ml of THF at 0° C. The reaction mixture was stirred for 2 hours at room temperature, and then NaBH$_4$ (93 mg, 2.45 mmol) was added at 0° C. After the resulting mixture was stirred for 2 hours at room temperature, it was concentrated under reduced pressure. The residue was purified by silica gel chromatography, eluted with DCM/MeOH (20/1). The combined organic fractions were concentrated under reduced pressure to give the title compound as a foam: LCMS [M+1]$^+$: 964.

Step B: (R)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-3-hydroxypropan-2-yl)carbamate Pd(Ph$_3$P)$_4$ (27.0 mg, 0.023 mmol) was added to a stirred mixture of (R)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl)carbamate (210 mg, crude), and (2-amino-1H-benzo[d]imidazol-4-yl)boronic acid (83 mg, 0.47 mmol) and Na$_2$CO$_3$ (74.2 mg, 0.70 mmol) in 1,4-Dioxane (3.0 ml)/water (0.6 ml) at room temperature under Ar condition. After the resulting mixture was degassed twice, it was heated for 12 hours at 80° C. The resulting mixture was cooled to room temperature, filtered and concentrated under vacuum. The residue was purified by Prep-TLC (DCM/MeOH=20/1) to afford the title compound as a solid: LCMS [M+1]$^+$: 969.

Step C: (R)-4-(2-amino-1H-benzo[d]imidazol-4-yl)-N1-(2-amino-3-hydroxypropyl)-N2-(4-methoxybenzyl)-3-(2-(4-methoxybenzyl)-2H-tetrazol-5-yl)benzene-1,2-disulfonamide TFA (1.0 ml) was added dropwise to a stirred solution of (R)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-3-hydroxypropan-2-yl)carbamate (150 mg, crude) in 1.0 ml of DCM at 0° C. The reaction solution was stirred for 2 hours at room temperature and then concentrated under reduced pressure to afford 110 mg crude of (R)-4-(2-amino-1H-benzo[d]imidazol-4-yl)-N1-(2-amino-3-hydroxypropyl)-N2-(4-methoxybenzyl)-3-(2-(4-methoxybenzyl)-2H-tetrazol-5-yl)benzene-1,2-disulfonamide as a foam: LCMS [M+1]$^+$: 749. 2.0 ml TFA was added to this foam at room temperature. The resulting solution was stirred for 2 hours at 80° C. and then concentrated under reduced pressure. The crude was purified by Prep-HPLC with the following conditions: Column, Xbridge C18, 19×150 mm; mobile phase: water (0.05% NH$_4$HCO$_3$) and acetonitrile (hold 30% acetonitrile for 8 min, hold 100% for 2 min, down to 30% in 2 min); Detector, UV 220 and 254 nm. The collected fractions were combined and concentrated under vacuum to give the title compound as a solid: LCMS [M+1]$^+$: 509. $^1$H NMR (MDOD, 400 MHZ): 7.62 (d, J=7.6 Hz, 1H), 7.09 (d, J=7.6 Hz, 1H), 6.21 (d, J=7.6 Hz, 1H), 6.00-5.90 (m, 1H), 5.62 (d, J=7.2 Hz, 1H), 2.78-2.75 (m, 2H), 2.49-2.40 (m, 1H), 2.30-2.20 (m, 1H).

Example 191

4-(2-amino-1H-benzo[d]imidazol-4-yl)-N$^1$—((S)-2-amino-3-hydroxypropyl)-3-(2H-tetrazol-5-yl)benzene-1,2-disulfonamide

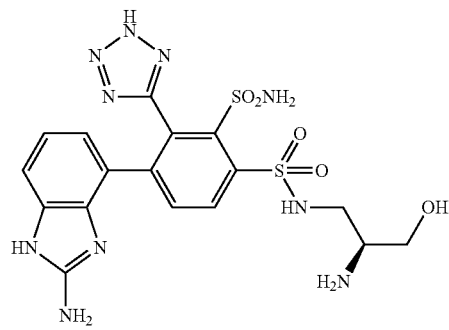 [SMILES: Nc1nc2c(-c3ccc(S(=O)(=O)NC[C@H](N)CO)c(S(N)(=O)=O)c3-c3nn[nH]n3)cccc2[nH]1]

Step A: (S)-benzyl tert-butyl (3-hydroxypropane-1,2-diyl)dicarbamate

TEA (4.1 ml) was added dropwise to a stirred solution of (S)-3-(((benzyloxy)carbonyl)amino)-2-((tert-butoxycarbonyl)amino)propanoic acid (5.0 g, 14.9 mmol) and isobutyl carbonochloridate (2.42 g, 17.7 mmol) in THF (50.0 ml) at 0° C. The resulting solution was stirred for 1 hour at room temperature, and then cooled to 0° C. and NaBH$_4$ (1.12 g, 29.6 mmol) was added. After the resulting mixture was stirred for 2 hours at room temperature, it was quenched with ice/water (100 ml), diluted with water (50 ml) and extracted with EA (3×80 ml). The combined organic layers were washed with brine (2×50 ml), dried over anhydrous sodium sulfate and filtered. The filtrate was concentrated under vacuum. The residue was purified by silica gel chromatography, eluted with DCM/MeOH (15/1). The combined organic fractions were concentrated under reduced pressure to give the title compound as a foam: LCMS [M+1]$^+$: 325. $^1$H NMR (400 MHz, CDCl$_3$): δ 7.67 (m, 5H), 5.53-5.33 (m, 2H), 4.07 (brs, 1H), 4.04-3.78 (m, 5H), 3.79-3.53 (m, 1H), 1.76 (brs, 9H), 1.38-1.16 (m, 1H).

Step B: (S)-tert-butyl (1-amino-3-hydroxypropan-2-yl)carbamate

To a stirred mixture of Pd(OH)$_2$/C (0.46 g) in 20 ml MeOH, (S)-benzyl tert-butyl (3-hydroxypropane-1,2-diyl)dicarbamate (2.1 g, 6.47 mmol) was added at ambient temperature. The resulting mixture was degassed with nitrogen 3 times and stirred under hydrogen (1.5 atm) for 12 hours at ambient temperature. The mixture was filtered. The filter cake was washed with methanol (3×20 ml). The combined organic layers were concentrated under reduced pressure. The residue was purified by silica gel chromatography, eluted with DCM/methanol (4/3). The combined organic fractions were concentrated under reduced pressure to give the title compound as a foam: LCMS [M+1]$^+$:

191. $^1$H NMR (400 MHz, CDCl$_3$): δ 5.76-5.23 (m, 3H), 4.02-3.79 (m, 2H), 3.80-3.63 (m, 1H), 3.39-3.17 (m, 1H), 1.44 (brs, 9H).

Step C: (S)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl)carbamate 1-Chloropyrrolidine-2,5-dione (207 mg, 1.55 mmol) was added batchwise to a stirred solution of 2-(N,N-bis(4-methoxybenzyl)sulfamoyl)-4-iodo-3-(2-(4-methoxybenzyl)-2H-tetrazol-5-yl)benzenesulfinic acid (600 mg, 0.77 mmol) in THF (5.0 ml) at 0° C. After the resulting solution was stirred for 2 hours at room temperature, (S)-tert-butyl (1-amino-3-hydroxypropan-2-yl)carbamate (294 mg, 1.55 mmol) was added and followed by the addition of triethylamine (235 mg, 2.32 mmol) dropwise at 0° C. The resulting mixture was stirred for 1 hour at room temperature and then concentrated under vacuum. The residue was purified by silica gel chromatography, eluted with methanol/DCM (1/50). The combined organic fractions were concentrated under reduced pressure to give the title compound as a foam: LCMS [M+1]$^+$: 963.

Step D: (S)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-3-hydroxypropan-2-yl)carbamate Pd(PPh$_3$)$_4$ (73.1 mg, 0.06 mmol) was added to a stirred mixture of (S)-tert-butyl (1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl)carbamate (610 mg, 0.633 mmol) and (2-amino-1H-benzo[d]imidazol-4-yl)boronic acid (224 mg, 1.27 mmol) and Na$_2$CO$_3$ (201 mg, 1.90 mmol) in 1,4-Dioxane (5.0 ml)/water (1.0 ml) at room temperature under Ar condition. The resulting mixture was heated for 12 hours at 80° C., and then cooled to room temperature, filtered and concentrated under reduced pressure. The residue was purified by Prep-TLC(DCM/MeOH=20/1) to afford the title compound as a solid: LCMS [M+1]$^+$: 969.

Step E: (S)-4-(2-amino-1H-benzo[d]imidazol-4-yl)-N$^1$-(2-amino-3-hydroxypropyl)-3-(2H-tetrazol-5-yl)-benzene-1,2-disulfonamide TFA (2.0 ml) was added dropwise to a stirred solution of (S)-tert-butyl (1-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-3-hydroxypropan-2-yl)carbamate (300 mg, crude) in DCM (2.0 ml) at 0° C. The reaction solution was stirred for 2 hours at room temperature, and then concentrated to afford crude (S)-4-(2-amino-1H-benzo[d]imidazol-4-yl)-N$^1$-(2-amino-3-hydroxypropyl)-N$^2$-(4-methoxybenzyl)-3-(2-(4-methoxybenzyl)-2H-tetrazol-5-yl)benzene-1,2-disulfonamide as a foam: LCMS [M+1]$^+$: 749.

TFA (2.0 ml) was added to this foam and the resulting mixture was heated for 2 hours at 80° C. After the resulting mixture was cooled to room temperature, it was concentrated under reduced pressure. The residue was purified by Prep-HPLC with the following conditions: Column, Xbridge C18, 19×150 mm; mobile phase: water (0.05% NH$_4$HCO$_3$) and acetonitrile (hold 34% acetonitrile for 8 min, hold 100% for 2 min, down to 34% in 2 min); Detector, UV 220 and 254 nm. The collected fractions were combined and concentrated under vacuum to give the title compound as a solid: LCMS [M+1]$^+$: 509. $^1$H NMR (CD$_3$OD, 400 MHZ): δ 8.45 (d, J=8.2 Hz, 1H), 7.92 (d, J=8.2 Hz, 1H), 7.05 (d, J=7.9 Hz, 1H), 6.79 (t, J=7.8 Hz, 1H), 6.49 (d, J=7.8 Hz, 1H), 3.74-3.67 (m, 1H), 3.63 (m, 1H), 3.30-3.20 (m, 3H).

Example 192

4-(3,4-disulfamoyl-2-(2H-tetrazol-5-yl)phenyl)benzo[d]thiazole-2-carboximidamide

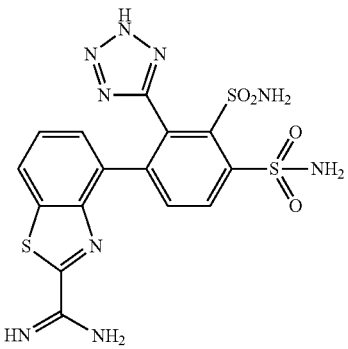 [SMILES: N=C(N)c1nc2c(-c3ccc(S(N)(=O)=O)c(S(N)(=O)=O)c3-c3nn[nH]n3)cccc2s1]

Step A: 5-(2-aminobenzo[d]thiazol-4-yl)-N1,N1-bis(4-methoxybenzyl)-6-(2-(4-methoxybenzyl)-2H-tetrazol-5-yl)benzene-1,2-disulfonamide Into a 50-mL round-bottom flask purged and maintained with an inert atmosphere of argon, was placed a solution of 5-iodo-N1,N1-bis(4-methoxybenzyl)-6-(2-(4-methoxybenzyl)-2H-tetrazol-5-yl)benzene-1,2-disulfonamide (1 g, 1.01 mmol), Pd(dppf)Cl$_2$CH$_2$Cl$_2$ (0.16 g, 0.20 mmol) and (2-aminobenzo[d]thiazol-4-yl)boronic acid (0.393 g, 2.024 mmol) in dioxane (10 mL). This was followed by the addition of sodium carbonate (0.32 g, 3.04 mmol) in water (1.5 mL) at ambient temperature. After the resulting mixture was stirred at 80° C. for 16 hours under argon, it was cooled to 20° C. and then quenched with water (50 mL), extracted with ethyl acetate (3×50 mL). The combined organic layers were washed with brine (3×100 mL), dried over anhydrous sodium sulfate and filtered. The filtrate was evaporated under reduced pressure and the residue was purified by silica gel chromatography, eluted with EA/DCM (2/3) to give the title compound as a solid: LCMS [M+H]$^+$: 813.0; $^1$H NMR (400 MHz, DMSO-d$_6$) δ 8.55 (d, J=8.4 Hz, 1H), 7.99 (d, J=8.4 Hz, 1H), 7.61 (s, 2H), 7.53-7.51 (m, 3H), 6.93 (d, J=8.4 Hz, 5H), 6.83 (d, J=8.8 Hz, 5H), 6.76 (d, J=7.6 Hz, 2H), 6.64 (br, 1H), 6.48 (br, 1H), 5.67 (s, 2H), 4.04-3.96 (m, 4H), 3.73 (s, 6H), 3.69 (s, 3H).

Step B: 5-(2-bromobenzo[d]thiazol-4-yl)-N1,N1-bis(4-methoxybenzyl)-6-(2-(4-methoxybenzyl)-2H-tetrazol-5-yl)benzene-1,2-disulfonamide Into a 25-mL round-bottom flask purged and maintained with an inert atmosphere of argon, was placed a solution of tert-butyl nitrite (81 mg, 0.79 mmol) and copper (II) bromide (0.13 g, 0.59 mmol) in acetonitrile (2 ml). This was followed by the addition of 5-(2-aminobenzo[d]thiazol-4- yl)-N1,N1-bis(4-methoxybenzyl)-6-(2-(4-methoxybenzyl)-2H-tetrazol-5-yl)benzene-1,2-disulfonamide (0.40 g, 0.49 mmol) in acetonitrile (5 mL) at 0° C. The resulting mixture was stirred at 0° C. for 16 hours under argon, and then the reaction was quenched with water (30 mL) and extracted with EA (3×30 mL). The combined organic layers were washed with brine (3×70 mL), dried over anhydrous sodium sulfate and filtered. The filtrate was evaporated under reduced pressure and the residue was purified by silica gel chromatography, eluted with EA/PE (2/3) to give the title compound as a solid: LCMS [M+H]$^+$: 878; $^1$H NMR (400 MHz, CDCl$_3$) δ 8.72 (d, J=8.4 Hz, 1H), 7.88 (d, J=8.4 Hz, 1H), 7.54 (d, J=8.0 Hz, 1H), 6.99 (d, J=8.4 Hz, 7H), 6.82 (d, J=8.8 Hz, 5H), 6.71 (d, J=7.6 Hz, 2H), 5.99 (s, 2H), 5.47-05.45 (m, 2H), 4.31-4.05 (m, 4H), 3.77 (s, 6H), 3.75 (s, 3H).

Step C: 5-(2-cyanobenzo[d]thiazol-4-yl)-N1,N1-bis(4-methoxybenzyl)-6-(2-(4-methoxybenzyl)-2H-tetrazol-5-yl)benzene-1,2-disulfonamide Into a 25-mL round-bottom flask purged and maintained with an inert atmosphere of argon, was placed a solution of 5-(2-bromobenzo[d]thiazol-4-yl)-N1,N1-bis(4-methoxybenzyl)-6-(2-(4-methoxybenzyl)-2H-tetrazol-5-yl)benzene-1,2-disulfonamide (0.40 g, 0.39 mmol) and copper(I) cyanide (0.10 g, 1.16 mmol) in DMSO (4 mL). The resulting mixture was stirred at 100° C. for 6 hours under argon. The reaction was quenched with water (30 mL), extracted with EA (3×30 mL). The combined organic layers were washed with brine (3×70 mL), dried over anhydrous sodium sulfate and filtered. The filtrate was evaporated under reduced pressure and the residue was purified by silica gel chromatography, eluted with EA/PE (2/3) to give the title compound as a solid: LCMS [M+H]$^+$: 823.0; $^1$H NMR (300 MHz, CDCl$_3$) δ 8.74 (d, J=8.4 Hz, 1H), 7.81 (d, J=8.4 Hz, 1H), 7.68 (d, J=8.1 Hz, 1H), 7.15-6.95 (m, 8H), 6.82-6.68 (m, 5H), 6.57-6.55 (m, 1H), 5.99-5.94 (m, 2H), 5.41 (brs, 2H), 4.31-4.05 (m, 4H), 3.77 (s, 6H), 3.74 (s, 3H).

Step D: 4-(3-(N,N-bis(4-methoxybenzyl)sulfamoyl)-2-(2-(4-methoxybenzyl)-2H-tetrazol-5-yl)-4-sulfamoylphenyl)benzo[d]thiazole-2-carboximidamide Into a 25-mL round-bottom flask purged and maintained with an inert atmosphere of argon, was placed a solution of 5-(2-cyanobenzo[d]thiazol-4-yl)-N1,N1-bis(4-methoxybenzyl)-6-(2-(4-methoxybenzyl)-2H-tetrazol-5-yl)benzene-1,2-disulfonamide (0.15 g, 0.18 mmol) in MeOH (3 mL) and THF (0.5 mL). This was followed by the addition of sodium methanolate (0.02 mL, 0.02 mmol) at ambient temperature. The resulting mixture was stirred at 20° C. for 0.5 hour under argon, and then was followed by the addition of NH$_4$Cl (0.98 g, 1.82 mmol) at ambient temperature. The resulting mixture was stirred at 40° C. for 16 hours under argon. The reaction was quenched with water (50 mL) and extracted with EA (3×100 mL). The combined organic layers were washed with brine (3×200 mL), dried over anhydrous sodium sulfate and filtered. The filtrate was evaporated under reduced pressure and the residue was purified by Prep-TLC, eluted with EA/PE (5/1) to give the title compound as a solid: LCMS [M+1]$^+$: 840; $^1$H NMR (300 MHz, CDCl$_3$) δ 8.74 (d, J=8.7 Hz, 1H), 7.88 (d, J=7.5 Hz, 1H), 7.69 (d, J=7.8 Hz, 1H), 7.05-6.88 (m, 9H), 6.79-6.76 (m, 5H), 6.70-6.67 (m, 2H), 6.52 (brs, 1H), 5.39 (brs, 2H), 4.85-4.61 (m, 1H), 4.25-4.23 (m, 3H), 3.77 (s, 6H), 3.74 (s, 3H), 3.73-3.65 (m, 2H).

Step E: 4-(3,4-disulfamoyl-2-(2H-tetrazol-5-yl)phenyl)benzo[d]thiazole-2-carboximidamide Into a 25-mL round-bottom flask, was placed a solution of 4-(3-(N,N-bis(4-methoxybenzyl)sulfamoyl)-2-(2-(4-methoxybenzyl)-2H-tetrazol-5-yl)-4-sulfamoylphenyl)benzo[d]thiazole-2-carboximidamide (0.80 g, 0.10 mmol) in TFA (3 mL). The resulting mixture was stirred at 80° C. for 1 hour. The solvent was evaporated and the residue was purified by Prep-HPLC with the following conditions: Column: Column: XBridge BEM 30 Prep C18 OBD Column 19×150 mm 5 μM 13 nm; Mobile Phase A: water with 10 mmol of NH$_4$HCO$_3$, Mobile Phase B: MeCN; Flow rate: 20 mL/min; Gradient: 5% B to 15% B in 8 min; RT: 5.0 Min; 254/220 nm. The collected fractions were combined and concentrated under reduced pressure to give the title compound as a solid: LCMS [M+1]$^+$: 480.0; $^1$H NMR (400 MHz, DMSO-d$_6$) δ 9.47 (br, 3H), 8.32 (d, J=8.4 Hz, 1H), 8.21 (d, J=8.4 Hz, 1H), 7.93 (d, J=8.4 Hz, 1H), 7.72 (br, 2H), 7.48 (t, J=8.0 Hz, 1H), 7.35 (br, 2H), 7.07 (d, J=7.6 Hz, 1H).

Example 193

4-(1H-benzo[d]imidazol-4-yl)-N1-((R)-pyrrolidin-3-yl)-3-(2H-tetrazol-5-yl)benzene-1,2-disulfonamide

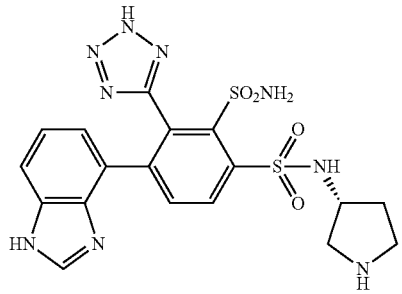 [SMILES: NS(=O)(=O)c1c(S(=O)(=O)N[C@@H]2CCNC2)ccc(-c2cccc3[nH]cnc23)c1-c1nn[nH]n1]

Step A: tert-butyl (R)-3-((4-(1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)pyrrolidine-1-carboxylate To a solution of tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate (300 mg, 0.349 mmol) in dioxane (6 ml) and water (2 ml) was added Na$_2$CO$_3$ (148 mg, 1.396 mmol) (1H-benzo[d]imidazol-4-yl)boronic acid (141 mg, 0.872 mmol) and Pd(dppf)Cl$_2$ (51.0 mg, 0.070 mmol) with stirring at room temperature. The resulting mixture was warmed to 80° C. and stirred overnight. After the reaction mixture was cooled to ambient temperature, it was diluted with water (15 mL) and extracted with ethyl acetate (3×15 mL). The combined organic layers were washed with brine (3×30 mL), dried over anhydrous sodium sulfate, filtered and concentrated under vacuum. The residue was purified by silica gel column chromatography 20 g, eluted with EtOAc/petroleum ether (1/2) to afford the title compound as a solid: LCMS [M+H]$^+$: 950.

Step B: (R)-4-(1H-benzo[d]imidazol-4-yl)-N$^1$-(pyrrolidin-3-yl)-3-(2H-tetrazol-5-yl)benzene-1,2-disulfonamide To a solution of tert-butyl (R)-3-((4-(1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)pyrrolidine-1-carboxylate in DCM (5 ml) was added TFA (1 ml) with stirring at room temperature. The resulting mixture was warmed to room temperature and stirred for 1 hour then concentrated under vacuum to afford an oil. To the oil was added TFA (5 ml) with stirring at room temperature. The resulting solution was warmed to 80° C. and stirred for 1 hour. The solution was concentrated under vacuum and the residue was purified by Prep-HPLC with the following conditions: Column: XBridge C18 OBD Prep Column, 100 Å, 5 μm, 19 mm×250 mm; Mobile Phase A: water with 10 mmol of NH$_4$HCO$_3$, Mobile Phase B: ACN; Flow rate: 20 mL/min; Gradient: 5% B to 30% B in 8 min; 254 nm. The collected fractions were combined and concentrated under vacuum to give the title compound as a solid: LCMS [M+H]$^+$: 490; $^1$H NMR (300 MHz, DMSO): δ 9.76 (s, 1H), 8.58-5.55 (m, 1H), 8.12-8.09 (m, 1H), 7.81-7.78 (m, 1H), 7.44-7.41 (m, 1H), 6.99 (s, 1H), 4.16-4.11 (m, 1H), 3.41-3.14 (m, 4H), 2.21-1.94 (m, 2H).

Example 194

(R)-4-(6-aminopyridin-3-yl)-N$^1$-(pyrrolidin-3-yl)-3-(2H-tetrazol-5-yl)benzene-1,2-disulfonamide

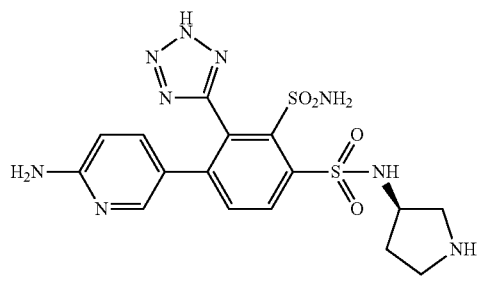 [SMILES: Nc1ccc(-c2ccc(S(=O)(=O)N[C@@H]3CCNC3)c(S(N)(=O)=O)c2-c2nn[nH]n2)cn1]

Step A: (R)-tert-butyl 3-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate To a solution of (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (250 mg, 0.260 mmol) in dioxane (2.7 ml)/water (0.3 ml) were added 5-(4,4,5,5-tetramethyl-1,3,2-dioxaborolan-2-yl)pyridin-2-amine (143 mg, 0.651 mmol), Na$_2$CO$_3$ (83 mg, 0.781 mmol) and PdCl$_2$ (dppf) (57.2 mg, 0.078 mmol) at ambient temperature. The flask was degassed with nitrogen three times. The reaction mixture was irradiated with microwave radiation at 130° C. for 0.5 hour under an atmosphere of nitrogen. The reaction mixture was quenched with water (20 mL) and extracted with ethyl acetate (3×15 mL). The combined organic layers were washed with water (3×15 mL) and brine (3×15 mL), dried over anhydrous sodium sulfate and filtered. The filtrate was concentrated under vacuum. The residue was purified by silica gel column chromatography with CH$_2$Cl$_2$/MeOH (1:10) to give the title compound as a solid: LCMS [M+H]$^+$: 926;

Step B: (R)-4-(6-aminopyridin-3-yl)-N$^1$-(pyrrolidin-3-yl)-3-(2H-tetrazol-5-yl)benzene-1,2-disulfonamide To a solution of (R)-tert-butyl 3-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate (140 mg, 0.151 mmol) in DCM (3 ml) was added TFA (1.00 ml) with stirring at 0° C. The resulting solution was warmed to room temperature and stirred for 1 hour. The reaction solution was filtered and the solvent was evaporated under reduced pressure. To the residue was added TFA (4 mL) and the mixture was stirred at 80° C. for 1 hour. The mixture was evaporated under reduced pressure. The product was purified by Prep-HPLC with the following conditions: Column: X Select CSH Prep C18 OBD Column, 5 μM, 19*150 mm; Mobile Phase A: water with 10 mmol NH$_4$HCO$_3$, Mobile Phase B: MeCN; Flow rate: 20 mL/min; Gradient: 5% B to 35% B in 8 min; 254/220 nm. The collected fractions were combined and concentrated under vacuum to afford the title compound as a solid: LCMS [M–H]$^+$: 464. $^1$H NMR (400 MHz, MeOD): δ 8.64 (d, J=8.0 Hz, 1H), 8.03-8.00 (m, 1H), 7.74-7.71 (m, 1H), 7.53 (d, J=8.0 Hz, 1H), 6.91-6.81 (m, 1H), 4.29-4.23 (m, 1H), 3.45-3.40 (m, 2H), 3.33-3.30 (m, 2H), 2.30-2.21 (m, 1H), 2.03-1.98 (m, 1H).

Example 195

(S)-4-(6-aminopyridin-3-yl)-N$^1$-(pyrrolidin-3-yl)-3-(2H-tetrazol-5-yl)benzene-1,2-disulfonamide

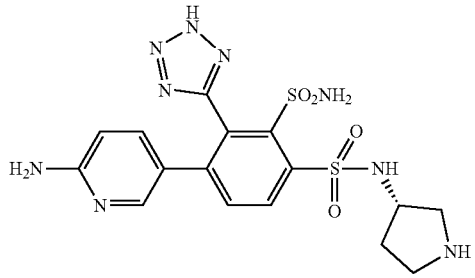 [SMILES: Nc1ccc(-c2ccc(S(=O)(=O)N[C@H]3CCNC3)c(S(N)(=O)=O)c2-c2nn[nH]n2)cn1]

Step A: (S)-tert-butyl 3-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate To a solution of (S)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (REFERENCE EXAMPLE 72, 2 g, 2.084 mmol) in dioxane (9 ml)/water (3 ml) was added 5-(4,4,5,5-tetramethyl-1,3,2-dioxaborolan-2-yl)pyridin-2-amine (0.917 g, 4.17 mmol), Na$_2$CO$_3$ (0.663 g, 6.25 mmol) and PdCl$_2$ (dppf) (0.305 g, 0.417 mmol) at ambient temperature. The flask was evacuated and backfilled with nitrogen three times. The reaction mixture was stirring at 80° C. for 16 hours under an atmosphere of nitrogen. The reaction mixture was quenched with water (50 mL) and extracted with ethyl acetate (3×100 mL). The combined organic layers were washed with water (3×100 mL) and brine (3×100 mL), dried over anhydrous sodium sulfate and filtered. The filtrate was concentrated under vacuum. The residue was applied onto silica gel column chromatography with $CH_2Cl_2$/MeOH (1:10) to afford the title compound as a solid: LCMS [M+H]$^+$: 926

Step B: (S)-4-(6-aminopyridin-3-yl)-N-(pyrrolidin-3-yl)-3-(2H-tetrazol-5-yl)benzene-1,2-disulfonamide To a solution of (S)-tert-butyl 3-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate (150 mg, 0.162 mmol) in DCM (3 ml) was added TFA (1.00 ml) with stirring at 0° C. The resulting solution was warmed to room temperature and stirred for 1 hour. The reaction solution was filtered and the solvent was evaporated under reduced pressure. To the residue was added TFA (4 ml) and the mixture was stirred at 80° C. for 1 hour. The mixture was evaporated under reduced pressure. The product was purified by Prep-HPLC with the following conditions: Column: X Bridge BEH130 Prep C18 OBD Column 19×150 mm 5 μM 13 nm; Mobile Phase A: water with 10 mmol $NH_4HCO_3$, Mobile Phase B: MeCN; Flow rate: 20 mL/min; Gradient: 3% B to 20% B in 8 min; 254 nm. The collected fractions were combined and concentrated under vacuum to afford the title compound as a solid: LCMS [M−H]$^+$: 464. $^1$H NMR (400 MHz, DMSO-d$_6$): δ 8.20 (d, J=8.0 Hz, 1H), 7.76-7.74 (d, J=8.0 Hz, 1H), 7.53 (s, 1H), 6.68-6.67 (m, 1H), 6.15-6.13 (m, 1H), 5.99-5.96 (brs, 2H), 4.08-4.02 (m, 1H), 3.30-3.22 (m, 2H), 3.19-3.10 (m, 2H), 2.08-2.01 (m, 1H), 1.89-1.80 (m, 1H).

Example 196

N$^1$-(2-aminoethyl)-4-(6-aminopyridin-3-yl)-3-(2H-tetrazol-5-yl)benzene-1,2-disulfonamide

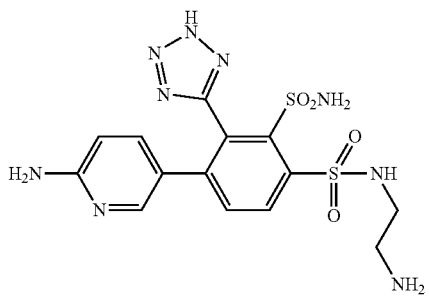 [SMILES: NCCNS(=O)(=O)c1ccc(-c2ccc(N)nc2)c(-c2nn[nH]n2)c1S(N)(=O)=O]

Step A: tert-butyl 2-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)ethylcarbamate To a solution of (S)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (250 mg, 0.260 mmol) in dioxane (2.7 ml)/water (0.300 ml) was added 5-(4,4,5,5-tetramethyl-1,3,2-dioxaborolan-2-yl)pyridin-2-amine (115 mg, 0.521 mmol), $Na_2CO_3$ (83 mg, 0.781 mmol) and PdCl$_2$ (dppf) (38.1 mg, 0.052 mmol) at ambient temperature. The flask was evacuated and back-filled with nitrogen three times. The reaction mixture was irradiated with microwave radiation at 80° C. for 3 hours under an atmosphere of nitrogen. The reaction mixture was quenched with water (50 mL) and extracted with ethyl acetate (3×15 mL). The combined organic layers were washed with water (3×15 mL) and brine (3×15 mL), dried over anhydrous sodium sulfate and filtered. The filtrate was concentrated under vacuum. The residue was applied onto silica gel column chromatography with MeOH/$CH_2Cl_2$ (1:10) to give the title compound as a solid: LCMS [M+H]$^+$: 900.

Step B: N$^1$-(2-aminoethyl)-4-(6-aminopyridin-3-yl)-3-(2H-tetrazol-5-yl)benzene-1,2-disulfonamide To a solution of tert-butyl (2-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)ethyl)carbamate (150 mg, 0.167 mmol) in DCM (3 ml) was added TFA (1.00 ml) with stirring at 0° C. The resulting solution was warmed to room temperature and stirred for 1 hour. The reaction solution was filtered and the solvent was evaporated under reduced pressure. To the residue was added TFA (4 ml) and the mixture was stirred at 80° C. for 1 hour. The mixture was evaporated under reduced pressure. The product was purified by Prep-HPLC with the following conditions: Column: X Bridge C18 OBD Prep Column, 100 Å, 5 μm, 19 mm×250 mm; Mobile Phase A: water with 10 mmol $NH_4HCO_3$, Mobile Phase B: MeCN; Flow rate: 20 mL/min; Gradient: 3% B to 20% B in 8 min; 254 nm. The collected fractions were combined and concentrated under vacuum to afford the title compound as a solid: LCMS [M+H]$^+$: 440. $^1$H NMR (400 MHz, DMSO-d$_6$): δ 8.18 (d, J=8.0 Hz, 1H), 7.75 (d, J=8.0 Hz, 1H), 7.53-7.52 (m, 1H), 6.71-6.68 (m, 1H), 6.15-6.13 (m, 1H), 5.99 (brs, 1H), 3.20-3.17 (m, 2H), 3.94-3.93 (m, 2H).

Example 197

4-(1H-benzo[d]imidazol-4-yl)-N$^1$—(S)-pyrrolidin-3-yl)-3-(2H-tetrazol-5-yl)benzene-1,2-disulfonamide

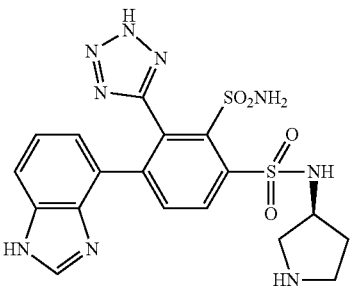 [SMILES: NS(=O)(=O)c1c(S(=O)(=O)N[C@H]2CCNC2)ccc(-c2cccc3[nH]cnc23)c1-c1nn[nH]n1]

Step A: 1H-benzo[d]imidazol-4-yl)boronic acid 4,4,4',4',5,5,5',5'-octamethyl-2,2'-bi(1,3,2-dioxaborolane) (5.16 g, 20.30 mmol), Pd(dppf)Cl$_2$ (1.485 g, 2.030 mmol) and potassium acetate (2.99 g, 30.5 mmol) were added to a stirred mixture of 4-bromo-1H-benzo[d]imidazole (2 g, 10.15 mmol) in dioxane (10 ml) and the mixture was degassed 3 times with N$_2$. The reaction mixture was stirred at 80° C. overnight. The resulting mixture was cooled to room temperature, diluted with ethyl acetate (50 mL), washed with brine (3×30 mL), dried over anhydrous Na$_2$SO$_4$ and filtered. The solvent was evaporated under reduced pressure. The residue was purified by column chromatography on silica gel chromatography, eluting with MeOH/AcOH to give the title compound as an oil: LCMS [M+H]+: 163; ¹H NMR (400 MHz, DMSO-d₆): δ 9.26 (s, 1H), 8.07-8.04 (m, 1H), 7.91-7.89 (m, 1H), 7.53-7.49 (m, 1H).

Step B: (S)-tert-butyl 3-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate (S)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (300 mg, 0.313 mmol), Pd(dppf)Cl₂ (45.7 mg, 0.063 mmol) and Na₂CO₃ (99 mg, 0.938 mmol) were added to a stirred mixture of (1H-benzo[d]imidazol-4-yl)boronic acid (152 mg, 0.938 mmol) in dioxane (10 ml) and water (2.5 ml). The reaction mixture was degassed 3 times with N₂, and stirred at 80° C. for 16 hours. The mixture was cooled, diluted with ethyl acetate (30 mL), washed with brine (3×20 mL), dried over anhydrous Na₂SO₄, filtered and the solvent was evaporated under reduced pressure. The residue was purified by column chromatography on silica gel chromatography, eluting with EA/PE (30-90%) to give the title compound as a solid: LCMS [M+H]+: 950.

Step C: (S)-4-(1H-benzo[d]imidazol-4-yl)-N1-(pyrrolidin-3-yl)-3-(2H-tetrazol-5-yl)benzene-1,2-disulfonamide (S)-tert-butyl 3-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate (220 mg, 0.232 mmol) was added to DCM (3 ml) and TFA (1 ml) at 0° C. and the solution was stirred at room temperature for 1 hour. The reaction solution was evaporated under reduced pressure. To the residue was added TFA (4 ml) and the mixture was stirred at 80° C. for 1 hour. The reaction solution was evaporated under reduced pressure. The crude product was purified by Prep-HPLC with the following conditions: Column: XBridge C18 OBD Prep Column, 100 Å, 5 μm, 19 mm×250 mm; Mobile Phase A: water with 10 mmol NH₄HCO₃, Mobile Phase B: MeCN; Flow rate: 20 mL/min; Gradient: 5% B to 30% B in 8 min; 254 nm. The collected fractions were concentrated under vacuum to afford the title compound as a solid: LCMS [M+H]+: 490; ¹H NMR (400 MHz, DMSO-d₆): δ 9.71 (s, 1H), 8.54 (d, J=8.0 Hz, 1H), 8.09 (d, J=8.0 Hz, 1H), 7.79-7.77 (m, 1H), 7.42-7.38 (m, 1H), 6.97-6.94 (m, 1H), 4.17-4.10 (m, 1H), 3.38-3.26 (m, 2H), 3.18-3.11 (m, 2H), 2.14-2.06 (m, 1H), 1.96-1.87 (m, 1H).

Example 198

N¹-(3-aminopropyl)-4-(1H-benzo[d]imidazol-4-yl)-3-(2H-tetrazol-5-yl)benzene-1,2-disulfonamide

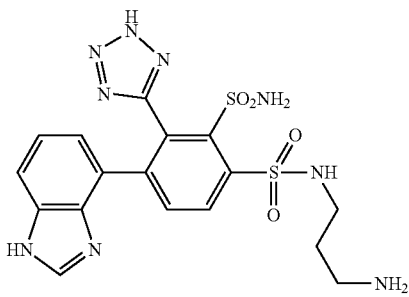 [SMILES: NCCCNS(=O)(=O)c1ccc(-c2cccc3[nH]cnc23)c(-c2nn[nH]n2)c1S(N)(=O)=O]

Step A: 3-(1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide 3-Iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (1 g, 1.142 mmol), Pd(dppf)Cl₂ (0.167 g, 0.228 mmol) and Na₂CO₃ (0.363 g, 3.43 mmol) were added to a stirred mixture of (1H-benzo[d]imidazol-4-yl)boronic acid (0.555 g, 3.43 mmol) in dioxane (10 ml) and water (2.5 ml). The mixture was evacuated and backfilled 3 times with N₂, and stirred at 80° C. for 6 hours. The mixture was cooled, diluted with ethyl acetate (30 mL), washed with brine (3×20 mL), dried (Na₂SO₄), filtered and the solvent was evaporated under reduced pressure. The residue was purified by silica-gel chromatography, eluted with EA/PE (30-90%) to give the title compound as a solid.: LCMS [M+H]+: 866.

Step B: 4-(1H-benzo[d]imidazol-4-yl)-2-(N,N-bis(4-methoxybenzyl)sulfamoyl)-3-(2-(4-methoxybenzyl)-2H-tetrazol-5-yl)benzenesulfinic acid TBAF (1M in THF) (3.00 ml, 3.00 mmol) was added to a stirred mixture of 3-(1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (650 mg, 0.750 mmol) in THF (10 ml) at 0° C. After the resulting mixture was stirred at 0° C. for 1 hour, it was diluted with ethyl acetate (30 mL), washed with saturated aqueous KHSO₄ (5×30 mL), dried over anhydrous Na₂SO₄, then filtered. The filtrate was evaporated under reduced pressure to give the title compound, which was used for the next step directly without further purification: LCMS [M+H]+: 766.

Step C: tert-butyl (3-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propyl)carbamate tert-butyl (3-aminopropyl)carbamate (150 mg, 0.862 mmol) and Et₃N (0.160 ml, 1.149 mmol) were added to a stirred, mixture of 4-(1H-benzo[d]imidazol-4-yl)-2-(N,N-bis(4-methoxybenzyl)sulfamoyl)-3-(2-(4-methoxybenzyl)-2H-tetrazol-5-yl)benzenesulfinic acid (220 mg, 0.287 mmol) in THF (20 ml) at 0° C. The resulting mixture was stirred at 0° C. for 5 minutes and then NCS (77 mg, 0.575 mmol) was added. After the resulting mixture was stirred at 0° C. for 16 hours, it was diluted with ethyl acetate (40 mL), washed with brine (3×30 mL), dried over anhydrous Na₂SO₄ and filtered. The filtrate was evaporated under reduced pressure and the residue was purified by silica-gel chromatography, eluted with EA/PE (0-80%) to give the title compound as a solid: LCMS [M+H]+: 938.

Step D: N¹-(3-aminopropyl)-4-(1H-benzo[d]imidazol-4-yl)-3-(2H-tetrazol-5-yl)benzene-1,2-disulfonamide tert-butyl 3-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propylcarbamate (220 mg, 0.235 mmol) was added to DCM (3 ml) and TFA (1 ml) at 0° C. and the solution was stirred at room temp. for 1 hour. The reaction solution was evaporated under reduced pressure. To the residue was added TFA (4 ml) and the mixture was stirred at 80° C. for 1 hour. The reaction solution was evaporated under reduced pressure. The crude product was purified by Prep-HPLC with the following conditions: Column: XBridge C18 OBD Prep Column, 100 Å, 5 μm, 19 mm×250 mm; Mobile Phase A: water with 10 mmol NH$_4$HCO$_3$, Mobile Phase B: MeCN; Flow rate: 20 mL/min; Gradient: 5% B to 30% B in 8 min; 254 nm. The collected fractions were concentrated under vacuum to afford the title compound as a solid: LCMS [M+H]$^+$: 478; $^1$H NMR (400 MHz, DMSO-d$_6$): δ 9.75 (s, 1H), 8.51 (d, J=8.0 Hz, 1H), 8.07 (d, J=8.0 Hz, 1H), 7.82-7.76 (m, 1H), 7.41-7.37 (m, 1H), 6.95-6.93 (m, 1H), 3.14-3.11 (m, 2H), 2.79-2.85 (m, 2H), 1.87-1.80 (m, 2H).

Example 199

N$^1$-(2-aminoethyl)-4-(1H-benzo[d]imidazol-4-yl)-3-(2H-tetrazol-5-yl)benzene-1,2-disulfonamide

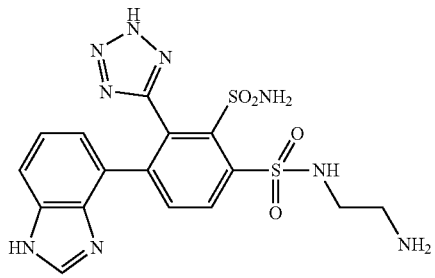 [SMILES: NCCNS(=O)(=O)c1ccc(-c2cccc3[nH]cnc23)c(-c2nn[nH]n2)c1S(N)(=O)=O]

Step A: tert-butyl (2-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)ethyl)carbamate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (300 mg, 0.321 mmol) in dioxane (6 ml) and water (2 ml) was added Na$_2$CO$_3$ (1H-benzo[d]imidazol-4-yl)boronic acid and Pd(dppf)Cl$_2$ with stirring at room temp. The resulting mixture was warmed to 80° C. and stirred overnight. The reaction mixture was cooled to ambient temperature, diluted with water (10 mL) and extracted with ethyl acetate (3×20 mL). The combined organic layers were washed with brine (3×20 mL), dried over anhydrous sodium sulfate and filtered. The filtrate was concentrated under vacuum to afford a residue. The residue was purified by silica gel column chromatography 20 g, eluted with ethyl acetate/petroleum ether (1/1) to afford the title compound as a solid: LCMS [M+H]$^+$: 924.

Step B: N$^1$-(2-aminoethyl)-4-(1H-benzo[d]imidazol-4-yl)-3-(2H-tetrazol-5-yl)benzene-1,2-disulfonamide To a solution of tert-butyl (2-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)ethyl)carbamate in DCM (2 ml) was added TFA (0.5 ml) with stirring at room temperature. After the resulting solution was stirred at room temperature for 1 hour, it was concentrated under vacuum to afford an oil. To the oil was added TFA (2 ml) with stirring at room temperature. The resulted solution was warmed to 80° C. and stirred for 1 hour. The resulting solution was concentrated under vacuum to afford a residue. The residue was purified by Prep-HPLC with the following conditions: Column: XBridge BEH130 Prep C18 OBD Column 19×150 mm 5 μM 13 nm; Mobile Phase A: water with 10 mmol NH$_4$HCO$_3$, Mobile Phase B: ACN; Flow rate: 20 mL/min; Gradient: 3% B to 25% B in 8 min; 254 nm. The collected fractions were combined and concentrated under vacuum to give the title compound as a solid: LCMS [M+H]$^+$: 464; $^1$H NMR (400 MHz, CD$_3$OD): δ 9.43 (s, 1H), 8.70 (d, J=8.0 Hz, 1H), 8.10-8.08 (m, 1H), 7.81 (d, J=8.0 Hz, 1H), 7.54 (d, J=8.0 Hz, 1H), 7.25-7.24 (m, 1H), 3.46-3.41 (m, 2H), 3.24-3.20 (m, 1H).

Example 200

N$^1$-((1r,3r)-3-aminocyclobutyl)-4-(1H-benzo[d]imidazol-4-yl)-3-(2H-tetrazol-5-yl)benzene-1,2-disulfonamide

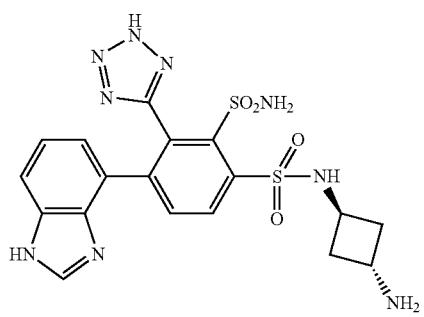 [SMILES: NS(=O)(=O)c1c(S(=O)(=O)N[C@H]2C[C@H](N)C2)ccc(-c2cccc3[nH]cnc23)c1-c1nn[nH]n1]

Step A: tert-butyl ((1r,3r)-3-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)cyclobutyl)carbamate tert-Butyl ((1R,3R)-3-aminocyclobutyl)carbamate (107 mg, 0.575 mmol) and Et$_3$N (0.160 ml, 1.149 mmol) were added to a stirred, cooled 0° C. mixture of 4-(1H-benzo[d]imidazol-4-yl)-2-(N,N-bis(4-methoxybenzyl)sulfamoyl)-3-(2-(4-methoxybenzyl)-2H-tetrazol-5-yl)benzenesulfinic acid (0.19 mmol) in THF (10 ml) and the mixture was stirred at 0° C. for 5 minutes. To the resulting reaction mixture, NCS (77 mg, 0.575 mmol) was added, and the mixture was stirred at 0° C. for 16 hours. The mixture was cooled, diluted with ethyl acetate (30 mL), washed with brine (3×30 mL), dried over anhydrous Na$_2$SO$_4$ and filtered. The solvent was evaporated under reduced pressure. The residue was purified by column chromatography on silica gel Isolute Flash Si; 10 g prepacked, eluting with EA/PE (0-80%) to give the title compound as a solid.: LCMS [M+H]$^+$: 950.

Step B: N$^1$-((1r,3r)-3-aminocyclobutyl)-4-(1H-benzo[d]imidazol-4-yl)-3-(2H-tetrazol-5-yl)benzene-1,2-disulfonamide tert-butyl ((1R,3R)-3-(4-(1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)cyclobutyl)carbamate (230 mg, 0.242 mmol) was added to DCM (3 ml) and TFA (1 ml) at 0° C. and the solution was stirred at room temperature for 1 hour. The reaction solution was evaporated under reduced pressure. To the residue was added TFA (4 ml) and the mixture was stirred at 80° C. for 1 hour. The reaction solution was evaporated under reduced pressure. The crude product was purified by Prep-HPLC with the following conditions: Column: XBridge BEH130 Prep C18 OBD Column 19×150 mm 5 μM 13 nm; Mobile Phase A: water with 10 mmol $NH_4HCO_3$, Mobile Phase B: MeCN; Flow rate: 20 mL/min; Gradient: 3% B to 23% B in 8 min; 254 nm. The collected fractions were concentrated under vacuum to afford the title compound as a solid: LCMS $[M+H]^+$: 490; $^1H$ NMR (400 MHz, MeOD): δ 9.43 (s, 1H), 8.65 (d, J=8.0 Hz, 1H), 8.07 (d, J=8.0 Hz, 1H), 7.81 (d, J=8.0 Hz, 1H), 7.56-7.52 (m, 1H), 7.26 (d, J=7.2 Hz, 1H), 4.45-4.41 (m, 1H), 3.85-3.83 (m, 1H), 2.59-2.47 (m, 4H).

Example 201

(S)—$N^1$-(1-amino-3-hydroxypropan-2-yl)-4-(2-aminobenzo[d]thiazol-4-yl)-3-(1H-tetrazol-5-yl)benzene-1,2-disulfonamide

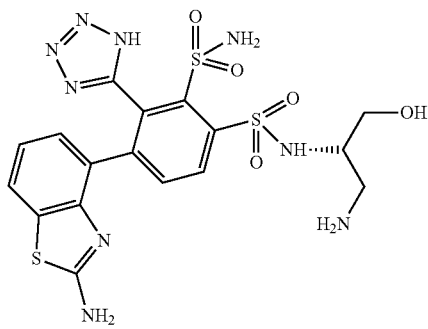

Step A: tert-Butyl (S)-(2-amino-3-hydroxypropyl)carbamate

To a solution of (S)-2-amino-3-((tert-butoxycarbonyl)amino)propanoic acid (888 mg, 4.35 mmol) in THF (1.67E+04 μl), was added a solution of $BH_3$.THF (13 mL, 13.04 mmol). The resulting mixture was stirred at 70° C. for 1 hour and then cooled to room temp. The reaction was quenched by dropwise addition of MeOH, and the mixture was stirred with CELITE and then filtered. The filtrates were concentrated to dryness. The residue was redissolved in MeOH, passed through an Agilent scx ion exchange cartridge. The cartridge was washed with ammonia MeOH solution. The eluents were concentrated to give an oil, which was lypholized from $CH_3CN$/water to give tert-butyl (S)-(2-amino-3-hydroxypropyl)carbamate.

Step B: tert-Butyl (S)-(2-((2-(N,N-bis(4-methoxybenzyl)sulfamoyl)-4-iodo-3-(1-(4-methoxybenzyl)-1H-tetrazol-5-yl)phenyl)sulfonamido)-3-hydroxypropyl)carbamate and tert-butyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)-3-hydroxypropyl)carbamate 2-(N,N-bis(4-methoxybenzyl)sulfamoyl)-4-iodo-3-(1-(4-methoxybenzyl)-1H-tetrazol-5-yl)benzenesulfinic acid and 2-(N,N-bis(4-methoxybenzyl)sulfamoyl)-4-iodo-3-(2-(4-methoxybenzyl)-2H-tetrazol-5-yl)benzenesulfinic acid (4.25 g, 5.48 mmol) was dissolved in THF (54.8 ml) and cooled to 0° C. NCS (1.464 g, 10.96 mmol) was added as solid. The mixture was kept at 0° C. for 1 hour. The reaction mixture was used directly for the next step. To 18 mL of the above reaction mixture was added (S)-tert-butyl (2-amino-3-hydroxypropyl)carbamate (381 mg, 2.002 mmol) and DIEA (699 μl, 4.00 mmol). The mixture was stirred at room temp. under $N_2$ for 12 hours. The reaction mixture was concentrated and redissolved in MeOH, and purified by column chromatography (0-70% EtOAc/Hexane) to give the title compounds. LC-MS $[M+H]^+$: 964.5.

Step C: tert-Butyl (S)-(2-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonamido)-3-hydroxypropyl)carbamate and tert-butyl (S)-(2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonamido)-3-hydroxypropyl)carbamate (2-aminobenzo[d]thiazol-4-yl)boronic acid (127 mg, 0.656 mmol), tert-butyl ((S)-2-(2-(N,N-bis(4-methoxybenzyl)sulfamoyl)-4-iodo-3-(1-(4-methoxybenzyl)-1H-tetrazol-5-yl)phenylsulfonamido)-3-hydroxypropyl)carbamate and tert-butyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)-3-hydroxypropyl)carbamate (527 mg, 0.547 mmol), sodium carbonate (116 mg, 1.094 mmol), $Pd(dppf)Cl_2$ (40.0 mg, 0.055 mmol) were placed in a reaction vial. Dioxane (4101 μl) and water (1367 μl) were added. The reaction mixture was degassed and heated at 80° C. for 12 hours. The reaction mixture was purified by silica gel column chromatography (0-15% meOH/EtOAc) to give the title compounds. LC-MS $[M+H]^+$: 986.7.

Step D: (S)—N1-(1-amino-3-hydroxypropan-2-yl)-4-(2-aminobenzo[d]thiazol-4-yl)-3-(1H-tetrazol-5-yl)benzene-1,2-disulfonamide (S)—N1-(1-amino-3-hydroxypropan-2-yl)-4-(2-aminobenzo[d]thiazol-4-yl)-3-(1H-tetrazol-5-yl)benzene-1,2-disulfonamide was prepared in a similar fashion to the synthesis of 4-(2-amino-1H-benzo[d]imidazol-4-yl)-$N^1$—((R)-pyrrolidin-3-yl)-3-(2H-tetrazol-5-yl)benzene-1,2-disulfonamide (EXAMPLE 161, Step C) from tert-butyl (S)-(2-((4-(2-aminobenzo[d]thiazol-4-yl)-2-(N,N-bis(4-methoxybenzyl)sulfamoyl)-3-(1-(4-methoxybenzyl)-1H-tetrazol-5-yl)phenyl)sulfonamido)-3-hydroxypropyl)carbamate and tert-butyl(S)-(2-((4-(2-aminobenzo[d]thiazol-4-yl)-2-(N,N-bis(4-methoxybenzyl)sulfamoyl)-3-(2-(4-methoxybenzyl)-2H-tetrazol-5-yl)phenyl)sulfonamido)-3-hydroxypropyl)carbamate. LC-MS $[M+H]^+$: 526.4.

Example 202

(R)—$N^1$-(1-amino-3-hydroxypropan-2-yl)-4-(2-aminobenzo[d]thiazol-4-yl)-3-(1H-tetrazol-5-yl)benzene-1,2-disulfonamide

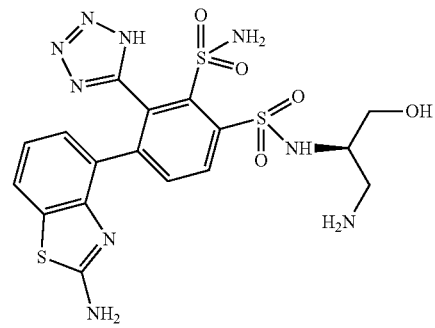 [SMILES: NC[C@H](CO)NS(=O)(=O)c1ccc(-c2cccc3sc(N)nc23)c(-c2nnn[nH]2)c1S(N)(=O)=O]

(R)—N¹-(1-amino-3-hydroxypropan-2-yl)-4-(2-aminobenzo[d]thiazol-4-yl)-3-(1H-tetrazol-5-yl)benzene-1,2-disulfonamide was prepared in an analogous way to (S)—N¹-(1-amino-3-hydroxypropan-2-yl)-4-(2-aminobenzo[d]thiazol-4-yl)-3-(1H-tetrazol-5-yl)benzene-1,2-disulfonamide (EXAMPLE 201) by using (R)-2-amino-3-((tert-butoxycarbonyl)amino)propanoic acid. LC-MS [M+H]⁺: 526.4.

Example 203

4-(2-aminobenzo[d]thiazol-4-yl)-N¹-(2-(2-aminoethoxy)ethyl)-3-(1H-tetrazol-5-yl)benzene-1,2-disulfonamide

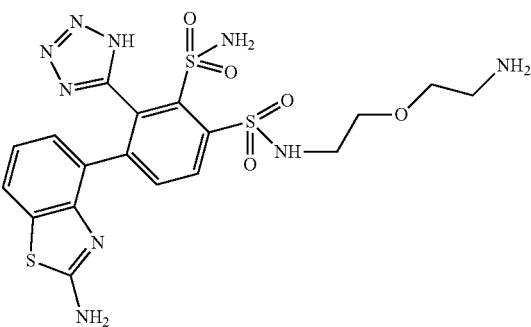 [SMILES: NCCOCCNS(=O)(=O)c1ccc(-c2cccc3sc(N)nc23)c(-c2nnn[nH]2)c1S(N)(=O)=O]

The title compound was prepared in an analogous way to EXAMPLES 85-127 by using tert-butyl (2-(2-aminoethoxy)ethyl)carbamate. LC-MS [M+H]⁺: 540.

Example 204

2-amino-N-(2-aminoethyl)-4'-(N-(2-aminoethyl)sulfamoyl)-5'-sulfamoyl-6'-(2H-tetrazol-5-yl)biphenyl-3-carboxamide

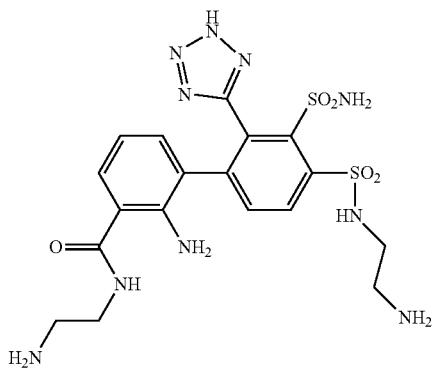 [SMILES: NCCNC(=O)c1cccc(-c2ccc(S(=O)(=O)NCCN)c(S(N)(=O)=O)c2-c2nn[nH]n2)c1N]

Step A: methyl 2-amino-3-(4,4,5,5-tetramethyl-1,3,2-dioxaborolan-2-yl)benzoate

To a solution of methyl 2-amino-3-bromobenzoate (15 g, 65.2 mmol) in dioxane (150 ml) was added 2nd Generation PCy₃ catalyst (11.55 g, 19.56 mmol), 4,4,4',4',5,5,5',5'-octamethyl-2,2'-bi(1,3,2-dioxaborolane) (33.1 g, 130 mmol) and potassium acetate (19.20 g, 196 mmol) with stirring at room temperature. The mixture was evacuated and backfilled with nitrogen 3 times and stirred at 80° C. for 16 hours. The reaction mixture was cooled to ambient temperature, diluted with water (200 mL) and extracted with ethyl acetate (3×200 mL). The combined organic layers were washed with brine (3×500 mL), dried over anhydrous sodium sulfate and filtered. The filtrate was concentrated under vacuum and the residue was purified by silica gel column chromatography 120 g, eluted with EtOAc/petroleum ether (1/20) to afford the title compound as an oil: ¹H NMR (300 MHz, CDCl₃): δ 7.97 (d, J=6.3 Hz, 1H), 7.79 (d, J=6.3 Hz, 1H), 6.58-6.53 (m, 1H), 3.85 (s, 3H), 1.34 (s, 12H).

Step B: methyl 2-amino-5'-(N,N-bis(4-methoxybenzyl)sulfamoyl)-4'-(N-(2-(tert-butoxycarbonylamino)ethyl)sulfamoyl)-6'-(2-(4-methoxybenzyl)-2H-tetrazol-5-yl)biphenyl-3-carboxylate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (850 mg, 0.910 mmol) in dioxane (20 ml) and water (7 ml) was added Pd(PPh₃)₄ (210 mg, 0.182 mmol), methyl 2-amino-3-(4,4,5,5-tetramethyl-1,3,2-dioxaborolan-2-yl)benzoate (757 mg, 2.73 mmol) and Na₂CO₃ (289 mg, 2.73 mmol) with stirring at room temperature. The resulting mixture was warmed to 80° C. and stirred overnight. The reaction mixture was cooled down to ambient temperature, diluted with water (50 mL) and extracted with ethyl acetate (3×50 mL). The combined organic layers were washed with brine (3×100 mL), dried over anhydrous sodium sulfate and filtered. The filtrate was concentrated under vacuum and the residue was purified by silica gel column chromatography and eluted with ethyl acetate/petroleum ether (1/1) to afford the title compound as a solid: LCMS [M+H]⁺: 957.

Step C: 2-amino-5'-(N,N-bis(4-methoxybenzyl)sulfamoyl)-4'-(N-(2-(tert-butoxycarbonylamino)ethyl)sulfamoyl)-6'-(2-(4-methoxybenzyl)-2H-tetrazol-5-yl)biphenyl-3-carboxylic acid To a solution of methyl 2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylate (600 mg, 0.627 mmol) in THF (3.00 ml) and MeOH (3 ml) was added sodium hydroxide with stirring at room temperature. The resulting solution was warmed to room temperature and stirred overnight. The pH value of the action solution was adjusted to 4 with hydrochloric acid (20%). The mixture was filtered and the filtrate was washed with water to give crude title compound as a solid, which was used in the next reaction without further purification. LCMS [M+H]⁺: 943.

Step D: tert-butyl N-[2-({[(4-{2-amino-3-[(2-{[(tert-butoxy)carbonyl]amino}ethyl)carbamoyl]phenyl}-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]phenyl)-{3}-oxidane]sulfinyl}amino)ethyl]carbamate To a solution of 2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid (500 mg, 0.530 mmol), HATU (302 mg, 0.795 mmol) and tert-butyl (2-aminoethyl)carbamate (340 mg, 2.121 mmol) in DMF (2 ml) was added DIEA (0.139 ml, 0.795 mmol) with stirring at 0° C. The resulting solution was degassed with nitrogen 3 times and then was warmed to 0° C. and stirred for 4 hours. The reaction solution was cooled to ambient temperature, diluted with water (5 mL) and extracted with ethyl acetate (3×10 mL). The combined organic layers were washed with brine (3×20 mL), dried over anhydrous sodium sulfate and filtered. The filtrate was concentrated under vacuum and the residue was purified by silica gel column chromatography, eluted with EtOAc/isohexane (1/1) to afford the title compound: LCMS [M+H]+: 1085.

Step E: 2-amino-N-(2-aminoethyl)-4'-(N-(2-amino-ethyl)sulfamoyl)-3'-sulfamoyl-2'-(2H-tetrazol-5-yl)-[1,1'-biphenyl]-3-carboxamide To a solution of tert-butyl N-[2-({[(4-{2-amino-3-[(2-{[(tert-butoxy)carbonyl]amino}ethyl)carbamoyl]phenyl}-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentan-3-yl]phenyl}-{3}-oxidane]sulfinyl}amino)ethyl]carbamate (300 mg, 0.276 mmol) in DCM (5 ml) was added TFA (1 ml) with stirring at room temperature. The resulting mixture was warmed to room temperature and stirred for 1 hour. The solution was concentrated under vacuum. To the residue was added TFA (5 ml) with stirring at room temperature. The resulting solution was warmed to 80° C. and stirred for 1 hour. The solution was concentrated under vacuum to afford a residue. The product was purified by Prep-HPLC with the following conditions: Column: XBridge Prep C18 OBD Column 19×250 mm 10 μM; Mobile Phase A: water with 10 mmol NH4HCO3, Mobile Phase B: MeCN; Flow rate: 25 mL/min; Gradient: 5% B to 30% B in 8 min; 254/220 nm. The collected fractions were combined and concentrated under vacuum to give the title compound. LCMS [M+H]+: 525; 1H NMR (400 MHz, CD3OD): δ 8.64 (d, J=8.4 Hz, 1H), 7.97 (d, J=8.4 Hz, 1H), 7.85 (d, J=6.4 Hz, 1H), 7.07 (d, J=6.4 Hz, 1H), 6.39-6.97 (m, 1H), 3.73-3.69 (m, 2H), 3.68-3.66 (m, 2H), 3.21-3.18 (m, 2H).

Example 205

3-(2-amino-1H-benzo[d]imidazol-4-yl)-6-(((3R,4R)-3-amino-4-fluoropiperidin-1-yl)sulfonyl)-2-(2H-tetrazol-5-yl)benzenesulfonamide

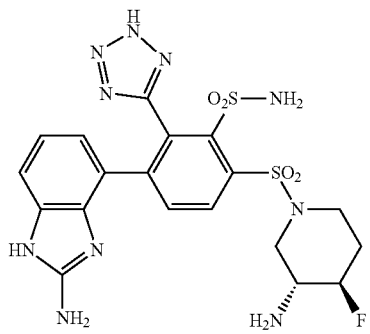 [SMILES: Nc1nc2c(-c3ccc(S(=O)(=O)N4CC[C@@H](F)[C@H](N)C4)c(S(N)(=O)=O)c3-c3nn[nH]n3)cccc2[nH]1]

Step A: tert-butyl (4-(3-(N,N-bis(4-methoxybenzyl)sulfamoyl)-4-(((3R,4R)-3-((tert-butoxycarbonyl)amino)-4-fluoropiperidin-1-yl)sulfonyl)-2-(2-(4-methoxybenzyl)-2H-tetrazol-5-yl)phenyl)-1H-benzo[d]imidazol-2-yl)carbamate Triethylamine (0.15 mL, 1.02 mmol), tert-butyl ((3R,4R)-4-fluoropiperidin-3-yl)carbamate (149 mg, 0.681 mmol) and 1-chloropyrrolidine-2,5-dione (91 mg, 0.681 mmol) were added to a stirred, cooled 0° C. solution of 2-(N,N-bis(4-methoxybenzyl)sulfamoyl)-4-(2-((tert-butoxycarbonyl)amino)-1H-benzo[d]imidazol-4-yl)-3-(2-(4-methoxybenzyl)-2H-tetrazol-5-yl)benzenesulfinic acid (300 mg, 0.341 mmol) in DCM (3 mL) and the mixture was stirred at 0° C. for 30 minutes. The mixture was diluted with water (30 mL) and extracted with DCM (2×30 mL). The combined organic fractions were washed with brine, dried (MgSO4), filtered and the solvent was evaporated under reduced pressure. LC/MS [M+H]+: 1097.

Step B: 3-(2-amino-1H-benzo[d]imidazol-4-yl)-6-(((3R,4R)-3-amino-4-fluoropiperidin-1-yl)sulfonyl)-2-(2H-tetrazol-5-yl)benzenesulfonamide To tert-butyl (4-(3-(N,N-bis(4-methoxybenzyl)sulfamoyl)-4-(((3R,4R)-3-((tert-butoxycarbonyl)amino)-4-fluoropiperidin-1-yl)sulfonyl)-2-(2-(4-methoxybenzyl)-2H-tetrazol-5-yl)phenyl)-1H-benzo[d]imidazol-2-yl)carbamate (222 mg, 0.202 mmol) in CH2Cl2 (2 mL) at RT was added anisole (0.2 mL, 1.83 mmol) and TFA (2 mL, 28.3 mmol). The reaction mixture was stirred for 2 hours. The reaction mixture was concentrated. The residue was redissolved in toluene and MeOH, and concentrated again. The residue was placed on high vacuum for 4 hours and redissolved in anisole (0.2 mL) and TFA (2 mL) at RT and stirred at 80° C. for 2 hours. The reaction mixture was concentrated. The residue was purified by preparative RP-HPLC (C-18), eluting with Acetonitrile/Water+0.1% NH4OH to give the title compound as a solid after lyophilization overnight. LC/MS [M+H]+: 537.

Example 206

4-(2-amino-1H-benzo[d]imidazol-4-yl)-N1-(morpholin-3-ylmethyl)-3-(2H-tetrazol-5-yl)benzene-1,2-disulfonamide

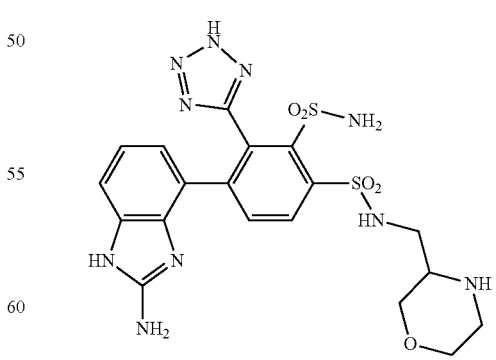

The title compound was prepared in an analogous fashion to that described for 3-(2-amino-1H-benzo[d]imidazol-4-yl)-6-(((3R,4R)-3-amino-4-fluoropiperidin-1-yl)sulfonyl)-2-(2H-tetrazol-5-yl)benzenesulfonamide, starting from 2-(N,N-bis(4-methoxybenzyl)sulfamoyl)-4-(2-((tert-butoxycarbonyl)amino)-1H-benzo[d]imidazol-4-yl)-3-(2-(4-methoxybenzyl)-2H-tetrazol-5-yl)benzenesulfinic acid and commercially available tert-butyl 3-(aminomethyl)morpholine-4-carboxylate. LC/MS [M+H]+: 535

Example 207

4-(2-amino-1H-benzo[d]imidazol-4-yl)-N1-(azetidin-2-ylmethyl)-3-(2H-tetrazol-5-yl)benzene-1,2-disulfonamide

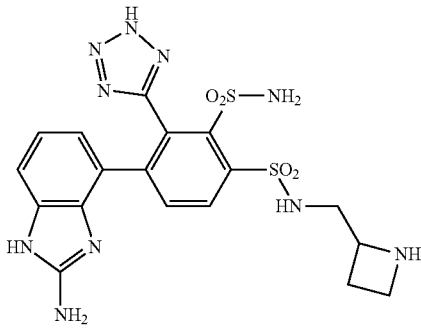 [SMILES: Nc1nc2c(-c3ccc(S(=O)(=O)NCC4CCN4)c(S(N)(=O)=O)c3-c3nn[nH]n3)cccc2[nH]1]

The title compound was prepared in an analogous fashion to that described for 3-(2-amino-1H-benzo[d]imidazol-4-yl)-6-(((3R,4R)-3-amino-4-fluoropiperidin-1-yl)sulfonyl)-2-(2H-tetrazol-5-yl)benzenesulfonamide, starting from 2-(N,N-bis(4-methoxybenzyl)sulfamoyl)-4-(2-((tert-butoxycarbonyl)amino)-1H-benzo[d]imidazol-4-yl)-3-(2-(4-methoxybenzyl)-2H-tetrazol-5-yl)benzenesulfinic acid and commercially available tert-butyl 2-(aminomethyl)azetidine-1-carboxylate. LC/MS [M+H]+: 505.

Example 208

(S)-3-amino-N-((4-(2-amino-1H-benzo[d]imidazol-4-yl)-2-sulfamoyl-3-(2H-tetrazol-5-yl)phenyl)sulfonyl)butanamide

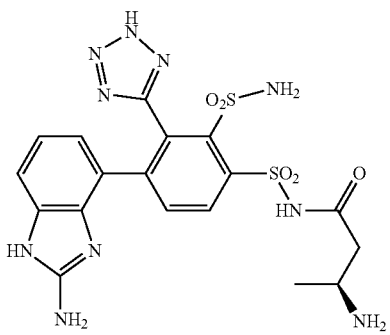 [SMILES: C[C@H](N)CC(=O)NS(=O)(=O)c1ccc(-c2cccc3[nH]c(N)nc23)c(-c2nn[nH]n2)c1S(N)(=O)=O]

Step A: tert-butyl (4-(3-(N,N-bis(4-methoxybenzyl)sulfamoyl)-2-(2-(4-methoxybenzyl)-2H-tetrazol-5-yl)-4-sulfamoylphenyl)-1H-benzo[d]imidazol-2-yl)carbamate Triethylamine (0.351 g, 3.47 mmol) and ammonia (0.496 mL, 3.47 mmol) were added to a stirred solution of starting material 2-(N,N-bis(4-methoxybenzyl)sulfamoyl)-4-(2-((tert-butoxycarbonyl)amino)-1H-benzo[d]imidazol-4-yl)-3-(2-(4-methoxybenzyl)-2H-tetrazol-5-yl)benzenesulfinic acid (1.02 g, 1.158 mmol) in DCM (10 mL) at 0° C. and 1-chloropyrrolidine-2,5-dione (0.340 g, 2.55 mmol) was added. The mixture was stirred at 0° C. for 1 hour. The mixture was diluted with water (30 mL) and extracted with DCM (2×25 mL). The residue was purified by column chromatography on silica gel 24 g, eluting with Heptane/Ethanol from 0-40% in 30 min to give the desired product as a solid after concentration. LC/MS [M+H]+: 896.

Step B: tert-butyl (S)-(4-(3-(N,N-bis(4-methoxybenzyl)sulfamoyl)-4-(N-(3-((tert-butoxycarbonyl)amino)butanoyl)sulfamoyl)-2-(2-(4-methoxybenzyl)-2H-tetrazol-5-yl)phenyl)-1H-benzo[d]imidazol-2-yl)carbamate N1-((ethylimino)methylene)-N3,N3-dimethylpropane-1,3-diamine hydrochloride (141 mg, 0.738 mmol) and N,N-dimethylpyridin-4-amine (30.1 mg, 0.246 mmol) were added to a stirred solution of (S)-3-((tert-butoxycarbonyl)amino)butanoic acid (50 mg, 0.246 mmol) in dimethylformamide (2 mL) at room temperature and the mixture was stirred at 60° C. for 1 hour. The mixture was cooled down to RT. tert-butyl (4-(3-(N,N-bis(4-methoxybenzyl)sulfamoyl)-2-(2-(4-methoxybenzyl)-2H-tetrazol-5-yl)-4-sulfamoylphenyl)-1H-benzo[d]imidazol-2-yl)carbamate (110 mg, 0.123 mmol) was added to the reaction and stirred for 15 minutes before adding DBU in dry THF. The reaction was stirred overnight. The mixture was diluted with water (30 mL) and the mixture was extracted with ethyl acetate (2×30 mL). The residue was purified by column chromatography on silica gel 12 g, eluting with EtOAc/isohexane from 0-100% in 30 min to give the desired product as a solid after concentration. LC/MS [M+H]+: 1081.

Step C: (S)-3-amino-N-((4-(2-amino-1H-benzo[d]imidazol-4-yl)-2-sulfamoyl-3-(2H-tetrazol-5-yl)phenyl)sulfonyl)butanamide To tert-butyl (S)-(4-(3-(N,N-bis(4-methoxybenzyl)sulfamoyl)-4-(N-(3-((tert-butoxycarbonyl)amino)butanoyl)sulfamoyl)-2-(2-(4-methoxybenzyl)-2H-tetrazol-5-yl)phenyl)-1H-benzo[d]imidazol-2-yl)carbamate (112 mg, 0.104 mmol) in CH2Cl2 (2 mL) at RT was added anisole (0.2 mL, 1.83 mmol) and TFA (2 mL, 26 mmol). The reaction mixture was stirred for 2 hours. The reaction mixture was concentrated. The residue was redissolved in toluene and MeOH, and concentrated again. The residue was placed on high vacuum for 4 hours and redissolved in anisole (0.2 mL) and TFA (2 mL) at RT and stirred at 80° C. for 2 hours. The residue was purified by preparative RP-HPLC (C-18), eluting with Acetonitrile/Water+0.1% NH4OH to give the title compound as a solid after lyophilization overnight. LC/MS [M+H]+: 521.

Example 209

(R)-4-(2-aminopyridin-3-yl)-N¹-(pyrrolidin-3-yl)-3-(2H-tetrazol-5-yl)benzene-1,2-disulfonamide

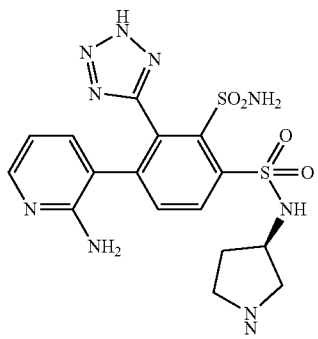

Step A: tert-butyl (R)-3-((2-(N,N-bis(4-methoxybenzyl)sulfamoyl)-4-(2-((tert-butoxycarbonyl)amino)pyridin-3-yl)-3-(2-(4-methoxybenzyl)-2H-tetrazol-5-yl)phenyl)sulfonamido)pyrrolidine-1-carboxylate TEA (0.100 mL, 0.720 mmol) and (R)-(+)-1-boc-3-aminopyrrolidine (0.122 mL, 0.720 mmol) were added to a stirred solution of 2-(N,N-bis(4-methoxybenzyl)sulfamoyl)-4-(2-((tert-butoxycarbonyl)amino)pyridin-3-yl)-3-(2-(4-methoxybenzyl)-2H-tetrazol-5-yl)benzenesulfinic acid, (202 mg, 0.240 mmol) in DCM (2 mL) at 0° C. and the mixture was stirred at 0° C. for 30 minutes. The mixture was diluted with water (40 mL), extracted with ethyl acetate (2×50 mL). The residue was purified by column chromatography on silica gel 12 g, eluting with heptane/ethanol to give the desired product as foam after concentration. LC/MS [M+H]+: 1026.

Step B: (R)-4-(2-aminopyridin-3-yl)-N1-(pyrrolidin-3-yl)-3-(2H-tetrazol-5-yl)benzene-1,2-disulfonamide To tert-butyl (R)-3-((2-(N,N-bis(4-methoxybenzyl)sulfamoyl)-4-(2-((tert-butoxycarbonyl)amino)pyridin-3-yl)-3-(2-(4-methoxybenzyl)-2H-tetrazol-5-yl)phenyl)sulfonamido)pyrrolidine-1-carboxylate (220 mg, 0.214 mmol) in CH2Cl2 (2 mL) at RT was added anisole (0.2 mL, 1.83 mmol) and TFA (2 mL, 28.3 mmol). The reaction mixture was stirred for 2 hours. The reaction mixture was concentrated. The residue was redissolved in toluene and MeOH, and concentrated again. The residue was redissolved in anisole (0.2 mL) and TFA (2 mL) at RT and stirred at 80° C. for 2 hours. The reaction mixture was concentrated. The residue was purified by preparative RP-HPLC (C-18), eluting with acetonitrile/water+0.1% NH4OH to give the title compound as a solid after lyophilization overnight. LC/MS [M+H]+: 466.

EXAMPLES 210-216 in the Table below were prepared in an analogous fashion to that described for (R)-4-(2-aminopyridin-3-yl)-N¹-(pyrrolidin-3-yl)-3-(2H-tetrazol-5-yl)benzene-1,2-disulfonamide (EXAMPLE 209) using 2-(N,N-bis(4-methoxybenzyl)sulfamoyl)-4-(2-((tert-butoxycarbonyl)amino)pyridin-3-yl)-3-(2-(4-methoxybenzyl)-2H-tetrazol-5-yl)benzenesulfinic acid, prepared as described above and the indicated right hand side protected amines, which were prepared as described herein, or which were available from commercial sources.

| EX NO | Structure | Name | Right Side Amine | LC/MS [M + H]+ |
|---|---|---|---|---|
| 210 | 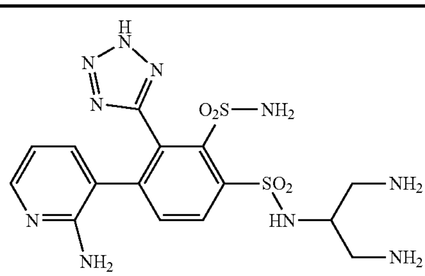 | 4-(2-aminopyridin-3-yl)-N1-(1,3-diaminopropan-2-yl)-3-(2H-tetrazol-5-yl)benzene-1,2-disulfonamide | | 469 |
| 211 | 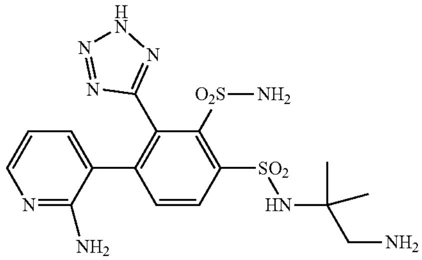 [SMILES: CC(C)(CN)NS(=O)(=O)c1ccc(-c2cccnc2N)c(-c2nn[nH]n2)c1S(N)(=O)=O] | N1-(1-amino-2-methylpropan-2-yl)-4-(2-aminopyridin-3-yl)-3-(2H-tetrazol-5-yl)benzene-1,2-disulfonamide | | 468 |

| EX NO | Structure | Name | Right Side Amine | LC/MS [M + H]+ |
|---|---|---|---|---|
| 212 | 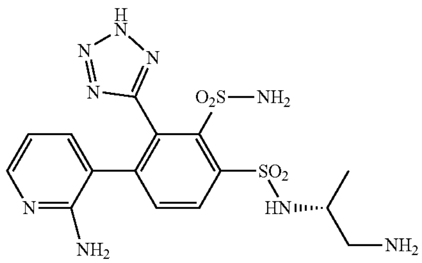 [SMILES: C[C@H](CN)NS(=O)(=O)c1ccc(-c2cccnc2N)c(-c2nn[nH]n2)c1S(N)(=O)=O] | (R)-N1-(1-amino-propan-2-yl)-4-(2-aminopyridin-3-yl)-3-(2H-tetrazol-5-yl)benzene-1,2-disulfonamide | | 554 |
| 213 | 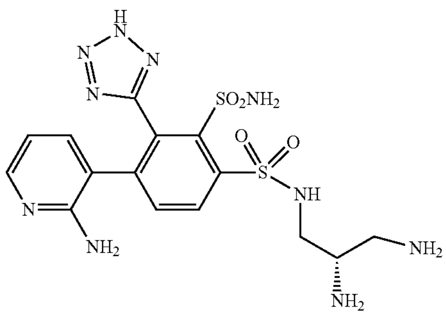 [SMILES: NC[C@H](N)CNS(=O)(=O)c1ccc(-c2cccnc2N)c(-c2nn[nH]n2)c1S(N)(=O)=O] | (S)-4-(2-aminopyridin-3-yl)-N1-(2,3-diaminopropyl)-3-(2H-tetrazol-5-yl)benzene-1,2-disulfonamide | | 469 |
| 214 | 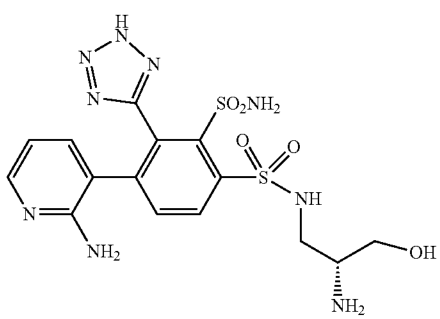 [SMILES: Nc1ncccc1-c1ccc(S(=O)(=O)NC[C@@H](N)CO)c(S(N)(=O)=O)c1-c1nn[nH]n1] | (R)-N1-(2-amino-3-hydroxypropyl)-4-(2-amino-pyridin-3-yl)-3-(2H-tetrazol-5-yl)benzene-1,2-disulfonamide | | 470 |
| 215 | 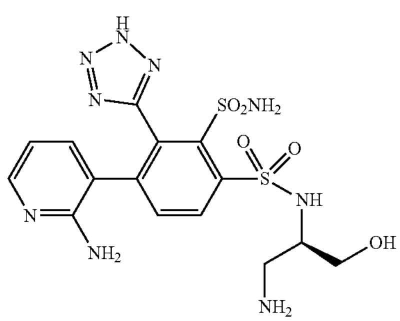 [SMILES: NC[C@H](CO)NS(=O)(=O)c1ccc(-c2cccnc2N)c(-c2nn[nH]n2)c1S(N)(=O)=O] | (R)-N1-(1-amino-3-hydroxypropan-2-yl)-4-(2-aminopyridin-3-yl)-3-(2H-tetrazol-5-yl)benzene-1,2-disulfonamide | | 470 |
| 216 | 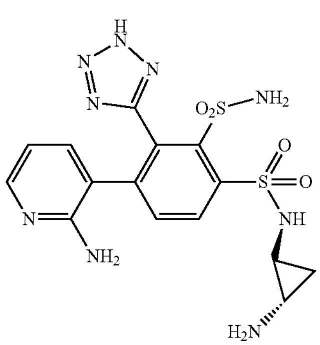 | N1-((1S)-2-amino-cyclopropyl)-4-(2-aminopyridin-3-yl)-3-(2H-tetrazol-5-yl)benzene-1,2-disulfonamide | | 452 |

Example 217

N$^1$-(2-(1H-imidazol-4-yl)ethyl)-4-(6-aminopyridin-3-yl)-3-(2H-tetrazol-5-yl)benzene-1,2-disulfonamide

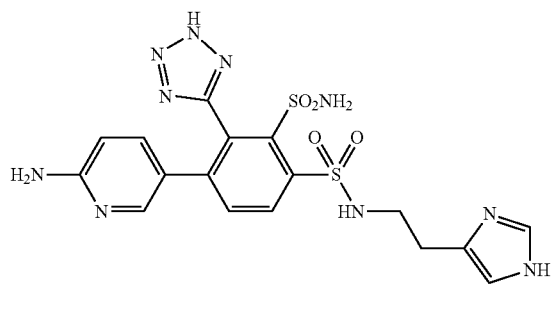 [SMILES: Nc1ccc(-c2ccc(S(=O)(=O)NCCc3c[nH]cn3)c(S(N)(=O)=O)c2-c2nn[nH]n2)cn1]

Step A: tert-butyl (5-(4-(N-(2-(1H-imidazol-4-yl)ethyl)sulfamoyl)-3-(N,N-bis(4-methoxybenzyl)sulfamoyl)-2-(2-(4-methoxybenzyl)-2H-tetrazol-5-yl)phenyl)pyridin-2-yl)carbamate Triethylamine (0.15 ml, 1.09 mmol), 2-(1H-imidazol-4-yl)ethanamine (81 mg, 0.732 mmol) and DMAP (44.7 mg, 0.366 mmol) were added to a stirred solution of starting material 2-(N,N-bis(4-methoxybenzyl)sulfamoyl)-4-(6-((tert-butoxycarbonyl)amino)pyridin-3-yl)-3-(2-(4-methoxybenzyl)-2H-tetrazol-5-yl)benzenesulfinic acid (308 mg, 0.366 mmol) in CH$_2$Cl$_2$ at 0° C. 1-chloropyrrolidine-2,5-dione (107 mg, 0.805 mmol) was then added and the mixture was stirred at 0° C. for 45 minutes. The mixture was diluted with water (40 mL), extracted with EtOAc (2×30 mL). The combined organic phases were washed with brine, dried (MgSO$_4$) and concentrated under reduced pressure. The residue was purified by column chromatography on silica gel 12 g, eluting with Heptane/Ethanol, 0-60% in 40 minutes to give the title compound. LC/MS [M+H]+: 951.

Step B: N1-(2-(1H-imidazol-4-yl)ethyl)-4-(6-aminopyridin-3-yl)-N2-(4-methoxybenzyl)-3-(2-(4-methoxybenzyl)-2H-tetrazol-5-yl)benzene-1,2-disulfonamide 1,4-dimethoxybenzene (129 mg, 0.936 mmol) and TFA (2 mL, 26.0 mmol) were added to a stirred solution of tert-butyl (5-(4-(N-(2-(1H-imidazol-4-yl)ethyl)sulfamoyl)-3-(N,N-bis(4-methoxybenzyl)sulfamoyl)-2-(2-(4-methoxybenzyl)-2H-tetrazol-5-yl)phenyl)pyridin-2-yl)carbamate (89 mg, 0.094 mmol) in CH$_2$Cl$_2$ (2 mL) at RT and the mixture was stirred at RT for 2 hours. The mixture was concentrated. The residue was used as is for next step. LC/MS [M+H]+: 731.

Step C: N1-(2-(1H-imidazol-4-yl)ethyl)-4-(6-aminopyridin-3-yl)-3-(2H-tetrazol-5-yl)benzene-1,2-disulfonamide 1,4-dimethoxybenzene (111 mg, 0.804 mmol) and TFA (3 mL, 38.9 mmol) were added to a stirred solution of N1-(2-(1H-imidazol-4-yl)ethyl)-4-(6-aminopyridin-3-yl)-N2-(4-methoxybenzyl)-3-(2-(4-methoxybenzyl)-2H-tetrazol-5-yl)benzene-1,2-disulfonamide (68.4 mg, 0.094 mmol) at RT and the mixture was stirred at 70° C. for 2 hours. The mixture was concentrated. The residue was purified by preparative RP-HPLC (C-18), eluting with Acetonitrile/Water+0.05% NH$_3$ to give the title compound. LC/MS [M+H]+: 491.

Example 218

N$^1$-(2-(1H-imidazol-2-yl)ethyl)-4-(6-aminopyridin-3-yl)-3-(2H-tetrazol-5-yl)benzene-1,2-disulfonamide

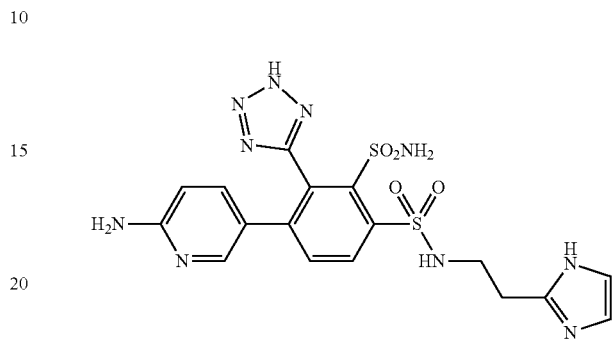

The title compound was made in an analogous fashion to that described for N$^1$-(2-(1H-imidazol-4-yl)ethyl)-4-(6-aminopyridin-3-yl)-3-(2H-tetrazol-5-yl)benzene-1,2-disulfonamide from 2-(N,N-bis(4-methoxybenzyl)sulfamoyl)-4-(6-((tert-butoxycarbonyl)amino)pyridin-3-yl)-3-(2-(4-methoxybenzyl)-2H-tetrazol-5-yl)benzenesulfinic acid. The corresponding right hand side amine, 2-(1H-imidazol-2-yl)ethan-1-amine was available from commercial sources. LC/MS [M+H]+: 491.

Example 219

(R)-4-(5-aminopyridin-3-yl)-N1-(pyrrolidin-3-yl)-3-(2H-tetrazol-5-yl)benzene-1,2-disulfonamide

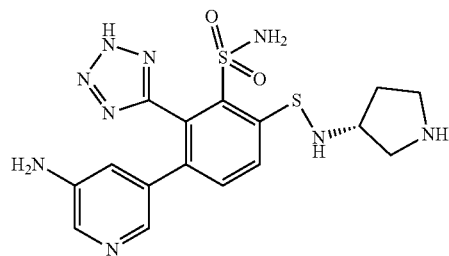 [SMILES: Nc1cncc(-c2ccc(SN[C@@H]3CCNC3)c(S(N)(=O)=O)c2-c2nn[nH]n2)c1]

Step A. tert-butyl (R)-3-((4-(5-aminopyridin-3-yl)-2-(N,N-bis(4-methoxybenzyl)sulfamoyl)-3-(2-(4-methoxybenzyl)-2H-tetrazol-5-yl)phenyl)sulfonamido)pyrrolidine-1-carboxylate The mixture of (R)-tert-butyl 3-(2-(N,N-bis(4-methoxybenzyl)sulfamoyl)-4-iodo-3-(2-(4-methoxybenzyl)-2H-tetrazol-5-yl)phenyl sulfonamido)pyrrolidine-1-carboxylate (588 mg, 0.613 mmol), 5-(4,4,5,5-tetramethyl-1,3,2-dioxaborolan-2-yl)pyridin-3-amine (337 mg, 1.531 mmol), Na$_2$CO$_3$ (195 mg, 1.838 mmol) and 1,1'-bis(diphenylphosphino)ferrocene-palladium(ii)dichloride dichloromethane complex (100 mg, 0.123 mmol) in dioxane (3 mL) and water (0.7 mL) was degassed with N$_2$ for 10 minutes. The resulting mixture was heated at 95° C. for 16 hours. This reaction was filtered and extracted with EtOAc (2×50 mL), organic phase was dried (MgSO₄), and concentrated. The residue was purified by column chromatography on silica gel 12 g, eluting with Heptane/Ethanol, 0-50% in 25 minutes to give the title compound as a solid. LC/MS [M+H]+: 926.

Step B. (R)-4-(5-aminopyridin-3-yl)-3-(2-(4-methoxybenzyl)-2H-tetrazol-5-yl)-N1-(pyrrolidin-3-yl)benzene-1,2-disulfonamide Anisole (0.3 mL, 2.75 mmol) and TFA (3 mL, 38.9 mmol) were added to a stirred solution of (R)-tert-butyl 3-(4-(5-aminopyridin-3-yl)-2-(N,N-bis(4-methoxybenzyl)sulfamoyl)-3-(2-(4-methoxybenzyl)-2H-tetrazol-5-yl)phenylsulfonamido)pyrrolidine-1-carboxylate (377 mg, 0.407 mmol) in CH₂Cl₂ (3 mL) at RT and the mixture was stirred at RT for 90 minutes. The mixture was concentrated and used as is. LC/MS [M+H]+: 585.

Step C. (R)-4-(5-aminopyridin-3-yl)-N1-(pyrrolidin-3-yl)-3-(2H-tetrazol-5-yl)benzene-1,2-disulfonamide Anisole (0.3 mL, 2.75 mmol) and TFA (4 mL, 0.406 mmol) were added to a stirred solution of (R)-4-(5-aminopyridin-3-yl)-3-(2-(4-methoxybenzyl)-2H-tetrazol-5-yl)-N1-(pyrrolidin-3-yl)benzene-1,2-disulfonamide (238 mg, 0.406 mmol) in TFA at RT and the mixture was stirred at 80° C. for 90 minutes. The mixture was concentrated. The residue was purified by preparative RP-HPLC (C-18), eluting with Acetonitrile/Water+0.05% NH₃, 0-30% to give the title compound as solid after lyophilization overnight. LC/MS [M+H]+: 466.

Example 220

(R)-4-(2-(piperazin-1-yl)pyridin-3-yl)-N1-(pyrrolidin-3-yl)-3-(2H-tetrazol-5-yl)benzene-1,2-disulfonamide

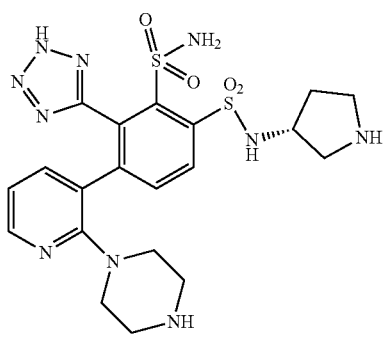 [SMILES: NS(=O)(=O)c1c(S(=O)(=O)N[C@@H]2CCNC2)ccc(-c2cccnc2N2CCNCC2)c1-c1nn[nH]n1]

The title compound was made in an analogous fashion to that described for (R)-4-(5-aminopyridin-3-yl)-N1-(pyrrolidin-3-yl)-3-(2H-tetrazol-5-yl)benzene-1,2-disulfonamide from (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate. The corresponding left hand side boronic acid, (2-(piperazin-1-yl)pyridin-3-yl)boronic acid was available from commercial sources. LC/MS [M+H]+: 535.

Example 221

(R)—N1-(1-aminopropan-2-yl)-4-(5-aminopyridin-3-yl)-3-(2H-tetrazol-5-yl)benzene-1,2-disulfonamide

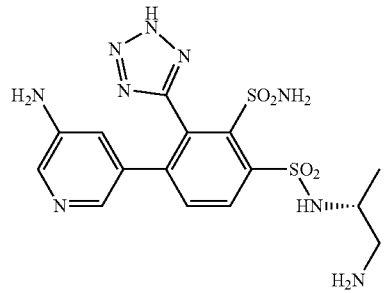 [SMILES: C[C@H](CN)NS(=O)(=O)c1ccc(-c2cncc(N)c2)c(-c2nn[nH]n2)c1S(N)(=O)=O]

Step A. tert-butyl (R)-(2-((4-(5-aminopyridin-3-yl)-2-(N,N-bis(4-methoxybenzyl)sulfamoyl)-3-(2-(4-methoxybenzyl)-2H-tetrazol-5-yl)phenyl)sulfonamido)propyl)carbamate (R)-tert-butyl (2-(2-(N,N-bis(4-methoxybenzyl)sulfamoyl)-4-iodo-3-(2-(4-methoxybenzyl)-2H-tetrazol-5-yl)phenylsulfonamido)propyl)carbamate (REFERENCE EXAMPLE 69, 315 mg, 0.332 mmol), 5-(4,4,5,5-tetramethyl-1,3,2-dioxaborolan-2-yl)pyridin-3-amine (146 mg, 0.665 mmol), Na₂CO₃ (106 mg, 0.997 mmol), 1,1'-bis(diphenylphosphino)ferrocene-palladium(ii)dichloride dichloromethane complex (54.3 mg, 0.066 mmol) were added to a 100 mL RBF in dioxane (2 mL) and water (0.5 mL) at RT and the mixture was stirred at 90° C. overnight. The mixture was filtered, washed with EtOAc, extracted with EtOAc (2×50 mL). The combined organic fractions were washed with brine (60 mL), dried (MgSO₄), filtered and the solvent was evaporated under reduced pressure. The residue was purified by column chromatography on silica gel 12 g, eluting with Heptane/Ethanol, 0-50% in 30 minutes to give product after concentration. LC/MS [M+H]+: 914.

Step B. (R)—N1-(1-aminopropan-2-yl)-4-(5-aminopyridin-3-yl)-N2-(4-methoxybenzyl)-3-(2-(4-methoxybenzyl)-2H-tetrazol-5-yl)benzene-1,2-disulfonamide Anisole (0.2 mL, 1.831 mmol) and TFA (2 mL, 26.0 mmol) were added to a stirred solution of starting material (R)-tert-butyl (2-(4-(5-aminopyridin-3-yl)-2-(N,N-bis(4-methoxybenzyl)sulfamoyl)-3-(2-(4-methoxybenzyl)-2H-tetrazol-5-yl)phenylsulfonamido)propyl)carbamate (240 mg, 0.263 mmol) in CH₂Cl₂ (2 mL) at RT and the mixture was stirred at RT for 1 hour. The mixture was concentrated and used as is for next step. LC/MS [M+H]+: 694.

Step C. (R)—N1-(1-aminopropan-2-yl)-4-(5-aminopyridin-3-yl)-3-(2H-tetrazol-5-yl)benzene-1,2-disulfonamide Anisole (0.2 mL, 1.831 mmol) and TFA (2 mL, 26.0 mmol) were added to a stirred solution of (R)—N1-(1-aminopropan-2-yl)-4-(5-aminopyridin-3-yl)-N2-(4-methoxybenzyl)-3-(2-(4-methoxybenzyl)-2H-tetrazol-5-yl)benzene-1,2-disulfonamide (182 mg, 0.263 mmol) in CH₂Cl₂ at RT and the mixture was stirred at RT for 1 hour.

The mixture was concentrated. The residue was purified by preparative RP-HPLC (C-18), eluting with Acetonitrile/Water+0.05% NH₃, 0-30% in 10 minutes to give the product as a solid. LC/MS [M+H]+: 454.

Example 222

(S)—N1-(3-amino-2-hydroxypropyl)-4-(3-aminopyridin-4-yl)-3-(2H-tetrazol-5-yl)benzene-1,2-disulfonamide

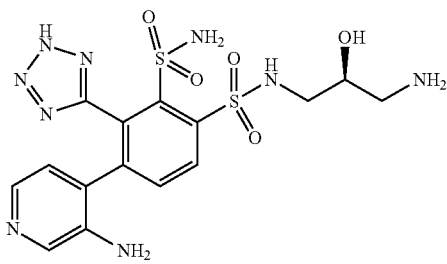 [SMILES: NC[C@H](O)CNS(=O)(=O)c1ccc(-c2ccncc2N)c(-c2nn[nH]n2)c1S(N)(=O)=O]

Step A. tert-butyl (S)-(3-((4-(3-aminopyridin-4-yl)-2-(N,N-bis(4-methoxybenzyl)sulfamoyl)-3-(2-(4-methoxybenzyl)-2H-tetrazol-5-yl)phenyl)sulfonamido)-2-hydroxypropyl)carbamate tert-butyl 2-(4-(4,4,5,5-tetramethyl-1,3,2-dioxaborolan-2-yl)pyridin-3-yl)hydrazinecarboxylate (250 mg, 0.747 mmol) and sodium carbonate (119 mg, 1.120 mmol) and Pd(dppf)Cl₂ (61.0 mg, 0.075 mmol) were added to a stirred solution of (S)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl)carbamate (REFERENCE EXAMPLE 75, 360 mg, 0.373 mmol) in dioxane (2 mL) and water (0.5 mL) at RT and the mixture was degased for 10 minutes and then stirred at 90° C. overnight. The mixture was diluted with water (50 mL) and extracted with EtOAc (2×50 mL). The combined organic phases were washed with brine, dried (MgSO₄) and concentrated under reduced pressure. The residue was purified by column chromatography on silica gel 12 g, eluting with Heptane/Ethanol, 0-90% in 30 min to give title compound. LC/MS [M+H]+: 930.

Step B. (S)—N1-(3-amino-2-hydroxypropyl)-4-(3-aminopyridin-4-yl)-N2-(4-methoxybenzyl)-3-(2-(4-methoxybenzyl)-2H-tetrazol-5-yl)benzene-1,2-disulfonamide 1,4-dimethoxybenzene (322 mg, 2.330 mmol) and TFA (2 mL, 26.0 mmol) were added to a stirred solution of tert-butyl (S)-(3-((4-(3-aminopyridin-4-yl)-2-(N,N-bis(4-methoxybenzyl)sulfamoyl)-3-(2-(4-methoxybenzyl)-2H-tetrazol-5-yl)phenyl)sulfonamido)-2-hydroxypropyl)carbamate (240 mg, 0.233 mmol) in CH₂Cl₂ (2 mL) at RT and the mixture was stirred at RT for 90 minutes. The mixture was concentrated under reduced pressure. The residue was used as is in next step. LC/MS [M+H]+: 710.

Step C. (S)—N1-(3-amino-2-hydroxypropyl)-4-(3-aminopyridin-4-yl)-3-(2H-tetrazol-5-yl)benzene-1,2-disulfonamide 1,4-dimethoxybenzene (321 mg, 2.323 mmol) and TFA (2 mL, 26.0 mmol) were added to a stirred solution of (S)—N1-(3-amino-2-hydroxypropyl)-4-(3-aminopyridin-4-yl)-N2-(4-methoxybenzyl)-3-(2-(4-methoxybenzyl)-2H-tetrazol-5-yl)benzene-1,2-disulfonamide (165 mg, 0.232 mmol) at RT and the mixture was stirred at 90° C. for 90 min. The mixture was concentrated. The residue was purified by preparative reverse phase HPLC (C-18), eluting with Acetonitrile/Water+0.05% NH₃, 0-30% in 10 minutes to give the title compound. LC/MS [M+H]+: 470.

Example 223

(S)-4-(4-aminopyridin-3-yl)-N1-(2,3-diaminopropyl)-3-(2H-tetrazol-5-yl)benzene-1,2-disulfonamide

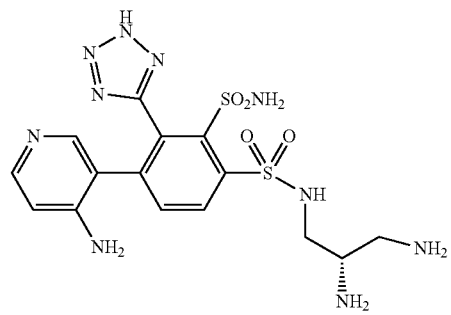 [SMILES: NC[C@H](N)CNS(=O)(=O)c1ccc(-c2cnccc2N)c(-c2nn[nH]n2)c1S(N)(=O)=O]

Step A. benzyl tert-butyl (3-((2-(N,N-bis(4-methoxybenzyl)sulfamoyl)-4-(4-((tert-butoxycarbonyl)amino)pyridin-3-yl)-3-(2-(4-methoxybenzyl)-2H-tetrazol-5-yl)phenyl)sulfonamido)propane-1,2-diyl)(S)-dicarbamate To (4-((tert-butoxycarbonyl)amino)pyridin-3-yl)boronic acid (130 mg, 0.547 mmol) and (S)-benzyl tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate (300 mg, 0.273 mmol), Na₂CO₃ (87 mg, 0.820 mmol), and Pd(dppf)Cl₂ (44.7 mg, 0.055 mmol) were added dioxane (2.4 mL) and water (0.6 mL) at RT and the mixture was degassed for 10 minutes, and stirred at 90° C. overnight. The mixture was diluted with water (50 mL), extracted with EtOAc (2×50 mL). The combined organic phases were washed with brine, dried (MgSO₄) and concentrated under reduced pressure. The residue was purified by column chromatography on silica gel 12 g, eluting with Heptane/Ethanol, 0-30% in 30 min to give title compound. LC/MS [M+H]+: 1163.

Step B. (S)-4-(4-aminopyridin-3-yl)-N1-(2,3-diaminopropyl)-N2,N2-bis(4-methoxybenzyl)-3-(2-(4-methoxybenzyl)-2H-tetrazol-5-yl)benzene-1,2-disulfonamide 1,4-dimethoxybenzene (166 mg, 1.203 mmol) and TFA (2 mL, 26.0 mmol) were added to a stirred solution of benzyl tert-butyl (3-((2-(N,N-bis(4-methoxybenzyl)sulfamoyl)-4-(4-((tert-butoxycarbonyl)amino)pyridin-3-yl)-3-(2-(4-methoxybenzyl)-2H-tetrazol-5-yl)phenyl)sulfonamido)propane-1,2-diyl)(S)-dicarbamate (140 mg, 0.120 mmol) in CH₂Cl₂ (2 mL) at RT and the mixture was stirred at RT for 90 minutes. The mixture was concentrated and used as is. LC/MS [M+H]+: 829.

Step C. (S)-4-(4-aminopyridin-3-yl)-N1-(2,3-diaminopropyl)-3-(2H-tetrazol-5-yl)benzene-1,2-disulfonamide 1,4-dimethoxybenzene (167 mg, 1.206 mmol) and TFA (2.5 mL, 32.4 mmol) were added to a stirred solution of starting material (S)-4-(4-aminopyridin-3-yl)-N1-(2,3-diaminopropyl)-N2,N2-bis(4-methoxybenzyl)-3-(2-(4-methoxybenzyl)-2H-tetrazol-5-yl)benzene-1,2-disulfonamide, from (100 mg, 0.121 mmol) at RT and the mixture was stirred at 80° C. overnight. The mixture was concentrated. The residue was purified by preparative reverse phase HPLC (C-18), eluting with Acetonitrile/Water+0.05% NH$_3$, 0-25% in 11 minutes to give the title compound. LC/MS [M+H]+: 469.

Example 224

$N^4$-(2-aminoethyl)-2-(2H-tetrazol-5-yl)-3'-(1H-1,2,4-triazol-3-yl)-[1,1'-biphenyl]-3,4-disulfonamide

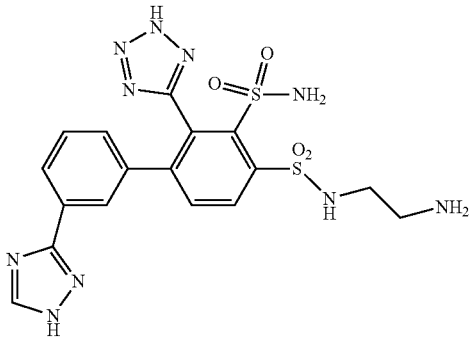 [SMILES: NCCNS(=O)(=O)c1ccc(-c2cccc(-c3nc[nH]n3)c2)c(-c2nn[nH]n2)c1S(N)(=O)=O]

Step A: (3-(1H-1,2,4-triazol-3-yl)phenyl)boronic acid

Potassium acetate (1.314 g, 13.39 mmol) and PCy3 Pd G2 (0.395 g, 0.669 mmol), 4,4,4',4',5,5,5',5'-octamethyl-2,2'-bi(1,3,2-dioxaborolane) (2.267 g, 8.93 mmol), were added to a stirred solution of 3-(3-bromophenyl)-1H-1,2,4-triazole (1.0 g, 4.46 mmol) in dioxane (10 mL) at room temperature and the mixture was stirred at 90° C. overnight. The mixture was filtered through a pad of CELITE, diluted with water (100 mL) and extracted with ethyl acetate (3×100 mL). The residue was purified by reverse phase column chromatography on silica gel 86 g C18, eluting with Acetonitrile/Water, 0-50% in 45 minutes to give the product as a solid after concentration. LC/MS [M+H]+: 190.

Step B: N,N-bis(4-methoxybenzyl)-2-(2-(4-methoxybenzyl)-2H-tetrazol-5-yl)-3'-(1H-1,2,4-triazol-3-yl)-4-((2-(trimethylsilyl)ethyl)sulfonyl)-[1,1'-biphenyl]-3-sulfonamide The mixture of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (2.0 g, 2.283 mmol), (3-(1H-1,2,4-triazol-3-yl)phenyl)boronic acid (0.777 g, 4.11 mmol), Na$_2$CO$_3$ (0.726 g, 6.85 mmol) and 1,1'-bis(diphenylphosphino)ferrocene-palladium(ii)dichloride dichloromethane complex (0.280 g, 0.343 mmol) in dioxane (20 mL) and water (5 mL) was degassed with N$_2$ for 5 minutes. The resulting mixture was heated at 95° C. for 16 hours. The reaction mixture was filtered and extracted with EtOAc (2×100 mL). The combined organic phases were dried (MgSO$_4$), and concentrated. The residue was purified by column chromatography on silica gel 120 g, eluting with EtOAc/isohexane, 0-100% in 45 minutes to give the title compound as a solid. LC/MS [M+H]+: 893.

Step C: 3-(N,N-bis(4-methoxybenzyl)sulfamoyl)-2-(2-(4-methoxybenzyl)-2H-tetrazol-5-yl)-3'-(1H-1,2,4-triazol-3-yl)-[1,1'-biphenyl]-4-sulfinic acid TBAF (0.719 mL, 0.719 mmol) was added to a stirred solution of starting material N,N-bis(4-methoxybenzyl)-2-(2-(4-methoxybenzyl)-2H-tetrazol-5-yl)-3'-(1H-1,2,4-triazol-3-yl)-4-((2-(trimethylsilyl)ethyl)sulfonyl)-[1,1'-biphenyl]-3-sulfonamide (292 mg, 0.327 mmol) in THF (4 mL) at room temperature and the mixture was stirred at room temperature for 45 min. The mixture was diluted with AcOEt (30 mL), washed with KHSO$_4$ aqueous (2×30 mL), dried over MgSO$_4$, and concentrated. LC/MS [M+H]+: 793.

Step D: tert-butyl (2-((3-(N,N-bis(4-methoxybenzyl)sulfamoyl)-2-(2-(4-methoxybenzyl)-2H-tetrazol-5-yl)-3'-(1H-1,2,4-triazol-3-yl)-[1,1'-biphenyl])-4-sulfonamido)ethyl)carbamate tert-butyl (2-aminoethyl)carbamate (100 mg, 0.626 mmol) and TEA (0.131 mL, 0.938 mmol) and NCS (92 mg, 0.688 mmol) were added to a stirred solution of 3-(N,N-bis(4-methoxybenzyl)sulfamoyl)-2-(2-(4-methoxybenzyl)-2H-tetrazol-5-yl)-3'-(1H-1,2,4-triazol-3-yl)-[1,1'-biphenyl]-4-sulfinic acid (248 mg, 0.313 mmol) in DCM (2 mL) at 0° C. The mixture was stirred at 0° C. for 45 minutes, diluted with water (50 mL) and extracted with ethyl acetate (2×50 mL). The combined organic phases were dried (MgSO$_4$) and concentrated. The residue was purified by column chromatography on silica gel 12 g, eluting with Heptane/Ethanol, 0-60% in 45 minutes to give the title product as a solid. LC/MS [M+H]+: 951.

Step E: N4-(2-aminoethyl)-N3-(4-methoxybenzyl)-2-(2-(4-methoxybenzyl)-2H-tetrazol-5-yl)-3'-(1H-1,2,4-triazol-3-yl)-[1,1'-biphenyl]-3,4-disulfonamide Anisole (0.276 mL, 2.52 mmol) and TFA (2 mL, 26.0 mmol) were added to a stirred solution of tert-butyl (2-(3-(N,N-bis(4-methoxybenzyl)sulfamoyl)-2-(2-(4-methoxybenzyl)-2H-tetrazol-5-yl)-3'-(1H-1,2,4-triazol-3-yl)-[1,1'-biphenyl]-4-ylsulfonamido)ethyl)carbamate (240 mg, 0.252 mmol) in DCM (2 mL) at RT and the mixture was stirred at RT for 30 minutes. The reaction mixture was concentrated. LC/MS [M+H]+: 731.

Step F: N4-(2-aminoethyl)-2-(2H-tetrazol-5-yl)-3'-(1H-1,2,4-triazol-3-yl)-[1,1'-biphenyl]-3,4-disulfonamide Anisole (0.3 mL, 2.75 mmol) and TFA (3 mL, 38.9 mmol) were added to $N^4$-(2-aminoethyl)-$N^3$-(4-methoxybenzyl)-2-(2-(4-methoxybenzyl)-2H-tetrazol-5-yl)-3'-(1H-1,2,4-triazol-3-yl)-[1,1'-biphenyl]-3,4-disulfonamide (184 mg, 0.252 mmol) at RT and the mixture was stirred at 80° C. for 90 min. The reaction mixture was concentrated. The residue was purified by preparative reverse phase HPLC (C-18) column, eluting with acetonitrile/water+0.05% NH$_3$, 3-40% to give the title compound as a solid after lyophilization overnight. LC/MS [M+H]+: 491.

EXAMPLES 225-231 in the Table below were prepared in an analogous fashion to that described for N$^4$-(2-aminoethyl)-2-(2H-tetrazol-5-yl)-3'-(1H-1,2,4-triazol-3-yl-[1,1'-biphenyl]-3,4-disulfonamide starting from 3-(N,N-bis(4-methoxybenzyl)sulfamoyl)-2-(2-(4-methoxybenzyl)-2H-tetrazol-5-yl)-3'-(1H-1,2,4-triazol-3-yl)-[1,1'-biphenyl]-4-sulfinic acid (EXAMPLE 224, Step C) or 3'-(5-amino-1H-1,2,4-triazol-3-yl)-3-(N,N-bis(4-methoxybenzyl)sulfamoyl)-2-(2-(4-methoxybenzyl)-2H-tetrazol-5-yl)-[1,1'-biphenyl]-4-sulfinic acid, prepared as described herein. The indicated right hand side protected amines were prepared as described herein, or were available from commercial sources.

| EX No. | Structure | Compound Name | LC/MS [M + H]$^+$ |
|---|---|---|---|
| 225 | 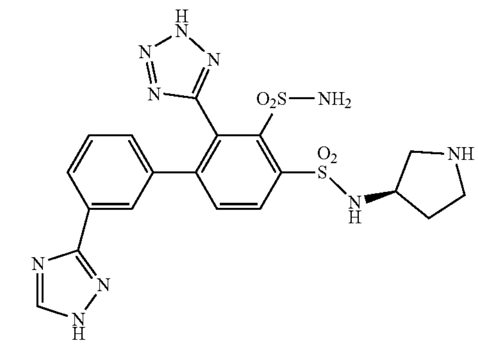 [SMILES: NS(=O)(=O)c1c(S(=O)(=O)N[C@@H]2CCNC2)ccc(-c2cccc(-c3nc[nH]n3)c2)c1-c1nn[nH]n1] | (R)-N4-(pyrrolidin-3-yl)-2-(2H-tetrazol-5-yl)-3'-(1H-1,2,4-triazol-3-yl)-[1,1'-biphenyl]-3,4-disulfonamide | 517 |
| 226 | 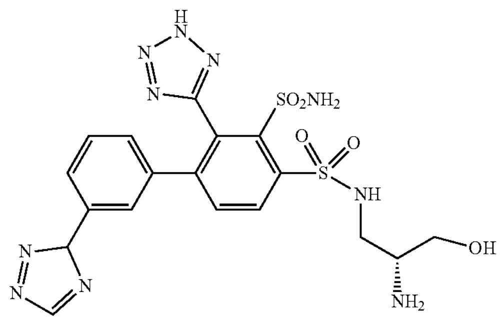 [SMILES: N[C@@H](CO)CNS(=O)(=O)c1ccc(-c2cccc(C3N=CN=N3)c2)c(-c2nn[nH]n2)c1S(N)(=O)=O] | N4-((R)-2-amino-3-hydroxypropyl)-2-(2H-tetrazol-5-yl)-3'-(3H-1,2,4-triazol-3-yl)-[1,1'-biphenyl]-3,4-disulfonamide | 521 |
| 227 | 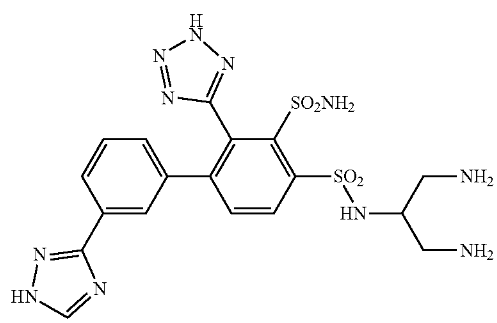 [SMILES: NCC(CN)NS(=O)(=O)c1ccc(-c2cccc(-c3nc[nH]n3)c2)c(-c2nn[nH]n2)c1S(N)(=O)=O] | N4-(1,3-diaminopropan-2-yl)-2-(2H-tetrazol-5-yl)-3'-(1H-1,2,4-triazol-3-yl)-[1,1'-biphenyl]-3,4-disulfonamide | 520 |
| 228 | 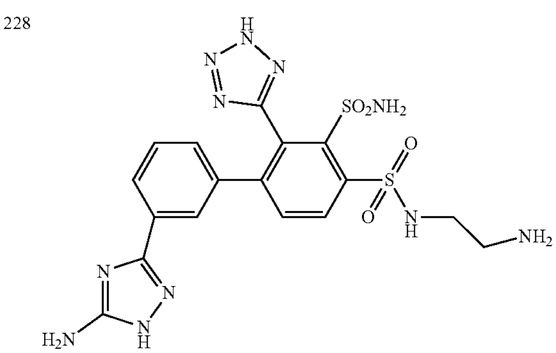 | 3'-(5-amino-1H-1,2,4-triazol-3-yl)-N4-(2-aminoethyl)-2-(2H-tetrazol-5-yl)-[1,1'-biphenyl]-3,4-disulfonamide | 506 |

| EX No. | Structure | Compound Name | LC/MS [M + H]+ |
|---|---|---|---|
| 229 | 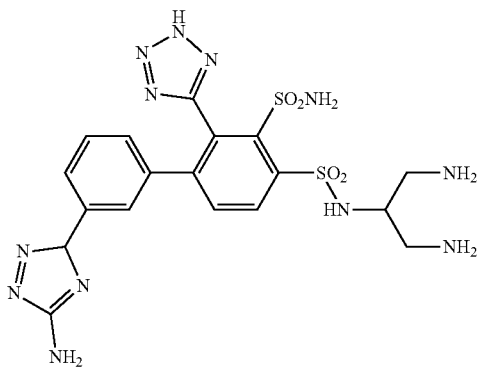 [SMILES: NCC(CN)NS(=O)(=O)c1ccc(-c2cccc(C3N=NC(N)=N3)c2)c(-c2nn[nH]n2)c1S(N)(=O)=O] | 3'-(5-amino-3H-1,2,4-triazol-3-yl)-N4-(1,3-diaminopropan-2-yl)-2-(2H-tetrazol-5-yl)-[1,1'-biphenyl]-3,4-disulfonamide | 535 |
| 230 | 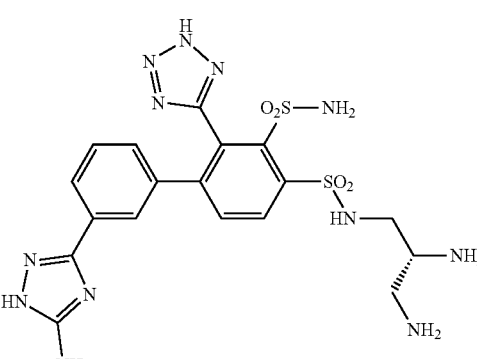 | (R)-3'-(5-amino-1H-1,2,4-triazol-3-yl)-N4-(2,3-diaminopropyl)-2-(2H-tetrazol-5-yl)-[1,1'-biphenyl]-3,4-disulfonamide | 535 |
| 231 | 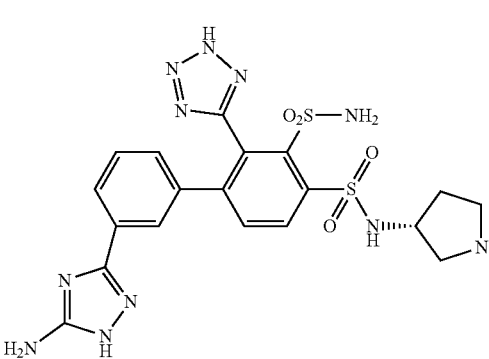 | (R)-3'-(5-amino-1H-1,2,4-triazol-3-yl)-N4-(pyrrolidin-3-yl)-2-(2H-tetrazol-5-yl)-[1,1'-biphenyl]-3,4-disulfonamide | 532 |

Example 232

(R)-4-(2-amino-1H-benzo[d]imidazol-4-yl)-N¹-(1-methylpyrrolidin-3-yl)-3-(2H-tetrazol-5-yl)benzene-1,2-disulfonamide

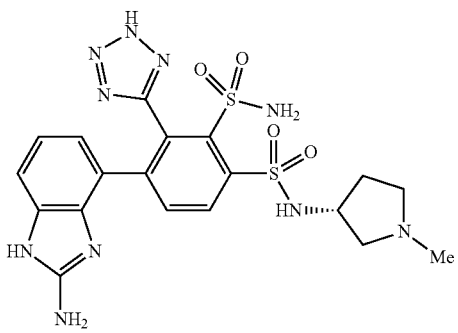 [SMILES: CN1CC[C@@H](NS(=O)(=O)c2ccc(-c3cccc4[nH]c(N)nc34)c(-c3nn[nH]n3)c2S(N)(=O)=O)C1]

Step A: (R)-4-iodo-N²,N²-bis(4-methoxybenzyl)-3-(2-(4-methoxybenzyl)-2H-tetrazol-5-yl)-N¹-(1-methylpyrrolidin-3-yl)benzene-1,2-disulfonamide and (R)-4-iodo-N²,N²-bis(4-methoxybenzyl)-3-(1-(4-methoxybenzyl)-1H-tetrazol-5-yl)-N¹-(1-methylpyrrolidin-3-yl)benzene-1,2-disulfonamide To a solution of 2-(N,N-bis(4-methoxybenzyl)sulfamoyl)-4-iodo-3-(2-(4-methoxybenzyl)-2H-tetrazol-5-yl)benzenesulfinic acid and 2-(N,N-bis(4-methoxybenzyl)sulfamoyl)-4-iodo-3-(1-(4-methoxybenzyl)-1H-tetrazol-5-yl)benzenesulfinic acid (3 g, 3.87 mmol) in THF (38.7 mL) was added (R)-1-methylpyrrolidin-3-amine (commercially available from Synnovator) (0.775 g, 7.74 mmol), triethylamine (1.078 mL, 7.74 mmol), and NCS (1.033 g, 7.74 mmol) in sequence at 0° C. under nitrogen. The mixture was stirred at the same temperature for 30 minutes, and monotored by LCMS. The reaction mixture was diluted with EtOAc, and washed with NaHCO₃ solution and brine. The organic layer was dried over MgSO₄, evaporated, and the crude product was purified by silica gel column chromatography eluting with 0-20% MeOH/DCM to give the title compound. LC/MS [M+H]⁺: 874.50.

Step B: (R)-4-(2-Amino-1H-benzo[d]imidazol-4-yl)-N²,N²-bis(4-methoxybenzyl)-3-(2-(4-methoxybenzyl)-2H-tetrazol-5-yl)-N¹-(1-methylpyrrolidin-3-yl)benzene-1,2-disulfonamide and (R)-4-(2-amino-1H-benzo[d]imidazol-4-yl)-N²,N²-bis(4-methoxybenzyl)-3-(1-(4-methoxybenzyl)-1H-tetrazol-5-yl)-N¹-(1-methylpyrrolidin-3-yl)benzene-1,2-disulfonamide A flask was charged with (R)-4-iodo-N²,N²-bis(4-methoxybenzyl)-3-(2-(4-methoxybenzyl)-2H-tetrazol-5-yl)-N¹-(1-methylpyrrolidin-3-yl)benzene-1,2-disulfonamide and (R)-4-iodo-N²,N²-bis(4-methoxybenzyl)-3-(1-(4-methoxybenzyl)-1H-tetrazol-5-yl)-N¹-(1-methylpyrrolidin-3-yl)benzene-1,2-disulfonamide (2.2 g, 2.52 mmol), (2-amino-1H-benzo[d]imidazol-4-yl)boronic acid (0.891 g, 5.04 mmol), Na₂CO₃ (0.801 g, 7.55 mmol) and PdCl₂ (dppf) (0.184 g, 0.252 mmol). The vial was sealed, degassed, and filled with dioxane (21 mL) and water (4.2 mL). The resulting mixture was heated overnight at 80° C. The reaction mixture was filtered over CELITE to removed palladium. The filtrate was concentrated and purified by silica gel column chromatography using (0-10)% MeOH/DCM as mobile phase to afford the title compound. LC/MS [M+H]⁺: 879.58.

Step C: R)-4-(2-amino-1H-benzo[d]imidazol-4-yl)-N¹-(1-methylpyrrolidin-3-yl)-3-(2H-tetrazol-5-yl)benzene-1,2-disulfonamide To a solution of (R)-4-(2-amino-1H-benzo[d]imidazol-4-yl)-N²,N²-bis(4-methoxybenzyl)-3-(2-(4-methoxybenzyl)-2H-tetrazol-5-yl)-N¹-(1-methylpyrrolidin-3-yl)benzene-1,2-disulfonamide and (R)-4-(2-amino-1H-benzo[d]imidazol-4-yl)-N²,N²-bis(4-methoxybenzyl)-3-(1-(4-methoxybenzyl)-1H-tetrazol-5-yl)-N¹-(1-methylpyrrolidin-3-yl)benzene-1,2-disulfonamide (250 mg, 0.284 mmol) in DCM (2.84 mL) was added TFA (2.19 mL, 28.4 mmol) at room temp. The resulting mixture was stirred at 80° C. for 1.0 hour. After removing the volatile, the residue was purified by reverse phase HPLC (3-40% MeCN/water as eluent, 0.1% TFA as additive) to give the TFA salt. The TFA salt was treated with HCl in MeOH to afford the title compound as an HCl salt. LC/MS [M+H]⁺: 519.47.

Example 233

(R)-3-((4-(2-amino-1H-benzo[d]imidazol-4-yl)-2-sulfamoyl-3-(2H-tetrazol-5-yl)phenyl)sulfonamido)-1,1-dimethylpyrrolidin-1-ium chloride

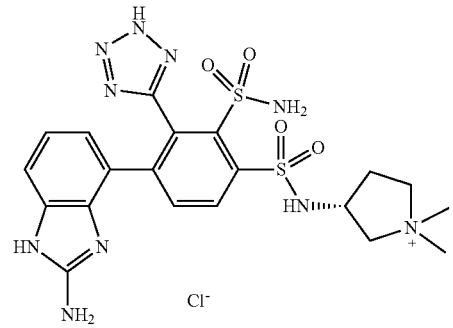

Step A: (R)-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)-1,1-dimethylpyrrolidin-1-ium and (R)-3-((4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfonamido)-1,1-dimethylpyrrolidin-1-ium chloride To a solution of (R)-4-(2-Amino-1H-benzo[d]imidazol-4-yl)-N²,N²-bis(4-methoxybenzyl)-3-(2-(4-methoxybenzyl)-2H-tetrazol-5-yl)-N¹-(1-methylpyrrolidin-3-yl)benzene-1,2-disulfonamide and (R)-4-(2-amino-1H-benzo[d]imidazol-4-yl)-N²,N²-bis(4-methoxybenzyl)-3-(1-(4-methoxybenzyl)-1H-tetrazol-5-yl)-N¹-(1-methylpyrrolidin-3-yl)benzene-1,2-disulfonamide (EXAMPLE 232, Step B; 250 mg, 0.284 mmol) in acetone (2.84 mL) was added K₂CO₃ (118 mg, 0.853 mmol) and MeI (0.021 mL, 0.341 mmol). The resulting mixture was stirred at room temp. for 90 minutes. After filtration and concentration the residue was purified on RP-HPLC using 10-100% acetonitrile/water (0.05% TFA as modifier) to give the title compound. LC/MS [M]⁺: 893.75.

Step B: (R)-3-((4-(2-amino-1H-benzo[d]imidazol-4-yl)-2-sulfamoyl-3-(2H-tetrazol-5-yl)phenyl)sulfonamido)-1,1-dimethylpyrrolidin-1-ium The title compound was obtained in a similar fashion to that of EXAMPLE 232, Step C starting from (R)-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)-1,1-dimethylpyrrolidin-1-ium trifluoroacetate and (R)-3-((4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfonamido)-1,1-dimethylpyrrolidin-1-ium trifluoroactetate except that the final compound was treated with excess HCl in MeOH (1.25 M) and then concentrated. LC/MS [M]⁺: 533.24.

Example 234

(R)-4-(2-amino-6-iodo-1H-benzo[d]imidazol-4-yl)-N¹-(pyrrolidin-3-yl)-3-(2H-tetrazol-5-yl)benzene-1,2-disulfonamide

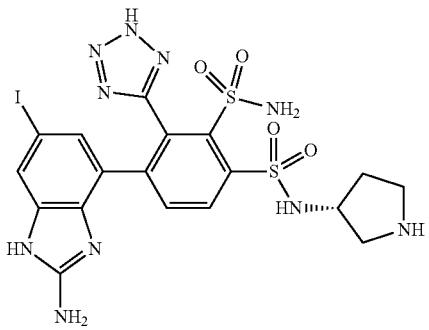 [SMILES: Nc1nc2c(-c3ccc(S(=O)(=O)N[C@@H]4CCNC4)c(S(N)(=O)=O)c3-c3nn[nH]n3)cc(I)cc2[nH]1]

To a solution of (R)-4-(2-amino-1H-benzo[d]imidazol-4-yl)-N¹-(pyrrolidin-3-yl)-3-(2H-tetrazol-5-yl)benzene-1,2-disulfonamide (200 mg, 0.396 mmol) in triflic acid (1.76 mL, 19.82 mmol) was added NIS (134 mg, 0.595 mmol) at 0° C. The reaction mixture was stirred at 0° C. for 30 minutes. Using ion exchange cartridge removed triflic acid, resulting in crude material before HPLC purification. After removing the volatile, the residue was purified by reverse phase HPLC (3-50% MeCN/water as eluent, 0.1% NH₄OH as additive) to give the title compound. LC/MS [M+H]⁺: 631.16.

Example 235

(R)-4-(1H-benzo[d][1,2,3]triazol-4-yl)-N¹-(pyrrolidin-3-yl)-3-(2H-tetrazol-5-yl)benzene-1,2-disulfonamide

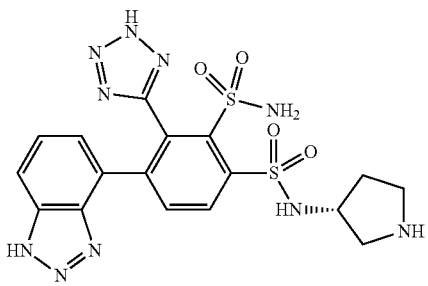 [SMILES: NS(=O)(=O)c1c(S(=O)(=O)N[C@@H]2CCNC2)ccc(-c2cccc3[nH]nnc23)c1-c1nn[nH]n1]

Step A: tert-butyl (R)-3-((4-(1H-benzo[d][1,2,3]triazol-4-yl)-2-(N,N-bis(4-methoxybenzyl)sulfamoyl)-3-(2-(4-methoxybenzyl)-2H-tetrazol-5-yl)phenyl)sulfonamido)pyrrolidine-1-carboxylate and tert-butyl (R)-3-((4-(1H-benzo[d][1,2,3]triazol-4-yl)-2-(N,N-bis(4-methoxybenzyl)sulfamoyl)-3-(1-(4-methoxybenzyl)-1H-tetrazol-5-yl)phenyl)sulfonamido)pyrrolidine-1-carboxylate A flask was charged with tert-Butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate (0.4 g, 0.417 mmol), (1H-benzo[d][1,2,3]triazol-4-yl)boronic acid (0.122 g, 0.750 mmol), Na₂CO₃ (0.133 g, 1.250 mmol) and PdCl₂ (dppf) (0.030 g, 0.042 mmol). The vial was sealed, degassed, and filled with dioxane (3.47 mL) and water (0.695 mL). The resulting mixture was heated overnight at 80° C. The reaction mixture was filtered over CELITE to removed palladium. The filtrate was concentrated and purified by silica gel column chromatography using (0-10)% MeOH/DCM as mobile phase to afford the title compound. LC/MS [M+H]⁺: 951.70.

Step B: (R)-4-(1H-benzo[d][1,2,3]triazol-4-yl)-N¹-(pyrrolidin-3-yl)-3-(2H-tetrazol-5-yl)benzene-1,2-disulfonamide To the solution of tert-butyl (R)-3-((4-(1H-benzo[d][1,2,3]triazol-4-yl)-2-(N,N-bis(4-methoxybenzyl)sulfamoyl)-3-(2-(4-methoxybenzyl)-2H-tetrazol-5-yl)phenyl)sulfonamido)pyrrolidine-1-carboxylate and tert-butyl (R)-3-((4-(1H-benzo[d][1,2,3]triazol-4-yl)-2-(N,N-bis(4-methoxybenzyl)sulfamoyl)-3-(1-(4-methoxybenzyl)-1H-tetrazol-5-yl)phenyl)sulfonamido)pyrrolidine-1-carboxylate (280 mg, 0.294 mmol) in DCM (2.9 mL) was added anisole (0.32 mL, 2.94 mmol) and TFA (2.27 mL, 29.4 mmol) at 0° C. The reaction was allowed to proceed at 0° C. for 30 minutes. After removing the volatile, the residue was treated with SCX ion exchange column (load sample and rinse with MeOH, rinse out product with 7 M NH₃ in MeOH) to give a free amine. The residue was dissolved in TFA (2.27 mL, 29.4 mmol). The resulting mixture was stirred at 80° C. for 1.0 hour. After removing the volatile, the residue was purified by reverse phase HPLC (3-40% ACN/water as eluent, 0.1% TFA as additive) to give the TFA salt. The TFA salt was treated with HCl in MeOH twice to give the title compound as an HCl salt. LC/MS [M+H]⁺: 491.31.

The following EXAMPLES 236-243 in the Table below were prepared in an analogous fashion to that described for EXAMPLE 235, starting from the corresponding boronic acid or boronic ester (commercially available or prepared as described herein) and the indicated aryl iodides which were prepared as described herein. Protective groups on the amines were simultaneously removed under the final deprotection conditions for the para-methoxybenzy, protective groups.

| EX. No. | Intermediates | Structure/Name | LC/MS |
|---|---|---|---|
| 236 | (1H-benzo[d][1,2,3]triazol-4-yl)boronic acid and tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate | N¹-(2-aminoethyl)-4-(1H-benzo[d][1,2,3]triazol-4-yl)-3-(2H-tetrazol-5-yl)benzene-1,2-disulfonide | [M + H]⁺: 465.29 |
| 237 | (1H-benzo[d][1,2,3]triazol-4-yl)boronic acid and tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate | (R)-N¹-(1-aminopropan-2-yl)-4-(1H-benzo[d][1,2,3]triazol-4-yl)-3-(2H-tetrazol-5-yl)benzene-1,2-disulfonamide | [M + H]⁺: 479.28 |
| 238 | benzo[c][1,2,5]oxadiazol-4-ylboronic acid and tert-Butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate | (R)-4-(benzo[c][1,2,5]oxadiazol-4-yl)-N¹-(pyrrolidin-3-yl)-3-(2H-tetrazol-5-yl)benzene-1,2-disulfonamide | [M + H]⁺: 492.25 |

| EX. No. | Intermediates | Structure/Name | LC/MS |
|---|---|---|---|
| 239 | benzo[c][1,2,5]oxadiazol-4-ylboronic acid and tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate | 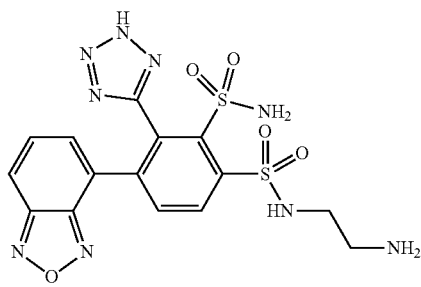<br>$N^1$-(2-aminoethyl)-4-(benzo[c][1,2,5]oxadiazol-4-yl)-3-(2H-tetrazol-5-yl)benzene-1,2-disulfonamide | [M + 1]$^+$: 466.35 |
| 240 | (2-amino-1H-benzo[d]imidazol-4-yl)boronic acid tert-butyl (3S,4R)-3-(((benzyloxy)carbonyl)amino)-4-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (3S,4R)-3-(((benzyloxy)carbonyl)amino)-4-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate | 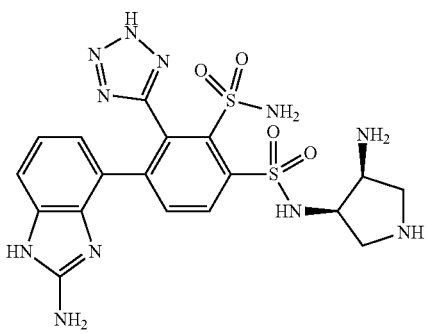<br>4-(2-amino-1H-benzo[d]imidazol-4-yl)-$N^1$-((3R,4S)-4-aminopyrrolidin-3-yl)-3-(2H-tetrazol-5-yl)benzene-1,2-disulfonamide | [M + 1]$^+$: 520.68 |
| 241 | (2-amino-1H-benzo[d]imidazol-4-yl)boronic acid and tert-butyl (3R,4S)-3-(((benzyloxy)carbonyl)amino)-4-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (3R,4S)-3-(((benzyloxy)carbonyl)amino)-4-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate | 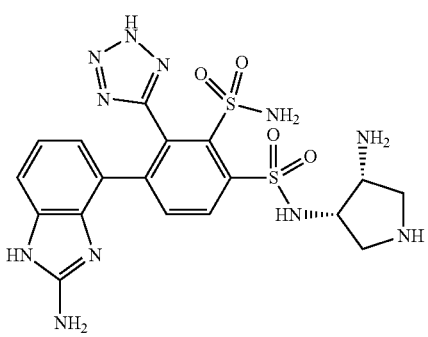<br>4-(2-amino-1H-benzo[d]imidazol-4-yl)-$N^1$-((3S,4R)-4-aminopyrrolidin-3-yl)-3-(2H-tetrazol-5-yl)benzene-1,2-disulfonamide | [M + 1]$^+$: 520.68 |

| EX. No. | Intermediates | Structure/Name | LC/MS |
|---|---|---|---|
| 242 | N-methyl-5-(4,4,5,5-tetramethyl-1,3,2-dioxaborolan-2-yl)pyridin-2-amine and tert-Butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate | (R)-4-(6-(methylamino)pyridin-3-yl)-N$^1$-(pyrrolidin-3-yl)-3-(2H-tetrazol-5-yl)benzene-1,2-disulfonamide | [M + 1]$^+$: 480.2 |
| 243 | N-methyl-5-(4,4,5,5-tetramethyl-1,3,2-dioxaborolan-2-yl)pyridin-2-amine and tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate | N$^1$-(2-aminoethyl)-4-(6-(methylamino)pyridin-3-yl)-3-(2H-tetrazol-5-yl)benzene-1,2-disulfonamide | [M + 1]$^+$: 454.2 |

Example 244

(S)-4-(2-amino-1H-benzo[d]imidazol-7-yl)-N1-methyl-N1-(pyrrolidin-3-yl)-3-(1H-tetrazol-5-yl)benzene-1,2-disulfonamide

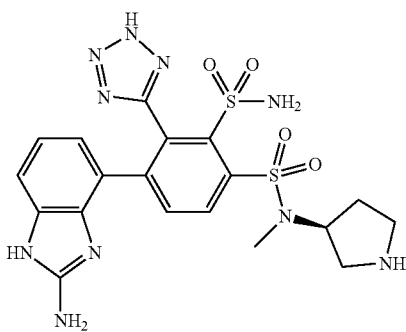 [SMILES: CN([C@H]1CCNC1)S(=O)(=O)c1ccc(-c2cccc3[nH]c(N)nc23)c(-c2nn[nH]n2)c1S(N)(=O)=O]

Step A: (3S)-tert-butyl-3-(2-(N,N-bis(4-methoxybenzyl)sulfamoyl)-4-iodo-3-(1-(4-methoxybenzyl)-1H-tetrazol-5-yl)-N-methylphenylsulfonamido)pyrrolidine-1-carboxylate To a solution of 2-(N,N-bis(4-methoxybenzyl)sulfamoyl)-4-iodo-3-(1-(4-methoxybenzyl)-1H-tetrazol-5-yl)benzenesulfinic acid (6.0 g, 7.74 mmol) in THF (30 mL) was added NCS (2.0 g, 15.47 mmol) at 0° C. The mixture was stirred at room temperature for 1 hour under nitrogen. To the reaction mixture was added (S)-tert-butyl 3-(methylamino)pyrrolidine-1-carboxylate (1.0 g, 4.94 mmol) and TEA (0.25 g, 2.50 mmol) at room temperature under nitrogen. The mixture was stirred at room temperature for 30 minutes under nitrogen. The resulting mixture was filtered. The filtrate was concentrated under vacuum. The residue was purified by silica gel column chromatography, eluted with 38% EA in PE. The fractions containing desired product were combined and concentrated under vacuum to afford the title compound: LCMS [M+1]$^+$: 974.

Step B: (3S)-tert-butyl-3-(4-(2-amino-1H-benzo[d]imidazol-7-yl)-2-(N,N-bis(4-methoxybenzyl) sulfamoyl)-3-(1-(4-methoxybenzyl)-1H-tetrazol-5-yl)-N-methylphenylsulfonamido)pyrrolidine-1-carboxylate To a stirred solution of (3S)-tert-butyl 3-(2-(N,N-bis(4-methoxybenzyl)sulfamoyl)-4-iodo-3-(1-(4-methoxybenzyl)-1H-tetrazol-5-yl)-N-methylphenylsulfonamido)pyrrolidine-1-carboxylate (0.50 g, 0.51 mmol) in 1,4-dioxane (3 mL) and water (0.50 mL) was added (2-amino-1H-benzo[d]imidazol-7-yl)boronic acid (0.27 g, 1.54 mmol), 2nd Generation XPhos precatalyst (81 mg, 0.10 mmol) and Na$_2$CO$_3$ (0.16 g, 1.54 mmol) under nitrogen at room temperature. The stirred mixture was degassed with nitrogen at room temperature three times. The reaction mixture was stirred at 80° C. for 16 hours under nitrogen. After cooling to room temperature, the resulting mixture was diluted with EA (50 mL) and washed with water (3×80 mL). The separated organic layer was washed with brine (3×80 mL), dried over anhydrous Na$_2$SO$_4$ and filtered. The filtrate was concentrated under vacuum. The residue was purified by silica gel column chromatography, eluted with 4% MeOH in DCM. The fractions containing desired product were combined and concentrated under vacuum to afford the title compound: LCMS [M+1]$^+$: 979.

Step C: (S)-4-(2-amino-1H-benzo[d]imidazol-7-yl)-N1-methyl-N1-(pyrrolidin-3-yl)-3-(1H-tetrazol-5-yl)benzene-1,2-disulfonamide A solution of (3S)-tert-butyl-3-(4-(2-amino-1H-benzo[d]imidazol-7-yl)-2-(N,N-bis(4-methoxybenzyl)sulfamoyl)-3-(1-(4-methoxybenzyl)-1H-tetrazol-5-yl)-N-methylphenylsulfonamido)pyrrolidine-1-carboxylate (0.23 g, 0.24 mmol) in TFA (5 mL) was stirred at room temperature for 1 hour. The resulting solution was concentrated under vacuum. The residue was co-evaporated with anisole (3×3 mL) and used in the next step without further purification. The crude product was dissolved in TFA (4 mL) and stirred at 80° C. for 1 hour. The resulting solution was concentrated under vacuum. The residue was purified by Prep-HPLC with the following conditions: Column: Xbridge C18, 19×150 mm; Mobile phase: ACN in water (10 mmol/L NH$_4$HCO$_3$), 5%-35% in 8 min; Detector: UV 254 nm. The fractions containing desired product were combined and concentrated under vacuum to afford the title compound: LCMS [M+1]$^+$: 519; $^1$H NMR (300 MHz, DMSO-d$_6$+D$_2$O): δ 8.02 (d, J=8.3 Hz, 1H), 7.92 (d, J=8.3 Hz, 1H), 6.93 (d, J=7.5 Hz, 1H), 6.53-6.49 (m, 1H), 6.07 (d, J=7.5 Hz, 1H), 4.69-4.64 (m, 1H), 3.30-3.17 (m, 2H), 3.09-3.05 (m, 2H), 3.02 (s, 3H), 2.11-2.03 (m, 2H).

Example 245

3-(4-(2-Amino-1H-benzo[d]imidazol-4-yl)-2-sulfamoyl-3-(2H-tetrazol-5-yl) phenylsulfonamido)-1,1-dimethylazetidin-1-ium hydrogencarbonate

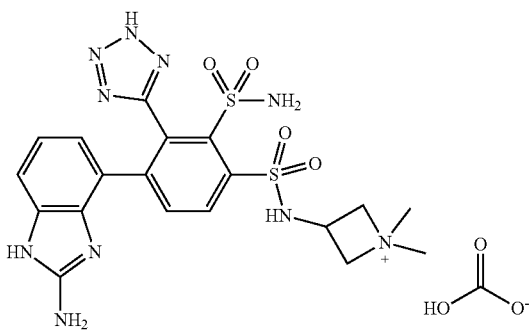

Step A: 4-Iodo-N2,N2-bis(4-methoxybenzyl)-3-(2-(4-methoxybenzyl)-2H-tetrazol-5-yl)-N1-(1-methylazetidin-3-yl)benzene-1,2-disulfonamide To a stirred solution of 1-methylazetidin-3-amine (0.32 g, 3.69 mmol) in THF (10 mL) was added 2-(N,N-bis(4-methoxybenzyl)sulfamoyl)-4-iodo-3-(2-(4-methoxybenzyl)-2H-tetrazol-5-yl) benzenesulfinic acid (1.3 g, 1.68 mmol) and TEA (0.70 mL, 5.03 mmol) at 0° C. under nitrogen. The solution was stirred for 15 minutes at 0° C., then NCS (0.45 g, 3.36 mmol) was added at 0° C. The mixture was stirred at 0° C. for 1.5 hours under nitrogen. The resulting mixture was concentrated under vacuum. The residue was diluted with EA (100 mL) and washed with brine (3×100 mL). The organic layer was dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 860.

Step B: 4-(2-Amino-1H-benzo[d]imidazol-4-yl)-N2,N2-bis(4-methoxybenzyl)-3-(2-(4-methoxybenzyl)-2H-tetrazol-5-yl)-N1-(1-methylazetidin-3-yl)benzene-1,2-disulfonamide To a solution of 4-iodo-N2,N2-bis(4-methoxybenzyl)-3-(2-(4-methoxybenzyl)-2H-tetrazol-5-yl)-N1-(1-methylazetidin-3-yl)benzene-1,2-disulfonamide (1.1 g, 1.28 mmol) in 1,4-dioxane (7 mL) and water (3 mL) was added (2-amino-1H-benzo[d]imidazol-4-yl)boronic acid (0.34 g, 1.92 mmol), Na$_2$CO$_3$ (0.41 g, 3.84 mmol) and Pd(PPh$_3$)$_4$ (0.15 g, 0.13 mmol) at room temp. The mixture was degassed with nitrogen three times. The reaction mixture was stirred at 80° C. for 16 hours under nitrogen. The resulting mixture was diluted with water (100 mL) and extracted with EA (3×100 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]$^+$: 865.

Step C: Tert-butyl-4-(3-(N,N-bis(4-methoxybenzyl)sulfamoyl)-4-(N-(tert-butoxycarbonyl)-N-(1-methylazetidin-3-yl)sulfamoyl)-2-(2-(4-methoxybenzyl)-2H-tetrazol-5-yl) phenyl)-2-(bis(tert-butoxycarbonyl)amino)-1H-benzo[d]imidazole-1-carboxylate To a solution of 4-(2-amino-1H-benzo[d]imidazol-4-yl)-N2,N2-bis(4-methoxybenzyl)-3-(2-(4-methoxybenzyl)-2H-tetrazol-5-yl)-N1-(1-methylazetidin-3-yl)benzene-1,2-disulfonamide (0.67 g, 0.78 mmol), TEA (0.34 mL, 2.30 mmol) and DMAP (19 mg, 0.16 mmol) in DCM (10 mL) was added Boc$_2$O (0.85 g, 3.87 mmol). The reaction mixture was stirred at room temperature for 1 hour. The resulting mixture was poured into water (50 mL). The aqueous phase was extracted with EA (3×50 mL). The combined organic layers were washed with water (3×50 mL) and brine (3×50 mL). The organic layer was dried over anhydrous Na$_2$SO$_4$ and filtered. The filtrate was concentrated under vacuum to afford the title compound, which was used in the next step without further purification: LCMS [M+1]$^+$: 1265.

Step D: 3-(2-(N,N-bis(4-methoxybenzyl)sulfamoyl)-4-(2-(bis(tert-butoxycarbonyl)amino)-1-(tert-butoxycarbonyl)-1H-benzo[d]imidazol-4-yl)-N-(tert-butoxycarbonyl)-3-(2-(4-methoxybenzyl)-2H-tetrazol-5-yl)phenylsulfonamido)-1,1-dimethylazetidin-1-ium To a solution of tert-butyl-4-(3-(N,N-bis(4-methoxybenzyl)sulfamoyl)-4-(N-(tert-butoxycarbonyl)-N-(1-methylazetidin-3-yl)sulfamoyl)-2-(2-(4-methoxybenzyl)-2H-tetrazol-5-yl)phenyl)-2-(bis(tert-butoxycarbonyl)amino)-1H-benzo[d]imidazole-1-carboxylate (0.90 g, 0.71 mmol) in DMF (10 mL) were added iodomethane (0.15 g, 1.07 mmol) and Cs$_2$CO$_3$ (0.70 g, 2.10 mmol). The reaction mixture was stirred at room temperature for 1 hour. The resulting mixture was poured into water (50 mL). The aqueous phase was extracted with EA (3×100 mL). The combined organic layers were washed with water (3×100 mL) and brine (3×100 mL), dried over anhydrous Na$_2$SO$_4$ and filtered. The filtrate was concentrated under vacuum to afford the title compound, which was used in the next step directly without further purification: LCMS [M]$^+$: 1279.

Step E: 3-(4-(2-Amino-1H-benzo[d]imidazol-4-yl)-2-sulfamoyl-3-(2H-tetrazol-5-yl)phenylsulfonamido)-1,1-dimethylazetidin-1-ium hydrogencarbonate The title compound was prepared as described for Example 244, step C, using 3-(2-(N,N-bis(4-methoxybenzyl)sulfamoyl)-4-(2-(bis(tert-butoxycarbonyl)amino)-1-(tert-butoxycarbonyl)-1H-benzo[d]imidazol-4-yl)-N-(tert-butoxycarbonyl)-3-(2-(4-methoxybenzyl)-2H-tetrazol-5-yl)phenylsulfonamido)-1,1-dimethylazetidin-1-ium (0.7 g, 0.55 mmol) to afford the crude product. The crude product was purified by Prep-HPLC with the following conditions: Column: X Bridge Shield RP18 OBD Column, 5 µm, 19×150 mm; Mobile Phase A: water with 10 mmol/L NH$_4$HCO$_3$, Mobile Phase B: ACN; Flow rate: 20 mL/min; Gradient: 5% B to 30% B in 8 min; Detector: 254 and 220 nm; Retention time: 6.12 min. The fractions containing desired product were combined and concentrated under vacuum to afford the title compound: LCMS [M−HCO$_3$$^-$]$^+$: 519; $^1$H NMR (400 MHz, DMSO-d$_6$): δ 10.76 (s, 1H), 8.27-8.18 (m, 1H), 8.16-8.02 (m, 1H), 7.89 (brs, 3H), 6.92-6.88 (m, 1H), 6.44-6.42 (m, 1H), 6.21 (brs, 2H), 6.04-5.84 (m, 1H), 4.75-4.62 (m, 1H), 4.44-4.39 (m, 4H), 3.17 (s, 3H), 3.16 (s, 3H).

Example 246

(R)-4-(2-amino-1H-benzo[d]imidazol-4-yl)-N1-(1-(2-aminoethyl) pyrrolidin-3-yl)-3-(2H-tetrazol-5-yl)benzene-1,2-disulfonamide

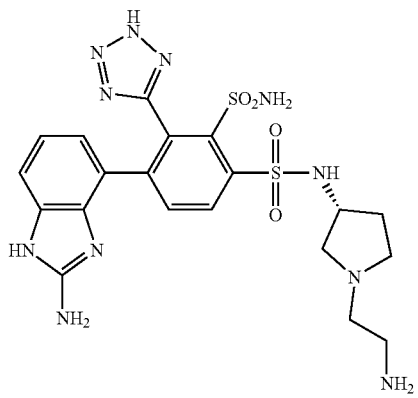 [SMILES: NCCN1CC[C@@H](NS(=O)(=O)c2ccc(-c3cccc4[nH]c(N)nc34)c(-c3nn[nH]n3)c2S(N)(=O)=O)C1]

Step A: (R)-4-iodo-N2-(4-methoxybenzyl)-3-(2-(4-methoxybenzyl)-2H-tetrazol-5-yl)-N1-(pyrrolidin-3-yl)benzene-1,2-disulfonamide To a stirred solution of (R)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (4.0 g, 4.17 mmol) in DCM (40 mL) was added TFA (8 mL) at 0° C. The solution was allowed to warm to room temperature and stirred for 0.5 hour. The pH value of reaction solution was adjusted to 8 with 7% aqueous NaHCO$_3$ solution and extracted with DCM (2×200 mL). The combined organic layers was washed with brine (3×400 mL), dried over anhydrous Na$_2$SO$_4$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]$^+$: 740.

Step B: (R)-tert-butyl (2-(3-(4-iodo-3-(2-(4-methoxybenzyl)-2H-tetrazol-5-yl)-2-(N-(4-methoxybenzyl)sulfamoyl)phenylsulfonamido)pyrrolidin-1-yl)ethyl)carbamate To a solution of (R)-4-iodo-N2-(4-methoxybenzyl)-3-(2-(4-methoxybenzyl)-2H-tetrazol-5-yl)-N1-(pyrrolidin-3-yl)benzene-1,2-disulfonamide (1.70 g, 2.30 mmol) and tert-butyl (2-oxoethyl)carbamate (0.73 g, 4.60 mmol) in MeOH (20 mL) was added NaBH(OAc)$_3$ (1.95 g, 9.19 mmol) at 0° C. The mixture was degassed with nitrogen three times. The mixture was stirred at room temperature for 1 hour under nitrogen. The resulting mixture was quenched with saturated aqueous NH$_4$Cl (50 mL) and extracted with EA (3×40 mL). The combined organic layers were washed with brine (3×100 mL), dried over anhydrous Na$_2$SO$_4$ and filtered. The filtrate was concentrated under vacuum. The residue was purified by silica gel column chromatography, eluted with 60% EA in PE. The fractions containing desired product were combined and concentrated under vacuum to afford the title compound: LCMS [M+1]$^+$: 883.

Step C: (R)-tert-butyl (2-(3-(4-(2-amino-1H-benzo[d]imidazol-4-yl)-3-(2-(4-methoxybenzyl)-2H-tetrazol-5-yl)-2-(N-(4-methoxybenzyl)sulfamoyl)phenylsulfonamido)pyrrolidin-1-yl)ethyl)carbamate To a solution of (R)-tert-butyl (2-(3-(4-iodo-3-(2-(4-methoxybenzyl)-2H-tetrazol-5-yl)-2-(N-(4-methoxybenzyl)sulfamoyl)phenylsulfonamido)pyrrolidin-1-yl)ethyl)carbamate (0.40 g, 0.45 mmol) in 1,4-dioxane (5 mL) and water (1 mL) was added (2-amino-1H-benzo[d]imidazol-4-yl)boronic acid (0.20 g, 1.13 mmol), Na$_2$CO$_3$ (0.14 g, 1.36 mmol) and Pd(dppf)Cl$_2$ adduct CH$_2$Cl$_2$ (74 mg, 0.09 mmol) at room temperature. The mixture was degassed with nitrogen three times. The reaction mixture was stirred at 80° C. for 16 hours under nitrogen. The resulting mixture was diluted with water (50 mL) and extracted with EA (3×50 mL). The combined organic layers were washed with brine (3×50 mL), dried over anhydrous Na$_2$SO$_4$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]$^+$: 888.

311

Step D: (R)-4-(2-amino-1H-benzo[d]imidazol-4-yl)-N1-(1-(2-aminoethyl)pyrrolidin-3-yl)-3-(2H-tetrazol-5-yl)benzene-1,2-disulfonamide The title compound was prepared as described for EXAMPLE 244, step C, using (R)-tert-butyl(2-(3-(4-(2-amino-1H-benzo[d]imidazol-4-yl)-3-(2-(4-methoxybenzyl)-2H-tetrazol-5-yl)-2-(N-(4-methoxybenzyl)sulfamoyl)phenylsulfonamido)pyrrolidin-1-yl)ethyl)carbamate (0.10 g, 0.11 mmol) to afford the crude product. The crude product was purified by Prep-HPLC with the following conditions: Column: X Select CSH Prep C18 OBD Column, 5 μm, 19×150 mm; Mobile Phase A: water with 10 mmol/L $NH_4HCO_3$, Mobile Phase B: ACN; Flow rate: 20 mL/min; Gradient: 5% B to 25% B in 8 min; 254 and 220 nm. The fractions containing desired product were combined and concentrated under vacuum to afford the title compound: LCMS [M+1]$^+$: 548; $^1$H NMR (400 MHz, DMSO-$d_6$): δ 8.23 (d, J=8.4 Hz, 1H), 7.96 (d, J=8.4 Hz, 1H), 7.57 (brs, 3H), 6.94 (d, J=7.6 Hz, 1H), 6.54 (t, J=7.6 Hz, 1H), 6.40 (brs, 2H), 6.10 (d, J=7.6 Hz, 1H), 3.98-3.94 (m, 1H), 2.88-2.81 (m, 2H), 2.75-2.71 (m, 1H), 2.70-2.58 (m, 4H), 2.38-2.32 (m, 1H), 2.11-2.06 (m, 1H), 1.72-1.66 (m, 1H).

Example 247

4-(2-amino-1H-benzo[d]imidazol-4-yl)-N-1-(1-amino-3-hydroxy-2-(hydroxymethyl) propan-2-yl)-3-(2H-tetrazol-5-yl)benzene-1,2-disulfonamide

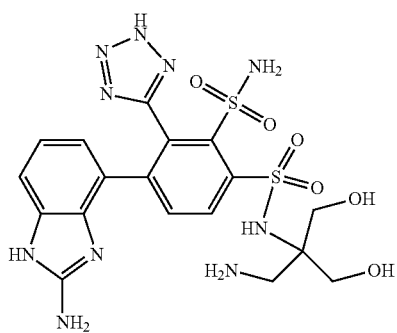 [SMILES: NCC(CO)(CO)NS(=O)(=O)c1ccc(-c2cccc3[nH]c(N)nc23)c(-c2nn[nH]n2)c1S(N)(=O)=O]

Step A: Benzyl (1,3-dihydroxy-2-(hydroxymethyl)propan-2-yl)carbamate

To a vigorously stirred mixture of 2-amino-2-(hydroxymethyl)propane-1,3-diol (25.0 g, 206 mmol) in EA (200 mL) and water (100 mL) was added $NaHCO_3$ (52.0 g, 619 mmol) and Cbz-Cl (59 mL, 413 mmol) at 0° C. The reaction mixture was stirred at room temp. for 4 hours under nitrogen. The resulting mixture was diluted with EA (300 mL), washed with water (3×150 mL) and brine (3×150 mL), dried over anhydrous $Na_2SO_4$ and filtered. The filtrate was concentrated under vacuum to afford the title compound, which was used in the next step without further purification: LCMS [M+1]$^+$: 256.

Step B: Benzyl (5-(hydroxymethyl)-2,2-dimethyl-1,3-dioxan-5-yl)carbamate

To a solution of benzyl (1,3-dihydroxy-2-(hydroxymethyl)propan-2-yl)carbamate (35.0 g, 137 mmol) in DMF

312

(100 mL) was added 4-methylbenzenesulfonic acid (4.7 g, 27.41 mmol) and 2,2-dimethoxypropane (28.6 g, 274 mmol) at 0° C. The reaction mixture was stirred at room temp. for 16 hours under nitrogen. The resulting mixture was diluted with EA (500 mL), washed with water (3×250 mL) and brine (3×300 mL), dried over anhydrous $Na_2SO_4$ and filtered. The filtrate was concentrated under vacuum. The residue was purified by silica gel column chromatography, eluted with 15% EA in PE. The fractions containing desired product were combined and concentrated under vacuum to afford the title compound: LCMS [M+1]$^+$: 296.

Step C: (5-(((benzyloxy)carbonyl)amino)-2,2-dimethyl-1,3-dioxan-5-yl)methyl methanesulfonate To a solution of benzyl(5-(hydroxymethyl)-2,2-dimethyl-1,3-dioxan-5-yl)carbamate (14.0 g, 47.4 mmol) in DCM (200 mL) was added TEA (20 mL, 142 mmol) and MsCl (7.4 mL, 95 mmol) at 0° C. The reaction mixture was stirred at room temperature for 4 hours under nitrogen. The resulting mixture was washed with water (3×300 mL) and brine (3×300 mL), dried over anhydrous $Na_2SO_4$ and filtered. The filtrate was concentrated under vacuum to afford the title compound, which was used in the next step without further purification: LCMS [M+1]$^+$: 374.

Step D: Benzyl (5-(aminomethyl)-2,2-dimethyl-1,3-dioxan-5-yl)carbamate

To a solution of (5-(((benzyloxy)carbonyl)amino)-2,2-dimethyl-1,3-dioxan-5-yl) methyl methanesulfonate (13.0 g, 34.80 mmol) in DMF (170 mL) was added potassium 1,3-dioxoisoindolin-2-ide (12.9 g, 69.60 mmol). The reaction mixture was stirred at 65° C. for 16 hours under nitrogen. The resulting mixtrue was diluted with EA (400 mL). The separated organic layer was washed with water (3×300 mL) and brine (3×300 mL), dried over anhydrous $Na_2SO_4$ and filtered. The filtrate was concentrated under vacuum. The residue was dissolved in a solution of hydrazine hydrate (80%, 100 mL) and EtOH (100 mL). The reaction mixture was stirred at 80° C. for 3 hours under nitrogen. The resulting mixture was diluted with EA (500 mL), and then washed with water (3×300 mL) and brine (3×300 mL). The organic layer was dried over anhydrous $Na_2SO_4$ and filtered. The filtrate was concentrated under vacuum to the title compound, which was used in the next step without further purification: [M+1]$^+$: 295.

Step E: Benzyl-N-[5-({[(tert-butoxy)carbonyl]amino}methyl)-2,2-dimethyl-1,3-dioxan-5-yl]carbamate To a solution of benzyl(5-(aminomethyl)-2,2-dimethyl-1,3-dioxan-5-yl)carbamate (10.0 g, 34.0 mmol) in DCM (150 mL) was added TEA (4.8 mL, 34.0 mmol) and $Boc_2O$ (7.4 g, 34.0 mmol) at 0° C. The reaction mixture was stirred at room temp. for 16 hours under nitrogen. The resulting mixture was diluted with DCM (300 mL), and then washed with water (3×250 mL) and brine (3×250 mL). The organic layer was dried over anhydrous $Na_2SO_4$ and filtered. The filtrate was concentrated under vacuum. The residue was purified by silica gel column chromatography, eluted with 20% EA in PE. The fractions containing desired product were combined and concentrated under vacuum to afford the title compound: LCMS [M+1]$^+$: 395.

Step F: Tert-butyl ((5-amino-2,2-dimethyl-1,3-dioxan-5-yl)methyl)carbamate

To a solution of benzyl-N-[5-({[(tert-butoxy)carbonyl]amino}methyl)-2,2-dimethyl-1,3-dioxan-5-yl]carbamate (2.6 g, 6.59 mmol) in MeOH (20 mL) was added Pd(OH)$_2$/C (20% wt, 0.93 g, 1.32 mmol). The reaction mixture was stirred at room temperature for 72 hours under hydrogen. The resulting mixture was filtered. The filtrate was concentrated under vacuum. The residue was purified by silica column chromatography, eluted with 33% EA in PE. The fractions containing desired product were combined and concentrated under vacuum to afford the title compound: LCMS [M+1 261.

Step G: Tert-butyl((5-(2-(N,N-bis(4-methoxybenzyl)sulfamoyl)-4-iodo-3-(2-(4-methoxy benzyl)-2H-tetrazol-5-yl)phenylsulfonamido)-2,2-dimethyl-1,3-dioxan-5-yl)methyl)carbamate To a solution of 2-(N,N-bis(4-methoxybenzyl)sulfamoyl)-4-iodo-3-(2-(4-methoxybenzyl)-2H-tetrazol-5-yl)benzenesulfinic acid (1.73 g, 2.23 mmol) in THF (15 mL) was added tert-butyl((5-amino-2,2-dimethyl-1,3-dioxan-5-yl) methyl)carbamate (1.2 g, 4.46 mmol) and TEA (0.9 mL, 6.69 mmol) at 0° C. for 10 min. The mixture was degassed with nitrogen three times. Then NCS (0.60 g, 4.46 mmol) was added and the mixture was stirred at 0° C. for 1.5 hours under nitrogen. The resulting mixture was concentrated under vacuum. The residue was diluted with EA (300 mL). The organic layer was washed with brine (3×200 mL), dried over anhydrous Na$_2$SO$_4$ and filtered. The filtrate was concentrated under vacuum. The residue was purified by silica gel column chromatography, eluted with 25% EA in PE. The fractions containing desired product were combined and concentrated under vacuum to afford the title compound: LCMS [M+1]$^+$: 1034.

Step H: Tert-butyl ((5-(4-(2-amino-1H-benzo[d]imidazol-4-yl)-2-(N,N-bis(4-methoxybenzyl) sulfamoyl)-3-(2-(4-methoxybenzyl)-2H-tetrazol-5-yl) phenylsulfonamido)-2,2-dimethyl-1,3-dioxan-5-yl) methyl)carbamate The title compound was prepared as described for EXAMPLE 246, step C, using tert-butyl((5-(2-(N,N-bis(4-methoxybenzyl)sulfamoyl)-4-iodo-3-(2-(4-methoxybenzyl)-2H-tetrazol-5-yl)phenylsulfonamido)-2,2-dimethyl-1,3-dioxan-5-yl)methyl) carbamate (1.24 g, 1.20 mmol) and (2-amino-1H-benzo[d]imidazol-4-yl)boronic acid (0.53 g, 3.00 mmol) to afford the title compound: LCMS [M+1]$^+$: 1039.

Step I: 4-(2-Amino-1H-benzo[d]imidazol-4-yl)-N-1-(1-amino-3-hydroxy-2-(hydroxymethyl) propan-2-yl)-3-(2H-tetrazol-5-yl)benzene-1,2-disulfonamide The title compound was prepared as described for EXAMPLE 244, step C, using tert-butyl((5-(4-(2-amino-1H-benzo[d]imidazol-4-yl)-2-(N,N-bis(4-methoxybenzyl) sulfamoyl)-3-(2-(4-methoxybenzyl)-2H-tetrazol-5-yl)phenylsulfonamido)-2,2-dimethyl-1,3-dioxan-5-yl)methyl)carbamate (0.50 g, 0.48 mmol) to afford the crude product. The crude product was purified by Prep-HPLC with the following conditions: Column: XBridge C18 OBD Prep Column, 100 Å, 5 µm, 19 mm×250 mm; Mobile Phase A: water with 10 mmol/L NH$_4$HCO$_3$, Mobile Phase B: ACN; Flow rate: 20 mL/min; Gradient: 3% B to 25% B in 9 min; Detector: 254 and 210 nm. The fractions containing desired product were combined and concentrated under vacuum to afford the title compound: LCMS [M+1]$^+$: 539; $^1$H NMR (300 MHz, DMSO-d$_6$): δ 8.19 (d, J=8.4 Hz, 1H), 7.98 (d, J=8.4 Hz, 1H), 7.49 (brs, 2H), 6.92 (dd, J=7.7 Hz, 1.1 Hz, 1H), 6.51 (t, J=7.8 Hz, 1H), 6.26 (s, 2H), 6.07 (d, J=7.7 Hz, 1H), 5.37 (brs, 2H), 3.57-3.39 (m, 4H), 3.19 (s, 2H).

Example 248

(3R)-3-{[4-(2-amino-1H-1,3-benzodiazol-4-yl)-2-sulfamoyl-3-(2H-1,2,3,4-tetrazol-5-yl)benzene]sulfonamido}-1-(2-aminoethyl)-1-methylpyrrolidin-1-ium; methaneperoxoate

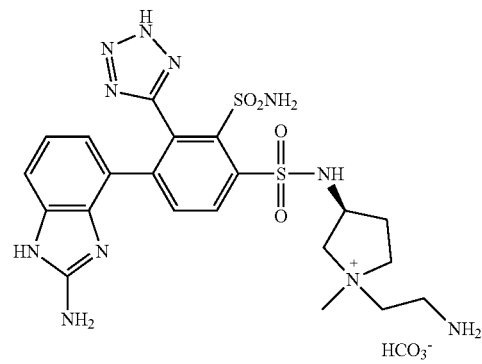

Step A: (R)-tert-butyl(2-(3-(2-(N,N-bis(4-methoxybenzyl)sulfamoyl)-4-iodo-3-(2-(4-methoxybenzyl)-2H-tetrazol-5-yl)phenylsulfonamido)pyrrolidin-1-yl) ethyl)carbamate To a solution of 2-(N,N-bis(4-methoxybenzyl)sulfamoyl)-4-iodo-3-(1-(4-methoxybenzyl)-1H-tetrazol-5-yl)benzenesulfinic acid (2.50 g, 3.22 mmol) in THF (40 mL) was added NCS (0.86 g, 6.45 mmol) at room temperature under nitrogen. The solution was stirred at room temperature for 1 hour. To the resulting solution was added (R)-tert-butyl (2-(3-aminopyrrolidin-1-yl)ethyl)carbamate (1.48 g, 6.45 mmol) and TEA (1.35 mL, 9.67 mmol) at 0° C. The resulting mixture was stirred for 1 hour at room temperature under nitrogen. The resulting solution was diluted with EA (100 mL), and then washed with saturated Na$_2$SO$_3$ (2×50 mL). The organic layer was dried over anhydrous Na$_2$SO$_4$ and filtered. The filtrate was concentrated under vacuum. The residue was purified by a silica gel column chromatography, eluted with 70% EA in PE. The fractions containing desired product were combined and concentrated under vacuum to afford the title compound: LCMS [M+1]$^+$: 1003.

Step B: (3R)-3-(2-(N,N-bis(4-methoxybenzyl)sulfamoyl)-4-iodo-3-(2-(4-methoxybenzyl)-2H-tetrazol-5-yl)phenylsulfonamido)-1-(2-((tert-butoxycarbonyl) amino)ethyl)-1-methylpyrrolidin-1-ium iodide To a solution of (R)-tert-butyl(2-(3-(2-(N,N-bis(4-methoxybenzyl)sulfamoyl)-4-iodo-3-(2-(4-methoxybenzyl)-2H-tetrazol-5-yl)phenylsulfonamido)pyrrolidin-1-yl) ethyl)carbamate (1.20 g, 1.20 mmol) in acetone (10 mL) was added iodomethane (0.68 g, 4.79 mmol). The reaction mixture was stirred for 3 hours at room temperature under nitrogen. The resulting solution was concentrated under vacuum to afford the title compound, which was used in the next step without further purification. LCMS [M−I+H]+: 1017.

Step C: (3R)-3-(4-(2-amino-1H-benzo[d]imidazol-4-yl)-2-(N,N-bis(4-methoxybenzyl) sulfamoyl)-3-(2-(4-methoxybenzyl)-2H-tetrazol-5-yl)phenylsulfonamido)-1-(2-((tert-butoxycarbonyl)amino)ethyl)-1-methylpyrrolidin-1-ium iodide To a solution of (3R)-3-(2-(N,N-bis(4-methoxybenzyl) sulfamoyl)-4-iodo-3-(2-(4-methoxybenzyl)-2H-tetrazol-5-yl)phenylsulfonamido)-1-(2-((tert-butoxycarbonyl)amino)ethyl)-1-methylpyrrolidin-1-ium iodide (1.60 g, 1.40 mmol) in 1,4-dioxane (20 mL) and water (5 mL) was added (2-amino-1H-benzo[d]imidazol-4-yl)boronic acid (0.62 g, 3.49 mmol), Pd(PPh₃)₄ (0.32 g, 0.28 mmol) and Na₂CO₃ (0.44 g, 4.19 mmol) at room temp. The reaction mixture was degassed with nitrogen three times and stirred for 4 hours at 80° C. under nitrogen. The resulting mixture was diluted with water (50 mL). The aqueous phase was extracted with EA (3×50 mL). The combined organic layers were washed with brine (2×50 mL), dried over anhydrous Na₂SO₄ and filtered. The filtrate was concentrated under vacuum to afford the title compound, which was used in the next step without further purification: LCMS [M−I+H]+: 1022.

Step D: (3R)-3-{[4-(2-amino-1H-1,3-benzodiazol-4-yl)-2-sulfamoyl-3-(2H-1,2,3,4-tetrazol-5-yl)benzene]sulfonamido}-1-(2-aminoethyl)-1-methylpyrrolidin-1-ium; methaneperoxoate The title compound was prepared as described for EXAMPLE 244, step C, using (3R)-3-(4-(2-amino-1H-benzo[d]imidazol-4-yl)-2-(N,N-bis(4-methoxybenzyl) sulfamoyl)-3-(2-(4-methoxybenzyl)-2H-tetrazol-5-yl)phenylsulfonamido)-1-(2-((tert-butoxycarbonyl)amino)ethyl)-1-methylpyrrolidin-1-ium iodide (1.40 g, 1.22 mmol) to afford the crude product. The crude product was purified by Prep-HPLC with the following conditions: Column: X Bridge C18 OBD Prep Column 100 Å, 10 μm, 19 mm×250 mm; Mobile Phase A: water with 10 mmol NH₄HCO₃, Mobile Phase B: ACN; Flow rate: 20 mL/min; Gradient: 5% B to 25% B in 8 min; Detector: 254 and 220 nm; Retention time: 6.72 min. The fractions containing desired product were combined and concentrated under vacuum to afford the title compound: LCMS [M−HCO₃−]+: 562; ¹H NMR (400 MHz, DCl): δ 6.59 (d, J=8.3 Hz, 1H), 6.08-5.96 (m, 1H), 5.29 (d, J=8.2 Hz, 1H), 5.10-5.04 (m, 1H), 4.81 (d, J=7.6 Hz, 0.5H), 4.65 (d, J=7.6 Hz, 0.5H), 2.53 (d, J=13.2 Hz, 1H), 2.13-1.97 (m, 1H), 1.97-1.61 (m, 5H), 1.58-1.55 (m, 2H), 1.32-1.29 (m, 1H), 1.19-1.17 (m, 2H), 0.72-0.65 (m, 1H), 0.50-0.27 (m, 1H).

Example 249

(3S)-3-{[4-(2-amino-1H-1,3-benzodiazol-4-yl)-2-sulfamoyl-3-(2H-1,2,3,4-tetrazol-5-yl)benzene]sulfonamido}-1-(2-aminoethyl)-1-methylpyrrolidin-1-ium methaneperoxoate

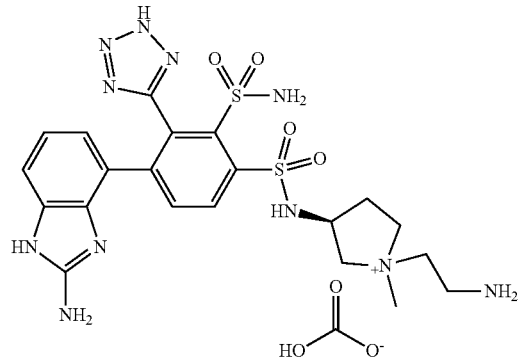

Step A: (S)-tert-butyl (2-(3-(2-(N,N-bis(4-methoxybenzyl)sulfamoyl)-4-iodo-3-(2-(4-methoxybenzyl)-2H-tetrazol-5-yl)phenylsulfonamido)pyrrolidin-1-yl)ethyl)carbamate To a solution of 2-(N,N-bis(4-methoxybenzyl)sulfamoyl)-4-iodo-3-(1-(4-methoxybenzyl)-1H-tetrazol-5-yl)benzenesulfinic acid (2.00 g, 2.58 mmol) in THF (40 mL) was added NCS (0.69 g, 5.16 mmol) at room temperature under nitrogen. The solution was stirred at room temperature for 1 hour. To the resulting solution was added (S)-tert-butyl (2-(3-aminopyrrolidin-1-yl)ethyl)carbamate (1.18 g, 5.16 mmol) and TEA (1.10 mL, 7.74 mmol) at 0° C. The mixture was stirred for 1 hour at room temperature under nitrogen. The resulting mixture was diluted with EA (100 mL), and then washed with saturated Na₂SO₃ (2×50 mL). The organic layer was dried over anhydrous Na₂SO₄ and filtered. The filtrate was concentrated under vacuum. The residue was purified by silica gel column chromatography, eluted with 70% EA in PE. The fractions containing desired product were combined and concentrated under vacuum to afford the title compound: LCMS [M+1]+: 1003.

Step B: (3S)-3-(2-(N,N-bis(4-methoxybenzyl)sulfamoyl)-4-iodo-3-(2-(4-methoxybenzyl)-2H-tetrazol-5-yl)phenylsulfonamido)-1-(2-((tert-butoxycarbonyl)amino)ethyl)-1-methylpyrrolidin-1-ium iodide To a solution of (S)-tert-butyl(2-(3-(2-(N,N-bis(4-methoxybenzyl)sulfamoyl)-4-iodo-3-(2-(4-methoxybenzyl)-2H-tetrazol-5-yl)phenylsulfonamido)pyrrolidin-1-yl)ethyl)carbamate (1.20 g, 1.20 mmol) in acetone (10 mL) was added iodomethane (0.68 g, 4.79 mmol). The reaction mixture was degassed nitrogen three times. The reaction mixture was stirred for 3 hours at room temperature under nitrogen. The resulting solution was concentrated under vacuum to afford the title compound, which was used in the next step without further purification: LCMS [M−I+H]+: 1017.

Step C: (3S)-3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-1-(2-((tert-butoxycarbonyl) amino)ethyl)-1-methylpyrrolidin-1-ium iodide To a solution of (3S)-3-(2-(N,N-bis(4-methoxybenzyl) sulfamoyl)-4-iodo-3-(2-(4-methoxybenzyl)-2H-tetrazol-5-yl)phenylsulfonamido)-1-(2-((tert-butoxycarbonyl)amino) ethyl)-1-methylpyrrolidin-1-ium iodide (1.50 g, 1.31 mmol) in 1,4-dioxane (20 mL) and water (5 mL) were added (2-amino-1H-benzo[d]imidazol-4-yl)boronic acid (0.58 g, 3.28 mmol), Pd(PPh$_3$)$_4$ (0.30 g, 0.26 mmol) and Na$_2$CO$_3$ (0.42 g, 3.93 mmol) at room temperature. The reaction mixture was degassed with nitrogen three times and stirred for 4 hours at 80° C. under nitrogen. The resulting mixture was diluted with water (50 mL). The aqueous phase was extracted with EA (3×50 mL). The combined organic layers were washed with brine (50 mL), dried over anhydrous Na$_2$SO$_4$ and filtered. The filtrate was concentrated under vacuum to afford the title compound, which was used in the next step without further purification: LCMS [M]$^+$: 1022.

Step D: (3S)-3-{[4-(2-amino-1H-1,3-benzodiazol-4-yl)-2-sulfamoyl-3-(2H-1,2,3,4-tetrazol-5-yl)benzene] sulfonamido}-1-(2-aminoethyl)-1-methylpyrrolidin-1-ium methaneperoxoate The title compound was prepared as described for EXAMPLE 244, step C, using (3S)-3-(4-(2-amino-1H-benzo[d]imidazol-4-yl)-2-(N,N-bis(4-methoxybenzyl) sulfamoyl)-3-(2-(4-methoxybenzyl)-2H-tetrazol-5-yl)phenylsulfonamido)-1-(2-((tert-butoxycarbonyl)amino)ethyl)-1-methylpyrrolidin-1-ium iodide (1.00 g, 0.87 mmol) to afford the crude product. The crude product was purified by Prep-HPLC with the following conditions: Column: X Bridge C18 OBD Prep Column 100 Å, 10 µm, 19 mm×250 mm; Mobile Phase A: water (10 mmol/L NH$_4$HCO$_3$), Mobile Phase B: ACN; Flow rate: 20 mL/min; Gradient: 5% B to 5% B in 2 min; Detector: 254 and 220 nm; Retention time: 6.72 min. The fractions containing desired product were combined and concentrated under vacuum to afford the title compound: LCMS [M−HCO$_3$$^-$]$^+$: 562; $^1$H NMR (400 MHz, DCl): δ 6.60 (d, J=8.3 Hz, 1H), 6.04 (d, J=8.2 Hz, 1H), 5.31 (d, J=8.1 Hz, 1H), 5.13-5.04 (m, 1H), 4.83 (d, J=8.0 Hz, 0.5H), 4.66 (d, J=8.0 Hz, 0.5H), 2.55-2.53 (m, 1H), 2.12-1.97 (m, 1H), 1.97-1.61 (m, 5H), 1.58-1.55 (m, 2H), 1.32-1.29 (m, 1H), 1.19-1.15 (m, 2H), 0.72-0.65 (m, 1H), 0.50-0.27 (m, 1H).

Example 250

(S)-4-(2-amino-1H-benzo[d]imidazol-4-yl)-N1-((3-aminopyrrolidin-3-yl)methyl)-3-(2H-tetrazol-5-yl) benzene-1,2-disulfonamide

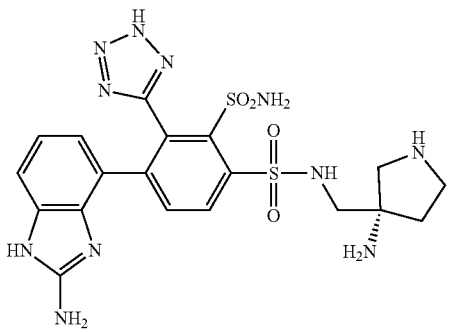 [SMILES: Nc1nc2c(-c3ccc(S(=O)(=O)NC[C@]4(N)CCNC4)c(S(N)(=O)=O)c3-c3nn[nH]n3)cccc2[nH]1]

Step A: 3-(2-Amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide The title compound was prepared as described for EXAMPLE 246, step C, using 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (2.0 g, 2.28 mmol) and (2-amino-1H-benzo[d]imidazol-4-yl)boronic acid (1.62 g, 9.13 mmol) to afford the title compound: LCMS [M+1]$^+$: 881.

Step B: 4-(2-Amino-1H-benzo[d]imidazol-4-yl)-2-(N,N-bis(4-methoxybenzyl)sulfamoyl)-3-(2-(4-methoxybenzyl)-2H-tetrazol-5-yl)benzenesulfinic acid To a stirred solution of 3-(2-amino-1H-benzo[d]imidazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzene sulfonamide (1.30 g, 1.48 mmol) in THF (13 mL) was added TBAF (1.54 g, 5.90 mmol) at 0° C. The reaction solution was stirred for 1 hour at room temp. The resulting solution was diluted with EA (100 mL), and then washed with saturated aqueous KHSO$_4$ (5×100 mL). The organic phase was dried over anhydrous Na$_2$SO$_4$ and filtered. The filtrate was concentrated under vacuum to afford the title compound: LCMS [M+1]$^+$: 781.

Step C: (S)-tert-butyl-3-amino-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl) phenyl sulfonamido) methyl)pyrrolidine-1-carboxylate To a stirred solution of 4-(2-amino-1H-benzo[d]imidazol-4-yl)-2-(N,N-bis(4-methoxybenzyl)sulfamoyl)-3-(2-(4-methoxybenzyl)-2H-tetrazol-5-yl) benzenesulfinic acid (0.50 g, 0.64 mmol) in THF (5 mL) were added (R)-tert-butyl 3-amino-3-(aminomethyl)pyrrolidine-1-carboxylate (0.28 g, 1.28 mmol) and TEA (0.27 mL, 1.92 mmol) at ice bath. The resulting solution was degassed under nitrogen three times and stirred for 15 minutes. NCS (0.17 g, 1.28 mmol) was added to the reaction solution slowly. The mixture was stirred for 2 hours at 15° C. under nitrogen. The resulting mixture was diluted with water (100 mL), and then extracted with EA (3×100 mL). The combined organic layers was washed with brine (3×100 mL), dried over anhydrous Na$_2$SO$_4$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]$^+$: 994.

Step D: (S)-4-(2-amino-1H-benzo[d]imidazol-4-yl)-N1-((3-aminopyrrolidin-3-yl)methyl)-3-(2H-tetrazol-5-yl)benzene-1,2-disulfonamide The title compound was prepared as described for EXAMPLE 244, step C, using (S)-tert-butyl-3-amino-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido) methyl)pyrrolidine-1-carboxylate (0.40 g, 0.40 mmol) to afford the crude product. The crude product was purified by Prep-HPLC with the following conditions: Column: X Bridge C18 OBD Prep Column 100 Å, 10 μm, 19 mm×250 mm; Mobile Phase A: water with 10 mmol/L NH₄HCO₃, Mobile Phase B: ACN; Flow rate: 20 mL/min; Gradient: 5% B to 30% B in 7 min; Detector: 254 and 220 nm. The fractions containing desired product were combined and concentrated under vacuum to afford the title compound: LCMS [M+1]$^+$: 534; $^1$H NMR (400 MHz, CD₃OD+DCl): δ 8.72 (d, J=8.0 Hz, 1H), 8.04 (d, J=8.4 Hz, 1H), 7.32 (dd, J=7.2 Hz, 0.8 Hz, 1H), 7.15 (t, J=8.0 Hz, 1H), 6.84-6.81 (m, 1H), 3.83-3.80 (m, 1H), 3.73-3.70 (m, 1H), 3.63-3.60 (m, 4H), 2.58-2.55 (m, 1H), 2.43-2.40 (m, 1H).

Example 251

(R)-4-(2-amino-1H-benzo[d]imidazol-4-yl)-N1-((3-aminopyrrolidin-3-yl)methyl)-3-(2H-tetrazol-5-yl)benzene-1,2-disulfonamide

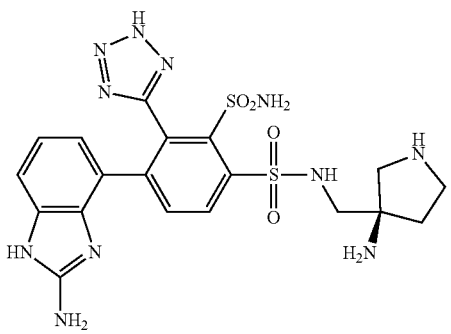 [SMILES: Nc1nc2c(-c3ccc(S(=O)(=O)NC[C@@]4(N)CCNC4)c(S(N)(=O)=O)c3-c3nn[nH]n3)cccc2[nH]1]

Step A: (R)-tert-butyl-3-amino-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)methyl)pyrrolidine-1-carboxylate The title compound was prepared as described for EXAMPLE 250, step C, using (S)-tert-butyl 3-amino-3-(aminomethyl)pyrrolidine-1-carboxylate (0.21 g, 0.96 mmol) to afford the title compound as a solid: LCMS [M+1] 994.

Step B: (R)-4-(2-amino-1H-benzo[d]imidazol-4-yl)-N1-((3-aminopyrrolidin-3-yl)methyl)-3-(2H-tetrazol-5-yl)benzene-1,2-disulfonamide The title compound was prepared as described for EXAMPLE 244, step C, using (R)-tert-butyl-3-amino-3-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido) methyl)pyrrolidine-1-carboxylate to afford the crude product. The crude product was purified by Prep-HPLC with the following conditions: Column: X Bridge C18 OBD Prep Column 100 Å, 10 μm, 19 mm×250 mm; Mobile Phase A: water with 10 mmol/L NH₄HCO₃, Mobile Phase B: ACN; Flow rate: 20 mL/min; Gradient: 5% B to 30% B in 7 min; Detector: 254 and 220 nm; Retention time: 5.81 min. The fractions containing desired product were combined and concentrated under vacuum to afford the title compound: LCMS [M+1]$^+$: 534; $^1$H NMR (400 MHz, CD₃OD+DCl): δ 8.72 (d, J=8.4 Hz, 1H), 8.04 (d, J=8.0 Hz, 1H), 7.32 (dd, J=7.2 Hz, 1.2 Hz, 1H), 7.15 (t, J=8.0 Hz, 1H), 6.82 (m 1H), 3.83-3.80 (m, 1H), 3.73-3.70 (m, 1H), 3.63-3.60 (m, 4H), 2.58-2.55 (m, 1H), 2.43-2.40 (m, 1H).

EXAMPLES 252-268 in the Table below were prepared in an analogous fashion to that described for EXAMPLE 244, starting from 2-(N,N-bis(4-methoxybenzyl) sulfamoyl)-4-iodo-3-(1-(4-methoxybenzyl)-1H-tetrazol-5-yl) benzenesulfinic acid and the corresponding boronic acids or boronic esters and protected amines (typically Boc protected), which were prepared as described herein, or which were available from commercial sources.

| EX. No. | Structure | Chemical Name | LC/MS [M + H]$^+$ |
|---|---|---|---|
| 252 | 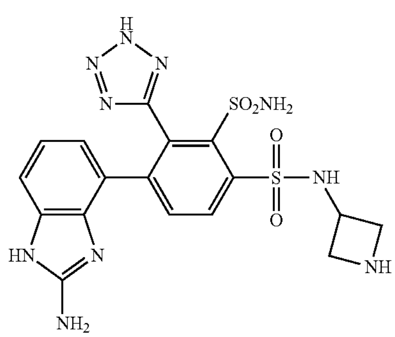 [SMILES: Nc1nc2c(-c3ccc(S(=O)(=O)NC4CNC4)c(S(N)(=O)=O)c3-c3nn[nH]n3)cccc2[nH]1] | 4-(2-amino-1H-benzo[d]imidazol-4-yl)-N1-(azetidin-3-yl)-3-(2H-tetrazol-5-yl)benzene-1,2-disulfonamide | 491 |

| EX. No. | Structure | Chemical Name | LC/MS [M + H]+ |
|---|---|---|---|
| 253 | 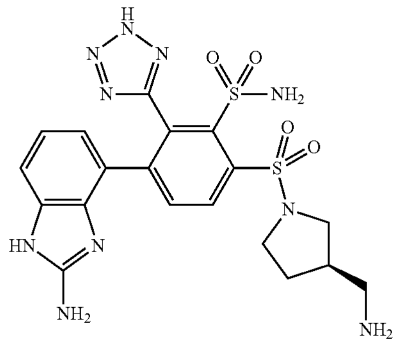 [SMILES: NC[C@H]1CCN(S(=O)(=O)c2ccc(-c3cccc4[nH]c(N)nc34)c(-c3nn[nH]n3)c2S(N)(=O)=O)C1] | (R)-3-(2-amino-1H-benzo[d]imidazol-4-yl)-6-((3-(aminomethyl)pyrrolidin-1-yl)sulfonyl)-2-(2H-tetrazol-5-yl)benzenesulfonamide | 519 |
| 254 | 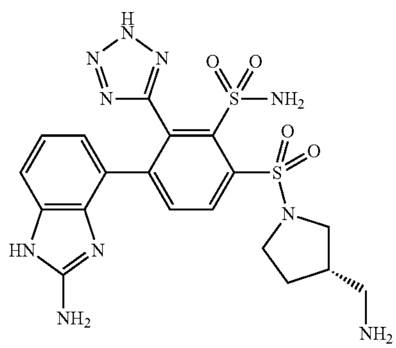 [SMILES: NC[C@@H]1CCN(S(=O)(=O)c2ccc(-c3cccc4[nH]c(N)nc34)c(-c3nn[nH]n3)c2S(N)(=O)=O)C1] | (S)-4-(2-amino-1H-benzo[d]imidazol-7-yl)-N1-methyl-N1-(pyrrolidin-3-yl)-3-(1H-tetrazol-5-yl)benzene-1,2-disulfonamide | 519 |
| 255 | 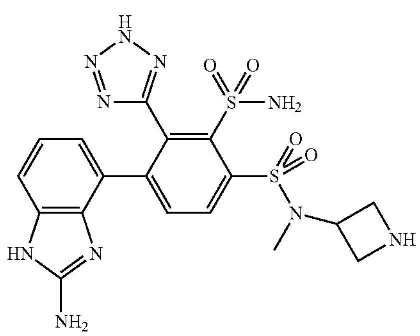 [SMILES: CN(C1CNC1)S(=O)(=O)c1ccc(-c2cccc3[nH]c(N)nc23)c(-c2nn[nH]n2)c1S(N)(=O)=O] | 4-(2-amino-1H-benzo[d]imidazol-4-yl)-N1-(azetidin-3-yl)-N1-methyl-3-(2H-tetrazol-5-yl)benzene-1,2-disulfonamide | 505 |
| 256 | 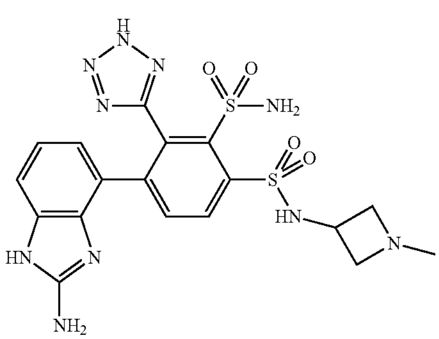 [SMILES: CN1CC(NS(=O)(=O)c2ccc(-c3cccc4[nH]c(N)nc34)c(-c3nn[nH]n3)c2S(N)(=O)=O)C1] | 4-(2-amino-1H-benzo[d]imidazol-4-yl)-N1-(1-methylazetidin-3-yl)-3-(2H-tetrazol-5-yl)benzene-1,2-disulfonamide | 505 |

| EX. No. | Structure | Chemical Name | LC/MS [M + H]+ |
|---|---|---|---|
| 257 | 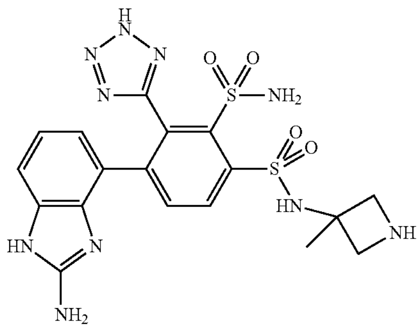 [SMILES: CC1(NS(=O)(=O)c2ccc(-c3cccc4[nH]c(N)nc34)c(-c3nn[nH]n3)c2S(N)(=O)=O)CNC1] | 4-(2-amino-1H-benzo[d]imidazol-4-yl)-N1-(3-methylazetidin-3-yl)-3-(2H-tetrazol-5-yl)benzene-1,2-disulfonamide | 505 |
| 258 | 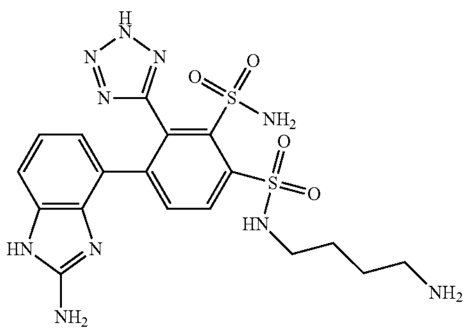 [SMILES: NCCCCNS(=O)(=O)c1ccc(-c2cccc3[nH]c(N)nc23)c(-c2nn[nH]n2)c1S(N)(=O)=O] | 4-(2-amino-1H-benzo[d]imidazol-7-yl)-N1-(4-aminobutyl)-3-(2H-tetrazol-5-yl)benzene-1,2-disulfonamide | 507 |
| 259 | 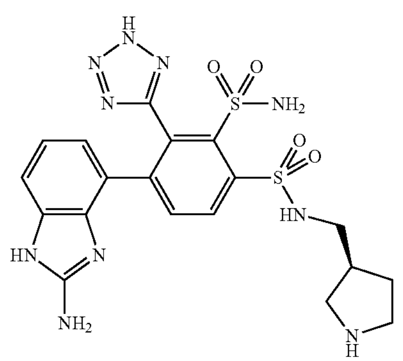 [SMILES: Nc1nc2c(-c3ccc(S(=O)(=O)NC[C@H]4CCNC4)c(S(N)(=O)=O)c3-c3nn[nH]n3)cccc2[nH]1] | (S)-4-(2-amino-1H-benzo[d]imidazol-4-yl)-N1-(pyrrolidin-3-ylmethyl)-3-(2H-tetrazol-5-yl)benzene-1,2-disulfonamide | 519 |
| 260 | 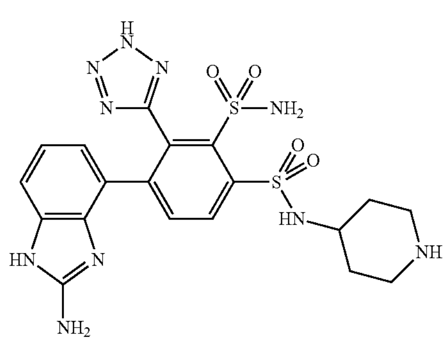 [SMILES: Nc1nc2c(-c3ccc(S(=O)(=O)NC4CCNCC4)c(S(N)(=O)=O)c3-c3nn[nH]n3)cccc2[nH]1] | 4-(2-amino-1H-benzo[d]imidazol-4-yl)-N1-(piperidin-4-yl)-3-(1H-tetrazol-5-yl)benzene-1,2-disulfonamide | 519 |

-continued

| EX. No. | Structure | Chemical Name | LC/MS [M + H]+ |
|---|---|---|---|
| 261 | 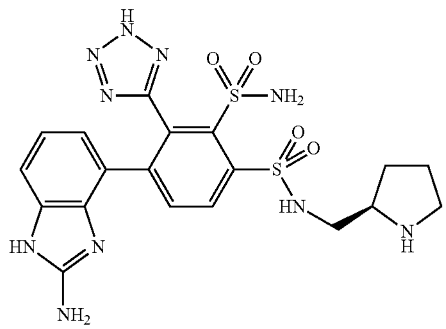 [SMILES: Nc1nc2c(-c3ccc(S(=O)(=O)NC[C@H]4CCCN4)c(S(N)(=O)=O)c3-c3nn[nH]n3)cccc2[nH]1] | (R)-4-(2-amino-1H-benzo[d]imidazol-4-yl)-N1-(pyrrolidin-2-ylmethyl)-3-(2H-tetrazol-5-yl)benzene-1,2-disulfonamide | 519 |
| 262 | 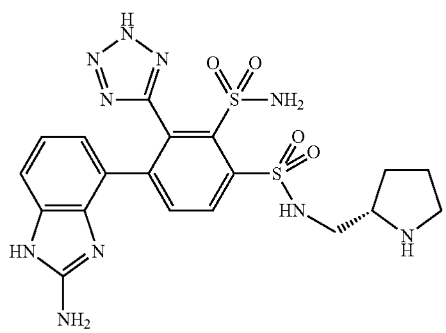 [SMILES: Nc1nc2c(-c3ccc(S(=O)(=O)NC[C@@H]4CCCN4)c(S(N)(=O)=O)c3-c3nn[nH]n3)cccc2[nH]1] | (S)-4-(2-amino-1H-benzo[d]imidazol-4-yl)-N1-(pyrrolidin-2-ylmethyl)-3-(2H-tetrazol-5-yl)benzene-1,2-disulfonamide | 519 |
| 263 | 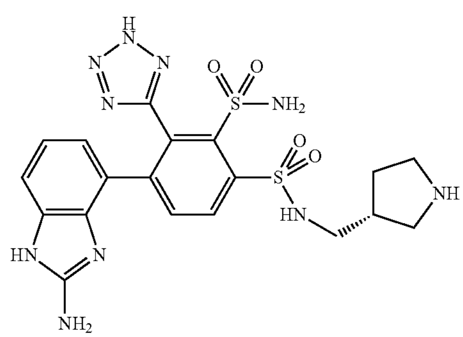 [SMILES: Nc1nc2c(-c3ccc(S(=O)(=O)NC[C@@H]4CCNC4)c(S(N)(=O)=O)c3-c3nn[nH]n3)cccc2[nH]1] | (R)-4-(2-amino-1H-benzo[d]imidazol-4-yl)-N1-(pyrrolidin-3-ylmethyl)-3-(2H-tetrazol-5-yl)benzene-1,2-disulfonamide | 519 |
| 264 | 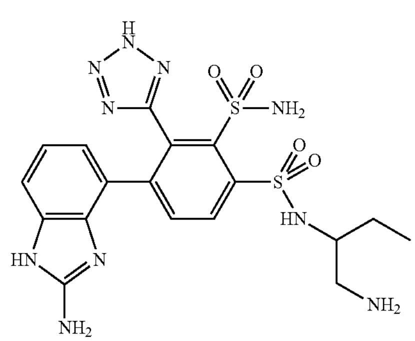 [SMILES: CCC(CN)NS(=O)(=O)c1ccc(-c2cccc3[nH]c(N)nc23)c(-c2nn[nH]n2)c1S(N)(=O)=O] | (S)-4-(2-amino-1H-benzo[d]imidazol-4-yl)-N1-(1-aminobutan-2-yl)-3-(2H-tetrazol-5-yl)benzene-1,2-disulfonamide | 507 |

| EX. No. | Structure | Chemical Name | LC/MS [M + H]+ |
|---|---|---|---|
| 265 | 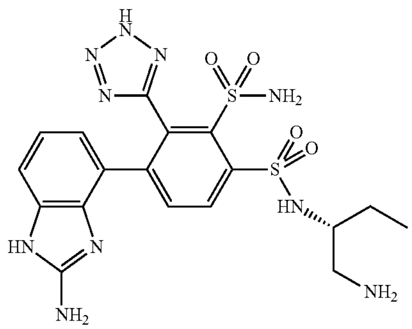 [SMILES: CC[C@H](CN)NS(=O)(=O)c1ccc(-c2cccc3[nH]c(N)nc23)c(-c2nn[nH]n2)c1S(N)(=O)=O] | (R)-4-(2-amino-1H-benzo[d]imidazol-4-yl)-N1-(1-aminobutan-2-yl)-3-(2H-tetrazol-5-yl)benzene-1,2-disulfonamide | 507 |
| 266 | 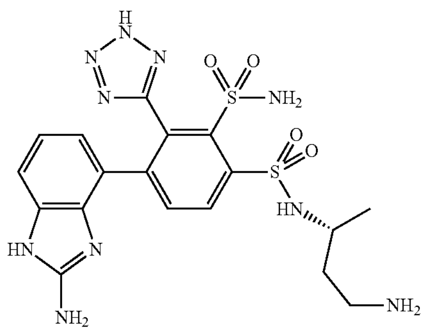 [SMILES: C[C@H](CCN)NS(=O)(=O)c1ccc(-c2cccc3[nH]c(N)nc23)c(-c2nn[nH]n2)c1S(N)(=O)=O] | (R)-4-(2-amino-1H-benzo[d]imidazol-4-yl)-N1-(4-aminobutan-2-yl)-3-(2H-tetrazol-5-yl)benzene-1,2-disulfonamide | 507 |
| 267 | 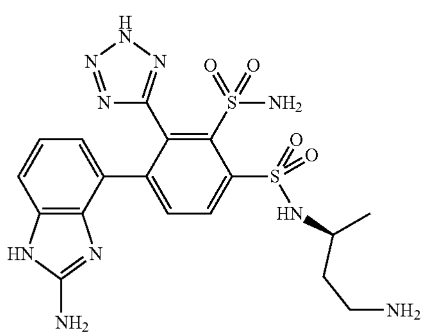 [SMILES: C[C@@H](CCN)NS(=O)(=O)c1ccc(-c2cccc3[nH]c(N)nc23)c(-c2nn[nH]n2)c1S(N)(=O)=O] | (S)-4-(2-amino-1H-benzo[d]imidazol-4-yl)-N1-(4-aminobutan-2-yl)-3-(2H-tetrazol-5-yl)benzene-1,2-disulfonamide | 507 |
| 268 | 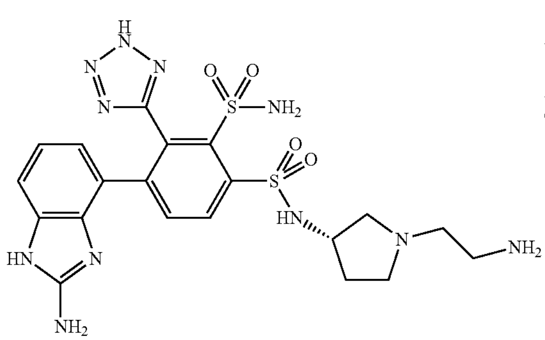 [SMILES: NCCN1CC[C@H](NS(=O)(=O)c2ccc(-c3cccc4[nH]c(N)nc34)c(-c3nn[nH]n3)c2S(N)(=O)=O)C1] | (S)-4-(2-amino-1H-benzo[d]imidazol-4-yl)-N1-(1-(2-aminoethyl)pyrrolidin-3-yl)-3-(2H-tetrazol-5-yl)benzene-1,2-disulfonamide | 548 |

Example 269

2-Amino-N-(4'-(N—((R)-pyrrolidin-3-yl)sulfamoyl)-3'-sulfamoyl-2'-(2H-tetrazol-5-yl)-3,4,5,6-tetrahydro-[1,1'-biphenyl]-3-yl)acetamide

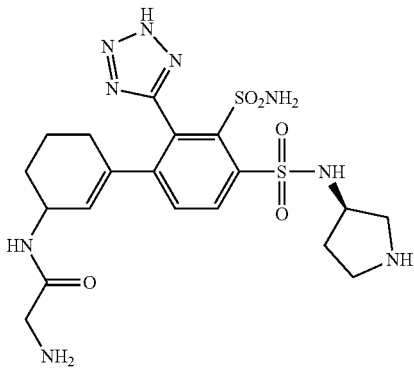 [SMILES: NCC(=O)NC1C=C(c2ccc(S(=O)(=O)N[C@@H]3CCNC3)c(S(N)(=O)=O)c2-c2nn[nH]n2)CCC1]

Step A: (R)-tert-butyl-3-(3-(N,N-bis(4-methoxybenzyl)sulfamoyl)-2-(2-(4-methoxybenzyl)-2H-tetrazol-5-yl)-5'-oxo-2',3',4',5'-tetrahydro-[1,1'-biphenyl]-4-ylsulfonamido) pyrrolidine-1-carboxylate To a solution of (R)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (5.0 g, 5.21 mmol) in 1,4-dioxane (12 mL) and water (3 mL) was added $Na_2CO_3$ (2.76 g, 26.00 mmol), 3-oxocyclohex-1-enylboronic acid (4.63 g, 33.07 mmol) and $Pd(PPh_3)_4$ (1.20 g, 1.00 mmol) at room temperature. The mixture was degassed with nitrogen three times and stirred at 80° C. for 6 hours under nitrogen. The resulting mixture was diluted with water (150 mL) and extracted with EA (3×200 mL). The combined organic layers were washed with water (3×500 mL) and brine (3×500 mL), dried over anhydrous $Na_2SO_4$ and filtered. The filtrate was concentrated under vacuum. The residue was purified by silica gel column chromatography, eluted with 70% EA in PE. The fractions containing desired product were combined and concentrated under vacuum to afford the title compound: LCMS $[M+1]^+$: 928.

Step B: (3R)-tert-butyl-3-(3-(N,N-bis(4-methoxybenzyl)sulfamoyl)-5'-hydroxy-2-(2-(4-pyrrolidine-1-carboxylate To a solution of (R)-tert-butyl-3-(3-(N,N-bis(4-methoxybenzyl)sulfamoyl)-2-(2-(4-methoxybenzyl)-2H-tetrazol-5-yl)-5'-oxo-2',3',4',5'-tetrahydro-[1,1'-biphenyl]-4-yl-sulfonamido)pyrrolidine-1-carboxylate (3.80 g, 4.09 mmol) in MeOH (20 mL) was added $NaBH_4$ (0.93 g, 24.60 mmol) at 0° C. The reaction mixture was stirred at room temperature 16 hours under nitrogen. The resulting mixture was quenched with water (150 mL), and then extracted with EA (3×150 mL). The combined organic layers were washed with water (3×300 mL) and brine (3×300 mL), dried over anhydrous $Na_2SO_4$ and filtered. The filtrate was concentrated under vacuum. The residue was purified by silica gel column chromatography, eluted with 50% EA in PE. The fractions containing desired product were combined and concentrated under vacuum to afford the title compound: LCMS $[M+1]^+$: 930.

Step C: (3R)-tert-butyl 3-(5'-azido-3-(N,N-bis(4-methoxybenzyl)sulfamoyl)-2-(2-(4-methoxy benzyl)-2H-tetrazol-5-yl)-2',3',4',5'-tetrahydro-[1,1'-biphenyl]-4-yl-sulfonamido) pyrrolidine-1-carboxylate To a solution of (3R)-tert-butyl-3-(3-(N,N-bis(4-methoxybenzyl)sulfamoyl)-5'-hydroxy-2-(2-(4-methoxybenzyl)-2H-tetrazol-5-yl)-2',3',4',5'-tetrahydro-[1,1'-biphenyl]-4-yl sulfonamido)pyrrolidine-1-carboxylate (2.60 g, 2.80 mmol) in toluene (15 mL) was added DBU (3.80 g, 25.20 mmol) and DPPA (4.60 g, 16.77 mmol). The reaction mixture was stirred at room temperature for 2 hours under nitrogen. The resulting mixture was quenched with water (100 mL), and then extracted with EA (3×100 mL). The combined organic layers were washed with water (3×200 mL) and brine (3×200 mL), dried over anhydrous $Na_2SO_4$ and filtered. The filtrate was concentrated under vacuum. The residue was purified by silica gel column chromatography, eluted with 20% EA in PE. The fractions containing desired product were combined and concentrated under vacuum to afford the title compound: $[M+1]^+$: 955.

Step D: (3R)-tert-butyl-3-(5'-amino-3-(N,N-bis(4-methoxybenzyl)sulfamoyl)-2-(2-(4-methoxybenzyl)-2H-tetrazol-5-yl)-2',3',4',5'-tetrahydro-[1,1'-biphenyl]-4-yl-sulfonamido) pyrrolidine-1-carboxylate To a solution of (3R)-tert-butyl 3-(5'-azido-3-(N,N-bis(4-methoxybenzyl)sulfamoyl)-2-(2-(4-methoxybenzyl)-2H-tetrazol-5-yl)-2',3',4',5'-tetrahydro-[1,1'-biphenyl]-4-yl-sulfonamido)pyrrolidine-1-carboxylate (2.0 g, 2.09 mmol) in THF (9 mL) and water (3 mL) was added triphenylphosphine (0.72 g, 2.7 mmol) and potassium hydroxide (0.18 g, 3.1 mmol) at room temp. The mixture was stirred at room temp for 4 hours. The resulting mixture was diluted with water (100 mL), and then extracted with EA (3×100 mL). The combined organic layers was washed with water (3×200 mL) and brine (3×200 mL), dried over anhydrous $Na_2SO_4$ and filtered. The filtrate was concentrated under vacuum. The residue was purified by silica gel column chromatography, eluted with 20% EA in PE. The fractions containing desired product were combined and concentrated under vacuum to afford the title compound: LCMS $[M+1]^+$: 929.

Step E: (3R)-tert-butyl-3-(3-(N,N-bis(4-methoxybenzyl)sulfamoyl)-5'-(2-((tert-butoxycarbonyl)amino)acetamido)-2-(2-(4-methoxybenzyl)-2H-tetrazol-5-yl)-2',3',4',5'-tetrahydro-[1,1'-biphenyl]-4-ylsulfonamido)pyrrolidine-1-carboxylate To a solution (3R)-tert-butyl 3-(5'-amino-3-(N,N-bis(4-methoxybenzyl) sulfamoyl)-2-(2-(4-methoxybenzyl)-2H-tetrazol-5-yl)-2',3',4',5'-tetrahydro-[1,1'-biphenyl]-4-yl-sulfonamido)pyrrolidine-1-carboxylate (1.50 g, 1.61 mmol) in THF (15 mL) was added TEA (0.70 mL, 4.84 mmol), 2-((tert-butoxycarbonyl)amino)acetic acid (0.28 g, 1.61 mmol) and HATU (1.80 g, 4.80 mmol) at room temp. The reaction mixture was degassed with nitrogen three times and stirred for 16 hours at room temp. The resulting mixture was diluted with water (100 mL), and then extracted with EA (3×100 mL). The combined organic layers were washed with water (3×200 mL) and brine (3×200 mL), dried over anhydrous Na$_2$SO$_4$ and filtered. The filtrate was concentrated under vacuum. The residue was purified by silica gel column chromatography, eluted with 60% EA in PE. The fractions containing desired product were combined and concentrated under vacuum to afford the title compound: LCMS [M+1]$^+$: 1086.

Step F: 2-Amino-N-(4'-(N—((R)-pyrrolidin-3-yl) sulfamoyl)-3'-sulfamoyl-2'-(2H-tetrazol-5-yl)-3,4,5, 6-tetrahydro-[1,1'-biphenyl]-3-yl)acetamide The title compound was prepared as described for EXAMPLE 244, step C, using (3R)-tert-butyl-3-(3-(N,N-bis(4-methoxybenzyl)sulfamoyl)-5'-(2-((tert-butoxycarbonyl)amino)acetamido)-2-(2-(4-methoxybenzyl)-2H-tetrazol-5-yl)-2',3',4',5'-tetrahydro-[1,1'-biphenyl]-4-ylsulfonamido)pyrrolidine-1-carboxylate (1.40 g, 1.30 mmol) to afford the crude product. The crude product was purified by Prep-HPLC with the following conditions: Column: C18 OBD column, 130 Å, 5 μm, 30 mm×50 mm; Mobile Phase A: water with 10 mmol/L NH$_4$HCO$_3$, Mobile Phase B: ACN; Flow rate: 50 mL/min; Gradient: 5% B to 17% B in 5 min; Detector: 254 and 220 nm. The fractions containing desired product were combined and concentrated under vacuum to afford the title compound: LCMS [M+1]$^+$: 526; $^1$H NMR (400 MHz, CD$_3$OD+DCl): δ 8.51 (d, J=8.2 Hz, 1H), 7.83 (d, J=8.2 Hz, 1H), 5.36-5.35 (m, 1H), 4.27-4.16 (m, 2H), 3.66 (s, 2H), 3.40-3.38 (m, 4H), 2.22-2.20 (m, 1H), 2.05-1.92 (m, 3H), 1.73-1.67 (m, 2H), 1.57-1.56 (m, 1H), 1.49-1.39 (m, 1H).

Example 270

2-Amino-N-((3R)-3-(4-(N—((R)-pyrrolidin-3-yl) sulfamoyl)-3-sulfamoyl-2-(2H-tetrazol-5-yl)phenyl) cyclohexyl)acetamide

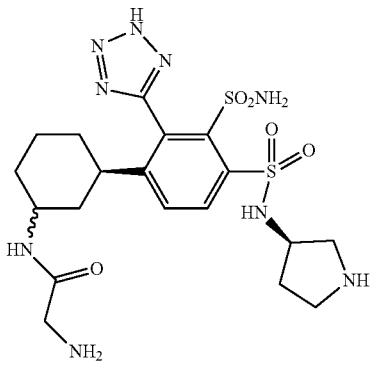 [SMILES: NCC(=O)NC1CCC[C@@H](c2ccc(S(=O)(=O)N[C@@H]3CCNC3)c(S(N)(=O)=O)c2-c2nn[nH]n2)C1]

Step A: 2-Amino-N-((3R)-3-(4-(N—((R)-pyrrolidin-3-yl)sulfamoyl)-3-sulfamoyl-2-(2H-tetrazol-5-yl) phenyl)cyclohexyl)acetamide To a suspension of 2-amino-N-(4'-(N—((R)-pyrrolidin-3-yl)sulfamoyl)-3'-sulfamoyl-2'-(2H-tetrazol-5-yl)-3,4,5,6-tetrahydro-[1,1'-biphenyl]-3-yl)acetamide (0.30 g, 0.57 mmol)) in MeOH (15 mL) was added PtO$_2$ (38.9 mg, 0.17 mmol) and conc. HCl (2.50 mL). The mixture was stirred at 45° C. for 16 hours under hydrogen (20 atm). The resulting mixture was filtered. The filtrate was concentrated under vacuum. The residue was purified by Prep-HPLC with the following conditions: Column: X Bridge BEH130 Prep C18 OBD Column 19×150 mm, 5 μm, 13 nm; Mobile Phase A: water (10 mmol/L NH$_4$HCO$_3$), Mobile Phase B: ACN; Flow rate: 20 mL/min; Gradient: 0% B to 4% B in 10 min, 4% B to 15% in 6 min; Detector: 254 and 220 nm. The fractions containing desired product were combined and concentrated under vacuum to afford the title compound: LCMS [M+1]$^+$: 528; $^1$H NMR (400 MHz, CD$_3$OD+DCl): δ 8.53 (d, J=8.0 Hz, 1H), 8.02 (d, J=8.0 Hz, 1H), 4.18-4.10 (m, 1H), 3.69-3.59 (m, 2H), 3.59-3.31 (m, 5H), 2.29-2.12 (m, 1H), 2.10-1.60 (m, 6H), 1.60-1.38 (m, 2H), 1.38-1.10 (m, 2H).

Example 271

(R)-4-(4-(N-(pyrrolidin-3-yl)sulfamoyl)-3-sulfamoyl-2-(2H-tetrazol-5-yl) phenyl)-1H-benzo[d]imidazole-2-carboxamide

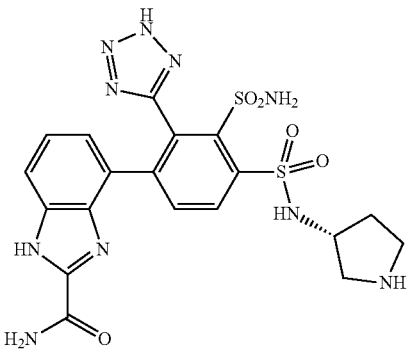 [SMILES: NC(=O)c1nc2c(-c3ccc(S(=O)(=O)N[C@@H]4CCNC4)c(S(N)(=O)=O)c3-c3nn[nH]n3)cccc2[nH]1]

Step A: (R)-tert-butyl-3-(2-(N,N-bis(4-methoxybenzyl)sulfamoyl)-4-(2-carbamoyl-1H-benzo[d]imidazol-4-yl)-3-(2-(4-methoxybenzyl)-2H-tetrazol-5-yl) phenylsulfonamido)pyrrolidine-1-carboxylate The title compound was prepared as described for EXAMPLE 246, step C, using (R)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (0.50 g, 0.52 mmol) and (2-carbamoyl-1H-benzo[d]imidazol-4-yl)boronic acid (0.21 g, 1.04 mmol) to afford the title compound: LCMS [M+1]$^+$: 993.

Step B: (R)-4-(4-(N-(pyrrolidin-3-yl)sulfamoyl)-3-sulfamoyl-2-(2H-tetrazol-5-yl)phenyl)-1H-benzo[d] imidazole-2-carboxamide The title compound was prepared as described for EXAMPLE 244, step C, using (R)-tert-butyl-3-(2-(N,N-bis(4-methoxybenzyl)sulfamoyl)-4-(2-carbamoyl-1H-benzo[d]imidazol-4-yl)-3-(2-(4-methoxybenzyl)-2H-tetrazol-5-yl) phenylsulfonamido)pyrrolidine-1-carboxylate (0.24 g, 0.24 mmol) to afford the crude product. The crude product was purified by Prep-HPLC with the following conditions: Column: X Bridge Prep C18 OBD Column 19×150 mm, 5 μm; Mobile Phase A: water with 10 mmol/L NH$_4$HCO$_3$, Mobile Phase B: ACN; Flow rate: 20 mL/min; Gradient: 5% B to 22% B in 8 min; Detector: 254 and 220 nm. The fractions containing desired product were combined and concentrated under vacuum to afford the title compound: LCMS [M+1]$^+$: 533; $^1$H NMR (400 MHz, DMSO-d$_6$): δ 8.25 (d, J=8.4 Hz, 1H), 7.99 (brs, 3H), 7.78-7.76 (m, 1H), 7.37-7.35 (m, 1H), 6.97 (t, J=8.0 Hz, 1H), 6.44-6.42 (m, 1H), 4.13-4.09 (m, 1H), 3.33-3.29 (m, 2H), 3.19-3.12 (m, 2H), 2.18-2.09 (m, 1H), 1.95-1.87 (m, 1H).

Example 272

4-(2-((S)-1-aminoethyl)-1H-benzo[d]imidazol-4-yl)-N1-((R)-pyrrolidin-3-yl)-3-(2H-tetrazol-5-yl)benzene-1,2-disulfonamide

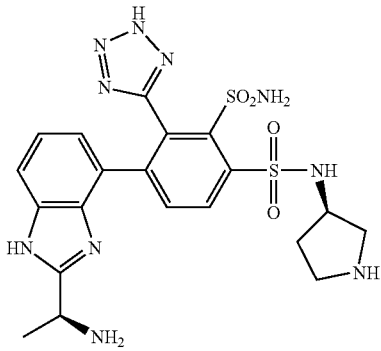 [SMILES: C[C@H](N)c1nc2c(-c3ccc(S(=O)(=O)N[C@@H]4CCNC4)c(S(N)(=O)=O)c3-c3nn[nH]n3)cccc2[nH]1]

Step A: (R)-tert-butyl-3-(2',3'-diamino-3-(N,N-bis(4-methoxybenzyl)sulfamoyl)-2-(2-(4-methoxybenzyl)-2H-tetrazol-5-yl-[1,1'-biphenyl]-4-ylsulfonamido)pyrrolidine-1-carboxylate To a solution of (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (1.80 g, 1.88 mmol) in 1,4-dioxane (12 mL) and water (3 mL) was added 3-(4,4,5,5-tetramethyl-1,3,2-dioxaborolan-2-yl)benzene-1,2-diamine (1.76 g, 7.50 mmol), Na₂CO₃ (0.56 g, 5.63 mmol) and Pd(PPh₃)₄ (0.43 g, 0.36 mmol) at room temperature. The mixture was degassed with nitrogen three times. The reaction mixture was irradiated with microwave radiation at 100° C. for 0.5 hours under nitrogen. The resulting mixture was diluted with water (200 mL), and then extracted with EA (3×200 mL). The combined organic layers were washed with water (3×200 mL) and brine (3×200 mL), dried over anhydrous Na₂SO₄ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]⁺: 940.

Step B: (R)-tert-butyl-3-(2'-amino-3-(N,N-bis(4-methoxybenzyl)sulfamoyl)-3'-((S)-2-((tert-butoxycarbonyl)amino)propanamido)-2-(2-(4-methoxybenzyl)-2H-tetrazol-5-yl-[1,1'-biphenyl]-4-yl-sulfonamido)pyrrolidine-1-carboxylate To a stirred solution of (R)-tert-butyl 3-(2',3'-diamino-3-(N,N-bis(4-methoxybenzyl) sulfamoyl)-2-(2-(4-methoxybenzyl)-2H-tetrazol-5-yl)-[1,1'-biphenyl]-4-yl-sulfamido)pyrrolidine-1-carboxylate (0.55 g, 0.59 mmol) in THF (5 mL) was added (S)-2-((tert-butoxycarbonyl)amino)propanoic acid (0.13 g, 0.70 mmol), TEA (0.18 g, 1.76 mmol) and HATU (0.45 g, 1.17 mmol). The mixture was degassed with nitrogen three times. The reaction mixture was stirred for 5 hours at room temperature under nitrogen. The resulting mixture was concentrated under vacuum. The residue was dissolved with EA (50 mL), washed with brine (3×50 mL), dried over anhydrous Na₂SO₄ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]⁺: 1111.

Step C: (R)-tert-butyl-3-(2-(N,N-bis(4-methoxybenzyl)sulfamoyl)-4-(2-((S)-1-((tert-butoxycarbonyl)amino)ethyl)-1H-benzo[d]imidazol-4-yl)-3-(2-(4-methoxybenzyl)-2H-tetrazol-5-yl)phenylsulfonamido)pyrrolidine-1-carboxylate A solution of (R)-tert-butyl 3-(2'-amino-3-(N,N-bis(4-methoxybenzyl)sulfamoyl)-3'-((S)-2-((tert-butoxycarbonyl)amino)propanamido)-2-(2-(4-methoxybenzyl)-2H-tetrazol-5-yl-[1,1'-biphenyl]-4-ylsulfonamido)pyrrolidine-1-carboxylate (0.45 g, 0.41 mmol) in AcOH (5 mL) was stirred at 60° C. for 30 minutes. The resulting mixture was concentrated under vacuum to afford the title compound, which was used in the next step without further purification: LCMS [M+1]⁺: 1093.

Step D: 4-(2-((S)-1-aminoethyl)-1H-benzo[d]imidazol-4-yl)-N¹—((R)-pyrrolidin-3-yl)-3-(2H-tetrazol-5-yl)benzene-1,2-disulfonamide The title compound was prepared as described for EXAMPLE 244, step C, using (R)-tert-butyl-3-(2-(N,N-bis(4-methoxybenzyl)sulfamoyl)-4-(2-((S)-1-((tert-butoxycarbonyl)amino)ethyl)-1H-benzo[d]imidazol-4-yl)-3-(2-(4-methoxybenzyl)-2H-tetrazol-5-yl)phenylsulfonamido) pyrrolidine-1-carboxylate (0.35 g, 0.32 mmol) to afford the crude product. The crude product was purified by Prep-HPLC with the following conditions: Column: X Select CSH Prep C18 OBD Column, 5 μm, 19×150 mm; Mobile Phase A: water with 10 mmol/L NH₄HCO₃, Mobile Phase B: ACN; Flow rate: 20 mL/min; Gradient: 10% B to 25% B in 8 min; Detector: 254 and 220 nm. The fractions containing desired product were combined and concentrated under vacuum to afford the title compound: LCMS [M−1]⁻: 531; ¹H NMR (400 MHz, CD₃OD+DCl): δ 8.72 (d, J=8.0 Hz, 1H), 8.14 (d, J=8.0 Hz, 1H), 7.83-7.81 (m, 1H), 7.52-7.48 (m, 1H), 7.17-7.15 (m, 1H), 5.18-5.15 (m, 1H), 4.34-4.31 (m, 1H), 3.59-3.40 (m, 4H), 2.37-2.34 (m, 1H), 1.97-1.95 (m, 4H).

Example 273

4-(2-((R)-1-aminoethyl)-1H-benzo[d]imidazol-4-yl)-N1-((R)-pyrrolidin-3-yl)-3-(2H-tetrazol-5-yl)benzene-1,2-disulfonamide

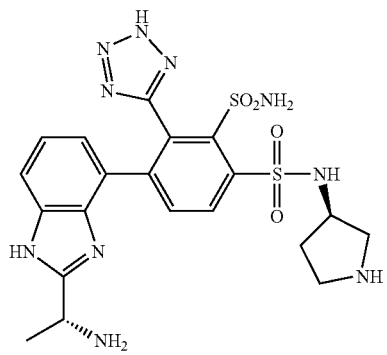 [SMILES: C[C@@H](N)c1nc2c(-c3ccc(S(=O)(=O)N[C@@H]4CCNC4)c(S(N)(=O)=O)c3-c3nn[nH]n3)cccc2[nH]1]

335

Step A: (R)-tert-butyl-3-(2'-amino-3-(N,N-bis(4-methoxybenzyl)sulfamoyl)-3'-((R)-2-((tert-butoxycarbonyl)amino)propanamido)-2-(2-(4-methoxybenzyl)-2H-tetrazol-5-yl)-[1,1'-biphenyl]-4-ylsulfonamido)pyrrolidine-1-carboxylate To a stirred solution of (R)-tert-butyl-3-(2',3'-diamino-3-(N,N-bis(4-methoxybenzyl) sulfamoyl)-2-(2-(4-methoxybenzyl)-2H-tetrazol-5-yl)-[1,1'-biphenyl]-4-yl-sulfonamido)pyrrolidine-1-carboxylate (0.55 g, 0.59 mmol) in THF (5 mL) was added (R)-2-((tert-butoxycarbonyl)amino)propanoic acid (0.11 g, 0.59 mmol), TEA (0.18 g, 1.76 mmol) and HATU (0.45 g, 1.17 mmol). The mixture was degassed with nitrogen three times. The reaction mixture was stirred for 5 hours at room temperature under nitrogen. The resulting mixture was concentrated under vacuum. The residue was dissolved in EA (50 mL), and then washed with brine (3×50 mL), dried over anhydrous Na$_2$SO$_4$ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]$^+$: 1111.

Step B: (R)-tert-butyl 3-(2-(N,N-bis(4-methoxybenzyl)sulfamoyl)-4-(2-((R)-1-((tert-butoxy carbonyl)amino)ethyl)-1H-benzo[d]imidazol-4-yl)-3-(2-(4-methoxybenzyl)-2H-tetrazol-5-yl) phenylsulfonamido)pyrrolidine-1-carboxylate A solution of (R)-tert-butyl 3-(2'-amino-3-(N,N-bis(4-methoxybenzyl)sulfamoyl)-3'-((R)-2-((tert-butoxycarbonyl)amino)propanamido)-2-(2-(4-methoxybenzyl)-2H-tetrazol-5-yl-[1,1'-biphenyl]-4-ylsulfonamido)pyrrolidine-1-carboxylate (0.48 g, 0.43 mmol) in AcOH (5 mL) was stirred at 60° C. for 30 minutes. The resulting mixture was concentrated under vacuum to afford the title compound, which was used in the next step without further purification: LCMS [M+1]$^+$: 1093.

Step C: 4-(2-((R)-1-aminoethyl)-1H-benzo[d]imidazol-4-yl)-N1-((R)-pyrrolidin-3-yl)-3-(2H-tetrazol-5-yl)benzene-1,2-disulfonamide The title compound was prepared as described for EXAMPLE 244, step C, using (R)-tert-butyl-3-(2-(N,N-bis(4-methoxybenzyl)sulfamoyl)-4-(2-((R)-1-((tert-butoxy carbonyl)amino)ethyl)-1H-benzo[d]imidazol-4-yl)-3-(2-(4-methoxybenzyl)-2H-tetrazol-5-yl)phenylsulfonamido) pyrrolidine-1-carboxylate (0.38 g, 0.35 mmol) to afford the crude product. The crude product was purified by Prep-HPLC with the following conditions: Column: X Select CSH Prep C18 OBD Column, 5 μm, 19×150 mm; Mobile Phase A: water with 10 mmol/L NH$_4$HCO$_3$, Mobile Phase B: ACN; Flow rate: 20 mL/min; Gradient: 10% B to 25% B in 8 min; Detector: 254 and 220 nm. The fractions containing desired product were combined and concentrated under vacuum to afford the title compound: LCMS [M+1]$^+$: 533; $^1$H NMR (400 MHz, CD$_3$OD+DCl): δ 8.72 (d, J=8.0 Hz, 1H), 8.14 (d, J=8.0 Hz, 1H), 7.83-7.81 (m, 1H), 7.52-7.48 (m, 1H), 7.17-7.15 (m, 1H), 5.18-5.15 (m, 1H), 4.34-4.31 (m, 1H), 3.59-3.40 (m, 4H), 2.37-2.34 (m, 1H), 1.97-1.95 (m, 4H).

336

Example 274

(R)-4-(2-(aminomethyl)-1H-benzo[d]imidazol-5-yl)-N1-(pyrrolidin-3-yl)-3-(2H-tetrazol-5-yl)benzene-1,2-disulfonamide

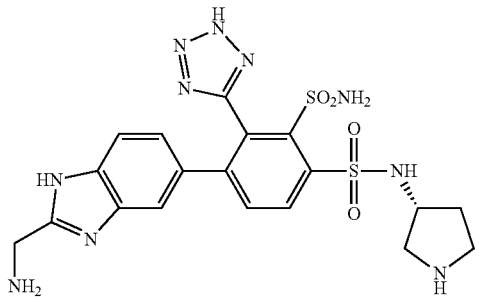 [SMILES: NCc1nc2cc(-c3ccc(S(=O)(=O)N[C@@H]4CCNC4)c(S(N)(=O)=O)c3-c3nn[nH]n3)ccc2[nH]1]

Step A: (R)-tert-butyl-3-(3',4'-diamino-3-(N,N-bis(4-methoxybenzyl)sulfamoyl)-2-(2-(4-methoxybenzyl)-2H-tetrazol-5-yl-[1,1'-biphenyl]-4-ylsulfonamido)pyrrolidine-1-carboxylate The title compound was prepared as described for EXAMPLE 246, step C, using (R)-tert-butyl-3-(2-(N,N-bis(4-methoxybenzyl)sulfamoyl)-4-iodo-3-(2-(4-methoxy benzyl)-2H-tetrazol-5-yl)phenylsulfonamido)pyrrolidine-1-carboxylate (1.50 g, 1.56 mmol) and 4-(4,4,5,5-tetramethyl-1,3,2-dioxaborolan-2-yl)benzene-1,2-diamine (0.55 g, 2.34 mmol), Na$_2$CO$_3$ (0.50 g, 4.69 mmol): LCMS [M+1]$^+$: 940.

Step B: (R)-tert-butyl-3-(3'-amino-3-(N,N-bis(4-methoxybenzyl)sulfamoyl)-4'-(2-((tert-butoxycarbonyl)amino)acetamido)-2-(2-(4-methoxybenzyl)-2H-tetrazol-5-yl)-[1,1'-biphenyl]-4-ylsulfonamido) pyrrolidine-1-carboxylate To a solution of 2-((tert-butoxycarbonyl)amino)acetic acid (0.22 g, 1.23 mmol) in DMF (15 mL) were added (R)-tert-butyl 3-(3',4'-diamino-3-(N,N-bis(4-methoxybenzyl) sulfamoyl)-2-(2-(4-methoxybenzyl)-2H-tetrazol-5-yl)-[1,1'-biphenyl]-4-yl-sulfonamido)pyrrolidine-1-carboxylate (1.49 mL, 1.17 mmol), HATU (0.53 g, 1.40 mmol) and DIEA (0.23 g, 1.76 mmol) at room temp. The reaction mixture was degassed with nitrogen three times. The reaction mixture was stirred for 2 hours at room temp. under nitrogen. The resulting mixture was diluted with water (100 mL), and then extracted with EA (3×80 mL). The combined organic layer was washed with brine (100 mL), dried over anhydrous Na$_2$SO$_4$ and filtered. The filtrate was concentrated under vacuum. The residue was purified by silica gel column chromatography, eluted with 70% EA in PE. The fractions containing desired product were combined and concentrated under vacuum to afford the title compound: LCMS [M+1]$^+$: 1097.

Step C: (R)-tert-butyl-3-(2-(N,N-bis(4-methoxybenzyl)sulfamoyl)-4-(2-(((tert-butoxycarbonyl) amino)methyl)-1H-benzo[d]imidazol-5-yl)-3-(2-(4-methoxybenzyl)-2H-tetrazol-5-yl) phenylsulfonamido)pyrrolidine-1-carboxylate A solution of (R)-tert-butyl 3-(3'-amino-3-(N,N-bis(4-methoxybenzyl)sulfamoyl)-4'-(2-((tert-butoxycarbonyl)

amino)acetamido)-2-(2-(4-methoxybenzyl)-2H-tetrazol-5-yl)-[1,1'-biphenyl]-4-ylsulfonamido)pyrrolidine-1-carboxylate (0.55 g, 0.50 mmol) in AcOH (10 mL) was stirred for 2 hours at 55° C. The resulting solution was diluted with water (50 mL), and then extracted with EA (3×50 mL). The combined organic layer was washed with brine (50 mL), dried over anhydrous Na$_2$SO$_4$ and filtered. The filtrate was concentrated under vacuum. The residue was purified by a silica gel column chromatography and eluted with 70% EA in PE. The fractions containing desired product were combined and concentrated under vacuum to afford the title compound: LCMS [M+1]$^+$: 1079.

Step D: (R)-4-(2-(aminomethyl)-1H-benzo[d]imidazol-5-yl)-N1-(pyrrolidin-3-yl)-3-(2H-tetrazol-5-yl)benzene-1,2-disulfonamide To a solution of (R)-tert-butyl 3-(2-(N,N-bis(4-methoxybenzyl)sulfamoyl)-4-(2-(((tert-butoxycarbonyl)amino)methyl)-1H-benzo[d]imidazol-5-yl)-3-(2-(4-methoxybenzyl)-2H-tetrazol-5-yl)phenylsulfonamido)pyrrolidine-1-carboxylate (0.38 g, 0.35 mmol) in DCM (6 mL) was added TFA (3 mL). The reaction mixture was stirred for 1 hour at room temperature. The reaction mixture co-evaporated with anisole (3×5 mL) under vacuum. The crude product was dissolved in TFA (10 mL). The solution was stirred at 80° C. for 1 hour. The resulting mixture was concentrated under vacuum to dryness, then was dissolved in EA (30 mL), extracted with aqueous HCl (1.0 M, 3×30 mL). The combined aqueous layers were concentrated under vacuum to dryness. The residue was purified by Prep-HPLC with the following conditions. Column: X Bridge Prep OBD C18 Column 30×150 mm, 5 μm; Mobile Phase A: water (10 mmol/L NH$_4$HCO$_3$+0.1% NH$_3$.H$_2$O), Mobile Phase B: ACN; Flow rate: 30 mL/min; Gradient: 5% B to 25% B in 6 min; Detector: 254 and 220 nm. The fractions were combined and concentrated under vacuum to afford the title compound: LCMS [M+1]$^+$: 519; $^1$H NMR (400 MHz, DMSO-d$_6$+DCl): δ 8.50 (d, J=8.3 Hz, 1H), 8.00 (d, J=8.3 Hz, 1H), 7.72 (d, J=8.5 Hz, 1H), 7.63-7.52 (m, 1H), 7.11 (dd, J=8.5 Hz, 1.6 Hz, 1H), 4.54 (s, 2H), 4.08-4.06 (m, 1H), 3.36-3.18 (m, 2H), 3.13-3.07 (m, 2H), 2.14-1.96 (m, 1H), 1.87-1.82 (m, 1H).

Example 275

(R)-4-(2-(aminomethyl)benzo[d]thiazol-5-yl)-N$^1$-(pyrrolidin-3-yl)-3-(2H-tetrazol-5-yl)benzene-1,2-disulfonamide

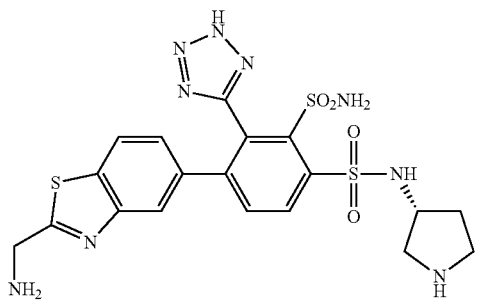 [SMILES: NCc1nc2cc(-c3ccc(S(=O)(=O)N[C@@H]4CCNC4)c(S(N)(=O)=O)c3-c3nn[nH]n3)ccc2s1]

Step A: (R)-tert-butyl-3-(4-(2-aminobenzo[d]thiazol-5-yl)-2-(N,N-bis(4-methoxybenzyl) sulfamoyl)-3-(2-(4-methoxybenzyl)-2H-tetrazol-5-yl)phenylsulfonamido)pyrrolidine-1-carboxylate The title compound was prepared as described for EXAMPLE 246, step C, using (R)-tert-butyl-3-(2-(N,N-bis(4-methoxybenzyl)sulfamoyl)-4-iodo-3-(2-(4-methoxy benzyl)-2H-tetrazol-5-yl)phenylsulfonamido)pyrrolidine-1-carboxylate (4.10 g, 4.27 mmol) and 5-(4,4,5,5-tetramethyl-1,3,2-dioxaborolan-2-yl)benzo[d]thiazol-2-amine (2.36 g, 8.54 mmol): LCMS [M+1]$^+$: 982.

Step B: (R)-tert-butyl-3-(2-(N,N-bis(4-methoxybenzyl)sulfamoyl)-4-(2-bromobenzo[d]thiazol-5-yl)-3-(2-(4-methoxybenzyl)-2H-tetrazol-5-yl)phenylsulfonamido)pyrrolidine-1-carboxylate To a solution of (R)-tert-butyl-3-(4-(2-aminobenzo[d]thiazol-5-yl)-2-(N,N-bis (4-methoxybenzyl)sulfamoyl)-3-(2-(4-methoxybenzyl)-2H-tetrazol-5-yl)phenyl sulfonamido) pyrrolidine-1-carboxylate (3.3 g, 3.36 mmol) in ACN (40 mL) was added CuBr$_2$ (0.90 g, 4.03 mmol). tert-butyl nitrite (0.55 g, 5.38 mmol) was then added dropwise at 0° C. The reaction mixture was stirred for 2 hours at room temp. under nitrogen. The resulting mixture was quenched with water (100 mL), and then extracted with EA (3×80 mL). The combined organic layers were washed with brine (2×50 mL), dried over anhydrous Na$_2$SO$_4$ and filtered. The filtrate was concentrated under vacuum. The residue was purified by silica gel column chromatography, eluted with 40% EA in PE. The fractions containing desired product were combined and concentrated under vacuum to afford the title compound: LCMS [M+1]$^+$: 1045, 1047 (1:1).

Step C: (R)-tert-butyl-3-(2-(N,N-bis(4-methoxybenzyl)sulfamoyl)-4-(2-cyanobenzo[d]thiazol-5-yl)-3-(2-(4-methoxybenzyl)-2H-tetrazol-5-yl)phenylsulfonamido)pyrrolidine-1-carboxylate To a solution of (R)-tert-butyl-3-(2-(N,N-bis(4-methoxybenzyl)sulfamoyl)-4-(2-bromobenzo[d]thiazol-5-yl)-3-(2-(4-methoxybenzyl)-2H-tetrazol-5-yl)phenyl sulfonamido) pyrrolidine-1-carboxylate (1.50 g, 1.43 mmol) in DMF (20 mL) was added t-BuXPhos palladium (II) biphenyl-2-amine mesylate (0.46 g, 0.57 mmol) and Zn(CN)$_2$ (0.51 g, 4.30 mmol) at room temperature. The reaction mixture was degassed with nitrogen three times and stirred for 16 hours at 55° C. under nitrgon. The resulting mixture was diluted with saturated Na$_2$CO$_3$ (100 mL), and then extracted with EA (3×80 mL). The combined organic layers were washed with the saturated aqueous FeSO$_4$ (3×50 mL) and brine (2×50 mL), dried over anhydrous Na$_2$SO$_4$ and filtered. The filtrate was concentrated under vacuum. The residue was purified by silica gel column chromatography, eluted with 40% EA in PE. The fractions containing desired product were combined and concentrated under vacuum to afford the title compound: LCMS [M+1]$^+$: 992.

Step D: (R)-tert-butyl-3-(4-(2-(aminomethyl)benzo[d]thiazol-5-yl)-2-(N,N-bis(4-methoxy benzyl)sulfamoyl)-3-(2-(4-methoxybenzyl)-2H-tetrazol-5-yl) phenylsulfonamido) pyrrolidine-1-carboxylate To a solution of (R)-tert-butyl-3-(2-(N,N-bis(4-methoxybenzyl)sulfamoyl)-4-(2-cyanobenzo[d]thiazol-5-yl)-3-(2-(4-methoxybenzyl)-2H-tetrazol-5-yl)phenyl sulfonamido)

pyrrolidine-1-carboxylate (0.85 g, 0.86 mmol) in MeOH (10 mL) and EA (5 mL) was added Pd(OH)$_2$/C (20% Pd, 0.12 g, 0.86 mmol) at room temperature. Then 4 drops conc. HCl was added. The reaction mixture was degassed with hydrogen three times and stirred for 16 hours at 25° C. under hydrogen (30 atm). The resulting solution was filtered. The filter cake was washed with MeOH (3×30 mL). The combined organic layers was concentrated under vacuum to afford the title compound, which was used in the next step without further purification: LCMS [M+1]$^+$: 996.

Step E: (R)-4-(2-(aminomethyl)benzo[d]thiazol-5-yl)-N1-(pyrrolidin-3-yl)-3-(2H-tetrazol-5-yl)benzene-1,2-disulfonamide The title compound was prepared as described for EXAMPLE 274 step D using (R)-tert-butyl-3-(4-(2-(aminomethyl)benzo[d]thiazol-5-yl)-2-(N,N-bis(4-methoxybenzyl)sulfamoyl)-3-(2-(4-methoxybenzyl)-2H-tetrazol-5-yl) phenylsulfonamido) pyrrolidine-1-carboxylate (0.70 g, 0.70 mmol) to afford the crude product. The crude product was purified by Prep-HPLC with the following conditions. Column: XBridge Prep Amide OBD Column 19×150 mm, 5 μm 13 nm; Mobile Phase A: water with 10 mmol NH$_4$HCO$_3$, Mobile Phase B: ACN; Flow rate: 20 mL/min; Gradient: 90% B to 65% B in 8 min; Detector: 254 and 220 nm; Retention time: 6.43 min. The fractions were combined and concentrated under vacuum to afford the title compound: LCMS [M+1]$^+$: 536; $^1$H NMR (400 MHz, DMSO-d$_6$): δ 8.27 (d, J=8.3 Hz, 1H), 7.85 (d, J=8.3 Hz, 2H), 7.40 (s, 1H), 6.88 (dd, J=8.3 Hz, 1.7 Hz, 1H), 6.70 (brs, 3H), 4.13 (s, 2H), 4.09-4.03 (m, 1H), 3.27-3.15 (m, 2H), 3.14-2.97 (m, 2H), 2.10-2.01 (m, 1H), 1.89-1.81 (m, 1H).

Example 276

(R)-4-(2-(aminomethyl)benzo[d]thiazol-4-yl)-N1-(pyrrolidin-3-yl)-3-(2H-tetrazol-5-yl)benzene-1,2-disulfonamide

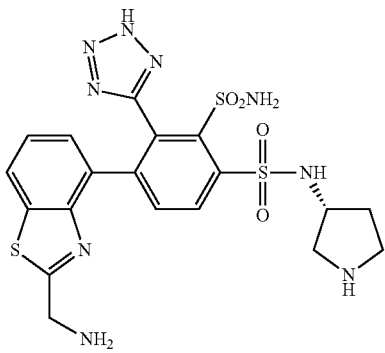 [SMILES: NCc1nc2c(-c3ccc(S(=O)(=O)N[C@@H]4CCNC4)c(S(N)(=O)=O)c3-c3nn[nH]n3)cccc2s1]

Step A: (R)-tert-butyl 3-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)pyrrolidine-1-carboxylate To a solution of (R)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (3.0 g, 3.13 mmol) in 1,4-dioxane (30 mL) and water (6 mL) were added (2-aminobenzo[d]thiazol-4-yl)boronic acid (1.52 g, 7.81 mmol), Na$_2$CO$_3$ (0.99 g, 9.38 mmol) and Pd(PPh$_3$)$_4$ (0.72 g, 0.63 mmol) at room temperature. The mixture was degassed with nitrogen for three times. The reaction mixture was stirred at 80° C. for 16 h under nitrogen. The resulting mixture was quenched with water (70 mL), and then extracted with EA (3×50 mL). The combined organic layers was washed with brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 982.

Step B: (R)-tert-butyl-3-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenylsulfonamido)pyrrolidine-1-carboxylate To a solution of (R)-tert-butyl-3-(4-(2-aminobenzo[d]thiazol-4-yl)-2-(N,N-bis (4-methoxybenzyl)sulfamoyl)-3-(2-(4-methoxybenzyl)-2H-tetrazol-5-yl)phenyl sulfonamide) pyrrolidine-1-carboxylate (2.30 g, 2.34 mmol) in ACN (20 mL) were added copper(II) bromide (0.63 g, 2.81 mmol) and tert-butyl nitrite (0.39 g, 3.75 mmol) dropwise at 0° C. The reaction mixture was stirred at room temperature for 2 h under nitrogen. The resulting mixture was quenched with water (50 mL), and then extracted with EA (3×50 mL). The combined organic layers was washed with brine (3×50 mL), dried over anhydrous Na$_2$SO$_4$ and filtered. The filtrate was concentrated under vacuum. The residue was purified by silica gel column chromatography, eluted with 40% EA in PE. The fractions containing desired product were combined and concentrated under vacuum to afford (R)-tert-butyl-3-(2-(N,N-bis(4-methoxybenzyl) sulfamoyl)-4-(2-bromobenzo[d]thiazol-4-yl)-3-(2-(4-methoxybenzyl)-2H-tetrazol-5-yl)phenylsulfonamido)pyrrolidine-1-carboxylate as a solid title compound: LCMS [M+1]$^+$: 1045, 1047.

Step C: Tert-butyl-3-(2-(N,N-bis(4-methoxybenzyl) sulfamoyl)-4-(2-cyanobenzo[d]thiazol-4-yl)-3-(2-(4-methoxybenzyl)-2H-tetrazol-5-yl)phenylsulfonamido)pyrrolidine-1-carboxylate To a solution of (R)-tert-butyl-3-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl sulfonamido) pyrrolidine-1-carboxylate (1.80 g, 1.72 mmol) in DMSO (8 mL) was added cyanocopper (0.46 g, 5.16 mmol) at room temperature. The mixture was degassed with nitrogen three times. The reaction mixture was stirred at 100° C. for 4 hours under nitrogen. The resulting mixture was quenched with the saturated aqueous Na$_2$CO$_3$ solution (100 mL), and then extracted with EA (3×50 mL). The combined organic layers were washed with brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 992

Step D: (R)-tert-butyl-3-(4-(2-(aminomethyl)benzo[d]thiazol-4-yl)-2-(N,N-bis(4-methoxy benzyl)sulfamoyl)-3-(2-(4-methoxybenzyl)-2H-tetrazol-5-yl) phenylsulfonamido) pyrrolidine-1-carboxylate To a solution of tert-butyl-3-(2-(N,N-bis(4-methoxybenzyl)sulfamoyl)-4-(2-cyanobenzo[d]thiazol-4-yl)-3-(2-(4- methoxybenzyl)-2H-tetrazol-5-yl)phenyl sulfonamido)pyrrolidine-1-carboxylate (0.70 g, 0.71 mmol) in EA (5 mL) and conc. HCl (2 drops) was added Pd(OH)$_2$/C (20% wt, 0.14 g, 0.20 mmol) at room temperature. The mixture was degassed with hydrogen three times. The reaction mixture was stirred at 25° C. for 16 hours under hydrogen (20 atm). The resulting mixture was filtered and the filtrate was concentrated under vacuum. The residue was purified by silica gel column chromatography, eluted with 80% EA in PE. The fractions containing desired product were combined and concentrated under vacuum to afford the title compound: LCMS [M+1]$^+$: 996.

Step E: (R)-4-(2-(aminomethyl)benzo[d]thiazol-4-yl)-N1-(pyrrolidin-3-yl)-3-(2H-tetrazol-5-yl)benzene-1,2-disulfonamide The title compound was prepared as described for EXAMPLE 244, step C, using (R)-tert-butyl-3-(4-(2-(aminomethyl)benzo[d]thiazol-4-yl)-2-(N,N-bis(4-methoxy benzyl)sulfamoyl)-3-(2-(4-methoxybenzyl)-2H-tetrazol-5-yl) phenylsulfonamido) pyrrolidine-1-carboxylate (0.30 g, 0.30 mmol) to afford the crude product. The crude product was purified by Prep-HPLC with the following conditions: X Bridge Prep C18 OBD Column, 19×150 mm, 5 μm, Mobile Phase A: water with 10 mmol/L NH$_4$HCO$_3$, Mobile Phase B: ACN; Flow rate: 20 mL/min; Gradient: 5% B to 25% B in 8 min; Detector: 254 and 220 nm. The fractions containing desired product were combined and concentrated under vacuum to afford the title compound: LCMS [M+1]$^+$: 536; $^1$H NMR (400 MHz, DMSO-d$_6$+D$_2$O): δ 8.28 (d, J=8.0 Hz, 1H), 7.89 (d, J=8.0 Hz, 2H), 7.10 (t, J=7.6 Hz, 1H), 6.69 (d, J=7.2 Hz, 1H), 4.15-4.12 (m, 1H), 4.09 (s, 2H), 3.35-3.24 (m, 2H), 3.17-3.09 (m, 2H), 2.20-2.06 (m, 1H), 1.94-1.86 (m, 1H).

Example 277

(R)-4-(6-aminopyridin-2-yl)-N1-(pyrrolidin-3-yl)-3-(2H-tetrazol-5-yl)benzene-1,2-disulfonamide

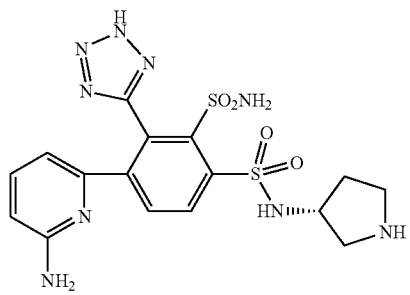 [SMILES: Nc1cccc(-c2ccc(S(=O)(=O)N[C@@H]3CCNC3)c(S(N)(=O)=O)c2-c2nn[nH]n2)n1]

Step A: (R)-tert-butyl-3-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)pyrrolidine-1-carboxylate The title compound was prepared as described for EXAMPLE 246, step C, using (R)-tert-butyl3-(2-(N,N-bis(4-methoxybenzyl)sulfamoyl)-4-iodo-3-(2-(4-methoxy benzyl)-2H-tetrazol-5-yl)phenylsulfonamido)pyrrolidine-1-carboxylate (0.50 g, 0.52 mmol) and (6-bromopyridin-2-yl) boronic acid (0.21 g, 1.04 mmol): LCMS [M+1]$^+$: 989, 991 (1:1).

Step B: (R)-tert-butyl-3-(2-(N,N-bis(4-methoxybenzyl)sulfamoyl)-4-(6-(((tert-butoxycarbonyl)amino) pyridin-2-yl)-3-(2-(4-methoxybenzyl)-2H-tetrazol-5-yl)phenylsulfonamido)pyrrolidine-1-carboxylate To a solution of (R)-tert-butyl3-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido) pyrrolidine-1-carboxylate (0.30 g, 0.30 mmol) in 1,4-dioxane (3 mL) was added tert-butyl carbamate (0.07 g, 0.61 mmol), Brettphos Pd G 3 (0.06 g, 0.06 mmol) and K$_3$PO$_4$ (0.19 g, 0.91 mmol) at room temperature. The mixture was degassed with nitrogen three times. The reaction mixture was stirred at 80° C. for 4 hours under nitrogen. The resulting mixture was quenched with water (50 mL) and extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford (R)-tert-butyl3-(2-(N,N-bis (4-methoxybenzyl)sulfamoyl)-4-(6-(((tert-butoxycarbonyl) amino)pyridin-2-yl)-3-(2-(4-methoxybenzyl)-2H-tetrazol-5-yl) phenylsulfonamido)pyrrolidine-1-carboxylate as a solid: LCMS [M+1]$^+$: 1026.

Step C: (R)-4-(6-aminopyridin-2-yl)-N1-(pyrrolidin-3-yl)-3-(2H-tetrazol-5-yl)benzene-1,2-disulfonamide The title compound was prepared as described for EXAMPLE 244, step C, using (R)-tert-butyl-3-(2-(N,N-bis (4-methoxybenzyl)sulfamoyl)-4-(6-(((tert-butoxycarbonyl) amino)pyridin-2-yl)-3-(2-(4-methoxybenzyl)-2H-tetrazol-5-yl)phenylsulfonamido) pyrrolidine-1-carboxylate (0.18 g, 0.18 mmol) to afford the crude product. The crude product was purified by Prep-HPLC with the following conditions: X Bridge Prep C18 OBD Column, 5 μm, 19×150 mm; Mobile Phase A: water with 10 mmol/L NH$_4$HCO$_3$, Mobile Phase B: ACN; Flow rate: 20 mL/min; Gradient: 0% B to 5% B in 8 min; Detector: 254 and 220 nm. The fractions containing desired product were combined and concentrated under vacuum to afford the title compound: LCMS [M+1]$^+$: 466; $^1$H NMR (400 MHz, DMSO-d$_6$): δ 8.30 (d, J=8.4 Hz, 1H), 7.98 (d, J=8.4 Hz, 1H), 7.97 (brs, 3H), 6.99 (t, J=8.0 Hz, 1H), 6.27 (d, J=8.4 Hz, 1H), 5.93 (brs, 2H), 5.50 (d, J=7.6 Hz, 1H), 4.19-4.13 (m, 1H), 3.27-3.16 (m, 2H), 3.09-3.00 (m, 2H), 1.92-1.85 (m, 1H), 1.79-1.71 (m, 1H).

EXAMPLES 278-291 in the Table below were prepared in an analogous fashion to that described for EXAMPLE 277, starting from (R)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate and the corresponding boronic acids or boronic esters, which were prepared as described herein, or which were available from commercial sources. In cases where the boronic acid or boronic ester intermediates have Boc-protected amines, the Boc groups where removed during the final TFA deprotection of the PMB groups as described for EXAMPLE 244, Step C.

| EX. No. | Structure | Chemical Name | MW | LC/MS [M + H]+ |
|---|---|---|---|---|
| 278 | 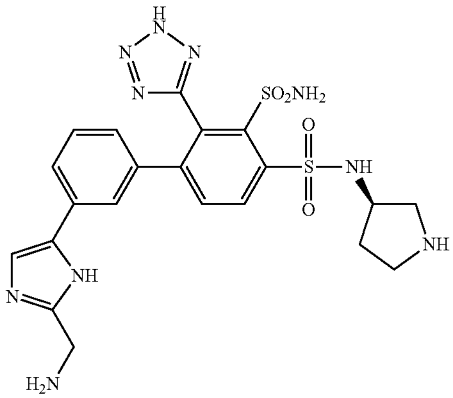 [SMILES: NCc1ncc(-c2cccc(-c3ccc(S(=O)(=O)N[C@@H]4CCNC4)c(S(N)(=O)=O)c3-c3nn[nH]n3)c2)[nH]1] | (R)-3'-(2-(aminomethyl)-1H-imidazol-5-yl)-N4-(pyrrolidin-3-yl)-2-(2H-tetrazol-5-yl)-[1,1'-biphenyl]-3,4-disulfonamide | 544 | 545 |
| 279 | 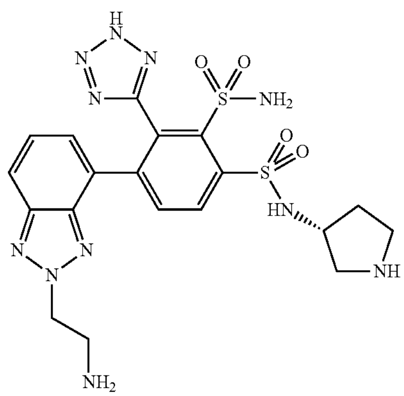 [SMILES: NCCn1nc2cccc(-c3ccc(S(=O)(=O)N[C@@H]4CCNC4)c(S(N)(=O)=O)c3-c3nn[nH]n3)c2n1] | (R)-4-(2-(2-aminoethyl)-2H-benzo[d][1,2,3]triazol-4-yl)-N1-(pyrrolidin-3-yl)-3-(2H-tetrazol-5-yl)benzene-1,2-disulfonamide | 533 | 534 |
| 280 | 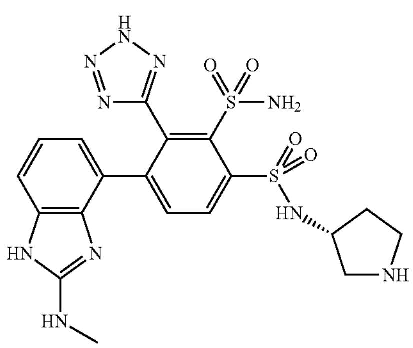 [SMILES: CNc1nc2c(-c3ccc(S(=O)(=O)N[C@@H]4CCNC4)c(S(N)(=O)=O)c3-c3nn[nH]n3)cccc2[nH]1] | (R)-4-(2-(methylamino)-1H-benzo[d]imidazol-4-yl)-N1-(pyrrolidin-3-yl)-3-(2H-tetrazol-5-yl)benzene-1,2-disulfonamide | 518 | 519 |
| 281 | 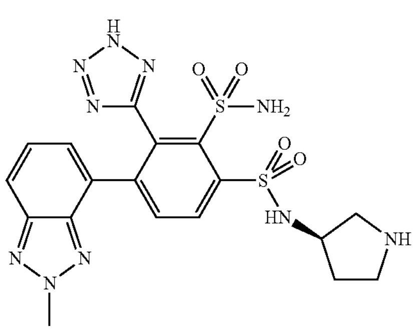 [SMILES: Cn1nc2cccc(-c3ccc(S(=O)(=O)N[C@@H]4CCNC4)c(S(N)(=O)=O)c3-c3nn[nH]n3)c2n1] | (R)-4-(2-methyl-2H-benzo[d][1,2,3]triazol-4-yl)-N1-(pyrrolidin-3-yl)-3-(2H-tetrazol-5-yl)benzene-1,2-disulfonamide | 504 | 505 |

| EX. No. | Structure | Chemical Name | MW | LC/MS [M + H]+ |
|---|---|---|---|---|
| 282 | 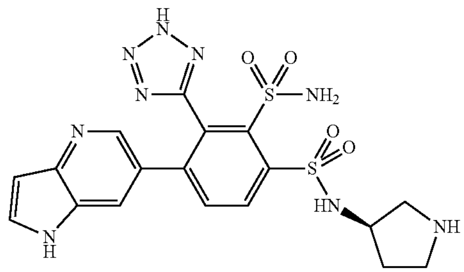 [SMILES: NS(=O)(=O)c1c(S(=O)(=O)N[C@@H]2CCNC2)ccc(-c2cnc3cc[nH]c3c2)c1-c1nn[nH]n1] | (R)-N1-(pyrrolidin-3-yl)-4-(1H-pyrrolo[3,2-b]pyridin-6-yl)-3-(2H-tetrazol-5-yl)benzene-1,2-disulfonamide | 489 | 490 |
| 283 | 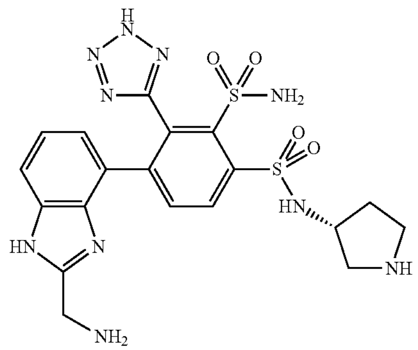 [SMILES: NCc1nc2c(-c3ccc(S(=O)(=O)N[C@@H]4CCNC4)c(S(N)(=O)=O)c3-c3nn[nH]n3)cccc2[nH]1] | (R)-4-(2-(aminomethyl)-1H-benzo[d]imidazol-4-yl)-N1-(pyrrolidin-3-yl)-3-(2H-tetrazol-5-yl)benzene-1,2-disulfonamide | 518 | 519 |
| 284 | 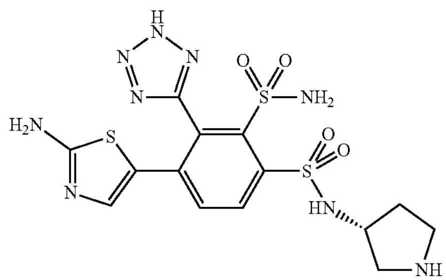 [SMILES: Nc1ncc(-c2ccc(S(=O)(=O)N[C@@H]3CCNC3)c(S(N)(=O)=O)c2-c2nn[nH]n2)s1] | (R)-4-(2-aminothiazol-5-yl)-N1-pyrrolidin-3-yl)-3-(2H-tetrazol-5-yl)benzene-1,2-disulfonamide | 471 | 472 |
| 285 | 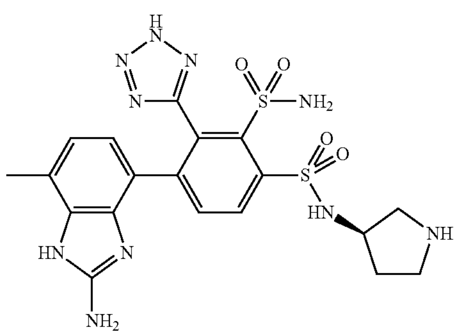 [SMILES: Cc1ccc(-c2ccc(S(=O)(=O)N[C@@H]3CCNC3)c(S(N)(=O)=O)c2-c2nn[nH]n2)c2nc(N)[nH]c12] | (R)-4-(2-amino-7-methyl-1H-benzo[d]imidazol-4-yl)-N1-(pyrrolidin-3-yl)-3-(2H-tetrazol-5-yl)benzene-1,2-disulfonamide | 518 | 519 |
| 286 | 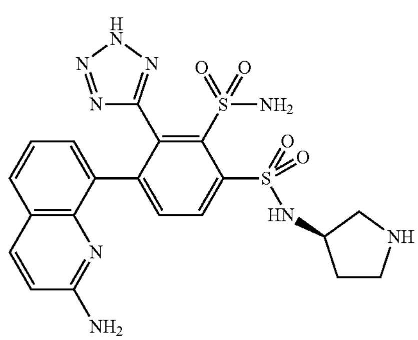 [SMILES: Nc1ccc2cccc(-c3ccc(S(=O)(=O)N[C@@H]4CCNC4)c(S(N)(=O)=O)c3-c3nn[nH]n3)c2n1] | (R)-4-(2-aminoquinolin-8-yl)-N1-(pyrrolidin-3-yl)-3-(2H-tetrazol-5-yl)benzene-1,2-disulfonamide | 515 | 516 |

| EX. No. | Structure | Chemical Name | MW | LC/MS [M + H]+ |
|---|---|---|---|---|
| 287 | 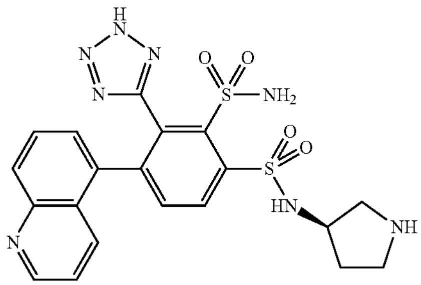 [SMILES: NS(=O)(=O)c1c(S(=O)(=O)N[C@@H]2CCNC2)ccc(-c2cccc3ncccc23)c1-c1nn[nH]n1] | (R)-N1-(pyrrolidin-3-yl)-4-(quinolin-5-yl)-3-(2H-tetrazol-5-yl)benzene-1,2-disulfonamide | 500 | 501 |
| 288 | 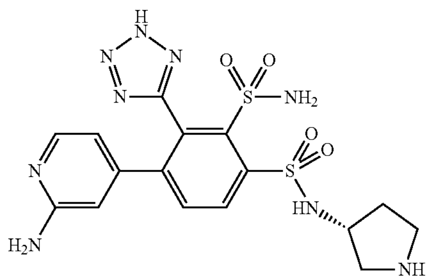 [SMILES: Nc1cc(-c2ccc(S(=O)(=O)N[C@@H]3CCNC3)c(S(N)(=O)=O)c2-c2nn[nH]n2)ccn1] | (R)-4-(2-aminopyridin-4-yl)-N1-(pyrrolidin-3-yl)-3-(2H-tetrazol-5-yl)benzene-1,2-disulfonamide | 465 | 466 |
| 289 | 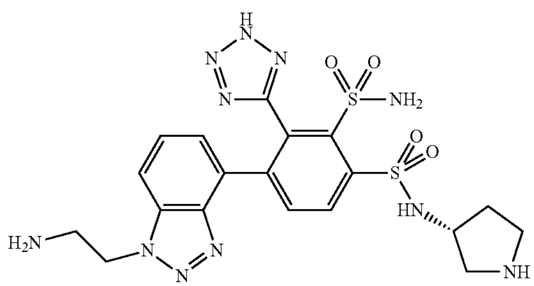 [SMILES: NCCn1nnc2c(-c3ccc(S(=O)(=O)N[C@@H]4CCNC4)c(S(N)(=O)=O)c3-c3nn[nH]n3)cccc21] | (R)-4-(1-(2-aminoethyl)-1H-benzo[d][1,2,3]triazol-4-yl)-N1-(pyrrolidin-3-yl)-3-(2H-tetrazol-5-yl)benzene-1,2-disulfonamide yl)benzene-1,2-disulfonamide | 533 | 534 |
| 290 | 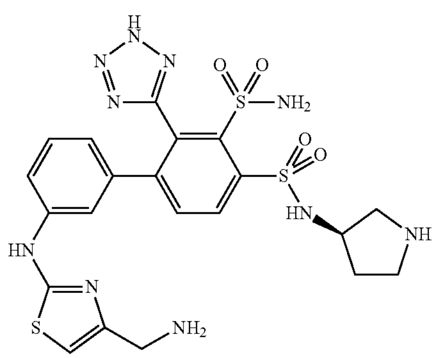 [SMILES: NCc1csc(Nc2cccc(-c3ccc(S(=O)(=O)N[C@@H]4CCNC4)c(S(N)(=O)=O)c3-c3nn[nH]n3)c2)n1] | (R)-3'-((4-(aminomethyl)thiazol-2-yl)amino)-N4-(pyrrolidin-3-yl)-2-(2H-tetrazol-5-yl)-[1,1'-biphenyl]-3,4-disulfonamide | 576 | 577 |
| 291 | 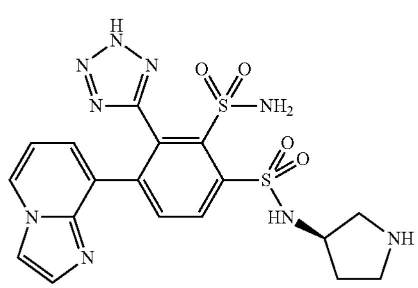 [SMILES: NS(=O)(=O)c1c(S(=O)(=O)N[C@@H]2CCNC2)ccc(-c2cccn3ccnc23)c1-c1nn[nH]n1] | (R)-4-(imidazo[1,2-a]pyridin-8-yl)-N1-(pyrrolidin-3-yl)-3-(2H-tetrazol-5-yl)benzene-1,2-disulfonamide | 489 | 490 |

Example 292

(S)-4-(4-(N-(pyrrolidin-3-yl)sulfamoyl)-3-sulfamoyl-2-(2H-tetrazol-5-yl)phenyl)-1H-benzo[d]imidazole-2-carboxamide

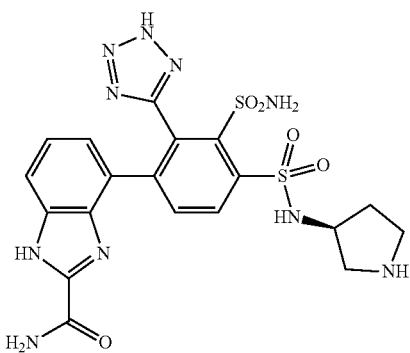 [SMILES: NC(=O)c1nc2c(-c3ccc(S(=O)(=O)N[C@H]4CCNC4)c(S(N)(=O)=O)c3-c3nn[nH]n3)cccc2[nH]1]

Step A: (S)-tert-butyl 3-(2-(N,N-bis(4-methoxybenzyl)sulfamoyl)-4-(2-carbamoyl-1H-benzo[d]imidazol-7-yl)-3-(2-(4-methoxybenzyl)-2H-tetrazol-5-yl)phenylsulfonamido)pyrrolidine-1-carboxylate To a solution of (S)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (0.60 g, 0.63 mmol) in 1,4-dioxane (5 mL) and water (1 mL) was added (2-carbamoyl-1H-benzo[d]imidazol-4-yl)boronic acid (0.26 g, 1.25 mmol), Na$_2$CO$_3$ (0.23 g, 2.19 mmol) and Pd(PPh$_3$)$_4$ (0.14 g, 0.13 mmol) at room temperature. The mixture was degassed with nitrogen three times. The reaction mixture was stirred at 80° C. for 16 hours under nitrogen. The resulting mixture was diluted with water (50 mL), and then extracted with EA (3×50 mL). The combined organic layers was washed with water (3×50 mL) and brine (3×50 mL), dried over anhydrous Na$_2$SO$_4$ and filtered. The filtrate was concentrated under vacuum. The residue was purified by silica gel column chromatography, eluted with 3% MeOH in EA. The fractions containing desired product were combined and concentrated under vacuum to afford the title compound: LCMS [M+1]$^+$: 993.

Step B: (S)-4-(4-(N-(pyrrolidin-3-yl)sulfamoyl)-3-sulfamoyl-2-(2H-tetrazol-5-yl)phenyl)-1H-benzo[d]imidazole-2-carboxamide The title compound was prepared as described for EXAMPLE 244, step C, using (S)-tert-butyl-3-(2-(N,N-bis(4-methoxybenzyl)sulfamoyl)-4-(2-carbamoyl-1H-benzo[d]imidazol-4-yl)-3-(2-(4-methoxybenzyl)-2H-tetrazol-5-yl)phenylsulfonamido) pyrrolidine-1-carboxylate (0.20 g, 0.20 mmol) to afford the crude product. The crude product was purified by Prep-HPLC with the following conditions: Column: X Bridge Prep C18 OBD Column 19×150 mm, 5 μm; Mobile Phase A: water with 10 mmol/L NH$_4$HCO$_3$, Mobile Phase B: ACN; Flow rate: 20 mL/min; Gradient: 5% B to 25% B in 8 min; Detector: 254 and 220 nm. The fractions containing desired product were combined and concentrated under vacuum to afford the title compound: LCMS [M+1]$^+$: 533; $^1$H NMR (300 MHz, DMSO-d$_6$): δ 8.25 (d, J=8.1 Hz, 1H), 8.03 (brs, 3H), 7.79 (d, J=8.1 Hz, 1H), 7.38 (d, J=7.6 Hz, 1H), 6.98 (t, J=8.1 Hz, 1H), 6.45 (d, J=7.6 Hz, 1H), 4.14-4.11 (m, 1H), 3.32-3.20 (m, 2H), 3.15-3.09 (m, 2H), 2.19-2.08 (m, 1H), 1.97-1.89 (m, 1H).

EXAMPLES 293-295 in the Table below were prepared in an analogous fashion to that described for EXAMPLE 292, starting from (S)-tert-butyl 3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate and the corresponding boronic acids or boronic esters, which were prepared as described herein, or which were available from commercial sources.

| EX. No. | Structure | Chemical Name | MW | LC/MS [M + H]$^+$ |
|---|---|---|---|---|
| 293 | 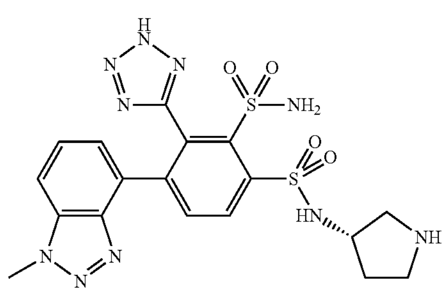 [SMILES: Cn1nnc2c(-c3ccc(S(=O)(=O)N[C@H]4CCNC4)c(S(N)(=O)=O)c3-c3nn[nH]n3)cccc21] | (S)-4-(1-methyl-1H-benzo[d][1,2,3]triazol-4-yl)-N1-(pyrrolidin-3-yl)-3-(2H-tetrazol-5-yl)benzene-1,2-disulfonamide | 504 | 505 |

| EX. No. | Structure | Chemical Name | MW | LC/MS [M + H]+ |
|---|---|---|---|---|
| 294 | 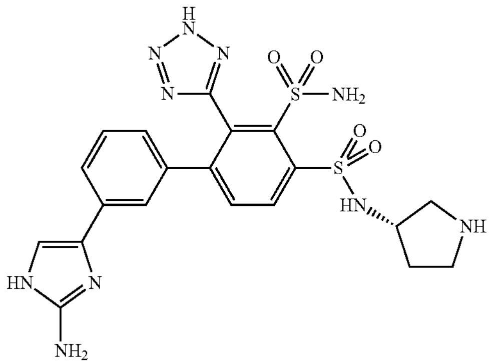 [SMILES: Nc1nc(-c2cccc(-c3ccc(S(=O)(=O)N[C@H]4CCNC4)c(S(N)(=O)=O)c3-c3nn[nH]n3)c2)c[nH]1] | (S)-3'-(2-amino-1H-imidazol-4-yl)-N4-(pyrrolidin-3-yl)-2-(2H-tetrazol-5-yl)-[1,1'-biphenyl]-3,4-disulfonamide | 530 | 529 [M − 1]− |
| 295 | 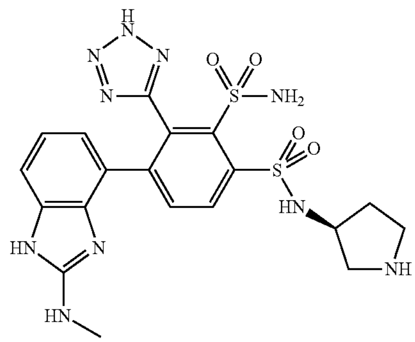 [SMILES: CNc1nc2c(-c3ccc(S(=O)(=O)N[C@H]4CCNC4)c(S(N)(=O)=O)c3-c3nn[nH]n3)cccc2[nH]1] | (S)-4-(2-(methylamino)-1H-benzo[d]imidazol-4-yl)-N1-(pyrrolidin-3-yl)-3-(2H-tetrazol-5-yl)benzene-1,2-disulfonamide | 518 | 519 |

Example 296

(S)—N1-(2-amino-3-hydroxypropyl)-4-(1H-benzo[d]imidazol-4-yl)-3-(2H-tetrazol-5-yl)benzene-1,2-disulfonamide

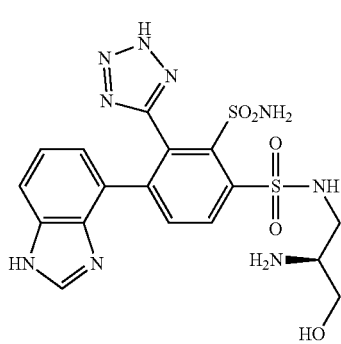 [SMILES: N[C@H](CO)CNS(=O)(=O)c1ccc(-c2cccc3[nH]cnc23)c(-c2nn[nH]n2)c1S(N)(=O)=O]

Step A: (S)-tert-butyl(1-(4-(1H-benzo[d]imidazol-4-yl)-2-(N,N-bis(4-methoxybenzyl) sulfamoyl)-3-(2-(4-methoxybenzyl)-2H-tetrazol-5-yl)phenylsulfonamido)-3-hydroxypropan-2-yl)carbamate The title compound was prepared as described for EXAMPLE 246, step C, using (S)-tert-butyl(1-(2-(N,N-bis(4-methoxybenzyl)sulfamoyl)-4-iodo-3-(2-(4-methoxy benzyl)-2H-tetrazol-5-yl)phenylsulfonamido)-3-hydroxypropan-2-yl)carbamate (1.1 g, 1.14 mmol) and (1H-benzo[d]imidazol-4-yl)boronic acid (0.37 g, 2.30 mmol) to afford the title compound: LCMS (ESI) [M+1]+: 954.

Step B: (S)—N1-(2-amino-3-hydroxypropyl)-4-(1H-benzo[d]imidazol-4-yl)-3-(2H-tetrazol-5-yl)benzene-1,2-disulfonamide The title compound was prepared as described for EXAMPLE 244, step C, using (S)-tert-butyl(1-(4-(1H-benzo[d]imidazol-4-yl)-2-(N,N-bis(4-methoxybenzyl) sulfamoyl)-3-(2-(4-methoxybenzyl)-2H-tetrazol-5-yl)phenylsulfonamido)-3-hydroxy propan-2-yl)carbamate (0.64 g, 0.67 mmol) to afford the crude product. The crude product was dissolved in TFA (4 mL). The solution was stirred at 80° C. for 1 hour. The resulting solution was concentrated under vacuum. The crude product was purified by Prep-HPLC with the following conditions: Column: X Bridge C18, 19×150 mm, 5 μm; Mobile Phase A: water (0.05% NH4HCO3), Mobile Phase B: ACN; Flow rate: 20 mL/min; Gradient: 30% B to 70% B in 10 min; Detector: 254 and 220 nm; Retention time: 8.25 min. The fractions containing desired product were combined and concentrated under vacuum to afford the title compound: LCMS [M+1]+: 494; 1H NMR (400 MHz, DMSO-d6): δ 8.25 (d, J=11.2 Hz, 1H), 8.17 (s, 1H), 8.00 (d, J=11.2 Hz, 1H), 7.77 (brs, 3H), 7.28 (d, J=10.0 Hz, 1H), 6.85 (t, J=10.0 Hz, 1H), 6.34 (d, J=10.0 Hz, 1H), 5.38 (s, 1H), 3.64-3.53 (m, 2H), 3.28-3.20 (m, 3H).

Example 297

(S)—N¹-(2-amino-3-hydroxypropyl)-4-(6-aminopyridin-3-yl)-3-(2H-tetrazol-5-yl) benzene-1,2-disulfonamide

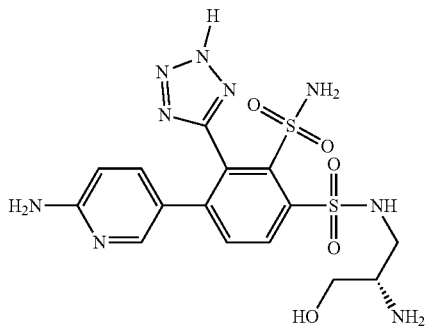 [SMILES: Nc1ccc(-c2ccc(S(=O)(=O)NC[C@H](N)CO)c(S(N)(=O)=O)c2-c2nn[nH]n2)cn1]

Step A: (S)-tert-butyl(1-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)-3-hydroxypropan-2-yl) carbamate To a mixture of (S)-tert-butyl(1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl) carbamate (0.80 g, 0.83 mmol), 5-(4,4,5,5-tetramethyl-1,3,2-dioxaborolan-2-yl)pyridin-2-amine (0.46 g, 2.08 mmol) and Pd(PPh₃)₄ (0.20 g, 0.17 mmol) in 1,4-dioxane (10 mL) was added a solution of Na₂CO₃ (0.27 g, 2.49 mmol) in water (2.5 mL) at room temperature. The mixture was degassed with nitrogen three times and stirred for 12 hours at 80° C. The resulting mixture was allowed to cool to room temperature, diluted with water (150 mL), and then extracted with EA (3×100 mL). The combined organic layers were washed with brine (200 mL), dried over anhydrous Na₂SO₄ and filtered. The filtrate was concentrated under vacuum. The residue was purified by a silica gel column chromatography, eluted with 10% MeOH in EA to afford the title compound: LCMS [M+1]⁺: 930.

Step B: (S)—N1-(2-amino-3-hydroxypropyl)-4-(6-aminopyridin-3-yl)-3-(2H-tetrazol-5-yl)benzene-1,2-disulfonamide The title compound was prepared as described for EXAMPLE 244, step C, using (S)-tert-butyl(1-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)-3-hydroxypropan-2-yl) carbamate (0.61 g, 0.66 mmol) to afford the crude product. The crude product was purified by Prep-HPLC with the following conditions: Column: X Bridge C18 OBD Prep Column 100 Å, 10 μm, 19 mm×250 mm; Mobile Phase A: water (10 mmol/L NH₄HCO₃), Mobile Phase B: ACN; Flow rate: 20 mL/min; Gradient: 2% B to 20% B in 10 min; Detector: 254 and 220 nm; Retention time: 8.3 min. The fractions containing desired product were combined and concentrated under vacuum to afford the title compound: LCMS [M+1]⁺: 470; ¹H NMR (400 MHz, DMSO-d₆): δ 8.18 (d, J=8.4 Hz, 1H), 7.75 (d, J=8.4 Hz, 1H), 7.54 (s, 1H), 7.49 (brs, 3H), 6.71 (d, J=6.4 Hz, 1H), 6.15 (d, J=8.8 Hz, 1H), 5.99 (brs, 2H), 5.29 (brs, 1H), 3.59-3.46 (m, 2H), 3.21-3.01 (m, 3H).

Example 298

(R)-4-(2-amino-1H-benzo[d]imidazol-4-yl)-N1-(3-amino-2-hydroxypropyl)-3-(2H-tetrazol-5-yl)-benzene-1,2-disulfonamide

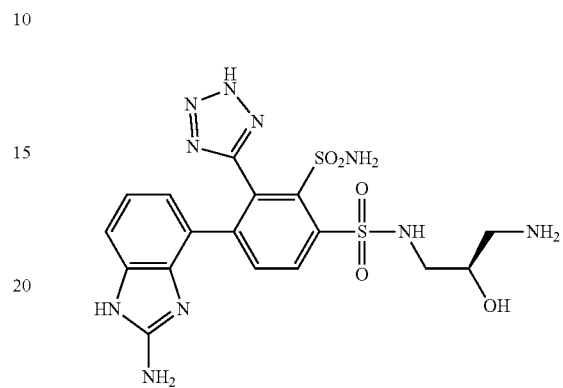

Step A: (R)-tert-butyl(3-(4-(2-amino-1H-benzo[d]imidazol-4-yl)-2-(N,N-bis(4-methoxybenzyl) sulfamoyl)-3-(2-(4-methoxybenzyl)-2H-tetrazol-5-yl) phenylsulfonamido)-2-hydroxy propyl) carbamate To a stirred solution of (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl) carbamate (1.0 g, 1.00 mmol) in 1,4-dioxane (5 mL) and water (1 mL) was added (2-amino-1H-benzo[d]imidazol-4-yl)boronic acid (0.37 g, 2.10 mmol), Na₂CO₃ (0.33 g, 3.10 mmol) and Pd(PPh₃)₄ (0.12 g, 0.10 mmol) at room temperature. The mixture was degassed with nitrogen three times. The reaction mixture was stirred for 12 hours at 80° C. under nitrogen. The resulting mixture was diluted with water (50 mL), and then extracted with EA (3×50 mL). The combined organic layers was washed with water (3×50 mL) and brine (3×50 mL), dried over anhydrous Na₂SO₄ and filtered. The filtrate was concentrated under vacuum. The residue was purified by silica gel column chromatography, eluted with 5% MeOH in DCM. The fractions containing desired product were combined and concentrated under vacuum to afford the title compound: LCMS [M+1]⁺: 969.

Step B: (R)-4-(2-amino-1H-benzo[d]imidazol-4-yl)-N1-(3-amino-2-hydroxypropyl)-3-(2H-tetrazol-5-yl)-benzene-1,2-disulfonamide The title compound was prepared as described for EXAMPLE 244, step C, using (R)-tert-butyl(3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-2-hydroxypropyl)carbamate (0.55 g, 0.57 mmol) to afford the crude product. The crude product was purified by Prep-HPLC with the following conditions: Column: X Bridge Prep C18 OBD Column 19×250 mm 10 μm; Mobile Phase A: water with 10 mmol/L NH₄HCO₃, Mobile Phase B: ACN; Flow rate: 25 mL/min; Gradient: 5% B to 35% B in 8 min; Detector: 254 and 220 nm; Retention time: 6.8 min. The fractions containing desired product were combined and concentrated under vacuum to afford the title compound: LCMS [M+1]$^+$: 509; $^1$H NMR (400 MHz, CD$_3$OD+DCl): δ 8.64 (d, J=8.2 Hz, 1H), 8.11-7.97 (m, 1H), 7.33 (dd, J=8.0 Hz, 1.0 Hz, 1H), 7.28-7.12 (m, 1H), 6.89 (d, J=7.2 Hz, 1H), 4.16-3.92 (m, 1H), 3.31-3.16 (m, 3H), 2.98-2.80 (m, 1H).

Example 299

(R)—N1-(3-amino-2-hydroxypropyl)-4-(2-(aminomethyl)-1H-benzo[d]imidazol-4-yl)-3-(2H-tetrazol-5-yl)benzene-1,2-disulfonamide

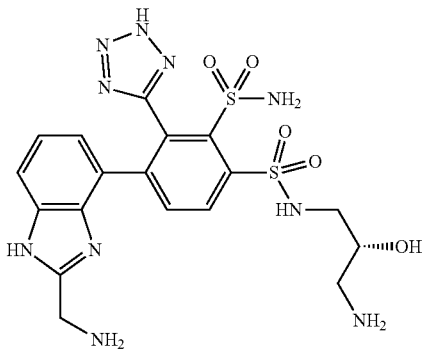 [SMILES: NCc1nc2c(-c3ccc(S(=O)(=O)NC[C@H](O)CN)c(S(N)(=O)=O)c3-c3nn[nH]n3)cccc2[nH]1]

Step A: Tert-butyl-N-{[4-(3-{bis[(4-methoxyphenyl)methyl]sulfamoyl}-4-{[(2R)-3-{[(tert-butoxy)carbonyl]amino}-2-hydroxypropyl]sulfamoyl}-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl}carbamate The title compound was prepared as described for EXAMPLE 246, step C, using (R)-tert-butyl(3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl) carbamate (0.70 g, 0.73 mmol) and tert-butyl ((4-(5,5-dimethyl-1,3,2-dioxaborinan-2-yl)-1H-benzo[d]imidazol-2-yl)methyl)carbamate (0.53 g, 1.48 mmol): LCMS [M+1]$^+$: 1083.

Step B: (R)—N1-(3-amino-2-hydroxypropyl)-4-(2-(aminomethyl)-1H-benzo[d]imidazol-4-yl)-3-(2H-tetrazol-5-yl)benzene-1,2-disulfonamide The title compound was prepared as described for EXAMPLE 244, step C, using tert-butyl-N-{[4-(3-{bis[(4-methoxyphenyl)methyl]sulfamoyl}-4-{[(2R)-3-{[(tert-butoxy)carbonyl]amino}-2-hydroxypropyl]sulfamoyl}-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl}carbamate (0.60 g, 0.55 mmol) to afford the crude product. The crude product was purified by Prep-HPLC with the following conditions: Column: X bridge C18, 19×150 mm; Mobile phase: ACN in water (10 mmol/L NH$_4$HCO$_3$), 5%-30% in 7 min; Detector: UV 254 nm. The fractions containing desired product were combined and concentrated under vacuum to afford the title compound: LCMS [M+1]$^+$: 523; $^1$H NMR (400 MHz, DMSO-d$_6$+D$_2$O): δ 8.24 (d, J=8.4 Hz, 1H), 7.92 (d, J=8.0 Hz, 1H), 7.34 (d, J=8.0 Hz, 1H), 6.84 (t, J=7.8 Hz, 1H), 6.35 (d, J=7.4 Hz, 1H), 3.97 (s, 2H), 3.90-3.81 (m, 1H), 3.17-3.12 (m, 1H), 3.09-3.03 (m, 1H), 2.96-2.93 (m, 1H), 2.76-2.71 (m, 1H).

Example 300

(R)—N1-(3-amino-2-hydroxypropyl)-4-(2-(aminoethyl)benzo[d]thiazol-4-yl)-3-(2H-tetrazol-5-yl)benzene-1,2-disulfonamide

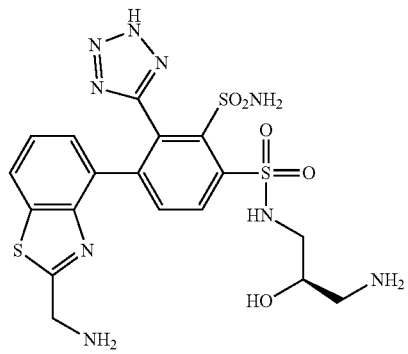 [SMILES: NCc1nc2c(-c3ccc(S(=O)(=O)NC[C@H](O)CN)c(S(N)(=O)=O)c3-c3nn[nH]n3)cccc2s1]

Step A: (R)-tert-butyl (3-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)-2-hydroxypropyl) carbamate The title compound was prepared as described for EXAMPLE 246, step C, using (R)-tert-butyl-(3-(2-(N,N-bis(4-methoxybenzyl)sulfamoyl)-4-iodo-3-(2-(4-methoxy benzyl)-2H-tetrazol-5-yl)phenylsulfonamido)-2-hydroxypropyl)carbamate (2.0 g, 2.08 mmol) and (2-aminobenzo[d]thiazol-4-yl)boronic acid (1.01 g, 5.19 mmol): LCMS [M+1]$^+$: 986.

Step B: (R)-tert-butyl (3-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenylsulfonamido)-2-hydroxypropyl)carbamate The title compound was prepared as described for EXAMPLE 275, step B, using (R)-tert-butyl(3-(4-(2-aminobenzo[d]thiazol-4-yl)-2-(N,N-bis (4-methoxybenzyl)sulfamoyl)-3-(2-(4-methoxybenzyl)-2H-tetrazol-5-yl)phenyl sulfonamido)-2-hydroxypropyl)carbamate (1.37 g, 1.39 mmol) to afford the title compound: LCMS [M+1]$^+$: 1049, 1051 (1:1).

Step C: (R)-tert-butyl (3-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenylsulfonamido)-2-hydroxypropyl)carbamate The title compound was prepared as described for Example 275, step C, using (R)-tert-butyl(3-(2-(N,N-bis(4-methoxybenzyl)sulfamoyl)-4-(2-bromobenzo[d]thiazol-4-yl)-3-(2-(4-methoxybenzyl)-2H-tetrazol-5-yl) phenyl sulfonamido)-2-hydroxypropyl)carbamate (0.86 g, 0.82 mmol): LCMS [M+1]$^+$: 996.

Step D: (R)-tert-butyl(3-(4-(2-(aminomethyl)benzo[d]thiazol-4-yl)-2-(N,N-bis(4-methoxybenzyl)sulfamoyl)-3-(2-(4-methoxybenzyl)-2H-tetrazol-5-yl)phenylsulfonamido)-2-hydroxypropyl) carbamate To a solution of (R)-tert-butyl (3-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl sulfonamido)-2-hydroxypropyl)carbamate (0.60 g, 0.60 mmol) in EA (4 mL) and MeOH (8 mL) was added Pd(OH)$_2$/C (20% Pd, 0.40 g, 0.60 mmol) at room temperature. Then 4 drops conc. HCl were added. The reaction mixture was degassed with hydrogen three times and stirred for 16 hours at 25° C. under hydrogen (about 30 atm). The resulting mixture was filtered and the filter cake was washed with MeOH (3×20 mL). The combined organic layers were concentrated under vacuum to afford the title compound, which was used in the next step without further purification: LCMS [M+1]$^+$: 1000.

Step E: (R)—N1-(3-amino-2-hydroxypropyl)-4-(2-(aminomethyl)benzo[d]thiazol-4-yl)-3-(2H-tetrazol-5-yl)benzene-1,2-disulfonamide The title compound was prepared as described for EXAMPLE 274, step D, using (R)-tert-butyl(3-(4-(2-(aminomethyl)benzo[d]thiazol-4-yl)-2-(N,N-bis(4-methoxy benzyl)sulfamoyl)-3-(2-(4-methoxybenzyl)-2H-tetrazol-5-yl)phenylsulfonamido)-2-hydroxypropyl)carbamate (0.55 g, 0.55 mmol) to afford the crude product. The crude product was purified by Prep-HPLC with the following conditions. Column: X Bridge Prep C18 OBD Column, 30×100 mm, 5 μm; Mobile Phase A: water with 10 mmol/L NH$_4$HCO$_3$, Mobile Phase B: ACN; Flow rate: 25 mL/min; Gradient: 5% B to 25% B in 10 min; Detector: 254 nm. The fractions containing desired product were combined and concentrated under vacuum to afford the title compound: LCMS [M+1]$^+$: 540; $^1$H NMR (400 MHz, DMSO-d$_6$): δ 8.19 (d, J=8.4 Hz, 1H), 7.93-7.74 (m, 2H), 7.02 (t, J=7.8 Hz, 1H), 6.54 (dd, J=7.6 Hz, 1.2 Hz, 1H), 6.31 (brs, 3H), 4.04 (s, 2H), 3.84-3.78 (m, 1H), 3.17-3.13 (m, 1H), 3.06-3.01 (m, 1H), 2.96-2.92 (m, 1H), 2.74-2.69 (m, 1H).

EXAMPLES 301-303 in the Table below were prepared in an analogous fashion to that described for EXAMPLE 298, starting from (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl) carbamate and the corresponding boronic acids or boronic esters, which were prepared as described herein, or which were available from commercial sources.

| EX. No. | Structure | Name | LC/MS [M + H]$^+$ |
|---|---|---|---|
| 301 | 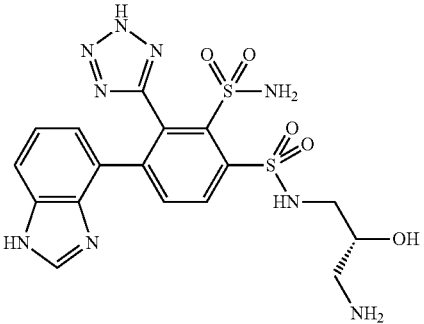 [SMILES: NC[C@@H](O)CNS(=O)(=O)c1ccc(-c2cccc3[nH]cnc23)c(-c2nn[nH]n2)c1S(N)(=O)=O] | (R)-4-(1H-benzo[d]imidazol-4-yl)-N1-(3-amino-2-hydroxypropyl)-3-(2H-tetrazol-5-yl)-benzene-1,2-disulfonamide | 494 |
| 302 | 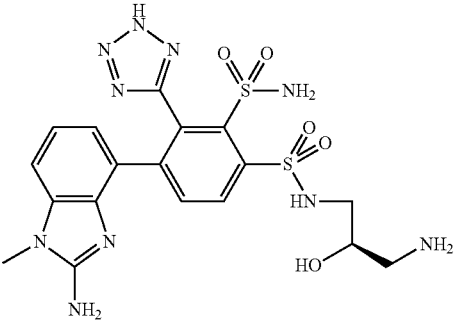 [SMILES: Cn1c(N)nc2c(-c3ccc(S(=O)(=O)NC[C@H](O)CN)c(S(N)(=O)=O)c3-c3nn[nH]n3)cccc21] | (R)-4-(2-amino-1-methyl-1H-benzo[d]imidazol-4-yl)-N1-(3-amino-2-hydroxypropyl)-3-(2H-tetrazol-5-yl)benzene-1,2-disulfonamide | 523 |

| EX. No. | Structure | Name | LC/MS [M + H]+ |
|---|---|---|---|
| 303 | 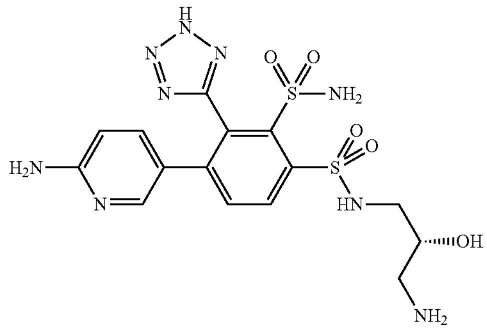 [SMILES: NC[C@@H](O)CNS(=O)(=O)c1ccc(-c2ccc(N)nc2)c(-c2nn[nH]n2)c1S(N)(=O)=O] | (R)-N1-(3-amino-2-hydroxypropyl)-4-(6-aminopyridin-3-yl)-3-(2H-tetrazol-5-yl)benzene-1,2-disulfonamide | 470 |

Example 304

(S)-4-(2-amino-1H-benzo[d]imidazol-4-yl)-N1-(3-amino-2-hydroxypropyl)-3-(2H-tetrazol-5-yl)-benzene-1,2-disulfonamide

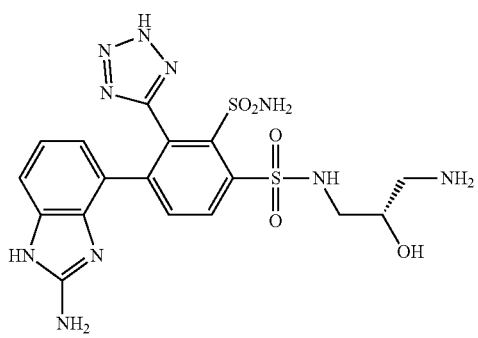 [SMILES: NC[C@H](O)CNS(=O)(=O)c1ccc(-c2cccc3[nH]c(N)nc23)c(-c2nn[nH]n2)c1S(N)(=O)=O]

Step A: (S)-tert-butyl(3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-2-hydroxypropyl)carbamate The title compound was prepared as described for EXAMPLE 298, step A, using (S)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl) carbamate (1.00 g, 1.00 mmol): LCMS [M+1]+: 969.

Step B: (S)-4-(2-amino-1H-benzo[d]imidazol-4-yl)-N1-(3-amino-2-hydroxypropyl)-3-(2H-tetrazol-5-yl)-benzene-1,2-disulfonamide The title compound was prepared as described for EXAMPLE 244, step C, using (S)-tert-butyl(3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-2-hydroxypropyl)carbamate to afford the crude product. The crude product was purified by Prep-HPLC with the following conditions: Column: X Bridge Prep C18 OBD Column 19×250 mm 10 μm; Mobile Phase A: water with 10 mmol/L NH4HCO3, Mobile Phase B: ACN; Flow rate: 25 mL/min; Gradient: 5% B to 35% B in 8 min; Detector: 254 and 220 nm. The fractions containing desired product were combined and concentrated under vacuum to afford the title compound: LCMS [M+1]+: 509; $^1$H NMR (400 MHz, CD$_3$OD+DCl): δ 8.64 (d, J=8.4 Hz, 1H), 8.11-7.97 (m, 1H), 7.33 (dd, J=8.0 Hz, 1.0 Hz, 1H), 7.28-7.12 (m, 1H), 6.89 (d, J=7.2 Hz, 1H), 4.16-3.92 (m, 1H), 3.31-3.16 (m, 3H), 2.98-2.82 (m, 1H).

Example 305

(S)—N1-(3-amino-2-hydroxypropyl)-4-(2-(aminomethyl)-1H-benzo[d]imidazole-4-yl)-3-(2H-tetrazol-5-yl)benzene-1,2-disulfonamide

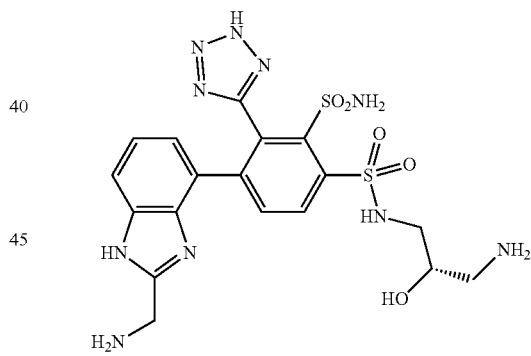

Step A: Tert-butyl-N-{[4-(3-{bis[(4-methoxyphenyl)methyl]sulfamoyl}-4-{[(2S)-3-{[(tert-butoxy)carbonyl]amino}-2-hydroxypropyl]sulfamoyl}-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl}carbamate The title compound was prepared as described for EXAMPLE 246, step C, using (S)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl)carbamate (0.56 g, 0.58 mmol) and tert-butyl ((4-(5,5-dimethyl-1,3,2-dioxaborinan-2-yl)-1H-benzo[d]imidazol-2-yl)methyl)carbamate (0.52 g, 1.45 mmol): LCMS [M+1]+: 1083.

Step B: (S)—N1-(3-amino-2-hydroxypropyl)-4-(2-(aminomethyl)-1H-benzo[d]imidazol-4-yl)-3-(2H-tetrazol-5-yl)benzene-1,2-disulfonamide The title compound was prepared as described for EXAMPLE 244, step C, using tert-butyl-N-{[4-(3-{bis[(4-methoxyphenyl)methyl]sulfamoyl}-4-{[(2S)-3-{[(tert-butoxy)carbonyl]amino}-2-hydroxypropyl]sulfamoyl}-2-[(2E, 4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl}carbamate (0.5 g, 0.46 mmol) to afford the crude product. The crude product was purified by Prep-HPLC with the following conditions: Column: X bridge C18, 19×150 mm; Mobile phase: ACN in water (10 mmol/L NH$_4$HCO$_3$), 5%-30% in 7 min; Detector: UV 254 nm. The fractions containing desired product were combined and concentrated under vacuum to afford the title compound: LCMS [M+1]$^+$: 523; $^1$H NMR (400 MHz, DMSO-d$_6$+D$_2$O): δ 8.23 (d, J=8.0 Hz, 1H), 7.92 (d, J=8.4 Hz, 1H), 7.31 (d, J=8.0 Hz, 1H), 6.81 (t, J=7.8 Hz, 1H), 6.30 (d, J=7.2 Hz, 1H), 3.91 (s, 2H), 3.82-3.76 (m, 1H), 3.18-3.13 (m, 1H), 3.06-3.00 (m, 1H), 2.92-2.89 (m, 1H), 2.73-2.68 (m, 1H).

Example 306

(S)—N1-(3-amino-2-hydroxypropyl)-4-(2-(aminomethyl) benzo[d]thiazol-4-yl)-(2H-tetrazol-5-yl)benzene-1,2-disulfonamide

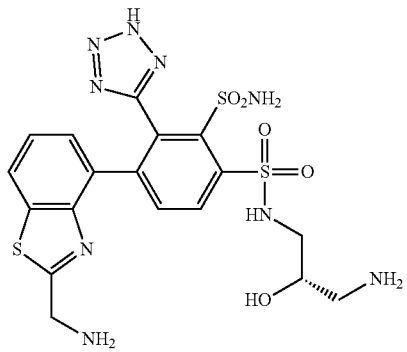 [SMILES: NCc1nc2c(-c3ccc(S(=O)(=O)NC[C@@H](O)CN)c(S(N)(=O)=O)c3-c3nn[nH]n3)cccc2s1]

Step A: (S)-tert-butyl (3-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)-2-hydroxy propyl)carbamate The title compound was prepared as described for EXAMPLE 246, step C, using (S)-tert-butyl(3-(2-(N,N-bis(4-methoxybenzyl)sulfamoyl)-4-iodo-3-(2-(4-methoxy benzyl)-2H-tetrazol-5-yl)phenylsulfonamido)-2-hydroxypropyl)carbamate (2.00 g, 2.08 mmol) and (2-aminobenzo[d]thiazol-4-yl)boronic acid (1.01 g, 5.19 mmol): LCMS [M+1]$^+$: 986.

Step B: (S)-tert-butyl(3-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenylsulfonamido)-2-hydroxypropyl)carbamate The title compound was prepared as described for EXAMPLE 275, step B, using (S)-tert-butyl-3-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)-2-hydroxypropyl)carbamate (1.50 g, 1.52 mmol) to afford the title compound: LCMS [M+1]$^+$: 1049, 1051 (1:1).

Step C: (S)-tert-butyl(3-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenylsulfonamido)-2-hydroxypropyl)carbamate The title compound was prepared as described for EXAMPLE 275, step C, using (S)-tert-butyl-3-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenylsulfonamido)-2-hydroxypropyl)carbamate (0.98 g, 0.93 mmol) to afford the title compound: LCMS [M+1]$^+$: 996.

Step D: (S)-tert-butyl(3-(4-(2-(aminomethyl)benzo[d]thiazol-4-yl)-2-(N,N-bis(4-methoxy benzyl)sulfamoyl)-3-(2-(4-methoxybenzyl)-2H-tetrazol-5-yl) phenylsulfonamido)-2-hydroxypropyl) carbamate To a solution of (S)-tert-butyl(3-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl sulfonamido)-2-hydroxypropyl)carbamate (0.60 g, 0.60 mmol) in EA (4 mL) and MeOH (8 mL) was added Pd(OH)$_2$/C (20% Pd, 0.40 g, 0.60 mmol) at room temperature. Then 4 drops conc. HCl were added. The reaction mixture was degassed with hydrogen three times and stirred for 16 hours at 25° C. under hydrogen (about 30 atm.). The resulting mixture was filtered and the filter cake was washed with MeOH (3×20 mL). The combined organic layers were concentrated under vacuum to afford (S)-tert-butyl (3-(4-(2-(aminomethyl)benzo[d]thiazol-4-yl)-2-(N,N-bis(4-methoxybenzyl)sulfamoyl)-3-(2-(4-methoxybenzyl)-2H-tetrazol-5-yl)phenylsulfonamido)-2-hydroxypropyl) carbamate as a solid, which was used in the next step without further purification: LCMS [M+1]$^+$: 1000.

Step E: (S)—N1-(3-amino-2-hydroxypropyl)-4-(2-(aminomethyl)benzo[d]thiazol-4-yl)-3-(2H-tetrazol-5-yl)benzene-1,2-disulfonamide The title compound was prepared as described for EXAMPLE 274, step D, using (S)-tert-butyl(3-(4-(2-(aminomethyl)benzo[d]thiazol-4-yl)-2-(N,N-bis(4-methoxy benzyl)sulfamoyl)-3-(2-(4-methoxybenzyl)-2H-tetrazol-5-yl) phenylsulfonamido)-2-hydroxypropyl)carbamate (0.58 g, 0.57 mmol) to afford the crude product. The crude product was purified by Prep-HPLC with the following conditions: Column: X Bridge C18 OBD Prep Column 100 Å, 10 μm, 19 mm×250 mm; Mobile Phase A: water with 10 mmol/L NH$_4$HCO$_3$, Mobile Phase B: ACN; Flow rate: 20 mL/min; Gradient: 3% B to 30% B in 10 min; Detector: 254 nm. The fractions were combined and concentrated under vacuum to afford the title compound: LCMS [M+1]$^+$: 540; $^1$H NMR (400 MHz, DMSO-d$_6$): δ 8.19 (d, J=8.4 Hz, 1H), 7.94-7.78 (m, 2H), 7.02 (t, J=7.6 Hz, 1H), 6.54 (dd, J=7.4 Hz, 1.2 Hz, 1H), 6.51-5.45 (brs, 5H), 4.04 (s, 2H), 3.84-3.81 (m, 1H), 3.18-3.12 (m, 1H), 3.08-3.02 (m, 1H), 2.98-2.92 (m, 1H), 2.75-2.71 (m, 1H).

EXAMPLES 307-309 in the Table below were prepared in an analogous fashion to that described for EXAMPLE 299, starting from (S)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl) carbamate and the corresponding boronic acids or boronic esters, which were prepared as described herein, or which were available from commercial sources.

| EX. No. | Structure | Chemical Name | LC/MS [M + H]+ |
|---|---|---|---|
| 307 | 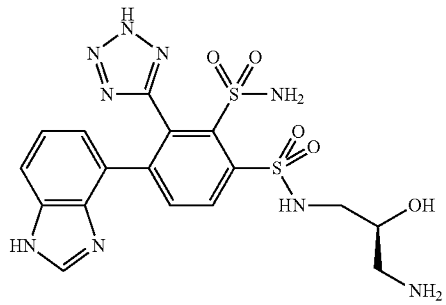 [SMILES: NC[C@H](O)CNS(=O)(=O)c1ccc(-c2cccc3[nH]cnc23)c(-c2nn[nH]n2)c1S(N)(=O)=O] | (S)-4-(1H-benzo[d]imidazol-4-yl)-N1-(3-amino-2-hydroxypropyl)-3-(2H-tetrazol-5-yl)-benzene-1,2-disulfonamide | 494 |
| 308 | 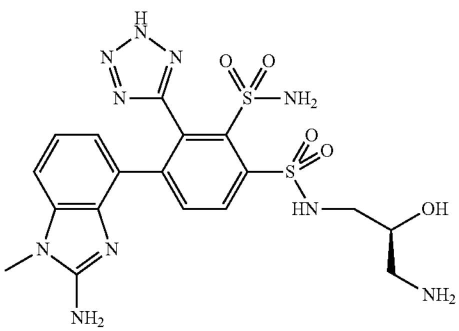 [SMILES: Cn1c(N)nc2c(-c3ccc(S(=O)(=O)NC[C@@H](O)CN)c(S(N)(=O)=O)c3-c3nn[nH]n3)cccc21] | (S)-4-(2-amino-1-methyl-1H-benzo[d]imidazol-4-yl)-N1-(3-amino-2-hydroxypropyl)-3-(2H-tetrazol-5-yl)benzene-1,2-disulfonamide | 523 |
| 309 | 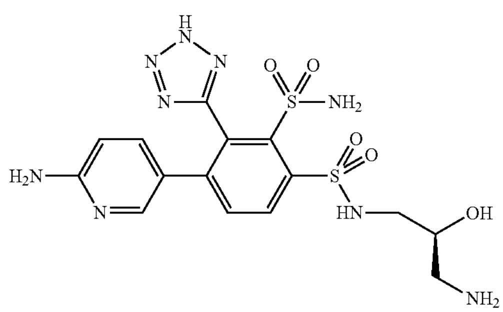 [SMILES: NC[C@H](O)CNS(=O)(=O)c1ccc(-c2ccc(N)nc2)c(-c2nn[nH]n2)c1S(N)(=O)=O] | (S)-N1-(3-amino-2-hydroxypropyl)-4-(6-aminopyridin-3-yl)-3-(2H-tetrazol-5-yl)benzene-1,2-disulfonamide | 470 |

Example 310

(S)-4-(2-amino-1H-benzo[d]imidazol-4-yl)-N1-(piperazin-2-ylmethyl)-3-(2H-tetrazol-5-yl)benzene-1,2-disulfonamide

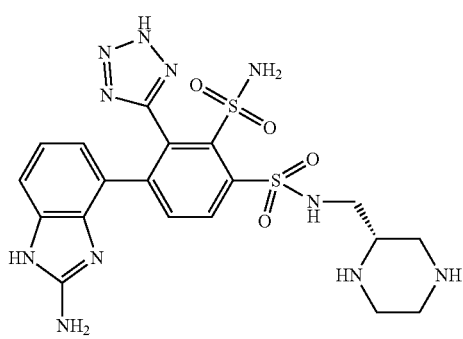 [SMILES: Nc1nc2c(-c3ccc(S(=O)(=O)NC[C@@H]4CNCCN4)c(S(N)(=O)=O)c3-c3nn[nH]n3)cccc2[nH]1]

Step A: (S)-di-tert-butyl 2-((4-(2-amino-1H-benzo[d]imidazol-4-yl)-2-(N,N-bis(4-methoxy benzyl)sulfamoyl)-3-(2-(4-methoxybenzyl)-2H-tetrazol-5-yl) phenylsulfonamido) methyl)piperazine-1,4-dicarboxylate The title compound was prepared as described for EXAMPLE 246, step C, using (S)-di-tert-butyl-2-((2-(N,N-bis(4-methoxybenzyl)sulfamoyl)-4-iodo-3-(2-(4-methoxy benzyl)-2H-tetrazol-5-yl)phenylsulfonamido)methyl)piperazine-1,4-dicarboxylate (1.00 g, 0.92 mmol) and (2-amino-1H-benzo[d]imidazol-4-yl)boronic acid (0.41 g, 2.30 mmol): LCMS [M+1]+: 1094.

Step B: (S)-4-(2-amino-1H-benzo[d]imidazol-4-yl)-N1-(piperazin-2-ylmethyl)-3-(2H-tetrazol-5-yl)benzene-1,2-disulfonamide The title compound was prepared as described for EXAMPLE 244, step C, using (S)-di-tert-butyl-2-((4-(2-amino-1H-benzo[d]imidazol-4-yl)-2-(N,N-bis(4-methoxy benzyl)sulfamoyl)-3-(2-(4-methoxybenzyl)-2H-tetrazol-5-yl)phenylsulfonamido) methyl)piperazine-1,4-dicarboxylate (0.70 g, 0.64 mmol) to afford the crude product. The crude product was purified by Prep-HPLC with the following conditions: Column: X Bridge Prep C18 OBD Column 19×250 mm 10 μm; Mobile Phase A: water with 5 mmol/L NH$_4$HCO$_3$, Mobile Phase B: ACN; Flow rate: 20 mL/min; Gradient: 5% B to 25% B in 7 min; Detector: 254 and 220 nm. The fractions containing desired product were combined and concentrated under vacuum to afford the title compound: LCMS [M+1]$^+$: 534; $^1$H NMR (400 MHz, DMSO-d$_6$): δ 8.17 (d, J=8.4 Hz, 1H), 7.97 (d, J=8.4 Hz, 1H), 7.55 (brs, 3H), 6.90 (d, J=7.6 Hz, 1H), 6.48 (t, J=7.6 Hz, 1H), 6.15 (brs, 2H), 6.04 (d, J=7.6 Hz, 1H), 3.23-3.16 (m, 1H), 3.06-2.89 (m, 5H), 2.73 (d, J=8.4 Hz, 2H), 2.69-2.53 (m, 1H).

Example 311

(S)-4-(2-(aminomethyl)-1H-benzo[d]imidazol-4-yl)-N-(piperazin-2-ylmethyl)-3-(2H-tetrazol-5-yl)benzene-1,2-disulfonamide

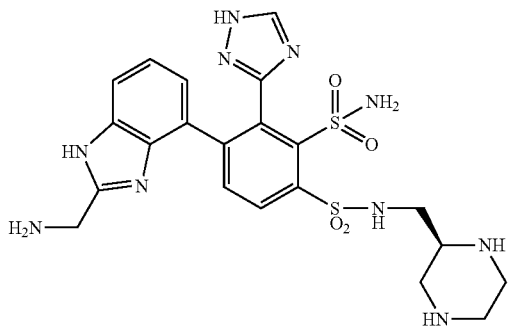 [SMILES: NCc1nc2c(-c3ccc(S(=O)(=O)NC[C@@H]4CNCCN4)c(S(N)(=O)=O)c3-c3nc[nH]n3)cccc2[nH]1]

Step A: (2S)-di-tert-butyl-2-((2-(N,N-bis(4-methoxybenzyl)sulfamoyl)-4-(2-(((tert-butoxy carbonyl)amino)methyl)-1H-benzo[d]imidazol-4-yl)-3-(1-(4-methoxybenzyl)-2H-tetrazol-5-yl)phenylsulfonamido)methyl)piperazine-1,4-dicarboxylate The title compound was prepared as described for EXAMPLE 246, step C, using (2S)-di-tert-butyl-2-((2-(N,N-bis(4-methoxybenzyl)sulfamoyl)-4-iodo-3-(1-(4-methoxybenzyl)-2H-tetrazol-5-yl)phenylsulfonamido)methyl) piperazine-1,4-dicarboxylate (0.50 g, 0.46 mmol) and tert-butyl ((4-(5,5-dimethyl-1,3,2-dioxaborinan-2-yl)-1H-benzo[d]imidazol-2-yl)methyl)carbamate (0.66 g, 1.84 mmol): LCMS [M+1]$^+$: 1208.

Step B: (S)-4-(2-(aminomethyl)-1H-benzo[d]imidazol-4-yl)-N1-(piperazin-2-ylmethyl)-3-(2H-tetrazol-5-yl)benzene-1,2-disulfonamide The title compound was prepared as described for EXAMPLE 244, step C, using (2S)-di-tert-butyl-2-((2-(N,N-bis(4-methoxybenzyl)sulfamoyl)-4-(2-(((tert-butoxycarbonyl)amino)methyl)-1H-benzo[d]imidazol-4-yl)-3-(1-(4-methoxybenzyl)-2H-tetrazol-5-yl)phenylsulfonamido) methyl)piperazine-1,4-dicarboxylate (0.3 g, 0.25 mmol) to afford the crude product. The crude product was purified by Prep-HPLC with the following conditions: Column: X Bridge Prep C18 OBD Column 19×250 mm, 10 μm; Mobile Phase A: water with 10 mmol/L NH$_4$HCO$_3$, Mobile Phase B: ACN; Flow rate: 20 mL/min; Gradient: 3% B to 25% B in 7 min; Detector: 254 and 220 nm. The fractions containing desired product were combined and concentrated under vacuum to afford the title compound. LCMS [M+1]$^+$: 548; $^1$H NMR (300 MHz, DMSO-d$_6$): δ 8.22 (d, J=8.3 Hz, 1H), 7.90 (d, J=8.4 Hz, 1H), 7.31 (d, J=8.0 Hz, 1H), 6.80 (t, J=7.9 Hz, 1H), 6.30 (d, J=7.6 Hz, 1H), 3.97 (s, 2H), 3.22-2.80 (m, 5H), 2.71-2.67 (m, 2H); 2.55-2.51 (m, 2H).

EXAMPLES 312-313 in the Table below were prepared in an analogous fashion to that described for EXAMPLE 310, starting from (S)-di-tert-butyl 2-((2-(N,N-bis(4-methoxybenzyl)sulfamoyl)-4-iodo-3-(2-(4-methoxybenzyl)-2H-tetrazol-5-yl)phenylsulfonamido) methyl)piperazine-1,4-dicarboxylate and the corresponding boronic acids or boronic esters, which were prepared as described herein, or which were available from commercial sources.

| EX. No. | Structure | Chemical Name | MW | LC/MS [M + H]$^+$ |
|---|---|---|---|---|
| 312 | 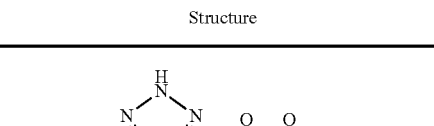 | (S)-4-(6-aminopyridin-3-yl)-N1-(piperazin-2-ylmethyl)-3-(2H-tetrazol-5-yl)benzene-1,2-disulfonamide | 494 | 495 |

| EX. No. | Structure | Chemical Name | MW | LC/MS [M + H]+ |
|---|---|---|---|---|
| 313 | 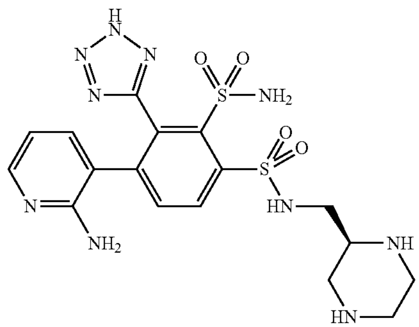 [SMILES: Nc1ncccc1-c1ccc(S(=O)(=O)NC[C@@H]2CNCCN2)c(S(N)(=O)=O)c1-c1nn[nH]n1] | (S)-4-(2-aminopyridin-3-yl)-N1-(piperazin-2-ylmethyl)-3-(2H-tetrazol-5-yl)benzene-1,2-disulfonamide | 494 | 495 |

Example 314

(R)-4-(2-amino-1H-benzo[d]imidazol-4-yl)-N1-(piperazin-2-ylmethyl)-3-(2H-tetrazol-5-yl)benzene-1,2-disulfonamide

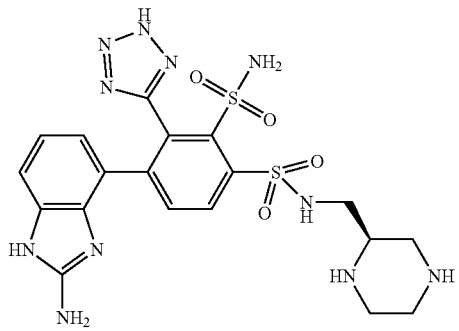 [SMILES: Nc1nc2c(-c3ccc(S(=O)(=O)NC[C@H]4CNCCN4)c(S(N)(=O)=O)c3-c3nn[nH]n3)cccc2[nH]1]

Step A: (R)-di-tert-butyl 2-((4-(2-amino-1H-benzo[d]imidazol-4-yl)-2-(N,N-bis(4-methoxy benzyl)sulfamoyl)-3-(2-(4-methoxybenzyl)-2H-tetrazol-5-yl)phenylsulfonamido) methyl)piperazine-1,4-dicarboxylate The title compound was prepared as described for EXAMPLE 246, step C, using (R)-di-tert-butyl-2-((2-(N,N-bis(4-methoxybenzyl)sulfamoyl)-4-iodo-3-(2-(4-methoxybenzyl)-2H-tetrazol-5-yl)phenylsulfonamido)methyl)piperazine-1,4-dicarboxylate (1.00 g, 0.92 mmol) and (2-amino-1H-benzo[d]imidazol-4-yl)boronic acid (0.33 g, 1.84 mmol): LCMS [M+1]+: 1094.

Step B: (R)-4-(2-amino-1H-benzo[d]imidazol-4-yl)-N1-(piperazin-2-ylmethyl)-3-(2H-tetrazol-5-yl)benzene-1,2-disulfonamide The title compound was prepared as described for EXAMPLE 244, step C, using (R)-di-tert-butyl-2-((4-(2-amino-1H-benzo[d]imidazol-4-yl)-2-(N,N-bis(4-methoxy benzyl)sulfamoyl)-3-(2-(4-methoxybenzyl)-2H-tetrazol-5-yl)phenylsulfonamido) methyl)piperazine-1,4-dicarboxylate (0.60 g, 0.55 mmol) to afford the crude product. The crude product was purified by Prep-HPLC with the following conditions: Column: X Bridge Prep C18 OBD Column 19×250 mm, 10 μm; Mobile Phase A: water with 5 mmol/L NH$_4$HCO$_3$, Mobile Phase B: ACN; Flow rate: 20 mL/min; Gradient: 5% B to 25% B in 7 min; Detector: 254 and 220 nm. The fractions containing desired product were combined and concentrated under vacuum to afford the title compound: LCMS [M+1]+: 534; $^1$H NMR (400 MHz, DMSO-d$_6$): δ 8.17 (d, J=8.4 Hz, 1H), 7.97 (d, J=8.4 Hz, 1H), 7.50 (brs, 3H), 6.90 (d, J=8.4 Hz, 1H), 6.48 (t, J=7.6 Hz, 1H), 6.15 (brs, 2H), 6.04 (d, J=7.6 Hz, 1H), 3.19-3.09 (m, 1H), 3.06-3.03 (m, 3H), 2.98-2.89 (m, 2H), 2.76-2.72 (m, 2H), 2.58-2.54 (m, 1H).

EXAMPLES 315-316 in the Table below were prepared in an analogous fashion to that described for EXAMPLE 314, starting from (R)-di-tert-butyl 2-((2-(N,N-bis(4-methoxybenzyl)sulfamoyl)-4-iodo-3-(2-(4-methoxybenzyl)-2H-tetrazol-5-yl)phenylsulfonamido)methyl)piperazine-1,4-dicarboxylate and the corresponding boronic acids or boronic esters, which were prepared as described herein, or which were available from commercial sources.

| EX. No. | Structure | Chemical Name | MW | LC/MS [M + H]+ |
|---|---|---|---|---|
| 315 | 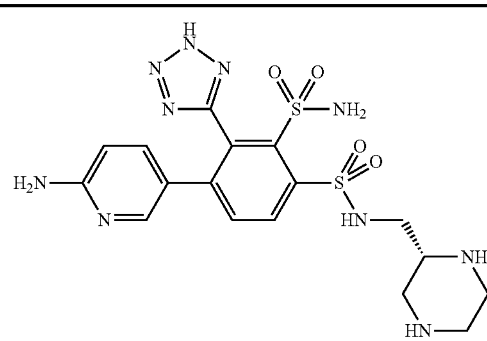 | (R)-4-(6-aminopyridin-3-yl)-N1-(piperazin-2-ylmethyl)-3-(1H-tetrazol-5-yl)benzene-1,2-disulfonamide | 494 | 495 |

| EX. No. | Structure | Chemical Name | MW | LC/MS [M + H]+ |
|---|---|---|---|---|
| 316 | 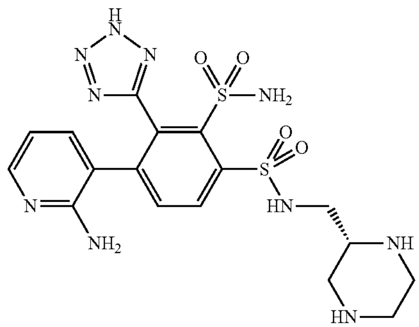 [SMILES: Nc1ncccc1-c1ccc(S(=O)(=O)NC[C@H]2CNCCN2)c(S(N)(=O)=O)c1-c1nn[nH]n1] | (R)-4-(2-aminopyridin-3-yl)-N1-(piperazin-2-ylmethyl)-3-(1H-tetrazol-5-yl)benzene-1,2-disulfonamide | 494 | 495 |

Example 317

(R)—N1-(1-aminopropan-2-yl)-4-(2-aminopyridin-4-yl)-3-(2H-tetrazol-5-yl) benzene-1,2-disulfonamide

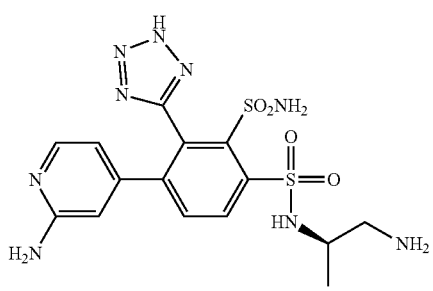 [SMILES: C[C@H](CN)NS(=O)(=O)c1ccc(-c2ccnc(N)c2)c(-c2nn[nH]n2)c1S(N)(=O)=O]

Step A: (R)-benzyl(2-(4-(2-aminopyridin-4-yl)-2-(N,N-bis(4-methoxybenzyl)sulfamoyl)-3-(2-(4-methoxybenzyl)-2H-tetrazol-5-yl)phenylsulfonamido)propyl)carbamate The title compound was prepared as described for EXAMPLE 246, step C, using (R)-benzyl2-(2-(N,N-bis(4-methoxybenzyl)sulfamoyl)-4-iodo-3-(2-(4-methoxybenzyl)-2H-tetrazol-5-yl)phenylsulfonamido)propyl)carbamate (0.70 g, 0.71 mmol) and 4-(4,4,5,5-tetramethyl-1,3,2-dioxaborolan-2-yl)pyridin-2-amine (0.39 g, 1.78 mmol): LCMS [M+1]+: 948.

Step B: (R)—N1-(1-aminopropan-2-yl)-4-(2-aminopyridin-4-yl)-3-(2H-tetrazol-5-yl)benzene-1,2-disulfonamide A solution of (R)-benzyl(2-(4-(2-aminopyridin-4-yl)-2-(N,N-bis (4-methoxybenzyl)sulfamoyl)-3-(2-(4-methoxybenzyl)-2H-tetrazol-5-yl) phenylsulfonamido)propyl)carbamate (0.40 g, 0.42 mmol) in TFA (5 mL) was stirred at 80° C. for 3 hours. The resulting solution was concentrated under vacuum. The crude product was purified by Prep-HPLC with the following conditions: Column: X Bridge Prep C18, 19 mm×250 mm, 10 μm; Mobile Phase A: water with 10 mmol/L NH4HCO3, Mobile Phase B: ACN; Flow rate: 20 mL/min; Gradient: 5% B to 20% B in 6 min; Detector: 254 and 220 nm. The fractions containing desired product were combined and concentrated under vacuum to afford the title compound: LCMS [M+1]+: 454; 1H NMR (400 MHz, CD3OD+DCl): δ 8.74 (d, J=8.4 Hz, 1H), 8.07 (d, J=8.4 Hz, 1H), 7.77 (d, J=6.8 Hz, 1H), 6.86 (s, 1H), 6.54 (dd, J=6.4 Hz, 1.6 Hz, 1H), 3.92-3.87 (m, 1H), 3.15-3.11 (m, 1H), 3.05-3.00 (m, 1H), 1.13 (d, J=6.8 Hz, 3H).

Example 318

(R)—N1-(1-aminopropan-2-yl)-4-(6-aminopyridin-2-yl)-3-(2H-tetrazol-5-yl) benzene-1,2-disulfonamide

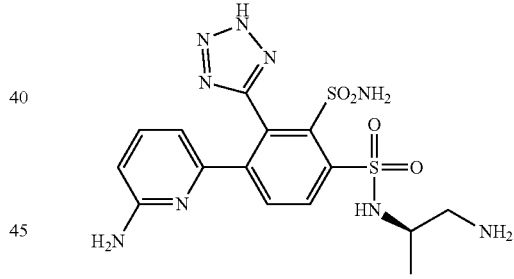

Step A: (R)-benzyl(2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)propyl)carbamate The title compound was prepared as described for EXAMPLE 246, step C, using (R)-benzyl(2-(2-(N,N-bis(4-methoxybenzyl)sulfamoyl)-4-iodo-3-(2-(4-methoxy benzyl)-2H-tetrazol-5-yl)phenylsulfonamido)propyl)carbamate (0.65 g, 0.66 mmol) and (6-bromopyridin-2-yl)boronic acid (0.13 g, 0.66 mmol): LCMS [M+1]+: 1011, 1013.

Step B: (R)-benzyl (2-(4-(6-aminopyridin-2-yl)-2-(N,N-bis(4-methoxybenzyl)sulfamoyl)-3-(2-(4-methoxybenzyl)-2H-tetrazol-5-yl)phenylsulfonamido)propyl)carbamate To a solution of (R)-benzyl(2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido) propyl)carbamate (0.20 g, 0.15 mmol) in 1,4-dioxane (2 mL) was added 2,2,2-trifluoroacetamide (0.08 g, 0.74 mmol), copper (I) iodide (14.11 mg, 0.07 mmol), $Cs_2CO_3$ (0.15 g, 0.45 mmol) and N1,N2-dimethylethane-1,2-diamine (13.07 mg, 0.15 mmol) at room temperature. The mixture was degassed with nitrogen three times. The reaction mixture was stirred at 80° C. for 4 hours under nitrogen. The resulting mixture was quenched with water (50 mL), and then extracted with EA (3×50 mL). The combined organic layers was washed with water (3×50 mL) and brine (3×50 mL), dried over anhydrous $Na_2SO_4$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]+: 948.

Step C: (R)—N1-(1-aminopropan-2-yl)-4-(6-aminopyridin-2-yl)-3-(2H-tetrazol-5-yl)benzene-1,2-disulfonamide A solution of (R)-benzyl (2-(4-(6-aminopyridin-2-yl)-2-(N,N-bis(4-methoxybenzyl) sulfamoyl)-3-(2-(4-methoxybenzyl)-2H-tetrazol-5-yl)phenylsulfonamido)propyl) carbamate (0.12 g, 0.13 mmol) in TFA (3 mL) was stirred at 80° C. for 2 hours. The resulting solution was concentrated under vacuum. The crude product was purified by Prep-HPLC with the following conditions: Column: X Bridge Prep C18 OBD Column 19×250 mm, 10 μm; Mobile Phase A: water with 10 mmol/L $NH_4HCO_3$, Mobile Phase B: ACN; Flow rate: 20 mL/min; Gradient: 5% B to 25% B in 7 min; Detector: 254 and 220 nm; Retention time: 5.51 min. The fractions containing desired product were combined and concentrated under vacuum to afford the title compound: LCMS [M+1]+: 454; $^1$H NMR (400 MHz, DMSO-$d_6$): δ 8.26 (d, J=8.4 Hz, 1H), 7.91 (d, J=8.4 Hz, 1H), 7.19 (brs, 3H), 6.97 (t, J=7.6 Hz, 1H), 6.25 (d, J=8.0 Hz, 1H), 5.88 (brs, 2H), 5.49 (d, J=7.6 Hz, 1H), 3.61-3.51 (m, 1H), 2.85-2.83 (m, 2H), 1.05 (d, J=6.4 Hz, 3H).

Example 319

$N^1$-((3R,4S)-4-aminopyrrolidin-3-yl)-4-(2-aminoquinolin-8-yl)-3-(2H-tetrazol-5-yl)benzene-1,2-disulfonamide

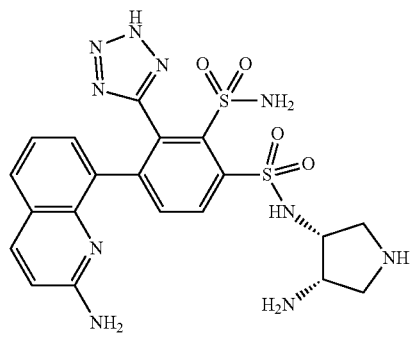 [SMILES: Nc1ccc2cccc(-c3ccc(S(=O)(=O)N[C@@H]4CNC[C@@H]4N)c(S(N)(=O)=O)c3-c3nn[nH]n3)c2n1]

Step A: (3R,4S)-tert-butyl-3-(2-(N,N-bis(4-methoxybenzyl)sulfamoyl)-3-(2-(4-methoxybenzyl)-2H-tetrazol-5-yl)-4-(2-((4-methoxybenzyl)amino)quinolin-8-yl)phenylsulfonamido)-4-((tert-butoxycarbonyl)amino)pyrrolidine-1-carboxylate The title compound was prepared as described for EXAMPLE 246, step C, using (3R,4S)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)-4-((tert-butoxycarbonyl) amino)pyrrolidine-1-carboxylate (0.45 g, 0.42 mmol) and (2-((4-methoxybenzyl) amino)quinolin-8-yl)boronic acid (0.15 g, 0.50 mmol) to afford the title compound: LCMS [M+1]+: 1211.

Step B: $N^1$-((3R,4S)-4-aminopyrrolidin-3-yl)-4-(2-aminoquinolin-8-yl)-3-(2H-tetrazol-5-yl)benzene-1,2-disulfonamide The title compound was prepared as described for EXAMPLE 244, step C, using (3R,4S)-tert-butyl-3-(2-(N,N-bis(4-methoxybenzyl)sulfamoyl)-3-(2-(4-methoxybenzyl)-2H-tetrazol-5-yl)-4-(2-((4-methoxybenzyl)amino)quinolin-8-yl)phenylsulfonamido)-4-((tert-butoxycarbonyl)amino)pyrrolidine-1-carboxylate (0.29 g, 0.24 mmol) to afford the crude product. The crude product was purified by Prep-HPLC with the following conditions: Column: X Bridge C18 OBD, 100 Å, 5 μm, 19 mm×250 mm; Mobile Phase A: water (10 mmol/L $NH_4HCO_3$), Mobile Phase B: ACN; Flow rate: 20 mL/min; Gradient: 7% B to 30% B in 7 min; Detector: 254 and 220 nm. The fractions containing desired product were combined and concentrated under vacuum to afford the title compound: LCMS [M+1]+: 531; $^1$H NMR (300 MHz, DMSO-$d_6$): δ 8.19 (d, J=8.4 Hz, 1H), 7.87 (d, J=8.4 Hz, 1H), 7.76 (d, J=8.4 Hz, 1H), 7.46 (d, J=6.6 Hz, 1H), 6.84-6.79 (m, 1H), 6.75-6.72 (m, 2H), 6.32 (brs, 2H), 3.86-3.77 (m, 1H), 3.52-3.23 (m, 4H), 2.90-2.83 (m, 1H).

Example 320

N1-((3R,4S)-4-aminopyrrolidin-3-yl)-4-(1H-pyrrolo[3,2-b]pyridin-6-yl-3-(2H-tetrazol-5-yl)benzene-1,2-disulfonamide

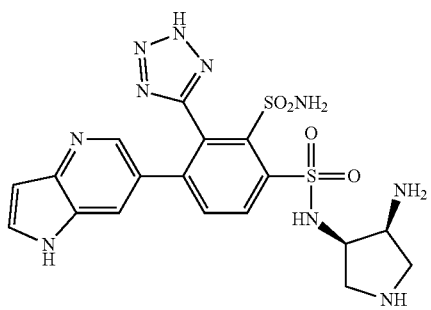 [SMILES: N[C@H]1CNC[C@H]1NS(=O)(=O)c1ccc(-c2cnc3cc[nH]c3c2)c(-c2nn[nH]n2)c1S(N)(=O)=O]

Step A: (3R,4S)-tert-butyl-3-(2-(N,N-bis(4-methoxybenzyl)sulfamoyl)-3-(2-(4-methoxybenzyl)-2H-tetrazol-5-yl)-4-(1H-pyrrolo[3,2-b]pyridin-6-yl)phenylsulfonamido)-4-((tert-butoxycarbonyl)amino)pyrrolidine-1-carboxylate The title compound was prepared as described for EXAMPLE 246, step C, using (3R,4S)-tert-butyl-3-(2-(N, N-bis(4-methoxybenzyl)sulfamoyl)-4-iodo-3-(2-(4-methoxybenzyl)-2H-tetrazol-5-yl)phenylsulfonamido)-4-((tert-butoxycarbonyl) amino)pyrrolidine-1-carboxylate (0.80 g, 0.74 mmol) and (1H-pyrrolo[3,2-b] pyridin-6-yl)boronic acid (0.27 g, 1.64 mmol) to afford the title compound: LCMS [M+1]⁺: 1065.

Step B: N1-((3R,4S)-4-aminopyrrolidin-3-yl)-4-(1H-pyrrolo[3,2-b]pyridin-6-yl)-3-(2H-tetrazol-5-yl) benzene-1,2-disulfonamide The title compound was prepared as described for EXAMPLE 274, step D, (3R,4S)-tert-butyl-3-(2-(N,N-bis (4-methoxybenzyl)sulfamoyl)-3-(2-(4-methoxybenzyl)-2H-tetrazol-5-yl)-4-(1H-pyrrolo[3,2-b]pyridin-6-yl)phenylsulfonamido)-4-((tert-butoxycarbonyl)amino)pyrrolidine-1-carboxylate (0.49 g, 0.46 mmol) to afford the crude product. The crude product was purified with the following conditions: Column: Sunfire Prep C18 OBD Column, 10 μm, 19×250 mm; Mobile Phase A: water with 10 mmol/L NH₄HCO₃, Mobile Phase B: ACN; Flow rate: 20 mL/min; Gradient: 6% B to 22% B in 9 min; Detector: 254 and 220 nm. The fractions containing desired product were combined and concentrated under vacuum to afford the title compound: LCMS [M+1]⁺: 505; ¹H NMR (400 MHz, DMSO-d₆): δ 11.42 (s, 1H), 8.27 (d, J=8.4 Hz, 1H), 7.96-7.76 (m, 2H), 7.58 (t, J=7.3 Hz, 1H), 7.20 (d, J=7.6 Hz, 1H), 6.45-6.41 (m, 1H), 3.77-3.72 (m, 1H), 3.54-3.37 (m, 1H), 3.23-3.07 (m, 3H), 2.79-2.74 (m, 1H).

Example 321

N¹-((3R,4S)-4-aminopyrrolidin-3-yl)-4-(2-aminothiazol-5-yl)-3-(2H-tetrazol-5-yl)benzene-1,2-disulfonamide

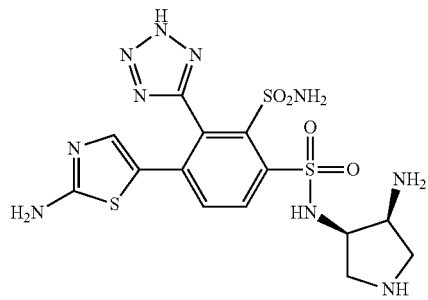 [SMILES: Nc1ncc(-c2ccc(S(=O)(=O)N[C@@H]3CNC[C@@H]3N)c(S(N)(=O)=O)c2-c2nn[nH]n2)s1]

Step A: (3R,4S)-tert-butyl-3-(4-(2-aminothiazol-5-yl)-2-(N,N-bis(4-methoxybenzyl)sulfamoyl)-3-(2-(4-methoxybenzyl)-2H-tetrazol-5-yl)phenyl sulfonamido)-4-((tert-butoxy carbonyl)amino) pyrrolidine-1-carboxylate The title compound was prepared as described for EXAMPLE 246, step C, using (3R,4S)-tert-butyl-3-(2-(N, N-bis(4-methoxybenzyl)sulfamoyl)-4-iodo-3-(2-(4-methoxybenzyl)-2H-tetrazol-5-yl)phenylsulfonamido)-4-((tert-butoxycarbonyl)amino) pyrrolidine-1-carboxylate (0.80 g, 0.74 mmol) and tert-butyl (5-(4,4,5,5-tetramethyl-1,3,2-dioxaborolan-2-yl)thiazol-2-yl)carbamate (0.36 g, 1.12 mmol) to afford the title compound: LCMS [M+1]⁺: 1147.

Step B: N1-((3R,4S)-4-aminopyrrolidin-3-yl)-4-(2-aminothiazol-5-yl)-3-(2H-tetrazol-5-yl) benzene-1, 2-disulfonamide The title compound was prepared as described for EXAMPLE 274, step D, using (3R,4S)-tert-butyl-3-(4-(2-aminothiazol-5-yl)-2-(N,N-bis(4-methoxybenzyl)sulfamoyl)-3-(2-(4-methoxybenzyl)-2H-tetrazol-5-yl)phenylsulfonamido)-4-((tert-butoxy carbonyl)amino)pyrrolidine-1-carboxylate (0.56 g, 0.54 mmol) to afford the crude product. The crude product was purified with the following conditions: Column: X Bridge Prep Amide OBD Column 19×150 mm, 5 μm 13 nm; Mobile Phase A: waters with 10 mmol/L NH₄HCO₃, Mobile Phase B: ACN; Flow rate: 20 mL/min; Gradient: 90% B to 60% B in 10 min; Detector: 254 nm. The fractions were combined and concentrated under vacuum to afford the title compound: LCMS [M+1]⁺: 487; ¹H NMR (400 MHz, DMSO-d₆+DCl): δ 8.13 (d, J=8.6 Hz, 1H), 7.87 (d, J=8.6 Hz, 1H), 6.68 (s, 1H), 3.68-3.60 (m, 1H), 3.46-3.40 (m, 1H), 3.22-3.09 (m, 3H), 2.80-2.76 (m, 1H).

Example 322

4-(2-Amino-1H-benzo[d]imidazol-4-yl)-N1-((3S, 4R)-4-aminopyrrolidin-3-yl)-3-(2H-tetrazol-5-yl) benzene-1,2-disulfonamide

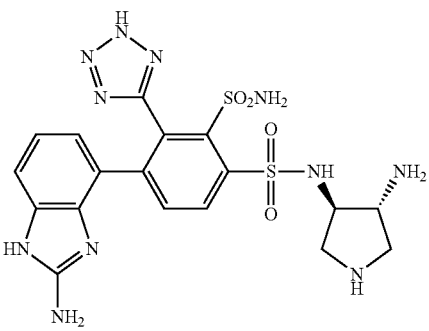 [SMILES: Nc1nc2c(-c3ccc(S(=O)(=O)N[C@@H]4CNC[C@H]4N)c(S(N)(=O)=O)c3-c3nn[nH]n3)cccc2[nH]1]

Step A: (3S,4R)-tert-butyl 3-(4-(2-amino-1H-benzo [d]imidazol-4-yl)-2-(N, N-bis (4-methoxybenzyl) sulfamoyl)-3-(2-(4-methoxybenzyl)-2H-tetrazol-5-yl)phenyl sulfonamido)-4-(((benzyloxy)carbonyl) amino)pyrrolidine-1-carboxylate To a solution of (3R,4S)-tert-butyl 3-(((benzyloxy)carbonyl)amino)-4-(2-(N,N-bis (4-methoxybenzyl)sulfamoyl)-4-iodo-3-(2-(4-methoxybenzyl)-2H-tetrazol-5-yl) phenylsulfonamido)pyrrolidine-1-carboxylate (9.50 g, 8.60 mmol) in 1,4-dioxane (100 mL) and water (25 mL) was added (2-amino-1H-benzo[d]imidazol-4-yl)boronic acid (3.79 g, 21.4 mmol), Na₂CO₃ (2.72 g, 25.7 mmol) and Pd(PPh₃)₄ (1.98 g, 1.70 mmol). The reaction mixture was degassed with nitrogen three times and stirred at 80° C. for 4 hours under nitrogen. The resulting mixture was diluted with water (100 mL) and extracted with EA (3×100 mL). The combined organic layers was washed with brine (3×100 mL), dried over anhydrous Na₂SO₄ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]⁺: 1114.

Step B: 4-(2-Amino-1H-benzo[d]imidazol-4-yl)-N1-((3S,4R)-4-aminopyrrolidin-3-yl)-3-(2H-tetrazol-5-yl)benzene-1,2-disulfonamide The title compound was prepared as described for EXAMPLE 274, step D, (3S,4R)-tert-butyl-3-(4-(2-amino-1H-benzo[d]imidazol-4-yl)-2-(N,N-bis(4-methoxy benzyl)sulfamoyl)-3-(2-(4-methoxybenzyl)-2H-tetrazol-5-yl)phenylsulfonamido)-4-(((benzyloxy)carbonyl)amino)pyrrolidine-1-carboxylate (5.80 g, 5.20 mmol) to afford the crude product. The crude product was purified by Prep-HPLC with the following conditions: Column: Atlantis Prep C18 Column, Mobile Phase A: water with 10 mmol/L NH$_4$HCO$_3$; Mobile Phase B: ACN; Flow rate: 100 mL/min; Gradient: 5% B to 5% B in 5 min, 5% B to 20% B in 15 min; Detector: 254 nm. The fractions containing desired product were combined and concentrated under vacuum to afford the title compound: LCMS [M+1]$^+$: 520; $^1$H NMR (400 MHz, DMSO-d$_6$): δ 8.20 (d, J=8.4 Hz, 1H), 7.97 (d, J=8.5 Hz, 1H), 6.89 (dd, J=7.7 Hz, 1.1 Hz, 1H), 6.46 (t, J=7.7 Hz, 1H), 6.13 (brs, 2H), 6.03 (d, J=7.7 Hz, 1H), 3.79 (q, J=5.9 Hz, 1H), 3.52 (q, J=6.2 Hz, 1H), 3.30-3.21 (m, 3H), 2.94-2.82 (m, 1H).

Example 323

4-(2-((S)-1-amino-2-hydroxyethyl)-1H-benzo[d]imidazol-4-yl)-N1-((3S,4R)-4-aminopyrrolidin-3-yl)-3-(2H-tetrazol-5-yl)benzene-1,2-disulfonamide

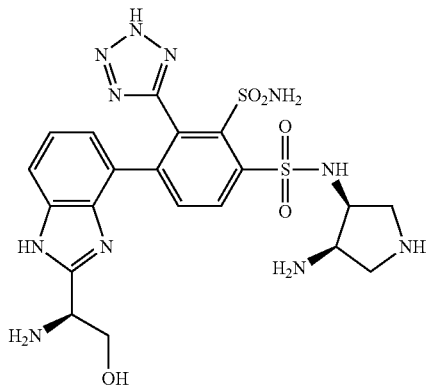 [SMILES: N[C@H](CO)c1nc2c(-c3ccc(S(=O)(=O)N[C@H]4CNC[C@H]4N)c(S(N)(=O)=O)c3-c3nn[nH]n3)cccc2[nH]1]

Step A: (3R,4S)-tert-butyl-3-(((benzyloxy)carbonyl)amino)-4-(2',3'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)pyrrolidine-1-carboxylate To a solution of (3R,4S)-tert-butyl-3-(((benzyloxy)carbonyl)amino)-4-(2-(N,N-bis(4-methoxybenzyl)sulfamoyl)-4-iodo-3-(2-(4-methoxybenzyl)-2H-tetrazol-5-yl) phenylsulfonamido) pyrrolidine-1-carboxylate (2.0 g, 1.80 mmol) in 1,4-dioxane (12 mL) and water (3 mL) was added 3-(4,4,5,5-tetramethyl-1,3,2-dioxaborolan-2-yl) benzene-1,2-diamine (1.67 g, 7.21 mmol), Na$_2$CO$_3$ (0.57 g, 5.41 mmol) and Pd(PPh$_3$)$_4$ (0.42 g, 0.36 mmol) at room temperature. The mixture was degassed with nitrogen three times. The reaction mixture was irradiated with microwave radiation at 100° C. for 0.5 hour under nitrogen. The resulting mixture was diluted with water (100 mL), and then extracted with EA (3×100 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS ([M+1]$^+$: 1089.

Step B: (3S,4R)-tert-butyl 3-(2'-amino-3'-((R)-3-(benzyloxy)-2-((tert-butoxycarbonyl) amino)propanamido)-3-(N,N-bis(4-methoxybenzyl)sulfamoyl)-2-(2-(4-methoxybenzyl)-2H-tetrazol-5-yl-[1,1'-biphenyl]-4-ylsulfonamido)-4-(((benzyloxy)carbonyl)amino)pyrrolidine-1-carboxylate To a stirred solution of (3R,4S)-tert-butyl-3-(((benzyloxy)carbonyl)amino)-4-(2',3'-diamino-3-(N,N-bis(4-methoxybenzyl)sulfamoyl)-2-(2-(4-methoxybenzyl)-2H-tetrazol-5-yl-[1,1'-biphenyl]-4-ylsulfonamido)pyrrolidine-1-carboxylate (0.75 g, 0.69 mmol) in THF (7 mL) was added (R)-3-(benzyloxy)-2-((tert-butoxycarbonyl)amino)propanoic acid (0.22 g, 0.76 mmol), HATU (0.52 g, 1.38 mmol), TEA (0.29 mL, 2.07 mmol) at 0° C. The reaction mixture was degassed with nitrogen three times. The reaction mixture was stirred for 3 hours at 50° C. under nitrogen. The resulting mixture was diluted with water (100 mL) and extracted with EA (3×100 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]+: 1366.

Step C: (3S,4R)-tert-butyl-3-(4-(2-((S)-2-(benzyloxy)-1-((tert-butoxycarbonyl)amino)ethyl)-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)-4-(((benzyloxy)carbonyl) amino) pyrrolidine-1-carboxylate A solution of (3S,4R)-tert-butyl-3-(2'-amino-3'-((R)-3-(benzyloxy)-2-((tert-butoxycarbonyl)amino)propanamido)-3-(N,N-bis(4-methoxybenzyl)sulfamoyl)-2-(2-(4-methoxybenzyl)-2H-tetrazol-5-yl)-[1,1'-biphenyl]-4-ylsulfonamido)-4-(((benzyloxy)carbonyl) amino) pyrrolidine-1-carboxylate (0.70 g, 0.51 mmol) in AcOH (8 mL) was stirred at 60° C. for 30 minutes. The resulting mixture was concentrated under vacuum to afford (3S,4R)-tert-butyl-3-(4-(2-((S)-2-(benzyloxy)-1-((tert-butoxycarbonyl)amino) ethyl)-1H-benzo[d]imidazol-4-yl)-2-(N,N-bis(4-methoxybenzyl)sulfamoyl)-3-(2-(4-methoxybenzyl)-2H-tetrazol-5-yl) phenylsulfonamido)-4-(((benzyloxy)carbonyl) amino)pyrrolidine-1-carboxylate as a solid, which was used in the next step without further purification: LCMS [M+1]$^+$: 1348.

Step D: (3R,4S)-tert-butyl-3-amino-4-(2-(N,N-bis(4-methoxybenzyl)sulfamoyl)-4-(2-((S)-1-((tert-butoxycarbonyl)amino)-2-hydroxyethyl)-1H-benzo[d]imidazol-4-yl)-3-(2-(4-methoxybenzyl)-2H-tetrazol-5-yl)phenylsulfonamido)pyrrolidine-1-carboxylate To a solution of (3S,4R)-tert-butyl 3-(4-(2-((S)-2-(benzyloxy)-1-((tert-butoxycarbonyl) amino)ethyl)-1H-benzo[d]

imidazol-4-yl)-2-(N,N-bis(4-methoxybenzyl)sulfamoyl)-3-(2-(4-methoxybenzyl)-2H-tetrazol-5-yl)phenylsulfonamido)-4-(((benzyloxy) carbonyl)amino)pyrrolidine-1-carboxylate (0.55 g, 0.48 mmol) in MeOH (7 mL) was added Pd(OH)$_2$/C (20% Pd, 0.8 g, 1.05 mmol) at room temperature. The mixture was degassed hydrogen three times. The mixture was stirred for three days under hydrogen at room temperature. The resulting mixture was filtered. The filtrate was concentrated under vacuum to afford the title compound: LCMS [M+1]$^+$: 1124.

Step E: 4-(2-((S)-1-amino-2-hydroxyethyl)-1H-benzo[d]imidazol-4-yl)-N1-((3S,4R)-4-amino pyrrolidin-3-yl)-3-(2H-tetrazol-5-yl)benzene-1,2-disulfonamide The title compound was prepared as described for EXAMPLE 244, step C, using (3R,4S)-tert-butyl-3-amino-4-(2-(N,N-bis(4-methoxybenzyl)sulfamoyl)-4-(2-((S)-1-((tert-butoxycarbonyl)amino)-2-hydroxyethyl)-1H-benzo[d]imidazol-4-yl)-3-(2-(4-methoxybenzyl)-2H-tetrazol-5-yl)phenylsulfonamido)pyrrolidine-1-carboxylate (0.30 g, 0.27 mmol) to afford the crude product. The crude product was purified by Prep-HPLC with the following conditions: Column: X Bridge Shield RP18 OBD Column 19×250 mm, 10 μm; Mobile Phase A: water with 10 mmol/L NH$_4$HCO$_3$, Mobile Phase B: ACN; Flow rate: 20 mL/min; Gradient: 1% B to 23% B in 16 min; Detector: 254 and 220 nm; Retention time: 14.0 min. The fractions containing desired product were combined and concentrated under vacuum to afford 4-(2-((S)-1-amino-2-hydroxyethyl)-1H-benzo[d]imidazol-4-yl)-N1-((3S,4R)-4-aminopyrrolidin-3-yl)-3-(2H-tetrazol-5-yl)benzene-1,2-disulfonamide as a solid: LCMS [M+1]$^+$: 564; $^1$H NMR (400 MHz, CD$_3$OD+DCl): δ 8.79 (d, J=8.2 Hz, 1H), 8.17 (d, J=8.3 Hz, 1H), 7.84 (d, J=8.3 Hz, 1H), 7.50 (m, 1H), 7.16 (m, 1H), 4.61 (m, 1H), 4.22 (m, 3H), 3.89 (m, 1H), 3.80 (m, 1H), 3.55 (m, 1H), 3.35 (m, 2H).

EXAMPLES 324-328 in the Table below were prepared in an analogous fashion to that described for EXAMPLE 323, starting from (3R,4S)-tert-butyl 3-(((benzyloxy)carbonyl)amino)-4-(2-(N,N-bis(4-methoxybenzyl)sulfamoyl)-4-iodo-3-(2-(4-methoxybenzyl)-2H-tetrazol-5-yl)phenylsulfonamido) pyrrolidine-1-carboxylate and the corresponding boronic acids or boronic esters, which were prepared as described herein, or which were available from commercial sources.

| EX. No. | Structure | Chemical Name | LC/MS [M + H]$^+$ |
|---|---|---|---|
| 324 | 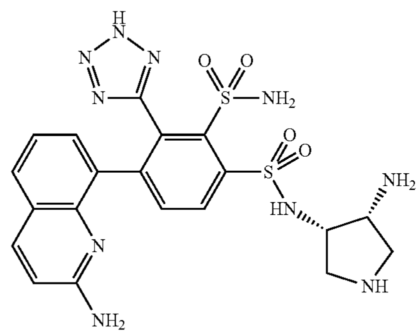 [SMILES: Nc1ccc2cccc(-c3ccc(S(=O)(=O)N[C@H]4CNC[C@H]4N)c(S(N)(=O)=O)c3-c3nn[nH]n3)c2n1] | N1-((3S,4R)-4-aminopyrrolidin-3-yl)-4-(2-aminoquinolin-8-yl)-3-(1H-tetrazol-5-yl)benzene-1,2-disulfonamide | 531 |
| 325 | 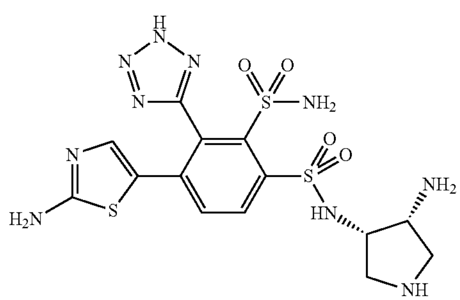 [SMILES: Nc1ncc(-c2ccc(S(=O)(=O)N[C@H]3CNC[C@H]3N)c(S(N)(=O)=O)c2-c2nn[nH]n2)s1] | N1-((3S,4R)-4-aminopyrrolidin-3-yl)-4-(2-aminothiazol-5-yl)-3-(2H-tetrazol-5-yl)benzene-1,2-disulfonamide | 487 |
| 326 | 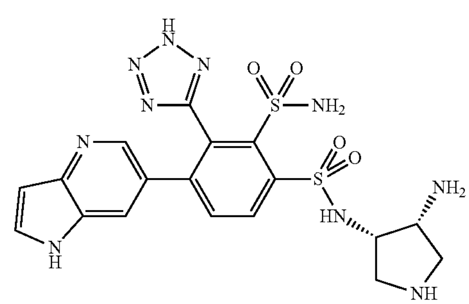 [SMILES: N[C@@H]1CNC[C@@H]1NS(=O)(=O)c1ccc(-c2cnc3cc[nH]c3c2)c(-c2nn[nH]n2)c1S(N)(=O)=O] | N1-((3S,4R)-4-aminopyrrolidin-3-yl)-4-(1H-pyrrolo[3,2-b]pyridin-6-yl)-3-(2H-tetrazol-5-yl)benzene-1,2-disulfonamide | 505 |

-continued

| EX. No. | Structure | Chemical Name | LC/MS [M + H]+ |
|---|---|---|---|
| 327 | 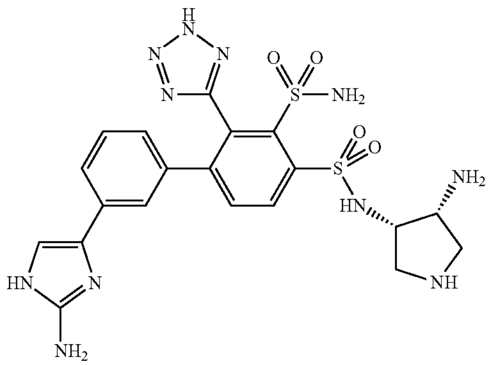 [SMILES: Nc1nc(-c2cccc(-c3ccc(S(=O)(=O)N[C@H]4CNC[C@H]4N)c(S(N)(=O)=O)c3-c3nn[nH]n3)c2)c[nH]1] | 3'-(2-amino-1H-imidazol-4-yl)-N4-((3S,4R)-4-aminopyrrolidin-3-yl)-2-(2H-tetrazol-5-yl)-[1,1'-biphenyl]-3,4-disulfonamide | 546 |
| 328 | 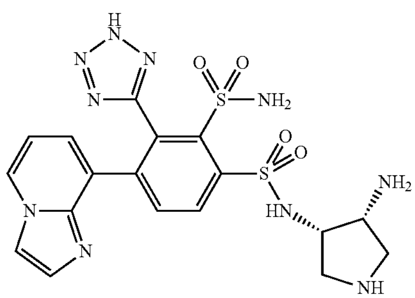 [SMILES: N[C@@H]1CNC[C@@H]1NS(=O)(=O)c1ccc(-c2cccn3ccnc23)c(-c2nn[nH]n2)c1S(N)(=O)=O] | N1-((3S,4R)-4-aminopyrrolidin-3-yl)-4-(imidazo[1,2-a]pyridin-8-yl)-3-(2H-tetrazol-5-yl)benzene-1,2-disulfonamide | 505 |

Example 329

4-(2-Amino-7-methyl-1H-benzo[d]imidazol-4-yl)-N1-(2-aminoethyl)-3-(2H-tetrazol-5-yl)benzene-1,2-disulfonamide

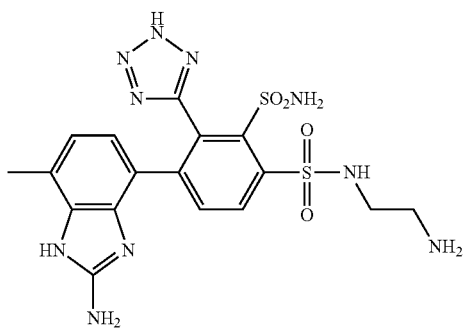 [SMILES: Cc1ccc(-c2ccc(S(=O)(=O)NCCN)c(S(N)(=O)=O)c2-c2nn[nH]n2)c2nc(N)[nH]c12]

Step A: Tert-butyl (2-(4-(2-amino-7-methyl-1H-benzo[d]imidazol-4-yl)-2-(N,N-bis (4-methoxybenzyl)sulfamoyl)-3-(2-((4-methoxybenzyl)-2H-tetrazol-5-yl)phenyl sulfonamido)ethyl)carbamate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (0.9 g, 0.96 mmol) in 1,4-dioxane (6 mL) and water (2 mL) was added (2-amino-7-methyl-1H-benzo[d]imidazol-4-yl)boronic acid (0.33 g, 1.73 mmol), Pd(PPh$_3$)$_4$ (0.17 g, 0.15 mmol), Na$_2$CO$_3$ (0.31 g, 2.89 mmol). The reaction mixture was degassed with nitrogen three times. The reaction mixture was irradiated with microwave radiation at 100° C. for 50 minutes. The resulting mixture was diluted with water (30 mL), and then extracted with EA (3×30 mL). The combined organic layers was washed with water (3×30 mL) and brine (3×30 mL), dried over Na$_2$SO$_4$ and filtered. The filtrate was concentrated under vacuum. The residue was purified by silica gel column chromatography, eluted with 10% MeOH in DCM. The fractions containing desired product were combined and concentrated under vacuum to afford tert-butyl (2-(4-(2-amino-7-methyl-1H-benzo[d]imidazol-4-yl)-2-(N,N-bis(4-methoxybenzyl) sulfamoyl)-3-(2-((4-methoxybenzyl)-2H-tetrazol-5-yl)phenylsulfonamido)ethyl) carbamate as a solid: [M+1]+: 953.

Step B: 4-(2-Amino-7-methyl-1H-benzo[d]imidazol-4-yl)-N1-(2-aminoethyl)-3-(2H-tetrazol-5-yl) benzene-1,2-disulfonamide The title compound was prepared as described for EXAMPLE 244, step C, using tert-butyl(2-(4-(2-amino-7-methyl-1H-benzo[d]imidazol-4-yl)-2-(N,N-bis (4-methoxybenzyl)sulfamoyl)-3-(2-((4-methoxybenzyl)-2H-tetrazol-5-yl)phenyl sulfonamido)ethyl)carbamate (0.50 g, 0.53 mmol) to afford the crude product. The crude product was purified by Prep-HPLC with the following conditions: Column: X Bridge Prep C18 OBD Column 19×250 mm 10 μm; Mobile Phase A: water with 10 mmol/L NH$_4$HCO$_3$, Mobile Phase B: ACN; Flow rate: 25 mL/min; Gradient: 5% B to 25% B in 8 min; Detector: 254 and 220 nm: The fractions containing desired product were combined and concentrated under vacuum to afford the title compound: LCMS [M+1]+: 493; $^1$H NMR (300 MHz, DMSO-d$_6$+D$_2$O): δ 8.17 (d, J=8.4

Hz, 1H), 7.80 (d, J=8.3 Hz, 1H), 6.36 (d, J=7.9 Hz, 1H), 6.03 (d, J=7.8 Hz, 1H), 3.20 (t, J=6.1 Hz, 2H), 2.92 (t, J=6.1 Hz, 2H), 2.19 (s, 3H).

Example 330

(S)-4-(2-(1-amino-2-hydroxyethyl)-1H-benzo[d]imidazol-4-yl)-N1-(2-aminoethyl)-3-(2H-tetrazol-5-yl)benzene-1,2-disulfonamide

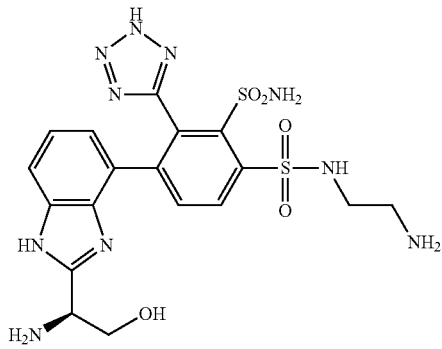 [SMILES: NCCNS(=O)(=O)c1ccc(-c2cccc3[nH]c([C@H](N)CO)nc23)c(-c2nn[nH]n2)c1S(N)(=O)=O]

Step A: (R)-tert-butyl (1-((2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-yl)amino)-3-hydroxy-1-oxopropan-2-yl)carbamate To a stirred solution of 2',3'-diamino-N,N-bis(4-methoxybenzyl)-2-(2-(4-methoxybenzyl)-2H-tetrazol-5-yl)-4-((2-(trimethylsilyl)ethyl)sulfonyl)-[1,1'-biphenyl]-3-sulfonamide (2.0 g, 2.34 mmol) in DCM (20 mL) was added (R)-2-((tert-butoxycarbonyl)amino)-3-hydroxypropanoic acid (0.53 g, 2.57 mmol), HATU (1.78 g, 4.67 mmol), TEA (0.98 mL, 7.01 mmol). The mixture was degassed with nitrogen three times. The mixture was stirred for 5 hours at room temperature under nitrogen. The resulting mixture was diluted with water (200 mL), and then extracted with DCM (3×200 mL). The combined organic layers was washed with water (3×200 mL) and brine (3×200 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1043.

Step B: (S)-tert-butyl (1-(4-(3-(N,N-bis(4-methoxybenzyl)sulfamoyl)-2-(2-(4-methoxybenzyl) 2H-tetrazol-5-yl)-4-((2-(trimethylsilyl)ethyl)sulfonyl)phenyl)-1H-benzo[d]imidazole-2-yl)-2-hydroxyethyl)carbamate A solution of (R)-tert-butyl(1-((2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-yl)amino)-3-hydroxy-1-oxopropan-2-yl)carbamate (2.0 g, 1.92 mmol) in AcOH was stirred at 60° C. for 30 min. The resulting mixture was concentrated under vacuum to afford the title compound, which was used in the next step without further purification: LCMS [M+1]$^+$: 1025.

Step C: 2-(N,N-bis(4-methoxybenzyl)sulfamoyl)-4-(2-((S)-1-((tert-butoxycarbonyl) amino)-2-hydroxyethyl)-1H-benzo[d]imidazol-4-yl)-3-(2-(4-methoxybenzyl)-2H-tetrazol-5-yl)benzenesulfinic acid To a stirred solution of (S)-tert-butyl(1-(4-(3-(N,N-bis(4-methoxybenzyl) sulfamoyl)-2-(2-(4-methoxybenzyl)-2H-tetrazol-5-yl)-4-((2-(trimethylsilyl)ethyl) sulfonyl)phenyl)-1H-benzo[d]imidazol-2-yl)-2-hydroxyethyl)carbamate (1.50 g, 1.50 mmol) in THF (10 mL) was added TBAF (1.90 g, 6 mmol) at 0° C. The mixture was stirred at room temperature for 2 hours. The mixture was diluted with EA (100 mL), washed with saturated aqueous KHSO$_4$ (5×100 mL), dried over anhydrous Na$_2$SO$_4$ and filtered. The filtrate was concentrated under vacuum to afford the title compound, which was used in the next step without further purification: LCMS [M+1]$^+$: 925.

Step D: Tert-butyl-N-[(1S)-1-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]-2-hydroxyethyl]carbamate To a stirred solution of 2-(N,N-bis(4-methoxybenzyl) sulfamoyl)-4-(2-((S)-1-((tert-butoxycarbonyl)amino)-2-hydroxyethyl)-1H-benzo[d]imidazol-4-yl)-3-(2-(4-methoxybenzyl)-2H-tetrazol-5-yl)benzenesulfinic acid (0.50 g, 0.54 mmol) was added tert-butyl (2-aminoethyl)carbamate (0.17 g, 1.10 mmol), TEA (0.22 mL, 1.60 mmol) at 0° C. for 10 minutes. The mixture was degassed with nitrogen three times. Then NCS (0.15 g, 1.10 mmol) was added to the mixture. The mixture was stirred at 0° C. for 1.5 hours under nitrogen. The resulting mixture was concentrated under vacuum. The residue was dissolved with EA (50 mL), washed with brine (3×50 mL), dried over anhydrous Na$_2$SO$_4$ and filtered. The filtrate was concentrated under vacuum. The residue was purified by silica gel column chromatography, eluted with 75% EA in PE. The fractions containing desired product were combined and concentrated under vacuum to afford the title compound: LCMS [M+1]$^+$: 1083.

Step E: (S)-4-(2-(1-amino-2-hydroxyethyl)-1H-benzo[d]imidazol-4-yl)-N1-(2-aminoethyl)-3-(2H-tetrazol-5-yl)benzene-1,2-disulfonamide The title compound was prepared as described for EXAMPLE 244, step C, using tert-butyl-N-[(1S)-1-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]-2-hydroxyethyl]carbamate (0.50 g, 0.46 mmol) to afford the crude product. The crude product was purified by Prep-HPLC with the following conditions: Column: X Bridge Prep C18 OBD Column, 5 μm, 19×250 mm; Mobile Phase A: water with 10 mmol/L NH$_4$HCO$_3$, Mobile Phase B: ACN; Flow rate: 25 mL/min; Gradient: 5% B to 25% B in 10 min; Detector: 254 and 220 nm. The fractions containing desired product were combined and concentrated under vacuum to afford the title compound: LCMS [M+1]$^+$: 523; $^1$H NMR (400 MHz, CD$_3$OD+DCl): δ 8.69-8.67 (m, 1H), 8.15-8.10 (m, 1H), 7.83-7.77 (m, 1H), 7.51-7.44 (m, 1H), 7.33-7.14 (m, 1H), 4.90-4.81 (m, 2H), 4.21-4.17 (m, 2H), 3.46 (t, J=6.0 Hz, 2H), 3.20 (t, J=6.0 Hz, 2H).

Example 331

(R)-4-(2-(1-amino-2-hydroxyethyl)-1H-benzo[d]imidazol-4-yl)-N1-(2-aminoethyl)-3-(2H-tetrazol-5-yl)benzene-1,2-disulfonamide

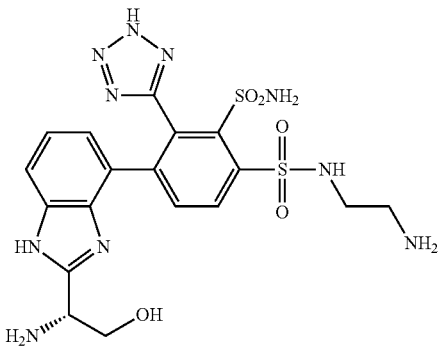 [SMILES: NCCNS(=O)(=O)c1ccc(-c2cccc3[nH]c([C@@H](N)CO)nc23)c(-c2nn[nH]n2)c1S(N)(=O)=O]

Step A: Tert-butyl-N-[(1S)-1-{[2-amino-3-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)phenyl] carbamoyl}-2-(benzyloxy)ethyl]carbamate The title compound was prepared as described for EXAMPLE 274, step D, using tert-butyl(2-(2',3'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)ethyl)carbamate and (S)-3-(benzyloxy)-2-((tert-butoxycarbonyl)amino)propanoic acid to afford the title compound as a solid: LCMS [M+1]$^+$: 1191.

Step B: Tert-butyl-N-[(1R)-2-(benzyloxy)-1-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]ethyl]carbamate The title compound was prepared as described for EXAMPLE 323, step C, using tert-butyl-N-[(1S)-1-{[2-amino-3-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)phenyl] carbamoyl}-2-(benzyloxy)ethyl]carbamate to afford the title compound: LCMS [M+1]$^+$: 1173.

Step C: Tert-butyl-N-[(1R)-1-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]-2-hydroxyethyl]carbamate The title compound was prepared as described for EXAMPLE 323, step D, using tert-butyl-N-[(1R)-2-(benzyloxy)-1-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]ethyl]carbamate to afford the title compound: LCMS [M+1]$^+$: 1083.

Step D: (R)-4-(2-(1-amino-2-hydroxyethyl)-1H-benzo[d]imidazol-4-yl)-N1-(2-aminoethyl)-3-(2H-tetrazol-5-yl)benzene-1,2-disulfonamide The title compound was prepared as described for EXAMPLE 244, step C, using tert-butyl-N-[(1R)-1-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]-2-hydroxyethyl]carbamate to afford the title compound: LCMS [M+1]$^+$: 523; $^1$H NMR (400 MHz, CD$_3$OD+DCl): δ 8.69 (d, J=8.0 Hz, 1H), 8.12 (d, J=8.4 Hz, 1H), 7.81 (d, J=8.8 Hz, 1H), 7.49 (d, J=7.6 Hz, 1H), 7.17 (d, J=7.6 Hz, 1H), 4.90-4.81 (m, 1H), 4.21-4.18 (m, 2H), 3.46 (t, J=6.0 Hz, 2H), 3.19 (t, J=5.6 Hz, 2H).

Example 332

(R)-2-amino-N-(2-amino-3-hydroxypropyl)-4'-(N-(2-aminoethyl)sulfamoyl)-3'-sulfamoyl-2'-(2H-tetrazol-5-yl-[1,1'-biphenyl]-3-carboxamide

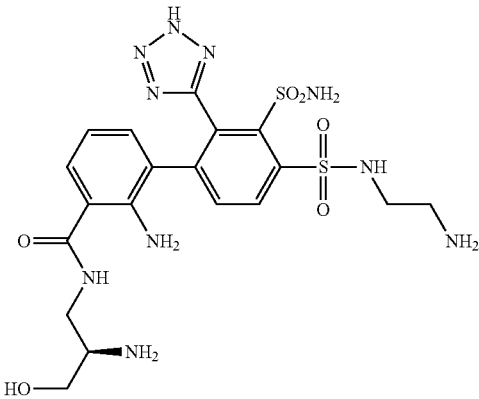 [SMILES: NCCNS(=O)(=O)c1ccc(-c2cccc(C(=O)NC[C@@H](N)CO)c2N)c(-c2nn[nH]n2)c1S(N)(=O)=O]

Step A: Methyl-2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (0.85 g, 0.91 mmol) in 1,4-dioxane (6 mL) and water (1.5 mL) were added Pd(PPh$_3$)$_4$ (0.21 g, 0.18 mmol), methyl 2-amino-3-(4,4,5,5-tetramethyl-1,3,2-dioxaborolan-2-yl) benzoate (0.76 g, 2.73 mmol, prepared by following details described in *Bioorganic and Medicinal Chemistry Letters*, 2012, 22: 3327-3331) and Na$_2$CO$_3$ (0.29 g, 2.73 mmol) at room temperature. The reaction mixture was degassed with nitrogen three times. The resulting mixture was warmed to 80° C. and stirred for 16 hours under nitrogen. The resulting mixture was diluted with water (50 mL), and then extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford methyl-2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylate as a solid: LCMS [M+1]$^+$: 957.

Step B: 2-Amino-3'-(N,N-bis(4-methoxybenzyl) sulfamoyl)-4'-(N-(2-((tert-butoxycarbonyl)amino) ethyl)sulfamoyl)-2'-(2-(4-methoxybenzyl)-2H-tetrazol-5-yl)-[1,1'-biphenyl]-3-carboxylic acid To a stirred solution of methyl-2-amino-3'-(N,N-bis(4-methoxybenzyl) sulfamoyl)-4'-(N-(2-((tert-butoxycarbonyl)amino)ethyl)sulfamoyl)-2'-(2-(4-methoxy benzyl)-2H-tetrazol-5-yl)-[1,1'-biphenyl]-3-carboxylate (0.6 g, 0.63 mmol) in THF (3 mL) and MeOH (3 mL) was added NaOH (0.40 g, 10 mmol) at room temp. The reaction solution was stirred for 16 hours. The pH value of the solution was adjusted to 4 with HCl (20%). The mixture was filtered. The filtrate was washed with water to afford 2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid as a solid: LCMS [M+1]$^+$: 943.

Step C: Benzyl-N-[(2R)-1-{[2-amino-3-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl) phenyl] formamido}-3-hydroxypropan-2-yl] carbamate To a solution of 2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylicacid (0.48 g, 0.51 mmol) in DMF (5 mL) were added (R)-benzyl (1-amino-3-hydroxypropan-2-yl)carbamate (0.23 g, 1.02 mmol), HATU (0.39 g, 1.02 mmol) and DIEA (0.13 g, 1.02 mmol) with stirring at 0° C. The reaction mixture was degassed with nitrogen three times. The resulting mixture was warmed to room temperature and stirred for 3 hours at room temp. The resulting mixture was diluted with water (50 mL), and then extracted with EA (3×50 mL). The combined organic layers was washed with water (3×50 mL) and brine (3×50 mL), dried over anhydrous Na$_2$SO$_4$ and filtered. The filtrate was concentrated under vacuum. The residue was purified by silica gel column chromatography, eluted with 67% EA in PE. The fractions containing desired product were combined and concentrated under vacuum to afford the title compound: LCMS [M+1]$^+$: 1149.

Step D: (R)-2-amino-N-(2-amino-3-hydroxypropyl)-4'-(N-(2-aminoethyl)sulfamoyl)-3'-sulfamoyl-2'-(2H-tetrazol-5-yl)-[1,1'-biphenyl]-3-carboxamide The title compound was prepared as described for EXAMPLE 244, step C, using benzyl N-[(2R)-1-{[2-amino-3-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)phenyl] formamido}-3-hydroxypropan-2-yl]carbamate (0.29 g, 0.25 mmol) to afford the crude product. The crude product was purified by Prep-HPLC with the following conditions: Column: X Bridge C18 OBD Prep Column 100 Å, 10 μm, 19×250 mm; 0° C. Mobile Phase A: water with 10 mmol/L NH$_4$HCO$_3$, Mobile Phase B: ACN; Flow rate: 20 mL/min; Gradient: 3% B to 3% B in 8 min; Detector: 254 and 220 nm; Retention time: 5.6 min. The fractions containing desired product were combined and concentrated under vacuum to afford the title compound: LCMS [M+1]$^+$: 555; $^1$H NMR (400 MHz, CD$_3$OD+DCl): δ 8.63 (d, J=8.4 Hz, 1H), 7.95 (d, J=8.4 Hz, 1H), 7.73 (dd, J=7.6 Hz, 1.6 Hz, 1H), 7.08-7.00 (m, 2H), 3.82 (dd, J=11.6 Hz, 4.0 Hz, 1H), 3.70 (dd, J=11.6 Hz, 6.0 Hz-1H), 3.66-3.63 (m, 2H), 3.50-3.48 (m, 1H), 3.43-3.39 (m, 2H), 3.18 (t, J=6.0 Hz, 2H).

Example 333

(S)-2-amino-N-(2-amino-3-hydroxypropyl)-4'-(N-(2-aminoethyl)sulfamoyl)-3'-sulfamoyl-2'-(2H-tetrazol-5-yl)-[1,1'-biphenyl]-3-carboxamide

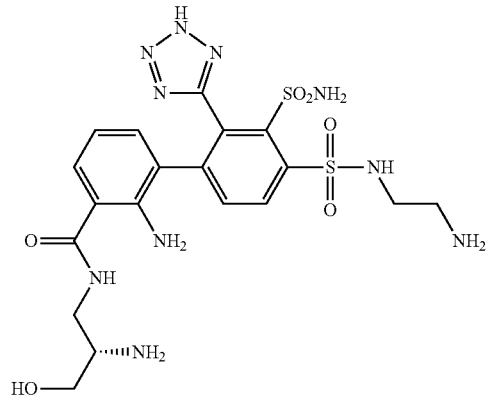 [SMILES: NCCNS(=O)(=O)c1ccc(-c2cccc(C(=O)NC[C@H](N)CO)c2N)c(-c2nn[nH]n2)c1S(N)(=O)=O]

Step A: Tert-butyl N-[(2S)-1-{[2-amino-3-(3-{bis[(4-methoxyphenyl)methyl]sulfamoyl}-4-[(2-{[(tert-butoxy)carbonyl]amino}ethyl)sulfamoyl]-2-{2-[(4-methoxyphenyl) methyl]-2H-1,2,3,4-tetrazol-5-yl}phenyl)phenyl]formamido}-3-hydroxypropan-2-yl] carbamate The title compound was prepared as described for EXAMPLE 332, step C, using (S)-tert-butyl (1-amino-3-hydroxypropan-2-yl)carbamate to afford the title compound: LCMS [M+1]$^+$: 1115.

Step B: (S)-2-amino-N-(2-amino-3-hydroxypropyl)-4'-(N-(2-aminoethyl)sulfamoyl)-3'-sulfamoyl-2'-(2H-tetrazol-5-yl)-[1,1'-biphenyl]-3-carboxamide The title compound was prepared as described for EXAMPLE 244, step C, using tert-butyl N-[(2S)-1-{[2-amino-3-(3-{bis[(4-methoxyphenyl)methyl]sulfamoyl}-4-[(2-{[(tert-butoxy)carbonyl]amino}ethyl)sulfamoyl]-2-{2-[(4-methoxyphenyl) methyl]-2H-1,2,3,4-tetrazol-5-yl}phenyl)phenyl]formamido}-3-hydroxypropan-2-yl] carbamate to afford the title compound: LCMS [M+1]$^+$: 555; $^1$H NMR (400 MHz, CD$_3$OD+DCl): δ 8.65 (d, J=8.4 Hz, 1H), 7.98 (d, J=8.0 Hz, 1H), 7.84-7.82 (m, 1H), 7.14-7.13 (m, 2H), 3.85-3.81 (m, 1H), 3.74-3.66 (m, 3H), 3.53-3.40 (m, 3H), 3.19-3.18 (m, 2H).

Example 334

N-(2-aminoethyl)-4'-(N-(2-aminoethyl)sulfamoyl)-3'-sulfamoyl-2'-(2H-tetrazol-5-yl)-[1,1'-biphenyl]-3-carboxamide

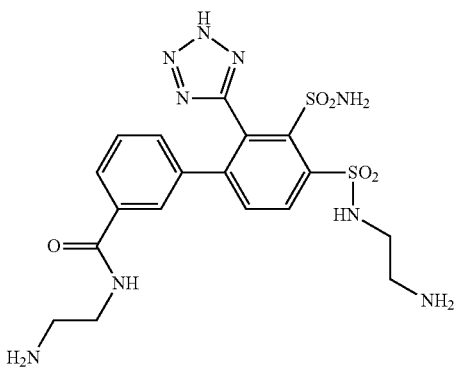 [SMILES: NCCNC(=O)c1cccc(-c2ccc(S(=O)(=O)NCCN)c(S(N)(=O)=O)c2-c2nn[nH]n2)c1]

Step A: Methyl-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (0.6 g, 0.64 mmol) in 1,4-dioxane (20 mL) and water (7 mL) were added Pd(PPh$_3$)$_4$ (0.15 g, 0.13 mmol), (3-(methoxycarbonyl)phenyl)boronic acid (0.35 g, 1.93 mmol, prepared by following the details described in *Organic Letters*, 2006, 8: 305-307) and Na$_2$CO$_3$ (0.20 g, 1.93 mmol) at room temperature. The mixture was degassed with nitrogen three times. The reaction mixture was stirred at 80° C. for 16 hours under nitrogen. The resulting mixture was diluted with water (200 mL), and then extracted with EA (3×200 mL). The combined organic layers was washed with water (3×200 mL) and brine (3×200 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 942.

Step B: 3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid To a stirred solution of methyl 3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylate (0.5 g, 0.53 mmol) in THF (5 mL) and MeOH (5 mL) was added aqueous LiOH solution (1 M) (5 mL, 5.00 mmol) at room temperature. The solution was stirred for 16 hours at room temperature. The pH value of the reaction solution was adjusted to 4 with aqueous HCl (20%). The resulting mixture was filtered. The filter cake was washed with water and dried in an oven to afford the title compound: LCMS [M+1]$^+$: 928.

Step C: Tert-butyl-N-[2-({[(2-{bis[(4-methoxyphenyl)methyl]sulfamoyl}-4-{3-[(2-{[(tert-butoxy)carbonyl]amino}ethyl)carbamoyl]phenyl}-3-[(2E,4E)-11-methoxy-2,4,5,6-tetraazabicyclo[6.3.1]dodeca-1(11),2,4,8(12),9-pentaen-3-yl]phenyl)-1{3}-oxidane]sulfinyl}amino)ethyl]carbamate To a stirred solution of 3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid (0.2 g, 0.22 mmol), HATU (0.12 g, 0.32 mmol) and tert-butyl (2-aminoethyl)carbamate (0.14 g, 0.86 mmol) in DMF (2 mL) was added DIEA (0.06 mL, 0.32 mmol) at 0° C. The reaction mixture was degassed with nitrogen three times. The solution was stirred at 0° C. for 4 hours under nitrogen. The resulting solution was diluted with water (50 mL) and extracted with EA (3×50 mL). The combined organic layers was washed with brine (3×50 mL), dried over anhydrous Na$_2$SO$_4$ and filtered. The filtrate was concentrated under vacuum. The residue was purified by silica gel column chromatography, eluted with 45% EA in PE. The fractions containing desired product were combined and concentrated under vacuum to afford the title compound: LCMS [M+1]$^+$: 1070.

Step D: N-(2-aminoethyl)-4'-(N-(2-aminoethyl)sulfamoyl)-3'-sulfamoyl-2'-(2H-tetrazol-5-yl)-[1,1'-biphenyl]-3-carboxamide The title compound was prepared as described for EXAMPLE 244, step C, using tert-butyl-N-[2-({[(2-{bis[(4-methoxyphenyl)methyl]sulfamoyl}-4-{3-[(2-{[(tert-butoxy)carbonyl]amino}ethyl)carbamoyl]phenyl}-3-[(2E,4E)-11-methoxy-2,4,5,6-tetraazabicyclo[6.3.1]dodeca-1(11),2,4,8(12),9-pentaen-3-yl]phenyl)-1{3}-oxidane]sulfinyl} amino)ethyl]carbamate (0.2 g, 0.20 mmol) to afford the crude product. The crude product was purified by Prep-HPLC with the following conditions: Column: X Bridge C18 OBD Prep Column, 100 Å, 5 µm, 19 mm×250 mm; Mobile Phase A: water (0.05% TFA), Mobile Phase B: ACN; Flow rate: 20 mL/min; Gradient: 5% B to 30% B in 8 min; Detector: 254 nm. The fractions containing desired product were combined and concentrated under vacuum to afford N-(2-aminoethyl)-4'-(N-(2-aminoethyl)sulfamoyl)-3'-sulfamoyl-2'-(2H-tetrazol-5-yl)-[1,1'-biphenyl]-3-carboxamide as a solid: LCMS [M+1]$^+$: 510; $^1$H NMR (400 MHz, CD$_3$OD+DCl): δ 8.58 (d, J=8.0 Hz, 1H), 7.97 (d, J=8.0 Hz, 1H), 7.84-7.82 (m, 1H), 7.69-7.68 (m, 1H), 7.41-7.37 (m, 1H), 7.21-7.19 (m, 1H), 3.67-3.64 (m, 2H), 3.67-3.64 (m, 2H), 3.18-3.12 (m, 4H).

Example 335

(R)—N1-(2-aminoethyl)-4-(2-(1,2-diaminoethyl)-1H-benzo[d]imidazole-4-yl)-3-(2H-tetrazol-5-yl)benzene-1,2-disulfonamide

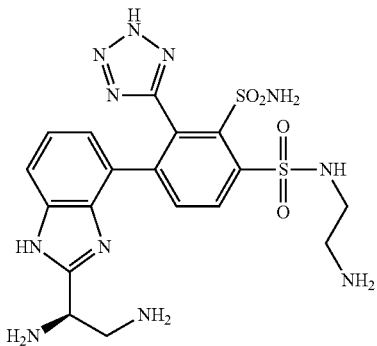 [SMILES: NCCNS(=O)(=O)c1ccc(-c2cccc3[nH]c([C@H](N)CN)nc23)c(-c2nn[nH]n2)c1S(N)(=O)=O]

Step A: Tert-butyl (2-(2',3'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)ethyl)carbamate To a solution of 3-(4,4,5,5-tetramethyl-1,3,2-dioxaborolan-2-yl)benzene-1,2-diamine (2.51 g, 10.71 mmol, prepared as described in WO2006/005915 or available commercially) in 1,4-dioxane (25 mL) and water (12 mL) were added Na$_2$CO$_3$ (1.70 g, 16.06 mmol), tert-butyl(2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (5.00 g, 5.35 mmol) and Pd(PPh$_3$)$_4$ (0.62 g, 0.54 mmol) at room temperature. The reaction mixture was degassed with nitrogen three times and stirred at 80° C. for 16 hours under nitrogen. The resulting mixture was diluted with water (200 mL) and extracted with EA (3×250 mL). The combined organic layers was washed with water (3×500 mL) and brine (3×500 mL), dried over anhydrous Na$_2$SO$_4$ and filtered. The filtrate was concentrated under vacuum. The residue was purified by silica gel column chromatography, eluted with 65% EA in PE. The fractions containing desired product were combined and concentrated under vacuum to afford the title compound: LCMS [M+1]$^+$: 914.

Step B: Tert-butyl-N-{2-[(4-{2-amino-3-[(2R)-2,3-bis({[(tert-butoxy)carbonyl]amino}) propanamido]phenyl}-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene)sulfonamido]ethyl}carbamate To a solution of tert-butyl (2-(2',3'-diamino-3-(N,N-bis(4-methoxybenzyl) sulfamoyl)-2-(2-(4-methoxybenzyl)-2H-tetrazol-5-yl)-[1,1'-biphenyl]-4-yl-sulfonamido)ethyl)carbamate (1.10 g, 1.20 mmol) in THF (15 mL) was added (R)-2,3-bis((tert-butoxycarbonyl)amino)propanoic acid (0.55 g, 1.8 mmol), TEA (0.5 mL, 3.60 mmol) and HATU (1.60 g, 4.21 mmol) at 0° C. for 10 minutes. The mixture was degassed with nitrogen three times and was stirred at 0° C. for 1.5 hours under nitrogen. The resulting mixture was filtered. The filtrate was concentrated under vacuum. The residue was diluted with EA (100 mL), and washed with water (3×40 mL) and brine (40 mL). The combined organic layers were dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1200.

Step C: Tert-butyl N-[(2R)-2-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]-2-{[(tert-butoxy)carbonyl]amino}ethyl]carbamate A solution of tert-butyl-N-{2-[(4-{2-amino-3-[(2R)-2,3-bis({[(tert-butoxy) carbonyl]amino})propanamido]phenyl}-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene)sulfonamido]ethyl}carbamate (1.10 g, 0.92 mmol) in AcOH (10 mL) was stirred for 0.5 hour at 60° C. The solvent was removed under vacuum to afford the title compound, which was used in the next step without further purification: LCMS [M+1]$^+$: 1182.

Step D: (R)—N1-(2-aminoethyl)-4-(2-(1,2-diaminoethyl)-1H-benzo[d]imidazol-4-yl)-3-(2H-tetrazol-5-yl)benzene-1,2-disulfonamide A solution of tert-butyl-N-[(2R)-2-[4-(3-{bis[(4-methoxyphenyl)methyl] sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl] phenyl)-1H-1,3-benzodiazol-2-yl]-2-{[(tert-butoxy)carbonyl]amino}ethyl]carbamate (1.00 g, 0.85 mmol) in TFA (10 mL) was stirred for 1 hour at room temperature. The resulting solution was concentrated under vacuum. The residue was co-evaporated with anisole (3×8 mL) under vacuum and used in the next step without further purification. The crude product was added to TFA (10 mL). The solution was stirred at 80° C. for 1 hour. The resulting solution was concentrated under vacuum and used in the next step without further purification. The crude product was dissolved in THF (10 mL) and water (10 mL). To the mixture was added NaOH (0.40 g, 10 mmol). The reaction mixture was stirred for 2 hours at room temp. The resulting solution was concentrated under vacuum. The crude product was purified by Prep-HPLC with the following conditions: Column: X Bridge BEH C18 OBD Prep Column, 19×250 mm, 10 μm; Mobile Phase A: waters with 10 mmol/L NH$_4$HCO$_3$, Mobile Phase B: ACN; Flow rate: 20 mL/min; Gradient: 3% B to 20% B in 8 min; Detector: 254 and 220 nm. The fractions containing desired product were combined and concentrated under vacuum to afford the title compound: LCMS [M+1]$^+$: 522; $^1$H NMR (400 MHz, CD$_3$OD+DCl): δ 8.58 (d, J=8.2 Hz, 1H), 7.99 (d, J=8.2 Hz, 1H), 7.62-7.55 (m, 1H), 7.33-7.24 (m, 1H), 7.04 (d, J=7.4 Hz, 1H), 4.86-4.81 (m, 1H), 3.69-3.64 (m, 1H), 3.54-3.47 (m, 1H), 3.43-3.40 (m, 2H), 3.18-3.12 (t, J=5.6 Hz, 2H).

Example 336

(S)—N1-(2-aminoethyl)-4-(2-(1,2-diaminoethyl)-1H-benzo[d]imidazol-4-yl)-3-(2H-tetrazol-5-yl)benzene-1,2-disulfonamide

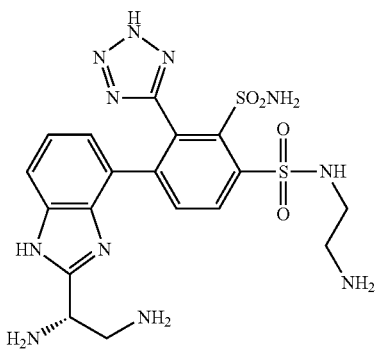 [SMILES: NCCNS(=O)(=O)c1ccc(-c2cccc3[nH]c([C@@H](N)CN)nc23)c(-c2nn[nH]n2)c1S(N)(=O)=O]

Step A: Tert-butyl-N-{2-[(4-{2-amino-3-[(2S)-2,3-bis({[(tert-butoxy)carbonyl]amino}) propanamido]phenyl}-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene)sulfonamido]ethyl}carbamate To a solution of tert-butyl(2-(2',3'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)ethyl) carbamate (1.00 g, 1.10 mmol) in THF (15 mL) was added (S)-2,3-bis((tert-butoxycarbonyl)amino)propanoic acid (0.50 g, 1.60 mmol), TEA (0.45 mL, 3.30 mmol) and HATU (1.45 g, 3.80 mmol) at 0° C. for 10 minutes. The mixture was degassed with nitrogen three times and was stirred at 0° C. for 1.5 hours under nitrogen. The resulting mixture was filtered. The filtrate was concentrated under vacuum. The residue was diluted with EA (100 mL). The organic phase was washed with water (3×60 mL) and brine (3×40 mL). The organic layer was dried over anhydrous $Na_2SO_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 1200.

Step B: Tert-butyl-N-[(1S)-1-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]-2-{[(tert-butoxy)carbonyl]amino}ethyl]carbamate A solution of tert-butyl-N-{2-[(4-{2-amino-3-[(2S)-2,3-bis({[(tert-butoxy) carbonyl]amino})propanamido]phenyl}-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene)sulfonamido]ethyl}carbamate (1.00 g, 0.83 mmol) in AcOH (10 mL) was stirred for 0.5 hour at 60° C. The solvent was removed under vacuum to afford crude title compound, which was used in the next step without further purification: LCMS [M+1]$^+$: 1182.

Step C: (S)—N1-(2-aminoethyl)-4-(2-(1,2-diaminoethyl)-1H-benzo[d]imidazol-4-yl)-3-(2H-tetrazol-5-yl)benzene-1,2-disulfonamide A solution of tert-butyl-N-[(1S)-1-[4-(3-{bis[(4-methoxyphenyl)methyl] sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]-2-{[(tert-butoxy)carbonyl]amino}ethyl]carbamate (0.90 g, 0.76 mmol) in TFA (10 mL) was stirred for 1 hour at room temperature. The resulting solution was concentrated under vacuum. The residue was co-evaporated with anisole (3×8 mL) under vacuum and used directly in the next step without further purification. The crude product was added TFA (10 mL). The solution was stirred at 80° C. for 1 hour. The resulting solution was concentrated under vacuum and used directly in the next step without further purification. The crude product was dissolved in THF (10 mL) and water (10 mL). To the mixture was added NaOH (400 mg, 10 mmol). The reaction mixture was stirred for 2 hours at room temperature. The resulting solution was concentrated under vacuum. The crude product was purified by Prep-HPLC with the following conditions: Column: XBridge BEH $C_{18}$ OBD Prep Column, 19×250 mm, 10 μm; Mobile Phase A: water with 10 mmol/L $NH_4HCO_3$, Mobile Phase B: ACN; Flow rate: 20 mL/min; Gradient: 3% B to 20% B in 8 min; Detector: 254 and 220 nm. The fractions containing desired product were combined and concentrated under vacuum to afford the title compound: LCMS [M+1]$^+$: 522; $^1$H NMR (400 MHz, $CD_3OD+DCl$): δ 8.57 (d, J=8.2 Hz, 1H), 7.99 (d, J=8.2 Hz, 1H), 7.57 (d, J=8.2 Hz, 1H), 7.28 (t, J=7.8 Hz, 1H), 7.04 (d, J=7.3 Hz, 1H), 4.72-4.70 (m, 1H), 3.64-3.59 (m, 1H), 3.42-3.40 (m, 2H), 3.20-3.18 (m, 3H).

Example 337

N1-(2-aminoethyl)-4-(2-(2-aminoethyl)-1H-benzo[d]imidazol-4-yl)-3-(2H-tetrazol-5-yl)benzene-1,2-disulfonamide

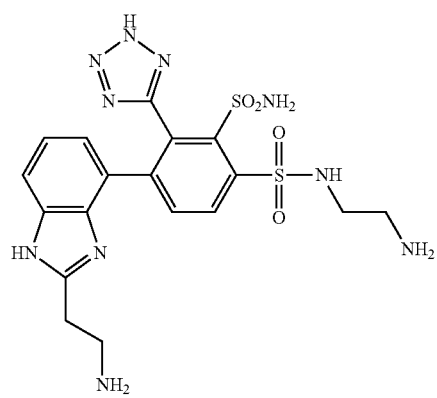 [SMILES: NCCNS(=O)(=O)c1ccc(-c2cccc3[nH]c(CCN)nc23)c(-c2nn[nH]n2)c1S(N)(=O)=O]

Step A: Tert-butyl(3-((2-amino-3'-(N,N-bis(4-methoxybenzyl)sulfamoyl)-2'-(2-(4-methoxy benzyl)-2H-tetrazol-5-yl)-4'-((2-(trimethylsilyl)ethyl)sulfonyl)-[1,1'-biphenyl]-3-yl) amino)-3-oxopropyl) carbamate The title compound was prepared as described for EXAMPLE 331, step A, using 3-((tert-butoxycarbonyl)amino)propanoic acid to afford the title compound: LCMS [M+1]⁺: 1027.

Step B: Tert-butyl (2-(4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)ethyl)carbamate The title compound was prepared as described for EXAMPLE 331, step B, using tert-butyl(3-((2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-yl)amino)-3-oxopropyl)carbamate to afford the title compound as a solid: LCMS [M+1]⁺: 1009.

Step C: 2-(N,N-bis(4-methoxybenzyl)sulfamoyl)-4-(2-(2-((tert-butoxycarbonyl)amino)ethyl)-1H-benzo[d]imidazol-4-yl)-3-(2-(4-methoxybenzyl)-2H-tetrazol-5-yl)benzenesulfinic acid The title compound was prepared as described for EXAMPLE 331, step C, using tert-butyl(2-(4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)ethyl)carbamate to afford the title compound as a solid: LCMS [M+1]⁺: 909.

Step D: Tert-butyl-N-{2-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]ethyl}carbamate The title compound was prepared as described for EXAMPLE 331, step D, using 2-(N,N-bis(4-methoxybenzyl)sulfamoyl)-4-(2-(2-((tert-butoxycarbonyl)amino)ethyl)-1H-benzo[d]imidazol-4-yl)-3-(2-(4-methoxybenzyl)-2H-tetrazol-5-yl)benzenesulfinic acid to afford the title compound as a solid LCMS [M+1]⁺: 1067.

Step E: N1-(2-aminoethyl)-4-(2-(2-aminoethyl)-1H-benzo[d]imidazol-4-yl)-3-(2H-tetrazol-5-yl)benzene-1,2-disulfonamide The title compound was prepared as described for EXAMPLE 244, step C, using tert-butyl-N-{2-[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]ethyl}carbamate to afford the title compound as a solid: LCMS [M+1]⁺: 507; ¹H NMR (400 MHz, CD₃OD+DCl): δ 8.70 (d, J=8.4 Hz, 1H), 8.11 (d, J=8.1 Hz, 1H), 7.74 (d, J=8.1 Hz, 1H), 7.43 (t, J=8.1 Hz, 1H), 7.11 (d, J=7.5 Hz, 1H), 3.67-3.62 (m, 2H), 3.58-3.53 (m, 2H), 3.47-3.43 (m, 2H), 3.20-3.16 (m, 2H).

Example 338

5'-Amino-N4-(2-aminoethyl)-2-(2H-tetrazol-5-yl)-2',3',4',5'-tetrahydro-[1,1'-biphenyl]-3,4-disulfonamide

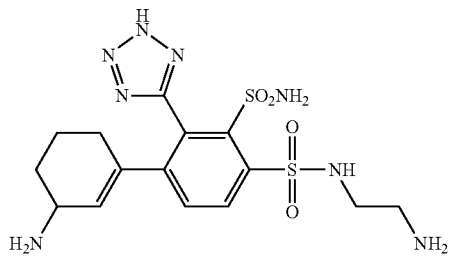 [SMILES: NCCNS(=O)(=O)c1ccc(C2=CC(N)CCC2)c(-c2nn[nH]n2)c1S(N)(=O)=O]

Step A: tert-butyl (2-(3-(N,N-bis(4-methoxybenzyl)sulfamoyl)-2-(2-(4-methoxybenzyl)-2H-tetrazol-5-yl)-5'-oxo-2',3',4',5'-tetrahydro-[1,1'-biphenyl]-4-ylsulfonamido)ethyl) carbamate To a solution of tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (3.00 g, 3.20 mmol) in 1,4-dioxane (35 mL) and water (8 mL) was added (3-oxocyclohex-1-en-1-yl)boronic acid (1.80 g, 12.80 mmol), Na₂CO₃ (1.02 g, 9.60 mmol) and Pd(PPh₃)₄ (0.74 g, 0.64 mmol) at room temperature. The mixture was degassed with nitrogen three times. The reaction mixture was stirred at 80° C. for 24 hours under nitrogen. The resulting mixture was diluted with water (50 mL), and then extracted with EA (3×50 mL). The combined organic layers were washed with water (3×50 mL) and brine (3×50 mL), dried over anhydrous Na₂SO₄ and filtered. The filtrate was concentrated under vacuum. The residue was purified by silica gel column chromatography, eluted with 50% EA in PE. The fractions containing desired product were combined and concentrated under vacuum to afford tert-butyl (2-(3-(N,N-bis(4-methoxybenzyl)sulfamoyl)-2-(2-(4-methoxybenzyl)-2H-tetrazol-5-yl)-5'-oxo-2',3',4',5'-tetrahydro-[1,1'-biphenyl]-4-ylsulfonamido)ethyl)carbamate as a solid: LCMS [M+1]⁺: 902.

Step B: Tert-butyl(2-(3-(N,N-bis(4-methoxybenzyl)sulfamoyl)-5'-((S)-1,1-dimethylethyl sulfinamido)-2-(2-(4-methoxybenzyl)-2H-tetrazol-5-yl)-2',3',4',5'-tetrahydro-[1,1'-biphenyl]-4-ylsulfonamido)ethyl) carbamate To a solution of tert-butyl(2-(3-(N,N-bis(4-methoxybenzyl)sulfamoyl)-2-(2-(4-methoxybenzyl)-2H-tetrazol-5-yl)-5'-oxo-2',3',4',5'-tetrahydro-[1,1'-biphenyl]-4-ylsulfonamido)ethyl)carbamate (2.50 g, 2.80 mmol) in THF (20 mL) was added (S)-2-methylpropane-2-sulfinamide (1.68 g, 12.80 mmol), Ti(OiPr)₄ (40 mL) at room temperature. The reaction mixture was stirred at 80° C. for 2 hours. Then the reaction mixture was cooled to the room temperature. NaBH₄ (0.42 g, 11.10 mmol) was added and the reaction mixture was stirred for 1 hour. The resulting mixture was quenched with water (100 mL) and extracted with EA (3×100 mL). The combined organic layers were washed with water (3×100 mL) and brine (3×100 mL), dried over anhydrous Na₂SO₄ and filtered. The filtrate was concentrated under vacuum. The residue was purified by silica gel column chromatography, eluted with 30% EA in PE. The fractions containing desired product were combined and concentrated under vacuum to afford tert-butyl (2-(3-(N,N-bis(4-methoxybenzyl)sulfamoyl)-5'-((S)-1,1-dimethylethylsulfinamido)-2-(2-(4-methoxybenzyl)-2H-tetrazol-5-yl)-2',3',4',5'-tetrahydro-[1,1'-biphenyl]-4-ylsulfonamido)ethyl)carbamate as an oil: LCMS [M+1]+: 1007.

Step C: 5'-Amino-N4-(2-aminoethyl)-2-(2H-tetrazol-5-yl)-2',3',4',5'-tetrahydro-[1,1'-biphenyl]-3,4-disulfonamide To a stirred solution of tert-butyl(2-(3-(N,N-bis(4-methoxybenzyl)sulfamoyl)-5'-((S)-1,1-dimethylethylsulfinamido)-2-(2-(4-methoxybenzyl)-2H-tetrazol-5-yl)-2',3',4',5'-tetrahydro-[1,1'-biphenyl]-4-ylsulfonamido)ethyl)carbamate (1.15 g, 1.31 mmol) in 1,4-dioxane (5 mL) was added a solution of saturated HCl in dioxane (20 mL). The reaction mixture was stirred at room temp. for 1 hour. The resulting solution was concentrated under vacuum. The residue was co-evaporated with anisole (3×3 mL) under vacuum and used directly in the next step without further purification. The crude product was added TFA (10 mL). The solution was stirred at 80° C. for 1 hour. The resulting solution was concentrated under vacuum. The crude product was purified by Prep-HPLC with the following conditions: Column: X Bridge Prep C18 OBD Column 19×250 mm 10 μm; Mobile Phase A: water with 10 mmol/L NH$_4$HCO$_3$, Mobile Phase B: ACN; Flow rate: 25 mL/min; Gradient: 5% B to 35% B in 8 min; Detector: 254 and 220 nm; Retention time: 6.51 min. The fractions containing desired product were combined and concentrated under vacuum to afford 5'-amino-N4-(2-aminoethyl)-2-(2H-tetrazol-5-yl)-2',3',4',5'-tetrahydro-[1,1'-biphenyl]-3,4-disulfonamide as a solid: LCMS [M+1]+: 443; $^1$H NMR (400 MHz, D$_2$O+DCl): δ 6.42 (d, J=8.3 Hz, 1H), 5.85 (d, J=8.3 Hz, 1H), 3.48 (d, J=2.5 Hz, 1H), 1.77 (s, 1H), 1.37 (t, J=5.6 Hz, 2H), 1.21 (t, J=5.6 Hz, 2H), −0.38-−0.14 (m, 6H).

Example S 339 and 340

(R)-5'-amino-N4-((R)-pyrrolidin-3-yl)-2-(2H-tetrazol-5-yl)-2',3',4',5'-tetrahydro-[1,1'-biphenyl]-3,4-disulfonamide and (S)-5'-amino-N4-((R)-pyrrolidin-3-yl)-2-(2H-tetrazol-5-yl)-2',3',4',5'-tetrahydro-[1,1'-biphenyl]-3,4-disulfonamide

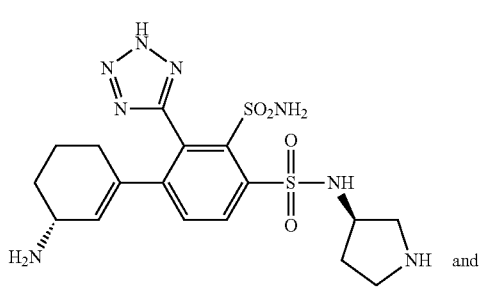

339 and

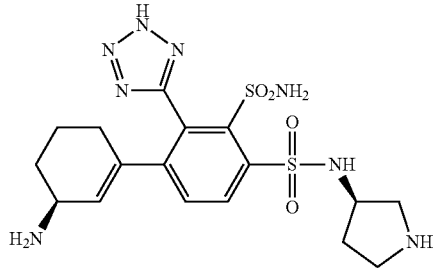

340

Step A: (R)-tert-butyl-3-(3-(N,N-bis(4-methoxybenzyl)sulfamoyl)-2-(2-(4-methoxybenzyl)-2H-tetrazol-5-yl)-5'-oxo-2',3',4',5'-tetrahydro-[1,1'-biphenyl]-4-ylsulfonamido)pyrrolidine-1-carboxylate The title compound was prepared as described for EXAMPLE 338, step A, using (R)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (1.00 g, 1.04 mmol) to afford the title compound as a solid: LCMS [M+1]+: 928.

Step B: (3R)-tert-butyl-3-(3-(N,N-bis(4-methoxybenzyl)sulfamoyl)-5'-((S)-1,1-dimethylethyl sulfinamido)-2-(2-(4-methoxybenzyl)-2H-tetrazol-5-yl)-2',3',4',5'-tetrahydro-[1,1'-biphenyl]-4-ylsulfonamido)pyrrolidine-1-carboxylate The title compound was prepared as described for EXAMPLE 338, step B, using (R)-tert-butyl-3-(3-(N,N-bis(4-methoxybenzyl)sulfamoyl)-2-(2-(4-methoxybenzyl)-2H-tetrazol-5-yl)-5'-oxo-2',3',4',5'-tetrahydro-[1,1'-biphenyl]-4-ylsulfonamido)pyrrolidine-1-carboxylate (0.60 g, 0.65 mmol) to afford the title compound as a foam: LCMS [M+1]+: 1033.

Step C: (R)-5'-amino-N4-((R)-pyrrolidin-3-yl)-2-(2H-tetrazol-5-yl)-2',3',4',5'-tetrahydro-[1,1'-biphenyl]-3,4-disulfonamide and (S)-5'-amino-N4-((R)-pyrrolidin-3-yl)-2-(2H-tetrazol-5-yl)-2',3',4',5'-tetrahydro-[1,1'-biphenyl]-3,4-disulfonamide The title compounds were prepared as described for EXAMPLE 338, step C, using (3R)-tert-butyl-3-(3-(N,N-bis(4-methoxybenzyl)sulfamoyl)-5'-((S)-1,1-dimethylethylsulfinamido)-2-(2-(4-methoxybenzyl)-2H-tetrazol-5-yl)-2',3',4',5'-tetrahydro-[1,1'-biphenyl]-4-ylsulfonamido)pyrrolidine-1-carboxylate (0.50 g, 0.50 mmol) to afford the crude isomers. The isomers were separated by Prep-HPLC with the following conditions: Column: X Bridge C18 OBD Prep Column 100 Å, 10 μm, 19 mm×250 mm; Mobile Phase A: water with 10 mmol/L NH$_4$HCO$_3$, Mobile Phase B: ACN; Flow rate: 25 mL/min; Gradient: 2% B to 18% B in 12 min; 254 nm/220 nm; retention time 6.50 min and 6.80 min; Temperature: 25° C. The faster-eluting enantiomer of (R)-5'-amino-N4-((R)-pyrrolidin-3-yl)-2-(2H-tetrazol-5-yl)-2',3',4',5'-tetrahydro-[1,1'-biphenyl]-3,4-disulfonamide was obtained: LCMS [M+1]+: 469; $^1$H NMR (400 MHz, D$_2$O+DCl): δ 5.91 (d, J=8.4 Hz, 1H), 5.30 (d, J=8.4 Hz, 1H), 2.93 (d, J=16.4 Hz, 1H), 1.65-1.60 (m, 1H), 1.20 (brs, 1H), 0.96-0.72 (m, 4H), −0.34-−0.39 (m, 1H), −0.41-−0.43 (m, 4H), −0.80-−1.20 (m, 3H). The slower-eluting enantiomer of (S)-5'-amino-N4-((R)-pyrrolidin-3-yl)-2-(2H-tetrazol-5-yl)-2',3',4',5'-tetrahydro-[1,1'-biphenyl]-3,4-disulfonamide was obtained: LCMS [M+1]+: 469; 1H NMR (400 MHz, D2O+ DCl): δ 5.91 (d, J=8.4 Hz, 1H), 5.30 (d, J=8.0 Hz, 1H), 2.93 (d, J=15.2 Hz, 1H), 1.67-1.61 (m, 1H), 1.23 (brs, 1H), 0.95-0.91 (m, 2H), 0.90-0.72 (m, 2H), −0.34--0.41 (m, 1H), −0.49--0.59 (m, 2H), −0.61--1.30 (m, 5H).

Example 341

4'-(N-(2-aminoethyl)sulfamoyl)-N-(3-aminopropyl)-3'-sulfamoyl-2'-(2H-tetrazol-5-yl)-[1,1'-biphenyl]-3-carboxamide

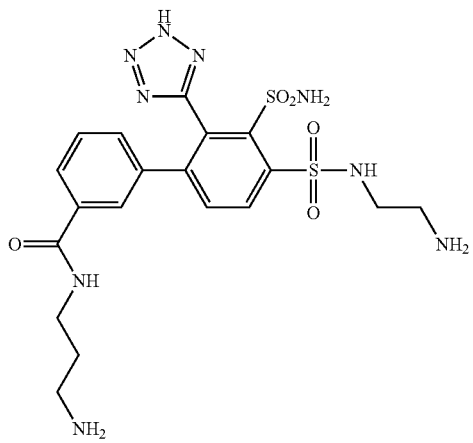 [SMILES: NCCCNC(=O)c1cccc(-c2ccc(S(=O)(=O)NCCN)c(S(N)(=O)=O)c2-c2nn[nH]n2)c1]

Step A: Tert-butyl-N-{2-[(2-{bis[(4-methoxyphenyl)methyl]sulfamoyl}-4-{3-[(3-{[(tert-butoxy)carbonyl]amino}propyl)carbamoyl]phenyl}-3-[(2E,4E)-11-methoxy-2,4,5,6-tetraazabicyclo[6.3.1]dodeca-1(11),2,4,8(12),9-pentaen-3-yl]benzene)sulfonamido] ethyl}carbamate To a stirred solution of 3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid (0.20 g, 0.22 mmol) in DMF (2 mL) was added tert-butyl (3-aminopropyl)carbamate (0.15 g, 0.86 mmol), HATU (0.12 g, 0.32 mmol) and DIEA (0.06 mL, 0.32 mmol) at 0° C. The reaction mixture was degassed with nitrogen three times. The mixture was stirred for 4 hours at room temp. under nitrogen. The resulting mixture was diluted with water (50 mL), and then extracted with EA (3×50 mL). The combined organic layers were washed with water (3×50 mL) and brine (3×50 mL), dried over anhydrous Na2SO4 and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]+: 1084.

Step B: 4'-(N-(2-aminoethyl)sulfamoyl)-N-(3-aminopropyl)-3'-sulfamoyl-2'-(2H-tetrazol-5-yl)-[1,1'-biphenyl]-3-carboxamide The title compound was prepared as described for EXAMPLE 244, step C, using tert-butyl-N-{2-[(2-{bis[(4-methoxyphenyl)methyl]sulfamoyl}-4-{3-[(3-{[(tert-butoxy)carbonyl]amino}propyl)carbamoyl]phenyl}-3-[(2E,4E)-11-methoxy-2,4,5,6-tetraazabicyclo[6.3.1]dodeca-1(11),2,4,8(12),9-pentaen-3-yl]benzene)sulfonamido] ethyl}carbamate (0.15 g, 0.14 mmol) to afford the crude product. The crude product was purified by Prep-HPLC with the following conditions: Column: X Select CSH Prep C18 OBD Column, 5 μm, 19×150 mm; Mobile Phase A: water with 0.05% NH4HCO3, Mobile Phase B: ACN; Flow rate: 20 mL/min; Gradient: 5% B to 35% B in 8 min; Detector: 254 and 220 nm; Retention time: 6.78 min. The fractions containing desired product were combined and concentrated under vacuum to afford the title compound: LCMS [M+1]+: 524. 1H NMR (300 MHz, CD3OD+DCl): δ 8.60 (d, J=8.1 Hz, 1H), 7.99 (d, J=8.1 Hz, 1H), 7.81-7.78 (m, 1H), 7.60-7.58 (m, 1H), 7.43-7.38 (m, 1H), 7.26-7.23 (m, 1H), 3.54-3.47 (m, 2H), 3.51-3.38 (m, 2H), 3.20-3.16 (m, 2H), 3.08-2.98 (m, 2H), 2.09-1.93 (m, 2H).

Example 342

4-((3S)-3-aminocyclohexyl)-N1-(2-aminoethyl)-3-(2H-tetrazol-5-yl)benzene-1,2-disulfonamide

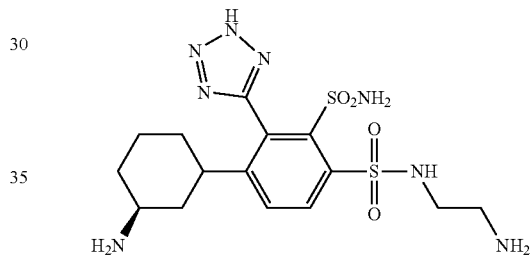

Step A: 4-((3S)-3-aminocyclohexyl)-N1-(2-aminoethyl)-3-(2H-tetrazol-5-yl)benzene-1,2-disulfonamide To a stirred solution of 5'-amino-N4-(2-aminoethyl)-2-(2H-tetrazol-5-yl)-2',3',4',5'-tetrahydro-[1,1'-biphenyl]-3,4-disulfonamide (0.10 g, 0.22 mmol) in conc. HCl (1 mL) and MeOH (6 mL) was added PtO2 (30 mg, 0.13 mmol). The reaction mixture was degassed with hydrogen three times and stirred for 18 hours at 45° C. under hydrogen (20 atm). The resulting solution was filtered. The filtrate was concentrated under vacuum. The crude product was purified by Prep-HPLC with the following conditions: Column: X Bridge Prep C18 OBD Column 19×250 mm, 10 μm; Mobile Phase A: water with 10 mmol/L NH4HCO3, Mobile Phase B: ACN; Flow rate: 25 mL/min; Gradient: 5% B to 35% B in 8 min; Detector: 254 and 220 nm. The fractions containing desired product were combined and concentrated under vacuum to afford the title compound: LCMS [M-1]−: 443; 1H NMR (400 MHz, D2O+DCl): δ 6.41 (d, J=8.5 Hz, 1H), 6.03 (d, J=8.7 Hz, 1H), 1.67 (s, 1H), 1.32 (t, J=5.6 Hz, 2H), 1.17 (d, J=7.0 Hz, 2H), 0.10 (s, 1H), −0.08 (s, 2H), −0.25 (s, 2H), −0.37 (d, J=17.0 Hz, 3H), −0.60 (d, J=12.8 Hz, 1H).

Example 343

N¹-(2-aminoethyl)-4-(2-(aminomethyl)-1H-benzo[d]imidazol-4-yl)-3-(2H-tetrazol-5-yl)benzene-1,2-disulfonamide

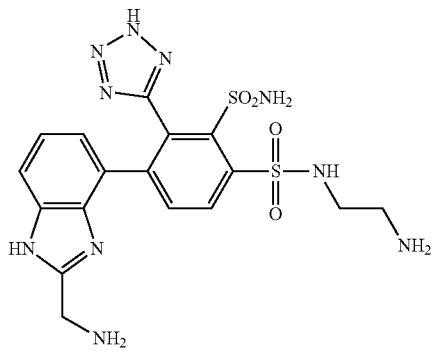 [SMILES: NCCNS(=O)(=O)c1ccc(-c2cccc3[nH]c(CN)nc23)c(-c2nn[nH]n2)c1S(N)(=O)=O]

Step A: 2',3'-Diamino-N,N-bis(4-methoxybenzyl)-2-(2-(4-methoxybenzyl)-2H-tetrazol-5-yl)-4-((2-(trimethylsilyl)ethyl)sulfonyl)-[1,1'-biphenyl]-3-sulfonamide To a stirred solution of 3-(4,4,5,5-tetramethyl-1,3,2-dioxaborolan-2-yl)benzene-1,2-diamine (2.7 g, 11.4 mmol) in dioxane (30 mL) and water (10 mL) was added Na$_2$CO$_3$ (1.8 g, 17.13 mmol), 3-iodo-N,N-bis(4-methoxybenzyl)-2-(2-(4-methoxybenzyl)-2H-tetrazol-5-yl)-6-((2-(trimethylsilyl)ethyl)sulfonyl) benzenesulfonamide (5.00 g, 5.71 mmol) and Pd(PPh$_3$)$_4$ (1.98 g, 1.71 mmol) at room temp. The mixture was degassed with nitrogen three times. The reaction mixture was stirred at 80° C. for 16 hours under nitrogen. The resulting mixture was diluted with water (200 mL), and then extracted with EA (3×200 mL). The combined organic layers were washed with water (3×200 mL) and brine (3×200 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 856.

Step B: Tert-butyl(2-((2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-yl)amino)-2-oxoethyl)carbamate To a solution of 2',3'-diamino-N,N-bis(4-methoxybenzyl)-2-(2-(4-methoxybenzyl)-2H-tetrazol-5-yl)-4-((2-(trimethylsilyl)ethyl)sulfonyl-[1,1'-biphenyl]-3-sulfonamide (2.00 g, 2.34 mmol) in DMF (10 mL) was added 2-((tert-butoxycarbonyl)amino)acetic acid (0.82 g, 4.67 mmol), HATU (1.33 g, 3.50 mmol) and DIEA (1.83 mL, 10.50 mmol) with stirring at 0° C. The mixture was degassed with nitrogen three times. The reaction mixture was stirred at 0° C. for 4 hours under nitrogen. The resulting mixture was diluted with water (50 mL), and then extracted with EA (3×20 mL). The combined organic layers was washed with water (3×20 mL) and brine (3×20 mL), dried over anhydrous Na$_2$SO$_4$ and filtered. The filtrate was concentrated under vacuum. The residue was purified by silica gel column chromatography, eluted with 75% EA in PE. The fractions containing desired product were combined and concentrated under vacuum to afford the title compound: LCMS [M+1]$^+$: 1013.

Step C: Tert-butyl ((4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)methyl)carbamate To AcOH (20 mL) was added tert-butyl (2-((2-amino-3'-(N,N-bis (4-methoxybenzyl)sulfamoyl)-2'-(2-(4-methoxybenzyl)-2H-tetrazol-5-yl)-4'-((2-(trimethylsilyl)ethyl)sulfonyl-[1,1'-biphenyl]-3-yl)amino)-2-oxoethyl)carbamate (2.4 g, 2.37 mmol) with stirring at room temp. The reaction mixture was stirred at 60° C. for 30 minutes. The resulting mixture was concentrated under vacuum. The residue was purified by silica gel column chromatography, eluted with 70% EA in PE. The fractions containing desired product were combined and concentrated under vacuum to afford the title compound: LCMS [M+1]$^+$: 995.

Step D: 2-(N,N-bis(4-methoxybenzyl)sulfamoyl)-4-(2-(((tert-butoxycarbonyl)amino)methyl)-1H-benzo[d]imidazol-4-yl)-3-(2-(4-methoxybenzyl)-2H-tetrazol-5-yl)benzenesulfinic acid To a solution of tert-butyl((4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)methyl)carbamate (1.20 g, 1.21 mmol) in THF (10 mL) was added TBAF (1 M solution in THF) (4.84 mL, 4.84 mmol) at 0° C. The reaction mixture was stirred at 0° C. for 1 hour. The resulting mixture was diluted with water (50 mL) and extracted with EA (3×20 mL). The combined organic layers was washed with KHSO$_4$ (saturated, 5×30 mL) and brine (3×20 mL), dried over anhydrous Na$_2$SO$_4$ and filtered. The filtrate was concentrated under vacuum to afford the title compound, which was used in the next step without further purification: LCMS [M+1]$^+$: 895.

Step E: Tert-butyl-N-{[4-(3-{bis[(4-methoxyphenyl)methyl]sulfamoyl}-4-[({[(tert-butoxy) carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl} carbamate To a solution of 2-(N,N-bis(4-methoxybenzyl)sulfamoyl)-4-(2-(((tert-butoxycarbonyl)amino)methyl)-1H-benzo[d]imidazol-4-yl)-3-(2-(4-methoxy benzyl)-2H-tetrazol-5-yl)benzenesulfinic acid (0.5 g, 0.56 mmol) in THF (20 mL) was added NCS (0.12 g, 1.12 mmol), TEA (0.24 mL, 1.68 mmol) and tert-butyl (2-aminoethyl)carbamate (90 mg, 0.56 mmol) with stirring at 0° C. The mixture was degassed with nitrogen three times. The reaction mixture was stirred at room temp. for 4 hours under nitrogen. The resulting mixture was diluted with water (50 mL) and extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography, eluted with 90% EA in PE. The fractions containing desired product were combined and concentrated under vacuum to afford the title compound: LCMS [M+1]$^+$: 1053.

Step F: N1-(2-aminoethyl)-4-(2-(aminomethyl)-1H-benzo[d]imidazol-4-yl)-3-(2H-tetrazol-5-yl)benzene-1,2-disulfonamide The title compound was prepared as described for EXAMPLE 244, step C, using tert-butyl-N-{[4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl]-1H-1,3-benzodiazol-2-yl]methyl}carbamate (0.37 g, 0.35 mmol) to afford the crude product. The crude product was purified by Prep-HPLC with the following conditions: Column: X Bridge C18 OBD Prep Column, 100 Å, 5 μm, 19 mm×250 mm; Mobile Phase A: water (0.05% NH$_4$HCO$_3$), Mobile Phase B: ACN; Flow rate: 20 mL/min; Gradient: 5% B to 30% B in 8 min; Detector: 254 nm; Retention time: 6.82 min. The fractions containing desired product were combined and concentrated under vacuum to afford the title compound: LCMS [M+1]$^+$: 493; $^1$H NMR (400 MHz, CD$_3$OD+DCl): δ 8.70 (d, J=8.0 Hz, 1H), 8.12 (d, J=8.0 Hz, 1H), 7.84-7.81 (m, 1H), 7.50-7.48 (m, 1H), 7.18-7.16 (m, 1H), 4.75 (s, 2H), 3.46-3.44 (m, 2H), 3.30-3.19 (m, 2H).

Example 344

4'-(N-(2-aminoethyl)sulfamoyl)-N-((3R,4R)-4-hydroxypyrrolidin-3-yl)-3'-sulfamoyl-2'-(2H-tetrazol-5-yl-[1,1'-biphenyl]-3-carboxamide

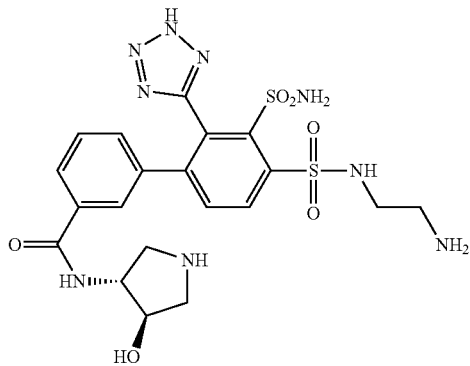 [SMILES: NCCNS(=O)(=O)c1ccc(-c2cccc(C(=O)N[C@@H]3CNC[C@H]3O)c2)c(-c2nn[nH]n2)c1S(N)(=O)=O]

Step A: (3R,4R)-tert-butyl-3-(3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-ylcarboxamido)-4-hydroxypyrrolidine-1-carboxylate The title compound was prepared as described for EXAMPLE 341, step A, using (3R,4R)-tert-butyl 3-amino-4-hydroxypyrrolidine-1-carboxylate to afford the title compound as a solid: LCMS [M+1]$^+$: 1112.

Step B: 4'-(N-(2-aminoethyl)sulfamoyl)-N-((3R,4R)-4-hydroxypyrrolidin-3-yl)-3'-sulfamoyl-2'-(2H-tetrazol-5-yl)-[1,1'-biphenyl]-3-carboxamide The title compound was prepared as described for EXAMPLE 244, step C, using (3R,4R)-tert-butyl-3-(3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-ylcarboxamido)-4-hydroxypyrrolidine-1-carboxylate to afford the title compound as a solid: LCMS [M+1]$^+$: 552; $^1$H NMR (400 MHz, CD$_3$OD+DCl): δ 8.58 (d, J=10.8 Hz, 1H), 7.99 (d, J=11.2 Hz, 1H), 7.82 (d, J=8.1 Hz, 1H), 7.75 (s, 1H), 7.33 (t, J=7.8 Hz, 1H), 7.13 (d, J=8.4 Hz, 1H), 4.48-4.32 (m, 2H), 3.78-3.50 (m, 3H), 3.40-3.37 (m, 2H), 3.33-3.31 (s, 1H), 3.16-3.13 (m, 2H).

Example 345

N$^1$-(2-aminoethyl)-4-(2-(aminomethyl)benzo[d]thiazol-4-yl)-3-(2H-tetrazol-5-yl)benzene-1,2-disulfonamide

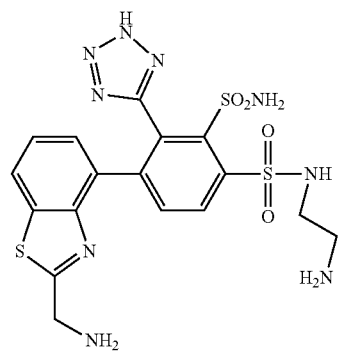 [SMILES: NCCNS(=O)(=O)c1ccc(-c2cccc3sc(CN)nc23)c(-c2nn[nH]n2)c1S(N)(=O)=O]

Step A: Tert-butyl (2-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)ethyl) carbamate To a solution of tert-butyl(2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (3.0 g, 3.21 mmol) in 1,4-dioxane (30 mL) and water (6 mL) was added (2-aminobenzo[d]thiazol-4-yl)boronic acid (1.56 g, 8.03 mmol), Na$_2$CO$_3$ (1.02 g, 9.64 mmol) and Pd(PPh$_3$)$_4$ (0.74 g, 0.64 mmol) at room temperature. The mixture was degassed with nitrogen three times. The reaction mixture was stirred at 80° C. for 16 hours under nitrogen. The resulting mixture was diluted with water (70 mL) and extracted with EA (3×50 mL). The combined organic layers were washed with brine (3×100 mL), dried over anhydrous Na$_2$SO$_4$ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]$^+$: 956.

Step B: Tert-butyl (2-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenylsulfonamido)ethyl)carbamate To a solution of tert-butyl(2-(4-(2-aminobenzo[d]thiazol-4-yl)-2-(N,N-bis(4-methoxybenzyl)sulfamoyl)-3-(2-(4-methoxybenzyl)-2H-tetrazol-5-yl) phenylsulfonamido)ethyl)carbamate (2.0 g, 2.09 mmol) and Cu$_2$Br (0.56 g, 2.51 mmol) in ACN (20 mL) was added tert-butyl nitrite (0.35 g, 3.35 mmol) dropwise at 0° C. The reaction mixture was stirred at room temperature for 2 hours under nitrogen. The resulting mixture was quenched with water (50 mL) and extracted with EA (3×50 mL). The combined organic layers was washed with brine (3×50 mL), dried over anhydrous $Na_2SO_4$ and filtered. The filtrate was concentrated under vacuum. The residue was purified by silica gel column chromatography, eluted with 40% EA in PE. The fractions containing desired product were combined and concentrated under vacuum to afford the title compound: LCMS [M+1]$^+$: 1019, 1021 (1:1).

Step C: Tert-butyl (2-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenylsulfonamido)ethyl)carbamate To a solution of tert-butyl(2-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl sulfonamido)ethyl)carbamate (1.20 g, 1.18 mmol) in DMSO (8 mL) was added cyanocopper (0.32 g, 3.53 mmol) at room temperature. The mixture was degassed with nitrogen three times. The reaction mixture was stirred at 100° C. for 4 hours under nitrogen. The resulting mixture was quenched with $Na_2CO_3$ aqueous solution (100 mL) and extracted with EA (3×50 mL). The combined organic layers were washed with brine (3×100 mL), dried over anhydrous $Na_2SO_4$ and filtered. The filtrate was concentrated under vacuum. The residue was purified by silica gel column chromatography and eluted with 50% EA in PE. The fractions containing desired product were combined and concentrated under vacuum to afford the title compound: LCMS [M+1]$^+$: 966.

Step D: Tert-butyl (2-(4-(2-(aminomethyl)benzo[d]thiazol-4-yl)-2-(N,N-bis(4-methoxybenzyl)sulfamoyl)-3-(2-(4-methoxybenzyl)-2H-tetrazol-5-yl)phenylsulfonamido)ethyl) carbamate To a solution of tert-butyl(2-(2-(N,N-bis(4-methoxybenzyl)sulfamoyl)-4-(2-cyanobenzo[d]thiazol-4-yl)-3-(2-(4-methoxybenzyl)-2H-tetrazol-5-yl) phenylsulfonamido)ethyl)carbamate (0.55 g, 0.57 mmol) in EA (5 mL) and conc. HCl (2 drops) was added Pd(OH)$_2$/C (20% wt, 0.11 g, 0.16 mmol) at room temperature. The mixture was degassed with hydrogen three times. The reaction mixture was stirred at 25° C. for 16 h under hydrogen (20 atm). The resulting mixture was filtered and the filtrate was concentrated under vacuum. The residue was purified by silica gel column chromatography, eluted with 80% EA in PE. The fractions containing desired product were combined and concentrated under vacuum to afford the title compound: LCMS [M+1]$^+$: 970.

Step E: N1-(2-aminoethyl)-4-(2-(aminomethyl)benzo[d]thiazol-4-yl)-3-(2H-tetrazol-5-yl) benzene-1,2-disulfonamide The title compound was prepared as described for EXAMPLE 244, step C, using tert-butyl(2-(4-(2-(aminomethyl)benzo[d]thiazol-4-yl)-2-(N,N-bis(4-methoxybenzyl)sulfamoyl)-3-(2-(4-methoxybenzyl)-2H-tetrazol-5-yl)phenylsulfonamido)ethyl) carbamate (0.20 g, 0.21 mmol) to afford the crude product. The crude product was purified by Prep-HPLC with the following conditions: X Bridge Prep C 18 OBD Column, 19×150 mm, 5 μm, Mobile Phase A: water with 10 mmol/L $NH_4HCO_3$, Mobile Phase B: ACN; Flow rate: 20 mL/min; Gradient: 5% B to 25% B in 8 min; Detector: 254 and 220 nm. The fractions containing desired product were combined and concentrated under vacuum to afford the title compound: LCMS [M+1]$^+$: 510; $^1$H NMR (400 MHz, DMSO-d$_6$+D$_2$O): δ 8.23 (d, J=8.4 Hz, 1H), 7.88 (t, J=6.3 Hz, 2H), 7.05 (t, J=7.8 Hz, 1H), 6.61 (d, J=7.5 Hz, 1H), 4.06 (s, 2H), 3.26 (t, J=6.3 Hz, 2H), 2.98 (t, J=6.0 Hz, 2H).

Example 346

(R)—N-(3-amino-2-hydroxypropyl)-4'-(N-(2-aminoethyl)sulfamoyl)-3'-sulfamoyl-2'-(2H-tetrazol-5-yl-[1,1'-biphenyl]-3-carboxamide

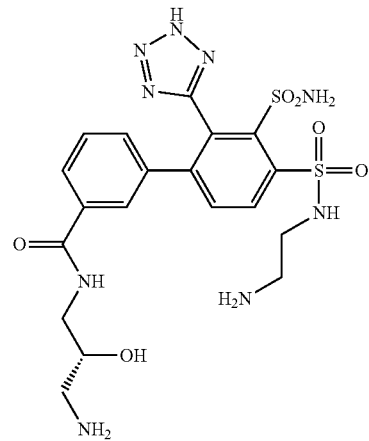 [SMILES: NCCNS(=O)(=O)c1ccc(-c2cccc(C(=O)NC[C@H](O)CN)c2)c(-c2nn[nH]n2)c1S(N)(=O)=O]

Step A: Tert-butyl-N-{2-[(2-{bis[(4-methoxyphenyl)methyl]sulfamoyl}-4-(3-{[(2S)-3-{[(tert-butoxy)carbonyl]amino}-2-hydroxypropyl]carbamoyl}phenyl)-3-[(4E)-11-methoxy-2,4,5,6-tetraazabicyclo[6.3.1]dodeca-1(11),2,4,8(12),9-pentaen-3-yl]benzene)sulfonamido]ethyl}carbamate The title compound was prepared as described for EXAMPLE 341, step A, using (S)-tert-butyl (3-amino-2-hydroxypropyl)carbamate to afford the title compound as a solid: LCMS [M+1]$^+$: 1100.

Step B: (R)—N-(3-amino-2-hydroxypropyl)-4'-(N-(2-aminoethyl)sulfamoyl)-3'-sulfamoyl-2'-((2H-tetrazol-5-yl-[1,1'-biphenyl]-3-carboxamide The title compound was prepared as described for EXAMPLE 341, step B, using tert-butyl-N-{2-[(2-{bis[(4-methoxyphenyl)methyl]sulfamoyl}-4-(3-{[(2S)-3-{[(tert-butoxy)carbonyl]amino}-2-hydroxypropyl]carbamoyl}phenyl)-3-[(4E)-11-methoxy-2,4,5,6-tetraazabicyclo[6.3.1]dodeca-1(11),2,4,8(12),9-pentaen-3-yl] benzene)sulfonamido]ethyl}carbamate to afford the title compound as a solid: LCMS [M+1]$^+$: 540; $^1$H NMR (300 MHz, CD$_3$OD+DCl): δ 8.61 (d, J=8.1 Hz, 1H), 7.99 (d, J=8.1 Hz, 1H), 7.83-7.80 (m, 1H), 7.64-7.63 (m, 1H), 7.43-7.37 (m, 1H), 7.28-7.24 (m, 1H), 4.05-3.99 (m, 1H), 3.54-3.52 (m, 2H), 3.49-3.41 (m, 2H), 3.25-3.08 (m, 3H), 2.91-2.85 (m, 1H).

Example 347

(S)—N-(3-amino-2-hydroxypropyl)-4'-(N-(2-amino-ethyl)sulfamoyl)-3'-sulfamoyl-2'-(2H-tetrazol-5-yl) [1,1'-biphenyl]-3-carboxamide

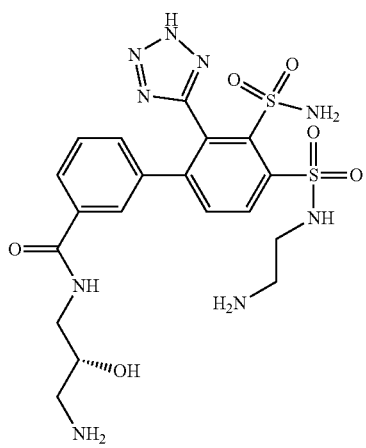 [SMILES: NCCNS(=O)(=O)c1ccc(-c2cccc(C(=O)NC[C@H](O)CN)c2)c(-c2nn[nH]n2)c1S(N)(=O)=O]

Step A: tert-butyl-N-{2-[(2-{bis[(4-methoxyphenyl) methyl]sulfamoyl}-4-(3-{[(2S)-3-{[(tert-butoxy) carbonyl]amino}-2-hydroxypropyl] carbamoyl}phenyl)-3-[(2E,4E)-11-methoxy-2,4,5,6-tetraazabicyclo[6.3.1]dodeca-1(11),2,4,8(12),9-pentaen-3-yl] benzene)sulfonamido]ethyl}carbamate To a solution of 3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid (0.25 g, 0.26 mmol) in DMF (5 mL) was added (R)-tert-butyl (3-amino-2-hydroxypropyl) carbamate (0.2 g, 1.08 mmol) and HATU (0.2 g, 0.54 mmol). DIEA (70 mg, 0.54 mmol) was added at 0° C. The resulting mixture was stirred at 50° C. for 3 hours under nitrogen. The resulting mixture was diluted with water (50 mL) and extracted with EA (3×50 mL). The combined organic layers were washed with brine (2×50 mL), dried over anhydrous Na$_2$SO$_4$ and filtered. The filtrate was concentrated under vacuum. The residue was purified by silica gel column chromatography, eluted with 60% EA in PE. The fractions containing desired product were combined and concentrated under vacuum to afford the title compound as a solid: LCMS [M+1]$^+$: 1100.

Step B: (R)—N-(3-amino-2-hydroxypropyl)-4'-(N-(2-aminoethyl)sulfamoyl)-3'-sulfamoyl-2'-(2H-tetrazol-5-yl-[1,1'-biphenyl]-3-carboxamide The title compound was prepared as described for EXAMPLE 244, step C, using tert-butyl-N-{2-[(2-{bis[(4-methoxyphenyl)methyl]sulfamoyl}-4-(3-{[(2S)-3-{[(tert-butoxy)carbonyl]amino}-2-hydroxypropyl]carbamoyl}phenyl)-3-[(2E,4E)-11-methoxy-2,4,5,6-tetraazabicyclo[6.3.1] dodeca-1(11),2,4,8(12),9-pentaen-3-yl] benzene)sulfonamido]ethyl}carbamate (0.27 g, 0.25 mmol) to afford the crude product. The crude product was purified by Prep-HPLC with the following conditions: Column: XBridge Prep C18 OBD Column 19×150 mm, 5 μm; Mobile Phase A: water (50 mmol/L NH$_4$HCO$_3$), Mobile Phase B: ACN; Flow rate: 20 mL/min; Gradient: 5% B to 25% B in 8 min; Detector: 254 and 220 nm. The fractions containing desired product were combined and concentrated under vacuum to afford the title compound: LCMS [M+1]$^+$: 540; $^1$H NMR (400 MHz, DMSO-d$_6$): δ 8.41-8.39 (m, 1H), 8.27 (d, J=8.0 Hz, 1H), 7.81 (d, J=8.4 Hz, 1H), 7.66 (d, J=8.0 Hz, 1H), 7.51 (s, 1H), 7.21 (t, J=7.6 Hz, 1H), 6.91 (d, J=7.6 Hz, 1H), 6.50 (brs, 3H), 3.89-3.69 (m, 1H), 3.32-3.28 (m, 3H), 3.04 (t, J=5.6 Hz, 2H), 2.91-2.82 (m, 1H), 2.75-2.58 (m, 2H).

Example 348

N$^1$-(2-aminoethyl)-4-(1-(2-aminoethyl)-1H-benzo[d] imidazol-6-yl)-3-(2H-tetrazol-5-yl)benzene-1,2-disulfonamide

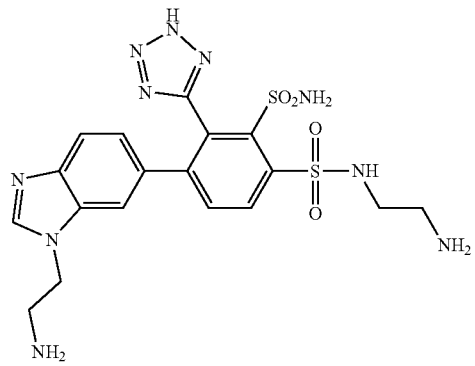 [SMILES: NCCNS(=O)(=O)c1ccc(-c2ccc3ncn(CCN)c3c2)c(-c2nn[nH]n2)c1S(N)(=O)=O]

Step A: tert-butyl (2-((4'-amino-3-(N,N-bis(4-methoxybenzyl)sulfamoyl)-3'-((2-((tert-butoxycarbonyl)amino)ethyl)amino)-2-(2-(4-methoxybenzyl)-2H-tetrazol-5-yl)-[1,1'-biphenyl])-4-sulfonamido) ethyl)carbamate To a stirred mixture of tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate (2 g, 2.14 mmol) in 1,4-dioxane (15 mL) and water (4 mL) were added Pd(PPh$_3$)$_4$ (0.50 g, 0.43 mmol), tert-butyl (2-((2-amino-5-(4,4,5,5-tetramethyl-1,3,2-dioxaborolan-2-yl) phenyl)amino)ethyl)carbamate (2.02 g, 5.35 mmol) and Na$_2$CO$_3$ (0.68 g, 6.43 mmol) at room temperature. The mixture was degassed with nitrogen three times. The reaction mixture was stirred at 80° C. for 16 hours under nitrogen. The resulting mixture was diluted with water (100 mL) and extracted with EA (3×50 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]$^+$: 1057.

Step B: tert-butyl (2-((2-(N,N-bis(4-methoxybenzyl) sulfamoyl)-4-(1-(2-((tert-butoxycarbonyl)amino) ethyl)-1H-benzo[d]imidazol-6-yl)-3-(2-(4-methoxybenzyl)-2H-tetrazol-5-yl)phenyl)sulfonamido)ethyl) carbamate To a stirred mixture of tert-butyl (2-((4'-amino-3-(N,N-bis(4-methoxybenzyl)sulfamoyl)-3'-((2-((tert-butoxycarbonyl)amino)ethyl)amino)-2-(2-(4-methoxybenzyl)-2H-tetrazol-5-yl-[1,1'-biphenyl])-4-sulfonamido)ethyl)carbamate (0.7 g, 0.66 mmol) in trimethyl orthoformate (5 mL, 45.2 mmol) was added a few drops of AcOH at room temperature. The reaction mixture was stirred at 60° C. for 1 hour. The resulting mixture was concentrated under vacuum. The residue was purified by silica gel column chromatography and eluted with 65% EA in PE. The fractions containing desired product were combined and concentrated under vacuum to afford the title compound: LCMS [M+1]$^+$: 1067.

Step C: N1-(2-aminoethyl)-4-(1-(2-aminoethyl)-1H-benzo[d]imidazol-6-yl)-3-(2H-tetrazol-5-yl)benzene-1,2-disulfonamide The title compound was prepared as described for EXAMPLE 244, step C, using tert-butyl (2-((2-(N,N-bis(4-methoxybenzyl)sulfamoyl)-4-(1-(2-((tert-butoxycarbonyl)amino)ethyl)-1H-benzo[d]imidazol-6-yl)-3-(2-(4-methoxybenzyl)-2H-tetrazol-5-yl)phenyl)sulfonamido)ethyl)carbamate (0.5 g, 0.47 mmol) to afford the crude product. The crude product was purified by Prep-HPLC with the following conditions: Column: X Bridge C18 OBD Prep Column 100 Å, 10 μm, 19 mm×250 mm; Mobile Phase A: water (10 mmol/L NH$_4$HCO$_3$), Mobile Phase B: ACN; Flow rate: 20 mL/min; Gradient: 1% B to 3% B in 10 min; Detector: 254 and 210 nm; Retention time: 6.31 min. The fractions containing desired product were combined and concentrated under vacuum to afford the title compound: LCMS [M+1]$^+$: 507; $^1$H NMR (400 MHz, CD$_3$OD+DCl): δ 9.64 (s, 1H), 8.62 (d, J=10.8 Hz, 1H), 8.07 (d, J=10.8 Hz, 1H), 7.99 (s, 1H), 7.77 (d, J=11.2 Hz, 1H), 7.31 (d, J=11.2 Hz, 1H), 4.90-4.80 (m, 2H), 3.60-3.56 (m, 2H), 3.47-3.44 (m, 2H), 3.17-3.13 (m, 2H).

EXAMPLES 349-361 in the Table below were prepared in an analogous fashion to that described for EXAMPLE 329, starting from tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate and the corresponding boronic acids or boronic esters, which were prepared as described herein, or which were available from commercial sources.

| EX. No. | Structure | Chemical Name | MW | LC/MS [M + H]$^+$ |
|---|---|---|---|---|
| 349 | 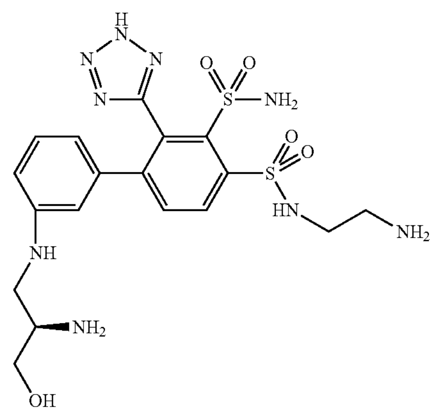 [SMILES: NCCNS(=O)(=O)c1ccc(-c2cccc(NC[C@@H](N)CO)c2)c(-c2nn[nH]n2)c1S(N)(=O)=O] | (R)-3'-((2-amino-3-hydroxypropyl)amino)-N4-(2-aminoethyl)-2-(2H-tetrazol-5-yl)-[1,1'-biphenyl]-3,4-disulfonamide | 511 | 512 |
| 350 | 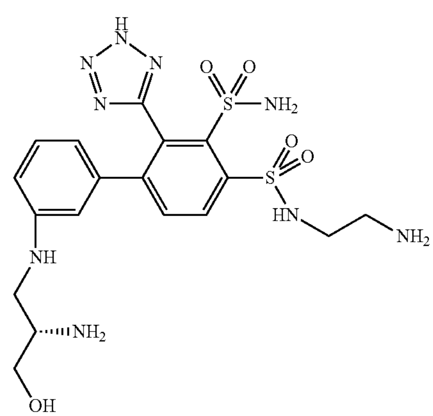 [SMILES: NCCNS(=O)(=O)c1ccc(-c2cccc(NC[C@H](N)CO)c2)c(-c2nn[nH]n2)c1S(N)(=O)=O] | (S)-3'-((2-amino-3-hydroxypropyl)amino)-N4-(2-aminoethyl)-2-(2H-tetrazol-5-yl)-[1,1'-biphenyl]-3,4-disulfonamide | 511 | 512 |

-continued

| EX. No. | Structure | Chemical Name | MW | LC/MS [M + H]+ |
|---|---|---|---|---|
| 351 | 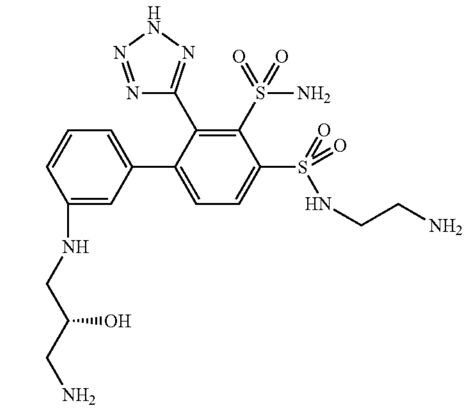 [SMILES: NCCNS(=O)(=O)c1ccc(-c2cccc(NC[C@H](O)CN)c2)c(-c2nn[nH]n2)c1S(N)(=O)=O] | (R)-3'-((3-amino-2-hydroxypropyl)amino)-N4-(2-aminoethyl)-2-(2H-tetrazol-5-yl)-[1,1'-biphenyl]-3,4-disulfonamide | 511 | 512 |
| 352 | 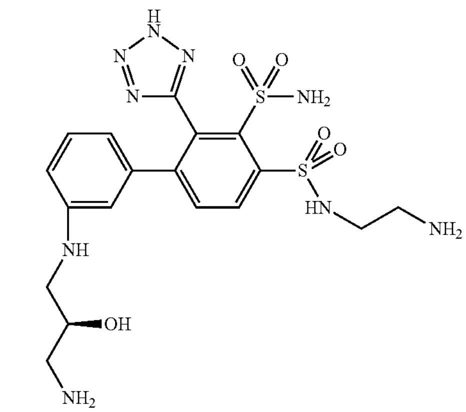 [SMILES: NCCNS(=O)(=O)c1ccc(-c2cccc(NC[C@@H](O)CN)c2)c(-c2nn[nH]n2)c1S(N)(=O)=O] | (S)-3'-((3-amino-2-hydroxypropyl)amino)N4-(2-aminoethyl)-2-(2H-tetrazol-5-yl)-[1,1'-biphenyl]-3,4-disulfonamide | 511 | 512 |
| 353 | 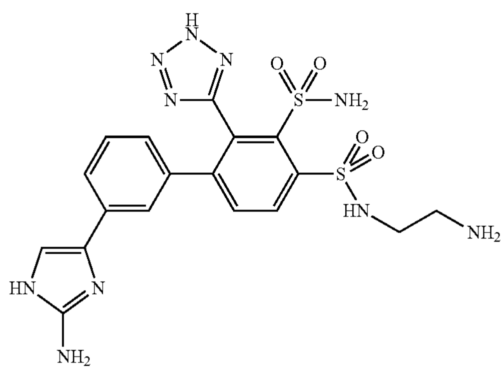 [SMILES: NCCNS(=O)(=O)c1ccc(-c2cccc(-c3c[nH]c(N)n3)c2)c(-c2nn[nH]n2)c1S(N)(=O)=O] | 3'-(2-amino-1H-imidazol-4-yl)-N4-(2-aminoethyl)-2-(2H-tetrazol-5-yl)-[1,1'-biphenyl]-3,4-disulfonamide | 504 | 505 |
| 354 | 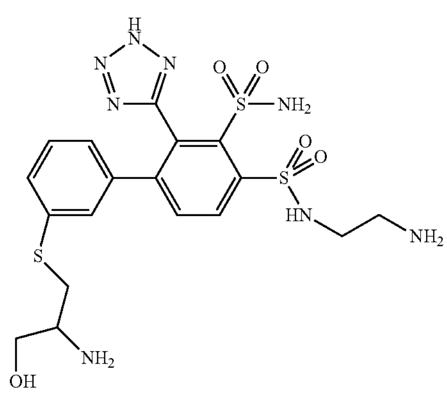 [SMILES: NCCNS(=O)(=O)c1ccc(-c2cccc(SCC(N)CO)c2)c(-c2nn[nH]n2)c1S(N)(=O)=O] | 3'-((2-amino-3-hydroxypropyl)thio)-N4-(2-aminoethyl)-2-(2H-tetrazol-5-yl)-[1,1'-biphenyl]-3,4-disulfonamide | 528 | 529 |

-continued

| EX. No. | Structure | Chemical Name | MW | LC/MS [M + H]+ |
|---|---|---|---|---|
| 355 | 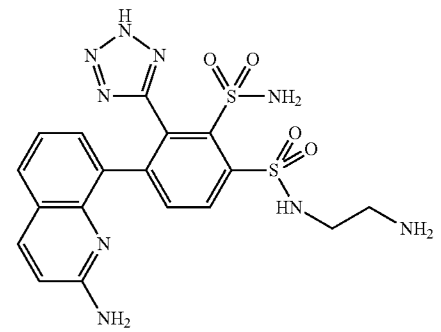 [SMILES: NCCNS(=O)(=O)c1ccc(-c2cccc3ccc(N)nc23)c(-c2nn[nH]n2)c1S(N)(=O)=O] | N1-(2-aminoethyl)-4-(2-aminoquinolin-8-yl)-3-(2H-tetrazol-5-yl)benzene-1,2-disulfonamide | 489 | 490 |
| 356 | 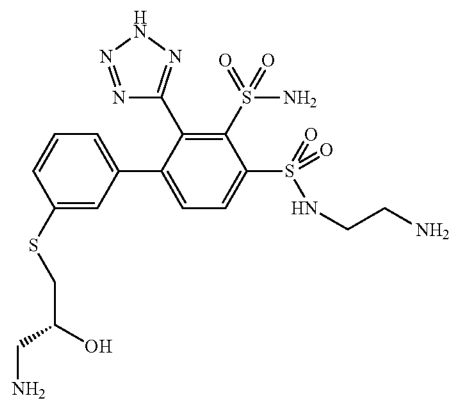 [SMILES: NCCNS(=O)(=O)c1ccc(-c2cccc(SC[C@H](O)CN)c2)c(-c2nn[nH]n2)c1S(N)(=O)=O] | (R)-3'-((3-amino-2-hydroxypropyl)thio)-N4-(2-aminoethyl)-2-(2H-tetrazol-5-yl)-[1,1'-biphenyl]-3,4-disulfonamide | 528 | 529 |
| 357 | 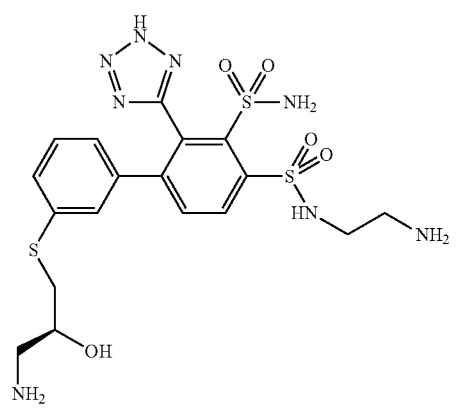 [SMILES: NCCNS(=O)(=O)c1ccc(-c2cccc(SC[C@@H](O)CN)c2)c(-c2nn[nH]n2)c1S(N)(=O)=O] | (S)-5'-(3-amino-2-hydroxypropylthio)-N4-(2-aminoethyl)-2-(2H-tetrazol-5-yl)biphenyl-3,4-disulfonamide | 528 | 529 |
| 358 | 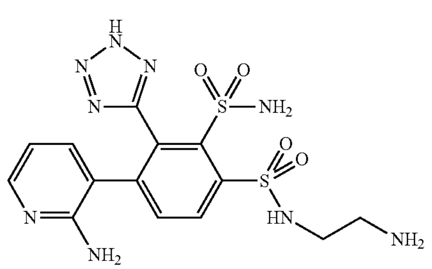 [SMILES: NCCNS(=O)(=O)c1ccc(-c2cccnc2N)c(-c2nn[nH]n2)c1S(N)(=O)=O] | N1-(2-aminoethyl)-4-(2-aminopyridin-3-yl)-3-(2H-tetrazol-5-yl)benzene-1,2-disulfonamide | 439 | 440 |

| EX. No. | Structure | Chemical Name | MW | LC/MS [M + H]⁺ |
|---|---|---|---|---|
| 359 | 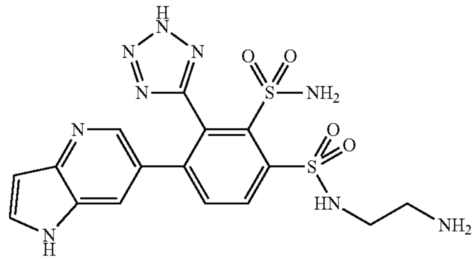 [SMILES: NCCNS(=O)(=O)c1ccc(-c2cnc3cc[nH]c3c2)c(-c2nn[nH]n2)c1S(N)(=O)=O] | N1-(2-aminoethyl)-4-(1H-pyrrolo[3,2-b]pyridin-6-yl)-3-(2H-tetrazol-5-yl)benzene-1,2-disulfonamide | 463 | 462 [M − 1]⁻ |
| 360 | 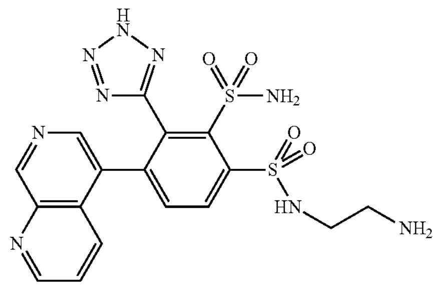 [SMILES: NCCNS(=O)(=O)c1ccc(-c2cncc3ncccc23)c(-c2nn[nH]n2)c1S(N)(=O)=O] | N1-(2-aminoethyl)-4-(quinolin-5-yl)-3-(2H-tetrazol-5-yl)benzene-1,2-disulfonamide | 474 | 475 |
| 361 | 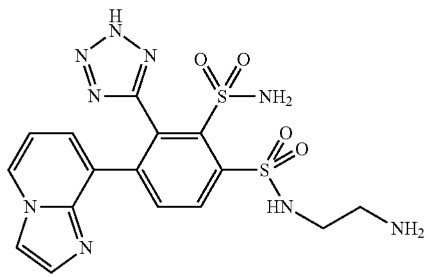 [SMILES: NCCNS(=O)(=O)c1ccc(-c2cccn3ccnc23)c(-c2nn[nH]n2)c1S(N)(=O)=O] | N1-(2-aminoethyl)-4-(imidazo[1,2-a]pyridin-8-yl)-3-(2H-tetrazol-5-yl)benzene-1,2-disulfonamide | 463 | 464 |

Example 362

(R)—N1-(1-amino-3-hydroxypropan-2-yl)-4-(2-aminopyridin-4-yl)-3-(2H-tetrazol-5-yl)benzene-1,2-disulfonamide

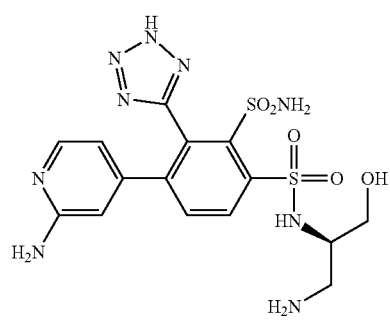 [SMILES: NC[C@H](CO)NS(=O)(=O)c1ccc(-c2ccnc(N)c2)c(-c2nn[nH]n2)c1S(N)(=O)=O]

Step A: (R)-tert-butyl(2-(4-(2-aminopyridin-4-yl)-2-(N,N-bis(4-methoxybenzyl)sulfamoyl)-3-(2-(4-methoxybenzyl)-2H-tetrazol-5-yl)phenylsulfonamido)-3-hydroxypropyl) carbamate The title compound was prepared as described for EXAMPLE 246, step C, using (R)-tert-butyl (2-(2-(N,N-bis (4-methoxybenzyl)sulfamoyl)-4-iodo-3-(2-(4-methoxy benzyl)-2H-tetrazol-5-yl)phenylsulfonamido)-3-hydroxypropyl)carbamate (1.0 g, 1.04 mmol) and 4-(4,4,5,5-tetramethyl-1,3,2-dioxaborolan-2-yl)pyridin-2-amine (0.46 g, 2.08 mmol): LCMS [M+1]⁺: 930.

Step B: (R)-3-amino-2-(4-(2-aminopyridin-4-yl)-2-sulfamoyl-3-(2H-tetrazol-5-yl)phenyl sulfonamido) propyl 2,2,2-trifluoroacetate The title compound was prepared as described for EXAMPLE 244, step C, using (R)-tert-butyl(2-(4-(2-aminopyridin-4-yl)-2-(N,N-bis(4-methoxybenzyl)sulfamoyl)-3-(2-(4-methoxybenzyl)-2H-tetrazol-5-yl)phenylsulfonamido)-3-hydroxypropyl) carbamate (0.39 g, 0.42 mmol) to afford the crude product of (R)-3-amino-2-(4-(2-aminopyridin-4-yl)-2-sulfamoyl-3-(2H-tetrazol-5-yl)phenylsulfonamido)propyl 2,2,2-trifluoroacetate as a solid: LCMS [M+1]⁺: 806.

Step C: (R)—N1-(1-amino-3-hydroxypropan-2-yl)-4-(2-aminopyridin-4-yl)-3-(2H-tetrazol-5-yl)benzene-1,2-disulfonamide To a solution of (R)-3-amino-2-(4-(2-aminopyridin-4-yl)-2-sulfamoyl-3-(2H-tetrazol-5-yl)phenylsulfonamido)propyl 2,2,2-trifluoroacetate (0.15 g, 0.265 mmol) in MeOH (3 mL) was added a solution of NaOH (42.4 mg, 1.061 mmol) in water (3 mL) at 0° C. The mixture was stirred at room temperature for 4 hours under nitrogen. The resulting mixture was concentrated under vacuum. The residue was purified by Prep-HPLC with the following conditions: Column: XBridge Shield RP18 OBD Column, 5 μm, 19×150 mm; Mobile Phase A: water with 10 mmol/L NH$_4$HCO$_3$, Mobile Phase B: ACN; Flow rate: 20 mL/min; Gradient: 2% B to 19% B in 8 min; Detector: 254 nm; Retention time: 6.67 min. The fractions containing desired product were combined and concentrated under vacuum to afford the title compound: LCMS [M+1]$^+$: 470; $^1$H NMR (400 MHz, CD$_3$OD+DCl) δ 8.37 (d, J=8.4 Hz, 1H), 7.68 (d, J=8.4 Hz, 1H), 7.54 (d, J=5.6 Hz, 1H), 6.15 (s, 1H), 6.05 (d, J=5.6 Hz, 1H), 3.76-3.62 (m, 1H), 3.49-3.41 (m, 1H), 3.39-3.31 (m, 1H), 3.11-3.01 (m, 1H), 3.01-2.89 (m, 1H).

Example 363

(R)—N1-(1-amino-3-hydroxypropan-2-yl)-4-(2-(aminomethyl)benzo[d]thiazol-4-yl)-3-(2H-tetrazol-5-yl)benzene-1,2-disulfonamide

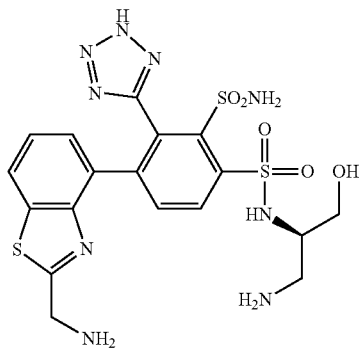 [SMILES: NCc1nc2c(-c3ccc(S(=O)(=O)N[C@H](CN)CO)c(S(N)(=O)=O)c3-c3nn[nH]n3)cccc2s1]

Step A: (R)-tert-butyl(2-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)-3-hydroxypropyl)carbamate The title compound was prepared as described for EXAMPLE 246, step C, using (R)-tert-butyl (2-(2-(N,N-bis (4-methoxybenzyl)sulfamoyl)-4-iodo-3-(2-(4-methoxybenzyl)-2H-tetrazol-5-yl)phenylsulfonamido)-3-hydroxypropyl)carbamate (2.80 g, 2.90 mmol) and 2-aminobenzo[d]thiazol-4-ylboronic acid (1.60 g, 5.81 mmol): LCMS [M+1]$^+$: 986.

Step B: (R)-tert-butyl (2-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl sulfonamido)-3-hydroxypropyl)carbamate 0.65 g, 0.62 mmol) in 1,4-dioxane To a suspension of tert-butyl nitrite (0.22 g, 2.11 mmol) and copper (II) cromide (0.36 g, 1.58 mmol) in ACN (15 mL) was added (R)-tert-butyl (2-(4-(2-aminobenzo[d]thiazol-4-yl)-2-(N,N-bis(4-methoxybenzyl)sulfamoyl)-3-(2-(4-methoxybenzyl)-2H-tetrazol-5-yl)phenylsulfonamido)-3-hydroxypropyl)carbamate (1.30 g, 1.32 mmol) at 0° C. The reaction mixture was stirred at room temperature for 4 hours under nitrogen. The resulting mixture was diluted with water (100 mL) and extracted with EA (3×100 mL). The combined organic layers were washed with water (3×200 mL) and brine (3×200 mL), dried over anhydrous Na$_2$SO$_4$ and filtered. The filtrate was concentrated under vacuum. The residue was purified by silica gel column chromatography and eluted with 50% EA in PE. The fractions containing desired product were combined and concentrated under vacuum to afford the title compound: LCMS [M+1]$^+$: 1049, 1051 (1:1).

Step C: (R)-tert-butyl (2-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl sulfonamido)-3-hydroxypropyl)carbamate To a solution of (R)-tert-butyl(2-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl sulfonamido)-3-hydroxypropyl)carbamate (0.65 g, 0.62 mmol) in 1,4-dioxane (6.0 mL) was added Zn(CN)$_2$ (0.22 g, 1.86 mmol), 3rd Generation t-Bu XPhos precatalyst (98 mg, 0.12 mmol) at room temperature. The mixture was degassed with nitrogen three times. The reaction mixture was stirred at 55° C. for 16 hours under nitrogen. The resulting mixture was concentrated under vacuum. The residue was purified by silica gel column chromatography and eluted with 50% EA in PE. The fractions containing desired product were combined and concentrated under vacuum to afford the title compound: LCMS [M+1]$^+$: 996.

Step D: (R)-tert-butyl(2-(4-(2-(aminomethyl)benzo[d]thiazol-4-yl)-2-(N,N-bis(4-methoxy benzyl)sulfamoyl)-3-(2-(4-methoxybenzyl)-2H-tetrazol-5-yl)phenylsulfonamido)-3-hydroxypropyl)carbamate To a solution of (R)-tert-butyl (2-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl sulfonamido)-3-hydroxypropyl)carbamate (0.20 g, 0.20 mmol) in MeOH (2.5 mL) and EA (2.5 mL) was added Pd(OH)$_2$/C (20% wt, 28.2 mg, 0.04 mmol). The mixture was degassed with hydrogen three times. The reaction mixture was stirred at room temperature for 4 hours under hydrogen. The resulting mixture was filtered and the filtrate was concentrated under vacuum. The residue was purified by silica gel column chromatography and eluted with 91% EA in MeOH. The fractions containing desired product were combined and concentrated under vacuum to afford the title compound: LCMS [M+1]$^+$: 1000.

Step E: (R)-3-amino-2-(4-(2-(aminomethyl)benzo[d]thiazol-4-yl)-2-sulfamoyl-3-(2H-tetrazol-5-yl)phenylsulfonamido)propyl 2,2,2-trifluoroacetate The title compound was prepared as described for EXAMPLE 244, step C, using (R)-tert-butyl (2-(4-(2-(aminomethyl)benzo[d]thiazol-4-yl)-2-(N,N-bis(4-methoxy benzyl)sulfamoyl)-3-(2-(4-methoxybenzyl)-2H-tetrazol-5-yl) phenylsulfonamido)-3-hydroxypropyl)carbamate (0.10 g, 0.10 mmol) to afford the crude product of (R)-3-amino-2-(4-(2-(aminomethyl)benzo[d]thiazol-4-yl)-2-sulfamoyl-3-(2H-tetrazol-5-yl)phenylsulfonamido)propyl 2,2,2-trifluoroacetate as a solid: LCMS [M+1]$^+$: 636.

Step F: (R)—N1-(1-amino-3-hydroxypropan-2-yl)-4-(2-(aminomethyl)benzo[d]thiazol-4-yl)-3-(2H-tetrazol-5-yl)benzene-1,2-disulfonamide To a solution of (R)-3-amino-2-(4-(2-(aminomethyl)benzo[d]thiazol-4-yl)-2-sulfamoyl-3-(2H-tetrazol-5-yl)phenylsulfonamido)propyl 2,2,2-trifluoroacetate (75 mg, 0.12 mmol) in MeOH (1 mL) was added a solution of NaOH (19 mg, 0.47 mmol) in water (1 mL) at 0° C. The reaction mixture was stirred at room temperature for 2 hours. The resulting mixture was concentrated under vacuum. The residue was purified by Prep-HPLC with the following conditions: Column: XBridge C18 OBD Prep Column 100 Å, 10 μm, 19 mm×250 mm; Mobile Phase A: water with 10 mmol/L NH$_4$HCO$_3$, Mobile Phase B: ACN; Flow rate: 20 mL/min; Gradient: 4% B to 23% B in 8 min; Detector: 254 and 220 nm. The fractions containing desired product were combined and concentrated under vacuum to afford the title compound: LCMS [M+1]$^+$: 540; $^1$H NMR (300 MHz, DMSO-d$_6$+DCl): δ 8.24 (d, J=4.5 Hz, 1H), 7.87-7.82 (m, 2H), 7.02 (t, J=7.5 Hz, 1H), 6.56 (d, J=7.8 Hz, 1H), 4.06 (s, 2H), 3.20-3.15 (m, 2H), 2.90-2.80 (m, 2H), 2.68-2.72 (m, 1H).

Example 364

(R)—N$^1$-(1-amino-3-hydroxypropan-2-yl)-4-(6-aminopyridin-2-yl)-3-(2H-tetrazol-5-yl)benzene-1,2-disulfonamide

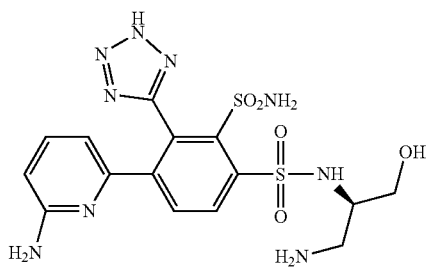 [SMILES: NC[C@H](CO)NS(=O)(=O)c1ccc(-c2cccc(N)n2)c(-c2nn[nH]n2)c1S(N)(=O)=O]

Step A: (R)-tert-butyl (2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)-3-hydroxypropyl) carbamate The title compound was prepared as described for EXAMPLE 246, step C, using (R)-tert-butyl (2-(2-(N,N-bis (4-methoxybenzyl)sulfamoyl)-4-iodo-3-(2-(4-methoxy benzyl)-2H-tetrazol-5-yl)phenylsulfonamido)-3-hydroxypropyl)carbamate (1.50 g, 1.56 mmol) and 2-bromo-6-(4,4,5,5-tetramethyl-1,3,2-dioxaborolan-2-yl)pyridine (0.89 g, 3.11 mmol): LCMS [M+1]$^+$: 993, 995 (1:1).

Step B: (R)-tert-butyl (2-(2-(N,N-bis(4-methoxybenzyl)sulfamoyl)-3-(2-(4-methoxybenzyl)-2H-tetrazol-5-yl)-4-(6-(2,2,2-trifluoroacetamido)pyridin-2-yl)phenylsulfonamido)-3-hydroxypropyl)carbamate To a solution of (R)-tert-butyl(2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)-3-hydroxypropyl)carbamate (0.72 g, 0.72 mmol) 1,4-dioxane (6 mL) was added 2,2,2-trifluoroacetamide (0.41 g, 3.62 mmol), N1,N2-dimethylethane-1,2-diamine (63.9 mg, 0.72 mmol), CuI (69.0 mg, 0.36 mmol) and Na$_2$CO$_3$ (0.23 g, 2.17 mmol) at room temperature. The reaction mixture was degassed with nitrogen three times and irradiated with microwave radiation at 120° C. for 1.5 hours. The resulting mixture was diluted with water (50 mL) and extracted with EA (3×50 mL). The combined organic layers were washed with water (3×100 mL) and brine (3×100 mL), dried over anhydrous Na$_2$SO$_4$ and filtered. The filtrate was concentrated under vacuum. The residue was purified by silica gel column chromatography, eluted with 60% EA in PE. The fractions containing desired product were combined and concentrated under vacuum to afford the title compound: LCMS [M+1]$^+$: 1026.

Step C: (R)—N1-(1-amino-3-hydroxypropan-2-yl)-4-(6-aminopyridin-2-yl)-3-(2H-tetrazol-5-yl)benzene-1,2-disulfonamide A solution of (R)-tert-butyl (2-(2-(N,N-bis(4-methoxybenzyl)sulfamoyl)-3-(2-(4-methoxybenzyl)-2H-tetrazol-5-yl)-4-(6-(2,2,2-trifluoroacetamido)pyridin-2-yl) phenylsulfonamido)-3-hydroxypropyl)carbamate (0.23 g, 0.22 mmol) in TFA (2 mL) was stirred for 1 hour at room temperature. The resulting solution was concentrated under vacuum. The residue was co-evaporated with anisole (3×5 mL) under vacuum and used in the next step without further purification. TFA (2 mL) was added to the crude product. The solution was stirred at 80° C. for 1 hour. The resulting solution was concentrated under vacuum. The residue was dissolved in THF (2 mL), and to the mixture was added NaOH (2 mL, 2 M). The reaction mixture was degassed with nitrogen 3 times and stirred for 2 hours at room temperature. The resulting solution was concentrated under vacuum. The crude product was purified by Prep-HPLC with the following conditions: Column: X Bridge C18 OBD Prep Column 100 Å, 10 μm, 19 mm×250 mm; Mobile Phase A: water with 10 mmol/L NH$_4$HCO$_3$, Mobile Phase B: ACN; Flow rate: 20 mL/min; Gradient: 5% B to 25% B in 7 min; Detector: 254 and 220 nm. The fractions containing desired product were combined and concentrated under vacuum to afford the title compound: LCMS [M+1]$^+$: 470; $^1$H NMR (400 MHz, CD$_3$OD+DCl) δ 8.46 (d, J=8.3 Hz, 1H), 7.93 (d, J=8.3 Hz, 1H), 7.15 (t, J=7.8 Hz, 1H), 6.39 (d, J=8.3 Hz, 1H), 6.01 (d, J=7.4 Hz, 1H), 3.74-3.71 (m, 1H), 3.57-3.39 (m, 2H), 3.05 (d, J=8.3 Hz, 2H).

Example 365

(R)—N1-(2-amino-3-hydroxypropyl)-4-(6-aminopyridin-3-yl)-3-(2H-tetrazol-5-yl) benzene-1,2-disulfonamide

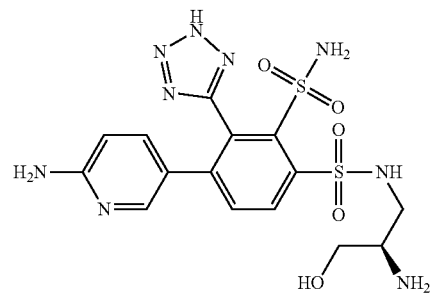 [SMILES: Nc1ccc(-c2ccc(S(=O)(=O)NC[C@@H](N)CO)c(S(N)(=O)=O)c2-c2nn[nH]n2)cn1]

Step A: (R)-benzyl (1-(4-(6-aminopyridin-3-yl)-2-(N,N-bis(4-methoxybenzyl)sulfamoyl)-3-((2-(4-methoxybenzyl)-2H-tetrazol-5-yl)phenylsulfonamido)-3-hydroxypropan-2-yl)carbamate To a mixture of (R)-benzyl (1-(2-(N,N-bis(4-methoxybenzyl)sulfamoyl)-4-iodo-3-(2-(4-methoxybenzyl)-2H-tetrazol-5-yl)phenylsulfonamido)-3-hydroxypropan-2-yl)carbamate (0.8 g, 0.8 mmol), 5-(4,4,5,5-tetramethyl-1,3,2-dioxaborolan-2-yl) pyridine-2-amine (0.44 g, 2.0 mmol) and Pd(PPh$_3$)$_4$ (0.19 g, 0.16 mmol) in 1,4-dioxane (10 mL) was added a solution of Na$_2$CO$_3$ (0.26 g, 2.4 mmol) in water (2.5 mL) at room temperature. The mixture was degassed with nitrogen three times and stirred for 12 hours at 80° C. under nitrogen. The resulting mixture was allowed to cool to room temperature, diluted with water (150 mL) and extracted with EA (3×100 mL). The combined organic layers were washed with brine (200 mL), dried over anhydrous Na$_2$SO$_4$ and filtered. The filtrate was concentrated under vacuum. The residue was purified by silica gel column chromatography, eluted with 10% MeOH in EA to afford the title compound: LCMS [M+1]$^+$: 964.

Step B: (R)—N1-(2-amino-3-hydroxypropyl)-4-(6-aminopyridin-3-yl)-3-(2H-tetrazol-5-yl) benzene-1,2-disulfonamide A solution of (R)-benzyl(1-(4-(6-aminopyridin-3-yl)-2-(N,N-bis(4-methoxybenzyl)sulfamoyl)-3-(2-(4-methoxybenzyl)-2H-tetrazol-5-yl)phenyl sulfonamido)-3-hydroxypropan-2-yl)carbamate (0.54 g, 0.56 mmol) in TFA (5 mL) was stirred at 80° C. for 1 hour. The resulting mixture was allowed to cool to room temperature. The residue was dissolved with HCl ((30 mL, 1 mol/L). The aqueous phase was extracted with EA (10 mL) and was concentrated under vacuum. The residue was purified by Prep-HPLC with the following conditions: Column: X Bridge C18 OBD Prep Column 100 Å, 10 μm, 19 mm×250 mm; Mobile Phase A: waters with 10 mmol/L NH$_4$HCO$_3$, Mobile Phase B: ACN; Flow rate: 20 mL/min; Gradient: 3% B to 20% B in 8 min; Detector: 254 and 220 nm, to afford the title compound: LCMS [M+1]$^+$: 470; $^1$H NMR (400 MHz, DMSO-d$_6$): δ 8.18 (d, J=8.4 Hz, 1H), 7.75 (d, J=8.4 Hz, 1H), 7.55 (s, 1H), 7.49-7.15 (brs, 3H), 6.72 (d, J=6.0 Hz, 1H), 6.15 (d, J=8.8 Hz, 1H), 5.99 (brs, 2H), 5.29-5.09 (brs, 1H), 3.59-3.42 (m, 2H), 3.21-3.15 (m, 2H), 3.11-3.02 (m, 1H).

Example 366

(S)-4-(2-aminobenzo[d]thiazol-4-yl)-N$^1$-((3-aminopyrrolidin-3-yl)methyl)-3-(2H-tetrazol-5-yl) benzene-1,2-disulfonamide

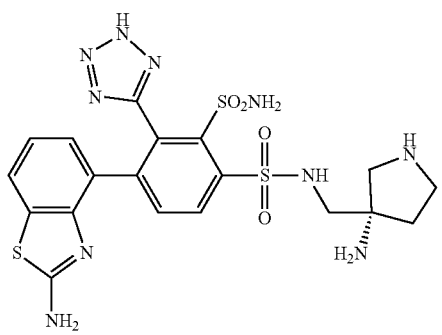 [SMILES: Nc1nc2c(-c3ccc(S(=O)(=O)NC[C@]4(N)CCNC4)c(S(N)(=O)=O)c3-c3nn[nH]n3)cccc2s1]

Step A: 3-(2-Aminobenzo[d]thiazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide The title compound was prepared as described for EXAMPLE 250, step A, using (2-aminobenzo[d]thiazol-4-yl)boronic acid (2.99 g, 15.41 mmol) to afford the desired compound as a solid: LCMS [M+1]$^+$: 898.

Step B: 4-(2-Aminobenzo[d]thiazol-4-yl)-2-(N,N-bis(4-methoxybenzyl)sulfamoyl)-3-(2-(4-methoxybenzyl)-2H-tetrazol-5-yl)benzenesulfinic acid The title compound was prepared as described for EXAMPLE 250, step B, using 3-(2-aminobenzo[d]thiazol-4-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (3.0 g, 3.34 mmol): LCMS [M+1]$^+$: 798.

Step C: (S)-tert-butyl-3-amino-3-((4-(2-aminobenzo[d]thiazol-4-yl)-2-(N,N-bis(4-methoxybenzyl)sulfamoyl)-3-(2-(4-methoxybenzyl)-2H-tetrazol-5-yl) phenyl sulfonamido)methyl)pyrrolidine-1-carboxylate The title compound was prepared as described for EXAMPLE 250, step C, using 4-(2-aminobenzo[d]thiazol-4-yl)-2-(N,N-bis(4-methoxybenzyl)sulfamoyl)-3-(2-(4-methoxybenzyl)-2H-tetrazol-5-yl)benzenesulfinic acid (0.50 g, 0.63 mmol): LCMS [M+1]$^+$: 1011.

Step D: (S)-4-(2-aminobenzo[d]thiazol-4-yl)-N1-((3-aminopyrrolidin-3-yl)methyl)-3-(2H-tetrazol-5-yl)benzene-1,2-disulfonamide The title compound was prepared as described for EXAMPLE 250, step D, using (S)-tert-butyl-3-amino-3-((4-(2-aminobenzo[d]thiazol-4-yl)-2-(N,N-bis(4-methoxy benzyl)sulfamoyl)-3-(2-(4-methoxybenzyl)-2H-tetrazol-5-yl) phenylsulfonamido) methyl)pyrrolidine-1-carboxylate (0.35 g, 0.35 mmol) to afford the desired compound as a solid: LCMS [M+1]$^+$: 551; $^1$H NMR (400 MHz, CD$_3$OD+DCl): δ 8.73 (dd, J=8.2 Hz, 2.4 Hz, 1H), 8.06 (d, J=8.2 Hz, 1H), 7.78 (dd, J=8.1 Hz, 1.0 Hz, 1H), 7.29-7.26 (m, 1H), 7.10-7.16 (m, 1H), 3.86-3.55 (m, 6H), 2.58 (m, 1H), 2.41 (m, 1H).

Example 367

(R)-4-(2-aminobenzo[d]thiazol-4-yl)-N1-((3-aminopyrrolidin-3-yl)methyl)-3-(2H-tetrazol-5-yl)benzene-1,2-disulfonamide

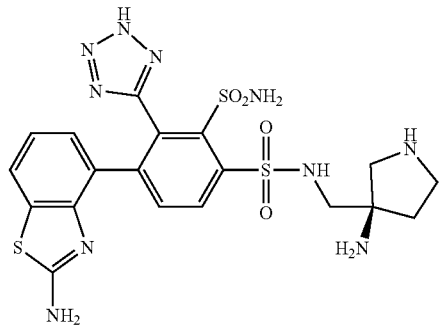 [SMILES: Nc1nc2c(-c3ccc(S(=O)(=O)NC[C@@]4(N)CCNC4)c(S(N)(=O)=O)c3-c3nn[nH]n3)cccc2s1]

Step A: (R)-tert-butyl-3-amino-3-((4-(2-aminobenzo[d]thiazol-4-yl)-2-(N,N-bis(4-methoxy benzyl)sulfamoyl)-3-(2-(4-methoxybenzyl)-2H-tetrazol-5-yl)phenylsulfonamido) methyl)pyrrolidine-1-carboxylate The title compound was prepared as described for EXAMPLE 250, step C, using 4-(2-aminobenzo[d]thiazol-4-yl)-2-(N,N-bis(4-methoxybenzyl)sulfamoyl)-3-(2-(4-methoxybenzyl)-2H-tetrazol-5-yl)benzenesulfinic acid (500 mg, 0.627 mmol) and (S)-tert-butyl 3-amino-3-(aminomethyl)pyrrolidine-1-carboxylate (202 mg, 0.940 mmol): LCMS (ESI) [M+1]$^+$: 1011.

Step B: (R)-4-(2-aminobenzo[d]thiazol-4-yl)-N1-((3-aminopyrrolidin-3-yl)methyl)-3-(2H-tetrazol-5-yl)benzene-1,2-disulfonamide The title compound was prepared as described for EXAMPLE 250, step D, using (R)-tert-butyl 3-amino-3-((4-(2-aminobenzo[d]thiazol-4-yl)-2-(N,N-bis(4-methoxy benzyl)sulfamoyl)-3-(2-(4-methoxybenzyl)-2H-tetrazol-5-yl)phenylsulfonamido) methyl)pyrrolidine-1-carboxylate (0.35 g, 0.35 mmol) to afford the desired compound as a solid: LCMS [M+1]$^+$: 551; $^1$H NMR (400 MHz, CD$_3$OD+DCl): δ 8.73 (dd, J=8.2 Hz, 2.3 Hz, 1H), 8.06 (d, J=8.2 Hz, 1H), 7.78 (dd, J=8.1 Hz, 1.0 Hz, 1H), 7.29-7.25 (m, 1H), 7.13-7.04 (m, 1H), 3.81 (dd, J=13.4 Hz, 3.6 Hz, 1H), 3.72-3.69 (m, 1H), 3.68-3.53 (m, 4H), 2.65-2.49 (m, 1H), 2.42-2.38 (m, 1H)

Example 368

(S)-4-(6-aminopyridin-3-yl)-N1-((3-aminopyrrolidin-3-yl)methyl)-3-(2H-tetrazol-5-yl)benzene-1,2-disulfonamide

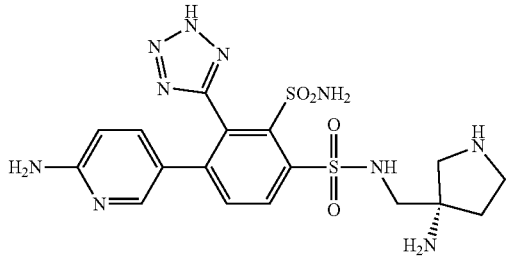 [SMILES: Nc1ccc(-c2ccc(S(=O)(=O)NC[C@]3(N)CCNC3)c(S(N)(=O)=O)c2-c2nn[nH]n2)cn1]

Step A: 3-(6-Aminopyridin-3-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamide The title compound was prepared as described for EXAMPLE 250, step A, using 5-(4,4,5,5-tetramethyl-1,3,2-dioxaborolan-2-yl)pyridin-2-amine (2.83 g, 12.84 mmol): LCMS ([M+1]$^+$: 842.

Step B: 4-(6-Aminopyridin-3-yl)-2-(N,N-bis(4-methoxybenzyl)sulfamoyl)-3-(2-(4-methoxybenzyl)-2H-tetrazol-5-yl)benzenesulfinic acid The title compound was prepared as described for EXAMPLE 250, step B, using 3-(6-aminopyridin-3-yl)-N,N-bis(4-methoxybenzyl)-2-(2-(4-methoxybenzyl)-2H-tetrazol-5-yl)-6-((2-(trimethylsilyl)ethyl)sulfonyl)benzenesulfonamideto (2.4 g, 2.85 mmol): LCMS [M+1]$^+$: 742.

Step C: (S)-tert-butyl-3-amino-3-((4-(6-aminopyridin-3-yl)-2-(N,N-bis(4-methoxybenzyl) sulfamoyl)-3-(2-(4-methoxybenzyl)-2H-tetrazol-5-yl)phenylsulfonamido)methyl) pyrrolidine-1-carboxylate The title compound was prepared as described for EXAMPLE 250, step C, using 4-(6-aminopyridin-3-yl)-2-(N,N-bis(4-methoxybenzyl)sulfamoyl)-3-(2-(4-methoxybenzyl)-2H-tetrazol-5-yl)benzenesulfinic acid (0.40 g, 0.54 mmol) to afford the desired compound as a solid: LCMS [M+1]$^+$: 955.

Step D: (S)-4-(6-aminopyridin-3-yl)-N1-((3-aminopyrrolidin-3-yl)methyl)-3-(2H-tetrazol-5-yl)benzene-1,2-disulfonamide The title compound was prepared as described for EXAMPLE 250, step D, using (S)-tert-butyl-3-amino-3-((4-(6-aminopyridin-3-yl)-2-(N,N-bis(4-methoxybenzyl) sulfamoyl)-3-(2-(4-methoxybenzyl)-2H-tetrazol-5-yl)phenylsulfonamido)methyl) pyrrolidine-1-carboxylate (0.28 g, 0.29 mmol): LCMS [M+1]$^+$: 495; $^1$H NMR (400 MHz, CD$_3$OD+DCl): δ 8.69 (d, J=8.4 Hz, 1H), 8.04 (d, J=8.0 Hz, 1H), 7.71 (d, J=2.0 Hz, 1H), 7.51 (dd, J=9.2 Hz, 2.0 Hz, 1H), 6.92 (d, J=9.2 Hz, 1H), 3.78 (d, J=13.2 Hz, 1H), 3.71 (m, 1H), 3.59 (m, 4H), 2.54 (m, 1H), 2.41 (m, 1H).

Example 369

(R)-4-(6-aminopyridin-3-yl)-N1-((3-aminopyrrolidin-3-yl)methyl)-3-(2H-tetrazol-5-yl)benzene-1,2-disulfonamide

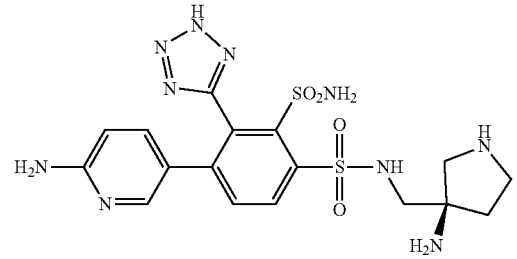 [SMILES: Nc1ccc(-c2ccc(S(=O)(=O)NC[C@@]3(N)CCNC3)c(S(N)(=O)=O)c2-c2nn[nH]n2)cn1]

Step A: (R)-tert-butyl 3-amino-3-((4-(6-aminopyridin-3-yl)-2-(N,N-bis(4-methoxybenzyl) sulfamoyl)-3-(2-(4-methoxybenzyl)-2H-tetrazol-5-yl)phenylsulfonamido)methyl) pyrrolidine-1-carboxylate The title compound was prepared as described for EXAMPLE 250, step C, using 4-(6-aminopyridin-3-yl)-2-(N,N-bis(4-methoxybenzyl)sulfamoyl)-3-(2-(4-methoxybenzyl)-2H-tetrazol-5-yl)benzenesulfinic acid (0.40 g, 0.54 mmol) and (S)-tert-butyl 3-amino-3-(aminomethyl)pyrrolidine-1-carboxylate (0.17 g, 0.81 mmol) to afford the desired compound as a solid: LCMS [M+1]$^+$: 955.

Step B: (R)-4-(6-aminopyridin-3-yl)-N1-((3-aminopyrrolidin-3-yl)methyl)-3-(2H-tetrazol-5-yl)benzene-1,2-disulfonamide The title compound was prepared as described for EXAMPLE 250, step D, using (R)-tert-butyl-3-amino-3-((4-(6-aminopyridin-3-yl)-2-(N,N-bis(4-methoxybenzyl) sulfamoyl)-3-(2-(4-methoxybenzyl)-2H-tetrazol-5-yl)phenylsulfonamido)methyl) pyrrolidine-1-carboxylate (0.26 g, 0.27 mmol): LCMS [M+1]$^+$: 495; $^1$H NMR (400 MHz, CD$_3$OD+DCl): δ 8.69 (d, J=8.4 Hz, 1H), 8.04 (d, J=8.4 Hz, 1H), 7.73-7.70 (m, 1H), 7.51 (dd, J=9.2 Hz, 2.0 Hz, 1H), 6.92 (d, J=9.2 Hz, 1H), 3.78 (d, J=13.2 Hz, 1H), 3.71 (m, 1H), 3.64-3.54 (m, 4H), 2.54 (m, 1H), 2.46-2.35 (m, 1H).

Example 370

(S)-4-(2-amino-1H-benzo[d]imidazol-4-yl)-N1-(2,3-diaminopropyl)-3-(2H-tetrazol-5-yl)benzene-1,2-disulfonamide

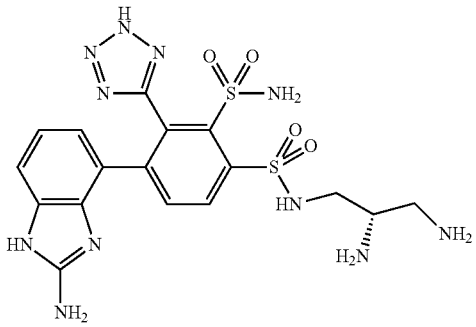 [SMILES: NC[C@H](N)CNS(=O)(=O)c1ccc(-c2cccc3[nH]c(N)nc23)c(-c2nn[nH]n2)c1S(N)(=O)=O]

Step A: (S)-benzyl-tert-butyl(3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl sulfonamido)propane-1,2-diyl)dicarbamate To a solution of (S)-benzyl-tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate (1.0 g, 0.91 mmol) in 1,4-dioxane (7 mL) and water (3 mL) was added (2-amino-1H-benzo[d]imidazol-4-yl)boronic acid (0.32 g, 1.82 mmol), $Na_2CO_3$ (0.29 g, 2.73 mmol) and $Pd(PPh_3)_4$ (0.21 g, 0.18 mmol) at room temperature. The mixture was degassed with nitrogen three times. The reaction mixture was stirred at 80° C. for 16 hours under nitrogen. The resulting mixture was diluted with water (100 mL) and extracted with EA (3×100 mL). The combined organic layers was washed with water (3×100 mL) and brine (3×100 mL), dried over anhydrous $Na_2SO_4$ and filtered. The filtrate was concentrated under vacuum. The residue was purified by silica gel column chromatography and eluted with 10% MeOH in DCM. The fractions containing desired product were combined and concentrated under vacuum to afford the title compound: LCMS [M+1]$^+$: 1102.

Step B: (S)-4-(2-amino-1H-benzo[d]imidazol-4-yl)-N1-(2,3-diaminopropyl)-3-(2H-tetrazol-5-yl)benzene-1,2-disulfonamide To a solution of (S)-benzyl tert-butyl (3-(4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenylsulfonamido)propane-1,2-diyl)dicarbamate (0.68 g, 0.62 mmol) was added conc. HCl (1 mL, 12.3 mmol). The mixture was stirred at 80° C. for 3 hours. The resulting solution was concentrated under vacuum. The crude product was purified by Prep-HPLC with the following conditions: Column: XBridge C18 OBD Prep Column 100 Å, 10 μm, 19 mm×250 mm; Mobile Phase A: water with 10 mmol/L $NH_4HCO_3$, Mobile Phase B: ACN; Flow rate: 20 mL/min; Gradient: 5% B to 5% B in 12 min; Detector: 254 nm; Retention time: 6.54 min. The fractions containing desired product were combind and concentrated under vacuum to afford the title compound: LCMS [M+1]$^+$: 508; $^1$H NMR (400 MHz, DMSO-$d_6$+$D_2O$): δ 8.24 (d, J=8.4 Hz, 1H), 7.96-7.81 (m, 1H), 6.95 (d, J=7.6 Hz, 1H), 6.62-6.53 (m, 1H), 6.13-6.07 (m, 1H), 3.14-2.80 (m, 4H), 2.54-2.53 (m, 1H).

Example 371

(S)-4-(2-aminoquinolin-8-yl)-N1-(2,3-diaminopropyl)-3-(2H-tetrazol-5-yl)benzene-1,2-disulfonamide

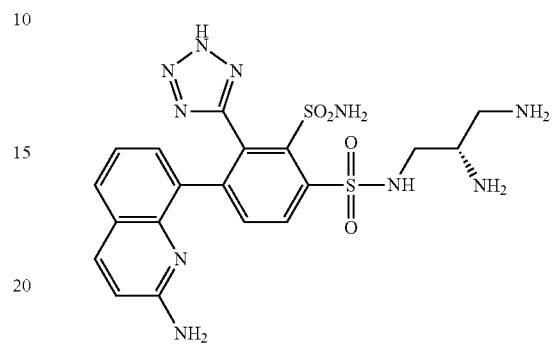

Step A: (S)-di-tert-butyl(3-(4-(2-aminoquinolin-8-yl)-2-(N,N-bis(4-methoxybenzyl)sulfamoyl)-3-(2-(4-methoxybenzyl)-2H-tetrazol-5-yl)phenylsulfonamido)propane-1,2-diyl)dicarbamate The title compound was prepared as described for EXAMPLE 246, step C, using (S)-di-tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl)dicarbamate (0.80 g, 0.75 mmol) and (2-aminoquinolin-8-yl)boronic acid (0.35 g, 1.80 mmol): LCMS [M+1]$^+$: 1079.

Step B: (S)-4-(2-aminoquinolin-8-yl)-N1-(2,3-diaminopropyl)-3-(2H-tetrazol-5-yl)benzene-1,2-disulfonamide The title compound was prepared as described for EXAMPLE 244, step C, using (S)-di-tert-butyl(3-(4-(2-aminoquinolin-8-yl)-2-(N,N-bis(4-methoxybenzyl)sulfamoyl)-3-(2-(4-methoxybenzyl)-2H-tetrazol-5-yl)phenylsulfonamido)propane-1,2-diyl) dicarbamate (0.17 g, 0.16 mmol) in DCM (6.0 mL). The crude product was purified by Prep-HPLC with the following conditions: Column: X Bridge Prep C18 OBD Column 19×250 mm 10 μm; Mobile Phase A: water with 10 mmol/L $NH_4HCO_3$, Mobile Phase B: ACN; Flow rate: 20 mL/min; Gradient: 5% B to 30% B in 8 min; 254/220 nm. The fractions containing desired product were combined and concentrated under vacuum to afford the title compound: LCMS [M+1]$^+$: 519; $^1$H NMR (300 MHz, DMSO-$d_6$): δ 8.10 (d, J=8.3 Hz, 1H), 7.82 (d, J=8.8 Hz, 1H), 7.69 (d, J=8.4 Hz, 1H), 7.41 (dd, J=7.9 Hz, 1.5 Hz, 1H), 6.77 (t, J=7.6 Hz, 1H), 6.70 (d, J=8.8 Hz, 1H), 6.67-6.58 (m, 1H), 6.39-6.27 (m, 2H), 5.85 (brs, 3H), 3.12-2.64 (m, 3H), 2.66-2.51 (m, 2H).

EXAMPLES 372-374 in the Table below were prepared in an analogous fashion to that described for EXAMPLE 371, starting from (S)-di-tert-butyl (3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl) dicarbamate or (S)-benzyl tert-butyl(3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl) dicarbamate and the corresponding boronic acids or boronic esters, which were prepared as described herein, or which were available from commercial sources.

| EX. No. | Structure | Chemical Name | LC/MS [M + H]+ |
|---|---|---|---|
| 372 | 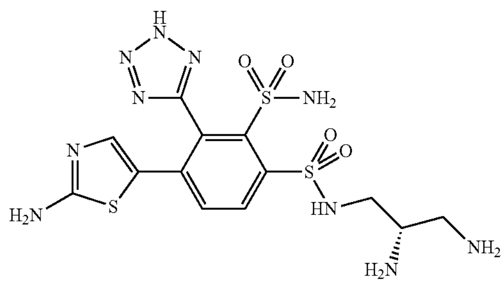 [SMILES: NC[C@H](N)CNS(=O)(=O)c1ccc(-c2cnc(N)s2)c(-c2nn[nH]n2)c1S(N)(=O)=O] | (S)-4-(2-aminothiazol-5-yl)-N1-(2,3-diaminopropyl)-3-(2H-tetrazol-5-yl)benzene-1,2-disulfonamide | 475 |
| 373 | 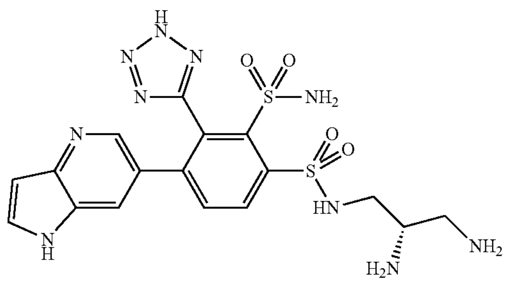 [SMILES: NC[C@H](N)CNS(=O)(=O)c1ccc(-c2cnc3cc[nH]c3c2)c(-c2nn[nH]n2)c1S(N)(=O)=O] | (S)-N1-(2,3-diaminopropyl)-4-(1H-pyrrolo[3,2-b]pyridin-6-yl)-3-(2H-tetrazol-5-yl)benzene-1,2-disulfonamide | 493 |
| 374 | 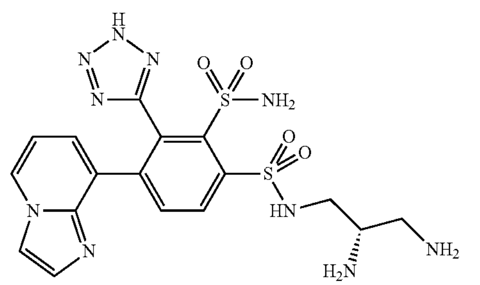 [SMILES: NC[C@H](N)CNS(=O)(=O)c1ccc(-c2cccn3ccnc23)c(-c2nn[nH]n2)c1S(N)(=O)=O] | (S)-N1-(2,3-diaminopropyl)-4-(imidazo[1,2-a]pyridin-8-yl)-3-(2H-tetrazol-5-yl)benzene-1,2-disulfonamide | 493 |

Example 375

(R)-4-(2-amino-1H-benzo[d]imidazol-4-yl)-N1-(2,3-diaminopropyl)-3-(2H-tetrazol-5-yl)benzene-1,2-disulfonamide

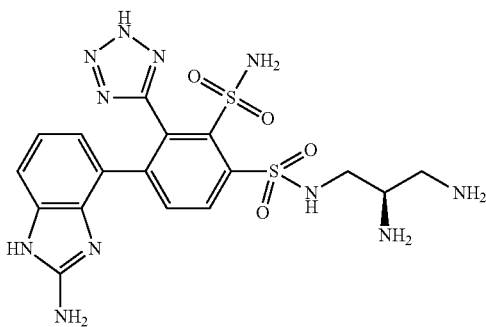 [SMILES: NC[C@@H](N)CNS(=O)(=O)c1ccc(-c2cccc3[nH]c(N)nc23)c(-c2nn[nH]n2)c1S(N)(=O)=O]

Step A: (R)-di-tert-butyl(3-(4-(2-amino-1H-benzo[d]imidazol-4-yl)-2-(N,N-bis(4-methoxy benzyl)sulfamoyl)-3-(2-(4-methoxybenzyl)-2H-tetrazol-5-yl)phenylsulfonamido) propane-1,2-diyl)dicarbamate To a solution of (R)-di-tert-butyl(3-(2-(N,N-bis(4-methoxybenzyl)sulfamoyl)-4-iodo-3-(2-(4-methoxybenzyl)-2H-tetrazol-5-yl)phenylsulfonamido)propane-1,2-diyl) dicarbamate (1.0 g, 0.94 mmol) in 1,4-dioxane (10 mL) and water (2.5 mL), was added (2-amino-1H-benzo[d]imidazol-4-yl)boronic acid (0.5 g, 2.82 mmol), Na$_2$CO$_3$ (0.29 g, 2.81 mmol) and Pd(PPh$_3$)$_4$ (0.22 g, 0.20 mmol) at room temperature. The mixture was degassed with nitrogen three times. The resulting mixture was stirred at 80° C. for 16 hours under nitrogen. The resulting mixture was diluted with water (100 mL) and extracted with EA (3×100 mL). The combined organic layers were washed with brine (1×100 mL), dried over anhydrous Na$_2$SO$_4$ and filtered. The filtrate was concentrated under vacuum. The residue was purified by silica gel column chromatography, eluted with 10% MeOH in EA. The fractions containing desired product were combined and concentrated under vacuum to afford the title compound: LCMS [M+1]+: 1068.

Step B: (R)-4-(2-amino-1H-benzo[d]imidazol-4-yl)-N1-(2,3-diaminopropyl)-3-(2H-tetrazol-5-yl)benzene-1,2-disulfonamide The title compound was prepared as described for EXAMPLE 244, step C, using (R)-di-tert-butyl (3-(4-(2-amino-1H-benzo[d]imidazol-4-yl)-2-(N,N-bis(4-methoxy benzyl)sulfamoyl)-3-(2-(4-methoxybenzyl)-2H-tetrazol-5-yl)phenylsulfonamido) propane-1,2-diyl)dicarbamate (0.80 g, 0.75 mmol) to afford the crude product. The crude product was added to TFA (4 mL). The mixture was stirred at 80°

Cfor 1 hour. The resulting mixture was concentrated under vacuum. The crude product was purified by Prep-HPLC with the following conditions: Column: Atlantis Prep T3 OBD Column, 19×250 mm, 10 μm; Mobile Phase A: waters with 50 mmol/L $NH_4HCO_3$, Mobile Phase B: ACN; Flow rate: 20 mL/min; Gradient: 0% B to 5% B in 5 min; 254 nm. The fractions containing desired product were combined and concentrated under vacuum to afford the title compound: LCMS ([M+1]$^+$: 508; $^1$H NMR (300 MHz, DMSO-$d_6$): δ 8.17 (d, J=8.1 Hz, 1H), 7.97 (d, J=8.7 Hz, 1H), 6.90 (d, J=7.8 Hz, 1H), 6.44 (t, J=7.5 Hz, 1H), 6.20 (brs, 3H), 6.02 (d, J=7.8 Hz, 1H), 3.09-2.83 (m, 4H), 2.65-2.61 (m, 1H).

EXAMPLES 376-378 in the Table below were prepared in an analogous fashion to that described for EXAMPLE 375, starting from (R)-di-tert-butyl (3-(2-(N,N-bis(4-methoxybenzyl)sulfamoyl)-4-iodo-3-(2-(4-methoxybenzyl)-2H-tetrazol-5-yl)phenylsulfonamido) propane-1,2-diyl) dicarbamate and the corresponding boronic acids or boronic esters, which were prepared as described herein, or which were available from commercial sources.

| EX. No. | Structure | Chemical Name | LC/MS [M + H]$^+$ |
|---|---|---|---|
| 376 | 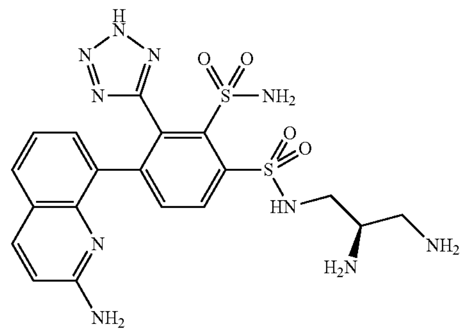 [SMILES: NC[C@@H](N)CNS(=O)(=O)c1ccc(-c2cccc3ccc(N)nc23)c(-c2nn[nH]n2)c1S(N)(=O)=O] | (R)-4-(2-aminoquinolin-8-yl)-N1-(2,3-diaminopropyl)-3-(2H-tetrazol-5-yl)benzene-1,2-disulfonamide | 519 |
| 377 | 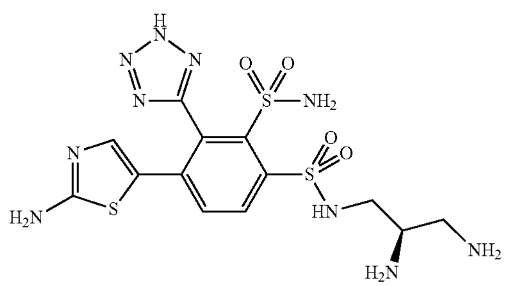 [SMILES: NC[C@@H](N)CNS(=O)(=O)c1ccc(-c2cnc(N)s2)c(-c2nn[nH]n2)c1S(N)(=O)=O] | (R)-4-(2-aminothiazol-5-yl)-N1-(2,3-diaminopropyl)-3-(2H-tetrazol-5-yl)benzene-1,2-disulfonamide | 475 |
| 378 | 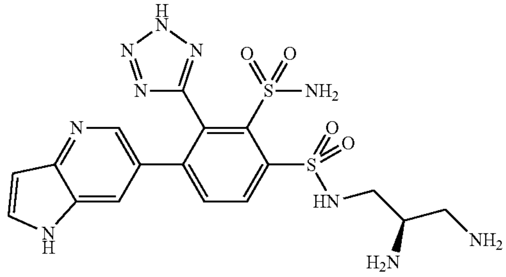 [SMILES: NC[C@@H](N)CNS(=O)(=O)c1ccc(-c2cnc3cc[nH]c3c2)c(-c2nn[nH]n2)c1S(N)(=O)=O] | (R)-N1-(2,3-diaminopropyl)-4-(1H-pyrrolo[3,2-b]pyridin-6-yl)-3-(2H-tetrazol-5-yl)benzene-1,2-disulfonamide | 493 |

Example 379

(S)—N1-(1-amino-3-hydroxypropan-2-yl)-4-(2-(aminomethyl)-1H-benzo[d]imidazol-4-yl)-3-(2H-tetrazol-5-yl)benzene-1,2-disulfonamide

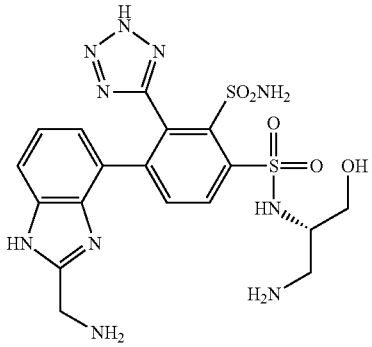 [SMILES: NCc1nc2c(-c3ccc(S(=O)(=O)N[C@@H](CN)CO)c(S(N)(=O)=O)c3-c3nn[nH]n3)cccc2[nH]1]

Step A: tert-butyl (S)-((4-(4-(N-(1-(((benzyloxy)carbonyl)amino)-3-hydroxypropan-2-yl)sulfamoyl)-3-(N,N-bis(4-methoxybenzyl)sulfamoyl)-2-(2-(4-methoxybenzyl)-2H-tetrazol-5-yl)phenyl)-1H-benzo[d]imidazol-2-yl)methyl)carbamate To a stirred solution of 2-(N,N-bis(4-methoxybenzyl)sulfamoyl)-4-(2-(((tert-butoxycarbonyl)amino)methyl)-1H-benzo[d]imidazol-4-yl)-3-(2-(4-methoxybenzyl)-2H-tetrazol-5-yl)benzenesulfinic acid (0.60 g, 0.89 mmol) in THF (6 mL) was added (S)-benzyl (3-hydroxy-2-(2,2,2-trifluoroacetamido)propyl)carbamate (0.43 g, 1.33 mmol) and TEA (0.37 mL, 2.67 mmol) at 0° C. The mixture was degassed with nitrogen three times. The reaction mixture was stirred for 10 min 0° C. Then NCS (0.24 g, 1.78 mmol) was added and the mixture was stirred at 0° C. for 1.5 hours under nitrogen. The resulting mixture was concentrated under vacuum. The residue was dissolved with EA (100 mL), washed with brine (3×100 mL), dried over anhydrous $Na_2SO_4$ and filtered. The filtrate was concentrated under vacuum. The residue was purified by silica gel column chromatography, eluted with 40% EA in PE. The fractions containing desired product were combined and concentrated under vacuum to afford the title compound: LCMS [M+1]$^+$: 1117.

Step B: (S)—N1-(1-amino-3-hydroxypropan-2-yl)-4-(2-(aminomethyl)-1H-benzo[d]imidazol-4-yl)-3-(2H-tetrazol-5-yl)benzene-1,2-disulfonamide The title compound was prepared as described for EXAMPLE 244, step C, using tert-butyl (S)-((4-(4-(N-(1-(((benzyloxy)carbonyl)amino)-3-hydroxypropan-2-yl)sulfamoyl)-3-(N,N-bis(4-methoxybenzyl)sulfamoyl)-2-(2-(4-methoxybenzyl)-2H-tetrazol-5-yl)phenyl)-1H-benzo[d]imidazol-2-yl)methyl)carbamate (0.35 g, 0.31 mmol) to afford the crude product. The crude product was purified by Prep-HPLC with the following conditions: Column: X Bridge C18 OBD Prep Column 100 Å, 10 μm, 19 mm×250 mm; Mobile Phase A: water with 10 mmol/L $NH_4HCO_3$, Mobile Phase B: ACN; Flow rate: 25 mL/min; Gradient: 3% B to 15% B in 8 min; Detector: 254 and 220 nm. The fractions containing desired product were combined and concentrated under vacuum to afford the title compound: LCMS [M+1 523; $^1$H NMR (400 MHz, $CD_3COCD_3$+DCl): δ 7.22 (d, J=8.0 Hz, 1H), 6.63 (d, J=8.0 Hz, 1H), 6.15-6.12 (d, J=8.0 Hz, 1H), 5.83-5.80 (d, J=8.0 Hz, 1H), 5.58-5.56 (d, J=8.0 Hz, 1H), 2.89 (s, 2H), 2.55-2.53 (m, 1H), 2.34-2.32 (m, 1H), 2.28-2.22 (m, 1H), 1.97-1.94 (m, 1H), 1.88-1.85 (m, 1H).

Example 380

(S)—N1-(1-amino-3-hydroxypropan-2-yl)-4-(2-aminopyridin-4-yl)-3-(2H-tetrazol-5-yl)benzene-1,2-disulfonamide

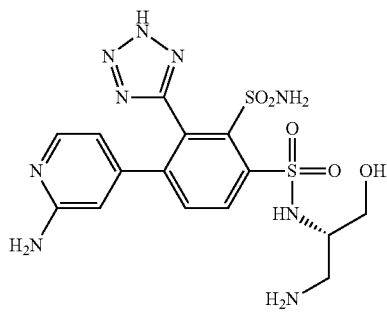 [SMILES: NC[C@@H](CO)NS(=O)(=O)c1ccc(-c2ccnc(N)c2)c(-c2nn[nH]n2)c1S(N)(=O)=O]

Step A: (S)-benzyl(2-(4-(2-aminopyridin-4-yl)-2-(N,N-bis(4-methoxybenzyl)sulfamoyl)-3-(2-(4-methoxybenzyl)-2H-tetrazol-5-yl)phenylsulfonamido)-3-hydroxypropyl)carbamate To a solution of (S)-benzyl (2-(2-(N,N-bis(4-methoxybenzyl)sulfamoyl)-4-iodo-3-(2-(4-methoxybenzyl)-2H-tetrazol-5-yl)phenylsulfonamido)-3-hydroxypropyl) carbamate (1.0 g, 1.00 mmol) in 1,4-dioxane (7 mL) and water (3 mL) was added 4-(4,4,5,5-tetramethyl-1,3,2-dioxaborolan-2-yl)pyridin-2-amine (0.41 g, 2.0 mmol), $Na_2CO_3$ (0.32 g, 3.01 mmol) and Pd(PPh$_3$)$_4$ (0.23 g, 0.20 mmol) at room temperature. The mixture was degassed with nitrogen three times. The reaction mixture was stirred at 80° C. for 16 hours under nitrogen. The resulting mixture was diluted with water (50 mL) and extracted with EA (3×50 mL). The combined organic layers were washed with water (3×50 mL) and brine (3×50 mL), dried over anhydrous $Na_2CO_3$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]$^+$: 964.

Step B: (S)—N1-(1-amino-3-hydroxypropan-2-yl)-4-(2-aminopyridin-4-yl)-3-(2H-tetrazol-5-yl)benzene-1,2-disulfonamide A solution of (S)-benzyl(2-(4-(2-aminopyridin-4-yl)-2-(N,N-bis (4-methoxybenzyl)sulfamoyl)-3-(2-(4-methoxybenzyl)-2H-tetrazol-5-yl)phenyl sulfonamido)-3-hydroxypropyl)carbamate (0.50 g, 0.52 mmol) in TFA (5 mL) was stirred at 80° C. for 2 hours. The resulting solution was concentrated under vacuum. The crude product was purified by Prep-HPLC with the following conditions: Column: X Select CSH Prep C18 OBD Column, 5 μm, 19×150 mm; Mobile Phase A: water with 10 mmol/L $NH_4HCO_3$, Mobile Phase B: ACN; Flow rate: 20 mL/min; Gradient: 5% B to 35% B in 8 min; Detector: 254 and 220 nm. The fractions containing desired product were combined and concentrated under vacuum to afford the title compound: LCMS [M+1]⁺: 470; ¹H NMR (400 MHz, CD₃OD+DCl): δ 8.47 (d, J=8.4 Hz, 1H), 7.78 (d, J=8.0 Hz, 1H), 7.65 (d, J=5.6 Hz, 1H), 6.23 (d, J=1.6 Hz, 1H), 6.15 (dd, J=5.6 Hz, 1.6 Hz, 1H), 3.74-3.71 (m, 1H), 3.55-3.52 (m, 1H), 3.45-3.42 (m, 1H), 3.18-3.14 (m, 1H), 3.08-3.03 (m, 1H).

Example 381

(S)—N1-(1-amino-3-hydroxypropan-2-yl)-4-(2-(aminomethyl)benzo[d]thiazol-4-yl)-3-(2H-tetrazol-5-yl)benzene-1,2-disulfonamide

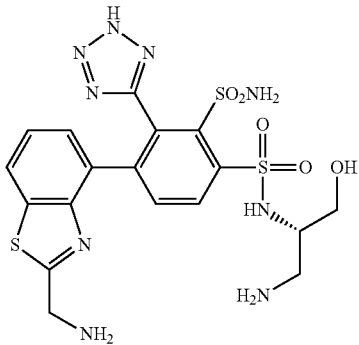 [SMILES: NCc1nc2c(-c3ccc(S(=O)(=O)N[C@@H](CN)CO)c(S(N)(=O)=O)c3-c3nn[nH]n3)cccc2s1]

Step A: (S)-benzyl(2-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)-3-hydroxy propyl)carbamate To solution of (S)-benzyl(2-(2-(N,N-bis(4-methoxybenzyl)sulfamoyl)-4-iodo-3-(2-(4-methoxybenzyl)-2H-tetrazol-5-yl)phenylsulfonamido)-3-hydroxy propyl)carbamate (1.7 g, 1.70 mmol) in 1,4-dioxane (10 mL) and water (2.5 mL) was added (2-aminobenzo[d]thiazol-4-yl)boronic acid (0.66 g, 3.41 mmol), PdCl₂ (dppf) adduct CH₂Cl₂ (0.28 g, 0.34 mmol) and Na₂CO₃ (0.54 g, 5.11 mmol). The mixture was degassed with nitrogen three times. The reaction mixture was stirred at 80° C. for 16 hours under nitrogen. The resulting mixture was diluted with water (50 mL) and extracted with EA (3×50 mL). The combined organic layers were washed with water (3×50 mL) and brine (3×50 mL), dried over anhydrous Na₂SO₄ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]⁺: 1020.

Step B: (S)-benzyl(2-(2-(N,N-bis(4-methoxybenzyl) sulfamoyl)-4-(2-bromobenzo[d]thiazol-4-yl)-3-(2-(4-methoxybenzyl)-2H-tetrazol-5-yl)phenylsulfonamido)-3-hydroxypropyl) carbamate The title compound was prepared as described for EXAMPLE 275, step B, using (S)-benzyl(2-(4-(2-aminobenzo[d]thiazol-4-yl)-2-(N,N-bis(4-methoxybenzyl) sulfamoyl)-3-(2-(4-methoxybenzyl)-2H-tetrazol-5-yl)phenylsulfonamido)-3-hydroxy propyl)carbamate (0.90 g, 0.88 mmol) LCMS [M+1]⁺: 1083, 1085 (1:1).

Step C: (S)-benzyl(2-(2-(N,N-bis(4-methoxybenzyl) sulfamoyl)-4-(2-cyanobenzo[d]thiazol-4-yl)-3-(2-(4-methoxybenzyl)-2H-tetrazol-5-yl)phenylsulfonamido)-3-hydroxypropyl) carbamate To a solution of (S)-benzyl(2-(2-(N,N-bis(4-methoxybenzyl)sulfamoyl)-4-(2-bromobenzo[d]thiazol-4-yl)-3-(2-(4-methoxybenzyl)-2H-tetrazol-5-yl)phenyl sulfonamido)-3-hydroxypropyl)carbamate (0.60 g, 0.55 mmol) and 3rd Generation t-BuXPhos precatalyst (0.09 g, 0.11 mmol) in DMF (5 mL) was added dicyanozinc (0.13 g, 1.11 mmol). The mixture was degassed with nitrogen three times. The reaction mixture was irradiated with microwave radiation at 55° C. for 6 hours under nitrogen. The resulting mixture was quenched with water (50 mL) and extracted with EA (3×50 mL). The combined organic layers were washed with water (3×50 mL) and brine (3×50 mL), dried over anhydrous Na₂SO₄ and filtered. The filtrate was concentrated under vacuum. The residue was purified by silica gel column chromatography, eluted with 50% EA in PE. The fractions containing desired product were combined and concentrated under vacuum to afford the title compound: LCMS [M+1]⁺: 1030.

Step D: (S)-benzyl(2-(4-(2-(aminomethyl)benzo[d] thiazol-4-yl)-2-(N,N-bis(4-methoxybenzyl)sulfamoyl)-3-(2-(4-methoxybenzyl)-2H-tetrazol-5-yl) phenylsulfonamido)-3-hydroxy propyl)carbamate To a solution of (S)-benzyl(2-(2-(N,N-bis(4-methoxybenzyl)sulfamoyl)-4-(2-cyanobenzo[d]thiazol-4-yl)-3-(2-(4-methoxybenzyl)-2H-tetrazol-5-yl)phenyl sulfonamido)-3-hydroxypropyl)carbamate (0.20 g, 0.19 mmol) in MeOH (10 mL) was added Pd(OH)₂/C (20% Pd, 1.48 mg, 9.71 μmol). The mixture was degassed with hydrogen three times and stirred at room temperature for 6 hours under hydrogen (30 atm). The resulting mixture was filtered and the filtrate was concentrated under vacuum to give title compound, which was directly used for next step without further purification: LCMS [M+1]⁺: 900.

Step E: (S)—N1-(1-amino-3-hydroxypropan-2-yl)-4-(2-(aminomethyl)benzo[d]thiazol-4-yl)-3-(2H-tetrazol-5-yl)benzene-1,2-disulfonamide A solution of (S)-benzyl(2-(4-(2-(aminomethyl)benzo[d]thiazol-4-yl)-2-(N,N-bis(4-methoxybenzyl)sulfamoyl)-3-(2-(4-methoxybenzyl)-2H-tetrazol-5-yl) phenylsulfonamido)-3-hydroxypropyl)carbamate (0.14 g, 0.13 mmol) in TFA (4 mL) was stirred at 60° C. for 1 hour. The resulting solution was concentrated under vacuum. The crude product was purified by Prep-HPLC with the following conditions: Column: X Bridge Prep C18 OBD Column 19×250 mm 10 μm; Mobile Phase A: water with 10 mmol/L NH₄HCO₃, Mobile Phase B: ACN; Flow rate: 20 mL/min; Gradient: 3% B to 21% B in 8 min; Detector: 254 and 220 nm. The fractions containing desired product were combined and concentrated under vacuum to afford the title compound: LCMS [M+1]⁺: 540; ¹H NMR (300 MHz, DMSO-d₆): δ 8.25 (d, J=8.1 Hz, 1H), 7.93-7.82 (m, 2H), 7.02 (t, J=7.7 Hz, 1H), 6.57 (d, J=7.6 Hz, 1H), 4.07 (s, 2H), 3.82-3.39 (m, 3H), 2.96-2.79 (m, 2H).

Example 382

(S)—N1-(1-amino-3-hydroxypropan-2-yl)-4-(6-aminopyridin-2-yl)-3-(2H-tetrazol-5-yl)benzene-1,2-disulfonamide

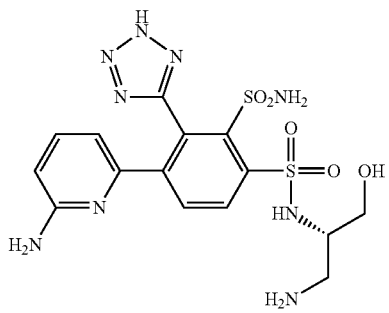 [SMILES: NC[C@@H](CO)NS(=O)(=O)c1ccc(-c2cccc(N)n2)c(-c2nn[nH]n2)c1S(N)(=O)=O]

Step A: (S)-benzyl(2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)-3-hydroxypropyl)carbamate The title compound was prepared as described for EXAMPLE 246, step C, using (S)-benzyl(2-(2-(N,N-bis(4-methoxybenzyl)sulfamoyl)-4-iodo-3-(2-(4-methoxybenzyl)-2H-tetrazol-5-yl)phenylsulfonamido)-3-hydroxypropyl)carbamate (1.50 g, 1.50 mmol) and (6-bromopyridin-2-yl)boronic acid (0.61 g, 3.01 mmol) to afford the title compound: LCMS [M+1]+: 1027, 1029.

Step B: benzyl((2S)-2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)-3-((tetrahydro-2H-pyran-2-yl)oxy)propyl)carbamate To a solution of (S)-benzyl(2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)-3-hydroxypropyl)carbamate (1.10 g, 1.07 mmol) in DCM (10 mL) were added 3,4-dihydro-2H-pyran (0.18 g, 2.14 mmol) and 4-methylbenzenesulfonic acid (37 mg, 0.214 mmol) at room temperature. The reaction mixture was degassed with nitrogen three times and stirred for 3 hours at room temperature. The resulting mixture was concentrated under vacuum and diluted with EA (200 mL). The organic layer was washed with water (3×150 mL) and brine (150 mL). The organic layer was dried over anhydrous Na$_2$SO$_4$ and filtered. The filtrate was concentrated under vacuum. The residue was purified by silica gel column chromatography, eluted with 60% EA in PE. The fractions containing desired product were combined and concentrated under vacuum to afford the title compound: LCMS [M+1]+: 1111,1113 (1:1).

Step C: Benzyl((2S)-2-(4-(6-aminopyridin-2-yl)-2-(N,N-bis(4-methoxybenzyl)sulfamoyl)-3-(2-(4-methoxybenzyl)-2H-tetrazol-5-yl)phenylsulfonamido)-3-((tetrahydro-2H-pyran-2-yl)oxy)propyl)carbamate To a solution of benzyl ((2S)-2-(2-(N,N-bis(4-methoxybenzyl) sulfamoyl)-4-(6-bromopyridin-2-yl)-3-(2-(4-meth-oxybenzyl)-2H-tetrazol-5-yl)phenylsulfonamido)-3-((tetrahydro-2H-pyran-2-yl)oxy)propyl)carbamate (0.60 g, 0.540 mmol) in 1,4-dioxane (10 mL) was added 2,2,2-trifluoroacetamide (0.61 g, 5.40 mmol), CuI (0.10 g, 0.54 mmol), Cs$_2$CO$_3$ (0.88 g, 2.70 mmol) and N1,N2-dimethylethane-1,2-diamine (95 mg, 1.08 mmol) at room temp. The mixture was degassed with nitrogen for three times and irradiated with microwave radiation for 3 hours at 100° C. The resulting reaction mixture was concentrated under vacuum, diluted with EA (150 mL). The organic layer was washed with water (3×100 mL) and brine (150 mL). The organic layer was dried over anhydrous Na$_2$SO$_4$ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]+: 1048.

Step D: (S)—N1-(1-amino-3-hydroxypropan-2-yl)-4-(6-aminopyridin-2-yl)-3-(2H-tetrazol-5-yl)benzene-1,2-disulfonamide The title compound was prepared as described for EXAMPLE 244, step C, using benzyl((2S)-2-(2-(N,N-bis(4-methoxybenzyl)sulfamoyl)-4-(6-bromopyridin-2-yl)-3-(2-(4-methoxybenzyl)-2H-tetrazol-5-yl)phenylsulfonamido)-3-((tetrahydro-2H-pyran-2-yl)oxy)propyl)carbamate (0.40 g, 0.360 mmol). The crude product was purified by Prep-HPLC with the following conditions: Column: X Bridge C18 OBD Prep Column 100 Å, 10 μm, 19 mm×250 mm; Mobile Phase A: water with 10 mmol/L NH$_4$HCO$_3$, Mobile Phase B: ACN; Flow rate: 20 mL/min; Gradient: 5% B to 25% B in 7 min; Detector: 254 and 220 nm; Retention time: 4.75 min. The fractions containing desired product were combined and concentrated under vacuum to afford the title compound: LCMS [M+1]+: 470; $^1$H NMR (400 MHz, CD$_3$OD+DCl) δ 8.46 (d, J=8.2 Hz, 1H), 7.93 (d, J=8.2 Hz, 1H), 7.15 (t, J=7.8 Hz, 1H), 6.38 (d, J=8.4 Hz, 1H), 6.02 (d, J=7.4 Hz, 1H), 3.70-3.69 (m, 1H), 3.56-3.40 (m, 2H), 3.14-2.97 (m, 2H).

Example 383

(R)-4-(2-(aminomethyl)-1H-benzo[d]imidazol-4-yl)-N1-(1-aminopropan-2-yl)-3-(2H-tetrazol-5-yl)benzene-1,2-disulfonamide

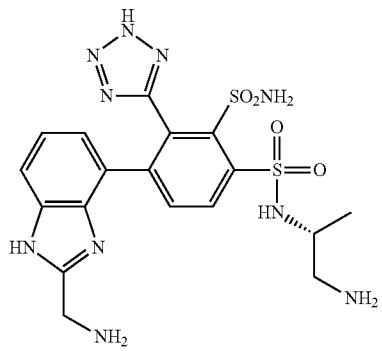 [SMILES: C[C@H](CN)NS(=O)(=O)c1ccc(-c2cccc3[nH]c(CN)nc23)c(-c2nn[nH]n2)c1S(N)(=O)=O]

Step A: Benzyl-N-[(2R)-2-[(2-{bis[(4-methoxyphenyl)methyl]sulfamoyl}-4-[2-({[(tert-butoxy)carbonyl]amino}methyl)-1H-1,3-benzodiazol-4-yl]-3-[(2E,4E)-11-methoxy-2,4,5,6-tetraazabicyclo[6.3.1]dodeca-1(11),2,4,8(12),9-pentaen-3-yl]benzene)sulfonamido]propyl]carbamate To a stirred solution of 4-(2-(aminomethyl)-1H-benzo[d]imidazol-4-yl)-3-(2-(4-methoxybenzyl)-2H-tetrazol-5-yl)-2-(N-(4-methoxybenzyl)sulfamoyl) benzenesulfinic acid (0.60 g, 0.89 mmol) in THF (6 mL) was added (R)-benzyl 2-aminopropylcarbamate (0.28 g, 1.34 mmol) and TEA (0.36 mL, 2.67 mmol) at 0° C. The mixture was degassed with nitrogen three times. The reaction mixture was stirred for 10 minutes at 0° C. Then NCS (0.24 g, 1.78 mmol) was added and the mixture was stirred at 0° C. for 1.5 hours under nitrogen. The resulting mixture was concentrated under vacuum. The residue was dissolved with EA (100 mL), and then washed with brine (3×100 mL). The combined organic layers was dried over anhydrous $Na_2SO_4$ and filtered. The filtrate was concentrated under vacuum. The residue was purified by silica gel column chromatography and eluted with 70% EA in PE. The fractions containing desired product were combined and concentrated under vacuum to afford the title compound: LCMS [M+1]$^+$: 1101.

Step B: (R)-4-(2-(aminomethyl)-1H-benzo[d]imidazol-4-yl)-N1-(1-aminopropan-2-yl)-3-(2H-tetrazol-5-yl)benzene-1,2-disulfonamide The title compound was prepared as described for EXAMPLE 244, step C, using benzyl-N-[(2R)-2-[(2-{bis[(4-methoxyphenyl)methyl]sulfamoyl}-4-[2-({[(tert-butoxy)carbonyl]amino}methyl)-1H-1,3-benzodiazol-4-yl]-3-[(2E,4E)-11-methoxy-2,4,5,6-tetraazabicyclo[6.3.1]dodeca-1(11),2,4,8(12),9-pentaen-3-yl]benzene)sulfonamido]propyl]carbamate (0.30 g, 0.27 mmol) to afford the crude product. The crude product was purified by Prep-HPLC with the following conditions: Column: X Bridge Shield RP18 OBD Column, 5 μm, 19×150 mm; Mobile Phase A: water with 10 mmol/L $NH_4HCO_3$, Mobile Phase B: ACN; Flow rate: 20 mL/min; Gradient: 5% B to 5% B in 8 min; Detector: 254 and 220 nm; Retention time: 5.4 min. The fractions containing desired product were combined and concentrated under vacuum to afford the title compound: LCMS [M+1]$^+$: 507. $^1$H NMR (400 MHz, $CD_3OD+DCl$): δ 8.48 (d, J=8.0 Hz, 1H), 7.92 (d, J=8.0 Hz, 1H), 7.39 (d, J=8.0 Hz, 1H), 7.03-7.01 (d, J=8.0 Hz, 1H), 6.75-6.72 (m, 1H), 3.97 (s, 2H), 3.95-3.92 (m, 1H), 2.99-2.98 (m, 1H), 2.92-2.86 (m, 1H), 1.18 (d, J=6.8 Hz, 3H).

Example 384

(R)—N1-(1-aminopropan-2-yl)-4-(imidazo[1,2-a]pyridin-8-yl)-3-(2H-tetrazol-5-yl) benzene-1,2-disulfonamide Step A: (R)-benzyl(2-(2-(N,N-bis(4-methoxybenzyl)sulfamoyl)-4-(imidazo[1,2-a]pyridin-8-yl)-3-(2-(4-methoxybenzyl)-2H-tetrazol-5-yl)phenylsulfonamido)propyl)carbamate To a solution of (R)-benzyl(2-(2-(N,N-bis(4-methoxybenzyl)sulfamoyl)-4-iodo-3-(2-(4-methoxybenzyl)-2H-tetrazol-5-yl)phenylsulfonamido)propyl)carbamate (0.75 g, 0.76 mmol) in 1,4-dioxane (10.0 mL) and water (2.5 mL) was added imidazo[1,2-a]pyridin-8-ylboronic acid (0.25 g, 1.53 mmol), $Na_2CO_3$ (0.24 g, 2.29 mmol) and $Pd(dppf)Cl_2$ adduct $CH_2Cl_2$ (0.13 g, 0.15 mmol) at room temp. The mixture was degassed with nitrogen three times. The reaction mixture was irradiated with microwave radiation at 130° C. for 1 hour under nitrogen. The resulting mixture was diluted with water (100 mL) and extracted with EA (3×100 mL). The combined organic layers were washed with water (3×200 mL) and brine (3×200 mL), dried over anhydrous $Na_2SO_4$ and filtered. The filtrate was concentrated under vacuum. The residue was purified by a silica gel column chromatography, eluted with EA. The fractions containing desired product were combined and concentrated under vacuum to afford the title compound: LCMS [M+1]$^+$: 972.

Step B: (R)—N1-(1-aminopropan-2-yl)-4-(imidazo[1,2-a]pyridin-8-yl)-3-(2H-tetrazol-5-yl)benzene-1,2-disulfonamide A stirred solution of (R)-benzyl(2-(2-(N,N-bis(4-methoxybenzyl)sulfamoyl)-4-(imidazo[1,2-c]pyridin-8-yl)-3-(2-(4-methoxybenzyl)-2H-tetrazol-5-yl)phenyl sulfonamido)propyl)carbamate (0.30 g, 0.31 mmol) in TFA (2 mL) was stirred for 1 hour under nitrogen. The resulting solution was concentrated under vacuum. The residue was co-evaporated with anisole (3×3 mL) under vacuum. The crude product was purified by Prep-HPLC with the following conditions: Column: X Bridge Prep Amide OBD Column 19×150 mm, 5 μm, 13 nm; Mobile Phase A: water with 10 mmol/L $NH_4HCO_3$, Mobile Phase B: ACN; Flow rate: 20 mL/min; Gradient: 90% B to 80% B in 8 min; Detector: 254 and 220 nm; Retention time: 6.15 min. The fractions containing desired product were combined and concentrated under vacuum to afford the title compound: LCMS [M+1]$^+$: 478; $^1$H NMR (300 MHz, $CD_3OD+DCl$) δ 8.40 (d, J=8.1 Hz, 1H), 8.39 (d, J=5.4 Hz, 1H), 8.05 (d, J=8.1 Hz, 1H), 7.93-7.91 (m, 1H), 7.61-7.58 (m, 1H), 6.95-6.79 (m, 2H), 3.98-3.69 (m, 1H), 3.10 (dd, J=13.2 Hz, 4.2 Hz, 1H), 3.06-2.91 (m, 1H), 1.18 (d, J=6.9 Hz, 3H).

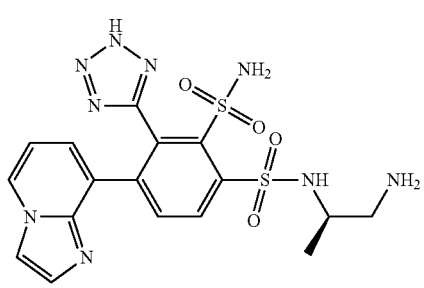 [SMILES: C[C@H](CN)NS(=O)(=O)c1ccc(-c2cccn3ccnc23)c(-c2nn[nH]n2)c1S(N)(=O)=O]

Example 385

4-(2-(Aminomethyl)-1H-benzo[d]imidazol-4-yl)-N1-(1,3-diaminopropan-2-yl)-3-(2H-tetrazol-5-yl)benzene-1,2-disulfonamide

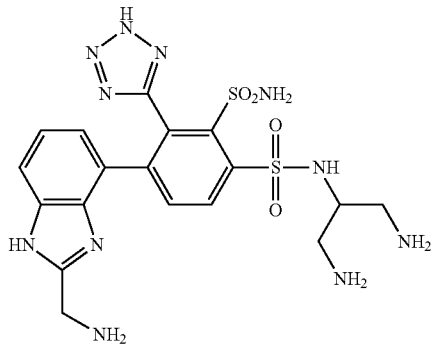 [SMILES: NCc1nc2c(-c3ccc(S(=O)(=O)NC(CN)CN)c(S(N)(=O)=O)c3-c3nn[nH]n3)cccc2[nH]1]

Step A: Di-tert-butyl(2-(2',3'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)propane-1,3-diyl)dicarbamate To a solution of di-tert-butyl(2-(2-(N,N-bis(4-methoxybenzyl)sulfamoyl)-4-iodo-3-(2-(4-methoxybenzyl)-2H-tetrazol-5-yl)phenylsulfonamido)propane-1,3-diyl)dicarbamate (4.00 g, 3.80 mmol) in 1,4-dioxane (40 mL) and water (10 mL) was added Pd(PPh$_3$)$_4$ (0.87 g, 0.75 mmol), 3-(4,4,5,5-tetramethyl-1,3,2-dioxaborolan-2-yl)benzene-1,2-diamine (2.20 g, 9.41 mmol) and Na$_2$CO$_3$ (1.20 g, 11.3 mmol) at room temp. The mixture was degassed with nitrogen for 3 times and stirred at 80° C. for 16 hours under nitrogen. The resulting mixture was quenched with water (100 mL) and extracted with EA (3×200 mL). The combined organic layers was washed with water (3×400 mL) and brine (3×400 mL), dried over anhydrous Na$_2$SO$_4$ and filtered. The filtrate was concentrated under vacuum. The residue was purified by silica gel column chromatography, eluted with 60% EA in PE. The fractions containing desired product were combined and concentrated under vacuum to afford the title compound: LCMS [M+1]$^+$: 1043.

Step B: Tert-butyl-N-[2-({4-[2-amino-3-(2-{[(tert-butoxy)carbonyl]amino}acetamido)phenyl]-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene}sulfonamido)-3-{[(tert-butoxy)carbonyl]amino}propyl]carbamate To a solution of di-tert-butyl(2-(2',3'-diamino-3-(N,N-bis(4-methoxybenzyl) sulfamoyl)-2-(2-(4-methoxybenzyl)-2H-tetrazol-5-yl)-[1,1'-biphenyl]-4-yl sulfonamido)propane-1,3-diyl)dicarbamate (1.0 g, 0.96 mmol) in THF (10 ml) was added 2-((tert-butoxycarbonyl)amino)acetic acid (0.17 g, 0.96 mmol), HATU (1.10 g, 2.9 mmol) and TEA (0.40 mL, 2.88 mmol) at room temp. The reaction mixture was degassed with nitrogen 3 times and stirred for overnight at room temp. The resulting mixture was quenched with water (100 mL), and then extracted with EA (3×100 mL). The combined organic layers was washed with water (3×200 mL) and brine (3×200 mL). The organic layer was dried over anhydrous Na$_2$SO$_4$ and filtered. The filtrate was concentrated under vacuum. The residue was purified by silica gel column chromatography, eluted with 60% EA in PE. The fractions containing desired product were combined and concentrated under vacuum to afford the title compound: LCMS [M+1]$^+$: 1200.

Step C: Tert-butyl N-{[4-(4-{[1,3-bis({[(tert-butoxy)carbonyl]amino})propan-2-yl]sulfamoyl}-2-[(2E,4E)-11-methoxy-2,4,5,6-tetraazabicyclo[6.3.1]dodeca-1(11),2,4,8(12),9-pentaen-3-yl]-3-{[(4-methoxyphenyl)methoxy]({[(4-methoxyphenyl)methyl]amino}) sulfinyl}phenyl)-1H-1,3-benzodiazol-2-yl]methyl}carbamate A solution of tert-butyl N-[2-({4-[2-amino-3-(2-{[(tert-butoxy)carbonyl]amino} acetamido)phenyl]-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene}sulfonamido)-3-{[(tert-butoxy)carbonyl]amino}propyl]carbamate (0.89 g, 0.74 mmol) in AcOH (8 mL) was stirred for 0.5 hour at 60° C. The solvent was removed under vacuum to afford crude product, which was used to next step without further purification: LCMS [M+1]$^+$: 1182.

Step D: 4-(2-(Aminomethyl)-1H-benzo[d]imidazol-4-yl)-N1-(1,3-diaminopropan-2-yl)-3-(2H-tetrazol-5-yl)benzene-1,2-disulfonamide The title compound was prepared as described for EXAMPLE 244, step C, using tert-butyl-N-{[4-(4-{[1,3-bis({[(tert-butoxy)carbonyl]amino})propan-2-yl]sulfamoyl}-3-{bis[(4-methoxyphenyl)methyl]sulfamoyl}-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl}carbamate (0.85 g, 0.72 mmol). The crude product was purified by Prep-HPLC with the following conditions: Column: X Bridge C$_{18}$ OBD Prep Column 100 Å, 10 µm, 19 mm×250 mm; Mobile Phase A: water with 10 mmol/L NH$_4$HCO$_3$, Mobile Phase B: ACN; Flow rate: 20 mL/min; Gradient: 5% B to 17.5% B in 6 min; Detector: 254 and 220 nm. The fractions containing desired product were combined and concentrated under vacuum to afford the title compound: LCMS [M+1]$^+$: 522; $^1$H NMR (400 MHz, CD$_3$OD+DCl): δ 8.49 (d, J=8.2 Hz, 1H), 7.91 (d, J=8.2 Hz, 1H), 7.39 (d, J=8.2 Hz, 1H), 7.02 (t, J=7.8 Hz, 1H), 6.75 (d, J=7.4 Hz, 1H), 4.02 (s, 2H), 3.68 (t, J=6.5 Hz, 1H), 2.93-2.75 (m, 4H).

Example 386

N1-(1,3-diaminopropan-2-yl)-4-(imidazo[1,2-c]pyridin-8-yl)-3-(2H-tetrazol-5-yl) benzene-1,2-disulfonamide

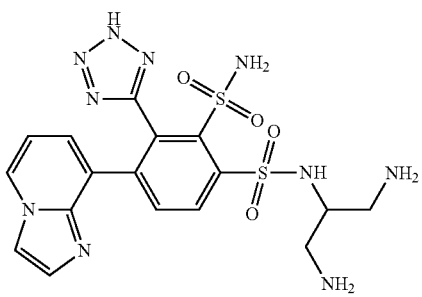 [SMILES: NCC(CN)NS(=O)(=O)c1ccc(-c2cccn3ccnc23)c(-c2nn[nH]n2)c1S(N)(=O)=O]

Step A: Di-tert-butyl(2-(2-(N,N-bis(4-methoxybenzyl)sulfamoyl)-4-(imidazo[1,2-c]pyridin-8-yl)-3-(2-(4-methoxybenzyl)-2H-tetrazol-5-yl)phenylsulfonamido)propane-1,3-diyl) dicarbamate To a solution of di-tert-butyl(2-(2-(N,N-bis(4-methoxybenzyl)sulfamoyl)-4-iodo-3-(1-(4-methoxybenzyl)-1H-tetrazol-5-yl)phenylsulfonamido)propane-1,3-diyl) dicarbamate (0.70 g, 0.66 mmol) in 1,4-dioxane (8 mL) and water (2 mL) was added imidazo[1,2-a]pyridin-8-ylboronic acid (0.11 g, 0.66 mmol), Na$_2$CO$_3$ (0.21 g, 1.98 mmol) and Pd(dppf)Cl$_2$ (0.11 g, 0.13 mmol) at room temperature. The mixture was degassed with nitrogen three times. The reaction mixture was irradiated with microwave radiation at 130° C. for 1.5 hours under nitrogen. The resulting mixture was quenched with water (50 mL), and then extracted with EA (3×50 mL). The combined organic layers was washed with water (3×50 mL) and brine (3×50 mL). The organic layer was dried over anhydrous Na$_2$SO$_4$ and filtered. The filtrate was concentrated under vacuum. The residue was purified by silica gel column chromatography, eluted with 80% EA in PE. The fractions containing desired product were combined and concentrated under vacuum to afford the title compound: LCMS [M+1]$^+$: 1054.

Step B: N1-(1,3-diaminopropan-2-yl)-4-(imidazo[1,2-c]pyridin-8-yl)-3-(2H-tetrazol-5-yl) benzene-1,2-disulfonamide The title compound was prepared as described for EXAMPLE 244, step C, using di-tert-butyl(2-(2-(N,N-bis(4-methoxybenzyl)sulfamoyl)-4-(imidazo[1,2-c]pyridin-8-yl)-3-(2-(4-methoxybenzyl)-2H-tetrazol-5-yl)phenylsulfonamido)propane-1,3-diyl) dicarbamate (0.24 g, 0.23 mmol). The crude product was purified by Prep-HPLC with the following conditions: Column: X Bridge Prep C18 OBD Column 19×250 mm, 10 μm; Mobile Phase A: water with 10 mmol/L NH$_4$HCO$_3$, Mobile Phase B: ACN; Flow rate: 20 mL/min; Gradient: 3% B to 33% B in 10 min; Detector: 254 and 220 nm. The fractions containing desired product were combined and concentrated under vacuum to afford the title compound: LCMS [M+1]$^+$: 493; $^1$H NMR (300 MHz, DMSO-d$_6$+DCl): δ 8.88-8.84 (m, 1H), 8.69 (d, J=8.1 Hz, 1H), 8.43 (d, J=2.1 Hz, 1H), 8.29-8.12 (m, 2H), 7.41-7.27 (m, 2H), 4.09-4.18 (m, 1H), 3.14-3.09 (m, 2H), 2.98-2.90 (m, 2H).

Example S 387-392

General procedure for parallel preparation of sulfonamide Examples 387-392:

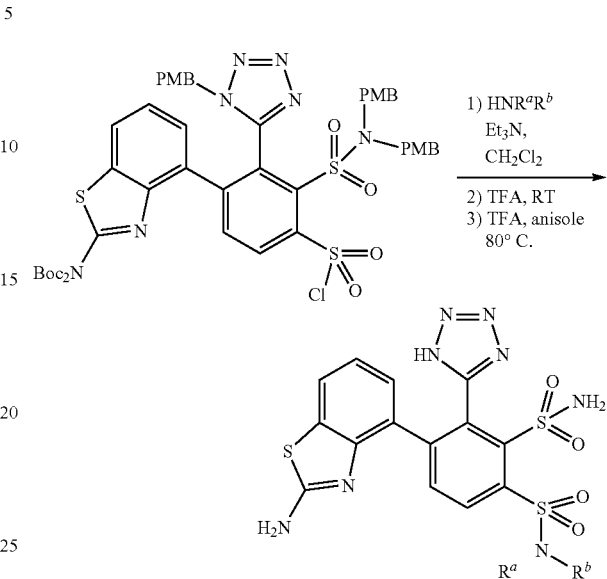

To a set of vials each containing the requisite commercially available or known amine (0.13 mmol) was added a solution of the sulfonyl chloride (45 mg, 0.044 mmol) followed by Et$_3$N (0.018 mL, 0.13 mmol). The vials were capped and the mixtures were stirred at RT for 5 hours. To the reaction mixture was then added TFA (0.5 mL) and the mixtures were stirred at RT for 1.5 hours. After that time, toluene (1 mL) was added to each vial and the mixtures were concentrated in vacuo. To each vial was then added TFA (1.0 mL) and anisole (0.019 mL, 0.17 mmol). The vials were capped and the reaction mixtures were heated to 80° C. with stirring for 45 min. After that time, the reaction mixtures were concentrated in vacuo. The crude residues were then dissolved in DMSO (1.0 mL) and filtered. The crude products were purified by mass triggered preparative HPLC [Waters Sunfire C18 column, 5 μm, 19×100 mm, using a gradient range from 8-10% initial to 21-36% final MeCN (0.1% TFA) in water (0.1% TFA), 25 mL/min, 8-12 min run time] to afford EXAMPLES 387-392.

| Ex. No. | HNR$^a$R$^b$ | Structure | Name | Calc'd Mass [M + H]$^+$ | LC/MS m/e [M + H]$^+$ |
|---|---|---|---|---|---|
| 387 | ![HO, H2N, NBoc azetidine] | ![structure] | 4-(2-amino-1,3-benzothiazol-4-yl)-N$^1$-[(3-hydroxyazetidin-3-yl)methyl]-3-(2H-tetrazol-5-yl)benzene-1,2-disulfonamide | 538.1 | 538.1 |

-continued

| Ex. No. | HNR$^a$R$^b$ | Structure | Name | Calc'd Mass [M + H]$^+$ | LC/MS m/e [M + H]$^+$ |
|---|---|---|---|---|---|
| 388 | H$_2$N,,,,△,,,,NHBoc | 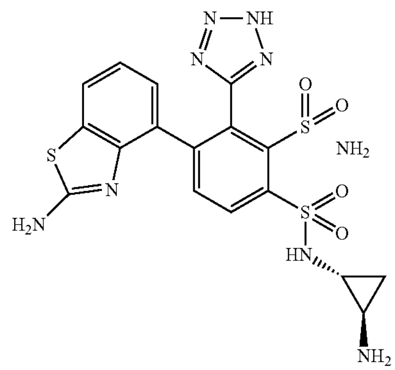 | 4-(2-amino-1,3-benzothiazol-4-yl)-N$^1$-[(1R,2R)-2-aminocyclopropyl]-3-(2H-tetrazol-5-yl)benzene-1,2-disulfonamide | 508.1.1 | 508.1 |
| 389 | H$_2$N,,,,NHBoc | 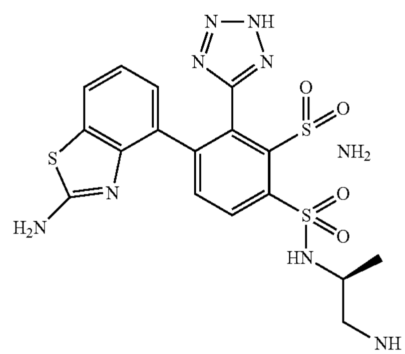 | 4-(2-amino-1,3-benzothiazol-4-yl)-N$^1$-[(1S)-2-amino-1-methylethyl]-3-(2H-tetrazol-5-yl)benzene-1,2-disulfonamide | 510.1 | 510.1 |
| 390 | H$_2$N,,,,NHBoc | 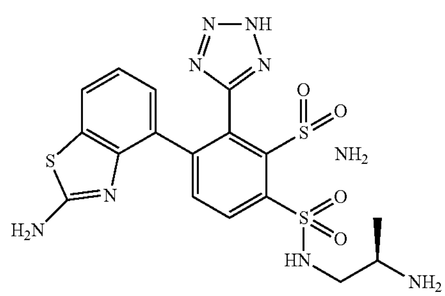 | 4-(2-amino-1,3-benzothiazol-4-yl)-N$^1$-[(2R)-2-aminopropyl]-3-(2H-tetrazol-5-yl)benzene-1,2-disulfonamide | 510.1 | 510.1 |
| 391 | H$_2$N~~N$^+$(CH$_3$)$_3$ | 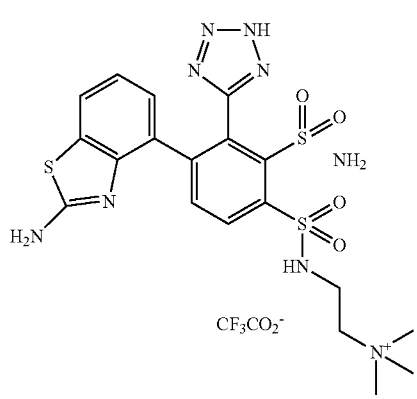 | 2-({[4-(2-amino-1,3-benzothiazol-4-yl)-2-sulfamoyl-3-(1H-tetrazol-5-yl)phenyl]sulfonyl}amino)-N,N,N-trimethylethanaminium trifluoroacetate | 539.0 | 539.0 |

| Ex. No. | HNR$^a$R$^b$ | Structure | Name | Calc'd Mass [M + H]$^+$ | LC/MS m/e [M + H]$^+$ |
|---|---|---|---|---|---|
| 392 | 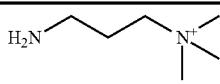 | 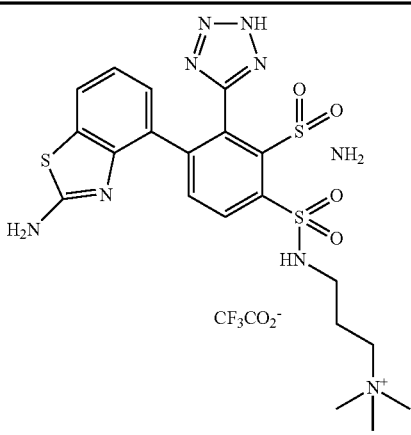 | 3-({[4-(2-amino-1,3-benzothiazol-4-yl)-2-sulfamoyl-3-(1H-tetrazol-5-yl)phenyl]sulfonyl}amino)-N,N,N-trimethylpropan-1-aminium trifluoroacetate | 553.0 | 553.0 |

Example 393

(R)—N$^1$-(1-aminopropan-2-yl)-4-(6-aminopyridin-3-yl)-3-(2H-tetrazol-5-yl)benzene-1,2-disulfonamide

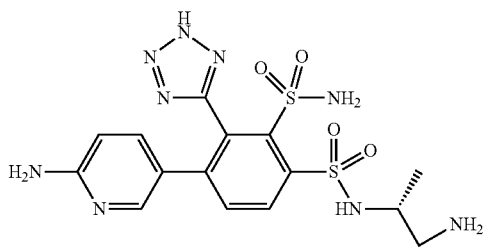 [SMILES: C[C@H](CN)NS(=O)(=O)c1ccc(-c2ccc(N)nc2)c(-c2nn[nH]n2)c1S(N)(=O)=O]

Step A: tert-butyl (R)-(2-((4-(6-aminopyridin-3-yl)-2-(N,N-bis(4-methoxybenzyl)sulfamoyl)-3-(1-(4-methoxybenzyl)-1H-tetrazol-5-yl)phenyl)sulfonamido)propyl)carbamate and tert-butyl (R)-(2-((4-(6-aminopyridin-3-yl)-2-(N,N-bis(4-methoxybenzyl)sulfamoyl)-3-(2-(4-methoxybenzyl)-2H-tetrazol-5-yl)phenyl)sulfonamido)propyl)carbamate A flask charged with tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate (4 g, 4.22 mmol), 5-(4,4,5,5-tetramethyl-1,3,2-dioxaborolan-2-yl)pyridin-2-amine (1.857 g, 8.44 mmol), sodium carbonate (1.342 g, 12.66 mmol) and PdCl$_2$ (dppf) (0.689 g, 0.844 mmol), dioxane (20 mL) and water (5 mL) was sealed and degassed. The resulting mixture was heated overnight at 80° C. The reaction mixture was filtered over CELITE to remove palladium. The filtrate was concentrated and purified by silica gel column chromatography using (0-10)% MeOH/DCM as mobile phase to afford the title compound. LC/MS [M+H]$^+$: 914.80.

Step B: (R)—N$^1$-(1-aminopropan-2-yl)-4-(6-aminopyridin-3-yl)-3-(2H-tetrazol-5-yl)benzene-1,2-disulfonamide To the solution of tert-butyl (R)-(2-((4-(6-aminopyridin-3-yl)-2-(N,N-bis(4-methoxybenzyl)sulfamoyl)-3-(1-(4-methoxybenzyl)-1H-tetrazol-5-yl)phenyl)sulfonamido)propyl)carbamate and tert-butyl (R)-(2-((4-(6-aminopyridin-3-yl)-2-(N,N-bis(4-methoxybenzyl)sulfamoyl)-3-(2-(4-methoxybenzyl)-2H-tetrazol-5-yl)phenyl)sulfonamido)propyl)carbamate (3.5 g, 3.83 mmol) in DCM (2 mL) was added anisole (2 g, 18.5 mmol) and TFA (10 g, 87.7 mmol) at 0° C. The reaction was stirred at 0° C. for 30 minutes. After removing the volatile the residue was treated with SCX ion exchange column (load sample and rinse with MeOH, rinse out product with 7 N amonia in MeOH) to give a free amine. The residue was dissolved in TFA (10 g, 87.7 mmol). The resulting mixture was stirred at 80° C. for 1.0 hour. After removing the volatile, the residue was purified by reverse phase HPLC (0-30% ACN/water as eluent, 0.05% ammonium hydroxide as additive) to give the desired product. LC/MS [M+H]$^+$: 454.30.

The following EXAMPLES in the Table below were prepared in an analogous fashion to that described for EXAMPLE 393, starting from the corresponding boronic acid or boronic ester and aryl iodide which were prepared as described herein, or which were available from commercial sources.

| EX. No. | Intermediates | Structure/Name | LC/MS |
|---|---|---|---|
| 394 | 5-(4,4,5,5-tetramethyl-1,3,2-dioxaborolan-2-yl)pyridin-2-amine and tert-butyl (S)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate | 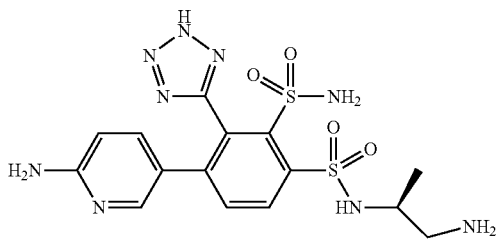<br>(S)-N¹-(1-aminopropan-2-yl)-4-(6-aminopyridin-3-yl)-3-(2H-tetrazol-5-yl)benzene-1,2-disulfonamide | [M + H]+: 454.26 |
| 395 | (2-amino-1-methyl-1H-benzo[d]imidazol-4-yl)boronic acid and tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate | 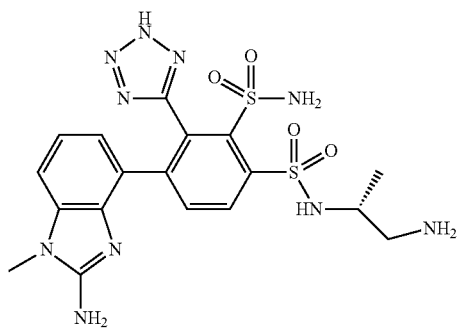<br>(R)-4-(2-amino-1-methyl-1H-benzo[d]imidazol-4-yl)-N¹-(1-aminopropan-2-yl)-3-(2H-tetrazol-5-yl)benzene-1,2-disulfonamide | [M + H]+: 507.34 |
| 396 | (2-amino-6-fluoro-1H-benzo[d]imidazol-4-yl)boronic acid and tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate | 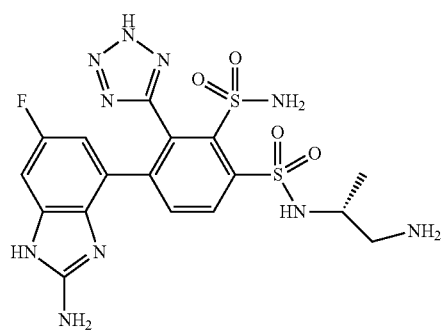<br>(R)-4-(2-amino-6-fluoro-1H-benzo[d]imidazol-4-yl)-N¹-(1-aminopropan-2-yl)-3-(2H-tetrazol-5-yl)benzene-1,2-disulfonamide | [M + H]+: 511.37 |

| EX. No. | Intermediates | Structure/Name | LC/MS |
|---|---|---|---|
| 397 | (2-amino-6-fluoro-1H-benzo[d]imidazol-4-yl)boronic acid and tert-butyl (S)-(2-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate | 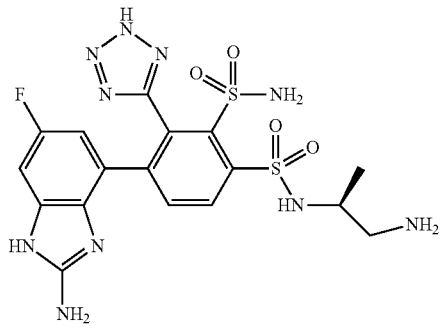<br>(S)-4-(2-amino-6-fluoro-1H-benzo[d]imidazol-4-yl)-$N^1$-(1-aminopropan-2-yl)-3-(2H-tetrazol-5-yl)benzene-1,2-disulfonamide | [M + H]+: 511.59 |
| 398 | 4-(4,4,5,5-tetramethyl-1,3,2-dioxaborolan-2-yl)pyridin-2-amine and tert-butyl (3S,4R)-3-(((benzyloxy)carbonyl)amino)-4-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (3S,4R)-3-(((benzyloxy)carbonyl)amino)-4-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate | 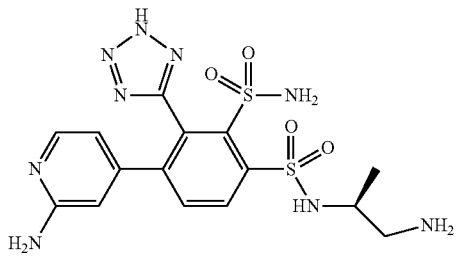<br>(S)-$N^1$-(1-aminopropan-2-yl)-4-(2-aminopyridin-4-yl)-3-(2H-tetrazol-5-yl)benzene-1,2-disulfonamide | [M + H]+: 454.27 |
| 399 | (2-amino-6-fluoro-1H-benzo[d]imidazol-4-yl)boronic acid and tert-butyl (S)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (S)-3-((2-(N,N-bis(4-methoxybenzyl)sulfamoyl)-4-iodo-3-(2-(4-methoxvbenzyl)-2H-tetrazol-5-yl)phenyl)sulfonamido)pyrrolidine-1-carboxylate | 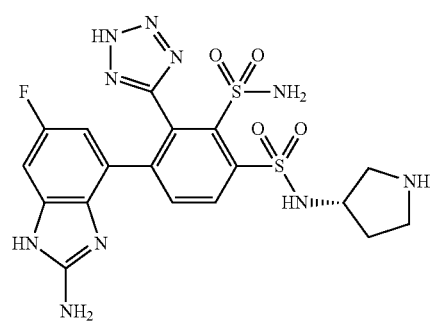<br>(S)-4-(2-amino-6-fluoro-1H-benzo[d]imidazol-4-yl)-$N^1$-(pyrrolidin-3-yl)-3-(2H-tetrazol-5-yl)benzene-1,2-disulfonamide | [M + H]+: 523.38 |

| EX. No. | Intermediates | Structure/Name | LC/MS |
|---|---|---|---|
| 400 | 4-(4,4,5,5-tetramethyl-1,3,2-dioxaborolan-2-yl)pyridin-2-amine and tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate | 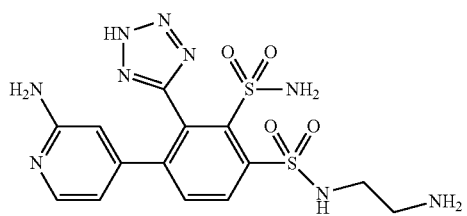<br>$N^1$-(2-aminoethyl)-4-(2-aminopyridin-4-yl)-3-(2H-tetrazol-5-yl)benzene-1,2-disulfonamide | [M + H]+: 440.18 |
| 401 | 6-(4,4,5,5-tetramethyl-1,3,2-dioxaborolan-2-yl)imidazo[1,2-a]pyridineamine and tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)ethyl)carbamate and tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)ethyl)carbamate | 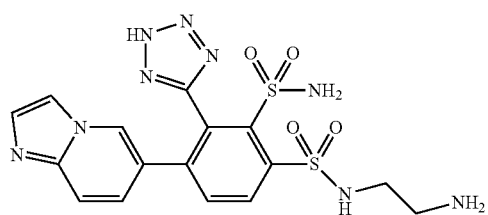<br>$N^1$-(2-aminoethyl)-4-(imidazo[1,2-a]pyridin-6-yl)-3-(2H-tetrazol-5-yl)benzene-1,2-disulfonamide | [M + H]+: 464.18 |
| 402 | (2-amino-6-fluoro-1H-benzo[d]imidazol-4-yl)boronic acid and tert-butyl (3-((2-(N,N-bis(4-methoxybenzyl)sulfamoyl)-4-iodo-3-(1-(4-methoxybenzyl)-1H-tetrazol-5-yl)phenyl)sulfonamido)propyl)carbamate and tert-butyl (3-((2-(N,N-bis(4-methoxybenzyl)sulfamoyl)-4-iodo-3-(2-(4-methoxybenzyl)-2H-tetrazol-5-yl)phenyl)sulfonamido)propyl)carbamate | 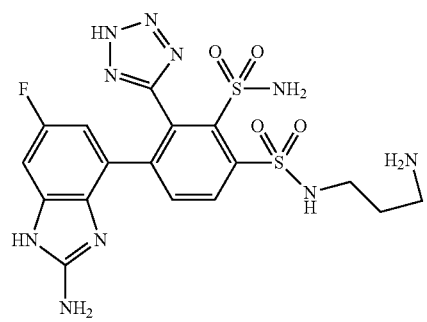<br>4-(2-amino-6-fluoro-1H-benzo[d]imidazol-4-yl)-N1-(3-aminopropyl)-3-(2H-tetrazol-5-yl)benzene-1,2-disulfonamide | [M + H]+: 511.00 |
| 403 | (1H-benzo[d][1,2,3]triazol-4-yl)boronic acid and di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 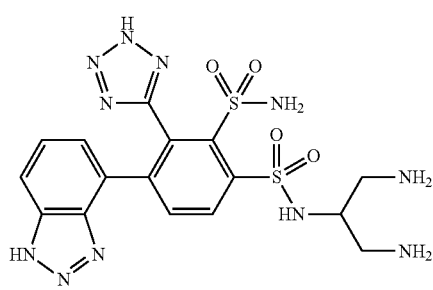<br>4-(1H-benzo[d][1,2,3]triazol-4-yl)-N1-(1,3-diaminopropan-2-yl)-3-(2H-tetrazol-5-yl)benzene-1,2-disulfonamide | [M + H]+: 494.55 |

-continued

| EX. No. | Intermediates | Structure/Name | LC/MS |
|---|---|---|---|
| 404 | 5-(4,4,5,5-tetramethyl-1,3,2-dioxaborolan-2-yl)pyridin-2-amine and di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 4-(6-aminopyridin-3-yl)-$N^1$-(1,3-diaminopropan-2-yl)-3-(2H-tetrazol-5-yl)benzene-1,2-disulfonamide | [M + H]+: 469.24 |
| 405 | 4-(4,4,5,5-tetramethyl-1,3,2-dioxaborolan-2-yl)pyridin-2-amine and di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 4-(2-aminopyridin-4-yl)-$N^1$-(1,3-diaminopropan-2-yl)-3-(2H-tetrazol-5-yl)benzene-1,2-disulfonamide | [M + H]+: 469.25 |
| 406 | 6-(4,4,5,5-tetramethyl-1,3,2-dioxaborolan-2-yl)imidazo[1,2-a]pyridineamine and di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | $N^1$-(1,3-diaminopropan-2-yl)-4-(imidazo[1,2-a]pyridin-6-yl)-3-(2H-tetrazol-5-yl)benzene-1,2-disulfonamide | [M + H]+: 493.10 |
| 407 | (1H-benzo[d][1,2,3]triazol-4-yl)boronic acid and tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)-3-hydroxypropyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)-3-hydroxypropyl)carbamate | (R)-$N^1$-(1-amino-3-hydroxypropan-2-yl)-4-(1H-benzo[d][1,2,3]triazol-4-yl)-3-(2H-tetrazol-5-yl)benzene-1,2-disulfonamide | [M + H]+: 495.43 |

| EX. No. | Intermediates | Structure/Name | LC/MS |
|---|---|---|---|
| 408 | 5-(4,4,5,5-tetramethyl-1,3,2-dioxaborolan-2-yl)pyridin-2-amine and tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)-3-hydroxypropyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)-3-hydroxypropyl)carbamate | 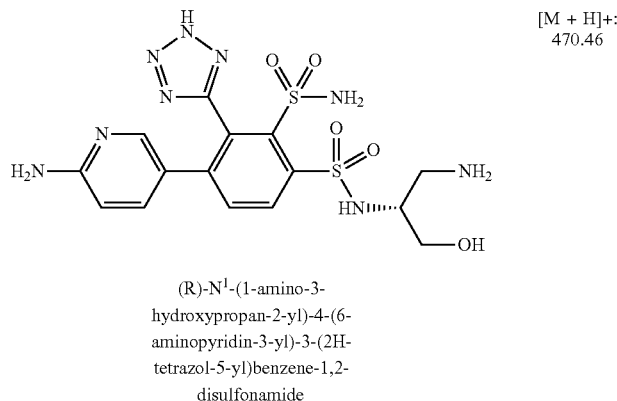 (R)-N$^1$-(1-amino-3-hydroxypropan-2-yl)-4-(6-aminopyridin-3-yl)-3-(2H-tetrazol-5-yl)benzene-1,2-disulfonamide | [M + H]+: 470.46 |
| 409 | 5-(4,4,5,5-tetramethyl-1,3,2-dioxaborolan-2-yl)pyridin-2-amine and tert-butyl (S)-(2-((2-(N,N-bis(4-methoxybenzyl)sulfamoyl)-4-iodo-3-(1-(4-methoxybenzyl)-1H-tetrazol-5-yl)phenyl)sulfonamido)-3-hydroxypropyl)carbamate and tert-butyl (S)-(2-((2-(N,N-bis(4-methoxybenzyl)sulfamoyl)-4-iodo-3-(2-(4-methoxybenzyl)-2H-tetrazol-5-yl)phenyl)sulfonamido)-3-hydroxypropyl)carbamate | 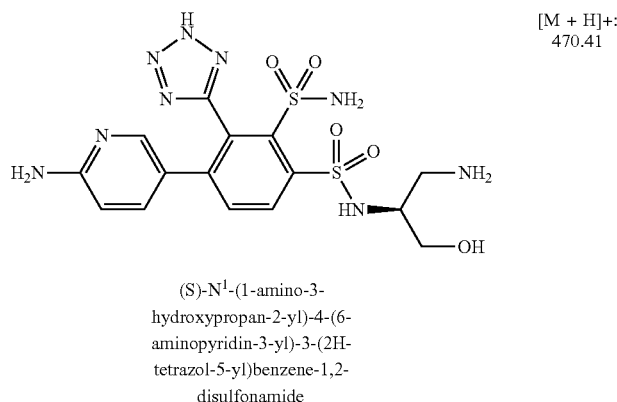 (S)-N$^1$-(1-amino-3-hydroxypropan-2-yl)-4-(6-aminopyridin-3-yl)-3-(2H-tetrazol-5-yl)benzene-1,2-disulfonamide | [M + H]+: 470.41 |
| 410 | 5-(4,4,5,5-tetramethyl-1,3,2-dioxaborolan-2-yl)pyridin-2-amine and tert-butyl (3S,4R)-3-((2-(N,N-bis(4-methoxybenzyl)sulfamoyl)-4-iodo-3-(1-(4-methoxybenzyl)-1H-1,2,3-triazol-5-yl)phenyl)sulfonamido)-4-hydroxypyrrolidine-1-carboxylate and tert-butyl (3S,4R)-3-((2-(N,N-bis(4-methoxybenzyl)sulfamoyl)-4-iodo-3-(2-(4-methoxybenzyl)-2H-1,2,3-triazol-5-yl)phenyl)sulfonamido)-4-hydroxypyrrolidine-1-carboxylate | 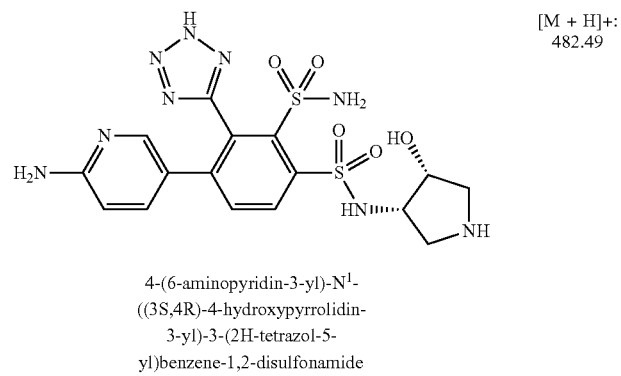 4-(6-aminopyridin-3-yl)-N$^1$-((3S,4R)-4-hydroxypyrrolidin-3-yl)-3-(2H-tetrazol-5-yl)benzene-1,2-disulfonamide | [M + H]+: 482.49 |

| EX. No. | Intermediates | Structure/Name | LC/MS |
|---|---|---|---|
| 411 | 5-(4,4,5,5-tetramethyl-1,3,2-dioxaborolan-2-yl)pyridin-2-amine and tert-butyl (2S,4R)-4-((2-(N,N-bis(4-methoxybenzyl)sulfamoyl)-4-iodo-3-(1-(4-methoxybenzyl)-1H-tetrazol-5-yl)phenyl)sulfonamido)-2-(hydroxymethyl)pyrrolidine-1-carboxylate and tert-butyl (2S,4R)-4-((2-(N,N-bis(4-methoxybenzyl)sulfamoyl)-4-iodo-3-(2-(4-methoxybenzyl)-2H-tetrazol-5-yl)phenyl)sulfonamido)-2-(hydroxymethyl)pyrrolidine-1-carboxylate | 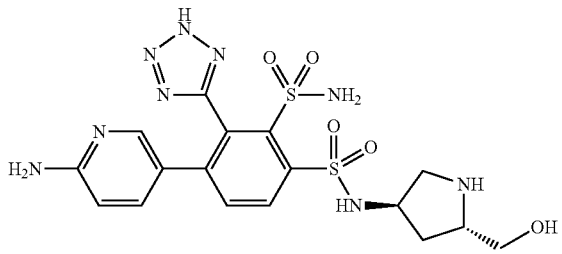<br>4-(6-aminopyridin-3-yl)-N$^1$-((3R,5S)-5-(hydroxymethyl)pyrrolidin-3-yl)-3-(2H-tetrazol-5-yl)benzene-1,2-disulfonamide | [M + H]+: 496.52 |
| 412 | (1H-benzo[d][1,2,3]triazol-4-yl)boronic acid and tert-butyl (3R,4S)-3-((2(N,N-bis(4-methoxybenzyl)sulfamoyl)-4-iodo-3-(1-(4-methoxybenzyl)-1H-1,2,3-triazol-5-yl)phenyl)sulfonamido)-4-hydroxypyrrolidine-1-carboxylate and tert-butyl (3R,4S)-3-((2-(N,N-bis(4-methoxybenzyl)sulfamoyl)-4-iodo-3-(2-(4-methoxybenzyl)-2H-1,2,3-triazol-5-yl)phenyl)sulfonamido)-4-hydroxypyrrolidine-1-carboxylate | 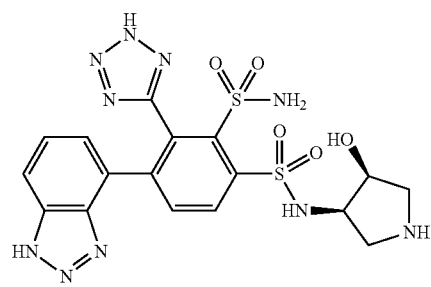<br>4-(1H-benzo[d][1,2,3]triazol-4-yl)-N$^1$-((3R,4S)-4-hydroxypyrrolidin-3-yl)-3-(2H-tetrazol-5-yl)benzene-1,2-disulfonamide | [M + H]+: 507.25 |
| 413 | 5-(4,4,5,5-tetramethyl-1,3,2-dioxaborolan-2-yl)pyridin-2-amine and tert-butyl (3S,4R)-3-(((benzyloxy)carbonyl)amino)-4-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (3S,4R)-3-(((benzyloxy)carbonyl)amino)-4-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate | 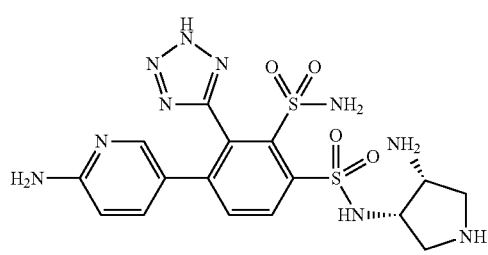<br>4-(6-aminopyridin-3-yl)-N$^1$-((3S,4R)-4-aminopyrrolidin-3-yl)-3-(2H-tetrazol-5-yl)benzene-1,2-disulfonamide | [M + H]+: 481.42 |
| 414 | 5-(4,4,5,5-tetramethyl-1,3,2-dioxaborolan-2-yl)pyridin-2-amine and tert-butyl (3R,4S)-3-(((benzyloxy)carbonyl)amino)-4-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate and tert-butyl (3R,4S)-3-(((benzyloxy)carbonyl)amino)-4-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate | 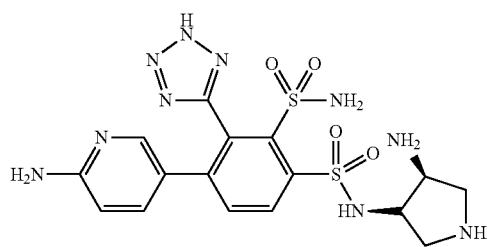<br>4-(6-aminopyridin-3-yl)-N$^1$-((3R,4S)-4-aminopyrrolidin-3-yl)-3-(2H-tetrazol-5-yl)benzene-1,2-disulfonamide | [M + H]+: 481.43 |

| EX. No. | Intermediates | Structure/Name | LC/MS |
|---|---|---|---|
| 415 | 5-(4,4,5,5-tetramethyl-1,3,2-dioxaborolan-2-yl)pyridin-2-amine and benzyl tert-butyl (3-((2-(N,N-bis(4-methoxybenzyl)sulfamoyl)-4-iodo-3-(2-(4-methoxybenzyl)-2H-tetrazol-5-yl)phenyl)sulfonamido)propane-1,2-diyl)(S)-dicarbamate and benzyl tert-butyl (3-((2-(N,N-bis(4-methoxybenzyl)sulfamoyl)-4-iodo-3-(1-(4-methoxybenzyl)-1H-tetrazol-5-yl)phenyl)sulfonamido)propane-1,2-diyl)(S)-dicarbamate | 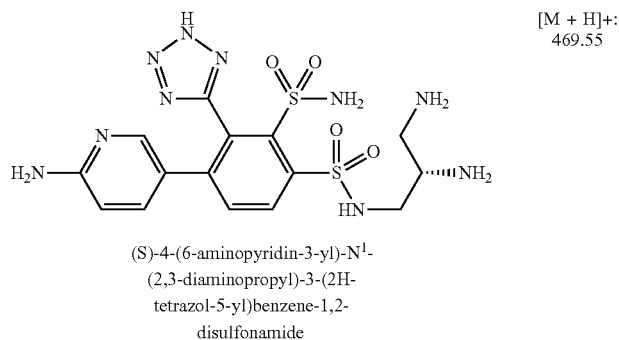<br>(S)-4-(6-aminopyridin-3-yl)-$N^1$-(2,3-diaminopropyl)-3-(2H-tetrazol-5-yl)benzene-1,2-disulfonamide | [M + H]+: 469.55 |
| 416 | 5-(4,4,5,5-tetramethyl-1,3,2-dioxaborolan-2-yl)pyridin-2-amine and benzyl tert-butyl (3-((2-(N,N-bis(4-methoxybenzyl)sulfamoyl)-4-iodo-3-(2-(4-methoxybenzyl)-2H-tetrazol-5-yl)phenyl)sulfonamido)propane-1,2-diyl)(R)-dicarbamate and benzyl tert-butyl (3-((2-(N,N-bis(4-methoxybenzyl)sulfamoyl)-4-iodo-3-(1-(4-methoxybenzyl)-1H-tetrazol-5-yl)phenyl)sulfonamido)propane-1,2-diyl)(R)-dicarbamate | 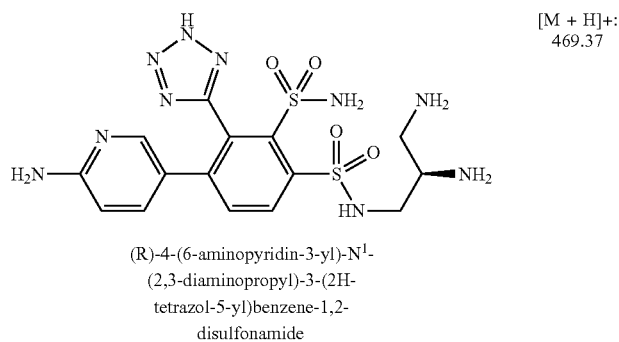<br>(R)-4-(6-aminopyridin-3-yl)-$N^1$-(2,3-diaminopropyl)-3-(2H-tetrazol-5-yl)benzene-1,2-disulfonamide | [M + H]+: 469.37 |
| 417 | 4-(4,4,5,5-tetramethyl-1,3,2-dioxaborolan-2-yl)pyridin-2-amine and tert-butyl (S)-(3-((2-(N,N-bis(4-methoxybenzyl)sulfamoyl)-4-iodo-3-(1-(4-methoxybenzyl)-1H-tetrazol-5-yl)phenyl)sulfonamido)-2-hydroxypropyl)carbamate and tert-butyl methoxybenzyl)sulfamoyl)-4-iodo-3-(2-(4-methoxybenzyl)-2H-tetrazol-5-yl)phenyl)sulfonamido)-2-hydroxypropyl)carbamate | 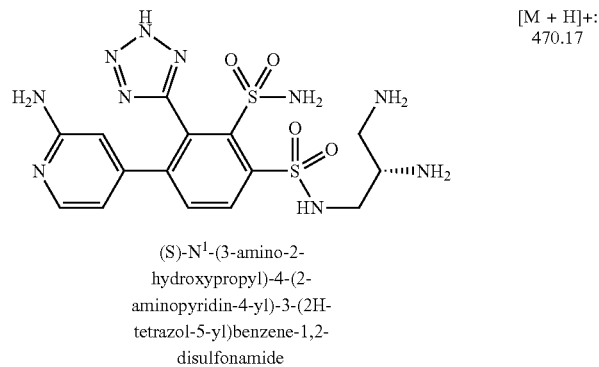<br>(S)-$N^1$-(3-amino-2-hydroxypropyl)-4-(2-aminopyridin-4-yl)-3-(2H-tetrazol-5-yl)benzene-1,2-disulfonamide | [M + H]+: 470.17 |
| 418 | 6-(4,4,5,5-tetramethyl-1,3,2-dioxaborolan-2-yl)imidazo[1,2-a]pyridineamine and tert-butyl (S)-(3-((2-(N,N-bis(4-methoxybenzyl)sulfamoyl)-4-iodo-3-(1-(4-methoxybenzyl)-1H-tetrazol-5-yl)phenyl)sulfonamido)-2-hydroxypropyl)carbamate and tert-butyl (S)-(3-((2-(N,N-bis(4-methoxybenzyl)sulfamoyl)-4-iodo-3-(2-(4-methoxybenzyl)-2H-tetrazol-5-yl)phenyl)sulfonamido)-2-hydroxypropyl carbamate | 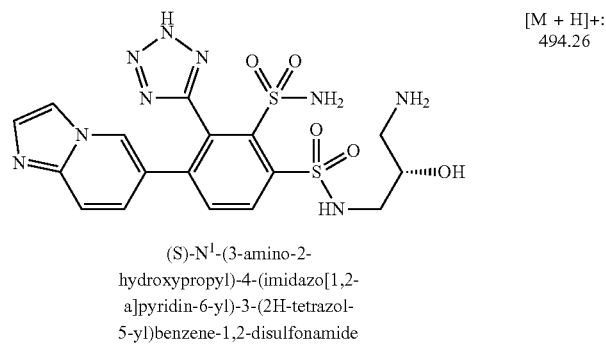<br>(S)-$N^1$-(3-amino-2-hydroxypropyl)-4-(imidazo[1,2-a]pyridin-6-yl)-3-(2H-tetrazol-5-yl)benzene-1,2-disulfonamide | [M + H]+: 494.26 |

| EX. No. | Intermediates | Structure/Name | LC/MS |
|---|---|---|---|
| 419 | 4-(4,4,5,5-tetramethyl-1,3,2-dioxaborolan-2-yl)pyridin-2-amine and tert-butyl (R)-(3-((2-(N,N-bis(4-methoxybenzyl)sulfamoyl)-4-iodo-3-(1-(4-methoxybenzyl)-1H-tetrazol-5-yl)phenyl)sulfonamido)-2-hydroxypropyl)carbamate and tert-butyl (R)-(3-((2-(N,N-bis(4-methoxybenzyl)sulfamoyl)-4-iodo-3-(2-(4-methoxybenzyl)-2H-tetrazol-5-yl)phenyl)sulfonamido)-2-hydroxypropyl)carbamate | 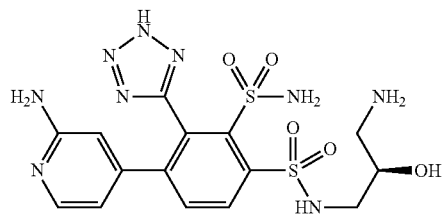<br>(R)-N¹-(3-amino-2-hydroxypropyl)-4-(2-aminopyridin-4-yl)-3-(2H-tetrazol-5-yl)benzene-1,2-disulfonamide | [M + H]+: 470.20 |
| 420 | 6-(4,4,5,5-tetramethyl-1,3,2-dioxaborolan-2-yl)imidazo[1,2-a]pyridineamine and tert-butyl (R)-(3-((2-(N,N-bis(4-methoxybenzyl)sulfamoyl)-4-iodo-3-(1-(4-methoxybenzyl)-1H-tetrazol-5-yl)phenyl)sulfonamido)-2-hydroxypropyl)carbamate and tert-butyl (R)-(3-((2-(N,N-bis(4-methoxybenzyl)sulfamoyl)-4-iodo-3-(2-(4-methoxybenzyl)-2H-tetrazol-5-yl)phenyl)sulfonamido)-2-hydroxypropyl)carbamate | 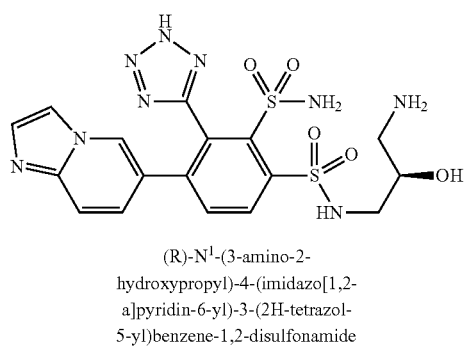 [SMILES: NC[C@@H](O)CNS(=O)(=O)c1ccc(-c2ccc3nccn3c2)c(-c2nn[nH]n2)c1S(N)(=O)=O]<br>(R)-N¹-(3-amino-2-hydroxypropyl)-4-(imidazo[1,2-a]pyridin-6-yl)-3-(2H-tetrazol-5-yl)benzene-1,2-disulfonamide | [M + H]+: 494.20 |
| 421 | 4-(4,4,5,5-tetramethyl-1,3,2-dioxaborolan-2-yl)pyridin-2-amine and tert-butyl (S)-(1-((2-(N,N-bis(4-methoxybenzyl)sulfamoyl)-4-iodo-3-(1-(4-methoxybenzyl)-1H-tetrazol-5-yl)phenyl)sulfonamido)propan-2-yl)carbamate and tert-butyl (S)-(1-((2-(N,N-bis(4-methoxybenzyl)sulfamoyl)-4-iodo-3-(2-(4-methoxybenzyl)-2H-tetrazol-5-yl)phenyl)sulfonamido)propan-2-yl)carbamate | 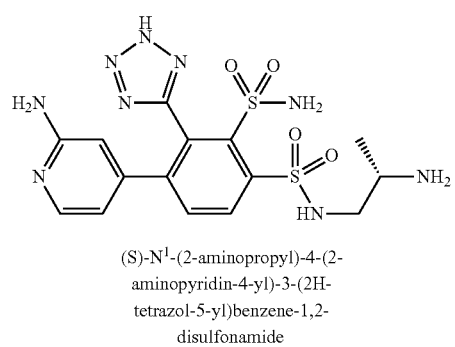 [SMILES: C[C@H](N)CNS(=O)(=O)c1ccc(-c2ccnc(N)c2)c(-c2nn[nH]n2)c1S(N)(=O)=O]<br>(S)-N¹-(2-aminopropyl)-4-(2-aminopyridin-4-yl)-3-(2H-tetrazol-5-yl)benzene-1,2-disulfonamide | [M + H]+: 454.36 |
| 422 | 4-(4,4,5,5-tetramethyl-1,3,2-dioxaborolan-2-yl)pyridin-2-amine and tert-butyl (R)-(1-((2-(N,N-bis(4-methoxybenzyl)sulfamoyl)-4-iodo-3-(1-(4-methoxybenzyl)-1H-tetrazol-5-yl)phenyl)sulfonamido)propan-2-yl)carbamate and tert-butyl (R)-(1-((2-(N,N-bis(4-methoxybenzyl)sulfamoyl)-4-iodo-3-(2-(4-methoxybenzyl)-2H-tetrazol-5-yl)phenyl)sulfonamido)propan-2-yl)carbamate | 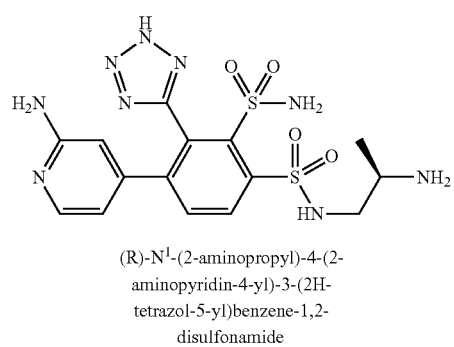 [SMILES: C[C@@H](N)CNS(=O)(=O)c1ccc(-c2ccnc(N)c2)c(-c2nn[nH]n2)c1S(N)(=O)=O]<br>(R)-N¹-(2-aminopropyl)-4-(2-aminopyridin-4-yl)-3-(2H-tetrazol-5-yl)benzene-1,2-disulfonamide | [M + H]+: 454.17 |

-continued

| EX. No. | Intermediates | Structure/Name | LC/MS |
|---|---|---|---|
| 423 | 6-(4,4,5,5-tetramethyl-1,3,2-dioxaborolan-2-yl)imidazo[1,2-a]pyridineamine and tert-butyl (R)-(1-((2-(N,N-bis(4-methoxybenzyl)sulfamoyl)-4-iodo-3-(1-(4-methoxybenzyl)-1H-tetrazol-5-yl)phenyl)sulfonamido)propan-2-yl)carbamate and tert-butyl (R)-(1-((2-(N,N-bis(4-methoxybenzyl)sulfamoyl)-4-iodo-3-(2-(4-methoxybenzyl)-2H-tetrazol-5-yl)phenyl)sulfonamido)propan-2-yl)carbamate | 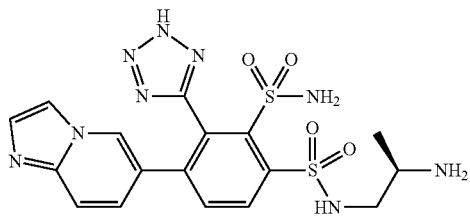<br>(R)-N¹-(2-aminopropyl)-4-(imidazo[1,2-a]pyridin-6-yl)-3-(2H-tetrazol-5-yl)benzene-1,2-disulfonamide | [M + H]+: 478.20 |
| 424 | (2-amino-1H-benzo[d]imidazol-4-yl)boronic acid and tert-butyl (3R,4R)-3-(((2-(N,N-bis(4-methoxybenzyl)sulfamoyl)-4-iodo-3-(1-(4-methoxybenzyl)-1H-tetrazol-5-yl)phenyl)sulfinyl)amino)-4-((tert-butoxycarbonyl)amino)pyrrolidine-1-carboxylate and tert-butyl (3R,4S-3-(((2-(N,N-bis(4-methoxybenzyl)sulfamoyl)-4-iodo-3-(2-(4-methoxybenzyl)-2H-tetrazol-5-yl)phenyl)sulfinyl)amino)-4-((tert-butoxycarbonyl)amino)pyrrolidine-1-carboxylate | 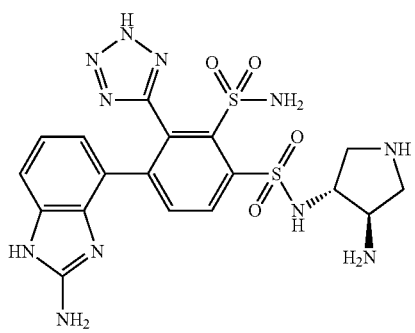<br>4-(2-amino-1H-benzo[d]imidazol-4-yl)-N¹-((3R,4R)-4-aminopyrrolidin-3-yl)-3-(2H-tetrazol-5-yl)benzene-1,2-disulfonamide | [M + H]+: 520.29 |

Example 425

4-(2-amino-1H-benzo[d]imidazol-4-yl)-N¹-((3R,5S)-5-(aminomethyl)pyrrolidin-3-yl)-3-(2H-tetrazol-5-yl)benzene-1,2-disulfonamide

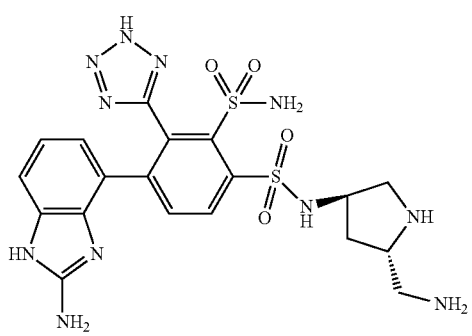 [SMILES: NC[C@@H]1C[C@@H](NS(=O)(=O)c2ccc(-c3cccc4[nH]c(N)nc34)c(-c3nn[nH]n3)c2S(N)(=O)=O)CN1]

Step A: tert-butyl (2S,4R)-4-(((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfinyl)amino)-2-((1,3-dioxoisoindolin-2-yl)methyl)pyrrolidine-1-carboxylate and tert-butyl (2S,4R)-4-(((4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfinyl)amino)-2-((1,3-dioxoisoindolin-2-yl)methyl)pyrrolidine-1-carboxylate A suspension of (2S,4R)-tert-butyl 4-(2-(N,N-bis(4-methoxybenzyl)sulfamoyl)-4-iodo-3-(2-(4-methoxybenzyl)-2H-tetrazol-5-yl)phenylsulfonamido)-2-((1,3-dioxoisoindolin-2-yl)methyl)pyrrolidine-1-carboxylate and (2S,4R)-tert-butyl 4-(2-(N,N-bis(4-methoxybenzyl)sulfamoyl)-4-iodo-3-(1-(4-methoxybenzyl)-1H-tetrazol-5-yl)phenylsulfonamido)-2-((1,3-dioxoisoindolin-2-yl)methyl)pyrrolidine-1-carboxylate (REFERENCE EXAMPLE 101, 1400 mg, 1.251 mmol), sodium carbonate (398 mg, 3.75 mmol), (2-amino-1H-benzo[d]imidazol-4-yl)boronic acid (332 mg, 1.877 mmol) and PdCl₂ (dppf) (204 mg, 0.250 mmol) in dioxane (10 ml) and water (2.5 ml) was heated at 100° C. for 17 hours. The mixture was diluted with EtOAc, washed with brine. The organic layer was dried (MgSO$_4$) and concentrated. The crude material was chromatographed via silica gel eluting with 0-20% MeOH in DCM to give the desired products. LCMS: 1124.9.

Step B: 3-(2-amino-1H-benzo[d]imidazol-4-yl)-6-(((((3R,5S)-5-(aminomethyl)pyrrolidin-3-yl)amino)sulfinyl)-2-(2H-tetrazol-5-yl)benzenesulfonamide To a solution of tert-butyl (2S,4R)-4-(((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfinyl)amino)-2-((1,3-dioxoisoindolin-2-yl)methyl)pyrrolidine-1-carboxylate and tert-butyl (2S,4R)-4-(((4-(2-amino-1H-benzo[d]imidazol-4-yl)-2-(N,N-bis(4-methoxybenzyl)sulfamoyl)-3-(1-(4-methoxybenzyl)-2H-tetrazol-5-yl)phenyl)sulfinyl)amino)-2-((1,3-dioxoisoindolin-2-yl)methyl)pyrrolidine-1-carboxylate (200 mg, 0.179 mmol) in EtOH (10 ml) was added hydrazine (17.18 mg, 0.536 mmol). The reaction mixture was heated to 60° C. for 2 hours. The solvent was removed in vacuo. The residue was dissolved in 5 ml of methanol and filtered through a 10 ml Agilent BE-SCX ino exchange resin column and washed with 7N ammonia in methanol. The filtrate was concentrated, then was dissolved in TFA (5 ml), heated to 80° C. for 1 hr. LC-MS shown deprotection completed. The reaction mixture was concentrated and purified via Gilson (3-60% Acetonitrile in water with 0.1% ammonia) to give the title compound. LC/MS [M+H]$^+$: 534.37.

Example 426

(S)-4-(2-Amino-1H-benzo[d]imidazol-4-yl)-N$^1$-(1-amino-3-hydroxypropan-2-yl)-3-(1H-tetrazol-5-yl)benzene-1,2-disulfonamide

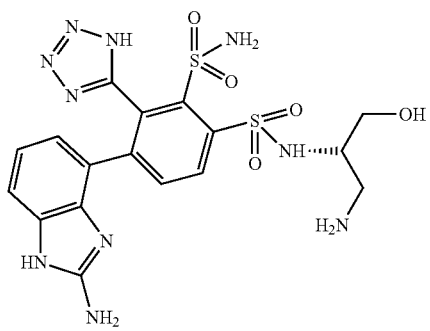

Step A: tert-Butyl (S)-(2-((4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfonamido)-3-hydroxypropyl)carbamate and tert-butyl (S)-(2-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)-3-hydroxypropyl)carbamate (2-Amino-1H-benzo[d]imidazol-4-yl)boronic acid (445 mg, 2.51 mmol), tert-butyl (S)-(2-((2-(N,N-bis(4-methoxybenzyl)sulfamoyl)-4-iodo-3-(1-(4-methoxybenzyl)-1H-tetrazol-5-yl)phenyl)sulfonamido)-3-hydroxypropyl)carbamate and tert-butyl (S)-(2-((2-(N,N-bis(4-methoxybenzyl)sulfomoyl)-4-iodo-3-(2-4-methoxybenzyl)-2H-tetrazol-5-yl)phenyl)sulfonamido)-3-hydroxypropyl)carbamate (REFERENCE EXAMPLE 88; 1010 mg, 1.048 mmol), sodium carbonate (222 mg, 2.096 mmol), Pd (dppf)Cl$_2$ (153 mg, 0.210 mmol) were placed in a reaction vial. Dioxane (7859 µl) and water (2620 µl) were added. The reaction was degassed and then heated at 80° C. for 12 hours. The reaction mixture was purified by column chromatography (0-100% EtOAc/EtOH (3/1) to hexane) to give the title compounds (mixture of two tetrazole regioisomers). LC/MS [M+H]+: 969.8.

Step B: (S)-4-(2-Amino-1H-benzo[d]imidazol-4-yl)-N$^1$-(1-amino-3-hydroxypropan-2-yl)-3-(1H-tetrazol-5-yl)benzene-1,2-disulfonamide A solution of tert-Butyl (S)-(2-((4-(2-amino-1H-benzo[d]imidazol-4-yl)-2-(N,N-bis(4-methoxybenzyl)sulfamoyl)-3-(1-(4-methoxybenzyl)-1H-tetrazol-5-yl)phenyl)sulfonamido)-3-hydroxypropyl)carbamate and tert-butyl (S)-(2-((4-(2-amino-1H-benzo[d]imidazol-4-yl)-2-(N,N-bis(4-methoxybenzyl)sulfamoyl)-3-(2-(4-methoxybenzyl)-2H-tetrazol-5-yl)phenyl)sulfonamido)-3-hydroxypropyl)carbamate (283 mg, 0.292 mmol) was stirred in TFA/DCM (1/1, 2 mL) at room temperature for 1 hour. The reaction was concentrated and co-evaporated with toluene 3 times. The residue was redissolved in TFA and heated at 80° C. for 1 hour, and then cooled to room temperature and concentrated. The residue was dissolved in DMSO (4 mL) and purified by Gilson (3-45% CH$_3$CN/water with 0.05% TFA). The correct fractions were combined and concentrtrated, redissolved in CH$_3$CN, and 300 uL of 1.25 M HCl in MeOH was added. The mixture was stirred at room temperature for 1 hour and then water was added. The product was lypholized to give the title compound. LC/MS [M+H]+: 509.3.

The EXAMPLES in the Table below were prepared in an analogous fashion to that described for (S)-4-(2-amino-1H-benzo[d]imidazol-4-yl)-N$^1$-(1-amino-3-hydroxypropan-2-yl)-3-(1H-tetrazol-5-yl)benzene-1,2-disulfonamide (immediately above), starting from the corresponding boronic acids or boronic esters and corresponding iodoaryl sulfonamides, which were nrenared as described herein or which were available from commercial sources.

| EX. No. | Intermediates | Structure/Name | LC/MS [M + H]+ |
|---|---|---|---|
| 427 | (2-amino-1H-benzo[d]imidazol-4-yl)boronic acid; tert-butyl (R)-(2-((2-(N,N-bis(4-methoxybenzyl)sulfamoyl)-4-iodo-3-(1-(4-methoxybenzyl)-1H-tetrazol-5-yl)phenyl)sulfonamido)-3-hydroxypropyl)carbamate and tert-butyl (R)-(2-((2-(N,N-bis(4-methoxybenzyl)sulfamoyl)-4-iodo-3-(2-(4-methoxybenzyl)-2H-tetrazol-5-yl)phenyl)sulfonamido)-3-hydroxypropyl)carbamate | (R)-4-(2-amino-1H-benzo[d]imidazol-4-yl)-N¹-(1-amino-3-hydroxypropan-2-yl)-3-(1H-tetrazol-5-yl)benzene-1,2-disulfonamide | 509 |
| 428 | (3-(2-amino-1H-imidazol-4-yl)phenyl)boronic acid; tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate | (R)-3'-(2-amino-1H-imidazol-4-yl)-N⁴-(pyrrolidin-3-yl)-2-(2H)-tetrazol-5-yl)-[1,1'-biphenyl]-3,4-disulfonamide | 531 |
| 429 | (2-amino-1H-benzo[d]imidazol-4-yl)boronic acid; di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 4-(2-amino-1H-benzo[d]imidazol-4-yl)-N1-(1,3-diaminopropan-2-yl)-3-(2H-tetrazol-5-yl)benzene-1,2-disulfonamide | 508 |

| EX. No. | Intermediates | Structure/Name | LC/MS [M + H]+ |
|---|---|---|---|
| 430 | (2-aminoquinolin-8-yl)boronic acid; di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 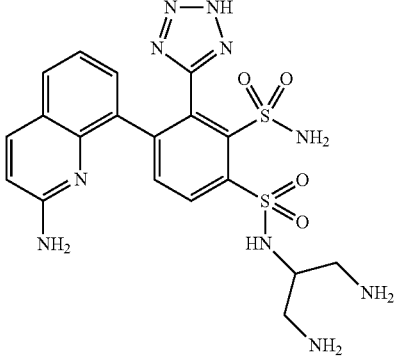<br>4-(2-aminoquinolin-8-yl)-N1-(1,3-diaminopropan-2-yl)-3-(2H-tetrazol-5-yl)benzene-1,2-disulfonamide | 519 |
| 431 | (3-(2-amino-5-(ethoxycarbonyl)thiazol-4-yl)phenyl)boronic acid;di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 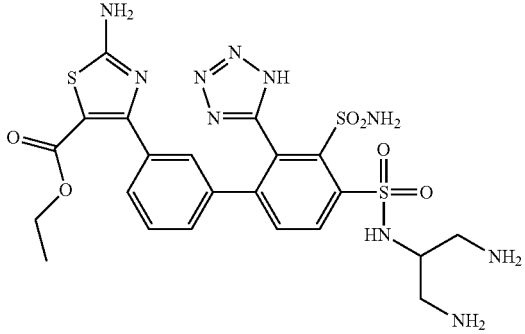<br>ethyl 2-amino-4-(4'-(N-(1,3-diaminopropan-2-yl)sulfamoyl)-3'-sulfamoyl-2'-(1H-tetrazol-5-yl)-[1,1'-biphenyl]-3-yl)thiazole-5-carboxylate | 623 |
| 432 | (3-(2-((tert-butoxycarbonyl)amino)-5-(((tert-butoxycarbonyl)amino)methyl)thiazol-4-yl)phenyl)boronic acid; tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate | 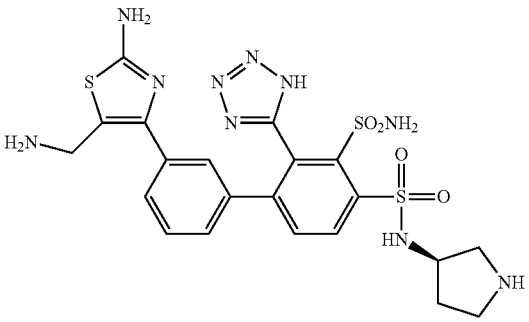<br>(R)-3'-(2-amino-5-(aminomethyl)thiazol-4-yl)-N4-(pyrrolidin-3-yl)-2-(1H-tetrazol-5-yl)-[1,1'-biphenyl]-3,4-disulfonamide | 578 |

| EX. No. | Intermediates | Structure/Name | LC/MS [M + H]+ |
|---|---|---|---|
| 433 | (3-(2-((tert-butoxycarbonyl)amino)-5-(((2-(tert-butoxycarbonyl)amino)ethyl)amino)methyl)thiazol-4-yl)phenyl)boronic acid; tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate | (R)-3'-(2-amino-5-(((2-(aminoethyl)amino)methyl)thiazol-4-yl)-N⁴-(pyrrolidin-3-yl)-2-(1H)-tetrazol-5-yl)-[1,1'-biphenyl]3,4-disulfonamide | 620 |
| 434 | (3-(2-amino-1H-imidazol-4-yl)phenyl)boronic acid; (S)-N¹-(2,3-diaminopropyl)-4-iodo-3-(1-(4-methoxy benzyl)-1H-tetrazol-5-yl)benzene-1,2-disulfonamide and (S)-N¹-(2,3-diaminopropyl)-4-iodo-3-(2-(4-methoxybenzyl)-2H-tetrazol-5-yl)benzene-1,2-disulfonamide (2H-tetrazol-5-yl)-[1,1'-biphenyl]-3,4-disulfonamide | (S)-3'-(2-amino-1H-imidazol-4-yl)-N⁴-(2,3-diaminopropyl)-2-(2H-tetrazol-5-yl)-[1,1'-biphenyl]-3,4-disulfonamide | 534 |
| 435 | (3-(2-amino-1H-imidazol-4-yl)phenyl)boronic acid; di-tert-butyl (2-(((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 3'-(2-amino-1H-imidazol-4-yl)-N4-(1,3-diaminopropan-2-yl)-2-(2H-tetrazol-5-yl)-[1,1'-biphenyl]-3,4-disulfonamide | 534 |

| EX. No. | Intermediates | Structure/Name | LC/MS [M + H]+ |
|---|---|---|---|
| 436 | (2-aminobenzo[d]thiazol-4-yl)boronic acid; di-tert-butyl (2-((2-(N,N-bis(4-methoxybenzyl)sulfamoyl)-4-iodo-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate | 4-(2-aminobenzo[d]thiazol-4-yl)-N1-(1,3-diaminopropan-2-yl)-3-(2H-tetrazol-5-yl)benzene-1,2-disulfonamide | 525 |

Example 437

4-(2-(2-Amino-1H-imidazol-5-yl)pyridin-4-yl)-N$^1$-(1,3-diaminopropan-2-yl)-3-(1H-tetrazol-5-yl)benzene-1,2-disulfonamide

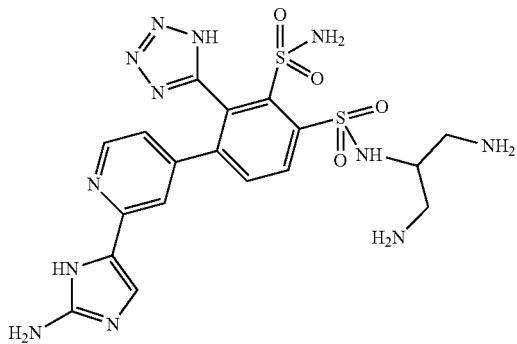 [SMILES: NCC(CN)NS(=O)(=O)c1ccc(-c2ccnc(-c3cnc(N)[nH]3)c2)c(-c2nnn[nH]2)c1S(N)(=O)=O]

Step A: di-tert-Butyl (2-((2-(N,N-bis(4-methoxybenzyl)sulfamoyl)-4-(2-chloropyridin-4-yl)-3-(1-(4-methoxybenzyl)-1H-tetrazol-5-yl)phenyl)sulfonamido)propane-1,3-diyl)dicarbamate and di-tert-butyl (2-((2-(N,N-bis(4-methoxybenzyl)sulfamoyl)-4-(2-chloropyridin-4-yl)-3-(2-(4-methoxybenzyl)-2H-tetrazol-5-yl)phenyl)sulfonamido)propane-1,3-diyl)dicarbamate Pd(dppf)Cl$_2$ (103 mg, 0.141 mmol), sodium carbonate (299 mg, 2.82 mmol), (2-chloropyridin-4-yl)boronic acid (244 mg, 1.552 mmol) and di-tert-butyl (2-(2-(N,N-bis(4-methoxybenzyl)sulfamoyl)-4-iodo-3-(1-(4-methoxybenzyl)-1H-tetrazol-5-yl)phenylsulfonamido)propane-1,3-diyl) dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate (1500 mg, 1.411 mmol) were placed in a reaction vial. Dioxane (10 mL) and water (3.5 mL) were added. The reaction was degassed and heated at 80° C. for 4 hours. The reaction was purified by column chromatography (0-60% hexane/EtOAc) to give the title compound. LC/MS [M+H]+: 1048.9.

Step B: 3-(Tributylstannyl)imidazo[1,2-c]pyrimidine

3-Bromoimidazo[1,2-a]pyrimidine (1.27 g, 6.41 mmol) was dissolved in anhydrous THF (32.1 ml) and cooled to −78° C. Isopropylmagnesium chloride (3.53 ml, 7.05 mmol) was added dropwise. The resulting mixture was stirred at −78° C. for 10 minutes, then tributylchlorostannane (2.422 g, 7.44 mmol) was added. The mixture was stirred at −78° C. for 10 minutes, then allowed to warm to room temperature. The reaction mixture was purified by column chromatography (100% hexane to 90% EtOAc/EtOH (3/1) over hexane) to give the title compound. LC/MS [M+H]+: 410.4.

Step C: di-tert-Butyl (2-((2-(N,N-bis(4-methoxybenzyl)sulfamoyl)-4-(2-(imidazo[1,2-a]pyrimidin-3-yl)pyridin-4-yl)-3-(1-(4-methoxybenzyl)-1H-tetrazol-5-yl)phenyl)sulfonamido)propane-1,3-diyl) and di-tert-butyl (2-((2-(N,N-bis(4-methoxybenzyl)sulfamoyl)-4-(2-(imidazo[1,2-c]pyrimidin-3-yl)pyridin-4-yl)-3-(2-(4-methoxybenzyl)-2H-tetrazol-5-yl)phenyl)sulfonamido)propane-1,3-diyl)dicarbamate di-tert-Butyl (2-((2-(N,N-bis(4-methoxybenzyl)sulfamoyl)-4-(2-(imidazo[1,2-a]pyrimidin-3-yl)pyridin-4-yl)-3-(1-(4-methoxybenzyl)-1H-tetrazol-5-yl)phenyl)sulfonamido)propane-1,3-diyl) and di-tert-butyl (2-((2-(N,N-bis(4-methoxybenzyl)sulfamoyl)-4-(2-(imidazo[1,2-c]pyrimidin-3-yl)pyridin-4-yl)-3-(2-(4-methoxybenzyl)-2H-tetrazol-5-yl)phenyl)sulfonamido)propane-1,3-diyl)dicarbamate (0.899 g, 0.857 mmol) in DMF (3 mL) were added to 3-(tributylstannyl)imidazo[1,2-a]pyrimidine (0.25 g, 0.612 mmol) followed by PalladiumTetrakis (0.071 g, 0.061 mmol). The reaction mixture was degassed and heated at 90° C. for 3 hours. The reaction was purified by column chromatography (100% hexane to 90% EtOAc/EtOH ((3/1) over hexane) to give the title compound. LC/MS [M+H]+: 1132.1.

Step D: di-tert-Butyl (2-((4-(2-(2-amino-1H-imidazol-5-yl)pyridin-4-yl)-2-(N,N-bis(4-methoxybenzyl)sulfamoyl)-3-(1-(4-methoxybenzyl)-1H-tetrazol-5-yl)phenyl)sulfonamido)propane-1,3-diyl)dicarbamate and di-tert-butyl (2-((4-(2-(2-amino-1H-imidazol-5-yl)pyridin-4-yl)-2-(N,N-bis(4-methoxybenzyl)sulfamoyl)-3-(2-(4-methoxybenzyl)-2H-tetrazol-5-yl)phenyl)sulfonamido)propane-1,3-diyl)dicarbamate di-tert-Butyl (2-(2-(N,N-bis(4-methoxybenzyl)sulfamoyl)-4-(2-(imidazo[1,2-a]pyrimidin-3-yl)pyridin-4-yl)-3-(1-(4-methoxybenzyl)-1H-tetrazol-5-yl)phenylsulfonamido)propane-1,3-diyl)dicarbamate and di-tert-butyl (2-((2-(N,N-bis(4-methoxybenzyl)sulfamoyl)-4-(2-(imidazo[1,2-a]pyrimidin-3-yl)pyridin-4-yl)-3-(2-(4-methoxybenzyl)-2H-tetrazol-5-yl)phenyl)sulfonamido)propane-1,3-diyl)dicarbamate (89 mg, 0.079 mmol) was dissolved in EtOH (1 mL). Hydrazine (24.69 µl, 0.787 mmol) and water (25 uL) were added. The mixture was heated at 80° C. for 30 minutes. The crude reaction mixture was concentrated and used directly in the next step. LC/MS [M+H]+: 1096.1.

Step E: 4-(2-(2-Amino-1H-imidazol-5-yl)pyridin-4-yl)-N$^1$-(1,3-diaminopropan-2-yl)-3-(1H-tetrazol-5-yl)benzene-1,2-disulfonamide di-tert-Butyl (2-(4-(2-(2-amino-1H-imidazol-5-yl)pyridin-4-yl)-2-(N,N-bis(4-methoxybenzyl)sulfamoyl)-3-(1-(4-methoxybenzyl)-1H-tetrazol-5-yl)phenylsulfonamido)propane-1,3-diyl)dicarbamate and di-tert-butyl (2-((4-(2-(2-amino-1H-imidazol-5-yl)pyridin-4-yl)-2-(N,N-bis(4-methoxybenzyl)sulfamoyl)-3-(2-(4-methoxybenzyl)-2H-tetrazol-5-yl)phenyl)sulfonamido)propane-1,3-diyl)dicarbamate (86 mg, 0.079 mmol) was stirred in DCM/TFA (2 mL/1 mL) at room temp. for 0.5 hour. The reaction mixture was concentrated and co-evaporated with toluene 3 times. The residue was heated in neat TFA (2 mL) at 80° C. for 45 minutes. The reaction was concentrated and the residue was purified with Gilson (2-30% CH$_3$CN/water with 0.1% TFA), and the correct fractions were concentrated and was free-based by purified again with Gilson (2-30% CH$_3$CN/water with 0.1% NH$_4$OH). The correct fractions were concentrated and lypholized to give the title compound. LC/MS [M+H]+: 535.7.

Example 438

4-(6-(2-Amino-1H-imidazol-5-yl)pyridin-2-yl)-N$^1$-(1,3-diaminopropan-2-yl)-3-(1H-tetrazol-5-yl)benzene-1,2-disulfonamide

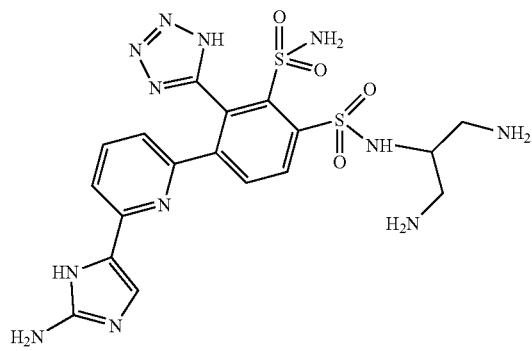 [SMILES: NCC(CN)NS(=O)(=O)c1ccc(-c2cccc(-c3cnc(N)[nH]3)n2)c(-c2nnn[nH]2)c1S(N)(=O)=O]

The title compound was prepared in a similar fashion to the synthesis of 4-(2-(2-amino-1H-imidazol-5-yl)pyridin-4-yl)-N$^1$-(1,3-diaminopropan-2-yl)-3-(1H-tetrazol-5-yl)benzene-1,2-disulfonamide (EXAMPLE 437) starting from (6-chloropyridin-2-yl)boronic acid and di-tert-butyl (2-(2-(N,N-bis(4-methoxybenzyl)sulfamoyl)-4-iodo-3-(1-(4-methoxybenzyl)-1H-tetrazol-5-yl)phenylsulfonamido)propane-1,3-diyl)dicarbamate and di-tert-butyl (2-((2-(N,N-bis(4-methoxybenzyl)sulfamoyl)-4-iodo-3-(2-(4-methoxybenzyl)-2H-tetrazol-5-yl)phenyl)sulfonamido)propane-1,3-diyl)dicarbamate. LC/MS [M+H]+: 535.4.

Example 439

(R)-4-(6-(2-Amino-1H-imidazol-5-yl)pyridin-2-yl)-N$^1$-(pyrrolidin-3-yl)-3-(1H-tetrazol-5-yl)benzene-1,2-disulfonamide

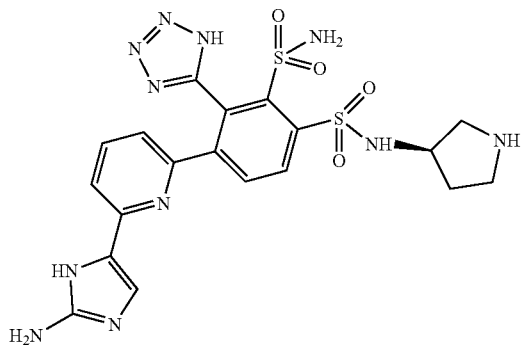 [SMILES: Nc1ncc(-c2cccc(-c3ccc(S(=O)(=O)N[C@@H]4CCNC4)c(S(N)(=O)=O)c3-c3nnn[nH]3)n2)[nH]1]

The title compound was prepared in a similar fashion to the synthesis of 4-(2-(2-amino-1H-imidazol-5-yl)pyridin-4-yl)-N$^1$-(1,3-diaminopropan-2-yl)-3-(1H-tetrazol-5-yl)benzene-1,2-disulfonamide, starting from (6-chloropyridin-2-yl)boronic acid and tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate. LC/MS [M+H]+: 532.5.

Example 440

(R)-4-(2-(2-Amino-1H-imidazol-5-yl)pyridin-4-yl)-N$^1$-(pyrrolidin-3-yl)-3-(1H-tetrazol-5-yl)benzene-1,2-disulfonamide

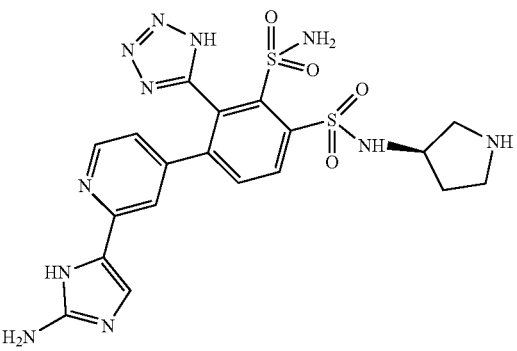 [SMILES: Nc1ncc(-c2cc(-c3ccc(S(=O)(=O)N[C@@H]4CCNC4)c(S(N)(=O)=O)c3-c3nnn[nH]3)ccn2)[nH]1]

The title compound was prepared in a similar fashion to the synthesis of 4-(2-(2-amino-1H-imidazol-5-yl)pyridin-4-yl)-N¹-(1,3-diaminopropan-2-yl)-3-(1H-tetrazol-5-yl)benzene-1,2-disulfonamide (Example 12), starting from (2-chloropyridin-4-yl)boronic acid and tert-butyl (R)-3-((2-(N,N-bis(4-methoxybenzyl)sulfamoyl)-4-iodo-3-(1-(4-methoxybenzyl)-1H-tetrazol-5-yl)phenyl)sulfonamido)pyrrolidine-1-carboxylate and tert-butyl (R)-3-((2-(N,N-bis(4-methoxybenzyl)sulfamoyl)-4-iodo-3-(2-(4-methoxybenzyl)-2H-tetrazol-5-yl)phenyl)sulfonamido)pyrrolidine-1-carboxylate. LC/MS [M+H]+: 532.2.

Example 441

4-(2-((S)-2-Aminopropyl)-1H-benzo[d]imidazol-4-yl)-N1-((R)-pyrrolidin-3-yl)-3-(2H-tetrazol-5-yl)benzene-1,2-disulfonamide

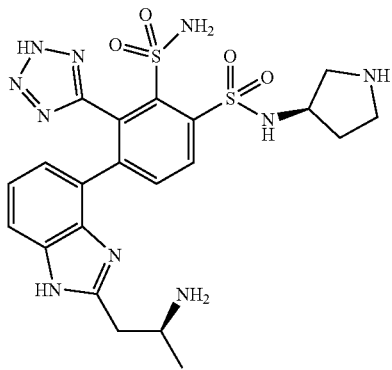 [SMILES: C[C@H](N)Cc1nc2c(-c3ccc(S(=O)(=O)N[C@@H]4CCNC4)c(S(N)(=O)=O)c3-c3nn[nH]n3)cccc2[nH]1]

Step A: 2',3'-Diamino-N,N-bis(4-methoxybenzyl)-2-(2-(4-methoxybenzyl)-2H-tetrazol-5-yl)-4-((2-(trimethylsilyl)ethyl)sulfonyl-[1,1'-biphenyl]-3-sulfonamide A suspension of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (8 g, 9.13 mmol), 2-nitro-3-(4,4,5,5-tetramethyl-1,3,2-dioxaborolan-2-yl)aniline (7.24 g, 27.4 mmol), tetrakis(triphenylphosphine)palladium (0) (1.055 g, 0.913 mmol) and sodium carbonate (2.90 g, 27.4 mmol) in dioxane (100 ml) and water (30 ml) was degassed and heated at 80° C. for 17 hours. The mixture was diluted with AcOEt. The organic layer was separated, washed with brine, dried (MgSO4) and concentrated to give about 1:1 mixture of 3'-amino-N,N-bis(4-methoxybenzyl)-2-(2-(4-methoxybenzyl)-2H-tetrazol-5-yl)-2'-nitro-4-((2-(trimethylsilyl)ethyl)sulfonyl-[1,1'-biphenyl]-3-sulfonamide and 2',3'-diamino-N,N-bis(4-methoxybenzyl)-2-(2-(4-methoxybenzyl)-2H-tetrazol-5-yl)-4-((2-(trimethylsilyl)ethyl)sulfonyl)-[1,1'-biphenyl]-3-sulfonamide which was separated by ISCO column (220 g, 0-30%, 30%, 30-100% EtOAc in Hexane). LC/MS [M+H]+: 856 and 886.

Step B: tert-butyl (S)-(4-((2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl-[1,1'-biphenyl]-3-yl)amino)-4-oxobutan-2-yl)carbamate 2',3'-Diamino-N,N-bis(4-methoxybenzyl)-2-(2-(4-methoxybenzyl)-2H-tetrazol-5-yl)-4-((2-(trimethylsilyl)ethyl)sulfonyl-[1,1'-biphenyl]-3-sulfonamide (1.5 g, 1.752 mmol), (S)-3-((tert-butoxycarbonyl)amino)butanoic acid (0.5 g, 2.46 mmol) and EDC (0.381 g, 2,452 mmol) were added to a 100 ml flask with 50 ml of DCM with the exception of N,N-dimethylpyridin-4-amine (0.321 g, 2.63 mmol) which was added after one minute of stirring. The solution was stirred at room temperature for 2 hours. Then the reaction solution was washed with KHSO4 and dried with magnesium sulfate. The solvent was removed to give a solid which was carried forward in the next step. LC/MS [M+H]+: 1042

Step C: tert-Butyl (S)-(1-(4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)propan-2-yl)carbamate tert-Butyl (S)-(4-((2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl-[1,1'-biphenyl]-3-yl)amino)-4-oxobutan-2-yl)carbamate (1.752 g, 1.824 mmol) was dissolved in acetic acid (40 ml) and stirred at 60° C. for two hours. The solvent was removed and the crude material was purified via column chromatography eluted with hexane/EtOAc. LC/MS [M+H]+: 1024

Step D: 2-(N,N-Bis(4-methoxybenzyl)sulfamoyl)-4-(2-((S)-2-((tert-butoxycarbonyl)amino)propyl)-1H-benzo[d]imidazol-4-yl)-3-(2-(4-methoxybenzyl)-2H-tetrazol-5-yl)benzenesulfinic acid tert-Butyl (S)-(1-(4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)-1H-benzo[d]imidazol-2-yl)propan-2-yl)carbamate (1.43 g, 1.397 mmol) was dissolved in 40 ml of THF to which 1M TBAF (7 ml, 7 mmol) was added and stirred for 30 minutes. The reaction was washed with KHSO4 and extracted with ethyl acetate and dried (MgSO4). The solvent was removed to give a solid. LC/MS [M+H]+: 924

Step E: tert-Butyl (R)-3-((2-(N,N-bis(4-methoxybenzyl)sulfamoyl)-4-(2-((S)-2-((tert-butoxycarbonyl)amino)propyl)-1H-benzo[d]imidazol-4-yl)-3-(2-(4-methoxybenzyl)-2H-tetrazol-5-yl)phenyl)sulfonamido)pyrrolidine-1-carboxylate 2-(N,N-Bis(4-methoxybenzyl)sulfamoyl)-4-(2-((S)-2-((tert-butoxycarbonyl)amino)propyl)-1H-benzo[d]imidazol-4-yl)-3-(2-(4-methoxybenzyl)-2H-tetrazol-5-yl)benzenesulfinic acid (0.2 g, 0.217 mmol), tert-butyl (R)-3-aminopyrrolidine-1-carboxylate (0.121 g, 0.650 mmol), TEA (0.091 ml, 0.650 mmol), and NCS (0.087 g, 0.650 mmol) were added to a 50 ml flask with 15 ml THF and stirred for 30 minutes at room temperature. The reaction mixture was stirred with Na2S2O3 aqueous for 30 minutes, diluted with ether. The organic layer was separated, washed with KHSO4 aqueous and dried over MgSO4 and concentrated to give a solid that was used in the next step. LC/MS [M+H]+: 1108.

Step F: 4-(2-((S)-2-Aminopropyl)-1H-benzo[d]imidazol-4-yl)-N1-((R)-pyrrolidin-3-yl)-3-(2H-tetrazol-5-yl)benzene-1,2-disulfonamide tert-Butyl (R)-3-((2-(N,N-bis(4-methoxybenzyl)sulfamoyl)- 4-(2-((S)-2-((tert-butoxycarbonyl)amino)propyl)-1H-benzo[d]imidazol-4-yl)-3-(2-(4-methoxybenzyl)-2H- tetrazol-5-yl)phenyl)sulfonamido)pyrrolidine-1-carboxylate (240 mg, 0.217 mmol) was dissolved in 10 ml of DCM to which 3 drops of anisole were added. After this, 2 ml of TFA were added and stirred at room temperature for two hours as a solution. The solvent was removed and toluene was added and the solvent was removed again under vacuum. 5 ml of TFA were added and the reaction was stirred at 80° C. for 1 hour. The solvent was removed to give the crude product as a sludge which was purified via HPLC RP HPLC Gilson (3-37% water in acetonitrile with 0.05% NH₄OH). LC/MS [M+H]+:274 (dication).

Compounds in the Table below were synthesized using the procedure described above for 4-(2-((S)-2-Aminopropyl)-1H-benzo[d]imidazol-4-yl)-N1-((R)-pyrrolidin-3-yl)-3-(2H-tetrazol-5-yl)benzene-1,2-disulfonamide using the indicated carboxylic acids as SM.

| EX No. | SM | Structure | Name | LC/MS [M + H]+ |
|---|---|---|---|---|
| 442 | | 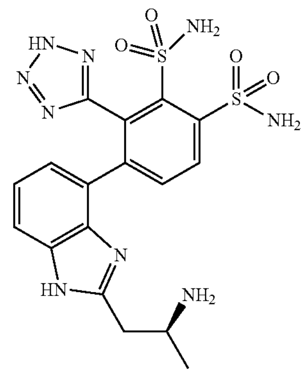 [SMILES: C[C@H](N)Cc1nc2c(-c3ccc(S(N)(=O)=O)c(S(N)(=O)=O)c3-c3nn[nH]n3)cccc2[nH]1] | (S)-4-(2-(2-aminopropyl)-1H-benzo[d]imidazol-4-yl)-3-(2H-tetrazol-5-yl)benzene-1,2-disulfonamide | 478 |
| 443 | | 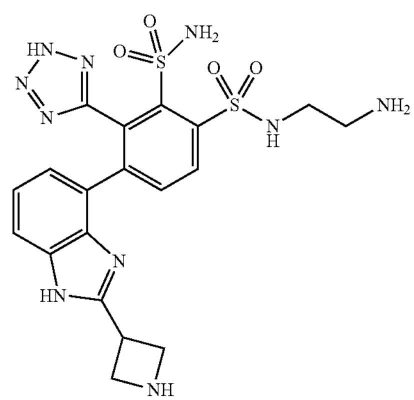 [SMILES: NCCNS(=O)(=O)c1ccc(-c2cccc3[nH]c(C4CNC4)nc23)c(-c2nn[nH]n2)c1S(N)(=O)=O] | N1-(2-aminoethyl)-4-(2-(azetidin-3-yl)-1H-benzo[d]imidazol-4-yl)-3-(2H-tetrazol-5-yl)benzene-1,2-disulfonamide | 519 |
| 444 | | 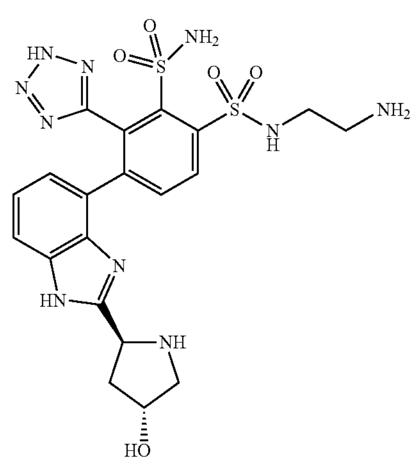 [SMILES: NCCNS(=O)(=O)c1ccc(-c2cccc3[nH]c([C@@H]4C[C@@H](O)CN4)nc23)c(-c2nn[nH]n2)c1S(N)(=O)=O] | N1-(2-aminoethyl)-4-(2-((2S,4R)-4-hydroxypyrrolidin-2-yl)-1H-benzo[d]imidazol-4-yl)-3-(2H-tetrazol-5-yl)benzene-1,2-disulfonamide | 549 |

| EX No. | SM | Structure | Name | LC/MS [M + H]+ |
|---|---|---|---|---|
| 445 | | 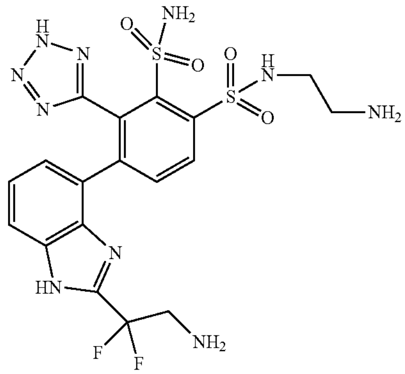 [SMILES: NCCNS(=O)(=O)c1ccc(-c2cccc3[nH]c(C(F)(F)CN)nc23)c(-c2nn[nH]n2)c1S(N)(=O)=O] | 4-(2-(2-amino-1,1-difluoroethyl)-1H-benzo[d]imidazol-4-yl)-N1-(2-aminoethyl)-3-(2H-tetrazol-5-yl)benzene-1,2-disulfonamide | 543 |
| 446 | | 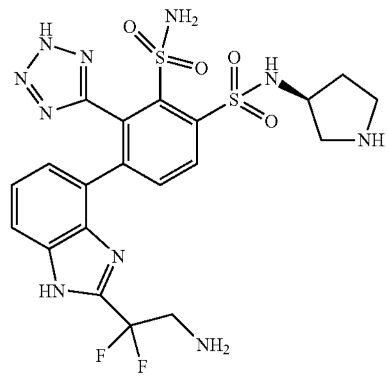 [SMILES: NCC(F)(F)c1nc2c(-c3ccc(S(=O)(=O)N[C@H]4CCNC4)c(S(N)(=O)=O)c3-c3nn[nH]n3)cccc2[nH]1] | (S)-4-(2-(2-amino-1,1-difluoroethyl)-1H-benzo[d]imidazol-4-yl)-N1-(pyrrolidin-3-yl)-3-(2H-tetrazol-5-yl)benzene-1,2-disulfonamide | 569 |

Example 447

2-Amino-N-(2-aminoethyl)-4'-(N-(2-aminoethyl) sulfamoyl)-5-chloro-3'-sulfamoyl-2'-(2H-tetrazol-5-yl)-[1,1'-biphenyl]-3-carboxamide

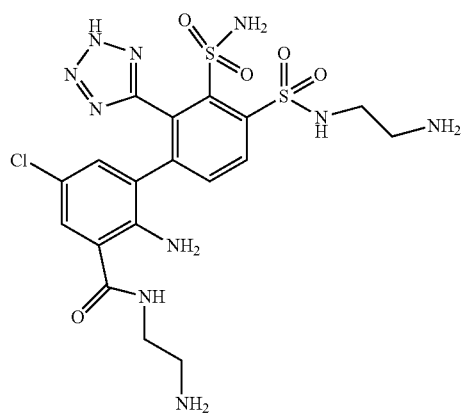 [SMILES: NCCNC(=O)c1cc(Cl)cc(-c2ccc(S(=O)(=O)NCCN)c(S(N)(=O)=O)c2-c2nn[nH]n2)c1N]

Step A: Methyl 2-amino-3'-(N,N-bis(4-methoxyben-zyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-carboxylate A suspension of 3-iodo-N,N-bis(4-methoxybenzyl)-2-(2-(4-methoxybenzyl)-2H-tetrazol-5-yl)-6-((2-(trimethylsilyl) ethyl)sulfonyl)benzenesulfonamide (7 g, 7.99 mmol), methyl 2-amino-3-(4,4,5,5-tetramethyl-1,3,2-dioxaborolan-2-yl)benzoate (6.64 g, 23.98 mmol), tetrakis(triphenylphosphine)palladium(0) (0.924 g, 0.799 mmol) and sodium carbonate (2.54 g, 23.98 mmol) in dioxane (120 ml) and water (40 ml) was degassed and heated at 80° C. for 17 hours. The mixture was diluted with AcOEt. The organic layer was washed with brine, dried (MgSO4) and concentrated. The residue was purified by ISCO column (220 g, 0-30%, 30%, 30%-100% EtOAc in Hexane). LC/MS [M+H]+: 899.53.

Step B: 2-Amino-3'-(N,N-bis(4-methoxybenzyl) sulfamoyl)-2'-(2-(4-methoxybenzyl)-2H-tetrazol-5-yl)-4'-((2-(trimethylsilyl)ethyl)sulfonyl-[1,1'-biphenyl]-3-carboxylic acid To a solution of methyl 2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-carboxylate (1.8 g, 2.002 mmol) in THF (20.00 ml) and MeOH (20 ml) was added LiOH (10.01 ml, 20.02 mmol) with stirring at room temperature. The resulting solution was warmed to room temperature and stirred overnight. The mixture was diluted with EtOAc (100 ml). The organic layer was separated, washed with KHSO4 aqueous and brine, dried (MgSO4) and concentrated. The crude material was directly used in the next step. LC/MS [M+H]+: 885.52

Step C: tert-Butyl (2-(2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl-[1,1'-biphenyl]-3-carboxamido)ethyl)carbamate To a solution of N1-((ethylimino)methylene)-N3,N3-dimethylpropane-1,3-diamine hydrochloride (0.650 g, 3.39 mmol), 2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-carboxylic acid (1.5 g, 1.695 mmol) and tert-butyl (2-aminoethyl)carbamate (0.543 g, 3.39 mmol) in DCM (30 ml) was added N,N-dimethylpyridin-4-amine (0.207 g, 1.695 mmol) at room temperature. The mixture was stirred at room temperature for 3 hours, diluted with ether (80 ml). The organic layer was separated, washed with KHSO$_4$ aqueous and brine, dried (MgSO$_4$) and concentrated. The crude material was used directly in the next step. LC/MS [M+H]+: 1027.73

Step D: 2'-Amino-3-(N,N-bis(4-methoxybenzyl)sulfamoyl)-3'-((2-((tert-butoxycarbonyl)amino)ethyl)carbamoyl)-2-(2-(4-methoxybenzyl)-2H-tetrazol-5-yl)-[1,1'-biphenyl]-4-sulfinic acid A solution of tert-butyl (2-(2-amino-3'-(N,N-bis(4-methoxybenzyl)sulfamoyl)-2'-(2-(4-methoxybenzyl)-2H-tetrazol-5-yl)-4'-((2-(trimethylsilyl)ethyl)sulfonyl)-[1,1'-biphenyl]-3-ylcarboxamido)ethyl)carbamate (1.73 g, 1.684 mmol) in THF (50 ml) was stirred with tetrabutylammonium fluoride (6.74 ml, 6.74 mmol) at room temp. under N2 for 0.5 hour. The mixture was diluted with AcOEt. The organic layer was separated, washed with KHSO$_4$ aqueous twice and brine, dried over MgSO$_4$ and concentrated. The crude material was directly used in the next step. LC/MS [M+H]+: 927.59.

Step E: tert-Butyl (2-(2-amino-3'-(N,N-bis(4-methoxybenzyl)sulfamoyl)-4'-(N-(2-((tert-butoxycarbonyl)amino)ethyl)sulfamoyl)-5-chloro-2'-(2-(4-methoxybenzyl)-2H-tetrazol-5-yl)-[1,1'-biphenyl]-3-carboxamido)ethyl)carbamate To a solution of 2'-amino-3-(N,N-bis(4-methoxybenzyl)sulfamoyl)-3'-((2-((tert-butoxycarbonyl)amino)ethyl)carbamoyl)-2-(2-(4-methoxybenzyl)-2H-tetrazol-5-yl)-[1,1'-biphenyl]-4-sulfinic acid (0.8 g, 0.863 mmol), tert-butyl (2-aminoethyl)carbamate (0.415 g, 2.59 mmol) and triethylamine (0.361 ml, 2.59 mmol) in THF (20 ml) was added NCS (0.346 g, 2.59 mmol) at 0° C. under nitrogen. The mixture was stirred at the same temperature for 30 minutes. The reaction mixture was diluted with ether (60 ml). The organic layer was separated, washed with 1 M Na$_2$CO$_3$, KHSO$_4$ aqueous and brine, dried (MgSO$_4$) and concentrated. LC/MS [M+H]+:1085.75. The residue was purified by column chromatography (80 g ISCO, 0-40%, 40%, then 40-100% EtOAc in Hexane). The purified compound showed LC/MS [M+H]+:1119.79: the excess of NCS was reacted in column with tert-butyl (2-(2-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxamido)ethyl)carbamate to form tert-butyl (2-(2-amino-3'-(N,N-bis(4-methoxybenzyl)sulfamoyl)-4'-(N-(2-((tert-butoxycarbonyl)amino)ethyl)sulfamoyl)-5-chloro-2'-(2-(4-methoxybenzyl)-2H-tetrazol-5-yl)-[1,1'-biphenyl]-3-carboxamido)ethyl)carbamate.

Step F: 2-Amino-N-(2-aminoethyl)-4'-(N-(2-aminoethyl)sulfamoyl)-5-chloro-3'-sulfamoyl-2'-(2H-tetrazol-5-yl-[1,1'-biphenyl]-3-carboxamide tert-Butyl (2-(2-amino-3'-(N,N-bis(4-methoxybenzyl)sulfamoyl)-4'-(N-(2-((tert-butoxycarbonyl)amino)ethyl)sulfamoyl)-5-chloro-2'-(2-(4-methoxybenzyl)-2H-tetrazol-5-yl)-[1,1'-biphenyl]-3-carboxamido)ethyl)carbamate (0.41 g, 0.366 mmol) was dissolved in DCM (20 ml) and stirred with 5 ml TFA in the presence of 0.2 ml anisole for 3 hours. The volatiles were removed under reduced pressure. The residue was separated on an ion-exchange column (washed with methanol first, then washed with 7N NH$_3$ in methanol to collect the desired product). The compound from the ion-exchange column was heated at 90° C. in TFA (10 ml) in a sealed tube for 60 minutes. TFA was removed, and the crude material was purified by Gilson (5-47% AcCN in water with 0.05% TFA) to give a mixture of 2-amino-N-(2-aminoethyl)-4'-(N-(2-aminoethyl)sulfamoyl)-5-chloro-3'-sulfamoyl-2'-(2H-tetrazol-5-yl-[1,1'-biphenyl]-3-carboxamide and N1-(2-aminoethyl)-4-(3-(2-aminoethyl)-6-chloro-4-oxo-2-(trifluoromethyl)-3,4-dihydroquinazolin-8-yl)-3-(2H-tetrazol-5-yl)benzene-1,2-disulfonamide. The solution was concentrated. The residue was separated by preparative TLC (1:1 DCM:7N NH3 in methanol). LC/MS [M+H]+: 559.38 and 637.43.

Example 448

4-(2-amino-1H-benzo[d]imidazol-4-yl)-N$^1$-((1R,2R)-2-aminocyclopropyl)-3-(1H-tetrazol-5-yl)benzene-1,2-disulfonamide

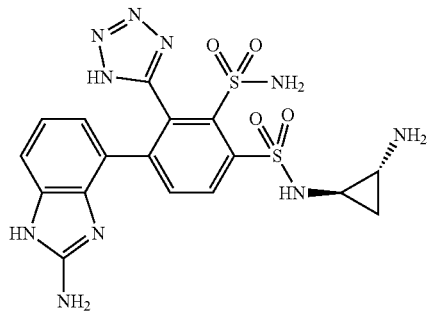 [SMILES: Nc1nc2c(-c3ccc(S(=O)(=O)N[C@@H]4C[C@H]4N)c(S(N)(=O)=O)c3-c3nnn[nH]3)cccc2[nH]1]

Step A: tert-butyl 4-(3-(N,N-bis(4-methoxybenzyl)sulfamoyl)-4-((((1R,2R)-2-((tert-butoxycarbonyl)amino)cyclopropyl)amino)sulfonyl)-2-(1-(4-methoxybenzyl)-1H-tetrazol-5-yl)phenyl)-2-(bis(tert-butoxycarbonyl)amino)-1H-benzo[d]imidazole-1-carboxylate and tert-butyl 4-(3-(N,N-bis(4-methoxybenzyl)sulfamoyl)-4-((((1R,2R)-2-((tert-butoxycarbonyl)amino)cyclopropyl)amino)sulfonyl)-2-(2-(4-methoxybenzyl)-1H-tetrazol-5-yl)phenyl)-2-(bis(tert-butoxycarbonyl)amino)-1H-benzo[d]imidazole-1-carboxylate To a solution of tert-butyl 4-(3-(N,N-bis(4-methoxybenzyl)sulfamoyl)-2-(1-(4-methoxybenzyl)-1H-tetrazol-5-yl)-4-((2-(trimethylsilyl)ethyl)sulfonyl)phenyl)-2-(bis(tert-butoxycarbonyl)amino)-1H-benzo[d]imidazole-1-carboxylate and tert-butyl 4-(3-(N,N-bis(4-methoxybenzyl)sulfamoyl)-2-(2-(4-methoxybenzyl)-1H-tetrazol-5-yl)-4-((2-(trimethylsilyl)ethyl)sulfonyl)phenyl)-2-(bis(tert-butoxycarbonyl) amino)-1H-benzo[d]imidazole-1-carboxylate (0.2 g, 0.169 mmol) in THF (10 ml) was added tetrabutylammonium fluoride (0.372 ml, 0.372 mmol) (1.0 M in THF) at 0° C. under $N_2$. The reaction mixture was diluted with 10 mL of EtOAc, washed with brine, dried over MgSO4, and concentrated. The residue was dissolved in 20 mL of DCM, followed by sequential addition of tert-butyl (((1R,2R)-2-aminocyclopropyl)carbamate (0.044 g, 0.254 mmol), triethylamine (0.034 g, 0.339 mmol), N,N-dimethylpyridin-4-amine (4.14 mg, 0.034 mmol) and 1-chloropyrrolidine-2,5-dione (0.045 g, 0.339 mmol). The reaction mixture was concentrated and chromatographed over silica gel eluting with 0-10% Methanol in DCM to give the title compounds. [M+H]$^+$: 1251.56.

Step B: 4-(2-amino-1H-benzo[d]imidazol-4-yl)-$N^1$-((1R,2R)-2-aminocyclopropyl)-3-(1H-tetrazol-5-yl) benzene-1,2-disulfonamide To the solution of tert-butyl 4-(3-(N,N-bis(4-methoxybenzyl)sulfamoyl)-4-((((1R,2R)-2-((tert-butoxycarbonyl) amino)cyclopropyl)amino)sulfonyl)-2-(1-(4-methoxybenzyl)-1H-tetrazol-5-yl)phenyl)-2-(bis(tert-butoxycarbonyl) amino)-1H-benzo[d]imidazole-1-carboxylate and tert-butyl 4-(3-(N,N-bis(4-methoxybenzyl)sulfamoyl)-4-((((1R,2R)-2-((tert-butoxycarbonyl)amino)cyclopropyl)amino)sulfonyl)-2-(2-(4-methoxybenzyl)-1H-tetrazol-5-yl)phenyl)-2-(bis(tert-butoxycarbonyl)amino)-1H-benzo[d]imidazole-1-carboxylate (98 mg, 0.078 mmol) in DCM (0.5 mL) was added anisole (85 mg, 0.783 mmol) and TFA (893 mg, 7.83 mmol) at 0° C. The reaction mixture was stirred at 0° C. for 30 minutes. After removing the volatile, the residue was treated with SCX ion exchange column (load sample and rinse with MeOH, rinse out product with 7 N amonia in MeOH) to give a free amine. The residue was dissolved in TFA (893 mg, 7.83 mmol). The resulting mixture was stirred at 80° C. for 0.5 hour. After removing the volatile the residue was purified by reverse phase HPLC (0-30% ACN/water as eluent, 0.05% ammonium hydroxide as additive) to give the desired product. LC/MS [M+H]$^+$: 491.37.

Example 449

4-(2-amino-1H-benzo[d]imidazol-4-yl)-$N^1$-(2-aminoethyl)-$N^1$-methyl-3-(2H-tetrazol-5-yl)benzene-1,2-disulfonamide

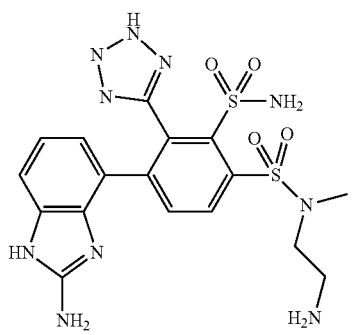 [SMILES: CN(CCN)S(=O)(=O)c1ccc(-c2cccc3[nH]c(N)nc23)c(C2=NNNN2)c1S(N)(=O)=O]

This compound was prepared in an analogous fashion to EXAMPLE 448, starting from tert-butyl (2-(methylamino) ethyl)carbamate. LC/MS [M+H]$^+$: 493.38.

Example 450

(R)-2-Amino-N-(2-aminoethyl)-5-chloro-4'-(N-(pyrrolidin-3-yl)sulfamoyl)-3'-sulfamoyl-2'-(2H-tetrazol-5-yl-[1,1'-biphenyl]-3-carboxamide

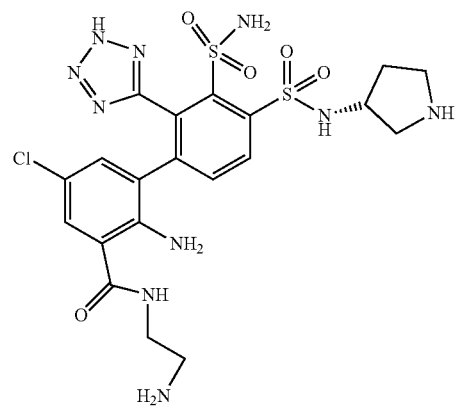

This compound was prepared follow the same procedure for EXAMPLE 447 using tert-butyl (R)-3-aminopyrrolidine-1-carboxylate to build the sulfonamide. LC/MS [M+H]+: 586.

Example 451

4-Amino-N-(2-aminoethyl)-4'-(N-(2-aminoethyl) sulfamoyl)-3'-sulfamoyl-2'-(2H-tetrazol-5-yl)-[1,1'-biphenyl]-3-carboxamide

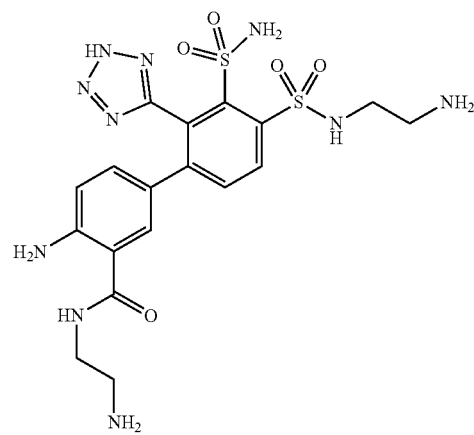 [SMILES: NCCNC(=O)c1cc(-c2ccc(S(=O)(=O)NCCN)c(S(N)(=O)=O)c2-c2nn[nH]n2)ccc1N]

Step A: Methyl 4-amino-3'-(N,N-bis(4-methoxybenzyl)sulfamoyl)-4'-(N-(2-((tert-butoxycarbonyl) amino)ethyl)sulfamoyl)-2'-(2-(4-methoxybenzyl)-2H-tetrazol-5-yl)-[1,1'-biphenyl]-3-carboxylate tert-Butyl (2-((2-(N,N-bis(4-methoxybenzyl)sulfamoyl)-4-iodo-3-(2-(4-methoxybenzyl)-2H-tetrazol-5-yl)phenyl) sulfonamido)ethyl)carbamate (1 g, 1.071 mmol), tetrakis (triphenylphosphine)palladium(0) (0.025 g, 0.021 mmol), sodium carbonate (0.34 g, 3.21 mmol) and methyl 2-amino-5-(4,4,5,5-tetramethyl-1,3,2-dioxaborolan-2-yl)benzoate (0.891 g, 3.21 mmol) were added to a 50 ml flask equipped with a stir bar and a reflux condenser. The flask was then put under nitrogen and solvent was added. The reaction was stirred overnight at 80° C. The reaction was diluted with ethyl acetate and washed with water. The organic layer was dried with magnesium sulfate and the solvent removed to give a sludge which was purified via column (ethyl acetate in hexane 0-30 hold 30-100%) to give the title compound. LC/MS [M+H]+: 958

Step B: 4-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid Methyl 4-amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylate (1 g, 1.025 mmol) was dissolved in methanol and dioxane and 1M LiOH (5.22 ml, 5.22 mmol) was added and stirred at 70° C. overnight. The solution was acidified with 2M HCl and the organic solvent was removed under vacuum. The organics were then extracted with ethyl acetate, dried and the solvent was removed to give a solid. LC/MS [M+H]+: 943.

Step C: tert-Butyl (2-((4'-amino-3-(N,N-bis(4-methoxybenzyl)sulfamoyl)-3'-((2-((tert-butoxycarbonyl)amino)ethyl)carbamoyl)-2-(2-(4-methoxybenzyl)-2H-tetrazol-5-yl)-[1,1'-biphenyl])-4-sulfonamido)ethyl)carbamate 4-Amino-3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-carboxylic acid (0.13 g, 0.138 mmol), tert-butyl (2-aminoethyl)carbamate (0.055 g, 0.345 mmol), N,N-dimethylpyridin-4-amine (0.025 g, 0.207 mmol), N1-((ethylimino)methylene)-N3,N3-dimethylpropane-1,3-diamine (0.053 g, 0.345 mmol) were added to a 50 ml flask with 20 ml of DCM with the exception of N,N-dimethylpyridin-4-amine which was added after one minute of stirring. The solution was stirred at room temperature for 2 hours. Then the reaction solution was washed with KHSO₄ and dried with magnesium sulfate. The solvent was removed under vacuum to give the product which was carried forward for the next step. LC/MS [M+H]+: 1086

Step D: 4-Amino-N-(2-aminoethyl)-4'-(N-(2-aminoethyl)sulfamoyl)-3'-sulfamoyl-2'-(2H-tetrazol-5-yl)-[1,1'-biphenyl]-3-carboxamide tert-Butyl (2-((4'-amino-3-(N,N-bis(4-methoxybenzyl)sulfamoyl)-3'-((2-((tert-butoxycarbonyl)amino)ethyl)carbamoyl)-2-(2-(4-methoxybenzyl)-2H-tetrazol-5-yl)-[1,1'-biphenyl])-4-sulfonamido)ethyl)carbamate (0.15 g, 0.138 mmol) was dissolved in 10 ml of DCM to which 3 drops of anisole were added. After this, 2 ml of TFA were added and the solution was stirred at room temp. for two hours. The solvent was removed, toluene was added, and the solvent was removed again. 5 ml of TFA were added and the reaction was stirred at 80° C. for 1 hour. The solvent was removed to give the crude product as a sludge which was purified via RP HPLC Gilson (3-37% water in acetonitrile with 0.05% NH₄OH) to give the title compound. LC/MS [M+H]+: 263 (dication).

Example 452

2-Amino-N-(4'-(N-(2-aminoethyl)sulfamoyl)-3'-sulfamoyl-2'-(2H-tetrazol-5-yl-[1,1'-biphenyl]-2-yl)acetamide

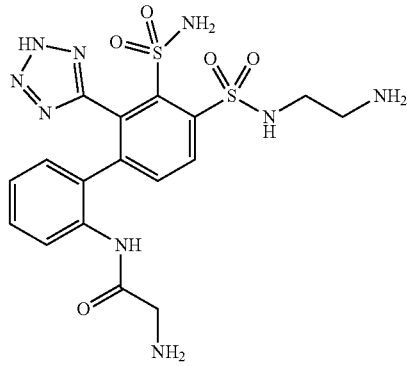 [SMILES: NCCNS(=O)(=O)c1ccc(-c2ccccc2NC(=O)CN)c(-c2nn[nH]n2)c1S(N)(=O)=O]

Step A: tert-Butyl (2-((2'-amino-3-(N,N-bis(4-methoxybenzyl)sulfamoyl)-2-(2-(4-methoxybenzyl)-2H-tetrazol-5-yl-[1,1'-biphenyl])-4-sulfonamido)ethyl)carbamate Sodium carbonate (0.17 g, 1.606 mmol), tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (0.50 g, 0.535 mmol), (2-aminophenyl)boronic acid (0.220 g, 1.606 mmol), and tetrakis(triphenylphosphine)palladium(0) (0.0069 g, 0.0054 mmol) were added to a 50 ml flask equipped with a stir bar and a reflux condenser. The flask was then put under nitrogen and solvent was added. The reaction was stirred overnight at 80° C. The reaction was diluted with ethyl acetate and washed with water. The organic layer was dried with magnesium sulfate and the solvent removed to give a sludge which was purified via column (ethyl acetate in hexane 0-30 hold 30-100%) to give the pure product as a solid. LC/MS [M+H]+: 899

Step B: tert-Butyl (2-((3-(N,N-bis(4-methoxybenzyl)sulfamoyl)-2'-(2-((tert-butoxycarbonyl)amino)acetamido)-2-(2-(4-methoxybenzyl)-2H-tetrazol-5-yl)-[1,1'-biphenyl])-4-sulfonamido)ethyl)carbamate 2-((tert-butoxycarbonyl)amino)acetic acid (0.146 g, 0.834 mmol), N1-((ethylimino)methylene)-N3,N3-dimethylpropane-1,3-diamine (0.13 g, 0.834 mmol), and tert-butyl (2-(2'-amino-3-(N,N-bis(4-methoxybenzyl)sulfamoyl)-2-(2-(4-methoxybenzyl)-2H-tetrazol-5-yl-[1,1'-biphenyl]-4-ylsulfonamido)ethyl)carbamate (0.25 g, 0.278 mmol) were added to a 50 ml flask with 25 ml of DCM with the exception of N,N-dimethylpyridin-4-amine (0.051 g, 0.417 mmol), which was added after one minute of stirring. The solution was stirred at room temperature over the weekend. The reaction solution was washed with KHSO₄ and dried with magnesium sulfate. The solvent was removed to give a liquid that was purified by column chromatography to give the pure product LC/MS [M+H]+: 1056

Step C: 2-Amino-N-(4'-(N-(2-aminoethyl)sulfamoyl)-3'-sulfamoyl-2'-(2H-tetrazol-5-yl-[1,1'-biphenyl]-2-yl)acetamide tert-Butyl (2-((3-(N,N-bis(4-methoxybenzyl)sulfamoyl)-2'-(2-((tert-butoxycarbonyl)amino)acetamido)-2-(2-(4-methoxybenzyl)-2H-tetrazol-5-yl)-[1,1'-biphenyl])-4-sulfonamido)ethyl)carbamate (0.206 g, 0.195 mmol) was dissolved in 10 ml of DCM to which 3 drops of anisole were added. 2 ml of TFA were added and the solution was stirred at room temperature for two hours. The solvent was removed, toluene was added, and the solvent was removed again. 5 ml of TFA were added and the reaction was stirred at 80° C. for 1 hour. The solvent was removed to give the crude product as a sludge which was purified via RP HPLC Gilson (3-37% water in acetonitrile with 0.05% NH$_4$OH) to give a solid. LC/MS [M+H]+: 248 (dication).

Example 453

(S)-2,3-Diamino-N-(4'-(N-(2-aminoethyl)sulfamoyl)-3'-sulfamoyl-2'-(2H-tetrazol-5-yl)-[1,1'-biphenyl]-3-yl)propanamide

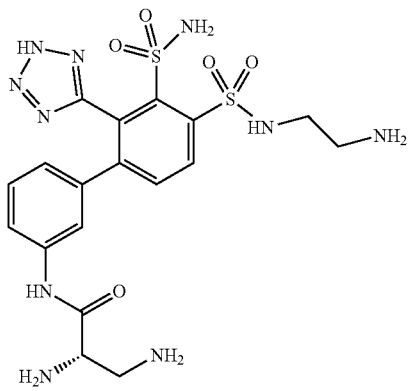 [SMILES: NCCNS(=O)(=O)c1ccc(-c2cccc(NC(=O)[C@@H](N)CN)c2)c(-c2nn[nH]n2)c1S(N)(=O)=O]

Step A: tert-Butyl (2-((3'-amino-3-(N,N-bis(4-methoxybenzyl)sulfamoyl)-2-(2-(4-methoxybenzyl)-2H-tetrazol-5-yl-[1,1'-biphenyl])-4-sulfonamido)ethyl)carbamate Sodium carbonate (0.34 g, 3.21 mmol), tert-Butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (1 g, 1.071 mmol), (3-aminophenyl)boronic acid (0.440 g, 3.21 mmol), and tetrakis(triphenylphosphine)palladium(0) (0.012 g, 0.0107 mmol) were added to a 100 ml flask equipped with a stir bar and a reflux condenser. The flask was put under nitrogen and solvent was added. The reaction was stirred for 5 hours at 80° C. The reaction was diluted with ethyl acetate and washed with water. The organic layer was dried with magnesium sulfate and the solvent removed to give a foam which was purified via column (ethyl acetate in hexanes 0-30 hold 30-100%) to give a solid LC/MS [M+H]+: 899.

Step B: di-tert-Butyl (3-((3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-yl)amino)-3-oxopropane-1,2-diyl)(S)-dicarbamate (S)-2,3-bis((tert-butoxycarbonyl)amino)propanoic acid (0.169 g, 0.556 mmol), N1-((ethylimino)methylene)-N3,N3-dimethylpropane-1,3-diamine (0.080 g, 0.556 mmol) and tert-butyl (2-(3'-amino-3-(N,N-bis(4-methoxybenzyl)sulfamoyl)-2-(2-(4-methoxybenzyl)-2H-tetrazol-5-yl)-[1,1'-biphenyl]-4-ylsulfonamido)ethyl)carbamate (0.2 g, 0.222 mmol) were added to a 50 ml flask with 25 ml of DCM with the exception of N,N-dimethylpyridin-4-amine (0.041 g, 0.334 mmol), which was added after one minute of stirring. The solution was stirred at room temperature for 2 hours. The reaction solution was washed with KHSO$_4$ and dried with magnesium sulfate. The solvent was removed to give an oil. LC/MS [M+H]+: 1186

Step C: (S)-2,3-Diamino-N-(4'-(N-(2-aminoethyl)sulfamoyl)-3'-sulfamoyl-2'-(2H-tetrazol-5-yl)-[1,1'-biphenyl]-3-yl)propanamide Di-tert-butyl (3-((3'-(N,N-bis(4-methoxybenzyl)sulfamoyl)-4'-(N-(2-((tert-butoxycarbonyl)amino)ethyl)sulfamoyl)-2'-(2-(4-methoxybenzyl)-2H-tetrazol-5-yl)-[1,1'-biphenyl]-3-yl)amino)-3-oxopropane-1,2-diyl)(S)-dicarbamate (0.263 g, 0.222 mmol) was dissolved in 10 ml of DCM to which 3 drops of anisole were added. 2 ml of TFA were then added and the solution was stirred at room temperature for two hours. The solvent was removed, toluene was added, and the solvent was removed again. 5 ml of TFA were added and the reaction was stirred at 80° C. for 1 hour. The solvent was removed to give the crude product as a sludge. LC/MS [M+H]+: 263 and 291. The product was purified with RP HPLC Gilson (3-37% water in acetonitrile with 0.05% NH$_4$OH) to give the product as a solid.

The compound in the Table below was synthesized using the procedure described above and the indicated carboxylic acid.

| EX No. | SM | Structure | Name | LC/MS [M + H]+ |
|---|---|---|---|---|
| 454 | HO-C(=O)-CH(NHBoc)-CH$_2$-OH | (structure shown) | (R)-2-amino-N-(4'-(N-(2-aminoethyl)sulfamoyl)-3'-sulfamoyl-2'-(2H-tetrazol-5-yl)-[1,1'-biphenyl]-3-yl)-3-hydroxypropanamide | 526 |

Example 455

N1-(2-Aminoethyl)-4-(1,2,3,4-tetrahydroquinolin-5-yl)-3-(2H-tetrazol-5-yl)benzene-1,2-disulfonamide

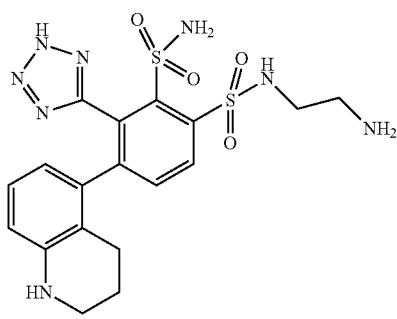 [SMILES: NCCNS(=O)(=O)c1ccc(-c2cccc3c2CCCN3)c(-c2nn[nH]n2)c1S(N)(=O)=O]

Step A: 5-(4,4,5,5-tetramethyl-1,3,2-dioxaborolan-2-yl)-1,2,3,4-tetrahydroquinoline A mixture of 5-bromo-1,2,3,4-tetrahydroquinoline (1.5 g, 7.07 mmol), 4,4,4',4',5,5,5',5'-octamethyl-2,2'-bi(1,3,2-dioxaborolane) (5.39 g, 21.22 mmol), PCy3 PdG2 (0.835 g, 1.415 mmol) and potassium acetate (2.082 g, 21.22 mmol) in dioxane (150 ml) was degassed and heated at 80° C. for 17 hours. The mixture was filtered and to the filtrate was added 100 ml water, and ether (100 ml). The organic was separated, dried (MgSO4), and concentrated. LC/MS [M+H]+: 260 (dication).

Step B: N,N-bis(4-methoxybenzyl)-2-(2-(4-methoxybenzyl)-2H-tetrazol-5-yl)-3-(1,2,3,4-tetrahydroquinolin-5-yl)-6-((2-(trimethylsilyl)ethyl)sulfonyl)benzenesulfonamide A suspension of 5-(4,4,5,5-tetramethyl-1,3,2-dioxaborolan-2-yl)-1,2,3,4-tetrahydroquinoline (1.775 g, 6.85 mmol), 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (3 g, 3.43 mmol), tetrakis(triphenylphosphine)palladium(0) (0.396 g, 0.343 mmol) and sodium carbonate (1.089 g, 10.28 mmol) in 1,4-dioxane (80 ml) and water (25.00 ml) was degassed and heated at 80° C. for 17 hours. The mixture was diluted with AcOEt. The organic layer was separated, washed with brine, dried (MgSO4) and concentrated. The crude material was purified by column (80 g, 0-30% EtAOc, then 30% EtOAc and 30-100% EtOAc in Hexane). LC/MS [M+H]+: 811.85

Step C: 2-(N,N-Bis(4-methoxybenzyl)sulfamoyl)-3-(2-(4-methoxybenzyl)-2H-tetrazol-5-yl)-4-(1,2,3,4-tetrahydroquinolin-5-yl)benzenesulfinic acid A solution of N,N-bis(4-methoxybenzyl)-2-(2-(4-methoxybenzyl)-2H-tetrazol-5-yl)-3-(1,2,3,4-tetrahydroquinolin-5-yl)-6-((2-(trimethylsilyl)ethyl)sulfonyl)benzenesulfonamide (2.3 g, 2.61 mmol) and THF (100 ml) was stirred with tetrabutylammonium fluoride (7.83 ml, 7.83 mmol) at room temp. under N2 for 0.5 hour. The mixture was diluted with AcOEt, washed with KHSO4 aqueous and brine, dried over MgSO4 and concentrated. The crude material was directly used in the next step LC/MS [M+H]+: 781.

Step D: tert-Butyl (2-((2-(N,N-bis(4-methoxybenzyl)sulfamoyl)-3-(2-(4-methoxybenzyl)-2H-tetrazol-5-yl)-4-(1,2,3,4-tetrahydroquinolin-5-yl)phenyl)sulfonamido)ethyl)carbamate To a solution of 2-(N,N-bis(4-methoxybenzyl)sulfamoyl)-3-(2-(4-methoxybenzyl)-2H-tetrazol-5-yl)-4-(1,2,3,4-tetrahydroquinolin-5-yl)benzenesulfinic acid (0.2 g, 0.256 mmol), and tert-butyl (2-aminoethyl)carbamate (0.123 g, 0.768 mmol) in THF (30 ml) was added NCS (0.103 g, 0.768 mmol) at room temp. The mixture was stirred for 30 minutes. The reaction mixture was stirred with Na2S2O3 aqueous for 30 minutes and diluted with ether 60 ml. The organic layer was separated, washed with KHSO4 aqueous and brine, dried over MgSO4 and concentrated. LC/MS [M+H]+: 939.94.

Step E: N1-(2-aminoethyl)-4-(1,2,3,4-tetrahydroquinolin-5-yl)-3-(2H-tetrazol-5-yl)benzene-1,2-disulfonamide tert-butyl (2-(2-(N,N-bis(4-methoxybenzyl)sulfamoyl)-3-(2-(4-methoxybenzyl)-2H-tetrazol-5-yl)-4-(1,2,3,4-tetrahydroquinolin-5-yl)phenylsulfonamido)ethyl)carbamate (0.21 g, 0.224 mmol) was dissolved in DCM (10 ml). The solution was stirred at room temp. for 2 hours with TFA (10 ml) and two drops anisole and concentrated. The residue was heated at 80° C. in 10 ml TFA for 40 minutes. TFA was removed, and the crude material was purified by Gilson (5-42% AcCN in water with 0.05% NH4OH). The solution was concentrated. Product was dried on vacuum (0.010 psi) LC/MS [M+H]+: 479.33.

Example 456

N1-(2-Aminoethyl)-4-(2-((2-aminoethyl)amino)pyridin-4-yl)-3-(2H-tetrazol-5-yl)benzene-1,2-disulfonamide

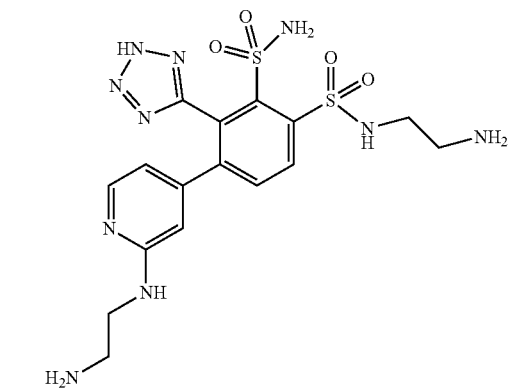 [SMILES: NCCNc1cc(-c2ccc(S(=O)(=O)NCCN)c(S(N)(=O)=O)c2-c2nn[nH]n2)ccn1]

Step A: tert-butyl (2-((4-bromopyridin-2-yl)amino)ethyl)carbamate

3-Bromo-2-fluoropyridine (3.46 g, 19.66 mmol), tert-butyl (2-aminoethyl)carbamate (3.15 g, 19.66 mmol) and K2CO3 (8.15 g, 59.0 mmol) in DMSO (40 ml) were stirred at 80° C. overnight. Excess of carbonate was filtered off, and washed with EtOAc. The mixture was diluted with water (60 ml), extracted with ether (100 ml). The extract was washed with brine, dried over MgSO4, and concentrated. The crude material was purified by column (120 g ISCO, 0-30, 30, 30-100% EtOAc in Hexane) LC/MS [M+H]+: 375.20, 373.25.

Step B: (2-((2-(((tert-Butoxycarbonyl)amino)ethyl) amino)pyridin-4-yl)boronic acid A mixture of tert-butyl (2-((4-bromopyridin-2-yl)amino) ethyl)carbamate (4.515 g, 14.28 mmol), 4,4,4',4',5,5,5',5'-octamethyl-2,2'-bi(1,3,2-dioxaborolane) (10.88 g, 42.8 mmol), PCy3 PdG2 (1.686 g, 2.86 mmol) and potassium acetate (4.20 g, 42.8 mmol) in dioxane (100 ml) was degassed and heated at 80° C. for 17 hours. The mixture was filtered, and to the filtrate was added 100 ml saturated KHSO4 aqueous, and ether (100 ml). The organic was separated, washed with brine, dried (MgSO4, and concentrated. LC/MS [M+H]+: 282.39

Step C: tert-Butyl (2-((4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)pyridin-2-yl)amino)ethyl)carbamate A suspension of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (7.45 g, 8.51 mmol), (2-((2-((tert-butoxycarbonyl)amino)ethyl)amino)pyridin-4-yl)boronic acid (7.17 g, 25.5 mmol), sodium carbonate (2.70 g, 25.5 mmol) and tetrakis(triphenylphosphine)palladium(0) (0.983 g, 0.851 mmol) in dioxane (100 ml) and water (30 ml) was degassed and heated at 80° C. for 17 hours. The mixture was diluted with EtOAc and washed with KHSO4 aqueous, and brine. The organic layer was dried (MgSO4) and concentrated. The residue was purified by ISCO (120 g, 0-30, 30, 30-100, 100% of EtOAc in Hexane). LC/MS [M+H]+: 986.09.

Step D: 2-(N,N-Bis(4-methoxybenzyl)sulfamoyl)-4-(2-((2-((tert-butoxycarbonyl)amino)ethyl)amino) pyridin-4-yl)-3-(2-(4-methoxybenzyl)-2H-tetrazol-5-yl)benzenesulfinic acid A solution of tert-Butyl (2-((4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)pyridin-2-yl) amino)ethyl)carbamate (5.6 g, 5.68 mmol) and THF (100 ml) was stirred with tetrabutylammonium fluoride (17.05 ml, 17.05 mmol) at room temp. for 0.5 hour. The mixture was diluted with AcOEt, washed with KHSO4 saturated aqueous and brine, dried over MgSO4, and concentrated. LC/MS [M+H]+: 885.86

Step E: tert-Butyl (2-((2-(N,N-bis(4-methoxybenzyl)sulfamoyl)-4-(2-((2-((tert-butoxycarbonyl) amino)ethyl)amino)pyridin-4-yl)-3-(2-(4-methoxybenzyl)-2H-tetrazol-5-yl)phenyl)sulfonamido)ethyl) carbamate tert-Butyl (2-aminoethyl)carbamate (0.0543, 0.339 mmol), NCS (0.0453 g, 0.339 mmol), and 2-(N,N-bis(4-methoxybenzyl)sulfamoyl)-4-(2-((2-((tert-butoxycarbonyl) amino)ethyl)amino)pyridin-4-yl)-3-(2-(4-methoxybenzyl)-2H-tetrazol-5-yl)benzenesulfinic acid (0.1 g, 0.113 mmol) were added to a 50 ml flask with 15 ml THF and stirred for 30 minutes at room temp. The reaction mixture was stirred with Na2S2O3 aqueous for 30 minutes and diluted with ethyl acetate. The organic layer was separated, washed with KHSO4 aqueous, dried over MgSO4 and concentrated to give a solid that was used in the next step. LC/MS [M+H]+: 1044

Step F: N1-(2-Aminoethyl)-4-(2-((2-aminoethyl) amino)pyridin-4-yl)-3-(2H-tetrazol-5-yl)benzene-1, 2-disulfonamide tert-Butyl (2-((2-(N,N-bis(4-methoxybenzyl)sulfamoyl)-4-(2-((2-((tert-butoxycarbonyl)amino)ethyl)amino)pyridin-4-yl)-3-(2-(4-methoxybenzyl)-2H-tetrazol-5-yl)phenyl)sulfonamido)ethyl)carbamate (0.118 g, 0.113 mmol) was dissolved in 10 ml of DCM to which 3 drops of anisole were added. 2 ml of TFA were added and the mixture was stirred at room temp. for two hours. The solvent was removed, toluene was added, and the solvent was removed again. 5 ml of TFA were added and the reaction was stirred at 80° C. for 1 hour. The solvent was removed to give the crude product as a sludge which was purified via HPLC to give a solid. LC/MS [M+H]+: 242 (dication).

The compounds in the Table below were synthesized using the procedure described above for EXAMPLE 456 and the corresnonding intermediates nrenared as described herein.

| EX No. | Structure | Name | MW | LC/MS [M + H]+ |
|---|---|---|---|---|
| 457 | 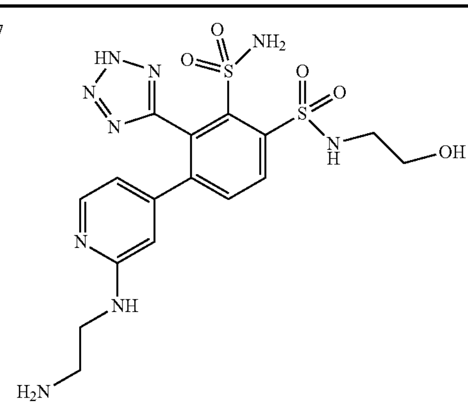 | 4-(2-((2-aminoethyl)amino)pyridin-4-yl)-N1-(2-hydroxyethyl)-3-(2H-tetrazol-5-yl)benzene-1,2-disulfonamide | 483 | 484 |

| EX No. | Structure | Name | MW | LC/MS [M + H]+ |
|---|---|---|---|---|
| 458 | 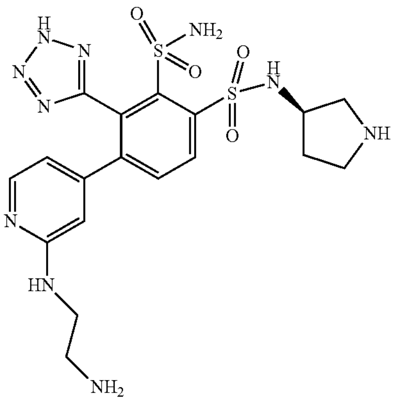 [SMILES: NCCNc1cc(-c2ccc(S(=O)(=O)N[C@@H]3CCNC3)c(S(N)(=O)=O)c2-c2nn[nH]n2)ccn1] | (R)-4-(2-((2-aminoethyl)amino)pyridin-4-yl)-N1-(pyrrolidin-3-yl)-3-(2H-tetrazol-5-yl)benzene-1,2-disulfonamide | 508 | 509 |
| 459 | 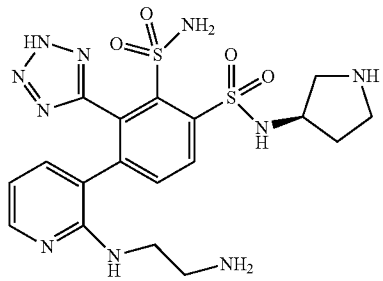 [SMILES: NCCNc1ncccc1-c1ccc(S(=O)(=O)N[C@@H]2CCNC2)c(S(N)(=O)=O)c1-c1nn[nH]n1] | (R)-4-(2-((2-Aminoethyl)amino)pyridin-3-yl)-N1-(pyrrolidin-3-yl)-3-(2H-tetrazol-5-yl)benzene-1,2-disulfonamide | 508 | 509 |
| 460 | 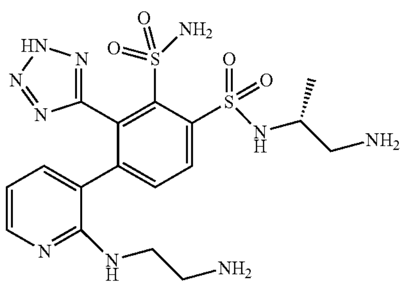 [SMILES: C[C@H](CN)NS(=O)(=O)c1ccc(-c2cccnc2NCCN)c(-c2nn[nH]n2)c1S(N)(=O)=O] | (R)-4-(2-((2-aminoethyl)amino)pyridin-3-yl)-N1-(1-aminopropan-2-yl)-3-(2H-tetrazol-5-yl)benzene-1,2-disulfonamide | 496 | 497 |

Example 461

N1-(2-Aminoethyl)-4-(2-(aminomethyl)pyridin-4-yl)-3-(2H-tetrazol-5-yl)benzene-1,2-disulfonamide

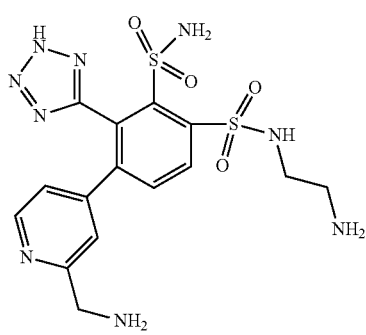 [SMILES: NCCNS(=O)(=O)c1ccc(-c2ccnc(CN)c2)c(-c2nn[nH]n2)c1S(N)(=O)=O]

Step A: (2-(((tert-butoxycarbonyl)amino)methyl)pyridin-4-yl)boronic acid

A mixture of tert-butyl ((4-bromopyridin-2-yl)methyl)carbamate (0.8 g, 2.79 mmol), 4,4,4',4',5,5,5',5'-octamethyl-2,2'-bi(1,3,2-dioxaborolane) (2.122 g, 8.36 mmol), PCy3 PdG2 (0.329 g, 0.557 mmol) and potassium acetate (0.820 g, 8.36 mmol) in dioxane (40 ml) was degassed and heated at 80° C. for 17 hours. The mixture was filtered and 100 ml saturated KHSO4 aqueous, and ether (100 ml) were added to the filtrate. The organic was separated, washed with brine, dried (MgSO4), and concentrated. LC/MS [M+H]+: 253,28.

Step B: tert-Butyl ((4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)pyridin-2-yl)methyl)carbamate A suspension of 3-iodo-N,N-bis(4-methoxybenzyl)-2-(2-(4-methoxybenzyl)-2H-tetrazol-5-yl)-6-((2-(trimethylsilyl)ethyl)sulfonyl)benzenesulfonamide (2 g, 2.283 mmol), (2-(((tert-butoxycarbonyl)amino)methyl)pyridin-4-yl)boronic acid (1.727 g, 6.85 mmol), tetrakis(triphenylphosphine)palladium(0) (0.264 g, 0.228 mmol) and sodium carbonate (0.726 g, 6.85 mmol) in dioxane (70 ml) and water (20 ml) was degassed and heated at 80° C. for 17 hours. The mixture was diluted with AcOEt and washed with brine. The organic layer was dried (MgSO$_4$) and concentrated. The residue was purified by ISCO column (80 g, 0-30%, 30%, 30-100% EtOAc in Hexane). The desired product was eluted at 100% EtOAc. LC/MS [M+H]+: 956.96.

Step C: 2-(N,N-bis(4-methoxybenzyl)sulfamoyl)-4-(2-(((tert-butoxycarbonyl)amino)methyl)pyridin-4-yl)-3-(2-(4-methoxybenzyl)-2H-tetrazol-5-yl)benzenesulfinic acid A solution of tert-butyl ((4-(3-(N,N-bis(4-methoxybenzyl)sulfamoyl)-2-(2-(4-methoxybenzyl)-2H-tetrazol-5-yl)-4-((2-(trimethylsilyl)ethyl)sulfonyl)phenyl)pyridin-2-yl) methyl)carbamate (0.6 g, 0.627 mmol) in THF (20 ml) was stirred with tetrabutylammonium fluoride (1.882 ml, 1.882 mmol) at room temp. for 0.5 hour. The mixture was diluted with AcOEt, washed with KHSO$_4$ saturated aqueous and brine, dried over MgSO$_4$, and concentrated. LC/MS [M+H]+: 856.85.

Step D: N1-(2-Aminoethyl)-4-(2-(aminomethyl) pyridin-4-yl)-3-(2H-tetrazol-5-yl)benzene-1,2-disulfonamide To a solution of tert-butyl ((4-(3-(N,N-bis(4-methoxybenzyl)sulfamoyl)-4-hydrosulfonyl-2-(2-(4-methoxybenzyl)-2H-tetrazol-5-yl)phenyl)pyridin-2-yl)methyl)carbamate (0.15 g, 0.175 mmol) and tert-butyl (2-aminoethyl)carbamate (0.112 g, 0.701 mmol) in THF (20 ml) was added NCS (0.068 g, 0.508 mmol) at room temp. The mixture was stirred for 30 minutes. The reaction mixture was stirred with Na$_2$S$_2$O$_3$ aqueous for 30 minutes and diluted with ether 60 ml. The organic layer was separated, washed with KHSO$_4$ aqueous and brine, dried over MgSO$_4$ and concentrated. LC/MS [M+H]+: 1015.11. The residue was dissolved in DCM (5 ml), and stirred at room temp. with 2 ml TFA and two drops anisole for 2 hours and concentrated. The residue was heated at 80° C. in 2 ml TFA for 40 minutes. TFA was removed, and the crude material was purified by Gilson (3-37% AcCN in water with 0.05% ammonium hydroxide). The solution was concentrated. LC/MS [M+H]+: 454.25.

Example 462

(R)-3'-(2-(aminomethyl)-1H-imidazol-4-yl)-N4-(2-aminopropyl)-2-(2H-tetrazol-5-yl-[1,1'-biphenyl]-3,4-disulfonamide

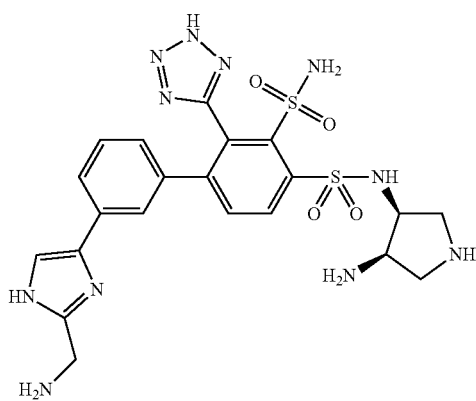 [SMILES: NCc1nc(-c2cccc(-c3ccc(S(=O)(=O)N[C@H]4CNC[C@H]4N)c(S(N)(=O)=O)c3-c3nn[nH]n3)c2)c[nH]1]

Step A: (3R,4S)-tert-butyl-3-(((benzyloxy)carbonyl) amino)-4-(3-(N,N-bis (4-methoxybenzyl) sulfamoyl)-3'-(2-(((tert-butoxycarbonyl)amino)methyl)-1H-imidazol-4-yl)-2-(2-(4-methoxybenzyl)-2H-tetrazol-5-yl-[1,1'-biphenyl]-4-ylsulfonamido) pyrrolidine-1-carboxylate To a solution of (3R,4S)-tert-butyl-3-(((benzyloxy)carbonyl)amino)-4-(2-(N,N-bis (4-methoxybenzyl)sulfamoyl)-4-iodo-3-(2H-tetrazol-5-yl)phenylsulfonamido) pyrrolidine-1-carboxylate (0.9 g, 0.81 mmol) in 1,4-dioxane (10 mL) and water (2.5 mL) was added tert-butyl ((5-(3-(4,4,5,5-tetramethyl-1,3,2-dioxaborolan-2-yl)phenyl)-1H-imidazol-2-yl) methyl)carbamate (0.5 g, 1.21 mmol), Na$_2$CO$_3$ (0.26 g, 2.43 mmol) and Pd(dppf)Cl$_2$ adduct CH$_2$Cl$_2$ (132 mg, 0.16 mmol) at room temperature. The mixture was degassed with nitrogen three times. The reaction mixture was stirred at 80° C. for 16 hours under nitrogen. The resulting mixture was quenched with water (25 mL) and extracted with EA (3×15 mL). The combined organic layers were washed with brine (3×20 mL), dried over Na$_2$SO$_4$ and filtered. The filtrate was concentrated under vacuum. The residue was purified by silica gel column chromatography, eluted with 60% EA in PE to afford the title compound: LCMS [M+1]$^+$: 1254.

Step B: 3'-(2-(Aminomethyl)-1H-imidazol-4-yl)-N4-((3S,4R)-4-aminopyrrolidin-3-yl)-2-(2H-tetrazol-5-yl-[1,1'-biphenyl]-3,4-disulfonamide To a stirred solution of (3R,4S)-tert-butyl-3-(((benzyloxy) carbonyl)amino)-4-(3-(N,N-bis(4-methoxybenzyl)sulfamoyl)-3'-(2-(((tert-butoxycarbonyl)amino) methyl)-1H-imidazol-4-yl)-2-(2-(4-methoxybenzyl)-2H-tetrazol-5-yl-[1,1'-biphenyl]-4-ylsulfonamido)pyrrolidine-1-carboxylate (0.48 g, 0.38 mmol) in DCM (5 mL) was added TFA (2 mL) at 0° C. The solution was allowed to warm to room temperature and stirred for 1 hour. The resulting solution was concentrated under vacuum. The residue was co-evaporated with anisole (3×3 mL) under vacuum and used in the next step without further purification. The crude product was dissolved in TFA (4 mL). The solution was stirred at 80° C. for 1 hour. The resulting solution was concentrated under vacuum. The crude product was purified by Prep-HPLC with the following conditions: Column: XBridge C18 OBD Prep Column 100 Å, 10 µm, 19 mm×250 mm; Mobile Phase A: water (10 mmol/L NH$_4$HCO$_3$), Mobile Phase B: ACN; Flow rate: 20 mL/min; Gradient: 5% B to 25% B in 6 min; Detector: UV 254 and 220 nm. The fractions containing desired product were combined and concentrated under vacuum to afford the title compound: LCMS [M+1]$^+$: 560; $^1$H NMR (400 MHz, CD$_3$OD+DCl): δ 8.74 (d, J=8.4 Hz, 1H), 8.08 (d, J=8.4 Hz, 1H), 8.03 (s, 1H), 7.81 (d, J=7.8 Hz, 1H), 7.66 (s, J=1.7 Hz, 1H), 7.49 (t, J=7.8 Hz, 1H), 7.21-7.17 (m, 1H), 4.65 (s, 2H), 4.63-4.59 (m, 1H), 4.26-4.21 (m, 1H), 3.93-3.88 (m, 1H), 3.73-3.68 (m, 1H), 3.60-3.55 (m, 1H), 3.51-3.46 (m, 1H).

By using the same general procedures described in Example 462, substituting the appropriate reactants and reagents, prepared as described herein or commercially available, the following compounds were synthesized and characterized by LC/MS.

| EX NO | Structure | Name | LC/MS [M + H]+ |
|---|---|---|---|
| 467 | 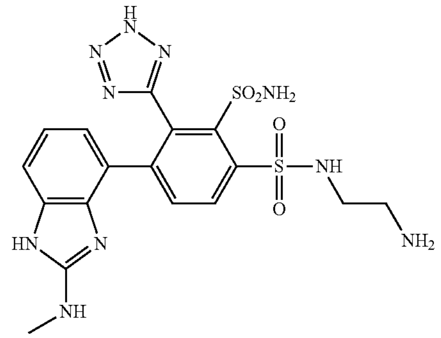 [SMILES: CNc1nc2c(-c3ccc(S(=O)(=O)NCCN)c(S(N)(=O)=O)c3-c3nn[nH]n3)cccc2[nH]1] | N1-(2-aminoethyl)-4-(2-(methylamino)-1H-benzo[d]imidazol-4-yl)-3-(2H-tetrazol-5-yl)benzene-1,2-disulfonamide | 491 |
| 468 | 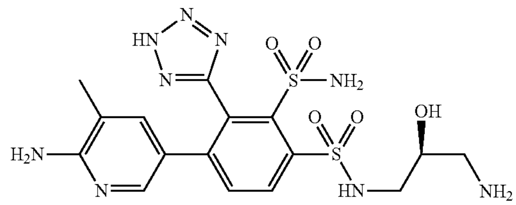 [SMILES: Cc1cc(-c2ccc(S(=O)(=O)NC[C@@H](O)CN)c(S(N)(=O)=O)c2-c2nn[nH]n2)cnc1N] | (S)-N1-(3-amino-2-hydroxypropyl)-4-(6-amino-5-methylpyridin-3-yl)-3-(2H-tetrazol-5-yl)benzene-1,2-disulfonamide | 484 |
| 469 | 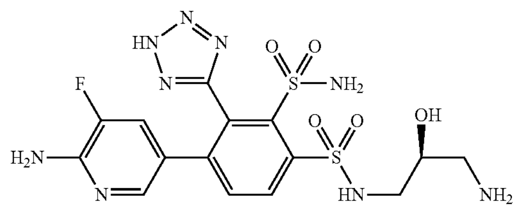 [SMILES: NC[C@H](O)CNS(=O)(=O)c1ccc(-c2cnc(N)c(F)c2)c(-c2nn[nH]n2)c1S(N)(=O)=O] | (S)-N1-(3-amino-2-hydroxypropyl)-4-(6-amino-5-fluoropyridin-3-yl)-3-(2H-tetrazol-5-yl)benzene-1,2-disulfonamide | 488 |
| 470 | 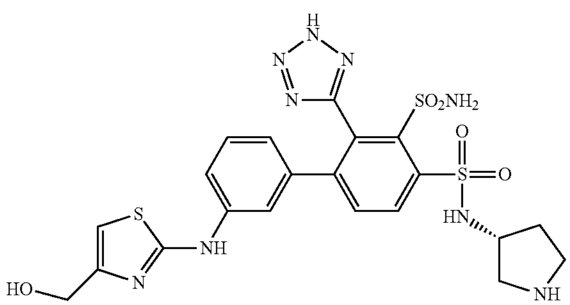 [SMILES: NS(=O)(=O)c1c(S(=O)(=O)N[C@@H]2CCNC2)ccc(-c2cccc(Nc3nc(CO)cs3)c2)c1-c1nn[nH]n1] | (R)-3'-((4-(hydroxymethyl)thiazol-2-yl)amino)-N4-(pyrrolidin-3-yl)-2-(2H-tetrazol-5-yl)-[1,1'-biphenyl]-3,4-disulfonamide | 578 |
| 472 | 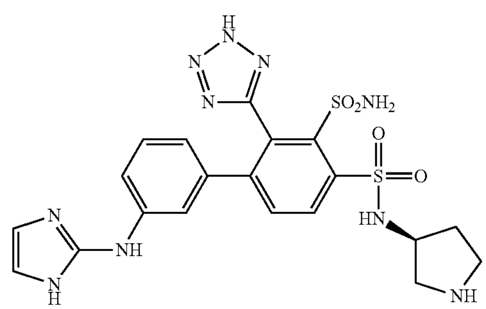 [SMILES: NS(=O)(=O)c1c(S(=O)(=O)N[C@H]2CCNC2)ccc(-c2cccc(Nc3ncc[nH]3)c2)c1-c1nn[nH]n1] | (R)-N1-(3-(aminomethyl)pyrrolidin-3-yl)-4-(6-aminopyridin-3-yl)-3-(2H-tetrazol-5-yl)benzene-1,2-disulfonamide dihydrochloride | 531 |
| 478 | 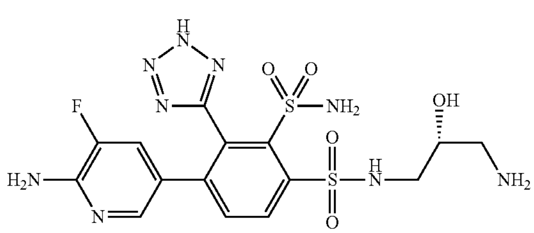 [SMILES: NC[C@@H](O)CNS(=O)(=O)c1ccc(-c2cnc(N)c(F)c2)c(-c2nn[nH]n2)c1S(N)(=O)=O] | (R)-N1-(3-amino-2-hydroxypropyl)-4-(6-amino-5-fluoropyridin-3-yl)-3-(2H-tetrazol-5-yl)benzene-1,2-disulfonamide | 488 |

| EX NO | Structure | Name | LC/MS [M + H]+ |
|---|---|---|---|
| 481 | 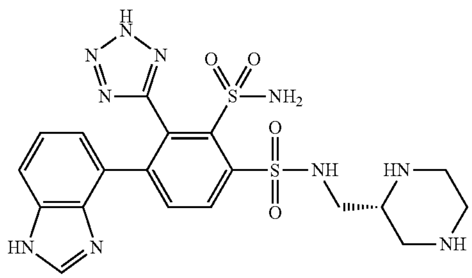 [SMILES: NS(=O)(=O)c1c(S(=O)(=O)NC[C@H]2CNCCN2)ccc(-c2cccc3[nH]cnc23)c1-c1nn[nH]n1] | (R)-4-(1H-benzo[d]imidazol-4-yl)-N1-(piperazin-2-ylmethyl)-3-(1H-tetrazol-5-yl)benzene-1,2-disulfonamide | 519 |

Example 463

(R)—N1-(3-amino-2-hydroxypropyl)-4-(2-(aminomethyl)benzo[d]thiazol-5-yl)-3-(2H-tetrazol-5-yl)benzene-1,2-disulfonamide

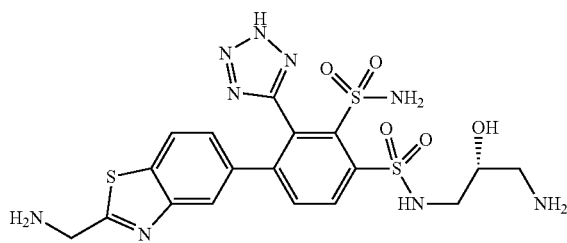 [SMILES: NCc1nc2cc(-c3ccc(S(=O)(=O)NC[C@H](O)CN)c(S(N)(=O)=O)c3-c3nn[nH]n3)ccc2s1]

Step A: (R)-tert-butyl(3-(4-(2-aminobenzo[d]thiazol-5-yl)-2-(N,N-bis(4-methoxybenzyl) sulfamoyl)-3-(2-(4-methoxybenzyl)-2H-tetrazol-5-yl)phenylsulfonamido)-2-hydroxypropyl)carbamate To a solution of (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl)carbamate (2.5 g, 2.59 mmol) in 1,4-dioxane (30 mL) and water (7 mL) was added 5-(4,4,5,5-tetramethyl-1,3,2-dioxaborolan-2-yl)benzo[d]thiazol-2-amine (1.3 g, 4.67 mmol), Na₂CO₃ (0.83 g, 7.78 mmol) and PdCl₂ (dppf) adduct CH₂Cl₂ (0.43 g, 0.52 mmol) at room temperature. The mixture was degassed with nitrogen 3 times and stirred for 12 hours at 80° C. under nitrogen. The resulting mixture was allowed to cool to room temperature, quenched with water (150 mL) and extracted with EA (3×150 mL). The combined organic layers were washed with brine (200 mL), dried over anhydrous Na₂SO₄ and filtered. The filtrate was concentrated under vacuum. The residue was purified by silica gel column chromatography, eluted with 80% EA in PE. The fractions containing desired product were combined and concentrated to afford the title compound: LCMS [M+1]+: 986.

Step B: (R)-tert-butyl(3-(2-(N,N-bis(4-methoxybenzyl)sulfamoyl)-4-(2-bromobenzo[d] thiazol-5-yl)-3-(2-(4-methoxybenzyl)-2H-tetrazol-5-yl)phenylsulfonamido)-2-hydroxypropyl)carbamate To a solution of (R)-tert-butyl (3-(4-(2-aminobenzo[d]thiazol-5-yl)-2-(N,N-bis(4-methoxybenzyl)sulfamoyl)-3-(2-(4-methoxybenzyl)-2H-tetrazol-5-yl) phenylsulfonamido)-2-hydroxypropyl)carbamate (2.0 g, 2.03 mmol) in ACN (20 mL) was added CuBr₂ (0.54 g, 2.43 mmol) and tert-butyl nitrite (0.34 g, 3.24 mmol) at 0° C. The mixture was stirred at room temperature for 1 hour. The resulting mixture was quenched with water (150 mL) and extracted with EA (3×150 mL). The combined organic layers were washed with brine (150 mL), dried over anhydrous Na₂SO₄ and filtered. The filtrate was concentrated under vacuum. The residue was purified by a silica gel column chromatography, eluting with 35% EA in PE. The fractions containing desired product were combined and concentrated to afford the title compound: LCMS [M+1]+: 1049:1051.

Step C: (R)-tert-butyl(3-(2-(N,N-bis(4-methoxybenzyl)sulfamoyl)-4-(2-cyanobenzo[d]thiazol-5-yl)-3-(2-(4-methoxybenzyl)-2H-tetrazol-5-yl)phenylsulfonamido)-2-hydroxypropyl)carbamate To a solution of (R)-tert-butyl(3-(2-(N,N-bis(4-methoxybenzyl)sulfamoyl)-4-(2-bromobenzo[d]thiazol-5-yl)-3-(2-(4-methoxybenzyl)-2H-tetrazol-5-yl)phenyl sulfonamido)-2-hydroxypropyl)carbamate (0.85 g, 0.81 mmol) in DMF (10 mL) was added Zn(CN)₂ (0.19 g, 1.62 mmol) and t-BuXPhos G3 precatalyst (0.13 g, 0.16 mmol) at room temperature. The resulting mixture was degassed with nitrogen 3 times and stirred for 1 hour at 55° C. The resulting mixture was allowed to cool to room temperature, quenched with water (100 mL) and extracted with EA (3×100 mL). The combined organic layers were washed with saturated aqueous Na₂CO₃ (2×100 mL) and FeSO₄ (2×100 mL), dried over anhydrous Na₂SO₄ and filtered. The filtrate was concentrated under vacuum. The residue was purified by silica gel column chromatography, eluting with 50% EA in PE. The fractions containing desired product were combined and concentrated to afford the title compound: LCMS [M+1]+: 996.

Step D: (R)-tert-butyl(3-(4-(2-(aminomethyl)benzo[d]thiazol-5-yl)-2-(N,N-bis(4-methoxy benzyl)sulfamoyl)-3-(2-(4-methoxybenzyl)-2H-tetrazol-5-yl)phenylsulfonamido)-2-hydroxypropyl)carbamate To a solution of (R)-tert-butyl(3-(2-(N,N-bis(4-methoxybenzyl)sulfamoyl)-4-(2-cyanobenzo[d]thiazol-5-yl)-3-(2-(4-methoxybenzyl)-2H-tetrazol-5-yl)phenyl sulfonamido)-2-hydroxypropyl)carbamate (0.54 g, 0.11 mmol) in MeOH (6 mL) was added Pd(OH)₂/C (20% wt, 0.3 g, 2.14 mmol, 20%) under nitrogen. This mixture was degassed with hydrogen three times. The mixture was stirred at 25° C. for 2 hours under hydrogen at 15 atm. The resulting mixture was filtered. The filtrate was concentrated under vacuum to afford the title compound, which was used in the next step without further purification: LCMS [M+1]$^+$: 1000.

Step E: (R)—N1-(3-amino-2-hydroxypropyl)-4-(2-(aminomethyl)benzo[d]thiazol-5-yl)-3-(2H-tetrazol-5-yl)benzene-1,2-disulfonamide The title compound was prepared as described for EXAMPLE 462, step B, using (R)-tert-butyl(3-(4-(2-(aminomethyl)benzo[d]thiazol-5-yl)-2-(N,N-bis(4-methoxy benzyl)sulfamoyl)-3-(2-(4-methoxybenzyl)-2H-tetrazol-5-yl) phenylsulfonamido)-2-hydroxypropyl)carbamate (0.34 g, 0.34 mmol) to afford crude product. The crude product was purified by Prep-HPLC with the following conditions: Column: XBridge C18 OBD Prep Column 100 Å, 10 μm, 19 mm×250 mm; Mobile Phase A: water (10 mmol/L, NH$_4$HCO$_3$), Mobile Phase B: ACN; Flow rate: 20 mL/min; Gradient: 5% B to 25% B in 8 min; Detector: UV 254 and 220 nm. The fractions containing desired product were combined and concentrated under vacuum to afford the title compound: LCMS [M+1]$^+$: 540; $^1$H NMR (400 MH$_z$, DMSO-d$_6$+DCl): δ 8.52 (d, J=7.2 Hz, 1H), 8.2-8.05 (m, 2H), 7.63 (s, 1H), 7.2 (d, J=7.2 Hz, 1H), 4.58 (s, 2H), 3.97-3.85 (m, 1H), 3.19-2.91 (m, 3H), 2.74 (t, J=10.8 Hz, 1H).

By using the same general procedures described in Example 463, substituting the appropriate reactants and reagents, prepared as described herein or commercially available, the following compounds were synthesized and characterized by LC/MS.

| EX NO | Structure | Name | LC/MS [M + H]$^+$ |
|---|---|---|---|
| 473 | 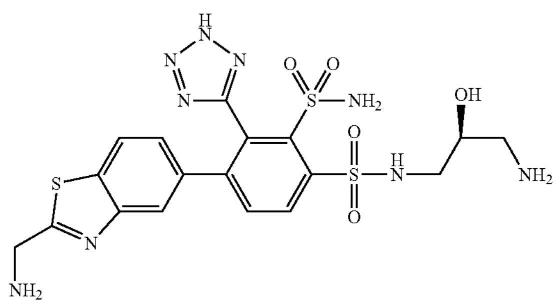 [SMILES: NCc1nc2cc(-c3ccc(S(=O)(=O)NC[C@@H](O)CN)c(S(N)(=O)=O)c3-c3nn[nH]n3)ccc2s1] | (S)-N1-(3-amino-2-hydroxypropyl)-4-(2-(aminomethyl)benzo[d]thiazol-5-yl)-3-(2H-tetrazol-5-yl)benzene-1,2-disulfonamide | 540 |
| 475 | 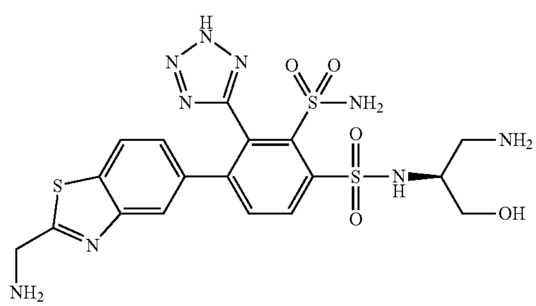 [SMILES: NCc1nc2cc(-c3ccc(S(=O)(=O)N[C@@H](CN)CO)c(S(N)(=O)=O)c3-c3nn[nH]n3)ccc2s1] | (S)-N1-(1-amino-3-hydroxypropan-2-yl)-4-(2-(aminomethyl)benzo[d]thiazol-5-yl)-3-(2H-tetrazol-5-yl)benzene-1,2-disulfonamide | 540 |
| 476 | 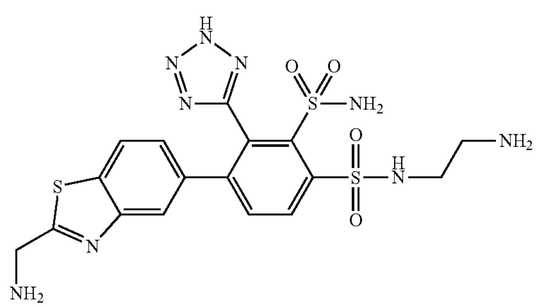 [SMILES: NCCNS(=O)(=O)c1ccc(-c2ccc3sc(CN)nc3c2)c(-c2nn[nH]n2)c1S(N)(=O)=O] | N1-(2-aminoethyl)-4-(2-(aminomethyl)benzo[d]thiazol-5-yl)-3-(2H-tetrazol-5-yl)benzene-1,2-disulfonamide | 510 |

Example 464

(R)—N1-(3-amino-2-hydroxypropyl)-4-(2-(aminomethyl)-1H-benzo[d]imidazole-5-yl)-3-(2H-tetrazol-5-yl)benzene-1,2-disulfonamide

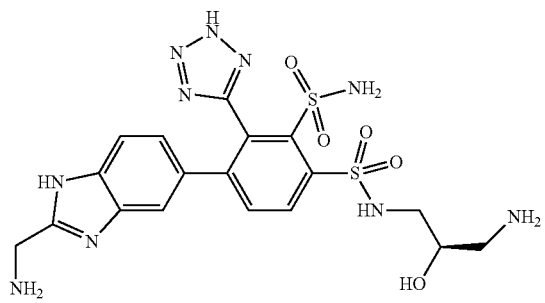 [SMILES: NCc1nc2cc(-c3ccc(S(=O)(=O)NC[C@H](O)CN)c(S(N)(=O)=O)c3-c3nn[nH]n3)ccc2[nH]1]

Step A: (R)-tert-butyl(3-(3',4'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)-2-hydroxypropyl)carbamate To a solution of (R)-tert-butyl (3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl) carbamate (1.50 g, 1.56 mmol) in 1,4-dioxane (15 mL) and water (3 mL) was added PdCl$_2$ (dppf) adduct CH$_2$Cl$_2$ (0.25 g, 0.31 mmol), 4-(4,4,5,5-tetramethyl-1,3,2-dioxaborolan-2-yl)benzene-1,2-diamine (0.55 g, 2.33 mmol) and Na$_2$CO$_3$ (0.50 g, 4.67 mmol) at room temperature. The mixture was degassed with nitrogen three times. The reaction mixture was stirred at 80° C. for 16 hours under nitrogen. The resulting mixture was quenched with water (50 mL) and extracted with EA (3×50 mL). The combined organic layers were washed with brine (3×50 mL), dried over anhydrous Na$_2$SO$_4$ and filtered. The filtrate was concentrated under vacuum. The residue was purified by silica gel column chromatography, eluted with 70% EA in PE. The fractions containing desired product were combined and concentrated to afford the title compound as a solid: LCMS [M+E]$^+$: 944.

Step B: tert-Butyl-N-[(2R)-3-({4-[3-amino-4-(2-{[(tert-butoxy)carbonyl]amino}acetamido)phenyl]-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene}sulfonamido)-2-hydroxypropyl]carbamate To a solution of 2-((tert-butoxycarbonyl)amino)acetic acid (0.23 g, 1.28 mmol) and HATU (0.53 g, 1.40 mmol) in DMF (10 mL) was added (R)-tert-butyl (3-(3',4'-diamino-3-(N,N-bis(4-methoxybenzyl)sulfamoyl)-2-(2-(4-methoxybenzyl)-2H-tetrazol-5-yl-[1,1'-biphenyl]-4-ylsulfonamido)-2-hydroxypropyl)carbamate (1.10 g, 1.17 mmol) and DIEA (0.31 mL, 1.75 mmol) at room temp. The mixture was stirred at room temp. for 2 hours under nitrogen. The resulting mixture was quenched with water (50 mL) and extracted with EA (3×50 mL). The combined organic layers was washed with brine (3×50 mL), dried over anhydrous Na$_2$SO$_4$ and filtered. The filtrate was concentrated under vacuum. The residue was purified by silica gel column chromatography, eluted with 70% EA in PE. The fractions containing desired product were combined and concentrated to afford the title compound: LCMS [M+H]$^+$: 1101.

Step C: tert-Butyl-N-{[5-(3-{bis[(4-methoxyphenyl)methyl]sulfamoyl}-4-{[(2R)-3-{[(tert-butoxy)carbonyl]amino}-2-hydroxypropyl]sulfamoyl}-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl}carbamate A solution of tert-butyl-N-[(2R)-3-({4-[3-amino-4-(2-{[(tert-butoxy)carbonyl]amino} acetamido)phenyl]-2-{bis[(4-methoxyphenyl)methyl]sulfamoyl}-3-[(2E,4E)-11-methoxy-2,4,5,6-tetraazabicyclo[6.3.1]dodeca-1(11),2,4,8(12),9-pentaen-3-yl]benzene}sulfonamido)-2-hydroxypropyl] carbamate (0.70 g, 0.64 mmol) in HOAc (10 mL) was stirred for 2 hours at 55° C. The resulting mixture was quenched with water (50 mL) and extracted with EA (3×50 mL). The combined organic layers were washed with brine (3×50 mL), dried over anhydrous sodium sulfate and filtered. The filtrate was concentrated under vacuum to afford the title compound: LCMS [M+H]$^+$: 1083.

Step D: (R)—N1-(3-amino-2-hydroxypropyl)-4-(2-(aminomethyl)-1H-benzo[d]imidazol-5-yl)-3-(2H-tetrazol-5-yl)benzene-1,2-disulfonamide The title compound was prepared as described for EXAMPLE 462, step B, using tert-butyl-N-{[5-(3-{bis[(4-methoxyphenyl)methyl]sulfamoyl}-4-{[(2R)-3-{[(tert-butoxy)carbonyl]amino}-2-hydroxypropyl]sulfamoyl}-2-[(2-E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl]methyl}carbamate (0.50 g, 0.46 mmol) to afford the crude product. The crude product was purified by Prep-HPLC with the following conditions: Column: X Bridge C18 OBD Prep Column 100 Å, 10 μm, 19 mm×250 mm; Mobile Phase A: water (10 mmol/L NH$_4$HCO$_3$), Mobile Phase B: ACN; Flow rate: 20 mL/min; Gradient: 0% B to 25% B in 8 min; Detector: UV 254 and 220 nm; Retention time: 3.5 min. The fractions containing desired product were combined and concentrated under vacuum to afford the title compound: LCMS [M+H]$^+$: 523; $^1$H NMR (300 MHz, CD$_3$OD+DCl): δ 8.58 (d, J=8.1 Hz, 1H), 7.99 (d, J=8.1 Hz, 1H), 7.78 (d, J=8.7 Hz, 1H), 7.63 (s, 1H), 7.34 (d, J=8.7 Hz, 1H), 4.74 (s, 2H), 4.00-3.95 (m, 1H), 3.29-3.22 (m, 3H), 2.95-2.87 (m, 1H).

The compounds in the Table below were synthesized using the procedure described above for EXAMPLE 464, and the corresponding intermediates prepared as described herein.

| EX No. | Structure | Name | LC/MS [M + H]+ |
|---|---|---|---|
| 465 | 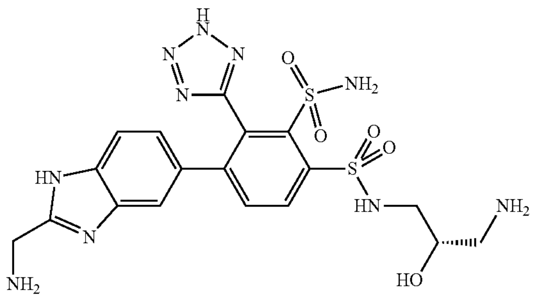 [SMILES: NCc1nc2cc(-c3ccc(S(=O)(=O)NC[C@@H](O)CN)c(S(N)(=O)=O)c3-c3nn[nH]n3)ccc2[nH]1] | S)-N1-(3-amino-2-hydroxypropyl)-4-(2-(aminomethyl)-1H-benzo[d]imidazol-5-yl)-3-(2H-tetrazol-5-yl)benzene-1,2-disulfonamide | 523 |
| 474 | 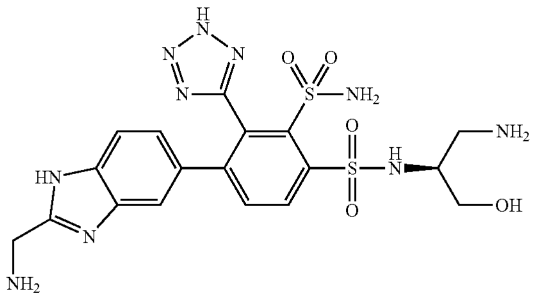 [SMILES: NCc1nc2cc(-c3ccc(S(=O)(=O)N[C@@H](CN)CO)c(S(N)(=O)=O)c3-c3nn[nH]n3)ccc2[nH]1] | (S)-N1-(1-amino-3-hydroxypropan-2-yl)-4-(2-(aminomethyl)-1H-benzo[d]imidazol-5-yl)-3-(2H-tetrazol-5-yl)benzene-1,2-disulfonamide | 523 |

Example 466

N1-(2-aminoethyl)-4-(2-(aminomethyl)-1H-benzo[d]imidazol-5-yl)-3-(2H-tetrazol-5-yl)benzene-1,2-disulfonamide

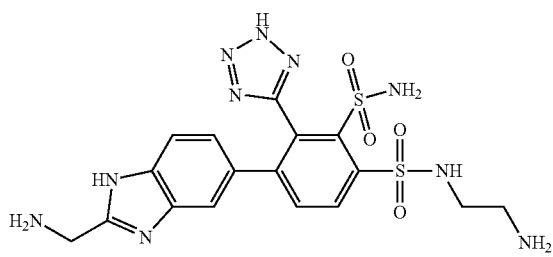 [SMILES: NCCNS(=O)(=O)c1ccc(-c2ccc3[nH]c(CN)nc3c2)c(-c2nn[nH]n2)c1S(N)(=O)=O]

Step A: tert-Butyl(2-(3',4'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)ethyl)carbamate The title compound was prepared as described for EXAMPLE 464, step A, using tert-butyl (2-(2-(N,N-bis(4-methoxybenzyl)sulfamoyl)-4-iodo-3-(2-(4-methoxybenzyl)-2H-tetrazol-5-yl)phenylsulfonamido)ethyl)carbamate (1.40 g, 1.50 mmol): LCMS [M+H]+: 914.

Step B: 2-Methoxybuta-1,3-diene; tert-butyl N-({[2-amino-4-(3-{bis[(4-methoxyphenyl) methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)phenyl]carbamoyl}methyl) carbamate The title compound was prepared as described for EXAMPLE 464, step B, using tert-butyl (2-(3',4'-diamino-3-(N,N-bis(4-methoxybenzyl)sulfamoyl)-2-(2-(4-methoxybenzyl)-2H-tetrazol-5-yl)-[1,1'-biphenyl]-4-ylsulfonamido)ethyl)carbamate (1 g, 1.09 mmol): LCMS [M+H]+: 1071.

Step C: tert-Butyl-N-{[5-(3-{bis[(4-methoxyphenyl)methyl]sulfamoyl}-4-[(2-{[(tert-butoxy) carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl] methyl} carbamate The title compound was prepared as described for EXAMPLE 464, step C, using tert-butyl-N-({[2-amino-4-(3-{bis[(4-methoxyphenyl)methyl]sulfamoyl}-4-[(2-{[(tert-butoxy)carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)phenyl] carbamoyl}methyl) carbamate (0.65 g, 0.61 mmol): LCMS [M+H]+: 1053.

Step D: N1-(2-aminoethyl)-4-(2-(aminomethyl)-1H-benzo[d]imidazol-5-yl)-3-(2H-tetrazol-5-yl)benzene-1,2-disulfonamide The title compound was prepared as described for EXAMPLE 462, step B, using tert-butyl-N-{[5-(3-{bis[(4-methoxyphenyl)methyl]sulfamoyl}-4-[(2-{[(tert-butoxy) carbonyl]amino}ethyl)sulfamoyl]-2-[(2E,4E)-11-methoxy-2,4,5,6-tetraazabicyclo[6.3.1]dodeca-1(11),2,4,8(12),9-pentaen-3-yl]phenyl)-1H-1,3-benzodiazol-2-yl] methyl}carbamate (0.46 g, 0.44 mmol) to afford the crude product. The crude product was purified by Prep-HPLC with the following conditions: Column: X Bridge Prep C18 OBD Column 19×250 mm 5 μm; Mobile Phase A: water (10 mmol/L NH4HCO3), Mobile Phase B: ACN; Flow rate: 20 mL/min; Gradient: 1% B to 20% B in 7 min; Dettector: UV 254 and 220 nm. The fractions containing desired product were combined and concentrated under vacuum to afford the title compound: LCMS [M+H]+: 493; 1H NMR (300 MHz, CD$_3$OD+DCl): δ 8.61 (d, J=8.1 Hz, 1H), 8.01 (d, J=8.1 Hz, 1H), 7.77 (d, J=8.1 Hz, 1H), 7.63 (s, 1H), 7.33 (dd, J=8.7 Hz, 1.5 Hz, 1H), 4.75 (s, 2H), 3.39 (t, J=6.0 Hz, 2H), 3.15 (t, J=6.0 Hz, 2H).

Example 471

(R)-2-((4'-(N-(pyrrolidin-3-yl)sulfamoyl)-3'-sulfamoyl-2'-(2H-tetrazol-5-yl)-[1,1'-biphenyl]-3-yl)amino)thiazole-4-carboxamide

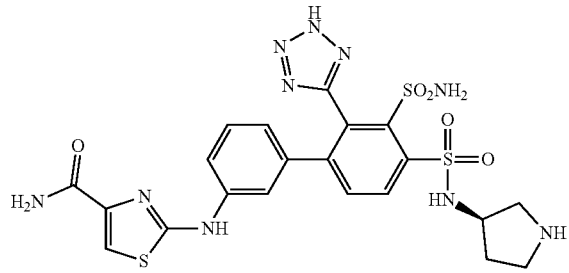 [SMILES: NC(=O)c1csc(Nc2cccc(-c3ccc(S(=O)(=O)N[C@@H]4CCNC4)c(S(N)(=O)=O)c3-c3nn[nH]n3)c2)n1]

Step A: (R)-methyl-2-((3'-(N-bis(4-methoxybenzyl)sulfamoyl)-4'-(N-(1-(tert-butoxy carbonyl)pyrrolidin-3-yl)sulfamoyl)-2'-(2-(4-methoxybenzyl)-2H-tetrazol-5-yl-[1,1'-biphenyl]-3-yl)amino)thiazole-4-carboxylate To a solution of (R)-tert-butyl-3-(2-(N,N-bis(4-methoxybenzyl)sulfamoyl)-4-iodo-3-(2-(4-methoxybenzyl)-2H-tetrazol-5-yl)phenylsulfonamido)pyrrolidine-1-carboxylate (2.0 g, 2.084 mmol) in 1,4-dioxane (16 mL) and water (4 mL) was added methyl-2-((3-(4,4,5,5-tetramethyl-1,3,2-dioxaborolan-2-yl)phenyl)amino)thiazole-4-carboxylate (0.75 g, 2.08 mmol), Na$_2$CO$_3$ (0.221 g, 2.08 mmol) and Pd(dppf)Cl$_2$ adduct CH$_2$Cl$_2$ (1.7 g, 2.084 mmol)) at room temperature. The mixture was degassed with nitrogen three times. The reaction mixture was stirred at 80° C. for 16 hours under nitrogen. The resulting mixture was diluted with water (200 mL) and extracted with EA (3×200 mL). The combined organic layers were washed with water (3×200 mL) and brine (3×200 mL), dried over anhydrous Na$_2$SO$_4$ and filtered. The filtrate was concentrated under vacuum. The residue was purified by silica gel column chromatography, eluted with 70% EA in PE. The fractions containing desired product were combined and concentrated under vacuum to afford the title compound: LCMS [M+H]$^+$: 1066.

Step B: (R)-2-((3'-(N,N-bis(4-methoxybenzyl)sulfamoyl)-4'-(N-(1-(tert-butoxycarbonyl) pyrrolidin-3-yl)sulfamoyl)-2'-(2-(4-methoxybenzyl)-2H-tetrazol-5-yl-[1,1'-biphenyl]-3-yl)amino)thiazole-4-carboxylic acid To a solution of (R)-methyl 2-((3'-(N,N-bis(4-methoxybenzyl)sulfamoyl)-4'-(N-(1-(tert-butoxycarbonyl)pyrrolidin-3-yl)sulfamoyl)-2'-(2-(4-methoxybenzyl)-2H-tetrazol-5-yl)-[1,1'-biphenyl]-3-yl)amino)thiazole-4-carboxylate (0.89 g, 0.84 mmol) in THF (4 mL) and MeOH (4 mL) was added aqueous solution NaOH (2 N, 1.67 mL, 3.34 mmol) slowly. The reaction solution was stirred for 5 hours at room temperature. The pH value of the solution was adjusted to 6-7 with 1 N aqueous HCl. The resulting mixture was concentrated under vacuum to afford a solid. The crude product was purified by Prep-HPLC with the following conditions: Column: XBridge Prep C18 OBD Column, 30×100 mm, 5 μm; Mobile Phase A: water (10 mmoL/L NH$_4$HCO$_3$), Mobile Phase B: ACN; Flow rate: 40 mL/min; Gradient: 0% B to 100% B in 30 min; Detector: UV 254 and 280 nm; Retention time: 8 min. The fractions containing desired product were combined and concentrated under vacuum to afford the title compound. LCMS [M+H]$^+$: 1052.

Step C: (R)-tert-butyl-3-(3-(N,N-bis(4-methoxybenzyl)sulfamoyl)-3'-((4-carbamoylthiazol-2-yl)amino)-2-(2-(4-methoxybenzyl)-2H-tetrazol-5-yl-[1,1'-biphenyl]-4-ylsulfonamido)pyrrolidine-1-carboxylate To a stirred solution of (R)-2-((3'-(N,N-bis(4-methoxybenzyl)sulfamoyl)-4'-(N-(1-(tert-butoxycarbonyl)pyrrolidin-3-yl)sulfamoyl)-2'-(2-(4-methoxybenzyl)-2H-tetrazol-5-yl)-[1,1'-biphenyl]-3-yl)amino)thiazole-4-carboxylic acid (0.4 g, 0.38 mmol) in THF (4 mL) was added ammonium chloride (0.10 g, 1.90 mmol), HATU (0.29 g, 0.76 mmol) and TEA (0.16 mL, 1.14 mmol) in an ice bath. The resulting mixture was stirred at room temperature for 16 hours. The resulting mixture was diluted with water (50 mL) and extracted with EA (3×50 mL). The combined organic layers were washed with water (3×50 mL) and brine (3×50 mL), dried over anhydrous Na$_2$SO$_4$ and filtered. The filtrate was concentrated under vacuum. The residue was purified by silica gel column chromatography and eluted with 80% EA in PE. The fractions containing desired product were combined and concentrated under vacuum to afford the title compound: LCMS [M+H]$^+$: 1051.

Step D: (R)-2-((4'-(N-(pyrrolidin-3-yl)sulfamoyl)-3'-sulfamoyl-2'-(2H-tetrazol-5-yl-[1,1'-biphenyl]-3-yl)amino)thiazole-4-carboxamide The title compound was prepared as described for EXAMPLE 462, step B, using (R)-tert-butyl-3-(3-(N,N-bis(4-methoxybenzyl)sulfamoyl)-3'-((4-carbamoylthiazol-2-yl)amino)-2-(2-(4-methoxybenzyl)-2H-tetrazol-5-yl)-[1,1'-biphenyl]-4-ylsulfonamido)pyrrolidine-1-carboxylate (0.32 g, 0.30 mmol) to afford the crude product. The crude product was purified by Prep-HPLC with the following conditions: Column: Atlantis Prep T3 OBD Column, 19×250 mm, 10 μm; Mobile Phase A: water (10 mmoL/L NH$_4$HCO$_3$), Mobile Phase B: ACN; Flow rate: 20 mL/min; Gradient: 15% B to 30% B in 8 min; Detector: UV 254 and 220 nm. The fractions containing desired product were combined and concentrated under vacuum to afford the title compound: LCMS [M+H]$^+$: 591; $^1$H NMR (400 MHz, CD$_3$OD): δ 8.61 (d, J=8.2 Hz, 1H), 7.97 (d, J=8.2 Hz, 1H), 7.62 (s, 1H), 7.50 (s, 1H), 7.37-7.34 (m, 2H), 6.91 (d, J=6.7 Hz, 1H), 4.33-4.18 (m, 1H), 3.55-3.42 (m, 2H), 3.43-3.34 (m, 2H), 2.27-2.24 (m, 1H), 2.05-1.94 (m, 1H).

Example 477

(R)—N1-(3-amino-2-hydroxypropyl)-4-(6-amino-5-methylpyridin-3-yl)-3-(2H-tetrazol-5-yl)benzene-1,2-disulfonamide

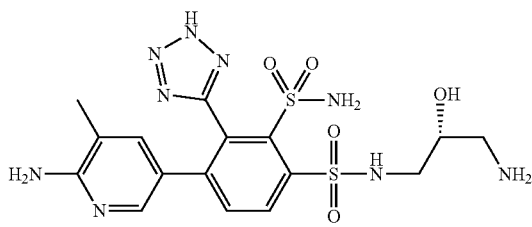 [SMILES: Cc1cc(-c2ccc(S(=O)(=O)NC[C@H](O)CN)c(S(N)(=O)=O)c2-c2nn[nH]n2)cnc1N]

Step A: (R)-tert-butyl (3-(2-(N,N-bis(4-methoxybenzyl)sulfamoyl)-4-iodo-3-(2-(4-methoxy benzyl)-2H-tetrazol-5-yl)phenylsulfonamido)-2-hydroxypropyl)carbamate To a solution of 2-(N,N-bis(4-methoxybenzyl)sulfamoyl)-4-iodo-3-(2-(4-methoxy benzyl)-2H-tetrazol-5-yl) benzenesulfinic acid (2.20 g, 2.84 mmol) in THF (20 mL) was added NCS (0.78 g, 7.51 mmol) at 0° C. The reaction mixture was stirred for 2 hours at room temperature under nitrogen. To the reaction mixture was added (S)-tert-butyl (3-amino-2-hydroxypropyl)carbamate (1.10 g, 5.79 mmol) and TEA (1.46 mL, 8.74 mmol) dropwise at 0° C. The reaction mixture was stirred for another 1 hour at room temperature under nitrogen. The resulting mixture was concentrated under vacuum. The residue was purified by silica gel chromatography, eluting with 50% EA in PE. The fractions containing desired product were combined and concentrated to afford the title compound: LCMS [M+H]$^+$: 964.

Step B: (R)-tert-butyl (3-(4-(6-amino-5-methylpyridin-3-yl)-2-(N,N-bis(4-methoxybenzyl) sulfamoyl)-3-(2-(4-methoxybenzyl)-2H-tetrazol-5-yl)phenylsulfonamido)-2-hydroxy propyl)carbamate To a solution of (R)-tert-butyl(3-(2-(N,N-bis(4-methoxybenzyl)sulfamoyl)-4-iodo-3-(2-(4-methoxybenzyl)-2H-tetrazol-5-yl)phenylsulfonamido)-2-hydroxypropyl) carbamate (1.10 g, 1.14 mmol), 3-methyl-5-(4,4,5,5-tetramethyl-1,3,2-dioxaborolan-2-yl)pyridin-2-amine (0.40 g, 1.72 mmol) in 1,4-dioxane (8 mL) and water (2 mL) was added Pd(dppf)Cl$_2$ adduct CH$_2$Cl$_2$ (0.19 g, 0.23 mmol) and Na$_2$CO$_3$ (0.36 g, 3.42 mmol). The reaction mixture was degassed with nitrogen three times and stirred for 4 hours at 80° C. The resulting mixture was diluted with water (20 mL), extracted with EA (3×30 mL). The combined organic layers were washed with brine (3×30 mL), dried over anhydrous Na$_2$SO$_4$ and filtered. The filtrate was concentrated under vacuum. The residue was purified by silica gel column chromatography, eluted with 80% EA in PE. The fractions containing desired product were combined and concentrated to afford the title compound: LCMS [M+H]$^+$: 944.

Step C: (R)—N1-(3-amino-2-hydroxypropyl)-4-(6-amino-5-methylpyridin-3-yl)-3-(2H-tetrazol-5-yl)benzene-1,2-disulfonamide The title compound was prepared as described for EXAMPLE 462, step B, using (R)-tert-butyl(3-(4-(6-amino-5-methylpyridin-3-yl)-2-(N,N-bis(4-methoxybenzyl) sulfamoyl)-3-(2-(4-methoxybenzyl)-2H-tetrazol-5-yl)phenylsulfonamido)-2-hydroxy propyl)carbamate (0.69 g, 0.73 mmol) to afford the crude product. The crude product was purified by Prep-HPLC with the following conditions: Column: X Bridge C18 OBD Prep Column 100 Å, 10 µm, 19 mm×250 mm; Mobile Phase A: water (10 mmol/L NH$_4$HCO$_3$), Mobile Phase B: ACN; Flow rate: 20 mL/min; Gradient: 0% B to 30% B in 8 min; Detector: UV 254 and 220 nm; Retention time: 5.82 min. The collected fractions containing desired product were combined and concentrated under vacuum to afford the title compound: LCMS [M+H]$^+$: 484; $^1$H NMR (300 MHz, DMSO-d$_6$): δ 8.17 (d, J=8.4 Hz, 1H), 7.74 (d, J=8.4 Hz, 1H), 7.35 (m, 4H), 6.63 (s, 1H), 5.79 (s, 2H), 3.78 (d, J=9.5 Hz, 1H), 3.12-3.04 (m, 1H), 3.03-2.82 (m, 2H), 2.74-2.67 (m, 1H), 1.86 (s, 3H).

Example 479

(S)—N1-(2-aminopropyl)-4-(6-aminopyridin-3-yl)-3-(2H-tetrazol-5-yl) benzene-1,2-disulfonamide

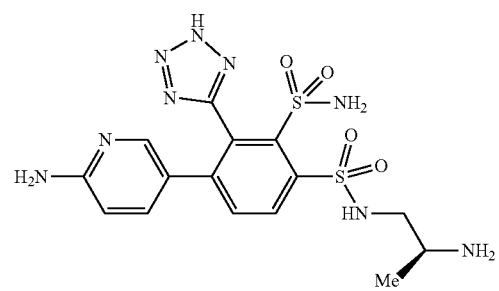 [SMILES: C[C@H](N)CNS(=O)(=O)c1ccc(-c2ccc(N)nc2)c(-c2nn[nH]n2)c1S(N)(=O)=O]

Step A: (S)-tert-butyl(1-(2-(N,N-bis(4-methoxybenzyl)sulfamoyl)-4-iodo-3-(2-(4-methoxy benzyl)-2H-tetrazol-5-yl)phenylsulfonamido)propan-2-yl)carbamate The title compound was prepared as described for EXAMPLE 477, step A, using (S)-tert-butyl (1-aminopropan-2-yl)carbamate (0.27 g, 1.55 mmol) to afford the title compound: LCMS [M+2]$^+$: 949.

Step B: (S)-tert-butyl (1-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)propan-2-yl)carbamate The title compound was prepared as described for EXAMPLE 477, step B, using (S)-tert-butyl(1-(2-(NA-bis(4-methoxybenzyl)sulfamoyl)-4-iodo-3-(2-(4-methoxybenzyl)-2H-tetrazol-5-yl)phenylsulfonamido)propan-2-yl)carbamate (0.81 g, 0.68 mmol) and 5-(4,4,5,5-tetramethyl-1,3,2-dioxaborolan-2-yl)pyridine-2-amine (0.28 g, 1.28 mmol: LCMS [M+H]$^+$: 914.

Step C: (S)—N1-(2-aminopropyl)-4-(6-aminopyridin-3-yl)-3-(2H-tetrazol-5-yl)benzene-1,2-disulfonamide The title compound was prepared as described for EXAMPLE 462, step B, using (S)-tert-butyl(1-(4-(6-aminopyridin-3-yl)-2-(N,N-bis(4-methoxybenzyl)sulfamoyl)-3-

(2-(4-methoxybenzyl)-2H-tetrazol-5-yl)phenylsulfonamido)propan-2-yl)carbamate (0.70 g, 0.76 mmol) to afford the crude product. The crude product was purified by Prep-HPLC with the following conditions: Column: X Bridge C18 OBD Prep Column 100 Å, 10 μm, 19 mm×250 mm; Mobile Phase A: water (10 mmol/L NH$_4$HCO$_3$), Mobile Phase B: ACN; Flow rate: 20 mL/min; Gradient: 0% B to 25% B in 8 min; Detector: UV 254 and 220 nm; Retention time: 6.67 min. The collected fractions containing desired product were combined and concentrated under vacuum to afford the title compound: LCMS [M+H]$^+$: 454; $^1$H NMR (400 MHz, CD$_3$OD): δ 8.42 (d, J=8.3 Hz, 1H), 7.82 (dd, J=8.5 Hz, 1.5 Hz, 1H), 7.61 (s, 1H), 6.97 (dd, J=8.6 Hz, 2.4 Hz, 1H), 6.36 (d, J=8.6 Hz, 1H), 3.25-2.88 (m, 1H), 3.28-3.11 (m, 2H), 1.30 (d, J=6.5 Hz, 3H).

Example 480

(R)—N1-(2-aminopropyl)-4-(6-aminopyridin-3-yl)-3-(2H-tetrazol-5-yl) benzene-1,2-disulfonamide

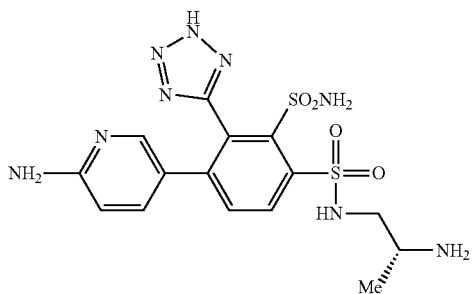 [SMILES: C[C@@H](N)CNS(=O)(=O)c1ccc(-c2ccc(N)nc2)c(-c2nn[nH]n2)c1S(N)(=O)=O]

Step A: (R)-tert-butyl(1-(2-(N,N-bis(4-methoxybenzyl)sulfamoyl)-4-iodo-3-(2-(4-methoxy benzyl)-2H-tetrazol-5-yl)phenylsulfonamido)propan-2-yl)carbamate The title compound was prepared as described for EXAMPLE 477, step A, using 2-(N,N-bis(4-methoxybenzyl)sulfamoyl)-4-iodo-3-(2-(4-methoxybenzyl)-2H-tetrazol-5-yl)benzenesulfinic acid (1.00 g, 1.29 mmol) and (R)-tert-butyl (1-aminopropan-2-yl)carbamate (0.34 g, 1.94 mmol) to afford the title compound: LCMS [M+1]$^+$: 948.

Step B: (R)-tert-butyl(1-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)propan-2-yl)carbamate The title compound was prepared as described for EXAMPLE 477, step B, using (R)-tert-butyl(1-(2-(N,N-bis(4-methoxybenzyl)sulfamoyl)-4-iodo-3-(2-(4-methoxybenzyl)-2H-tetrazol-5-yl)phenylsulfonamido)propan-2-yl)carbamate (0.9 g, 0.95 mmol) and 5-(4,4,5,5-tetramethyl-1,3,2-dioxaborolan-2-yl)pyridine-2-amine (0.39 g, 1.78 mmol): LCMS [M+2]$^+$: 915.

Step C: (R)—N1-(2-aminopropyl)-4-(6-aminopyridin-3-yl)-3-(2H-tetrazol-5-yl)benzene-1,2-disulfonamide The title compound was prepared as described for EXAMPLE 462, step B, using (R)-tert-butyl(1-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)propan-2-yl)carbamate (0.84 g, 0.92 mmol) to afford the crude product. The crude product was purified by Prep-HPLC with the following conditions: Column: X Bridge C18 OBD Prep Column 100 Å, 10 μm, 19 mm×250 mm; Mobile Phase A: water (10 mmol/L NH$_4$HCO$_3$), Mobile Phase B: ACN; Flow rate: 20 mL/min; Gradient: 0% B to 35% B in 8 min; Detector: UV 254 and 220 nm. The collected fractions were combined and concentrated under vacuum to afford the title compound: LCMS [M+H]$^+$: 454; $^1$H NMR (400 MHz, CD$_3$OD): δ 8.42 (d, J=8.1 Hz, 1H), 7.81 (d, J=8.3 Hz, 1H), 7.61 (s, 1H), 6.97 (d, J=8.8 Hz, 1H), 6.36 (d, J=8.7 Hz, 1H), 3.45 (d, J=6.7 Hz, 1H), 3.33-3.13 (m, 2H), 1.30 (d, J=6.6 Hz, 3H).

Example 482

N1-(2-(-2-amineoethylamino)ethyl)-4-(6-aminopyridin-3-yl)-3-(2H-tetrazol-5-yl)benzene-1,2-disulfonamide

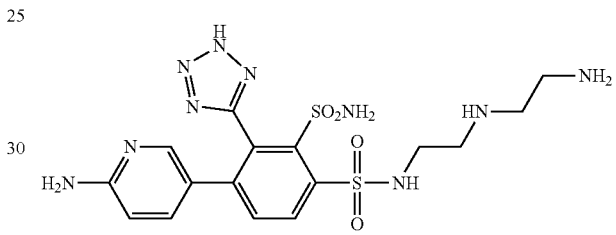

Step A: tert-Butyl(2-(2-(N,N-bis(4-methoxybenzyl)sulfamoyl)-4-iodo-3-(2-(4-methoxybenzyl)-2H-tetrazol-5-yl)phenylsulfonamido)ethyl)(2-((tert-butoxycarbonyl)amino)ethyl)carbamate To a solution of 2-(N,N-bis(4-methoxybenzyl)sulfamoyl)-4-iodo-3-(2-(4-methoxybenzyl)-2H-tetrazol-5-yl)benzenesulfinic acid (1.0 g, 1.29 mmol) in THF (4 mL) was added NCS (0.35 g, 2.59 mmol). The stirred mixture was stirred at room temperature for 1 hour under nitrogen. To the reaction mixture was added tert-butyl (2-aminoethyl)(2-((tert-butoxycarbonyl)amino)ethyl)carbamate (0.59 g, 1.94 mmol) and TEA (0.35 g, 3.43 mmol). The mixture was stirred at room temperature for 30 minutes. The resulting mixture was filtered and concentrated under vacuum. The residue was purified by silica gel column chromatography, eluted with 40% EA in PE. The fractions containing desired product were combined and concentrated to afford the title compound: LCMS [M+1]$^+$: 1077.

Step B: tert-Butyl(2-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)ethyl)(2-((tert-butoxycarbonyl)amino) ethyl) carbamate The title compound was prepared as described for EXAMPLE 477, step B using tert-butyl(2-(2-(N,N-bis(4-methoxybenzyl)sulfamoyl-4-iodo-3-(2-(4-methoxybenzyl)-2H-tetrazol-5-yl)phenylsulfonamido)ethyl)(2-((tert-butoxycarbonyl)amino)ethyl) carbamate (0.90 g, 0.86 mmol) and 5-(4,4,5,5-tetramethyl-1,3,2-dioxaborolan-2-yl) pyridin-2-amine (0.27 g, 1.34 mmol) to afford the title compound: LCMS [M+1]+: 1043.

Step C: N1-(2-(-2-amineoethylamino)ethyl)-4-(6-aminopyridin-3-yl)-3-(2H-tetrazol-5-yl)benzene-1,2-disulfonamide The title compound was prepared as described for EXAMPLE 462, step B, using tert-butyl(2-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido) ethyl)(2-((tert-butoxy carbonyl) amino)ethyl)carbamate (0.60 g, 0.58 mmol) to afford the crude product. The crude product was purified by Prep-HPLC with the following conditions: Column: XBridge Prep C18 OBD Column, 30×100 mm, 5 μm; Mobile Phase A: water (10 mmoL/L NH$_4$HCO$_3$), Mobile Phase B: ACN; Flow rate: 20 mL/min; Gradient: 0% B to 30% B in 11 min; Detector: UV 254 and 210 nm; Retention time: 9.73 min. The fractions containing desired product were combined and concentrated under vacuum to afford the title compound: LCMS [M+1]+: 483; $^1$H NMR (300 MHz, DMSO-d$_6$+DCl) δ 8.50 (d, J=8.3 Hz, 1H), 8.00 (d, J=8.3 Hz, 1H), 7.77 (d, J=2.2 Hz, 1H), 7.35 (dd, J=9.3 Hz, 2.3 Hz, 1H), 6.87 (d, J=9.3 Hz, 1H), 3.30-3.13 (m, 8H).

EXAMPLES 483-499 in the Table below were prepared in an analogous fashion to that described for EXAMPLE 482, starting from 2-(N,N-bis(4-methoxybenzyl)sulfamoyl)-4-iodo-3-(1-(4-methoxybenzyl)-1H-tetrazol-5-yl)benzenesulfinic acid and the corresponding boronic acids or boronic esters and amines and Boc-protected diamines, which were all either prepared as described herein, or which were available from commercial sources.

| EX. No. | Structure | Chemical Name | LC/MS [M + H]+ |
|---|---|---|---|
| 483 | 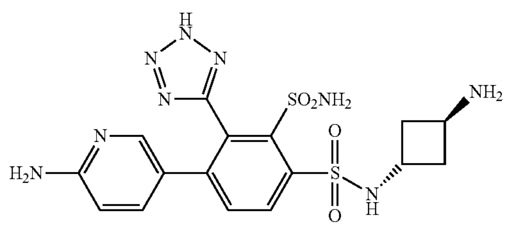 | N1-((1R,3R)-3-aminocyclobutyl)-4-(6-aminopyridin-3-yl)-3-(2H-tetrazol-5-yl)benzene-1,2-disulfonamide | 466 |
| 484 | 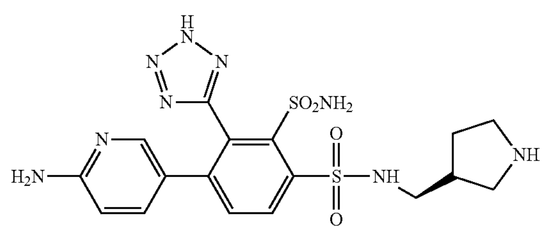 | (S)-4-(6-aminopyridin-3-yl)-N1-(pyrrolidin-3-ylmethyl)-3-(2H-tetrazol-5-yl)benzene-1,2-disulfonamide | 480 |
| 485 | 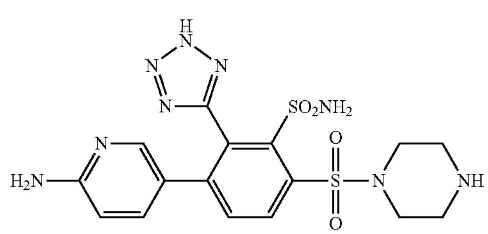 [SMILES: Nc1ccc(-c2ccc(S(=O)(=O)N3CCNCC3)c(S(N)(=O)=O)c2-c2nn[nH]n2)cn1] | 3-(6-aminopyridin-3-yl)-6-(piperazin-1-ylsulfonyl)-2-(2H-tetrazol-5-yl)benzenesulfonamide | 466 |
| 486 | 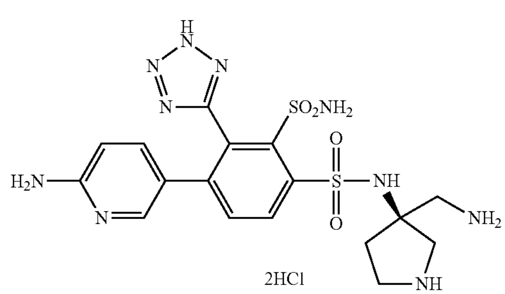 [SMILES: NC[C@@]1(NS(=O)(=O)c2ccc(-c3ccc(N)nc3)c(-c3nn[nH]n3)c2S(N)(=O)=O)CCNC1] | (R)-N1-(3-(aminomethyl)pyrrolidin-3-yl)-4-(6-aminopyridin-3-yl)-3-(2H-tetrazol-5-yl)benzene-1,2-disulfonamide dihydrochloride | 495 |

| EX. No. | Structure | Chemical Name | LC/MS [M + H]+ |
|---|---|---|---|
| 487 | 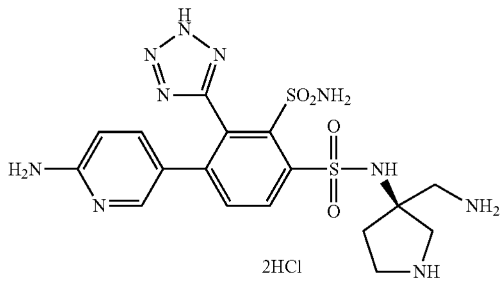 [SMILES: NC[C@@]1(NS(=O)(=O)c2ccc(-c3ccc(N)nc3)c(-c3nn[nH]n3)c2S(N)(=O)=O)CCNC1] | (S)-N1-(3-(aminomethyl)pyrrolidin-3-yl)-4-(6-aminopyridin-3-yl)-3-(2H-tetrazol-5-yl)benzene-1,2-disulfonamide dihydrochloride | 495 |
| 488 | 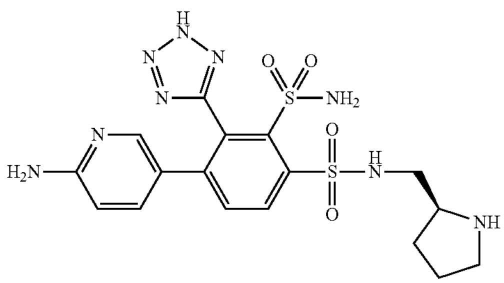 [SMILES: Nc1ccc(-c2ccc(S(=O)(=O)NC[C@@H]3CCCN3)c(S(N)(=O)=O)c2-c2nn[nH]n2)cn1] | (S)-4-(6-aminopyridin-3-yl)-N1-(pyrrolidin-2-ylmethyl)-3-(2H-tetrazol-5-yl)benzene-1,2-disulfonamide | 480 |
| 489 | 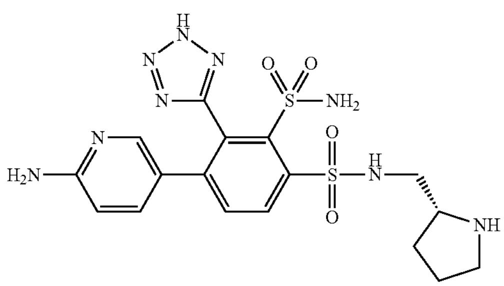 [SMILES: Nc1ccc(-c2ccc(S(=O)(=O)NC[C@H]3CCCN3)c(S(N)(=O)=O)c2-c2nn[nH]n2)cn1] | (R)-4-(6-aminopyridin-3-yl)-N1-(pyrrolidin-2-ylmethyl)-3-(2H-tetrazol-5-yl)benzene-1,2-disulfonamide | 480 |
| 490 | 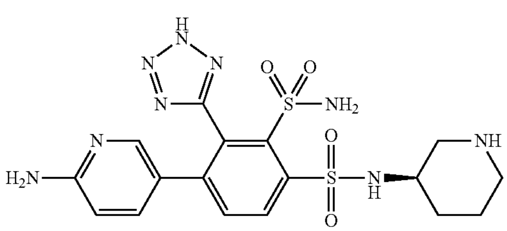 [SMILES: Nc1ccc(-c2ccc(S(=O)(=O)N[C@@H]3CCCNC3)c(S(N)(=O)=O)c2-c2nn[nH]n2)cn1] | (R)-4-(6-aminopyridin-3-yl)-N1-(piperidin-3-yl)-3-(2H-tetrazol-5-yl)benzene-1,2-disulfonamide | 480 |
| 491 | 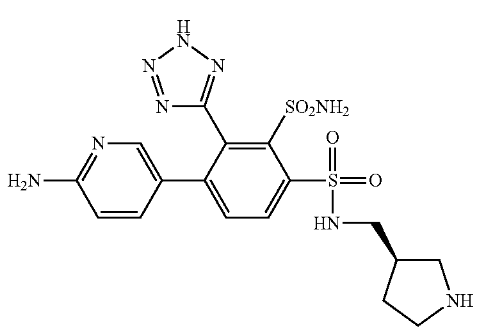 [SMILES: Nc1ccc(-c2ccc(S(=O)(=O)NC[C@@H]3CCNC3)c(S(N)(=O)=O)c2-c2nn[nH]n2)cn1] | (R)-4-(6-aminopyridin-3-yl)-N1-(pyrrolidin-3-ylmethyl)-3-(2H-tetrazol-5-yl)benzene-1,2-disulfonamide | 480 |

-continued

| EX. No. | Structure | Chemical Name | LC/MS [M + H]+ |
|---|---|---|---|
| 492 | 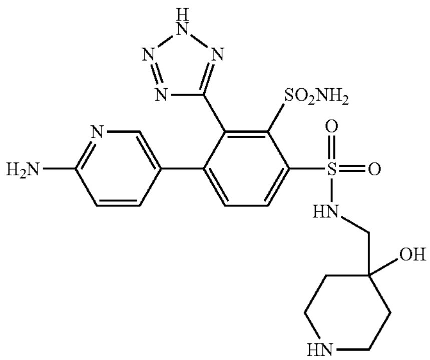 [SMILES: Nc1ccc(-c2ccc(S(=O)(=O)NCC3(O)CCNCC3)c(S(N)(=O)=O)c2-c2nn[nH]n2)cn1] | 4-(6-aminopyridin-3-yl)-N1-((4-hydroxypiperidin-4-yl)methyl)-3-(2H-tetrazol-5-yl)benzene-1,2 disulfonamide | 510 |
| 493 | 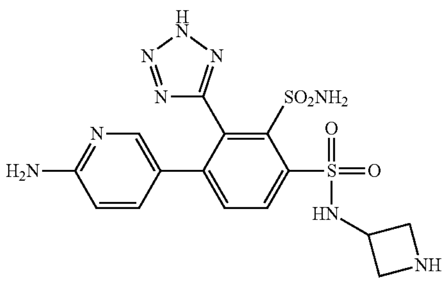 [SMILES: Nc1ccc(-c2ccc(S(=O)(=O)NC3CNC3)c(S(N)(=O)=O)c2-c2nn[nH]n2)cn1] | 4-(6-aminopyridin-3-yl)-N1-(azetidin-3-yl)-3-(2H-tetrazol-5-yl)benzene-1,2-disulfonamide | 452 |
| 494 | 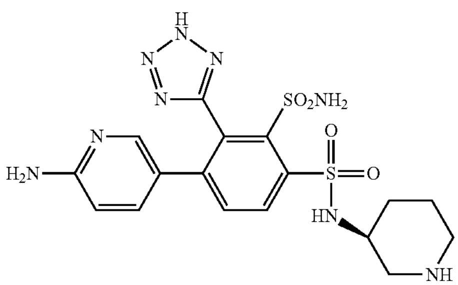 [SMILES: Nc1ccc(-c2ccc(S(=O)(=O)N[C@H]3CCCNC3)c(S(N)(=O)=O)c2-c2nn[nH]n2)cn1] | (S)-4-(6-aminopyridin-3-yl)-N1-(piperidin-3-yl)-3-(2H-tetrazol-5-yl)benzene-1,2-disulfonamide | 480 |
| 495 | 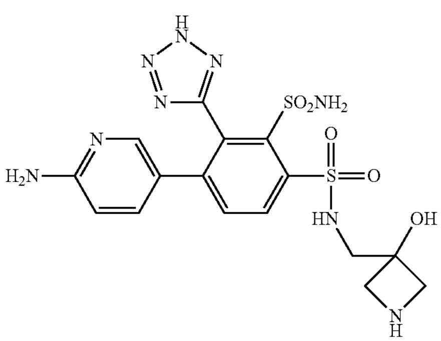 [SMILES: Nc1ccc(-c2ccc(S(=O)(=O)NCC3(O)CNC3)c(S(N)(=O)=O)c2-c2nn[nH]n2)cn1] | 4-(6-aminopyridin-3-yl)-N1-((3-hydroxyazetidin-3-yl)methyl)-3-(2H-tetrazol-5-yl)benzene-1,2-disulfonamide | 482 |
| 496 | 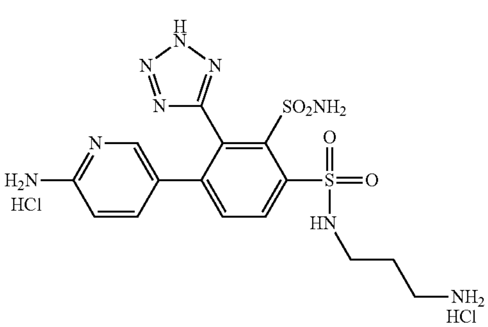 [SMILES: Cl ; NCCCNS(=O)(=O)c1ccc(-c2ccc(N)nc2)c(-c2nn[nH]n2)c1S(N)(=O)=O ; Cl] | N1-(3-aminopropyl)-4-(6-aminopyridin-3-yl)-3-(2H-tetrazol-5-yl)benzene-1,2-disulfonamide hydrogen chloride | 454 |

| EX. No. | Structure | Chemical Name | LC/MS [M + H]+ |
|---|---|---|---|
| 497 | 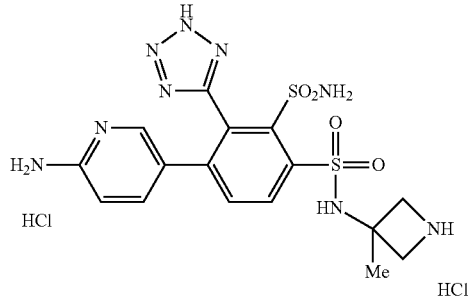 [SMILES: Cl ; CC1(NS(=O)(=O)c2ccc(-c3ccc(N)nc3)c(-c3nn[nH]n3)c2S(N)(=O)=O)CNC1 ; Cl] | 4-(6-aminopyridin-3-yl)-1-N-(3-methylazetidin-3-yl)-3-(2H-1,2,3,4-tetrazol-5-yl)benzene-1,2-disulfonamide hydrogen | 466 |
| 498 | 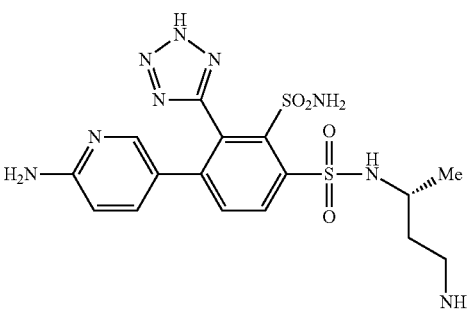 | (R)-N1-(4-aminobutan-2-yl)-4-(6-aminopyridin-3-yl)-3-(1H-tetrazol-5-yl)benzene-1,2-disulfonamide | 468 |
| 499 | 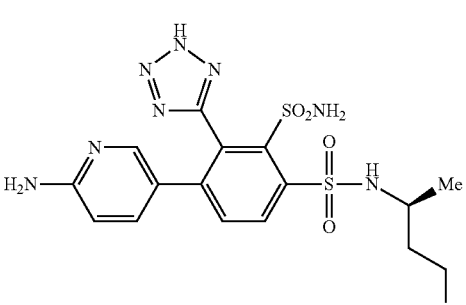 | (S)-N1-(4-aminobutan-2-yl)-4-(6-aminopyridin-3-yl)-3-(1H-tetrazol-5-yl)benzene-1,2-disulfonamide | 468 |

Example 500

(R)—N1-(1-(2-aminoethyl)pyrrolidin-3-yl)-4-(6-aminopyridin-3-yl)-3-(2H-tetrazol-5-yl)benzene-1,2-disulfonamide

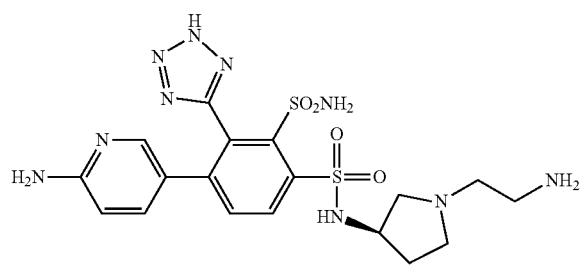 [SMILES: NCCN1CC[C@@H](NS(=O)(=O)c2ccc(-c3ccc(N)nc3)c(-c3nn[nH]n3)c2S(N)(=O)=O)C1]

Step A: Benzyl-N-[(3R)-1-(2-{[(tert-butoxy)carbonyl]amino}ethyl)pyrrolidin-3-yl]carbamate To a mixture of (R)-benzyl-pyrrolidin-3-ylcarbamate (1.92 g, 8.72 mmol) and anhydrous K$_2$CO$_3$ (3.61 g, 26.2 mmol) in DMF (35 mL) was added tert-butyl (2-bromoethyl)carbamate (4.88 g, 21.79 mmol) at room temperature. The reaction mixture was stirred for 18 hours at room temperature under nitrogen. The resulting mixture was poured into water (100 mL). The aqueous phase was extracted with EA (3×50 mL). The combined organic layers was washed with brine (2×30 mL), dried over anhydrous Na$_2$SO$_4$ and filtered. The filtrate was concentrated under vacuum. The residue was purified by silica gel column chromatography, eluted with 75% EA in PE. The fractions containing desired product were combined and concentrated under vacuum to afford the title compound: LCMS [M+1]+: 364.

Step B: (R)-tert-butyl (2-(3-aminopyrrolidin-1-yl)ethyl)carbamate

To a solution of benzyl-N-[(3R)-1-(2-{[(tert-butoxy)carbonyl]amino}ethyl)pyrrolidin-3-yl]carbamate (2.28 g, 6.28 mmol) in MeOH (35 mL) was added Pd(OH)$_2$/C (20% wt., 0.42 g, 2.95 mmol) under nitrogen at room temperature. The reaction mixture was stirred for 24 hours at room temperature under hydrogen (1.5 atm). The resulting mixture was filtered. The filtrate was concentrated under vacuum to afford the title compound, which was used in the next step without any further purification: LCMS [M+1]$^+$: 230.

Step C: tert-Butyl (2-((3R)-3-(2-(N,N-bis(4-methoxybenzyl)sulfamoyl)-4-iodo-3-(2-(4-methoxybenzyl)-2H-tetrazol-5-yl)phenylsulfinamido)pyrrolidin-1-yl)ethyl)carbamate The title compound was prepared as described for EXAMPLE 477, step A, using (R)-tert-butyl (2-(3-aminopyrrolidin-1-yl)ethyl)carbamate (1.38 g, 6.02 mmol): LCMS [M+1]$^+$: 1003.

Step D: tert-butyl (R)-(2-(3-((4-(6-aminopyridin-3-yl)-2-(N,N-bis(4-methoxybenzyl)sulfamoyl)-3-(2-(4-methoxybenzyl)-2H-tetrazol-5-yl)phenyl)sulfonamido)pyrrolidin-1-yl)ethyl)carbamate To a solution of tert-butyl (2-((3R)-3-(2-(N,N-bis(4-methoxybenzyl)sulfamoyl)-4-iodo-3-(2-(4-methoxybenzyl)-2H-tetrazol-5-yl)phenylsulfinamido)pyrrolidin-1-yl)ethyl)carbamate (0.70 g, 0.70 mmol), 5-(4,4,5,5-tetramethyl-1,3,2-dioxaborolan-2-yl)pyridin-2-amine (0.38 g, 1.74 mmol) in 1,4-dioxane (8.5 mL) and water (1.5 mL) was added Pd(PPh$_3$)$_4$ (0.16 g, 0.14 mmol) and Na$_2$CO$_3$ (0.22 g, 2.09 mmol). The reaction mixture was degassed with nitrogen three times and stirred for 4 hours at 80° C. under nitrogen. The resulting mixture was diluted with water (15 mL), extracted with EA (3×20 mL). The combined organic layers was washed with brine (3×30 mL), dried over anhydrous Na$_2$SO$_4$ and filtered. The filtrate was concentrated under vacuum. The residue was purified by silica gel column chromatography, eluted with 10% MeOH in DCM. The fractions containing desired product were combined and concentrated under vacuum to afford the title compound: LCMS [M+1]$^+$: 969.

Step E: (R)—N1-(1-(2-aminoethyl)pyrrolidin-3-yl)-4-(6-aminopyridin-3-yl)-3-(2H-tetrazol-5-yl)benzene-1,2-disulfonamide The title compound was prepared as described for EXAMPLE 462, step B using (R)-tert-butyl(2-(3-(4-(6-aminopyridin-3-yl)-2-(N,N-bis(4-methoxybenzyl)sulfamoyl)-3-(2-(4-methoxybenzyl)-2H-tetrazol-5-yl)phenylsulfonamido)pyrrolidin-1-yl)ethyl) carbamate (0.68 g, 0.70 mmol) to afford the crude product. The crude product was purified by Prep-HPLC with the following conditions: Column: X Bridge C18 OBD Prep Column 100 Å, 10 µm, 19 mm×250 mm; Mobile Phase A: water (10 mmol/L NH$_4$HCO$_3$), Mobile Phase B: ACN; Flow rate: 20 mL/min; Gradient: 0% B to 25% B in 9 min; Detector: UV 254 and 220 nm; Retention time: 8.05 min. The fractions containing desired product were combined and concentrated under vacuum to afford the title compound: LCMS [M+H]$^+$: 509; $^1$H NMR (300 MHz, DMSO-d$_6$+D$_2$O): δ 8.25 (d, J=9.0 Hz, 1H), 7.70 (d, J=8.4 Hz, 1H), 7.45 (d, J=2.4 Hz, 1H), 6.78-6.67 (m, 1H), 6.17 (dd, J=8.8 Hz, 2.0 Hz, 1H), 2.76-2.70 (m, 2H), 2.65-2.58 (m, 1H), 2.56-2.48 (m, 3H), 2.42-2.36 (m, 2H), 2.32-2.21 (m, 1H), 2.09-1.93 (m, 1H), 1.58-1.54 (m, 1H).

BIOLOGICAL ASSAYS

Enzyme Activity: Determination of IC$_{50}$

The Class B enzyme activities were measured in the presence of the test inhibitor in a fluorescence assay against a commercially available substrate consisting of a cephalosporin core linking 7-hydroxycoumarin to fluorescein (CCF2-FA). The enzyme (NDM-1, IMP-1 or VIM-1; for a review, see: Meine, M.-R.; Llarrull, L. I.; Vila, A. J. *Antibiotics*, 2014, 3, 285-316) and the substrate were diluted in 100 mM KH$_2$PO$_4$ buffer (pH 7) containing 0.005% Tween-20 and 10 µM ZnSO$_4$. In the assay, the final concentration of enzyme was 1 pM, 2 pM and 30 pM for NDM-1, IMP-1 and VIM-1, respectively, and the final concentration of CCF2-FA was 1.25 µM. The test inhibitor was dissolved in dimethylsulfoxide and diluted 1:50 in the assay, resulting in a final concentration range of 20 µM to 0.00063 µM. In a 384-well microplate, the test inhibitor was incubated with the metallo-β-lactamase enzyme and the substrate for 2 hours at 25° C. Fluorescence at 460 nm following excitation at 405 nm was measured. The IC$_{50}$ value was determined from semi-logarithmic plots of enzyme inhibition versus inhibitor concentration, with a curve generated using a 4-parameter fit.

Representative compounds of the present invention exhibit inhibition of Class B β-lactamases in this assay. For example, the compounds of Examples 1-500 were tested in this assay and were found to have the IC$_{50}$ values shown in Assay Table 1.

Antibiotic Potentiation Activity: Determination of Synergistic Concentration

The concentrations of metallo-β-lactamase inhibitors required to restore the susceptibility of various strains of bacteria to inactive concentrations of antibiotics were determined in an assay that assessed bacterial growth by measuring the optical density at 600 nm (OD$_{600}$). The bacterial strains tested included the clinical strains *Escherichia coli* expressing NDM-1 (CLB30005, CLB30016), *Serratia marcescens* expressing IMP-1 (CL5741), and *Klebsiella pneumoniae* expressing VIM-1 (IHMA599644). Inhibitor activity was measured in the presence and absence of imipenem in a 384-well microplate.

The clinical strains CLB30016, CL5741 and IHMA599644 were grown on trypticase soy agar containing 5% sheep's blood. The bacteria on agar plates were incubated at 35° C. with humidity overnight. The following day, individual colonies from each clinical strain were picked and resuspended in 5 ml saline to attain an OD$_{600}$ of 0.14, 0.11, 0.15 and 0.13, for CLB30016, CL5741 and IHMA599644, respectively. These were further diluted 1:100 into 1.1× CAMHB and used to inoculate the test wells as described below.

Imipenem in 10 mM 3-(N-morpholino)propanesulfonic acid (MOPS, pH 7) was stored in single use aliquots at −80° C. Test inhibitors were dissolved in dimethylsulfoxide and diluted 1:50 in the assay, resulting in a final concentration range of 200 µM to 0.195 µM. On the day of the assay, 4 µl of antibiotic was added to 45 ul of bacteria followed by 1 µl of test compound and mixed by pipetting and with an orbital shaker. The concentration of antibiotic used in the assay was 1 µg/ml. Microplates were covered and incubated at 35° C. for 22 hours to 24 hours. At the end of the incubation, absorbance was determined using a spectrophotometer. The synergistic concentration of MBLI was determined by identifying the lowest concentration of test compound in the presence of a given concentration of antibiotic that was required to inhibit 95% of the growth of the bacteria. The results for Examples 1-500 are reported in Table 1, expressed as the concentration of compound that potentiated the action of antibiotic (imipenem) affecting 95% inhibition of bacterial growth (MITC95).

Representative compounds of the present invention do not have any or have minimal intrinsic antibacterial activity but display a synergistic effect when used in combination with a beta-lactam antibiotic. For example, in general, the compounds of Examples 1-500 were determined to restore susceptibility to imipenem for one or more of the test organisms at concentrations of 100 μM or less.

ASSAY TABLE 1

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 1 | 0.5805 | 0.08531 | 0.2642 | 0.8542 | 0.5156 | 1.448 |
| 2 | 0.2789 | 0.1625 | 0.4615 | 0.7813 | 0.7813 | 1.563 |
| 3 | 0.2334 | 0.1507 | 0.2575 | 1.563 | 3.125 | 6.25 |
| 4 | 0.3538 | 0.1355 | 0.2371 | 1.563 | 3.125 | 3.125 |
| 5 | 0.3459 | 0.1972 | 0.1456 | 0.8906 | 0.25 | 1.781 |
| 6 | 0.06479 | 0.02689 | 0.09149 | 1.563 | 6.25 | 6.25 |
| 7 | 0.2144 | 0.1005 | 0.1085 | 3.125 | 6.25 | 6.25 |
| 8 | 0.3609 | 0.1227 | 0.2866 | 3.125 | 1.563 | 6.25 |
| 9 | 0.1711 | 0.08439 | 0.1328 | 1.563 | 0.7813 | 1.563 |
| 10 | 0.2346 | 0.09015 | 0.1772 | 0.6406 | 0.1875 | 1.531 |
| 11 | 0.1054 | 0.01854 | 0.05017 | 0.7813 | 0.7813 | 1.563 |
| 12 | 0.3161 | 0.04291 | 0.1025 | 0.6302 | 0.25 | 0.5703 |
| 13 | 2.139 | 0.07573 | 0.4117 | 12.5 | 12.5 | 25 |
| 14 | 0.1731 | 0.02553 | 0.1761 | 3.125 | 12.5 | 12.5 |
| 15 | 0.4514 | 0.0926 | 0.3939 | 12.5 | 50 | 25 |
| 16 | 0.4422 | 0.09208 | 0.4609 | 12.5 | 25 | 25 |
| 17 | 0.4305 | 0.08886 | 0.4099 | 6.25 | 12.5 | 12.5 |
| 18 | 0.268 | 0.04877 | 0.2709 | 3.125 | 6.25 | 6.25 |
| 19 | 0.486 | 0.09527 | 0.3348 | 6.25 | 50 | 25 |
| 20 | 0.8174 | 0.09725 | 0.4936 | 6.25 | 25 | 25 |
| 21 | 0.3828 | 0.06416 | 0.243 | 3.125 | 6.25 | 6.25 |
| 22 | 0.413 | 0.03484 | 0.2326 | 3.125 | 6.25 | 3.125 |
| 23 | 0.2941 | 0.05108 | 0.224 | 6.25 | 25 | 12.5 |
| 24 | 0.2347 | 0.07315 | 0.2053 | 3.125 | 25 | 12.5 |
| 25 | 2.242 | 3.023 | 4.516 | 6.25 | 25 | 25 |
| 26 | 1.154 | 0.9741 | 1.659 | 3.125 | 12.5 | 12.5 |
| 27 | 1.59 | 0.8253 | 1.916 | 6.25 | 12.5 | 25 |
| 28 | 0.6464 | 0.6463 | 0.7257 | 6.25 | 25 | 12.5 |
| 29 | 2.085 | 1.354 | 3.059 | 6.25 | 25 | 25 |
| 30 | 0.369 | 0.06858 | 0.3078 | 3.125 | 6.25 | 6.25 |
| 31 | 2.022 | 2.591 | 8.181 | 2.344 | 9.375 | 6.25 |
| 32 | 0.3395 | 0.06904 | 0.2962 | 1.563 | 6.25 | 3.125 |
| 33 | 0.2752 | 0.0731 | 0.299 | 6.25 | 25 | 25 |
| 34 | 0.4289 | 0.08163 | 0.3294 | 6.25 | 25 | 50 |
| 35 | 0.349 | 0.05085 | 0.2563 | 3.125 | 12.5 | 12.5 |
| 36 | 0.2466 | 0.03688 | 0.166 | 3.125 | 25 | 12.5 |
| 37 | 0.2871 | 0.00769 | 0.1983 | 3.125 | 12.5 | 12.5 |
| 38 | 1.431 | 0.4241 | 2.517 | 3.125 | 12.5 | 12.5 |
| 39 | 0.8785 | 0.5057 | 0.9078 | 6.25 | 12.5 | 12.5 |
| 40 | 1.859 | 1.704 | 2.657 | 6.25 | 25 | 25 |
| 41 | 0.8105 | 0.9382 | 1.753 | 6.25 | 25 | 25 |
| 42 | 0.7002 | 0.6967 | 0.6695 | 3.125 | 12.5 | 12.5 |
| 43 | 1.234 | 2.068 | 1.859 | 6.25 | 25 | 100 |
| 44 | 2.217 | 0.8716 | 2.058 | 6.25 | 25 | 25 |
| 45 | 1.651 | 2.395 | 2.39 | 6.25 | 50 | 25 |
| 46 | 0.2889 | 0.05716 | 0.321 | 1.563 | 6.25 | 3.125 |
| 47 | 0.4836 | 0.06578 | 0.3041 | 3.125 | 6.25 | 12.5 |
| 48 | 0.9514 | 0.2583 | 0.4898 | 3.125 | 6.25 | 3.125 |
| 49 | 0.4127 | 0.06731 | 0.3284 | 12.5 | 25 | 25 |
| 50 | 0.2629 | 0.04077 | 0.2496 | 12.5 | 25 | 25 |
| 51 | 0.3926 | 0.09705 | 0.4408 | 12.5 | 25 | 25 |
| 52 | 5.939 | 15.28 | 25.29 | 3.125 | 12.5 | 50 |
| 53 | 0.2978 | 0.04148 | 0.1919 | 1.563 | 3.125 | 3.125 |
| 54 | 1.928 | 0.19 | 3.635 | 3.125 | 6.25 | 6.25 |
| 55 | 0.8595 | 0.5101 | 1.461 | 3.125 | 3.125 | 6.25 |
| 56 | 0.342 | 0.05187 | 0.2454 | 3.125 | 1.563 | 3.125 |
| 57 | 0.5542 | 0.08529 | 0.3549 | 6.25 | 3.125 | 3.125 |

ASSAY TABLE 1-continued

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 58 | 0.7589 | 0.06858 | 0.4038 | 1.563 | 1.563 | 3.125 |
| 59 | 0.5584 | 0.03572 | 0.3086 | 1.563 | 1.563 | 3.125 |
| 60 | 0.6792 | 0.07653 | 0.2362 | 1.563 | 3.125 | 3.125 |
| 61 | 1.473 | 0.9756 | 1.44 | 3.125 | 3.125 | 3.125 |
| 62 | 1.28 | 0.8432 | 1.633 | 1.563 | 3.125 | 3.125 |
| 63 | 0.3071 | 0.04452 | 0.2571 | 1.563 | 1.563 | 1.563 |
| 64 | 2.158 | 1.488 | 5.694 | 1.563 | 12.5 | 12.5 |
| 65 | 0.7032 | 0.4639 | 1.433 | 3.125 | 6.25 | 3.125 |
| 66 | 2.263 | 1.089 | 4.015 | 3.125 | 3.125 | 6.25 |
| 67 | 0.4882 | 0.0407 | 0.2714 | 1.563 | 1.563 | 3.125 |
| 68 | 1.97 | 1.01 | 3.697 | 1.563 | 3.125 | 3.125 |
| 69 | 0.1841 | 0.03231 | 0.1846 | 1.563 | 0.7813 | 3.125 |
| 70 | 2.309 | 1.954 | 2.79 | 3.125 | 6.25 | 12.5 |
| 71 | 0.3554 | 0.06119 | 0.2235 | 3.125 | 1.563 | 3.125 |
| 72 | 0.27 | 0.02 | 0.26 | 1.563 | 1.563 | 3.125 |
| 73 | 0.1603 | 0.03323 | 0.1253 | 1.563 | 1.563 | 3.125 |
| 74 | 0.8404 | 0.6458 | 1.143 | 2.344 | 2.344 | 3.125 |
| 75 | 0.1576 | 0.02071 | 0.1153 | 1.563 | 1.563 | 3.125 |
| 76 | 0.1948 | 0.02846 | 0.1288 | 1.563 | 3.125 | 3.125 |
| 77 | 0.1662 | 0.03408 | 0.1332 | 1.563 | 3.125 | 6.25 |
| 78 | 0.2345 | 0.0225 | 0.1834 | 1.563 | 3.125 | 3.125 |
| 79 | 0.2827 | 0.04273 | 0.1813 | 1.563 | 1.563 | 3.125 |
| 80 | 0.3356 | 0.0488 | 0.1581 | 1.563 | 1.563 | 3.125 |
| 81 | 0.1907 | 0.02858 | 0.1349 | 1.563 | 1.563 | 1.563 |
| 82 | 0.2063 | 0.04932 | 0.1965 | 12.5 | 6.25 | 12.5 |
| 83 | 0.2608 | 0.04826 | 0.2083 | 3.125 | 3.125 | 3.125 |
| 84 | 0.4033 | 0.06189 | 0.2701 | 3.125 | 1.563 | 3.125 |
| 85 | 0.2051 | 0.0351 | 0.1473 | 3.125 | 6.25 | 6.25 |
| 86 | 0.1291 | 0.02748 | 0.07563 | 1.563 | 1.563 | 6.25 |
| 87 | 0.2605 | 0.03672 | 0.1969 | 3.125 | 3.125 | 6.25 |
| 88 | 0.1722 | 0.02028 | 0.1647 | 3.125 | 3.125 | 6.25 |
| 89 | 0.5676 | 0.05813 | 0.2296 | 3.125 | 6.25 | 6.25 |
| 90 | 0.4108 | 0.0795 | 0.2704 | 1.563 | 3.125 | 3.125 |
| 91 | 0.326 | 0.07691 | 0.3266 | 1.563 | 1.563 | 3.125 |
| 92 | 1.174 | 0.609 | 1.413 | 12.5 | 12.5 | 12.5 |
| 93 | 5.291 | 6.351 | 12.44 | 3.125 | 6.25 | 12.5 |
| 94 | 0.7296 | 0.5742 | 0.9732 | 2.083 | 3.646 | 3.125 |
| 95 | 0.1927 | 0.02701 | 0.1732 | 3.125 | 1.563 | 3.125 |
| 96 | 0.4015 | 0.07571 | 0.2986 | 3.125 | 6.25 | 6.25 |
| 97 | 0.3826 | 0.02142 | 0.2223 | 3.125 | 3.125 | 3.125 |
| 98 | 0.209 | 0.03651 | 0.1693 | 1.563 | 1.823 | 2.604 |
| 99 | 0.5656 | 0.09939 | 0.4991 | 6.25 | 12.5 | 25 |
| 100 | 3.262 | 3.878 | 12.63 | 25 | 50 | 200 |
| 101 | 1.246 | 0.2883 | 0.7443 | 3.125 | 3.125 | 6.25 |
| 102 | 0.2634 | 0.0324 | 0.1944 | 1.563 | 3.125 | 3.125 |
| 103 | 0.2261 | 0.02932 | 0.1961 | 3.125 | 3.125 | 3.125 |
| 104 | 1.237 | 0.2285 | 1.588 | 3.125 | 1.563 | 6.25 |
| 105 | 1.182 | 0.2057 | 1.136 | 1.563 | 1.563 | 6.25 |
| 106 | 0.3794 | 0.07327 | 0.2365 | 3.125 | 6.25 | 12.5 |
| 107 | 1.401 | 0.1841 | 1.687 | 3.125 | 3.125 | 6.25 |
| 108 | 0.3364 | 0.05123 | 0.2681 | 3.125 | 1.563 | 3.125 |
| 109 | 0.4396 | 0.08209 | 0.3223 | 1.563 | 1.563 | 3.125 |
| 110 | 0.3462 | 0.08153 | 0.3091 | 3.125 | 1.563 | 3.125 |
| 111 | 0.4291 | 0.07456 | 0.2981 | 1.563 | 1.563 | 3.125 |
| 112 | 0.3179 | 0.04604 | 0.2187 | 1.563 | 1.563 | 3.125 |
| 113 | 1.12 | 0.6465 | 0.7727 | 3.125 | 1.563 | 3.125 |
| 114 | 0.298 | 0.06486 | 0.3064 | 3.125 | 3.125 | 6.25 |
| 115 | 0.3242 | 0.0602 | 0.3878 | 3.125 | 3.125 | 6.25 |
| 116 | 0.2665 | 0.02387 | 0.2648 | 1.563 | 1.563 | 3.125 |
| 117 | 0.243 | 0.01259 | 0.1828 | 3.125 | 6.25 | 3.125 |
| 118 | 0.331 | 0.02604 | 0.2888 | 6.25 | 25 | 12.5 |
| 119 | 0.2228 | 0.04074 | 0.2536 | 1.563 | 1.563 | 3.125 |
| 120 | 0.2575 | 0.04946 | 0.2018 | 1.563 | 1.563 | 3.125 |
| 121 | 2.844 | 1.423 | 7.084 | 3.125 | 6.25 | 12.5 |
| 122 | 0.2823 | 0.03292 | 0.193 | 1.563 | 1.563 | 3.125 |
| 123 | 0.2194 | 0.03601 | 0.1885 | 1.563 | 1.563 | 3.125 |
| 124 | 0.2223 | 0.00652 | 0.2535 | 3.125 | 12.5 | 12.5 |
| 125 | 0.286 | 0.04653 | 0.1956 | 1.563 | 1.563 | 3.125 |
| 126 | 0.222 | 0.05687 | 0.1803 | 1.563 | 1.563 | 3.125 |

ASSAY TABLE 1-continued

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 127 | 0.3216 | 0.04212 | 0.2363 | 1.563 | 3.125 | 3.125 |
| 128 | 0.1767 | 0.04427 | 0.1988 | 6.25 | 3.125 | 12.5 |
| 129 | 9.075 | 0.2785 | 0.969 | 6.25 | 6.25 | 12.5 |
| 130 | 0.6842 | 0.05295 | 0.1514 | 1.563 | 1.563 | 3.125 |
| 131 | 1.827 | 0.2747 | 0.1198 | 3.125 | 1.563 | 1.563 |
| 132 | 1.401 | 0.1139 | 0.1237 | 1.563 | 0.7813 | 1.563 |
| 133 | 0.8158 | 0.3414 | 0.1183 | 1.563 | 0.7813 | 1.563 |
| 134 | 2.072 | 0.3012 | 0.1401 | 3.125 | 1.563 | 3.125 |
| 135 | 0.2294 | 0.1361 | 0.1071 | 1.563 | 1.563 | 1.563 |
| 136 | 0.0755 | 0.03684 | 0.1055 | 3.125 | 1.563 | 1.563 |
| 137 | 0.2653 | 0.126 | 0.1572 | 3.125 | 3.125 | 3.125 |
| 138 | 0.2748 | 0.1238 | 0.1501 | 3.125 | 3.125 | 3.125 |
| 139 | 0.4096 | 0.05818 | 0.1405 | 1.563 | 0.7813 | 3.125 |
| 140 | 0.7792 | 0.08674 | 0.1111 | 1.563 | 0.7813 | 1.563 |
| 141 | 0.04083 | 0.01864 | 0.06229 | 6.25 | 3.125 | 6.25 |
| 142 | 0.6363 | 0.1851 | 0.5585 | 1.563 | 3.906 | 3.125 |
| 143 | 0.2662 | 0.08486 | 0.2203 | 1.563 | 3.125 | 12.5 |
| 144 | 0.2884 | 0.08981 | 0.1619 | 3.125 | 12.5 | 12.5 |
| 145 | 0.2208 | 0.03427 | 0.1818 | 0.7813 | 0.7813 | 1.563 |
| 146 | 0.3557 | 0.03717 | 0.2236 | 0.7813 | 3.125 | 1.563 |
| 147 | 0.4936 | 0.5501 | 0.5589 | 6.25 | 25 | 12.5 |
| 148 | 0.4905 | 0.2134 | 0.7486 | 3.125 | 12.5 | 6.25 |
| 149 | 0.9927 | 0.2159 | 0.7386 | 6.25 | 12.5 | 6.25 |
| 151 | 2.428 | 5.943 | 9.218 | 6.25 | 12.5 | 50 |
| 152 | 0.2639 | 0.07201 | 0.1954 | 3.125 | 3.125 | 6.25 |
| 153 | 0.7036 | 0.2799 | 1.053 | 25 | 50 | 100 |
| 154 | 0.1547 | 0.06702 | 0.2803 | 6.25 | 50 | 25 |
| 155 | 0.6583 | 1.637 | 0.8044 | 0.6406 | 0.0625 | 2.563 |
| 156 | 0.8978 | 0.2898 | 1.738 | 12.5 | 6.25 | 25 |
| 157 | 3.087 | 0.3198 | 0.8269 | 0.8906 | 0.125 | 1.281 |
| 158 | 1.707 | 0.6013 | 1.267 | 0.8906 | 0.25 | 1.781 |
| 159 | 1.294 | 0.1948 | 0.5099 | 1.563 | 1.563 | 3.125 |
| 160 | 1.389 | 0.599 | 1.067 | 1.563 | 3.125 | 3.125 |
| 161 | 0.4012 | 0.03138 | 0.1057 | 0.5295 | 0.2995 | 0.8542 |
| 162 | 0.7334 | 0.06075 | 0.1542 | 0.5573 | 0.3203 | 0.9844 |
| 163 | 0.4503 | 0.06048 | 0.1184 | 0.7813 | 0.3906 | 0.7813 |
| 164 | 0.2718 | 0.03776 | 0.1055 | 0.7813 | 0.3906 | 0.7813 |
| 165 | 24.38 | 17.69 | 1.17 | 1.563 | 0.3906 | 3.125 |
| 166 | 0.82 | 0.05809 | 0.2331 | 1.563 | 0.7813 | 3.125 |
| 167 | 0.346 | 0.05911 | 0.169 | 1.563 | 1.563 | 3.125 |
| 168 | 0.5436 | 0.05152 | 0.1605 | 0.668 | 0.375 | 0.8906 |
| 169 | 2.081 | 0.1367 | 0.5805 | 1.563 | 0.7813 | 3.125 |
| 170 | 1.116 | 0.08032 | 0.2565 | 1.563 | 0.7813 | 1.563 |
| 171 | 1.393 | 0.1247 | 0.506 | 1.563 | 0.7813 | 3.125 |
| 172 | 0.5093 | 0.05003 | 0.1587 | 0.7813 | 0.5859 | 1.563 |
| 173 | 0.9335 | 0.09484 | 0.2844 | 0.7813 | 0.7813 | 3.125 |
| 174 | 1.66 | 0.1167 | 0.3895 | 1.563 | 3.125 | 3.125 |
| 175 | 1.003 | 0.1269 | 0.334 | 1.563 | 0.7813 | 3.125 |
| 176 | 0.7279 | 0.0524 | 0.1915 | 0.7813 | 0.3906 | 1.563 |
| 177 | 0.8615 | 0.0669 | 0.2457 | 1.563 | 0.7813 | 1.563 |
| 178 | 0.8696 | 0.06395 | 0.2663 | 1.563 | 1.563 | 3.125 |
| 179 | 2.997 | 0.2189 | 0.9041 | 3.125 | 1.563 | 3.125 |
| 180 | 0.3869 | 0.04716 | 0.1614 | 0.7813 | 0.3906 | 1.563 |
| 181 | 0.2726 | 0.03718 | 0.133 | 0.7813 | 0.3906 | 1.563 |
| 182 | 0.4531 | 0.03934 | 0.09036 | 0.5573 | 0.2578 | 0.6875 |
| 183 | 0.3384 | 0.05395 | 0.1102 | 0.7813 | 0.3906 | 0.7813 |
| 184 | 0.6733 | 0.03465 | 0.1893 | 0.7813 | 0.3906 | 0.7813 |
| 185 | 0.5239 | 0.04762 | 0.1896 | 0.7688 | 0.2135 | 1.025 |
| 186 | 4.094 | 0.3664 | 0.9014 | 1.563 | 0.7813 | 1.563 |
| 187 | 0.2304 | 0.02124 | 0.09821 | 0.7813 | 0.5859 | 1.172 |
| 188 | 0.6127 | 0.07557 | 0.2127 | 1.563 | 1.563 | 3.125 |
| 189 | 0.6154 | 0.0718 | 0.2158 | 1.563 | 0.7813 | 3.125 |
| 190 | 0.6235 | 0.05898 | 0.2811 | 0.3906 | 0.3906 | 0.7813 |
| 191 | 0.4334 | 0.04688 | 0.1728 | 0.8906 | 0.25 | 0.8906 |
| 192 | 0.6993 | 0.2738 | 0.126 | 0.7813 | 1.563 | 1.563 |
| 193 | 0.2112 | 0.03916 | 0.1126 | 1.563 | 1.563 | 2.344 |
| 194 | 0.2418 | 0.1053 | 0.1235 | 0.5573 | 0.3203 | 2.229 |
| 195 | 0.5234 | 0.1689 | 0.1824 | 0.5859 | 0.5859 | 1.563 |
| 196 | 0.4795 | 0.3283 | 0.2179 | 0.2969 | 0.03125 | 1.336 |

ASSAY TABLE 1-continued

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | Serratia marcescens expressing IMP-1 (CL5741) MITC95 µM | Escherichia coli expressing NDM-1 (CLB30016) MITC95 µM | Klebsiella pneumoniae expressing VIM-1 (IHMA599644) MITC95 µM |
|---|---|---|---|---|---|---|
| 197 | 0.3951 | 0.07636 | 0.1446 | 1.172 | 2.344 | 3.125 |
| 198 | 0.2929 | 0.05916 | 0.1346 | 1.172 | 1.172 | 2.344 |
| 199 | 0.102 | 0.02569 | 0.04709 | 1.042 | 1.042 | 2.865 |
| 200 | 0.2755 | 0.05275 | 0.1138 | 1.563 | 1.563 | 3.125 |
| 201 | 0.109 | 0.01987 | 0.1253 | 1.563 | 1.563 | 3.125 |
| 202 | 0.7129 | 0.1241 | 0.3284 | 1.563 | 3.125 | 3.125 |
| 203 | 0.1987 | 0.05004 | 0.1853 | 1.563 | 3.125 | 3.125 |
| 204 | 2.56 | 0.5202 | 0.2263 | 1.563 | 1.563 | 1.563 |
| 205 | 5.886 | 1.204 | 3.628 | 3.125 | 1.563 | 3.125 |
| 206 | 0.4978 | 0.07293 | 0.2108 | 1.563 | 0.3906 | 1.563 |
| 207 | 0.9988 | 0.2735 | 0.6897 | 1.563 | 3.125 | 3.125 |
| 208 | 3.117 | 0.4487 | 1.228 | 3.125 | 1.563 | 6.25 |
| 209 | 3.103 | 0.1483 | 0.1769 | 0.7813 | 0.293 | 1.563 |
| 210 | 1.499 | 0.1262 | 0.1967 | 0.7813 | 0.1953 | 3.125 |
| 211 | 2.247 | 0.1556 | 0.1818 | 3.125 | 1.563 | 6.25 |
| 212 | 1.067 | 0.07068 | 0.1543 | 0.7813 | 0.3906 | 1.563 |
| 213 | 1.544 | 0.07586 | 0.1134 | 0.7813 | 0.3906 | 1.563 |
| 214 | 8.489 | 0.5663 | 0.7324 | 1.563 | 0.7813 | 3.125 |
| 215 | 2.125 | 0.1746 | 0.2224 | 0.3906 | 0.1953 | 3.125 |
| 216 | 1.834 | 0.2371 | 0.2694 | 0.7813 | 0.1953 | 3.125 |
| 217 | 0.5049 | 0.4471 | 0.487 | 1.563 | 0.3906 | 3.125 |
| 218 | 0.6936 | 0.7858 | 0.5492 | 0.7813 | 0.1953 | 3.125 |
| 219 | 1.931 | 0.3657 | 0.2094 | 1.563 | 1.563 | 1.563 |
| 220 | 35.8 | 1.575 | 0.4419 | 3.125 | 1.563 | 1.563 |
| 221 | 0.6884 | 0.281 | 0.1522 | 1.563 | 1.563 | 6.25 |
| 222 | 1.193 | 0.3108 | 0.4448 | 1.563 | 0.3906 | 3.125 |
| 223 | 4.513 | 1.746 | 1.407 | 0.3906 | 0.09766 | 0.3906 |
| 224 | 0.4119 | 0.1424 | 0.187 | 1.563 | 1.563 | 3.125 |
| 225 | 0.1098 | 0.02561 | 0.0561 | 1.563 | 3.125 | 3.125 |
| 226 | 3.24 | 0.7467 | 0.9477 | 3.125 | 6.25 | 12.5 |
| 227 | 0.1645 | 0.04799 | 0.1373 | 1.563 | 1.563 | 3.125 |
| 228 | 0.562 | 0.08643 | 0.1503 | 1.563 | 0.7813 | 3.125 |
| 229 | 0.1726 | 0.03078 | 0.1199 | 3.125 | 0.7813 | 3.125 |
| 230 | 0.3568 | 0.05927 | 0.1988 | 1.563 | 1.563 | 3.125 |
| 231 | 0.3764 | 0.02884 | 0.1145 | 1.563 | 1.563 | 3.125 |
| 232 | 0.6094 | 0.05054 | 0.1603 | 0.7813 | 0.3906 | 1.563 |
| 233 | 0.3052 | 0.02253 | 0.08969 | 0.3906 | 0.3906 | 1.563 |
| 234 | 0.14 | 0.01573 | 0.08291 | 0.7813 | 0.7813 | 0.7813 |
| 235 | 0.4403 | 0.03077 | 0.1049 | 0.7813 | 1.563 | 3.125 |
| 236 | 0.5439 | 0.06471 | 0.1299 | 0.7813 | 3.125 | 1.563 |
| 237 | 0.1201 | 0.01335 | 0.05519 | 1.563 | 3.125 | 1.563 |
| 238 | 0.8005 | 0.1106 | 0.0653 | 0.7813 | 1.563 | 1.563 |
| 239 | 1.056 | 0.4389 | 0.1126 | 1.563 | 0.7813 | 3.125 |
| 240 | 0.7453 | 0.05686 | 0.1686 | 0.7813 | 0.1953 | 1.563 |
| 241 | 0.7381 | 0.05357 | 0.1817 | 1.042 | 0.5208 | 1.302 |
| 242 | 0.157 | 0.06112 | 0.08408 | 0.7813 | 0.7813 | 1.563 |
| 243 | 0.3125 | 0.2756 | 0.1935 | 0.3906 | 0.3906 | 1.563 |
| 244 | 6.584 | 1.304 | 6.755 | 1.563 | 0.7813 | 1.563 |
| 245 | 1.141 | 0.04935 | 0.3426 | 1.563 | 0.7813 | 3.125 |
| 246 | 0.8525 | 0.04052 | 0.1201 | 1.563 | 0.7813 | 1.563 |
| 247 | 0.5042 | 0.03308 | 0.1486 | 1.563 | 0.7813 | 3.125 |
| 248 | 0.147 | 0.01053 | 0.0345 | 1.563 | 0.3906 | 0.7813 |
| 249 | 0.3419 | 0.01529 | 0.06079 | 1.563 | 0.3906 | 1.563 |
| 250 | 0.5127 | 0.03352 | 0.1999 | 0.7813 | 0.3906 | 1.563 |
| 251 | 0.7554 | 0.0567 | 0.1938 | 0.7813 | 0.7813 | 1.563 |
| 252 | 0.6538 | 0.04264 | 0.1492 | 0.7383 | 0.4271 | 0.8359 |
| 253 | 2.681 | 0.8845 | 1.531 | 0.7813 | 1.563 | 1.563 |
| 254 | 2.134 | 0.4532 | 1.547 | 0.7813 | 0.7813 | 1.563 |
| 255 | 2.844 | 0.1127 | 0.9363 | 0.7813 | 0.3906 | 0.7813 |
| 256 | 0.6088 | 0.04165 | 0.1676 | 0.7813 | 0.3906 | 1.563 |
| 257 | 0.6425 | 0.033 | 0.1567 | 0.7813 | 0.3906 | 0.7813 |
| 258 | 0.6907 | 0.05354 | 0.1562 | 0.7813 | 0.1953 | 1.563 |
| 259 | 0.8359 | 0.05554 | 0.229 | 0.7813 | 0.3906 | 1.563 |
| 260 | 0.648 | 0.04312 | 0.1507 | 1.563 | 0.7813 | 1.563 |
| 261 | 0.6484 | 0.0691 | 0.224 | 0.7813 | 0.1953 | 0.7813 |
| 262 | 0.9246 | 0.07679 | 0.2952 | 0.7813 | 0.1953 | 0.7813 |
| 263 | 0.8636 | 0.04611 | 0.2047 | 0.7813 | 0.3906 | 1.563 |
| 264 | 5.931 | 0.1998 | 0.4701 | 1.563 | 0.7813 | 1.563 |
| 265 | 0.2918 | 0.02413 | 0.09272 | 0.7813 | 1.563 | 1.563 |

ASSAY TABLE 1-continued

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | *Serratia marcescens* expressing IMP-1 (CL5741) MITC95 μM | *Escherichia coli* expressing NDM-1 (CLB30016) MITC95 μM | *Klebsiella pneumoniae* expressing VIM-1 (IHMA599644) MITC95 μM |
|---|---|---|---|---|---|---|
| 266 | 0.4775 | 0.02816 | 0.1152 | 0.7813 | 0.7813 | 0.7813 |
| 267 | 1.633 | 0.179 | 0.2786 | 1.563 | 0.7813 | 1.563 |
| 268 | 1.097 | 0.06117 | 0.1497 | 1.563 | 0.7813 | 1.563 |
| 269 | 4.033 | 1.173 | 0.392 | 1.563 | 1.563 | 3.125 |
| 270 | 2.316 | 0.2439 | 0.2017 | 3.125 | 1.563 | 3.125 |
| 271 | 0.271 | 0.01958 | 0.09888 | 0.7813 | 1.563 | 3.125 |
| 272 | 1.361 | 0.0667 | 0.1096 | 1.563 | 3.125 | 1.563 |
| 273 | 1.411 | 0.05652 | 0.1244 | 1.563 | 1.563 | 1.563 |
| 274 | 0.4864 | 0.08334 | 0.1025 | 1.563 | 0.7813 | 1.563 |
| 275 | 0.1706 | 0.06333 | 0.09024 | 0.7813 | 0.7813 | 1.563 |
| 276 | 0.5417 | 0.05605 | 0.08805 | 0.7813 | 1.172 | 0.7813 |
| 277 | 1.27 | 0.1481 | 0.1291 | 1.563 | 0.7813 | 1.563 |
| 278 | 0.6402 | 0.05665 | 0.1442 | 0.7813 | 0.7813 | 0.7813 |
| 279 | 3.033 | 0.2319 | 0.1327 | 0.7813 | 0.7813 | 0.7813 |
| 280 | 0.6103 | 0.04075 | 0.1584 | 0.7813 | 0.7813 | 1.563 |
| 281 | 0.7501 | 0.0166 | 0.05154 | 1.563 | 1.563 | 3.125 |
| 282 | 1.128 | 0.04457 | 0.1332 | 0.7813 | 0.7813 | 1.563 |
| 283 | 1.201 | 0.07209 | 0.1242 | 0.6836 | 0.7813 | 1.172 |
| 284 | 0.4112 | 0.1793 | 0.183 | 0.7813 | 1.563 | 1.563 |
| 285 | 0.318 | 0.02952 | 0.09161 | 0.7813 | 0.7813 | 0.7813 |
| 286 | 0.1221 | 0.02068 | 0.08769 | 0.7813 | 1.953 | 1.172 |
| 287 | 0.6166 | 0.04217 | 0.1651 | 1.563 | 1.563 | 3.125 |
| 288 | 0.4618 | 0.09854 | 0.07805 | 1.563 | 0.7813 | 1.563 |
| 289 | 1.218 | 0.2487 | 0.104 | 1.563 | 0.7813 | 1.563 |
| 290 | 0.4476 | 0.08732 | 0.1041 | 0.7813 | 0.1953 | 0.7813 |
| 291 | 0.1687 | 0.05051 | 0.06936 | 1.563 | 0.7813 | 3.125 |
| 292 | 0.6716 | 0.04533 | 0.1465 | 3.125 | 1.563 | 3.125 |
| 293 | 1.296 | 0.2853 | 0.187 | 3.125 | 3.125 | 3.125 |
| 294 | 1.722 | 0.1967 | 0.7423 | 0.7813 | 0.3906 | 1.563 |
| 295 | 0.7746 | 0.05608 | 0.1724 | 0.7813 | 0.7813 | 1.563 |
| 296 | 0.1977 | 0.04089 | 0.1837 | 1.563 | 1.563 | 3.125 |
| 297 | 0.5692 | 0.3313 | 0.4229 | 0.7813 | 0.3906 | 1.563 |
| 298 | 0.671 | 0.05727 | 0.1348 | 0.4531 | 0.2786 | 1.031 |
| 299 | 2.647 | 0.2647 | 0.1541 | 1.563 | 0.7813 | 1.563 |
| 300 | 0.3184 | 0.07028 | 0.06785 | 1.563 | 1.563 | 1.563 |
| 301 | 0.1285 | 0.01635 | 0.05281 | 0.3906 | 1.563 | 3.125 |
| 302 | 0.3413 | 0.04491 | 0.1411 | 0.7813 | 0.7813 | 1.563 |
| 303 | 0.5363 | 0.2549 | 0.169 | 0.5859 | 0.2197 | 1.953 |
| 304 | 0.6169 | 0.06081 | 0.2077 | 0.7813 | 0.3906 | 1.563 |
| 305 | 2.065 | 0.1363 | 0.1751 | 1.172 | 1.172 | 1.563 |
| 306 | 0.2933 | 0.05872 | 0.05636 | 0.7813 | 0.7813 | 1.563 |
| 307 | 0.2575 | 0.03389 | 0.1134 | 1.563 | 1.563 | 1.563 |
| 308 | 0.4028 | 0.06192 | 0.1789 | 0.7813 | 0.3906 | 1.563 |
| 309 | 0.5009 | 0.1974 | 0.2 | 0.5208 | 0.2279 | 1.563 |
| 310 | 0.6674 | 0.05211 | 0.1693 | 0.7813 | 0.7813 | 1.563 |
| 311 | 1.27 | 0.0986 | 0.1095 | 1.563 | 1.563 | 3.125 |
| 312 | 0.5858 | 0.2158 | 0.2804 | 0.7813 | 0.3906 | 3.125 |
| 313 | 1.301 | 0.0817 | 0.1488 | 0.7813 | 0.3906 | 3.125 |
| 314 | 0.4849 | 0.03263 | 0.1142 | 1.563 | 0.7813 | 1.563 |
| 315 | 0.4594 | 0.169 | 0.2106 | 0.7813 | 0.3906 | 6.25 |
| 316 | 2.333 | 0.1749 | 0.2115 | 0.7813 | 0.3906 | 6.25 |
| 317 | 0.4949 | 0.1698 | 0.1327 | 1.563 | 0.7813 | 3.125 |
| 318 | 0.7042 | 0.1581 | 0.1425 | 3.125 | 0.7813 | 3.125 |
| 319 | 0.2649 | 0.04833 | 0.2057 | 1.563 | 1.563 | 1.563 |
| 320 | 1.209 | 0.09024 | 0.2958 | 0.7813 | 0.7813 | 3.125 |
| 321 | 1.248 | 0.3759 | 0.958 | 1.563 | 0.7813 | 3.125 |
| 322 | 0.7381 | 0.05357 | 0.1817 | 1.042 | 0.5208 | 1.302 |
| 323 | 3.387 | 0.2191 | 0.3212 | 3.125 | 1.563 | 3.125 |
| 324 | 0.2127 | 0.03874 | 0.1301 | 0.7813 | 1.563 | 1.563 |
| 325 | 1.22 | 0.7241 | 0.8965 | 1.563 | 0.7813 | 3.125 |
| 326 | 0.6505 | 0.05022 | 0.1147 | 1.563 | 0.7813 | 1.563 |
| 327 | 1.411 | 0.2594 | 0.6494 | 3.125 | 3.125 | 1.563 |
| 328 | 0.3401 | 0.1396 | 0.1651 | 1.563 | 0.7813 | 3.125 |
| 329 | 0.1284 | 0.01526 | 0.04297 | 1.563 | 1.563 | 1.563 |
| 330 | 2.759 | 0.2945 | 0.3078 | 1.563 | 3.125 | 3.125 |
| 331 | 2.279 | 0.2275 | 0.1802 | 3.125 | 1.563 | 3.125 |
| 332 | 3.001 | 0.6609 | 0.2296 | 1.563 | 1.563 | 3.125 |
| 333 | 3.209 | 1.011 | 0.4718 | 1.563 | 1.563 | 3.125 |
| 334 | 4.602 | 1.316 | 0.2468 | 0.7813 | 0.3906 | 0.7813 |

ASSAY TABLE 1-continued

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | Serratia marcescens expressing IMP-1 (CL5741) MITC95 μM | Escherichia coli expressing NDM-1 (CLB30016) MITC95 μM | Klebsiella pneumoniae expressing VIM-1 (IHMA599644) MITC95 μM |
|---|---|---|---|---|---|---|
| 335 | 4.777 | 0.4588 | 0.2866 | 3.125 | 1.563 | 3.125 |
| 336 | 2.899 | 0.3251 | 0.2325 | 3.125 | 1.563 | 3.125 |
| 337 | 2.228 | 0.208 | 0.2004 | 0.7813 | 0.7813 | 0.7813 |
| 338 | 91.05 | 37.63 | 6.424 | 1.563 | 1.563 | 1.563 |
| 339 | 34.11 | 11.92 | 2.102 | 1.563 | 0.7813 | 0.7813 |
| 340 | 46.74 | 6.291 | 2.894 | 1.563 | 0.3906 | 0.7813 |
| 341 | 4.134 | 1.706 | 0.4736 | 1.563 | 0.7813 | 3.125 |
| 342 | 88.68 | 32.72 | 5.309 | 3.125 | 1.563 | 1.563 |
| 343 | 1.369 | 0.195 | 0.2067 | 0.7813 | 0.7813 | 0.7813 |
| 344 | 4.257 | 1.393 | 0.52 | 1.563 | 0.7813 | 1.563 |
| 345 | 0.6757 | 0.1928 | 0.1293 | 0.7813 | 0.5859 | 0.7813 |
| 346 | 3.648 | 1.488 | 0.4673 | 1.563 | 1.563 | 1.563 |
| 347 | 3.974 | 2.038 | 0.5358 | 1.563 | 1.563 | 1.563 |
| 348 | 3.326 | 1.474 | 0.5356 | 1.563 | 1.563 | 1.563 |
| 349 | 5.651 | 1.62 | 0.4332 | 1.563 | 1.563 | 1.563 |
| 350 | 4.396 | 1.722 | 0.4122 | 0.7813 | 0.7813 | 0.7813 |
| 351 | 3.549 | 1.361 | 0.4526 | 1.563 | 0.7813 | 1.563 |
| 352 | 4.395 | 1.414 | 0.3787 | 1.563 | 0.7813 | 1.563 |
| 353 | 1.154 | 0.2594 | 0.5709 | 0.7813 | 0.3906 | 1.563 |
| 354 | 0.4531 | 0.8168 | 0.1081 | 1.563 | 0.3906 | 0.7813 |
| 355 | 0.2001 | 0.05094 | 0.1415 | 0.7813 | 0.1953 | 1.563 |
| 356 | 1.406 | 1.821 | 0.2438 | 0.7813 | 0.7813 | 0.7813 |
| 357 | 1.213 | 1.256 | 0.2242 | 0.7813 | 0.7813 | 0.7813 |
| 358 | 4.055 | 0.3189 | 0.2045 | 0.3906 | 0.2441 | 1.563 |
| 359 | 1.613 | 0.1545 | 0.2535 | 0.3906 | 0.09766 | 1.563 |
| 360 | 0.3807 | 0.04854 | 0.1348 | 1.563 | 1.563 | 3.125 |
| 361 | 0.1471 | 0.1429 | 0.09533 | 0.7813 | 0.3906 | 1.563 |
| 362 | 9.507 | 3.083 | 1.879 | 1.563 | 1.563 | 3.125 |
| 363 | 3.672 | 0.6486 | 0.5911 | 1.563 | 3.125 | 3.125 |
| 364 | 14.59 | 3.248 | 3.239 | 3.125 | 3.125 | 6.25 |
| 365 | 0.5899 | 0.2593 | 0.2463 | 0.3906 | 0.1953 | 3.125 |
| 366 | 0.07528 | 0.02251 | 0.1047 | 1.563 | 0.7813 | 3.125 |
| 367 | 0.0766 | 0.01932 | 0.09753 | 1.563 | 1.563 | 3.125 |
| 368 | 0.3036 | 0.2026 | 0.2527 | 0.7813 | 0.7813 | 3.125 |
| 369 | 0.508 | 0.2758 | 0.3018 | 0.7813 | 0.3906 | 3.125 |
| 370 | 0.6632 | 0.04589 | 0.2087 | 1.172 | 0.3906 | 1.563 |
| 371 | 0.2886 | 0.0807 | 0.1878 | 3.125 | 0.7813 | 3.125 |
| 372 | 1.275 | 0.5745 | 0.9145 | 1.563 | 1.563 | 3.125 |
| 373 | 0.4954 | 0.05162 | 0.1207 | 1.563 | 0.3906 | 3.125 |
| 374 | 0.2777 | 0.1574 | 0.121 | 3.125 | 0.7813 | 6.25 |
| 375 | 0.5997 | 0.05877 | 0.233 | 1.563 | 0.3906 | 1.563 |
| 376 | 0.2725 | 0.05515 | 0.2744 | 3.125 | 0.7813 | 3.125 |
| 377 | 1.179 | 0.5728 | 0.8851 | 1.563 | 0.7813 | 3.125 |
| 378 | 0.3538 | 0.0511 | 0.09847 | 1.563 | 0.7813 | 3.125 |
| 379 | 0.6265 | 0.09558 | 0.1354 | 1.563 | 1.563 | 1.563 |
| 380 | 0.5444 | 0.1783 | 0.1786 | 0.7813 | 0.4883 | 1.563 |
| 381 | 0.2411 | 0.06023 | 0.1174 | 1.172 | 0.7813 | 2.344 |
| 382 | 0.6514 | 0.2197 | 0.2708 | 1.563 | 1.563 | 3.125 |
| 383 | 0.5364 | 0.05685 | 0.1017 | 1.563 | 0.7813 | 1.563 |
| 384 | 0.05385 | 0.02335 | 0.05392 | 3.125 | 1.563 | 3.125 |
| 385 | 0.7818 | 0.111 | 0.1303 | 0.7813 | 0.7813 | 1.563 |
| 386 | 0.1408 | 0.1334 | 0.1682 | 1.563 | 0.9766 | 3.125 |
| 387 | 0.2445 | 0.06461 | 0.339 | 1.563 | 1.563 | 6.25 |
| 388 | 0.324 | 0.08838 | 0.3747 | 3.125 | 3.125 | 6.25 |
| 389 | 1.806 | 0.2894 | 0.744 | 3.125 | 3.125 | 3.125 |
| 390 | 0.3408 | 0.06052 | 0.3299 | 1.563 | 3.125 | 3.125 |
| 391 | 0.2093 | 0.02799 | 0.09653 | 3.125 | 3.125 | 6.25 |
| 392 | 0.2214 | 0.03181 | 0.101 | 3.125 | 3.125 | 12.5 |
| 393 | 0.0629 | 0.02189 | 0.04542 | 1.042 | 0.651 | 2.083 |
| 394 | 1.996 | 1.893 | 1.244 | 1.563 | 0.3906 | 3.125 |
| 395 | 0.1558 | 0.03153 | 0.1077 | 1.563 | 0.3906 | 1.563 |
| 396 | 0.2205 | 0.02687 | 0.1693 | 0.3906 | 0.7813 | 3.125 |
| 397 | 1.601 | 0.161 | 0.532 | 0.7813 | 3.125 | 3.125 |
| 398 | 7.449 | 2.544 | 0.9388 | 1.563 | 3.125 | 3.125 |
| 399 | 0.5331 | 0.08224 | 0.1122 | 1.563 | 0.7813 | 1.563 |
| 400 | 1.423 | 0.5983 | 0.2437 | 0.3906 | 0.1953 | 1.563 |
| 401 | 0.483 | 0.197 | 0.08968 | 0.3906 | 0.7813 | 1.563 |
| 402 | 0.3184 | 0.05238 | 0.1587 | 0.7813 | 0.3906 | 1.563 |
| 403 | 0.531 | 0.06326 | 0.175 | 1.563 | 1.563 | 3.125 |

ASSAY TABLE 1-continued

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | *Serratia marcescens* expressing IMP-1 (CL5741) MITC95 μM | *Escherichia coli* expressing NDM-1 (CLB30016) MITC95 μM | *Klebsiella pneumoniae* expressing VIM-1 (IHMA599644) MITC95 μM |
|---|---|---|---|---|---|---|
| 404 | 0.3545 | 0.2319 | 0.2969 | 0.5859 | 0.293 | 1.172 |
| 405 | 17.92 | 7.687 | 5.938 | 6.25 | 3.125 | 25 |
| 406 | 0.5918 | 0.1641 | 0.1719 | 0.7813 | 0.3906 | 3.125 |
| 407 | 1.347 | 0.1404 | 0.3352 | 1.563 | 0.7813 | 3.125 |
| 408 | 0.6841 | 0.4209 | 0.3937 | 0.7813 | 0.09766 | 3.125 |
| 409 | 0.1702 | 0.1123 | 0.1836 | 1.563 | 0.1953 | 3.125 |
| 410 | 0.6815 | 0.322 | 0.3741 | 0.7813 | 0.3906 | 1.563 |
| 411 | 0.4079 | 0.1171 | 0.1774 | 1.563 | 0.7813 | 3.125 |
| 412 | 2.572 | 0.1081 | 0.3208 | 3.125 | 3.125 | 6.25 |
| 413 | 0.8005 | 0.2484 | 0.3 | 1.563 | 0.7813 | 3.125 |
| 414 | 0.7862 | 0.3292 | 0.3473 | 0.7813 | 0.3906 | 3.125 |
| 415 | 0.8006 | 0.3612 | 0.4246 | 1.172 | 0.1953 | 3.125 |
| 416 | 1.342 | 0.9175 | 0.6803 | 1.563 | 0.3906 | 6.25 |
| 417 | 1.282 | 0.3854 | 0.234 | 0.7813 | 0.1953 | 1.563 |
| 418 | 0.8337 | 0.1518 | 0.1135 | 0.7813 | 0.3906 | 1.563 |
| 419 | 1.513 | 0.4964 | 0.207 | 0.7813 | 0.1953 | 1.563 |
| 420 | 0.974 | 0.2296 | 0.1248 | 1.563 | 0.3906 | 3.125 |
| 421 | 1.138 | 0.1958 | 0.2477 | 0.7813 | 0.3906 | 1.563 |
| 422 | 0.9819 | 0.3857 | 0.279 | 0.7813 | 0.3906 | 1.563 |
| 423 | 1.154 | 0.3029 | 0.1805 | 0.7813 | 0.3906 | 1.563 |
| 424 | 0.8135 | 0.08695 | 0.3012 | 1.563 | 0.7813 | 1.563 |
| 425 | 0.8859 | 0.04186 | 0.1603 | 3.125 | 0.7813 | 3.125 |
| 426 | 0.2734 | 0.03217 | 0.1675 | 0.7813 | 0.3906 | 1.563 |
| 427 | 2.608 | 0.2212 | 0.5475 | 0.7813 | 0.3906 | 1.563 |
| 428 | 0.4072 | 0.04729 | 0.1329 | 0.7813 | 0.3906 | 1.563 |
| 429 | 0.489 | 0.0819 | 0.2278 | 1.563 | 0.5208 | 1.563 |
| 430 | 0.1017 | 0.03252 | 0.1029 | 1.563 | 1.172 | 1.563 |
| 431 | 0.1326 | 0.07387 | 0.169 | 3.125 | 3.125 | 6.25 |
| 432 | 1.515 | 0.3961 | 0.3873 | 0.7813 | 0.7813 | 1.563 |
| 433 | 1.329 | 0.5105 | 0.4044 | 1.563 | 0.7813 | 1.563 |
| 434 | 1.529 | 0.1995 | 0.3368 | 1.563 | 0.7813 | 1.563 |
| 435 | 1.784 | 0.4598 | 1.207 | 3.125 | 1.563 | 3.125 |
| 436 | 0.1033 | 0.02464 | 0.1157 | 1.563 | 0.7813 | 1.563 |
| 437 | 2.412 | 1.175 | 0.9522 | 3.125 | 0.7813 | 3.125 |
| 438 | 17.95 | 2.043 | 3.906 | 3.125 | 3.125 | 3.125 |
| 439 | 6.719 | 0.254 | 0.6293 | 1.563 | 3.125 | 1.563 |
| 440 | 3.955 | 0.3331 | 0.5706 | 1.563 | 0.7813 | 1.563 |
| 441 | 1.227 | 0.08106 | 0.15 | 1.563 | 1.563 | 1.563 |
| 442 | 1.331 | 0.4315 | 0.2489 | 1.563 | 1.563 | 3.125 |
| 443 | 0.79 | 0.08142 | 0.127 | 1.563 | 0.7813 | 1.172 |
| 444 | 1.586 | 0.2358 | 0.2352 | 3.125 | 1.563 | 3.125 |
| 445 | 0.3705 | 0.04458 | 0.1139 | 3.125 | 3.125 | 3.125 |
| 446 | 0.4457 | 0.05694 | 0.1531 | 3.125 | 1.563 | 3.125 |
| 447 | 1.6 | 0.6457 | 0.1799 | 0.7813 | 0.7813 | 1.563 |
| 448 | 0.9877 | 0.1506 | 0.5566 | 1.563 | 0.7813 | 6.25 |
| 449 | 11.81 | 7.733 | 27.76 | 1.563 | 0.7813 | 12.5 |
| 450 | 3.418 | 0.5193 | 0.2757 | 1.563 | 1.563 | 1.563 |
| 451 | 4.023 | 1.698 | 0.5573 | 0.7813 | 0.7813 | 0.7813 |
| 452 | 6.206 | 1.718 | 0.9936 | 3.125 | 3.125 | 6.25 |
| 453 | 3.516 | 0.87 | 0.2437 | 3.125 | 1.563 | 3.125 |
| 454 | 3.456 | 0.7573 | 0.2623 | 3.125 | 1.563 | 6.25 |
| 455 | 0.5298 | 0.216 | 0.1625 | 3.125 | 1.563 | 3.125 |
| 456 | 3.769 | 1.56 | 0.5448 | 0.7813 | 0.7813 | 1.563 |
| 457 | 5.295 | 3.678 | 0.4898 | 3.125 | 1.563 | 6.25 |
| 458 | 3.772 | 0.5323 | 0.1315 | 1.563 | 0.7813 | 1.563 |
| 459 | 12.5 | 1.174 | 0.1717 | 1.563 | 0.3906 | 1.563 |
| 460 | 4.63 | 0.6034 | 0.1476 | 1.563 | 0.7813 | 1.563 |
| 461 | 50.43 | 42.1 | 4.766 | 3.125 | 1.563 | 6.25 |
| 462 | 1.289 | 0.09535 | 0.2266 | 1.563 | 1.563 | 1.563 |
| 463 | 0.3254 | 0.1449 | 0.09096 | 0.7813 | 0.7813 | 1.563 |
| 464 | 1.836 | 0.2736 | 0.1975 | 1.563 | 0.7813 | 1.563 |
| 465 | 1.154 | 0.2228 | 0.1329 | 1.563 | 0.7813 | 1.563 |
| 466 | 0.9665 | 0.3586 | 0.1383 | 1.563 | 0.7813 | 1.563 |
| 467 | 0.4367 | 0.04263 | 0.1197 | 0.7813 | 0.7813 | 1.563 |
| 468 | 0.5686 | 0.133 | 0.08688 | 0.7813 | 0.3906 | 3.125 |
| 469 | 0.554 | 0.1527 | 0.08684 | 3.125 | 1.563 | 3.125 |
| 470 | 0.1342 | 0.04957 | 0.1101 | 1.563 | 0.7813 | 3.125 |
| 471 | 0.1114 | 0.03032 | 0.07337 | 1.563 | 1.563 | 3.125 |
| 472 | 0.8471 | 0.1143 | 0.189 | 0.7813 | 0.7813 | 0.7813 |

ASSAY TABLE 1-continued

Inhibition of metallo-β-lactamases (IMP-1, NDM-1, VIM-1) and antibiotic potentiation vs. MBL-expressing bacteria by Examples 1-500.

| Ex. No. | IMP-1 IC50 nM | NDM-1 IC50 nM | VIM-1 IC50 nM | Serratia marcescens expressing IMP-1 (CL5741) MITC95 µM | Escherichia coli expressing NDM-1 (CLB30016) MITC95 µM | Klebsiella pneumoniae expressing VIM-1 (IHMA599644) MITC95 µM |
|---|---|---|---|---|---|---|
| 473 | 0.3285 | 0.1357 | 0.1092 | 1.563 | 0.7813 | 1.563 |
| 474 | 0.5219 | 0.1045 | 0.1408 | 1.563 | 0.7813 | 1.563 |
| 475 | 0.1297 | 0.06045 | 0.08695 | 1.563 | 0.7813 | 1.563 |
| 476 | 0.2809 | 0.2695 | 0.1214 | 0.7813 | 1.563 | 1.563 |
| 477 | 0.8424 | 0.2795 | 0.1321 | 0.7813 | 0.1953 | 1.563 |
| 478 | 0.6766 | 0.1594 | 0.09144 | 1.563 | 1.563 | 3.125 |
| 479 | 0.6641 | 0.2241 | 0.2994 | 0.7813 | 0.1953 | 1.563 |
| 480 | 0.3195 | 0.2272 | 0.2488 | 0.3906 | 0.1953 | 1.563 |
| 481 | 0.2505 | 0.04553 | 0.1191 | 1.563 | 3.125 | 3.125 |
| 482 | 1.139 | 0.5373 | 0.3333 | 0.7813 | 0.1953 | 1.563 |
| 483 | 0.3297 | 0.09267 | 0.1153 | 0.7813 | 1.758 | 1.563 |
| 484 | 0.2484 | 0.1023 | 0.1313 | 0.3906 | 0.1953 | 3.125 |
| 485 | 3.585 | 2.217 | 2.303 | 0.7813 | 0.1953 | 1.563 |
| 486 | 0.4218 | 0.1757 | 0.3214 | 0.7813 | 0.7813 | 1.563 |
| 487 | 0.8033 | 0.2744 | 0.5273 | 0.7813 | 0.3906 | 1.563 |
| 488 | 0.3552 | 0.2059 | 0.2104 | 0.1953 | 0.1953 | 1.563 |
| 489 | 0.5655 | 0.2459 | 0.2667 | 0.3906 | 0.3906 | 1.563 |
| 490 | 0.1759 | 0.0439 | 0.101 | 1.563 | 0.7813 | 3.125 |
| 491 | 0.2711 | 0.09392 | 0.1324 | 0.7813 | 0.1953 | 1.563 |
| 492 | 0.5199 | 0.3048 | 0.2401 | 1.563 | 0.3906 | 3.125 |
| 493 | 0.4032 | 0.1885 | 0.1786 | 0.3906 | 0.3906 | 1.563 |
| 494 | 0.8078 | 0.2756 | 0.4829 | 1.563 | 0.7813 | 3.125 |
| 495 | 0.3277 | 0.2152 | 0.3014 | 0.7813 | 0.1953 | 1.563 |
| 496 | 0.5762 | 0.1997 | 0.1749 | 0.7813 | 0.09766 | 1.563 |
| 497 | 0.6451 | 0.1314 | 0.2194 | 0.7813 | 0.3906 | 1.563 |
| 498 | 0.07629 | 0.01464 | 0.05117 | 1.563 | 1.563 | 3.125 |
| 499 | 1.023 | 0.5552 | 0.2915 | 1.563 | 0.7813 | 3.125 |
| 500 | 0.1643 | 0.03472 | 0.07099 | 1.563 | 1.563 | 3.125 |

Efflux

In order to assess the contribution of efflux to lack of whole cell inhibition of metallo-beta-lactamase inhibitors of Formula I, tool strains were constructed. The strain background was *Pseudomonas aeruginosa* PAO1. A wild-type (MB5919) and an isogenic strain in which multiple efflux pumps have been disrupted genetically were used. The MBL imipenem beta-lactamase-1 (IMP-1), obtained from a clinical isolate was introduced into the strain pair by the following process:

Plasmid DNA (encoding IMP-1) was extracted from CL 5673 (IMP-1, *P. aeruginosa* clinical strain) by standard techniques. The plasmid DNA was transformed into parental MB5919 (oprD+, efflux+, inducible AmpC) and MB5890 (oprD+, efflux−, inducible AmpC) isogenic strains by electroporation. These transformed strains were plated onto cation-adjusted Muller-Hinton agar plates containing ceftazidime at 32 µg/ml (MB5919) and 16 µg/ml (MB5890) to select for those cells in which the IMP-1-expressing plasmid was introduced successfully, resulting in resistance to ceftazidime. Agarose-gel electrophoresis of PCR product for IMP-1from the successful transformants was used to compare to control and to the original strain from which the plasmid was obtained, confirming transfer of the IMP-1 gene (data not shown).

Minimum inhibitory concentrations of sentinel antibiotics were performed to quality control the new strains. The imipenem MIC went up dramatically, as expected, due to presence of the IMP-1, also meropenem (MEM) and ceftazidime (CAZ). The efflux+/− set behaved similarly with non-BL antibiotics as they should with the efflux− strain exhibiting increased sensitivity to chloramphenicol (CAM) and ciprofloxacin (Cipro).

| | | | CL 5673 (IMP-1) plasmid | | pFlP-Vim1 plasmid | | pFlP-Vim2 plasmid | |
|---|---|---|---|---|---|---|---|---|
| | MB 5919 | MB 5890 | MB 9798 | MB 9799 | MB 9861 | MB9862 | | |
| OprD efflux | OprD+ efflux+ | OprD+ efflux− | OprD+ efflux+ | OprD+ efflux− | OprD+ efflux+ | OprD+ efflux− | OprD+ efflux+ | OprD+ efflux− |
| | MB 5919 | MB 5890 | MB 5919 Trans IMP1 plasmid | MB 5890 Trans IMP1 plasmid | MB 5919 Trans pIFp-Vim1 plasmid | MB 5890 Trans pFlp-Vim1 | MB 5919 Trans pFlp-Vim2 plasd | MB 5890 Trans pFlp-Vim2 plasd |
| Imipenem | 4 | 2 | 64 | 32 | >64 | 64 | >64 | 32 |
| Meropenem | 2 | 0.5 | >64 | 64 | >64 | 64 | >64 | 32 |

-continued

| | | | | | | | | |
|---|---|---|---|---|---|---|---|---|
| PiperaIln | 2 | 1 | 4 | 4 | >256 | 128 | >256 | 128 |
| Chloroamphenicol | >64 | 1 | >64 | 1 | >64 | 2 | >64 | 1 |
| Ciprofloxicin | 0.5 | 0.008 | 0.5 | 0.008 | 1 | 0.008 | 1 | 0.008 |
| CAZ | 1 | 0.5 | 256 | 256 | >256 | >256 | 128 | 64 |
| Azithromycin | 16 | 1 | 16 | 2 | 32 | 1 | 32 | 1 |

The strain set was then used as a pair to determine the effect of metallo-β-lactamase inhibitors of Formula I on the MIC of imipenem and/or ceftazidime. A fixed concentration of antibiotic was included in standard microbroth MIC tests, usually at the CLSI (Clinical and Laboratory Standards Institute) breakpoint concentration. A fixed amount of a class A/C beta-lactamase inhibitor was also included to inhibit the resident *Pseudomonas* AmpC enzyme. A serial titration of the metallo-β-lactamase inhibitor was included and the concentration of metallo-β-lactamase inhibitor which restores susceptibility of the strain to the included antibiotic was recorded. That concentration of metallo-β-lactamase inhibitor was then compared between the two strains to determine the fold difference between the efflux+ (MB9798) and efflux– (MB9799) strains. This was taken as an indication of the extent to which the MBLi is subject to efflux.

ASSAY TABLE 2

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam. In the Table below, Efflux ratio is the ratio MITC95 PA_9798/MITC95 PA_9799

| EX. No. | *P. aeruginosa* expressing IMP-1, efflux + (MB9798) MITC95 μM | *P. aeruginosa* expressing IMP-1, efflux − (MB9799) MITC95 μM | Efflux ratio |
|---|---|---|---|
| 1 | 0.5573 | 0.8542 | 0.65 |
| 2 | 0.7813 | 0.7813 | 1.00 |
| 3 | 3.125 | 1.563 | 2.00 |
| 4 | 1.563 | 1.563 | 1.00 |
| 5 | 1.781 | 0.8906 | 2.00 |
| 6 | 1.563 | 1.563 | 1.00 |
| 7 | 25 | 1.563 | 15.99 |
| 8 | 1.563 | 1.563 | 1.00 |
| 9 | 0.3906 | 0.7813 | 0.50 |
| 10 | 0.7656 | 0.7656 | 1.00 |
| 11 | 0.3906 | 0.3906 | 1.00 |
| 12 | 0.375 | 0.5 | 0.75 |
| 13 | 12.5 | 6.25 | 2.00 |
| 14 | 3.125 | 3.125 | 1.00 |
| 15 | 12.5 | 12.5 | 1.00 |
| 16 | 100 | 6.25 | 16.00 |
| 17 | 12.5 | 6.25 | 2.00 |
| 18 | 3.125 | 3.125 | 1.00 |
| 19 | 6.25 | 6.25 | 1.00 |
| 20 | 6.25 | 6.25 | 1.00 |
| 21 | 1.563 | 1.563 | 1.00 |
| 22 | 1.563 | 1.563 | 1.00 |
| 23 | 3.125 | 3.125 | 1.00 |
| 24 | 12.5 | 3.125 | 4.00 |
| 25 | 50 | 3.125 | 16.00 |
| 26 | 6.25 | 3.125 | 2.00 |
| 27 | 12.5 | 6.25 | 2.00 |
| 28 | 12.5 | 3.125 | 4.00 |
| 29 | 50 | 3.125 | 16.00 |
| 30 | 1.563 | 1.563 | 1.00 |
| 31 | 2.344 | 1.563 | 1.50 |
| 32 | 0.7813 | 1.563 | 0.50 |
| 33 | 12.5 | 3.125 | 4.00 |
| 34 | 25 | 6.25 | 4.00 |
| 35 | 6.25 | 3.125 | 2.00 |
| 36 | 3.125 | 3.125 | 1.00 |
| 37 | 6.25 | 6.25 | 1.00 |
| 38 | 3.125 | 3.125 | 1.00 |
| 39 | 50 | 3.125 | 16.00 |
| 40 | 50 | 3.125 | 16.00 |
| 41 | 25 | 3.125 | 8.00 |
| 42 | 25 | 1.563 | 15.99 |
| 43 | 100 | 1.563 | 63.98 |
| 44 | 12.5 | 6.25 | 2.00 |
| 45 | 25 | 3.125 | 8.00 |
| 46 | 0.7813 | 1.563 | 0.50 |
| 47 | 3.125 | 3.125 | 1.00 |
| 48 | 1.563 | 1.563 | 1.00 |
| 49 | 50 | 6.25 | 8.00 |
| 50 | 12.5 | 6.25 | 2.00 |
| 51 | 25 | 6.25 | 4.00 |
| 52 | 6.25 | 3.125 | 2.00 |
| 53 | 1.563 | 1.563 | 1.00 |
| 54 | 6.25 | 3.125 | 2.00 |
| 55 | 3.125 | 3.125 | 1.00 |
| 56 | 1.563 | 1.563 | 1.00 |
| 57 | 3.125 | 3.125 | 1.00 |
| 58 | 1.563 | 1.563 | 1.00 |
| 59 | 1.563 | 1.563 | 1.00 |
| 60 | 0.7813 | 1.563 | 0.50 |
| 61 | 1.563 | 1.563 | 1.00 |
| 62 | 1.563 | 1.563 | 1.00 |
| 63 | 0.7813 | 1.563 | 0.50 |
| 64 | 3.125 | 1.563 | 2.00 |
| 65 | 3.125 | 1.563 | 2.00 |
| 66 | 3.125 | 1.563 | 2.00 |
| 67 | 1.563 | 1.563 | 1.00 |
| 68 | 3.125 | 1.563 | 2.00 |
| 69 | 0.7813 | 1.563 | 0.50 |
| 70 | 3.125 | 3.125 | 1.00 |
| 71 | 1.563 | 1.563 | 1.00 |
| 72 | | | |
| 73 | 0.7813 | 1.563 | 0.50 |
| 74 | 1.172 | 1.172 | 1.00 |
| 75 | 0.7813 | 0.7813 | 1.00 |
| 76 | 0.7813 | 1.563 | 0.50 |
| 77 | 0.7813 | 1.563 | 0.50 |
| 78 | 0.7813 | 1.563 | 0.50 |
| 79 | 0.7813 | 1.563 | 0.50 |
| 80 | 1.563 | 1.563 | 1.00 |
| 81 | 0.7813 | 1.563 | 0.50 |
| 82 | 3.125 | 6.25 | 0.50 |
| 83 | 0.7813 | 1.563 | 0.50 |
| 84 | 1.563 | 1.563 | 1.00 |
| 85 | 1.563 | 1.563 | 1.00 |
| 86 | 0.7813 | 1.563 | 0.50 |
| 87 | 0.7813 | 1.563 | 0.50 |
| 88 | 1.563 | 3.125 | 0.50 |
| 89 | 1.563 | 1.563 | 1.00 |
| 90 | 0.7813 | 1.563 | 0.50 |

ASSAY TABLE 2-continued

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam. In the Table below, Efflux ratio is the ratio MITC95 PA_9798/MITC95 PA_9799

| EX. No. | P. aeruginosa expressing IMP-1, efflux + (MB9798) MITC95 μM | P. aeruginosa expressing IMP-1, efflux − (MB9799) MITC95 μM | Efflux ratio |
|---|---|---|---|
| 91 | 1.563 | 1.563 | 1.00 |
| 92 | 25 | 6.25 | 4.00 |
| 93 | 3.125 | 3.125 | 1.00 |
| 94 | 1.563 | 1.563 | 1.00 |
| 95 | 1.563 | 1.563 | 1.00 |
| 96 | 3.125 | 3.125 | 1.00 |
| 97 | 1.563 | 1.563 | 1.00 |
| 98 | 0.7813 | 1.042 | 0.75 |
| 99 | 25 | 3.125 | 8.00 |
| 100 | 200 | 6.25 | 32.00 |
| 101 | 3.125 | 3.125 | 1.00 |
| 102 | 0.7813 | 1.563 | 0.50 |
| 103 | 3.125 | 1.563 | 2.00 |
| 104 | 3.125 | 1.563 | 2.00 |
| 105 | 1.563 | 1.563 | 1.00 |
| 106 | 12.5 | 3.125 | 4.00 |
| 107 | 6.25 | 1.563 | 4.00 |
| 108 | 1.563 | 1.563 | 1.00 |
| 109 | 0.7813 | 1.563 | 0.50 |
| 110 | 1.563 | 1.563 | 1.00 |
| 111 | 0.7813 | 1.563 | 0.50 |
| 112 | 1.563 | 1.563 | 1.00 |
| 113 | 1.563 | 1.563 | 1.00 |
| 114 | 3.125 | 3.125 | 1.00 |
| 115 | 3.125 | 3.125 | 1.00 |
| 116 | 0.7813 | 1.563 | 0.50 |
| 117 | 1.563 | 1.563 | 1.00 |
| 118 | 12.5 | 3.125 | 4.00 |
| 119 | 0.7813 | 1.563 | 0.50 |
| 120 | 0.7813 | 1.563 | 0.50 |
| 121 | 12.5 | 3.125 | 4.00 |
| 122 | 3.125 | 1.563 | 2.00 |
| 123 | 1.563 | 1.563 | 1.00 |
| 124 | 12.5 | 3.125 | 4.00 |
| 125 | 0.7813 | 1.563 | 0.50 |
| 126 | 0.7813 | 1.563 | 0.50 |
| 127 | 1.563 | 1.563 | 1.00 |
| 128 | 6.25 | 6.25 | 1.00 |
| 129 | 12.5 | 3.125 | 4.00 |
| 130 | 0.7813 | 1.563 | 0.50 |
| 131 | 12.5 | 0.7813 | 16.00 |
| 132 | 3.125 | 0.7813 | 4.00 |
| 133 | 6.25 | 0.7813 | 8.00 |
| 134 | 25 | 1.563 | 15.99 |
| 135 | 0.7813 | 0.7813 | 1.00 |
| 136 | 1.563 | 0.7813 | 2.00 |
| 137 | 0.7813 | 0.7813 | 1.00 |
| 138 | 1.563 | 1.563 | 1.00 |
| 139 | 0.7813 | 0.7813 | 1.00 |
| 140 | 1.563 | 0.7813 | 2.00 |
| 141 | 1.563 | 1.563 | 1.00 |
| 142 | 1.563 | 1.172 | 1.33 |
| 143 | 0.7813 | 1.563 | 0.50 |
| 144 | 3.125 | 3.125 | 1.00 |
| 145 | 0.3906 | 0.7813 | 0.50 |
| 146 | 0.3906 | 0.7813 | 0.50 |
| 147 | 3.125 | 3.125 | 1.00 |
| 148 | 3.125 | 1.563 | 2.00 |
| 149 | 3.125 | 3.125 | 1.00 |
| 151 | 50 | 3.125 | 16.00 |
| 152 | 12.5 | 1.563 | 8.00 |
| 153 | 12.5 | 12.5 | 1.00 |
| 154 | 3.125 | 6.25 | 0.50 |
| 155 | 6.25 | 1.281 | 4.88 |
| 156 | 12.5 | 6.25 | 2.00 |
| 157 | 1.781 | 0.4453 | 4.00 |
| 158 | 3.125 | 0.8906 | 3.51 |
| 159 | 3.125 | 1.563 | 2.00 |
| 160 | 6.25 | 1.563 | 4.00 |
| 161 | 0.3993 | 0.5139 | 0.78 |
| 162 | 0.4271 | 0.4922 | 0.87 |
| 163 | 0.7813 | 0.7813 | 1.00 |
| 164 | 0.7813 | 0.7813 | 1.00 |
| 165 | 6.25 | 1.563 | 4.00 |
| 166 | 1.563 | 1.563 | 1.00 |
| 167 | 3.125 | 1.563 | 2.00 |
| 168 | 0.3828 | 0.543 | 0.70 |
| 169 | 1.563 | 1.563 | 1.00 |
| 170 | 0.7813 | 0.7813 | 1.00 |
| 171 | 0.7813 | 1.563 | 0.50 |
| 172 | 0.3906 | 0.7813 | 0.50 |
| 173 | 1.563 | 1.563 | 1.00 |
| 174 | 1.563 | 1.563 | 1.00 |
| 175 | 0.7813 | 1.563 | 0.50 |
| 176 | 0.7813 | 0.7813 | 1.00 |
| 177 | 0.7813 | 1.563 | 0.50 |
| 178 | 1.563 | 1.563 | 1.00 |
| 179 | 3.125 | 1.563 | 2.00 |
| 180 | 0.3906 | 0.7813 | 0.50 |
| 181 | 0.3906 | 0.7813 | 0.50 |
| 182 | 0.3438 | 0.4271 | 0.80 |
| 183 | 0.7813 | 0.7813 | 1.00 |
| 184 | 0.7813 | 0.7813 | 1.00 |
| 185 | 0.3844 | 0.5906 | 0.65 |
| 186 | 1.563 | 0.7813 | 2.00 |
| 187 | 0.3906 | 0.7813 | 0.50 |
| 188 | 0.7813 | 1.563 | 0.50 |
| 189 | 0.7813 | 1.563 | 0.50 |
| 190 | 0.3906 | 0.7813 | 0.50 |
| 191 | 0.4453 | 0.4453 | 1.00 |
| 192 | 1.563 | 0.7813 | 2.00 |
| 193 | 0.7813 | 0.7813 | 1.00 |
| 194 | 0.6875 | 0.8542 | 0.80 |
| 195 | 0.7813 | 0.7813 | 1.00 |
| 196 | 0.7656 | 0.7656 | 1.00 |
| 197 | 0.7813 | 0.7813 | 1.00 |
| 198 | 0.7813 | 0.7813 | 1.00 |
| 199 | 0.7813 | 1.432 | 0.55 |
| 200 | 0.7813 | 0.7813 | 1.00 |
| 201 | 0.7813 | 1.563 | 0.50 |
| 202 | 1.563 | 1.563 | 1.00 |
| 203 | 0.7813 | 1.563 | 0.50 |
| 204 | 0.7813 | 0.7813 | 1.00 |
| 205 | 12.5 | 1.563 | 8.00 |
| 206 | 3.125 | 1.563 | 2.00 |
| 207 | 3.125 | 1.563 | 2.00 |
| 208 | 3.125 | 3.125 | 1.00 |
| 209 | 1.563 | 1.172 | 1.33 |
| 210 | 3.125 | 1.563 | 2.00 |
| 211 | 12.5 | 3.125 | 4.00 |
| 212 | 1.563 | 1.563 | 1.00 |
| 213 | 3.125 | 1.563 | 2.00 |
| 214 | 12.5 | 1.563 | 8.00 |
| 215 | 1.563 | 1.563 | 1.00 |
| 216 | 6.25 | 1.563 | 4.00 |
| 217 | 12.5 | 1.563 | 8.00 |
| 218 | 25 | 1.563 | 15.99 |
| 219 | 1.563 | 1.563 | 1.00 |
| 220 | 6.25 | 1.563 | 4.00 |
| 221 | 1.563 | 1.563 | 1.00 |
| 222 | 1.563 | 1.563 | 1.00 |
| 223 | 1.563 | 0.7813 | 2.00 |
| 224 | 1.563 | 0.7813 | 2.00 |
| 225 | 1.563 | 1.563 | 1.00 |
| 226 | 6.25 | 3.125 | 2.00 |
| 227 | 1.563 | 1.563 | 1.00 |

ASSAY TABLE 2-continued

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam. In the Table below, Efflux ratio is the ratio MITC95 PA_9798/MITC95 PA_9799

| EX. No. | P. aeruginosa expressing IMP-1, efflux + (MB9798) MITC95 μM | P. aeruginosa expressing IMP-1, efflux − (MB9799) MITC95 μM | Efflux ratio |
|---|---|---|---|
| 228 | 1.563 | 1.563 | 1.00 |
| 229 | 1.563 | 3.125 | 0.50 |
| 230 | 1.563 | 1.563 | 1.00 |
| 231 | 1.563 | 1.563 | 1.00 |
| 232 | 1.563 | 0.7813 | 2.00 |
| 233 | 1.563 | 1.563 | 1.00 |
| 234 | 0.7813 | 0.7813 | 1.00 |
| 235 | 0.7813 | 1.563 | 0.50 |
| 236 | 0.7813 | 0.7813 | 1.00 |
| 237 | 0.7813 | 1.563 | 0.50 |
| 238 | 3.125 | 0.7813 | 4.00 |
| 239 | 6.25 | 0.7813 | 8.00 |
| 240 | 0.7813 | 0.7813 | 1.00 |
| 241 | 0.651 | 0.7813 | 0.83 |
| 242 | 0.7813 | 0.7813 | 1.00 |
| 243 | 0.7813 | 0.7813 | 1.00 |
| 244 | 1.563 | 0.7813 | 2.00 |
| 245 | 1.563 | 1.563 | 1.00 |
| 246 | 1.563 | 0.7813 | 2.00 |
| 247 | 1.563 | 0.7813 | 2.00 |
| 248 | 0.7813 | 0.7813 | 1.00 |
| 249 | 0.7813 | 0.7813 | 1.00 |
| 250 | 0.7813 | 0.7813 | 1.00 |
| 251 | 0.7813 | 0.7813 | 1.00 |
| 252 | 0.418 | 0.6133 | 0.68 |
| 253 | 1.563 | 0.7813 | 2.00 |
| 254 | 0.7813 | 0.7813 | 1.00 |
| 255 | 1.563 | 0.7813 | 2.00 |
| 256 | 0.7813 | 0.7813 | 1.00 |
| 257 | 0.7813 | 0.7813 | 1.00 |
| 258 | 0.7813 | 0.7813 | 1.00 |
| 259 | 0.7813 | 0.7813 | 1.00 |
| 260 | 0.7813 | 0.7813 | 1.00 |
| 261 | 0.7813 | 0.7813 | 1.00 |
| 262 | 0.7813 | 0.7813 | 1.00 |
| 263 | 0.7813 | 0.7813 | 1.00 |
| 264 | 3.125 | 0.7813 | 4.00 |
| 265 | 0.7813 | 0.7813 | 1.00 |
| 266 | 0.3906 | 0.7813 | 0.50 |
| 267 | 0.7813 | 0.7813 | 1.00 |
| 268 | 0.7813 | 0.7813 | 1.00 |
| 269 | 3.125 | 1.563 | 2.00 |
| 270 | 1.563 | 1.563 | 1.00 |
| 271 | 0.7813 | 1.563 | 0.50 |
| 272 | 1.563 | 0.7813 | 2.00 |
| 273 | 0.7813 | 0.7813 | 1.00 |
| 274 | 0.7813 | 0.7813 | 1.00 |
| 275 | 0.7813 | 0.7813 | 1.00 |
| 276 | 0.7813 | 0.7813 | 1.00 |
| 277 | 0.7813 | 0.7813 | 1.00 |
| 278 | 0.7813 | 0.7813 | 1.00 |
| 279 | 0.7813 | 0.7813 | 1.00 |
| 280 | 0.3906 | 0.7813 | 0.50 |
| 281 | 3.125 | 1.563 | 2.00 |
| 282 | 0.7813 | 0.7813 | 1.00 |
| 283 | 0.7813 | 0.7813 | 1.00 |
| 284 | 0.7813 | 0.7813 | 1.00 |
| 285 | 0.3906 | 0.3906 | 1.00 |
| 286 | 0.9766 | 0.7813 | 1.25 |
| 287 | 1.563 | 1.563 | 1.00 |
| 288 | 1.563 | 0.7813 | 2.00 |
| 289 | 1.563 | 0.7813 | 2.00 |
| 290 | 0.7813 | 0.3906 | 2.00 |
| 291 | 0.7813 | 0.7813 | 1.00 |
| 292 | 0.7813 | 1.563 | 0.50 |
| 293 | 3.125 | 1.563 | 2.00 |
| 294 | 1.563 | 0.7813 | 2.00 |
| 295 | 0.7813 | 0.7813 | 1.00 |
| 296 | 0.7813 | 0.7813 | 1.00 |
| 297 | 0.7813 | 0.7813 | 1.00 |
| 298 | 0.3555 | 0.5156 | 0.69 |
| 299 | 0.7813 | 0.7813 | 1.00 |
| 300 | 0.7813 | 0.7813 | 1.00 |
| 301 | 0.7813 | 0.7813 | 1.00 |
| 302 | 0.7813 | 0.7813 | 1.00 |
| 303 | 0.7813 | 0.7813 | 1.00 |
| 304 | 0.3906 | 0.7813 | 0.50 |
| 305 | 0.7813 | 0.7813 | 1.00 |
| 306 | 0.7813 | 0.7813 | 1.00 |
| 307 | 0.7813 | 0.7813 | 1.00 |
| 308 | 0.7813 | 0.7813 | 1.00 |
| 309 | 0.7813 | 0.7813 | 1.00 |
| 310 | 0.7813 | 0.7813 | 1.00 |
| 311 | 1.563 | 1.563 | 1.00 |
| 312 | 1.563 | 1.563 | 1.00 |
| 313 | 3.125 | 1.563 | 2.00 |
| 314 | 0.7813 | 0.7813 | 1.00 |
| 315 | 1.563 | 1.563 | 1.00 |
| 316 | 3.125 | 1.563 | 2.00 |
| 317 | 1.563 | 3.125 | 0.50 |
| 318 | 1.563 | 1.563 | 1.00 |
| 319 | 0.7813 | 0.7813 | 1.00 |
| 320 | 1.563 | 0.7813 | 2.00 |
| 321 | 1.563 | 0.7813 | 2.00 |
| 322 | 0.651 | 0.7813 | 0.83 |
| 323 | 1.563 | 1.563 | 1.00 |
| 324 | 0.7813 | 0.7813 | 1.00 |
| 325 | 1.563 | 0.7813 | 2.00 |
| 326 | 1.563 | 1.563 | 1.00 |
| 327 | 1.563 | 0.7813 | 2.00 |
| 328 | 1.563 | 1.563 | 1.00 |
| 329 | 1.563 | 0.7813 | 2.00 |
| 330 | 1.563 | 1.563 | 1.00 |
| 331 | 1.563 | 1.563 | 1.00 |
| 332 | 1.563 | 1.563 | 1.00 |
| 333 | 1.563 | 1.563 | 1.00 |
| 334 | 1.563 | 0.7813 | 2.00 |
| 335 | 3.125 | 1.563 | 2.00 |
| 336 | 3.125 | 1.563 | 2.00 |
| 337 | 0.7813 | 0.3906 | 2.00 |
| 338 | 6.25 | 1.563 | 4.00 |
| 339 | 6.25 | 1.563 | 4.00 |
| 340 | 6.25 | 1.563 | 4.00 |
| 341 | 1.563 | 0.7813 | 2.00 |
| 342 | 25 | 6.25 | 4.00 |
| 343 | 0.7813 | 0.7813 | 1.00 |
| 344 | 1.563 | 0.7813 | 2.00 |
| 345 | 0.7813 | 0.7813 | 1.00 |
| 346 | 1.563 | 0.7813 | 2.00 |
| 347 | 1.563 | 0.7813 | 2.00 |
| 348 | 3.125 | 0.7813 | 4.00 |
| 349 | 1.563 | 0.7813 | 2.00 |
| 350 | 0.7813 | 0.7813 | 1.00 |
| 351 | 1.563 | 0.7813 | 2.00 |
| 352 | 1.563 | 0.7813 | 2.00 |
| 353 | 1.563 | 0.7813 | 2.00 |
| 354 | 1.563 | 0.3906 | 4.00 |
| 355 | 0.7813 | 0.7813 | 1.00 |
| 356 | 0.7813 | 0.3906 | 2.00 |
| 357 | 0.7813 | 0.3906 | 2.00 |
| 358 | 1.563 | 0.7813 | 2.00 |
| 359 | 1.563 | 0.7813 | 2.00 |
| 360 | 1.563 | 1.563 | 1.00 |
| 361 | 0.7813 | 0.7813 | 1.00 |
| 362 | 3.125 | 1.563 | 2.00 |
| 363 | 3.125 | 0.7813 | 4.00 |

ASSAY TABLE 2-continued

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam. In the Table below, Efflux ratio is the ratio MITC95 PA_9798/MITC95 PA_9799

| EX. No. | P. aeruginosa expressing IMP-1, efflux + (MB9798) MITC95 μM | P. aeruginosa expressing IMP-1, efflux − (MB9799) MITC95 μM | Efflux ratio |
| --- | --- | --- | --- |
| 364 | 3.125 | 1.563 | 2.00 |
| 365 | 1.563 | 0.7813 | 2.00 |
| 366 | 0.7813 | 0.7813 | 1.00 |
| 367 | 0.7813 | 1.563 | 0.50 |
| 368 | 1.563 | 1.563 | 1.00 |
| 369 | 1.563 | 1.563 | 1.00 |
| 370 | 0.7813 | 0.7813 | 1.00 |
| 371 | 1.563 | 1.563 | 1.00 |
| 372 | 1.563 | 0.7813 | 2.00 |
| 373 | 1.563 | 1.563 | 1.00 |
| 374 | 1.563 | 1.563 | 1.00 |
| 375 | 1.563 | 1.563 | 1.00 |
| 376 | 1.563 | 1.563 | 1.00 |
| 377 | 1.563 | 0.7813 | 2.00 |
| 378 | 3.125 | 1.563 | 2.00 |
| 379 | 1.563 | 0.7813 | 2.00 |
| 380 | 0.7813 | 0.7813 | 1.00 |
| 381 | 1.172 | 0.7813 | 1.50 |
| 382 | 1.563 | 1.563 | 1.00 |
| 383 | 0.7813 | 0.7813 | 1.00 |
| 384 | 0.7813 | 1.563 | 0.50 |
| 385 | 0.7813 | 0.7813 | 1.00 |
| 386 | 1.563 | 1.563 | 1.00 |
| 387 | 0.7813 | 1.563 | 0.50 |
| 388 | 1.563 | 3.125 | 0.50 |
| 389 | 1.563 | 1.563 | 1.00 |
| 390 | 0.7813 | 1.563 | 0.50 |
| 391 | 1.563 | 1.563 | 1.00 |
| 392 | 1.563 | 3.125 | 0.50 |
| 393 | 0.7813 | 1.042 | 0.75 |
| 394 | 3.125 | 1.563 | 2.00 |
| 395 | 1.563 | 0.7813 | 2.00 |
| 396 | 0.7813 | 1.563 | 0.50 |
| 397 | 1.563 | 1.563 | 1.00 |
| 398 | 6.25 | 1.563 | 4.00 |
| 399 | 0.7813 | 0.7813 | 1.00 |
| 400 | 1.563 | 0.7813 | 2.00 |
| 401 | 1.563 | 0.7813 | 2.00 |
| 402 | 0.7813 | 0.7813 | 1.00 |
| 403 | 1.563 | 1.563 | 1.00 |
| 404 | 1.172 | 0.9766 | 1.20 |
| 405 | 25 | 12.5 | 2.00 |
| 406 | 1.563 | 1.563 | 1.00 |
| 407 | 3.125 | 1.563 | 2.00 |
| 408 | 1.563 | 1.563 | 1.00 |
| 409 | 1.563 | 1.563 | 1.00 |
| 410 | 0.7813 | 0.7813 | 1.00 |
| 411 | 1.563 | 1.563 | 1.00 |
| 412 | 1.563 | 3.125 | 0.50 |
| 413 | 1.563 | 1.563 | 1.00 |
| 414 | 1.563 | 1.563 | 1.00 |
| 415 | 1.563 | 1.563 | 1.00 |
| 416 | 3.125 | 3.125 | 1.00 |
| 417 | 1.563 | 0.7813 | 2.00 |
| 418 | 1.563 | 0.7813 | 2.00 |
| 419 | 1.563 | 0.7813 | 2.00 |
| 420 | 1.563 | 0.7813 | 2.00 |
| 421 | 1.563 | 0.7813 | 2.00 |
| 422 | 1.563 | 0.7813 | 2.00 |
| 423 | 3.125 | 0.7813 | 4.00 |
| 424 | 1.563 | 1.563 | 1.00 |
| 425 | 1.563 | 1.563 | 1.00 |
| 426 | 0.3906 | 0.7813 | 0.50 |
| 427 | 0.7813 | 0.7813 | 1.00 |
| 428 | 0.7813 | 0.7813 | 1.00 |
| 429 | 0.7813 | 0.7813 | 1.00 |
| 430 | 1.563 | 1.563 | 1.00 |
| 431 | 12.5 | 1.563 | 8.00 |
| 432 | 0.7813 | 0.7813 | 1.00 |
| 433 | 1.563 | 0.7813 | 2.00 |
| 434 | 1.563 | 0.7813 | 2.00 |
| 435 | 3.125 | 1.563 | 2.00 |
| 436 | 0.7813 | 0.7813 | 1.00 |
| 437 | 1.563 | 0.7813 | 2.00 |
| 438 | 6.25 | 3.125 | 2.00 |
| 439 | 6.25 | 1.563 | 4.00 |
| 440 | 1.563 | 0.7813 | 2.00 |
| 441 | 1.563 | 0.7813 | 2.00 |
| 442 | 0.7813 | 1.563 | 0.50 |
| 443 | 0.7813 | 0.7813 | 1.00 |
| 444 | 1.563 | 1.563 | 1.00 |
| 445 | 1.563 | 1.563 | 1.00 |
| 446 | 3.125 | 1.563 | 2.00 |
| 447 | 1.563 | 0.7813 | 2.00 |
| 448 | 1.563 | 3.125 | 0.50 |
| 449 | 6.25 | 1.563 | 4.00 |
| 450 | 1.563 | 0.7813 | 2.00 |
| 451 | 1.563 | 0.7813 | 2.00 |
| 452 | 6.25 | 1.563 | 4.00 |
| 453 | 3.125 | 1.563 | 2.00 |
| 454 | 3.125 | 1.563 | 2.00 |
| 455 | 12.5 | 1.563 | 8.00 |
| 456 | 1.563 | 0.7813 | 2.00 |
| 457 | 50 | 1.563 | 31.99 |
| 458 | 3.125 | 0.7813 | 4.00 |
| 459 | 3.125 | 1.563 | 2.00 |
| 460 | 3.125 | 1.563 | 2.00 |
| 461 | 12.5 | 3.125 | 4.00 |
| 462 | 1.563 | 0.7813 | 2.00 |
| 463 | 0.7813 | 0.7813 | 1.00 |
| 464 | 0.7813 | 0.7813 | 1.00 |
| 465 | 0.7813 | 0.7813 | 1.00 |
| 466 | 0.7813 | 0.7813 | 1.00 |
| 467 | 0.3906 | 0.7813 | 0.50 |
| 468 | 1.563 | 0.7813 | 2.00 |
| 469 | 0.7813 | 0.7813 | 1.00 |
| 470 | 1.563 | 0.7813 | 2.00 |
| 471 | 3.125 | 0.7813 | 4.00 |
| 472 | 1.563 | 0.3906 | 4.00 |
| 473 | 0.7813 | 0.7813 | 1.00 |
| 474 | 0.7813 | 0.7813 | 1.00 |
| 475 | 0.7813 | 0.7813 | 1.00 |
| 476 | 0.7813 | 0.7813 | 1.00 |
| 477 | 1.563 | 0.7813 | 2.00 |
| 478 | 0.7813 | 0.7813 | 1.00 |
| 479 | 0.7813 | 0.7813 | 1.00 |
| 480 | 0.7813 | 0.7813 | 1.00 |
| 481 | 1.563 | 1.563 | 1.00 |
| 482 | 1.563 | 0.7813 | 2.00 |
| 483 | 0.7813 | 0.7813 | 1.00 |
| 484 | 0.7813 | 0.7813 | 1.00 |
| 485 | 6.25 | 0.7813 | 8.00 |
| 486 | 1.563 | 0.7813 | 2.00 |
| 487 | 1.563 | 1.563 | 1.00 |
| 488 | 0.7813 | 0.7813 | 1.00 |
| 489 | 1.563 | 0.7813 | 2.00 |
| 490 | 1.563 | 1.563 | 1.00 |
| 491 | 0.7813 | 0.7813 | 1.00 |
| 492 | 1.563 | 1.563 | 1.00 |
| 493 | 0.3906 | 0.7813 | 0.50 |
| 494 | 3.125 | 1.563 | 2.00 |
| 495 | 0.7813 | 0.7813 | 1.00 |
| 496 | 0.7813 | 0.7813 | 1.00 |
| 497 | 0.7813 | 0.7813 | 1.00 |
| 498 | 0.7813 | 0.7813 | 1.00 |

ASSAY TABLE 2-continued

Concentration of metallo-β-lactamase inhibitors of Formula I which restores susceptibility of efflux + (MB9798) and efflux − (MB9799) strains to imipenem at 2 μg/mL in the presence of a class A, C, D serine β-lactamase inhibitor closely related to relebactam. In the Table below, Efflux ratio is the ratio MITC95 PA_9798/MITC95 PA_9799

| EX. No. | P. aeruginosa expressing IMP-1, efflux + (MB9798) MITC95 μM | P. aeruginosa expressing IMP-1, efflux − (MB9799) MITC95 μM | Efflux ratio |
|---|---|---|---|
| 499 | 0.7813 | 0.7813 | 1.00 |
| 500 | 1.563 | 1.563 | 1.00 |

Representative compounds of Formula I of the instant invention generally have a lower *Pseudomonas* efflux ratio than compounds in which the atom or linker at the C-6 position is a carbon or hydrogen instead of —$SO_2^-$.

What is claimed:

1. A compound of Formula I

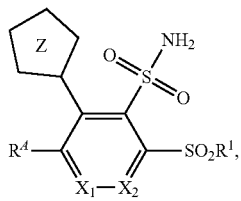

(I)

or a pharmaceutically acceptable salt thereof,
wherein:
$X^1$ is N or CH;
$X^2$ is N or CH;
Z is tetrazolyl, wherein Z is linked through a carbon to carbon bond to the six-membered core ring having $X_1$ and $X_2$;
$R^A$ is $(CH_2)_n$-AryA1, $(CH_2)_n$-HetA1, —$(CH_2)_n$—$C_4$-$C_6$cycloalkyl, or —$(CH_2)_n$—$C_4$-$C_6$cycloalkenyl, wherein said —$(CH_2)_n$—$C_4$-$C_6$cycloalkyl and —$(CH_2)_n$—$C_4$-$C_6$cycloalkenyl are optionally substituted with 1, 2, or 3 substituents independently selected from —$NH_2$, —OH, —F, and —$NR^aC(O)C_1$-$C_6$alkyl optionally substituted with 1 or 2 substituents independently selected from —F, —$CF_3$, —$NR^aR^b$, and –$OR^a$;
$R^1$ is
1) —$NH_2$;
2) —$NR^a$—$C_1$-$C_6$alkyl optionally substituted with 1, 2, 3, or 4 substituents independently selected from: —F, —$CF_3$, $C_1$-$C_6$alkyl, —$CH(NH_2)C(O)NH_2$, —$C(O)NR^aR^b$, —$C(O)OH$, —$(CH_2)_{1-2}NH_2$, —$NR^a(CH_2)_{2-3}NH_2$, —$NR^aR^b$, —$N^+R^aR^bCH_3$, —$NHCH_2CH_2OCH_3$, —$OR^a$, and —$O(CH_2)_{2-3}NH_2$;
3) —$NR^aC(O)C_1$-$C_6$alkyl optionally substituted with 1 or 2 substituents independently selected from: —F, —$CF_3$, —$C(O)NR^aR^b$, —$C(O)OH$, —$NR^aR^b$, —$N^+R^aR^bCH_3$, —$NHCH_2CH_2OCH_3$, —$OR^a$, and —$O(CH_2)_{2-3}NH_2$;
4) —$NR^a(CH_2)_n$—$C_3$-$C_6$cycloalkyl, wherein the $C_3$-$C_6$cycloalkyl is optionally substituted with —$CH_2OH$ or —$NH_2$;
5) a nitrogen-linked 4-6 membered monocyclic heterocycloalkyl with 0, 1, or 2, additional heteroatom ring atoms independently selected from N, O and S, or a nitrogen-linked 6- to 10-membered bicyclic heterocycloalkyl with 0, 1, 2, or 3 additional heteroatom ring atoms selected from N, O and S wherein the bicyclic ring may be bridged, fused or spirocyclic, wherein the 4-6 membered monocyclic heterocycloalkyl and the 6- to 10-membered bicyclic heterocycloalkyl are optionally substituted with one to three substituents, independently selected from: —F, —$NR^aR^b$, oxo, —$(CH_2)_{1-2}OH$, —$CH_2NH_2$, —$SO_2CH_3$, and $C_1$-$C_6$ alkyl and wherein a ring sulfur atom is optionally substituted with one or two oxo;
6) —$NR^a$—$(C_1$-$C_3$alkyl$)_n$-AryB1, wherein the $C_1$-$C_3$alkyl is optionally substituted with —$NH_2$; and
7) —$NR^a$—$(C_1$-$C_3$alkyl$)_n$-HetB1;
AryA1 is an aromatic ring system selected from:
1) a 5-6 membered monocyclic ring with 0, 1, 2, or 3 heteroatom ring atoms independently selected from N, O, and S, optionally substituted with 1, 2, or 3 substituents independently selected from:
a) halogen,
b) —$C_1$-$C_6$alkyl,
c) —CN,
d) —$CH_2OH$,
e) —$C(O)NR^aR^b$,
f) —$C(O)NH(CH_2)_{2-4}NH_2$ optionally substituted with one or two substituents independently selected from —$NR^aR^b$ and —$(CH_2)_nOR^a$,
g) —$C(O)OR^a$,
h) —$(CH_2)_pNHR^a$ optionally substituted with one or two substituents independently selected from —$NR^aR^b$ or —$OR^a$,
i) —$(CH_2)_pNR^aC(=NH)NH_2$,
j) —$NR^aC(O)C_1$-$C_6$ alkyl optionally substituted with one or two substituents independently selected from —$NR^aR^b$ or —$OR^a$,
k) —$NR^aSO_2$—$C_1$-$C_6$alkyl,
l) —$NR^aSO_2$-cyclopropyl,
m) —$OR^a$,
n) oxo,
o) —$SC_1$-$C_6$ alkyl optionally substituted with one or two substituents independently selected from —$NR^aR^b$ or —$OR^a$;
p) —$SO_2R^a$,
q) —$SO_2NR^aR^b$,
r) —$SO_2NH$-cyclopropyl,
s) -AryA2,
t) —$(CH_2)_nNR^aAryA2$,
u) —$C(O)NR^aHetA2$ and
v) -HetA2, and
2) an 8- to 10-membered bicyclic ring with 1, 2, 3 or 4 heteroatom ring atoms selected from N, O and S, wherein an S atom optionally has one or two oxo substituents and a N atom is optionally in the form of an N-oxide, and wherein the ring is optionally substituted with 1 or 2 substituents independently selected from
a) halogen;
b) $C_1$-$C_6$alkyl optionally substituted with one to three substituents independently selected from —$NR^aR^b$, —F and —$OR^a$;
c) —$(CH_2)_nCF_3$;
d) —$C(=NH)NH_2$;
e) —CN;
f) —$C(O)CF_3$;

g) —C(O)NR$^a$R$^b$;
h) —C(O)NHCH$_2$C(O)OR$^a$;
i) —C(O)NH—C$_2$-C$_4$alkyl-NH$_2$,
j) —C(O)OR$^a$;
k) —NR$^a$R$^b$;
l) —NHCH$_2$SO$_3$H;
m) —(CH$_2$)$_n$NHC(=NH)NH$_2$;
n) —NHC(O)C$_1$-C$_6$alkyl;
o) —NHC(O)NH$_2$;
p) —NHC(O)OR$^a$;
q) —NHSO$_2$CH$_3$;
r) —OR$^a$;
s) oxo;
t) —SO$_2$R$^a$,
u) —CH$_2$-phenyl-OCH$_3$; and
v) -HetA2;

HetA1 is dihydrothiopyranyl or tetrahydropyranyl;

AryA2 is a 5-6-membered aromatic monocyclic ring with 1, 2, or 3 heteroatom ring atoms independently selected from N, N as a quaternary salt, and S, or 4 N ring atoms, optionally substituted with —CH$_2$OH, —COOH, —CONH$_2$, —C(O)OC$_1$-C$_6$alkyl, and —(CH$_2$)$_p$NHR$^a$ optionally substituted with one or two substituents independently selected from —NR$^a$R$^b$ and —OR$^a$;

HetA2 is a 4-6-membered saturated monocyclic ring with 1 or 2 heteroatom ring atoms independently selected from N, O and S, wherein the S is optionally substituted with two oxo groups, and wherein the ring is optionally substituted with 1 or 2 substituents independently selected from C$_1$-C$_6$alkyl, —CN, —OH, and oxo;

AryB1 is an aromatic ring selected from:
1) a 5-6 membered monocyclic aromatic ring with 0, 1, 2, or 3 N ring atoms, optionally substituted with 1 substituent selected from —CF$_3$, C$_1$-C$_6$ alkyl, —(CH$_2$)$_n$NH$_2$ and —OCH$_3$; or
2) a 9-membered bicyclic ring with 2 N ring atoms;

HetB1 is a saturated ring selected from:
1) a 4-6 membered saturated monocyclic ring with 1 or 2 heteroatom ring atoms independently selected from N, O and S, wherein a N ring atom is optionally in the form of a quaternary amine, wherein the S is substituted with two oxo groups, and wherein the ring is optionally substituted with 1 or 2 substituents independently selected from —F, C$_1$-C$_6$ alkyl, C$_1$-C$_6$ hydroxyalkyl, —C(O)OR$^a$, —(CH$_2$)$_k$NR$^a$R$^b$, —OR$^a$, and oxo; or
2) a 6-10-membered bicyclic ring with 1 or 2 heteroatom ring atoms independently selected from N and O, optionally substituted with —OH or —NH$_2$, wherein the bicyclic ring is bridged or fused;

R$^a$ and R$^b$ are independently H or C$_1$-C$_6$ alkyl;
k is 0, 1, 2, 3, or 4;
each n is independently 0 or 1; and
each p is independently 0, 1, 2, or 3.

2. The compound of claim 1, or a pharmaceutically acceptable salt thereof, wherein X$^1$ and X$^2$ are CH.

3. The compound of claim 1, or a pharmaceutically acceptable salt thereof, having the Formula IA

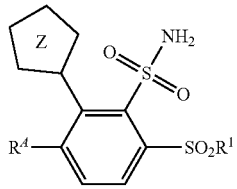

(IA)

wherein:
R$^A$ is AryA1, C$_4$-C$_6$cycloalkyl, or C$_4$-C$_6$cycloalkenyl, wherein said C$_4$-C$_6$cycloalkyl and C$_4$-C$_6$cycloalkenyl are optionally substituted with —NH$_2$ or NHC(O)(CH$_2$)$_{1-3}$NH$_2$;

AryA1 is an aromatic ring system selected from:
1) a 5-6 membered monocyclic ring with 0, 1, or 2 heteroatom ring atoms independently selected from N and S, optionally substituted with 1 or 2 substituents independently selected from:
a) F,
b) —C$_1$-C$_6$ alkyl,
c) —CN,
d) —CH$_2$OH,
e) —C(O)NR$^a$R$^b$,
f) —C(O)NH(CH$_2$)$_{2-4}$NH$_2$,
g) —C(O)OR$^a$,
h) —(CH$_2$)$_p$NHR$^a$,
i) —NHC(=NH)NH$_2$;
j) —NHC(O)CH$_3$;
k) —NR$^a$SO$_2$—C$_1$-C$_6$alkyl,
l) —NHSO$_2$-cyclopropyl,
m) —OR$^a$,
n) —SO$_2$NR$^a$R$^b$,
o) —SC$_1$-C$_6$alkyl,
p) —SO$_2$NH-cyclopropyl,
q) -AryA2,
r) —(CH$_2$)$_n$NR$^a$AryA2,
s) —C(O)NR$^a$HetA2 and
t) -HetA2, and 2) a 8- to 10-membered bicyclic ring with 1, 2, 3 or 4 heteroatom ring atoms selected from N, O and S, wherein an S atom is optionally substituted with one or two oxo substituents and a N atom is optionally in the form of an N-oxide, and wherein the ring is optionally substituted with 1 or 2 substituents independently selected from F, C$_1$-C$_6$ alkyl, —CH$_2$CF$_3$, —CF$_2$CH$_2$NH$_2$, —CF$_3$, —C(=NH)NH$_2$, —CH(NH$_2$)CH$_3$, —CN, —C(O)CF$_3$, —C(O)NR$^a$R$^b$, —C(O)NHCH$_2$C(O)OR$^a$, —C(O)OR$^a$, —(CH$_2$)$_{0-2}$NR$^a$R$^b$, —NHC(O)CH$_3$, —NHC(O)NH$_2$, —NHC(O)OR$^a$, —NHCH$_2$SO$_3$H, —NHSO$_2$CH$_3$, —OR$^a$, oxo, —CH$_2$-phenyl-OCH$_3$, and -HetA2; and all other variables are defined in claim 1.

4. The compound of claim 1, or a pharmaceutically acceptable salt thereof, wherein R$^A$ is AryA1.

5. The compound of claim 4, or a pharmaceutically acceptable salt thereof, wherein AryA1 is 1) pyridyl optionally substituted with —NH$_2$, 2) benzoimidazolyl substituted with 1 or 2 substituents independently selected from F, —CH$_3$ and —(CH$_2$)NH$_2$; or 3) benzothiazolyl substituted with 1 or 2 substituents independently selected from —CH$_3$ and —(CH$_2$)$_n$NH$_2$.

6. The compound of claim 1, or a pharmaceutically acceptable salt thereof, wherein R$^1$ is:
1) —NH$_2$;
2) —NR$^a$—C$_1$-C$_6$alkyl optionally substituted with 1, 2, 3 or 4 substituents independently selected from —F, —CF$_3$, C$_1$-C$_6$alkyl, —CH(NH$_2$)C(O)NH$_2$, —C(O)NR$^a$R$^b$, —C(O)OH, —(CH$_2$)$_{1-2}$NH$_2$, —NR$^a$R$^b$, —N$^+$R$^a$R$^b$CH$_3$, —NHCH$_2$CH$_2$OCH$_3$, —OR$^a$, —NR$^a$(CH$_2$)$_{2-3}$NH$_2$, and —O(CH$_2$)$_{2-3}$NH$_2$;
3) —NR$^a$(CH$_2$)$_n$—C$_3$-C$_6$cycloalkyl, wherein the C$_3$-C$_6$cycloalkyl is optionally substituted with —CH$_2$OH or —NH$_2$,
4) —NR$^a$—(C$_1$-C$_3$alkyl)$_n$-AryB1, wherein the C$_1$-C$_3$alkyl is optionally substituted with —NH$_2$; and
5) —NR$^a$—(C$_1$-C$_3$alkyl)$_n$-HetB1.

7. The compound of claim 1, or a pharmaceutically acceptable salt thereof, wherein $R^1$ is: —$NH_2$, —NH-HetB1 optionally substituted with —$NH_2$, or —NH—$C_2$-$C_3$alkyl$NH_2$, optionally substituted with —$CH_3$, —OH or —$NH_2$.

8. The compound of claim 1, or a pharmaceutically acceptable salt thereof, having the Formula IB:

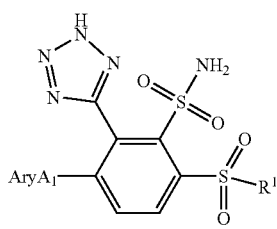

(IB)

wherein:

AryA1 is an aromatic ring system selected from:
1) a 5-6 membered monocyclic ring with 0 or 1 N ring atoms substituted with 1 or 2 substituents independently selected from F, —$C_1$-$C_6$ alkyl, —CONH—$C_{2-4}$alkyl-$NH_2$, or —$NHR^a$; or
2) a 9-membered bicyclic ring with 2 heteroatom ring atoms selected from N and S, wherein the ring is optionally substituted with 1 or 2 substituents independently selected from F, $C_1$-$C_6$ alkyl, and —$(CH_2)_xNR^aR^b$ $R^1$ is
1) —$NH_2$,
2) —$NR^a$—$C_{1-6}$alkyl optionally substituted with 1 or 2 F substituents and optionally substituted with 1 or 2 substituents independently selected from —$CF_3$, —$CH(NH_2)C(O)NH_2$; —$C(O)NR^aR^b$; —$C(O)OH$; —$NR^a(CH_2)_{2-3}NH_2$, —$NR^aR^b$, —$N^+R^aR^bCH_3$, —$NHCH_2CH_2OCH_3$, —$OR^a$, and —$O(CH_2)_{2-3}NH_2$;
3) —$NR^a(CH_2)_n$—$C_3$-$C_6$cycloalkyl, wherein the $C_3$-$C_6$cycloalkyl is optionally substituted with —$CH_2OH$ or —$NH_2$;
4) —$NR^a$—$(C_1$-$C_3$alkyl)$_n$-AryB1; and
5) —$NR^a$—$(C_1$-$C_3$alkyl)$_n$-HetB1;

$R^a$ and $R^b$ are H or —$CH_3$; and
x is 0, 1 or 2.

9. A compound of claim 1 having the structure

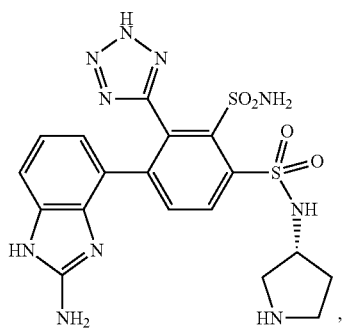

-continued

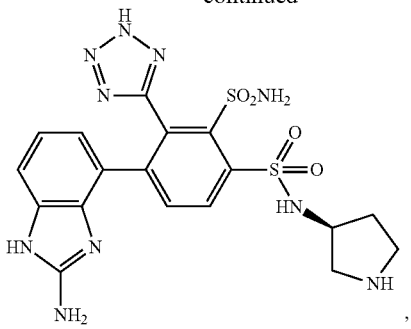

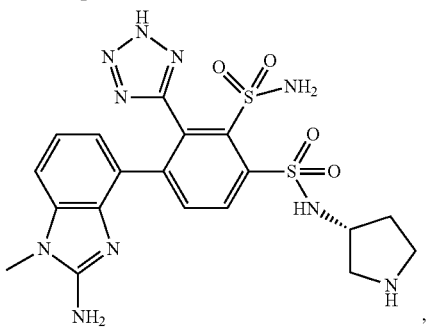

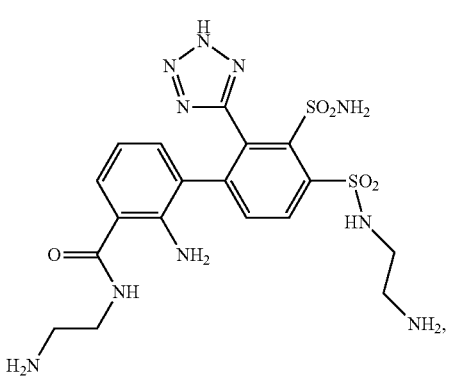

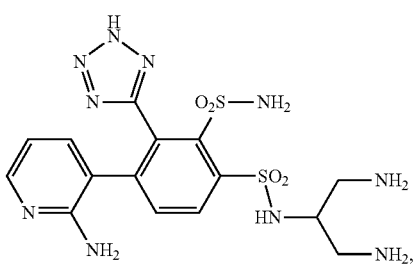

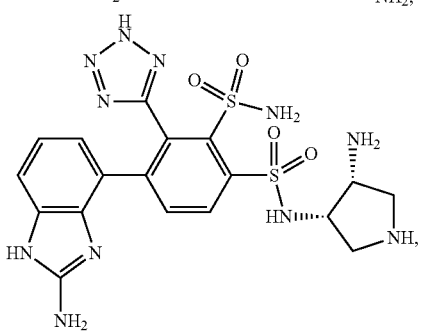

553
-continued
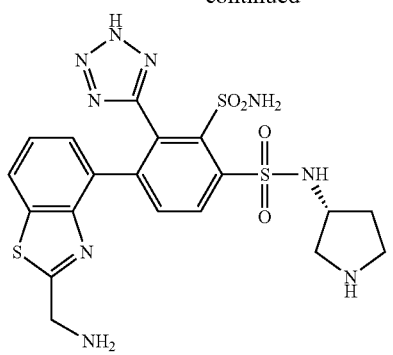
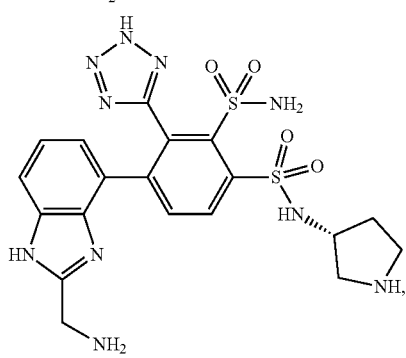
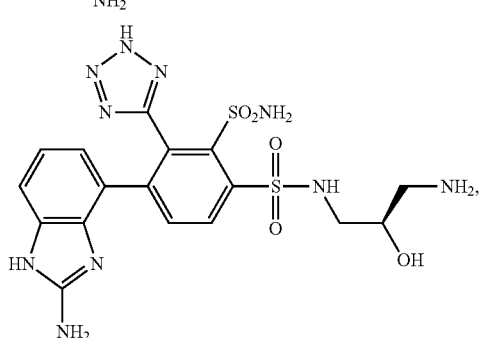
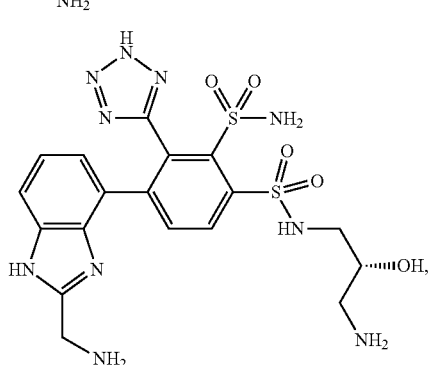
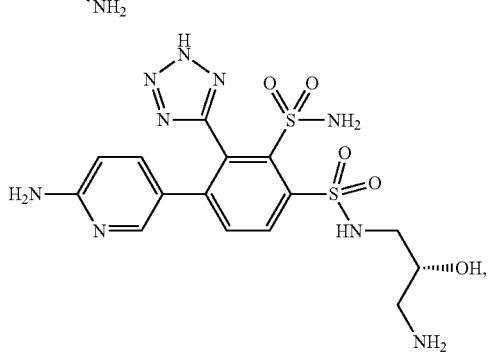
554
-continued
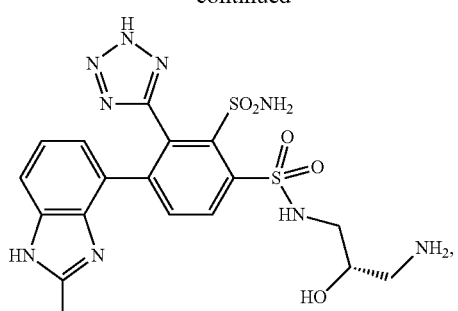
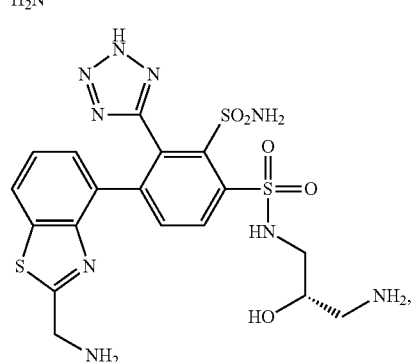
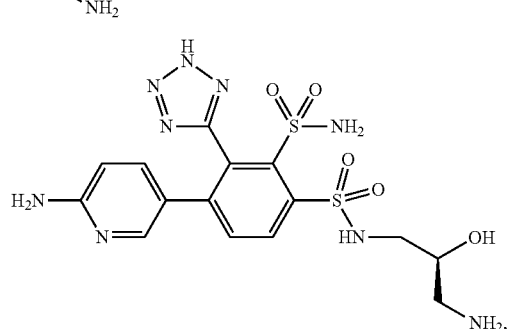
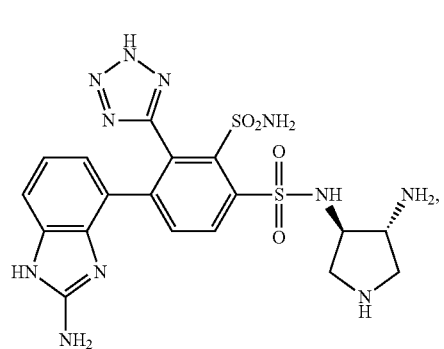
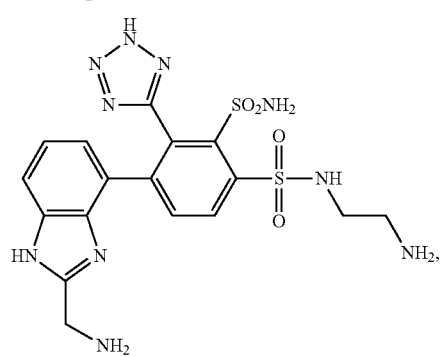

-continued

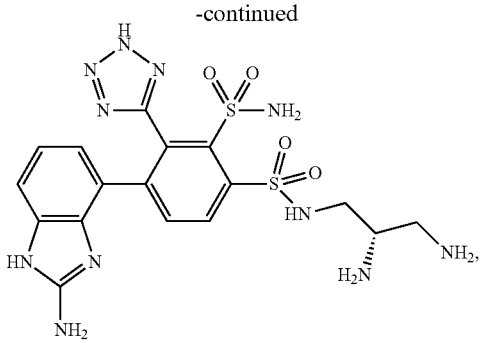

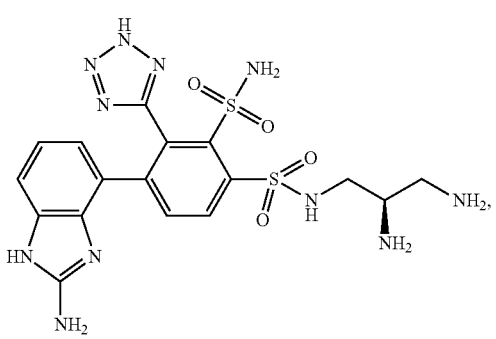

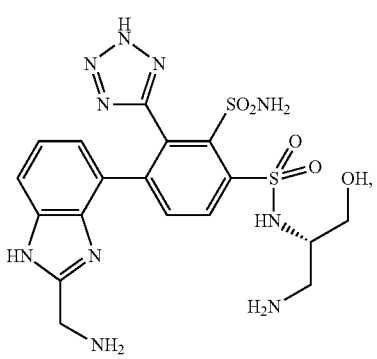

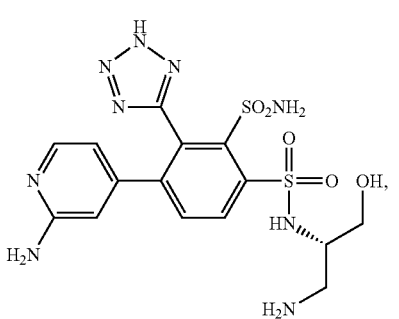

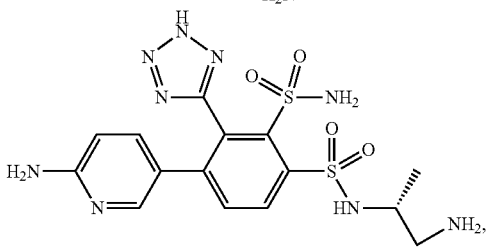

-continued

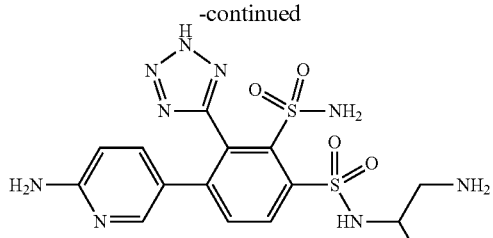

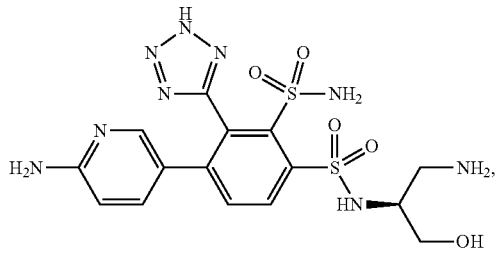

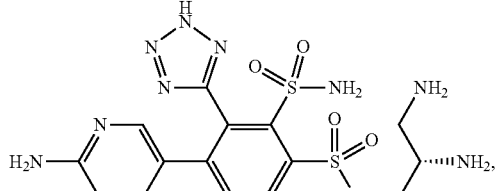

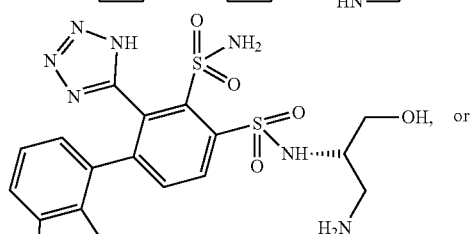

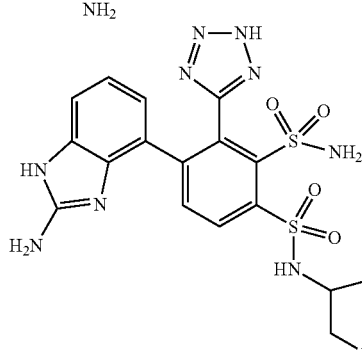

or a pharmaceutically acceptable salt thereof.

10. A zwitterion of the compound of claim 9.

11. A pharmaceutical composition which comprises a compound according to claim 1, or a pharmaceutically acceptable salt thereof, and a pharmaceutically acceptable carrier.

12. A pharmaceutical composition according to claim 11, which further comprises an effective amount of a beta-lactam antibiotic.

13. The pharmaceutical composition according to claim 12, which further comprises an effective amount of one or more beta-lactamase inhibitor compounds.

14. The pharmaceutical composition according to claim 13, wherein the composition comprises a beta-lactamase inhibitor compound selected from the group consisting of: relebactam, avibactam, vaborbactam, tazobactam, sulbactam, and clavulanic acid.

15. The pharmaceutical composition according to claim 14, wherein the beta-lactamase inhibitor compound is tazobactam and the beta-lactam antibiotic is ceftolozane.

16. The pharmaceutical composition according to claim 14, wherein the beta-lactamase inhibitor compound is relebactam.

17. The pharmaceutical composition according to claim 12, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, cefoperazone, cefotaxime, ceftriaxone, cefipime, ceftolozane, and ceftazidime.

18. The pharmaceutical composition according to claim 12, wherein the beta-lactam antibiotic is imipenem.

19. The pharmaceutical composition according to claim 18, further comprising cilastatin or a pharmaceutically acceptable salt thereof.

20. A method for inhibiting a bacterial beta-lactamase in a subject which comprises administering to the subject an effective amount of a compound according to claim 1, or a pharmaceutically acceptable salt thereof, optionally in combination with a beta-lactam antibiotic.

21. A method for treating a bacterial infection which comprises administering to a subject in need of such treatment a therapeutically effective amount of a compound according to claim 1, or a pharmaceutically acceptable salt thereof, in combination with a beta-lactam antibiotic.

22. The method of claim 21, wherein the beta-lactam antibiotic is selected from the group consisting of imipenem, ertapenem, meropenem, doripenem, biapenem, panipenem, ticarcillin, ampicillin, amoxicillin, carbenicillin, piperacillin, azlocillin, mezlocillin, cefoperazone, cefotaxime, ceftriaxone, cefipime, ceftolozane, and ceftazidime.

23. The method of claim 21, wherein the beta-lactam antibiotic is imipenem.

24. A method for treating a bacterial infection which comprises administering to a subject in need of such treatment a therapeutically effective amount of a compound according to claim 1, or a pharmaceutically acceptable salt thereof, and a therapeutically effective amount of imipenem, cilastatin, and relebactam.

25. The method of claim 21, wherein the bacterial infection is due to *Pseudomonas* spp., *Klebsiella* spp., *Enterobacter* spp., *Escherichi* spp., *Morganella* spp., *Citrobacter* spp., *Serratia*, spp. or *Acinetobacter* spp.

26. The compound of claim 1, or a pharmaceutically acceptable salt thereof, wherein:
$X^1$ and $X^2$ are CH; and
$R^A$ is:

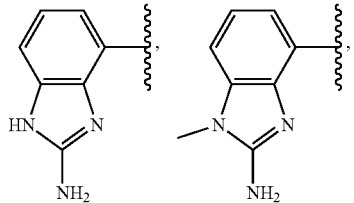

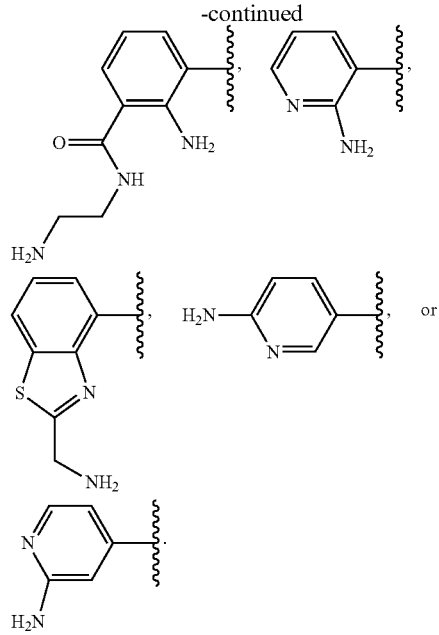

27. The compound of claim 26, or a pharmaceutically acceptable salt thereof, wherein $R^1$ is —$NR^a$—$(C_1$-$C_3$ alkyl)$_n$-HetB1.

28. The compound of claim 27, or a pharmaceutically acceptable salt thereof, wherein $R^a$ is H and HetB1 is:

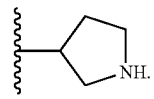

29. The compound of claim 26, or a pharmaceutically acceptable salt thereof, wherein $R^1$ is —$NHCH(CH_2NH_2)CH_2NH_2$.

30. The compound of claim 26, or a pharmaceutically acceptable salt thereof, wherein $R^1$ is —$NHCH_2CH(OH)CH_2NH_2$.

31. The compound of claim 26, or a pharmaceutically acceptable salt thereof, wherein $R^1$ is —$NHCH_2CH(NH_2)CH_2NH_2$.

32. A compound having the structure

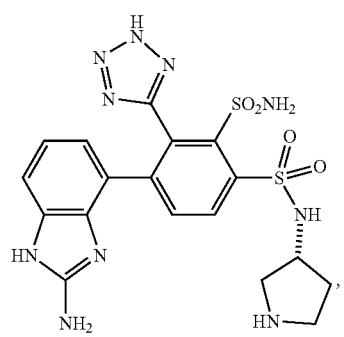

or a pharmaceutically acceptable salt thereof.

33. A pharmaceutically acceptable salt of the compound of claim 32.

34. A pharmaceutical composition comprising the compound of claim 32 or a pharmaceutically acceptable salt thereof and a pharmaceutically acceptable carrier.

35. The pharmaceutical composition of claim 34 further comprising relebactam.

36. A method for treating a bacterial infection which comprises administering to a subject in need of such treatment a therapeutically effective amount of a compound according to claim 32, or a pharmaceutically acceptable salt thereof, in combination with a beta-lactam antibiotic.

37. A compound having the structure or a pharmaceutically acceptable salt thereof.

38. A pharmaceutically acceptable salt of the compound of claim 37.

39. A pharmaceutical composition comprising the compound of claim 37 or a pharmaceutically acceptable salt thereof and a pharmaceutically acceptable carrier.

40. The pharmaceutical composition of claim 39 further comprising relebactam.

41. A method for treating a bacterial infection which comprises administering to a subject in need of such treatment a therapeutically effective amount of a compound according to claim 37, or a pharmaceutically acceptable salt thereof, in combination with a beta-lactam antibiotic.

42. A compound having the structure or a pharmaceutically acceptable salt thereof.

43. A pharmaceutically acceptable salt of the compound of claim 42.

44. A pharmaceutical composition comprising the compound of claim 42 or a pharmaceutically acceptable salt thereof and a pharmaceutically acceptable carrier.

45. The pharmaceutical composition of claim 44 further comprising relebactam.

46. A method for treating a bacterial infection which comprises administering to a subject in need of such treatment a therapeutically effective amount of a compound according to claim 42, or a pharmaceutically acceptable salt thereof, in combination with a beta-lactam antibiotic.

47. A compound having the structure or a pharmaceutically acceptable salt thereof.

48. A pharmaceutically acceptable salt of the compound of claim 47.

49. A pharmaceutical composition comprising the compound of claim 47 or a pharmaceutically acceptable salt thereof and a pharmaceutically acceptable carrier.

50. The pharmaceutical composition of claim 49 further comprising relebactam.

51. A method for treating a bacterial infection which comprises administering to a subject in need of such treatment a therapeutically effective amount of a compound according to claim 47, or a pharmaceutically acceptable salt thereof, in combination with a beta-lactam antibiotic.

52. A compound having the structure or a pharmaceutically acceptable salt thereof.

53. A pharmaceutically acceptable salt of the compound of claim 52.

54. A pharmaceutical composition comprising the compound of claim 52 or a pharmaceutically acceptable salt thereof and a pharmaceutically acceptable carrier.

55. The pharmaceutical composition of claim 54 further comprising relebactam.

56. A method for treating a bacterial infection which comprises administering to a subject in need of such treatment a therapeutically effective amount of a compound according to claim 52, or a pharmaceutically acceptable salt thereof, in combination with a beta-lactam antibiotic.

57. A compound having the structure

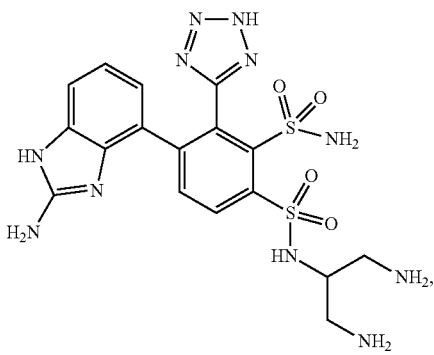

or a pharmaceutically acceptable salt thereof.

58. A pharmaceutically acceptable salt of the compound of claim 57.

59. A pharmaceutical composition comprising the compound of claim 57 or a pharmaceutically acceptable salt thereof and a pharmaceutically acceptable carrier.

60. The pharmaceutical composition of claim 59 further comprising relebactam.

61. A method for treating a bacterial infection which comprises administering to a subject in need of such treatment a therapeutically effective amount of a compound according to claim 57, or a pharmaceutically acceptable salt thereof, in combination with a beta-lactam antibiotic.

62. A compound having the structure

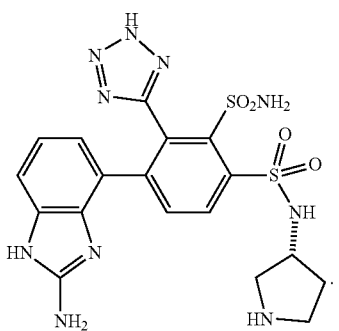

63. A compound having the structure

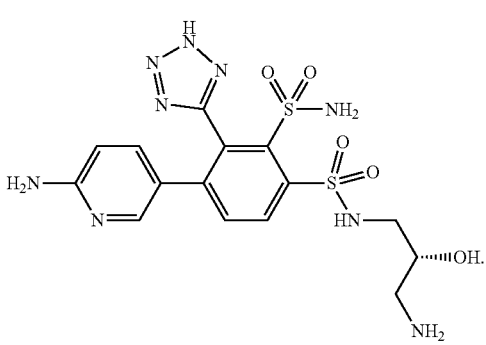 [SMILES: NC[C@@H](O)CNS(=O)(=O)c1ccc(-c2ccc(N)nc2)c(-c2nn[nH]n2)c1S(N)(=O)=O]

64. A compound having the structure

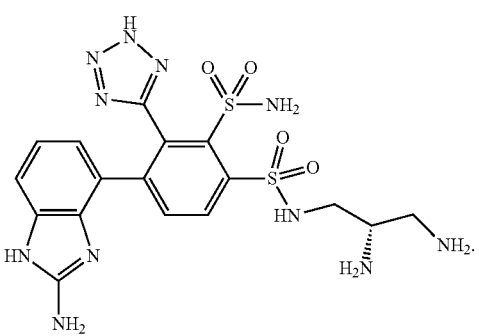 [SMILES: NC[C@H](N)CNS(=O)(=O)c1ccc(-c2cccc3[nH]c(N)nc23)c(-c2nn[nH]n2)c1S(N)(=O)=O]

65. A compound having the structure

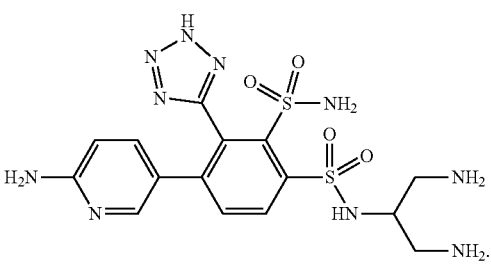 [SMILES: NCC(CN)NS(=O)(=O)c1ccc(-c2ccc(N)nc2)c(-c2nn[nH]n2)c1S(N)(=O)=O]

66. A compound having the structure

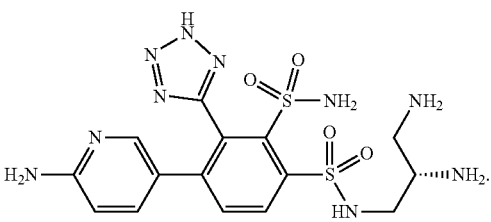 [SMILES: NC[C@H](N)CNS(=O)(=O)c1ccc(-c2ccc(N)nc2)c(-c2nn[nH]n2)c1S(N)(=O)=O]

67. A compound having the structure

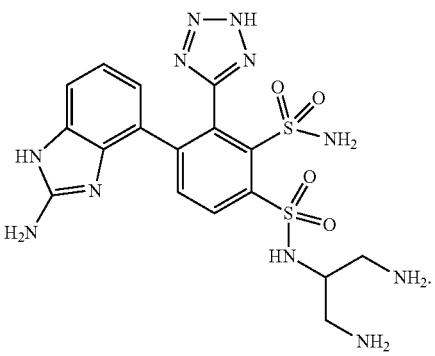 [SMILES: NCC(CN)NS(=O)(=O)c1ccc(-c2cccc3[nH]c(N)nc23)c(-c2nn[nH]n2)c1S(N)(=O)=O]

* * * * *